United States Patent
Kim et al.

(10) Patent No.: US 11,812,658 B2
(45) Date of Patent: Nov. 7, 2023

(54) COMPOUND AND ORGANIC LIGHT EMITTING DIODE COMPRISING SAME

(71) Applicant: LG CHEM, LTD., Seoul (KR)

(72) Inventors: Minjun Kim, Daejeon (KR); Kongkyeom Kim, Daejeon (KR); Min Woo Lee, Daejeon (KR); Donghee Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 589 days.

(21) Appl. No.: 16/982,229

(22) PCT Filed: Apr. 19, 2019

(86) PCT No.: PCT/KR2019/004757
§ 371 (c)(1),
(2) Date: Sep. 18, 2020

(87) PCT Pub. No.: WO2019/203613
PCT Pub. Date: Oct. 24, 2019

(65) Prior Publication Data
US 2021/0036236 A1    Feb. 4, 2021

(30) Foreign Application Priority Data

Apr. 19, 2018 (KR) .................. 10-2018-0045682

(51) Int. Cl.
*C07D 405/14* (2006.01)
*H10K 85/60* (2023.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
None
See application file for complete search history.

(56) References Cited

U.S. PATENT DOCUMENTS

| 2004/0251816 A1 | 12/2004 | Leo et al. |
| 2011/0240983 A1 | 10/2011 | Sekiguchi et al. |
| 2019/0157560 A1 | 5/2019 | Lee et al. |

FOREIGN PATENT DOCUMENTS

| JP | 2010-138121 | 6/2010 |
| KR | 10-2011-0107681 | 10/2011 |

(Continued)

OTHER PUBLICATIONS

Machine translation of KR-20160062603, translation generated Apr. 2023, 15 pages. (Year: 2023).*

(Continued)

*Primary Examiner* — Robert S Loewe
(74) *Attorney, Agent, or Firm* — Bryan Cave Leighton Paisner LLP

(57) ABSTRACT

Provided is a compound of Chemical Formula 1:

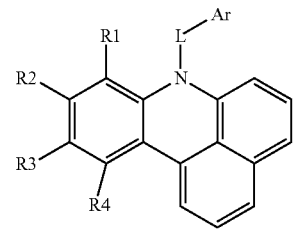

wherein:
R1 to R4 are each independently hydrogen, or groups adjacent to each other can bond to form a substituted or unsubstituted monocyclic or polycyclic ring;
L is a direct bond or a substituted or unsubstituted arylene group; and (Continued)

| 4 |
|---|
| 3 |
| 2 |
| 1 |

Ar is Chemical Formula D:

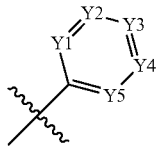

wherein:
Y1 to Y5 each independently is N or CR;
at least one of Y1 to Y5 is N;
R is hydrogen, deuterium, a halogen group, a substituted or unsubstituted alkyl group, a substituted or unsubstituted alkenyl group, a substituted or unsubstituted aryl group, or a substituted or unsubstituted heteroaryl group, and adjacent Rs can bond to each other to form a substituted or unsubstituted ring; and
when R is two or more, the Rs are the same as or different from each other, and an organic light emitting device comprising the same.

10 Claims, 1 Drawing Sheet

(51) Int. Cl.
| | | |
|---|---|---|
| *C07D 409/14* | (2006.01) | |
| *C07D 491/048* | (2006.01) | |
| *C07D 495/04* | (2006.01) | |
| *H10K 50/11* | (2023.01) | |
| *H10K 50/15* | (2023.01) | |
| *H10K 50/16* | (2023.01) | |
| *H10K 50/17* | (2023.01) | |

(52) U.S. Cl.
CPC ....... *C07D 491/048* (2013.01); *C07D 495/04* (2013.01); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/17* (2023.02); *H10K 50/171* (2023.02)

(56) References Cited

FOREIGN PATENT DOCUMENTS

| KR | 10-2013-0076223 | | 7/2013 | |
|---|---|---|---|---|
| KR | 10-2015-0053027 | | 5/2015 | |
| KR | 20150086071 | A * | 7/2015 | ........... C07D 401/04 |
| KR | 10-2015-0096152 | | 8/2015 | |
| KR | 10-2016-0004566 | | 1/2016 | |
| KR | 10-2016-0062603 | | 6/2016 | |
| KR | 10-2016-0064029 | | 6/2016 | |
| KR | 20160062603 | A * | 6/2016 | ........... C07D 471/04 |
| KR | 10-2016-0123176 | | 10/2016 | |
| WO | 2003-012890 | | 2/2003 | |

OTHER PUBLICATIONS

Machine translation of KR-20150086071, translation generated Apr. 2023, 16 pages. (Year: 2023).*

* cited by examiner

【FIG. 1】
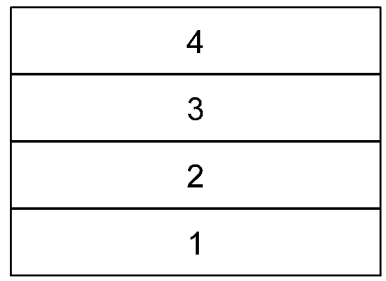
【FIG. 2】
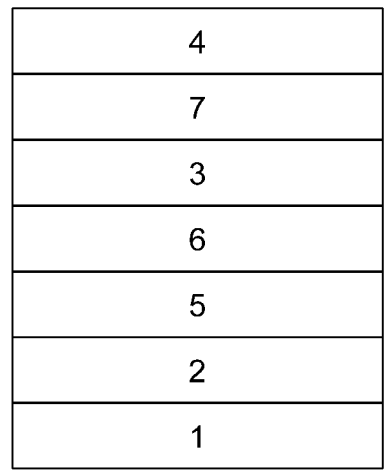
【FIG. 3】
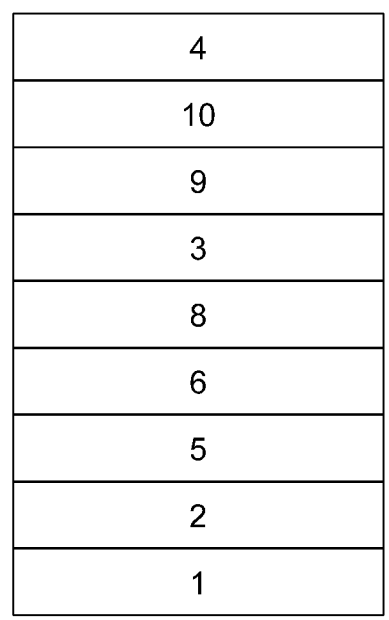

COMPOUND AND ORGANIC LIGHT EMITTING DIODE COMPRISING SAME

CROSS-REFERENCE TO RELATED APPLICATION(S)

This application is a National Stage Application of International Application No. PCT/KR2019/004757 filed on Apr. 19, 2019, which claims priority to and the benefits of Korean Patent Application No. 10-2018-0045682, filed with the Korean Intellectual Property Office on Apr. 19, 2018, the entire contents of which are incorporated herein by reference.

TECHNICAL FIELD

The present application relates to a compound of Chemical Formula 1, and an organic light emitting device comprising the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are famed, and light emits when these excitons fall back to the ground state.

Development of new materials for such an organic light emitting device has been continuously required.
<Prior Art Documents> Korean Patent Application Laid-Open Publication No. 10-2011-0107681

BRIEF DESCRIPTION

Technical Problem

The present application is directed to providing a compound of Chemical Formula 1, and an organic light emitting device comprising the same.

Technical Solution

One embodiment of the present application provides a compound of the following Chemical Formula 1:

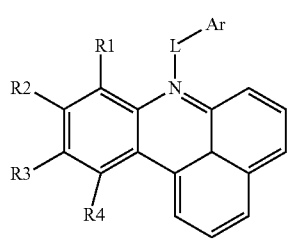

Chemical Formula 1

In Chemical Formula 1:
R1 to R4 are each independently hydrogen, or adjacent groups can bond to each other to form a substituted or unsubstituted monocyclic or polycyclic ring;
L is a direct bond or a substituted or unsubstituted arylene group; and
Ar is a group of the following Chemical Formula D:

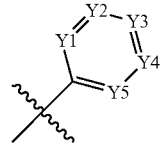

Chemical Formula D wherein in Chemical Formula D:
Y1 to Y5 are the same as or different from each other, and each independently is N or CR;
at least one of Y1 to Y5 is N;
R is hydrogen, deuterium, a halogen group, a substituted or unsubstituted alkyl group, a substituted or unsubstituted alkenyl group, a substituted or unsubstituted aryl group, or a substituted or unsubstituted heteroaryl group, and adjacent Rs can bond to each other to form a substituted or unsubstituted ring; and
when R is two or more, the Rs are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the compound of Chemical Formula 1 described above.

Advantageous Effects

An organic light emitting device using a compound according to one embodiment of the present application is capable of having low driving voltage, high light emission efficiency and/or long lifetime.

DESCRIPTION OF DRAWINGS

FIG. 1 illustrates an example of an organic light emitting device in which a substrate (1), a first electrode (2), a light emitting layer (3) and a second electrode (4) are consecutively laminated.

FIG. 2 illustrates an example of an organic light emitting device in which a substrate (1), a first electrode (2), a hole injection layer (5), a hole transfer layer (6), a light emitting layer (3), an electron transfer layer (7) and a second electrode (4) are consecutively laminated.

FIG. 3 illustrates an example of an organic light emitting device in which a substrate (1), a first electrode (2), a hole injection layer (5), a hole transfer layer (6), an electron blocking layer (8), a light emitting layer (3), a hole blocking layer (9), a layer carrying out electron transfer and electron injection at the same time (10) and a second electrode (4) are consecutively laminated.

REFERENCE NUMERALS

1: Substrate
2: First Electrode

3: Light Emitting Layer
4: Second Electrode
5: Hole Injection Layer
6: Hole Transfer Layer
7: Electron Transfer Layer
8: Electron Blocking Layer
9: Hole Blocking Layer
10: Layer Carrying Out Electron Transfer and Electron Injection At The Same Time

DETAILED DESCRIPTION

Hereinafter, the present specification will be described in more detail.

One embodiment of the present specification provides a compound of Chemical Formula 1.

In the present specification,

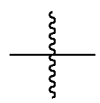

means a linking site or a bonding site.

According to one embodiment of the present application, the compound of Chemical Formula 1 can have properties of long lifetime and high efficiency by having a core structure as above.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of hydrogen, a halogen group, a nitrile group, a nitro group, a hydroxyl group, an alkyl group, a cycloalkyl group, an alkenyl group, an amine group, an aryl group, and a heterocyclic group, or being substituted with a substituent linking two or more substituents among the substituents illustrated above, or having no substituents. For example, "a substituent linking two or more substituents" can include a biphenyl group. In other words, a biphenyl group can be an aryl group, or interpreted as a substituent linking two phenyl groups.

In the present specification, examples of the halogen group include fluorine, chlorine, bromine or iodine.

In the present specification, the alkyl group can be linear or branched, and although not particularly limited thereto, the number of carbon atoms is preferably from 1 to 50. Specific examples thereof can include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms. Specific examples thereof can include cyclopropyl, cyclobutyl, cyclopentyl, cyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 20. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group can be linear or branched, and although not particularly limited thereto, the number of carbon atoms is preferably from 2 to 40. Specific examples thereof can include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the aryl group means a totally or partially unsaturated substituted or unsubstituted monocyclic or polycyclic. The number of carbon atoms is not particularly limited, but is preferably from 6 to 60. According to one embodiment, the number of carbon atoms of the aryl group is from 6 to 40. According to one embodiment, the number of carbon atoms of the aryl group is from 6 to 30. The aryl group can be a monocyclic aryl group or a polycyclic aryl group.

Examples of the monocyclic aryl group can include a phenyl group, a biphenyl group, a terphenyl group and the like, but are not limited thereto.

Examples of the polycyclic aryl group can include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group and the like, but are not limited thereto.

In the present specification, the fluorenyl group can be substituted, and adjacent substituents can bond to each other to form a ring.

When the fluorenyl group is substituted,

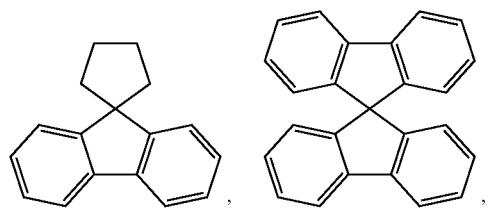

-continued

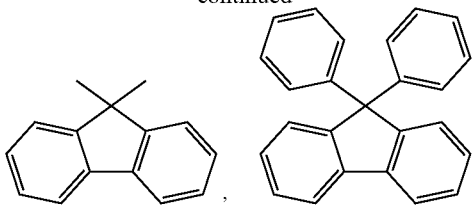

and the like can be included, however, the structure is not limited thereto.

In the present specification, the heterocyclic group includes one or more atoms that are not carbon, that is, heteroatoms, and specifically, the heteroatom can include one or more atoms selected from the group consisting of O, N, Se and S. The number of carbon atoms of the heterocyclic group is not particularly limited, but is preferably from 2 to 60. Examples of the heterocyclic group can include a thiophene group, a furanyl group, a pyrrolyl group, an imidazolyl group, a triazolyl group, an oxazolyl group, an oxadiazolyl group, a triazolyl group, a pyridinyl group, a bipyridinyl group, a pyrimidinyl group, a triazinyl group, an acridinyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, an isoxazolyl group, a thiadiazolyl group, a benzothiazolyl group, a phenothiazinyl group, a dibenzofuranyl group and the like, but are not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, adjacent groups bonding to each other to form a ring means, as described above, adjacent groups bonding to each other to form a 5-membered to 8-membered hydrocarbon ring; or a 5-membered to 8-membered heteroring. The formed ring can be monocyclic or polycyclic, and aliphatic, aromatic or a fused type thereof, but is not limited thereto.

In the present specification, adjacent groups bonding to each other to form a ring means adjacent groups being linked to each other through a chemical bond. For example, in the following reaction formula, G1 and G2 being adjacent groups and G1 and G2 bonding to each other to form a ring means a position linking G1 and G2 being linked by an organic group to form a ring. It means, even when G1 and G2 are hydrogen, a ring is formed at a position linking G1 and G2:

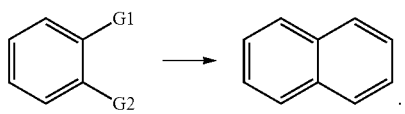

According to one embodiment of the present application, R1 to R4 are each independently hydrogen, or groups adjacent to each other can bond to form a substituted or unsubstituted hydrocarbon ring.

According to one embodiment of the present application, R1 to R4 are each independently hydrogen, or groups adjacent to each other can bond to form a substituted or unsubstituted benzene ring.

According to one embodiment of the present application, R1 to R4 are each independently hydrogen, or groups adjacent to each other can bond to form a benzene ring.

According to one embodiment of the present application, R1 to R4 are each hydrogen, or (R1 and R2), (R2 and R3), or (R3 and R4) can bond to each other to form a benzene ring.

According to one embodiment of the present application, L is a direct bond or a substituted or unsubstituted arylene group.

According to one embodiment of the present application, L is a direct bond or an arylene group.

According to one embodiment of the present application, L is a direct bond or a substituted or unsubstituted $C_{6-15}$ arylene group.

According to one embodiment of the present application, L is a direct bond or a $C_{6-15}$ arylene group.

According to one embodiment of the present application, L is a direct bond or a $C_{6-10}$ arylene group.

According to one embodiment of the present application, L is a direct bond, a phenylene group, or a divalent naphthyl group.

According to one embodiment of the present application, Ar is a group of the following Chemical Formula D:

Chemical Formula D

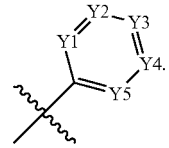

In Chemical Formula D:
Y1 to Y5 are the same as or different from each other, and each independently is N or CR;
at least one of Y1 to Y5 is N;
R is hydrogen; deuterium, a halogen group, a substituted or unsubstituted alkyl group, a substituted or unsubstituted alkenyl group, a substituted or unsubstituted aryl group, or a substituted or unsubstituted heteroaryl group, and adjacent Rs can bond to each other to form a substituted or unsubstituted ring; and
when R is two or more, the Rs are the same as or different from each other.

According to one embodiment of the present application, at least two of Y1 to Y5 are N.

According to one embodiment of the present application, at least three of Y1 to Y5 are N.

According to one embodiment of the present application, Y1 is N, and at least one of Y2 to Y5 is N.

According to one embodiment of the present application, R is hydrogen, deuterium, a halogen group, an alkyl group, an alkenyl group, an aryl group that is unsubstituted or substituted with R32, or a heteroaryl group that is unsubstituted or substituted with R33, and R32 and R33 are the same as or different from each other and each independently is deuterium, a halogen group, a substituted or unsubstituted alkyl group, a substituted or unsubstituted alkenyl group, a substituted or unsubstituted aryl group, or a substituted or unsubstituted heteroaryl group, and adjacent Rs bond to each other to form an aromatic hydrocarbon ring or an aromatic heteroring.

According to one embodiment of the present application, the ring formed by adjacent Rs bonding to each other can be a substituted or unsubstituted benzene, a substituted or unsubstituted indene, a substituted or unsubstituted benzofuran, or a substituted or unsubstituted benzothiophene.

According to one embodiment of the present application, the ring formed by adjacent Rs bonding to each other can be a substituted or unsubstituted benzene, a substituted or unsubstituted benzofuran, or a substituted or unsubstituted benzothiophene.

According to one embodiment of the present application, Ar is a group of any one of the following Chemical Formulae Ar-1 to Ar-4:

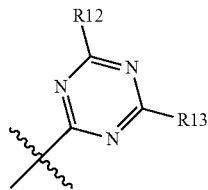

Chemical Formula Ar-1 wherein in Chemical Formula Ar-1:
R12 and R13 are the same as or different from each other, and each independently is hydrogen, deuterium, a halogen group, a substituted or unsubstituted alkyl group, a substituted or unsubstituted aryl group, or a substituted or unsubstituted heteroaryl group;

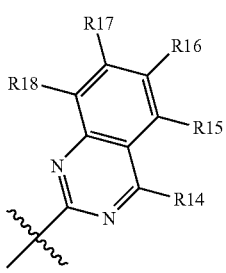

Chemical Formula Ar-2 wherein in Chemical Formula Ar-2:
R14 to R18 are the same as or different from each other, and each independently is hydrogen, deuterium, a halogen group, a substituted or unsubstituted alkyl group, a substituted or unsubstituted alkenyl group, a substituted or unsubstituted aryl group, or a substituted or unsubstituted heteroaryl group, or bond to adjacent groups to form a substituted or unsubstituted ring;

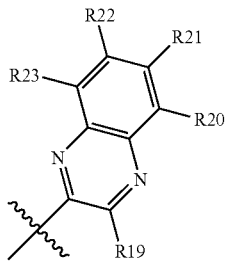

Chemical Formula Ar-3 wherein in Chemical Formula Ar-3:
R19 to R23 are the same as or different from each other, and each independently is hydrogen, deuterium, a halogen group, a substituted or unsubstituted alkyl group, a substituted or unsubstituted alkenyl group, a substituted or unsubstituted aryl group, or a substituted or unsubstituted heteroaryl group;

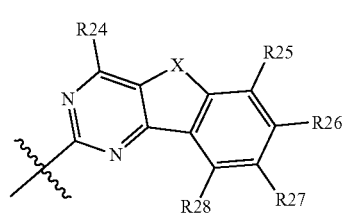

Chemical Formula Ar-4 wherein in Chemical Formula Ar-4:
X is S, O, or C(Rm) (Rn);
Rm and Rn are the same as or different from each other, and each independently is hydrogen, deuterium, an alkyl group, or an aryl group; and
R24 to R28 are the same as or different from each other, and each independently is hydrogen, deuterium, a halogen group, a substituted or unsubstituted alkyl group, a substituted or unsubstituted aryl group, or a substituted or unsubstituted heteroaryl group.

According to one embodiment of the present application, X is O or S.

According to one embodiment of the present application, R12 and R13 are the same as or different from each other, and each independently is hydrogen, deuterium, a halogen group, a substituted or unsubstituted $C_{1-10}$ alkyl group, a substituted or unsubstituted $C_{6-20}$ aryl group, or a substituted or unsubstituted $C_{2-20}$ heteroaryl group.

According to one embodiment of the present application, R12 and R13 are the same as or different from each other, and each independently is hydrogen, deuterium, a halogen group, a substituted or unsubstituted $C_{1-6}$ alkyl group, a substituted or unsubstituted $C_{6-16}$ aryl group, or a substituted or unsubstituted $C_{2-16}$ heteroaryl group.

According to one embodiment of the present application, R12 and R13 are the same as or different from each other, and each independently is hydrogen, deuterium, a halogen group, a substituted or unsubstituted $C_{1-6}$ alkyl group, a substituted or unsubstituted $C_{6-12}$ aryl group, or a substituted or unsubstituted $C_{2-12}$ heteroaryl group.

According to one embodiment of the present application, R12 and R13 are the same as or different from each other, and each independently is hydrogen, deuterium, an alkyl group, an aryl group that is unsubstituted or substituted with deuterium or an aryl group, or a heteroaryl group that is unsubstituted or substituted with an aryl group.

According to one embodiment of the present application, R12 and R13 are the same as or different from each other, and each independently is hydrogen, a phenyl group, a phenyl(d5) group

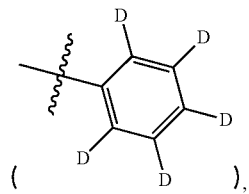

a biphenyl group, a biphenyl(d8) group

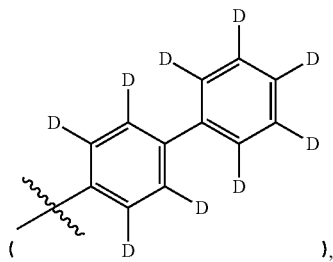

a 3-(phenyl(d5))phenyl group

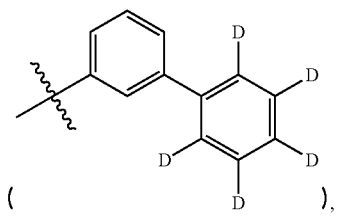

a naphthyl group, a naphthalen(d7)-2-yl group

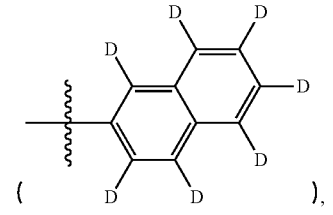

a phenanthrenyl group, a dibenzofuranyl group, a dibenzothiophenyl group, a 9-phenylcarbazolyl group, or a carbazol-9-yl group.

According to one embodiment of the present application, R12 is a substituted or unsubstituted heteroaryl group. When R12 is a substituted or unsubstituted heteroaryl group, a device comprising the compound of Chemical Formula 1 has more superior lifetime properties.

According to one embodiment of the present application, R12 is a heteroaryl group substituted or unsubstituted, and comprising at least one element selected from the group consisting of O, N and S.

According to one embodiment of the present application, R12 is a heteroaryl group that is unsubstituted or substituted with an aryl group.

According to one embodiment of the present application, R12 is a substituted or unsubstituted dibenzofuranyl group, a substituted or unsubstituted dibenzothiophenyl group, or a substituted or unsubstituted carbazolyl group.

According to one embodiment of the present application, R12 is a dibenzofuranyl group, a dibenzothiophenyl group, a 9-phenylcarbazolyl group, or a carbazol-9-yl group.

According to one embodiment of the present application, R14 is hydrogen, deuterium, a halogen group, a substituted or unsubstituted alkyl group, a substituted or unsubstituted alkenyl group, a substituted or unsubstituted aryl group, or a substituted or unsubstituted heteroaryl group; and R15 and R18 are the same as or different from each other, and each independently is hydrogen, deuterium, a halogen group, a substituted or unsubstituted alkyl group, a substituted or unsubstituted alkenyl group, a substituted or unsubstituted aryl group, or a substituted or unsubstituted heteroaryl group, or bond to adjacent groups to form a substituted or unsubstituted ring.

According to one embodiment of the present application, R14 is a substituted or unsubstituted aryl group or a substituted or unsubstituted heteroaryl group.

According to one embodiment of the present application, R14 is an aryl group that is unsubstituted or substituted with R40, or a heteroaryl group that is unsubstituted or substituted with R41.

According to one embodiment of the present application, R14 is a $C_{6-20}$ aryl group that is unsubstituted or substituted with R40, or a $C_{2-16}$ heteroaryl group that is unsubstituted or substituted with R41.

According to one embodiment of the present application, R14 is a $C_{6-15}$ aryl group that is unsubstituted or substituted with R40, or a $C_{2-12}$ heteroaryl group that is unsubstituted or substituted with R41.

According to one embodiment of the present application, R14 is a substituted aryl group, or a substituted or unsubstituted heteroaryl group.

According to one embodiment of the present application, R14 is an aryl group substituted with R40, or a heteroaryl group that is unsubstituted or substituted with R41.

According to one embodiment of the present application, R14 is a $C_{6-15}$ aryl group substituted with R40, or a $C_{2-12}$ heteroaryl group that is unsubstituted or substituted with R41.

According to one embodiment of the present application, R14 is a substituted or unsubstituted heteroaryl group.

According to one embodiment of the present application, R14 is a heteroaryl group that is unsubstituted or substituted with R41.

According to one embodiment of the present application, R14 is a $C_{2-12}$ heteroaryl group that is unsubstituted or substituted with R41.

According to some embodiments of the present application, R40 is deuterium or a heteroaryl group.

According to some embodiments of the present application, R40 is deuterium or a $C_{2-12}$ heteroaryl group.

According to some embodiments of the present application, R40 is a heteroaryl group.

According to some embodiments of the present application, R41 is deuterium or an aryl group.

According to some embodiments of the present application, R41 is deuterium or a $C_{6-15}$ aryl group.

According to some embodiments of the present application, R41 is an aryl group.

According to one embodiment of the present application, R14 is a substituted phenyl group, a substituted or unsubstituted dibenzofuranyl group, a substituted or unsubstituted dibenzothiophenyl group, a substituted or unsubstituted carbazolyl group, a substituted or unsubstituted pyridinyl group, or a substituted or unsubstituted quinolinyl group.

According to one embodiment of the present application, R14 is a dibenzofuranyl group, a dibenzothiophenyl group, a 9-phenylcarbazolyl group, a carbazol-9-yl group, a pyridinyl group, a quinolin-8-yl group, a 4-(pyridin-2-yl)phenyl group, or a 4-(quinolin-8-yl)phenyl group.

According to one embodiment of the present application, R15 to R18 are the same as or different from each other, and each independently is hydrogen or deuterium, or bond to adjacent groups to form a benzene ring unsubstituted or substituted with deuterium.

According to one embodiment of the present application, R15 to R18 are the same as or different from each other, and each independently is hydrogen or deuterium.

According to one embodiment of the present application, R15 to R18 are hydrogen.

According to one embodiment of the present application, R19 is a substituted or unsubstituted aryl group, or a substituted or unsubstituted heteroaryl group.

According to one embodiment of the present application, R19 is an aryl group that is unsubstituted or substituted with R50, or a heteroaryl group that is unsubstituted or substituted with R51.

According to one embodiment of the present application, R19 is a $C_{6-20}$ aryl group that is unsubstituted or substituted with R50, or a $C_{2-16}$ heteroaryl group that is unsubstituted or substituted with R51.

According to one embodiment of the present application, R19 is a $C_{6-15}$ aryl group that is unsubstituted or substituted with R50, or a $C_{2-12}$ heteroaryl group that is unsubstituted or substituted with R51.

According to one embodiment of the present application, R19 is a substituted aryl group, or a substituted or unsubstituted heteroaryl group.

According to one embodiment of the present application, R19 is an aryl group substituted with R50, or a heteroaryl group that is unsubstituted or substituted with R51.

According to one embodiment of the present application, R19 is a $C_{6-15}$ aryl group substituted with R50, or a $C_{2-12}$ heteroaryl group that is unsubstituted or substituted with R51.

According to one embodiment of the present application, R19 is a substituted or unsubstituted heteroaryl group.

According to one embodiment of the present application, R19 is a heteroaryl group that is unsubstituted or substituted with R51.

According to one embodiment of the present application, R19 is a $C_{2-12}$ heteroaryl group that is unsubstituted or substituted with R51.

According to some embodiments of the present application, R50 is deuterium, an aryl group, or a heteroaryl group.

According to some embodiments of the present application, R50 is deuterium or an aryl group.

According to some embodiments of the present application, R50 is deuterium or a $C_{6-12}$ aryl group.

According to some embodiments of the present application, R51 is deuterium or an aryl group.

According to some embodiments of the present application, R51 is deuterium or a $C_{2-12}$ aryl group.

According to one embodiment of the present application, R19 is a substituted or unsubstituted phenyl group, a substituted or unsubstituted biphenyl group, a substituted or unsubstituted phenanthrenyl group, a substituted or unsubstituted dibenzofuranyl group, a substituted or unsubstituted dibenzofuranyl group, or a substituted or unsubstituted carbazolyl group.

According to one embodiment of the present application, R19 is a phenyl group, a phenyl(d5) group, a naphthyl group, a biphenyl group, a phenanthrenyl group, a dibenzofuranyl group, a dibenzothiophenyl group, a 9-phenylcarbazolyl group, or a carbazol-9-yl group.

According to one embodiment of the present application, R20 to R23 are the same as or different from each other, and each independently is hydrogen or deuterium.

According to one embodiment of the present application, R20 to R23 are each hydrogen.

According to one embodiment of the present application, R24 is a substituted or unsubstituted aryl group, or a substituted or unsubstituted heteroaryl group.

According to one embodiment of the present application, R24 is an aryl group that is unsubstituted or substituted with R60, or a heteroaryl group that is unsubstituted or substituted with R61.

According to one embodiment of the present application, R24 is a $C_{6-16}$ aryl group that is unsubstituted or substituted with R60, or a $C_{2-16}$ heteroaryl group that is unsubstituted or substituted with R61.

According to one embodiment of the present application, R24 is a $C_{6-12}$ aryl group that is unsubstituted or substituted with R60, or a $C_{2-12}$ heteroaryl group that is unsubstituted or substituted with R61.

According to one embodiment of the present application, R24 is a substituted aryl group, or a substituted or unsubstituted heteroaryl group.

According to one embodiment of the present application, R24 is an aryl group substituted with R60, or a heteroaryl group that is unsubstituted or substituted with R61.

According to one embodiment of the present application, R24 is a $C_{6-12}$ aryl group substituted with R60, or a $C_{2-12}$ heteroaryl group that is unsubstituted or substituted with R61.

According to some embodiments of the present application, R60 is deuterium, an aryl group, or a heteroaryl group.

According to some embodiments of the present application, R60 is deuterium, a $C_{2-12}$ aryl group, or a $C_{2-12}$ heteroaryl group.

According to some embodiments of the present application, R61 is hydrogen or an aryl group.

According to some embodiments of the present application, R61 is hydrogen or a $C_{2-12}$ aryl group.

According to one embodiment of the present application, R24 is a substituted naphthyl group, a substituted phenyl group, a substituted or unsubstituted dibenzofuranyl group, a substituted or unsubstituted dibenzothiophenyl group, a substituted or unsubstituted carbazolyl group, a substituted or unsubstituted pyridinyl group, or a substituted or unsubstituted quinolinyl group.

According to one embodiment of the present application, R24 is a 4-phenylnaphthalen-1-yl group, a 4-(naphthyl-2-yl)phenyl group, a 4-(pyridin-2-yl)phenyl group, a 4-(quinolin-8-yl)phenyl group, a biphenyl group, a dibenzofuranyl group, a dibenzothiophenyl group, a 9-phenylcarbazolyl group, a carbazol-9-yl group; a pyridinyl group, or a quinolin-8-yl group.

According to one embodiment of the present application, R25 to R28 are the same as or different from each other, and each independently is hydrogen or deuterium.

According to one embodiment of the present application, R25 to R28 are each hydrogen.

According to one embodiment of the present application, when R1 to R4 are each hydrogen, R12 is a substituted or unsubstituted heteroaryl group, and R14 is a substituted aryl group, or a substituted or unsubstituted heteroaryl group.

According to one embodiment of the present application, when R1 to R4 are each hydrogen, R12 is a substituted or unsubstituted heteroaryl group, and R14 is a substituted or unsubstituted heteroaryl group.

According to one embodiment of the present application, when R1 to R4 are each hydrogen, R12 is a substituted or unsubstituted heteroaryl group, R14 is a substituted aryl group, or a substituted or unsubstituted heteroaryl group, and R19 is a substituted aryl group, or a substituted or unsubstituted heteroaryl group.

According to one embodiment of the present application, when R1 to R4 are each hydrogen, R12 is a substituted or unsubstituted heteroaryl group, R14 is a substituted or unsubstituted heteroaryl group, and R19 is a substituted aryl group, or a substituted or unsubstituted heteroaryl group.

According to one embodiment of the present application, when R1 to R4 are each hydrogen, R12 is a substituted or unsubstituted heteroaryl group, R14 is a substituted or unsubstituted heteroaryl group, and R19 is a substituted or unsubstituted heteroaryl group.

In one embodiment of the present application, Chemical Formula 1 is any one of the following Chemical Formulae 3 to 6:

Chemical Formula 3

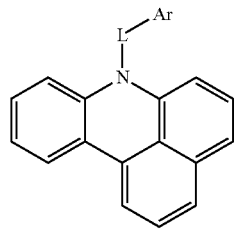

Chemical Formula 4

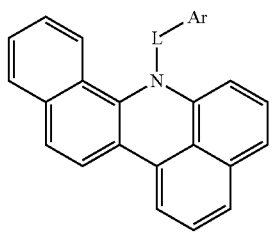

Chemical Formula 5

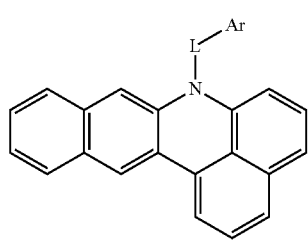

Chemical Formula 6

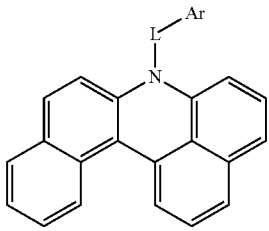

wherein in Chemical Formulae 3 to 6, Ar and L have the same definitions as in Chemical Formula 1.

In addition, in one embodiment of the present application, the compound of Chemical Formula 1 is any one compound selected from among the following compounds:

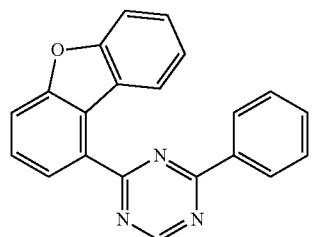

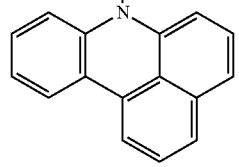
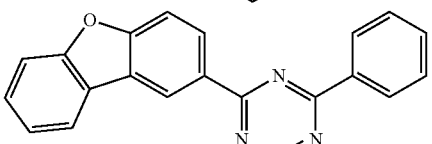

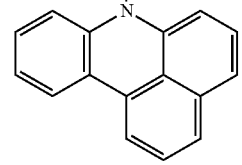
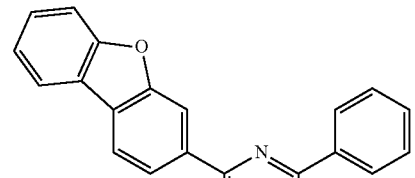

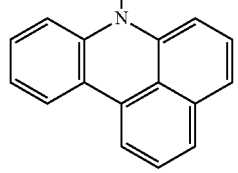

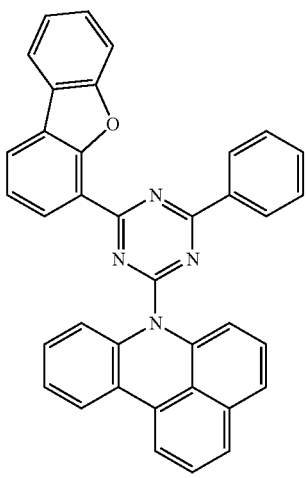
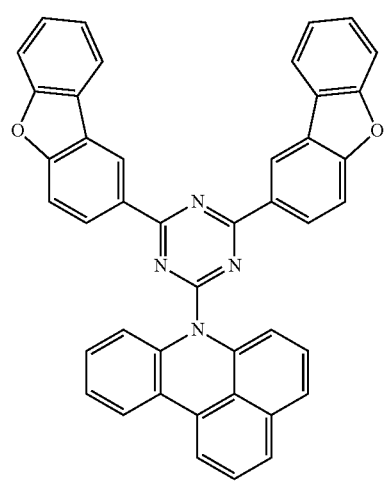
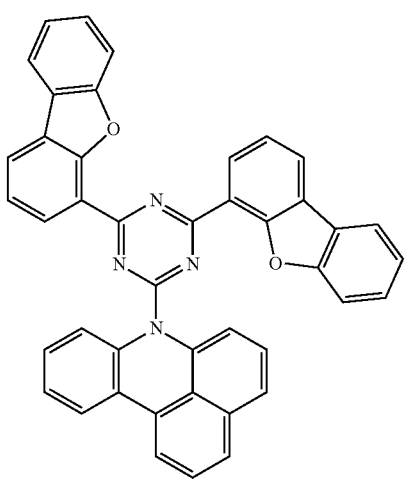
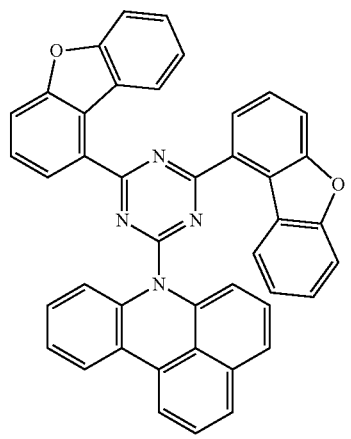
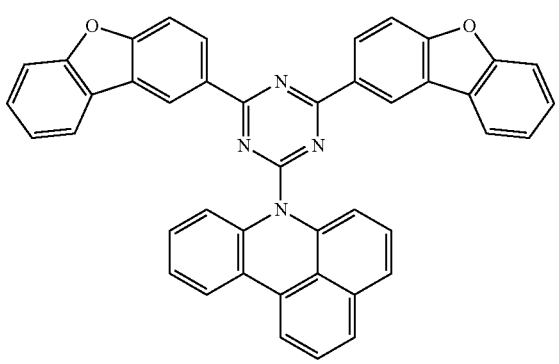
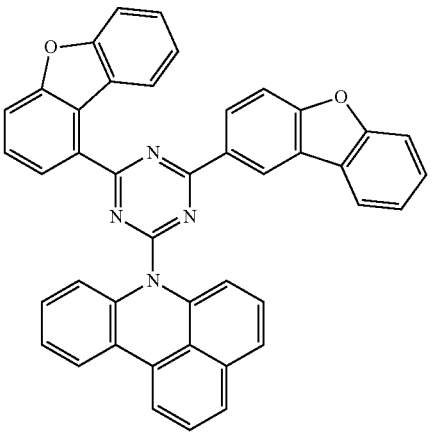
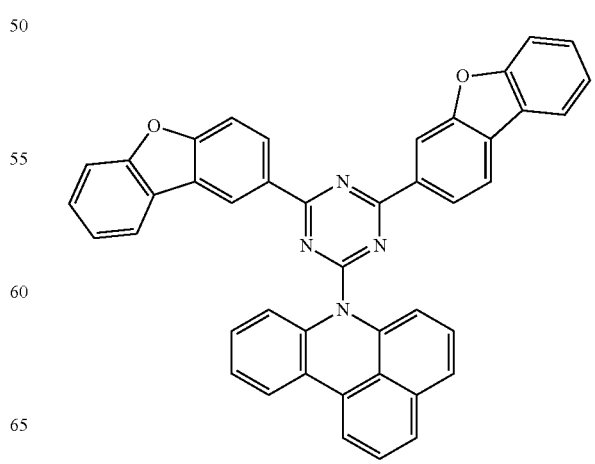

17
-continued
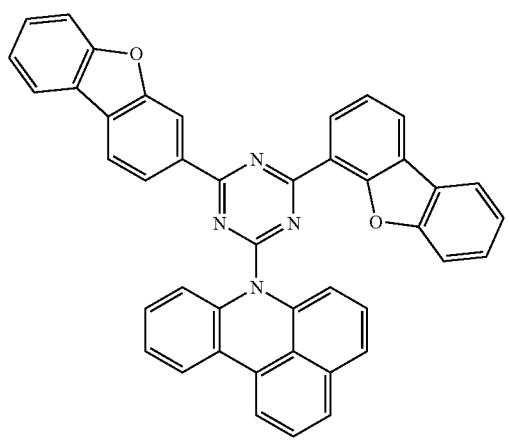
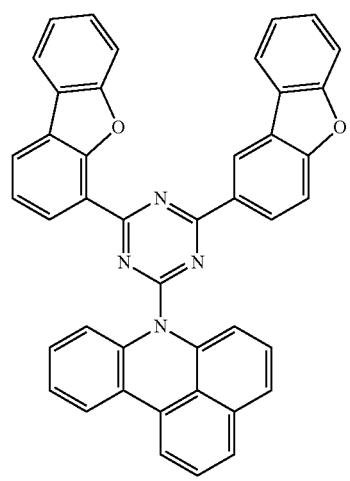
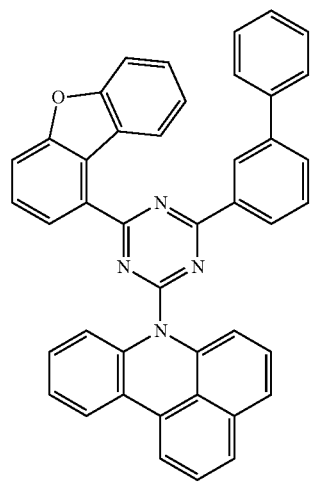
18
-continued
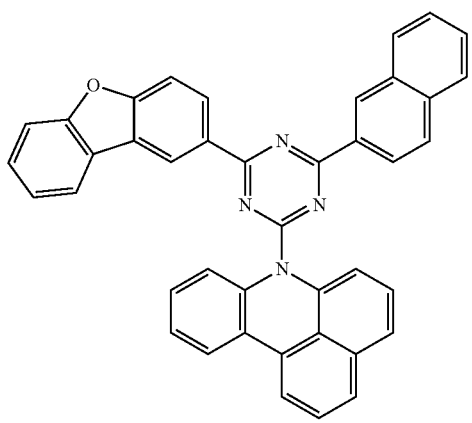
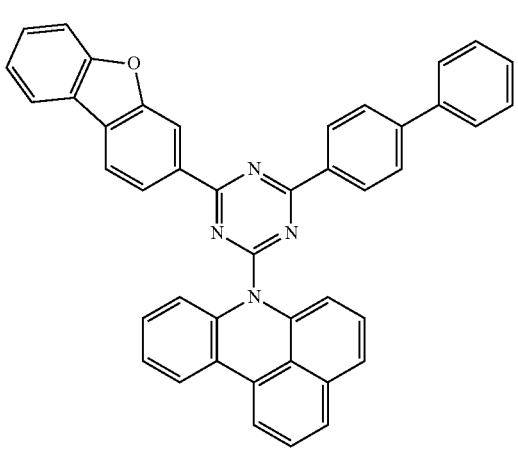
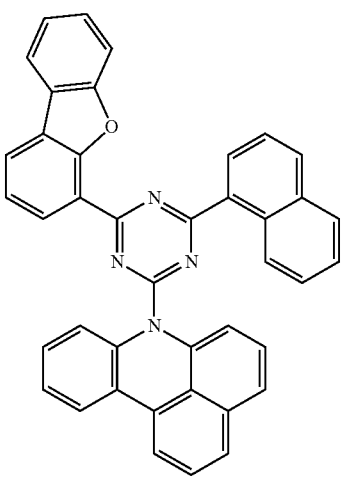

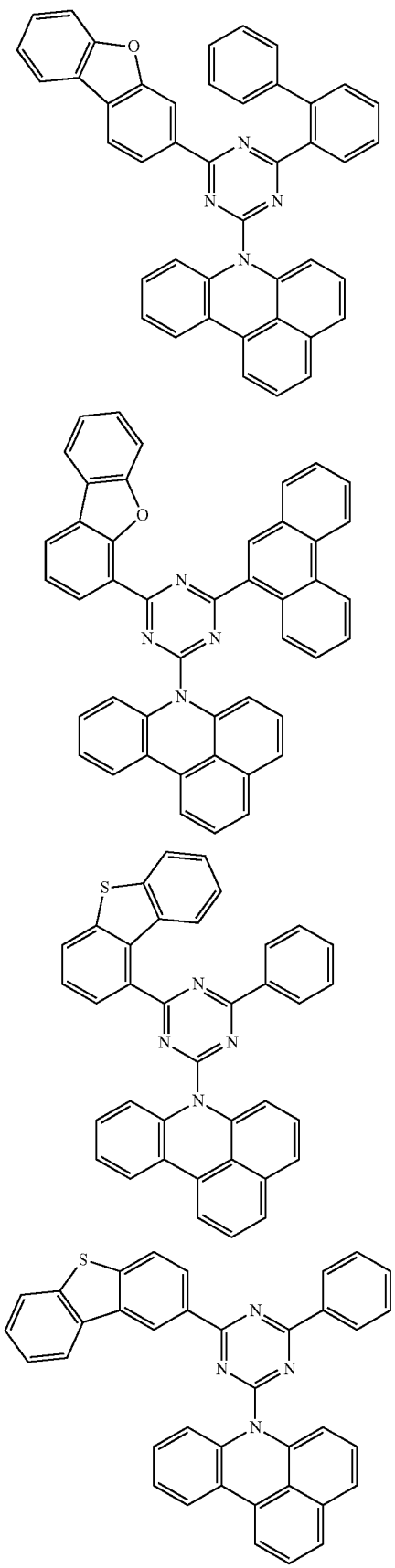
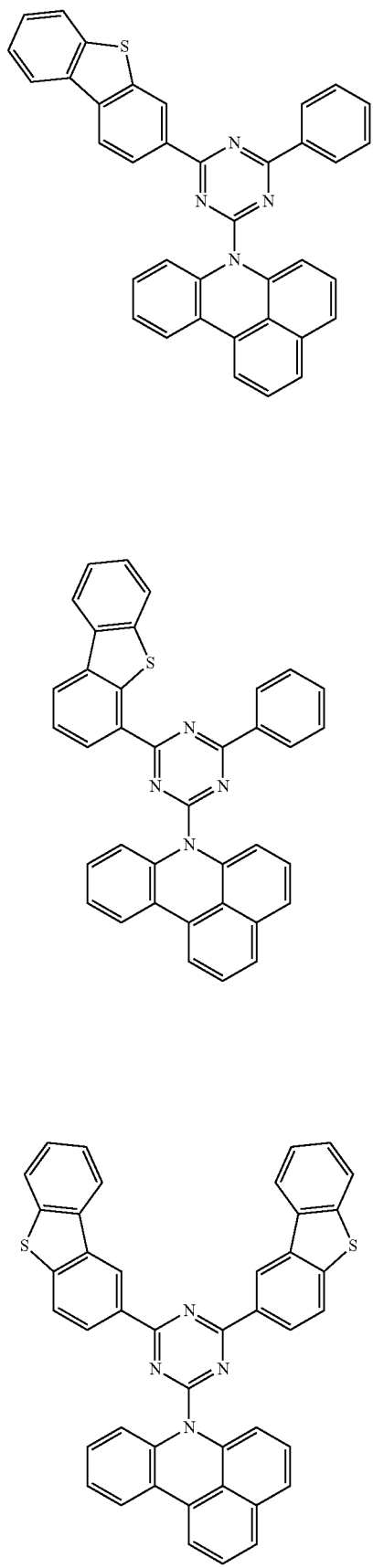

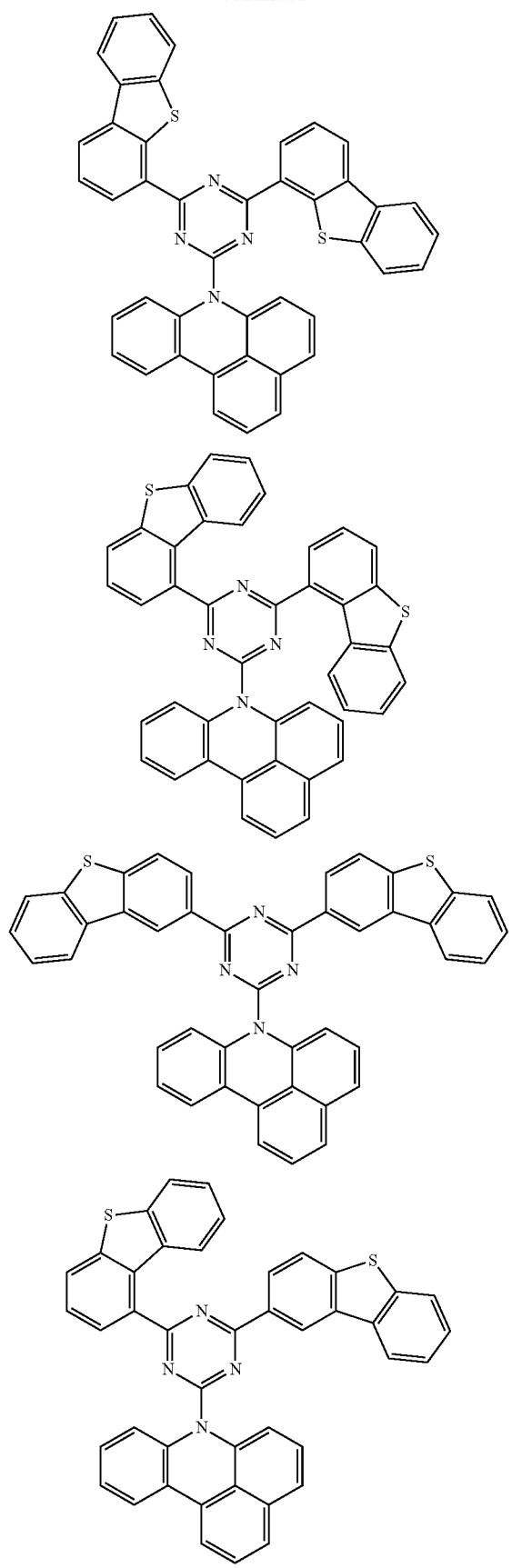
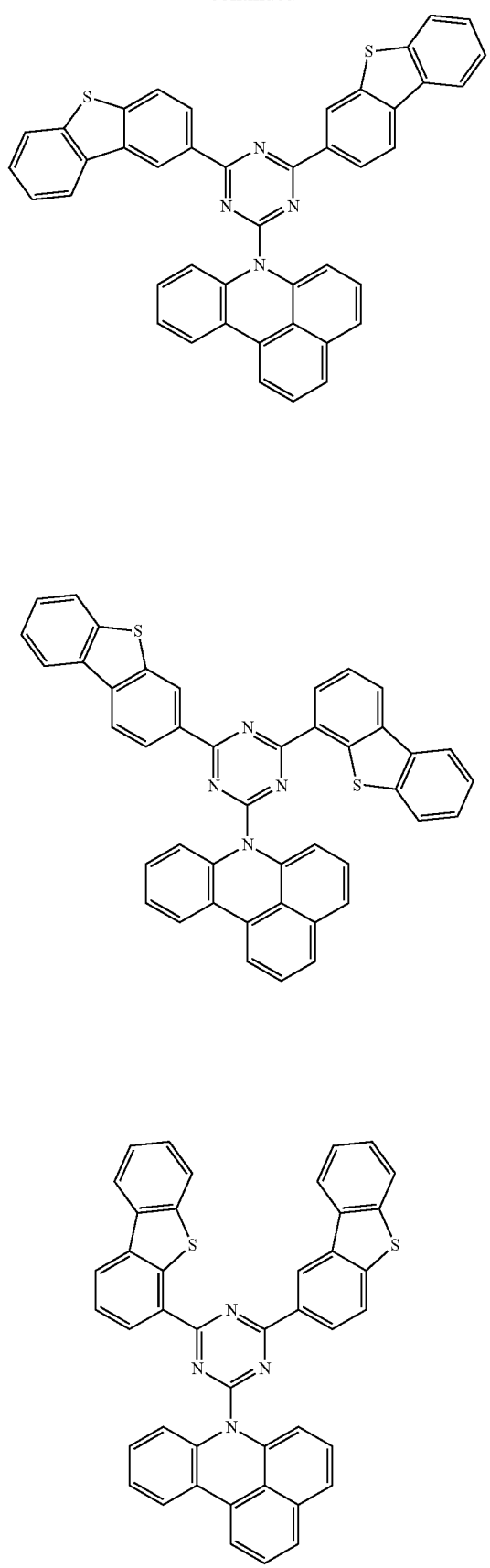

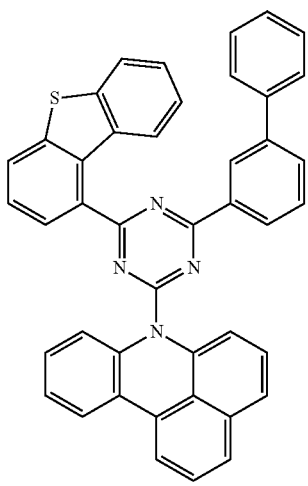
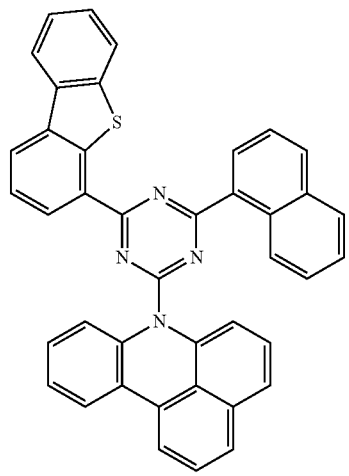
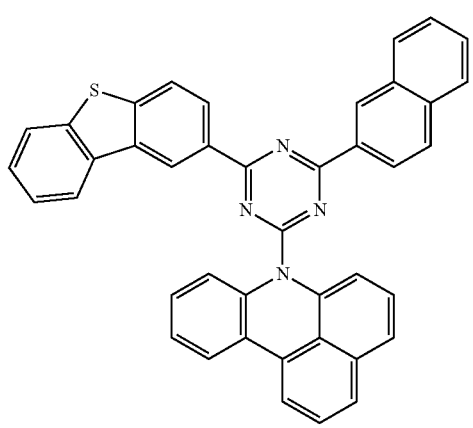
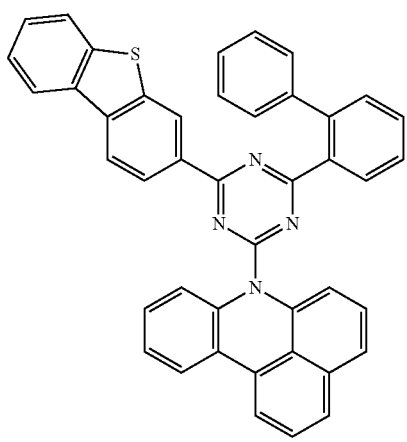
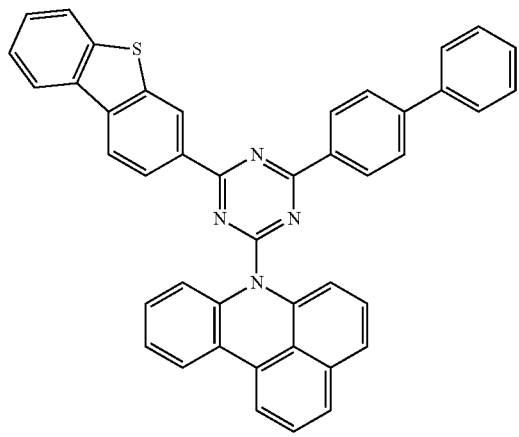
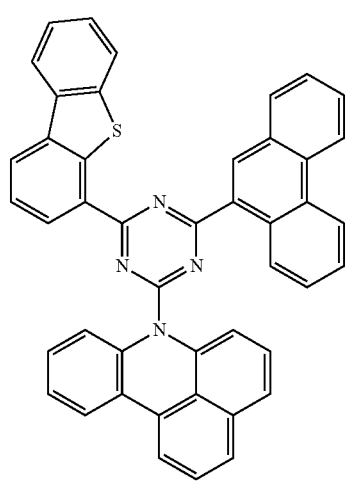

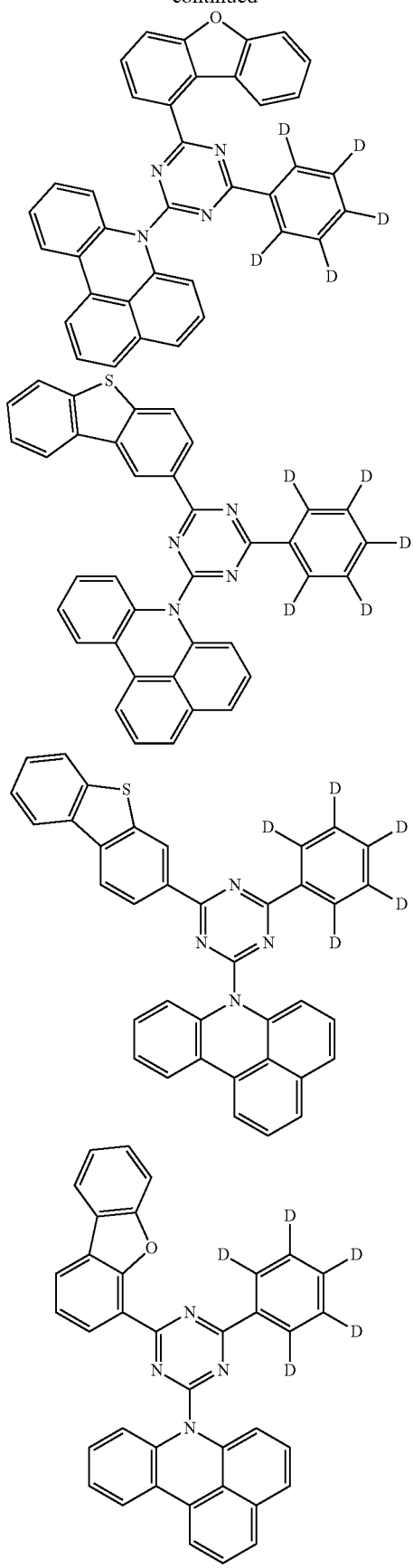
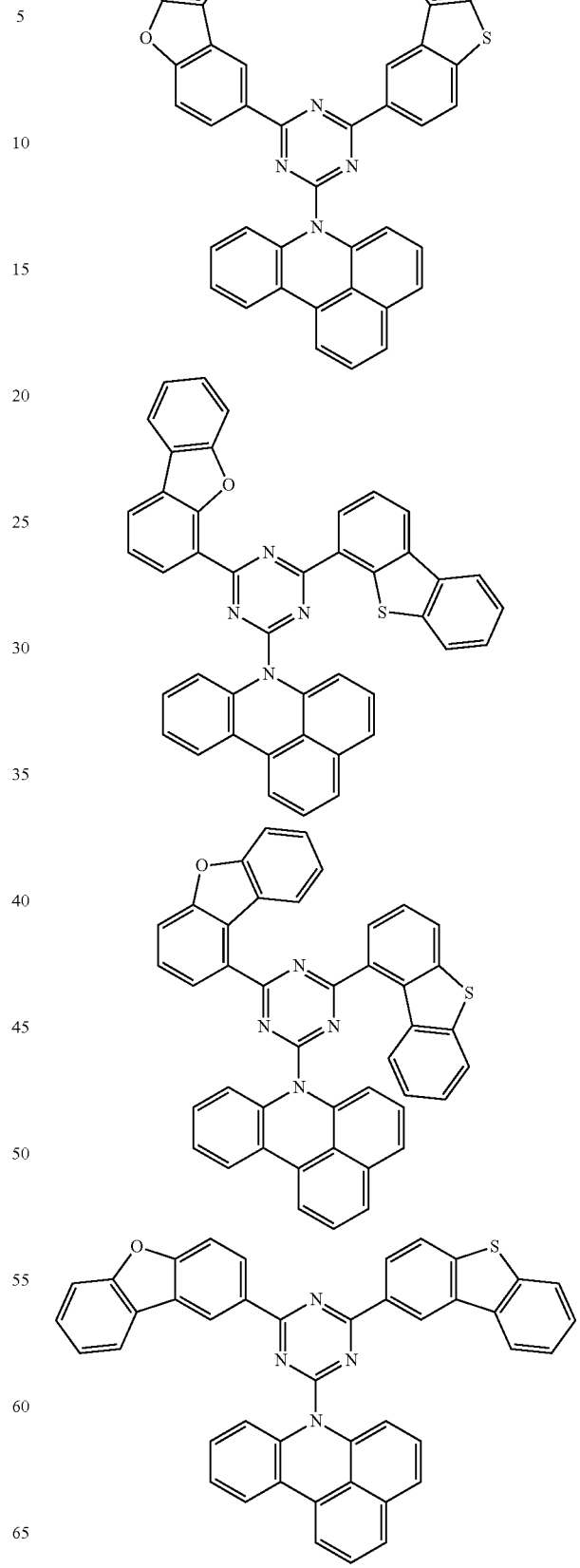

27
-continued
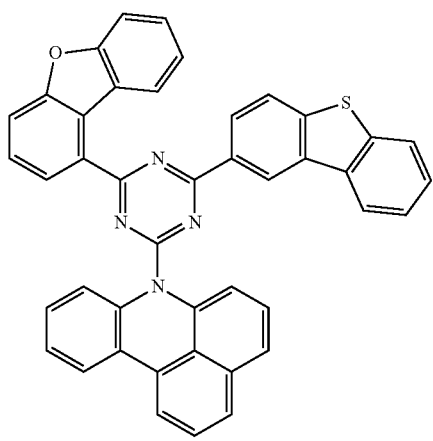
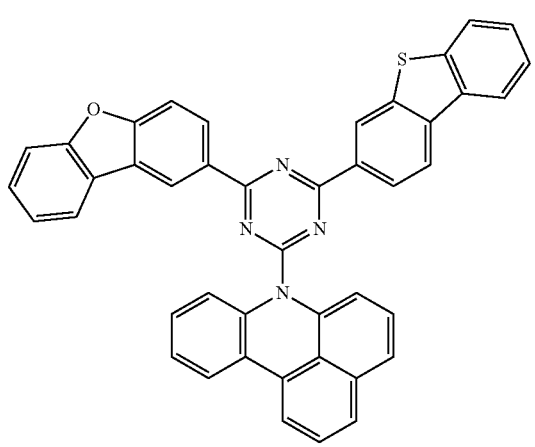
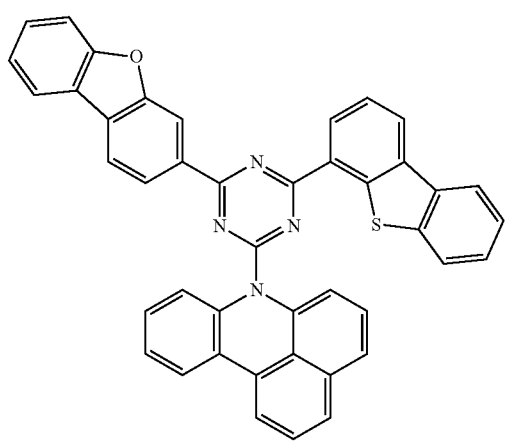
28
-continued
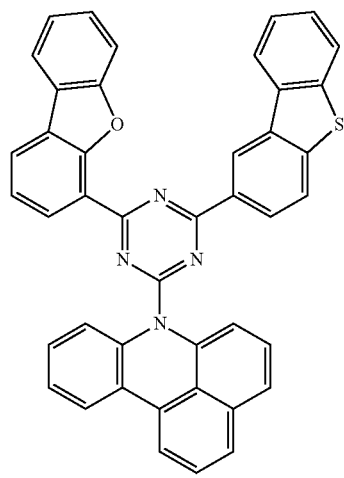
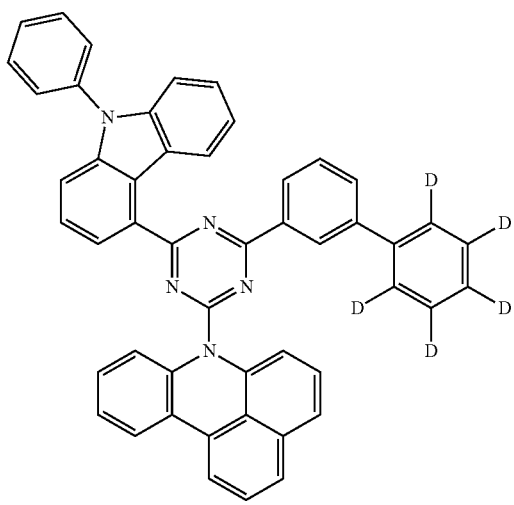
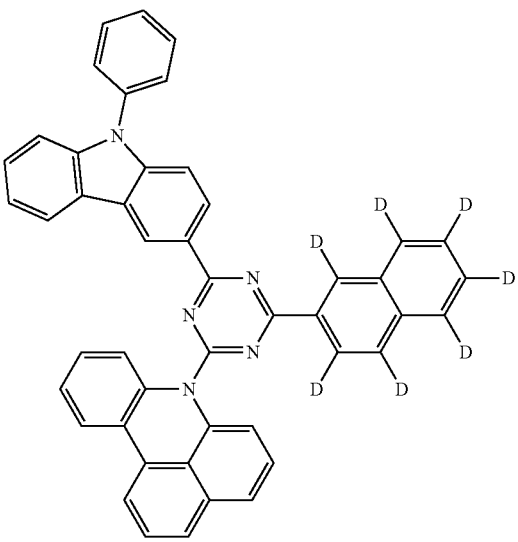

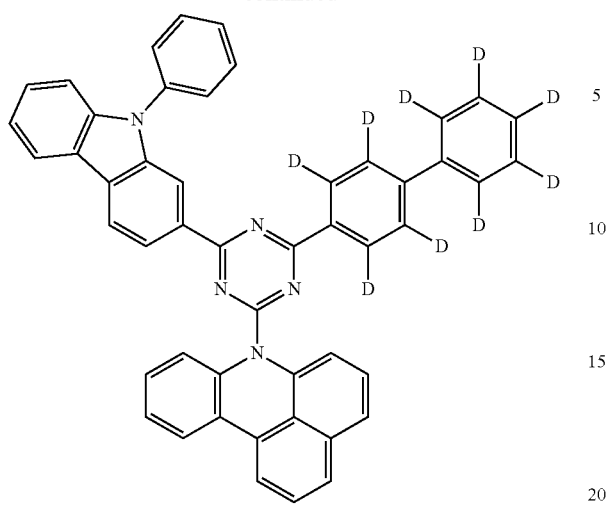
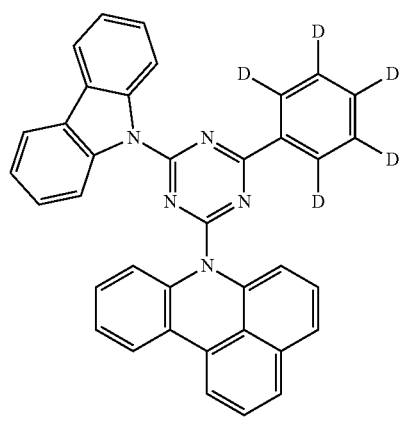
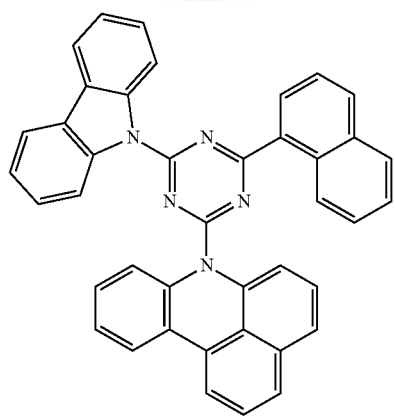
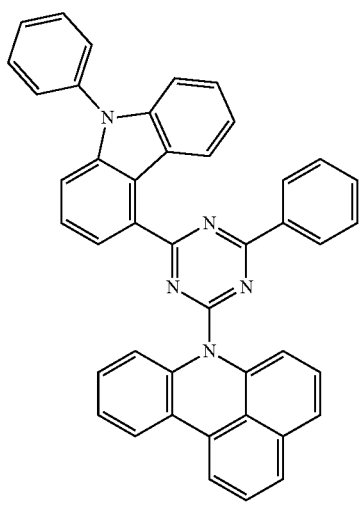
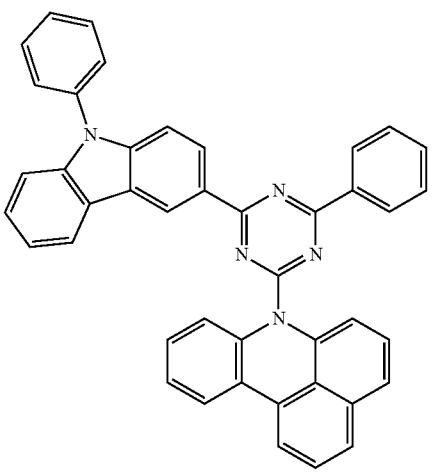

31
-continued
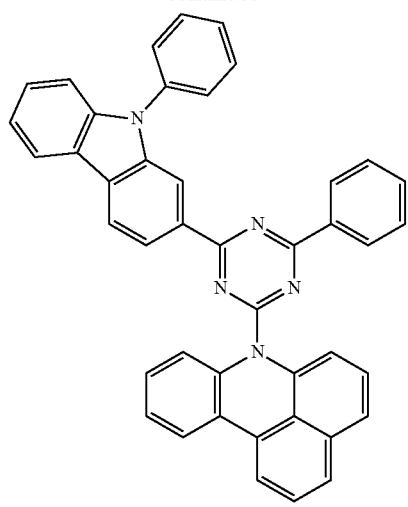
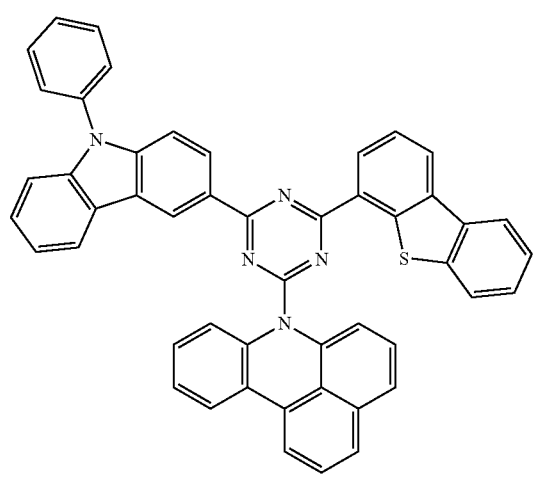
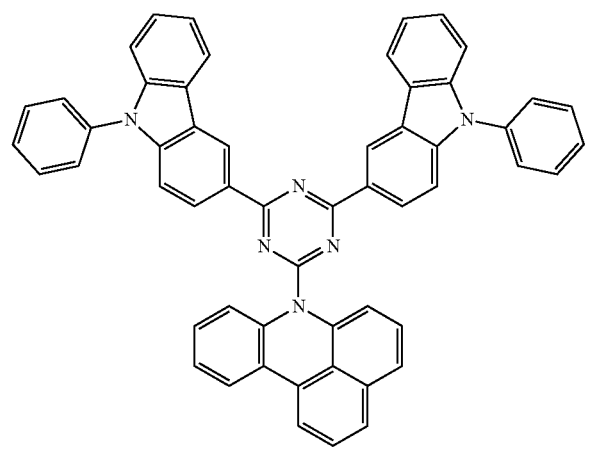
32
-continued
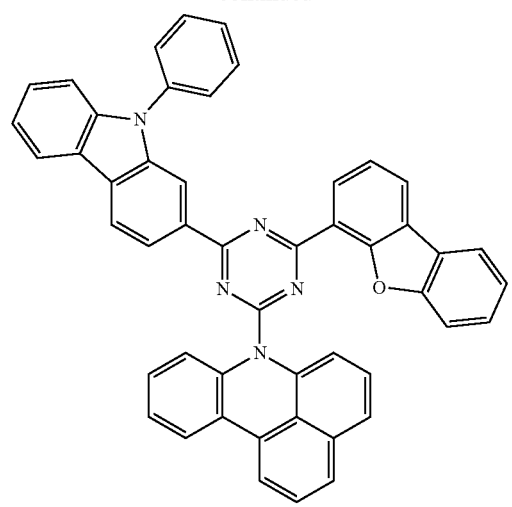
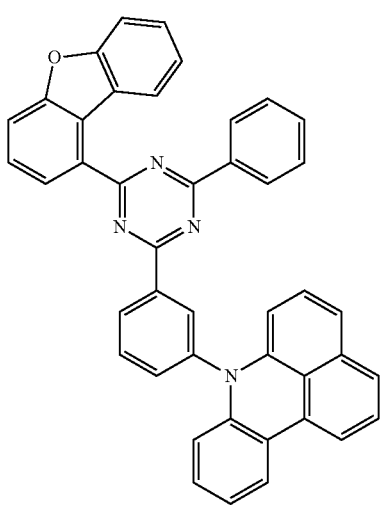
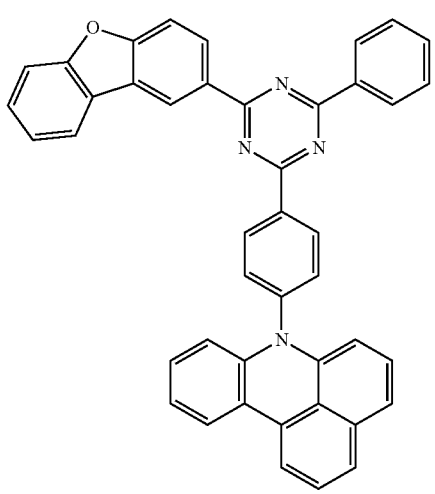

33
-continued
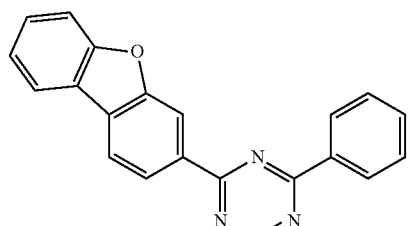
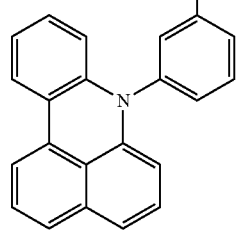
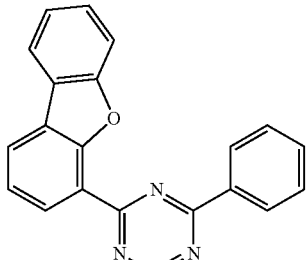
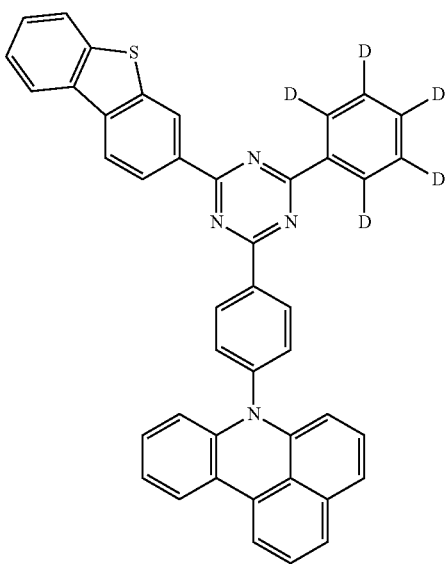
34
-continued
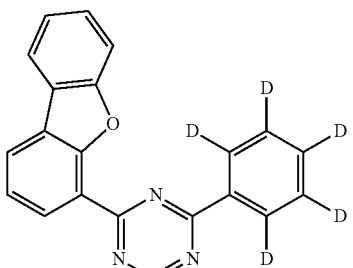
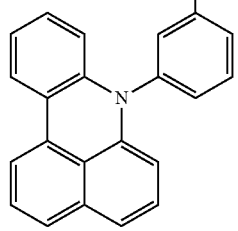
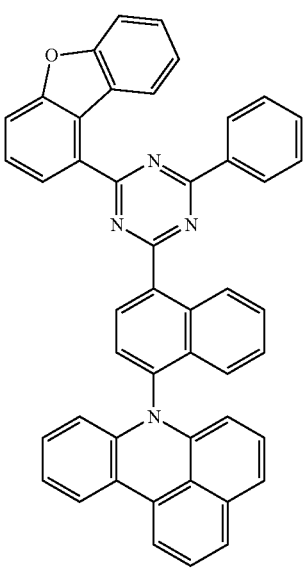
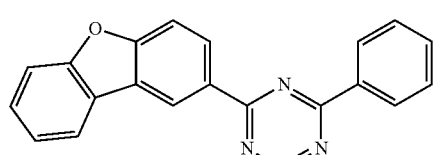

-continued
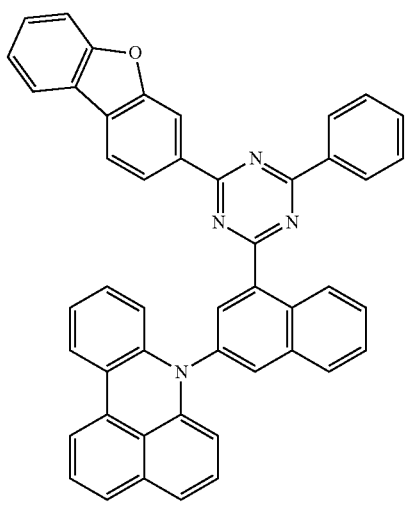
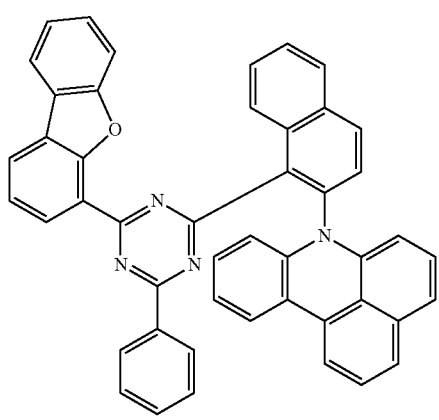
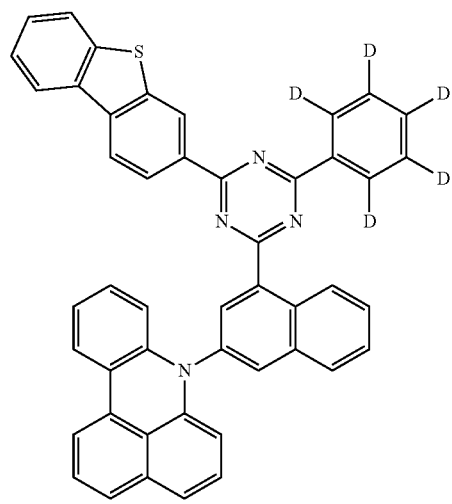
-continued
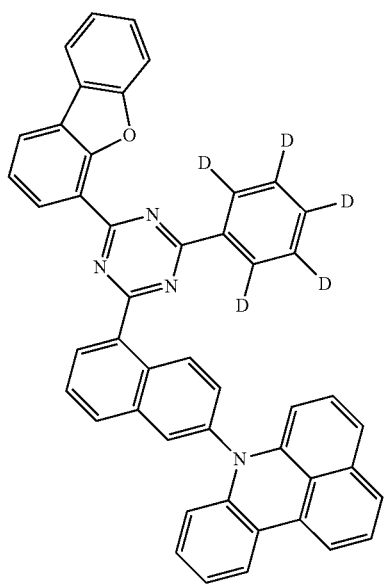
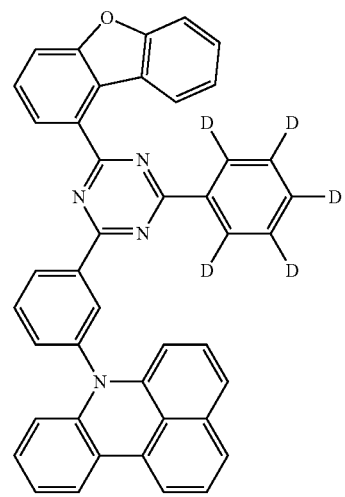
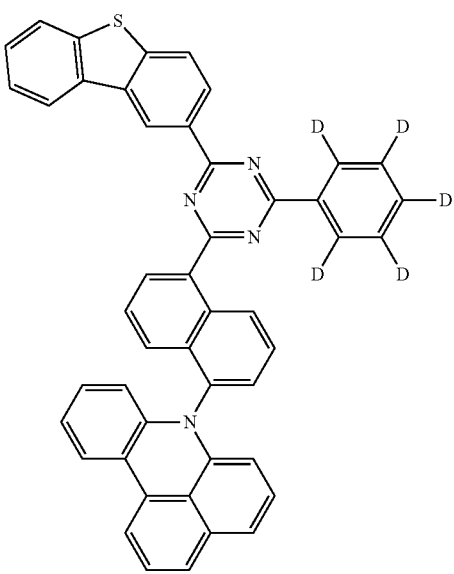

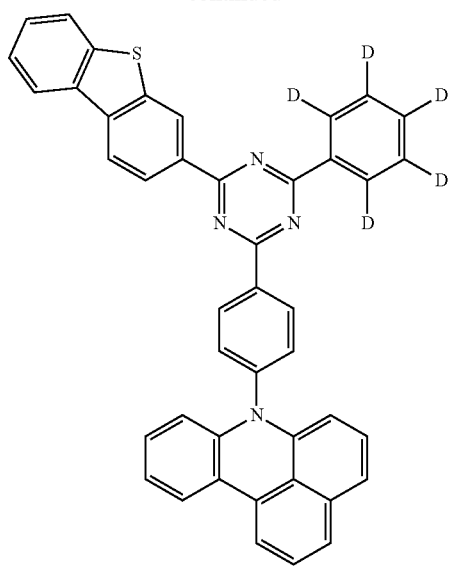
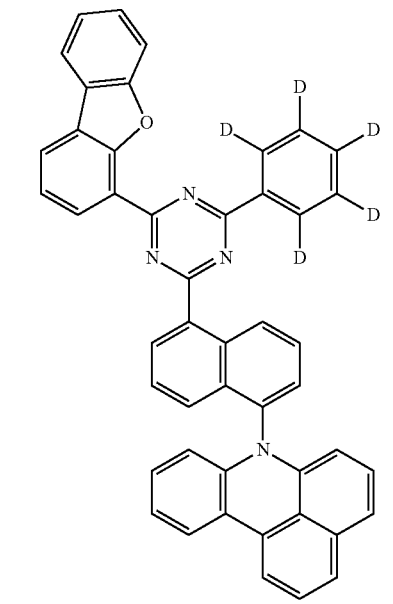
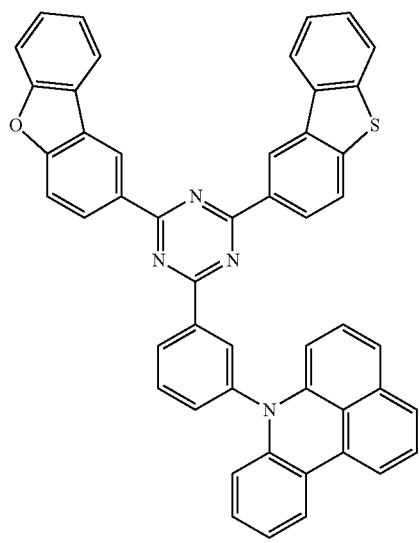
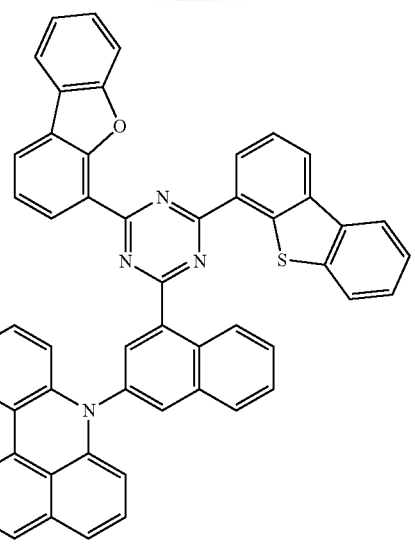
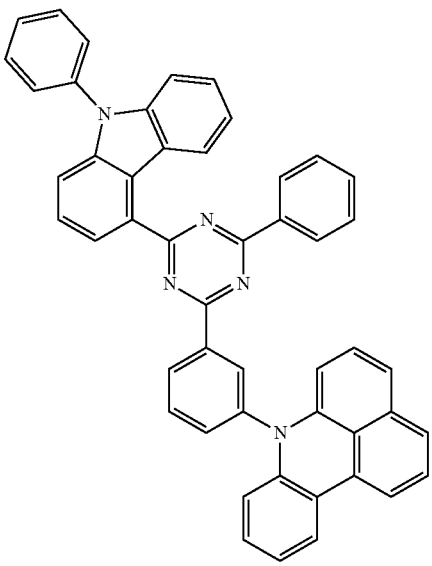
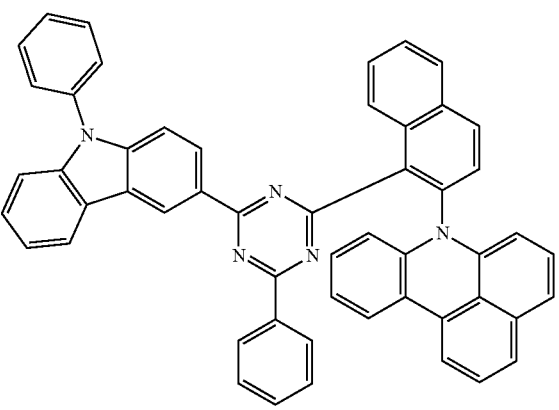

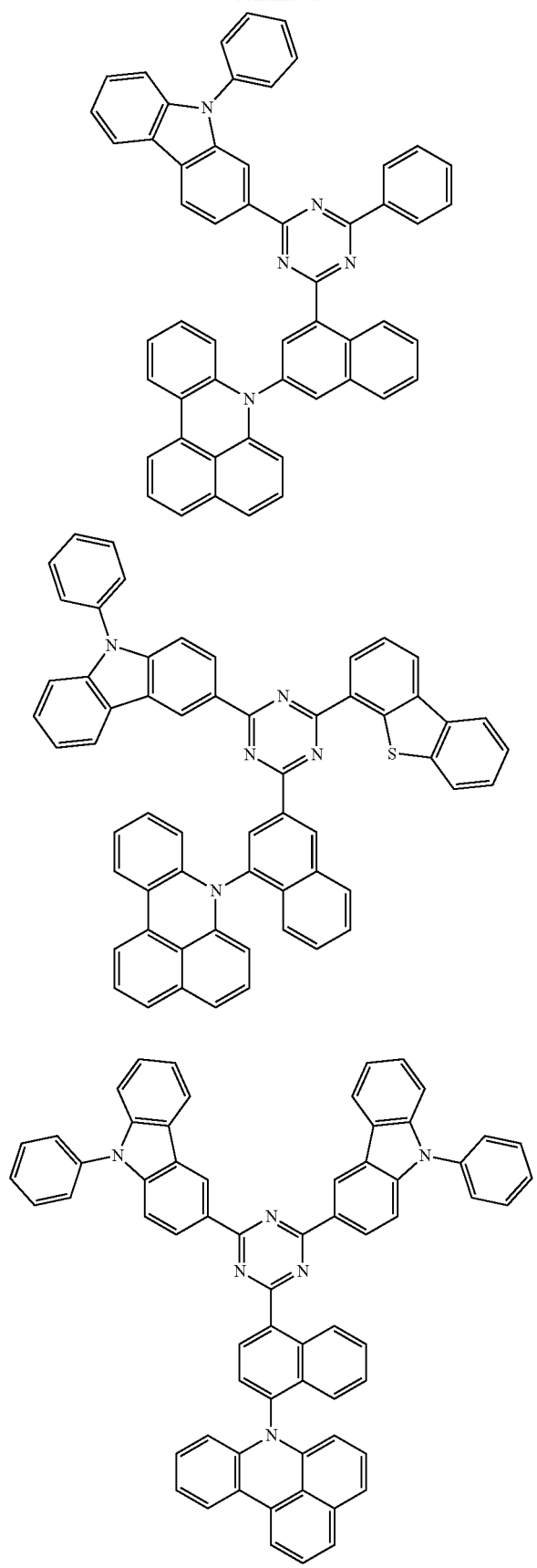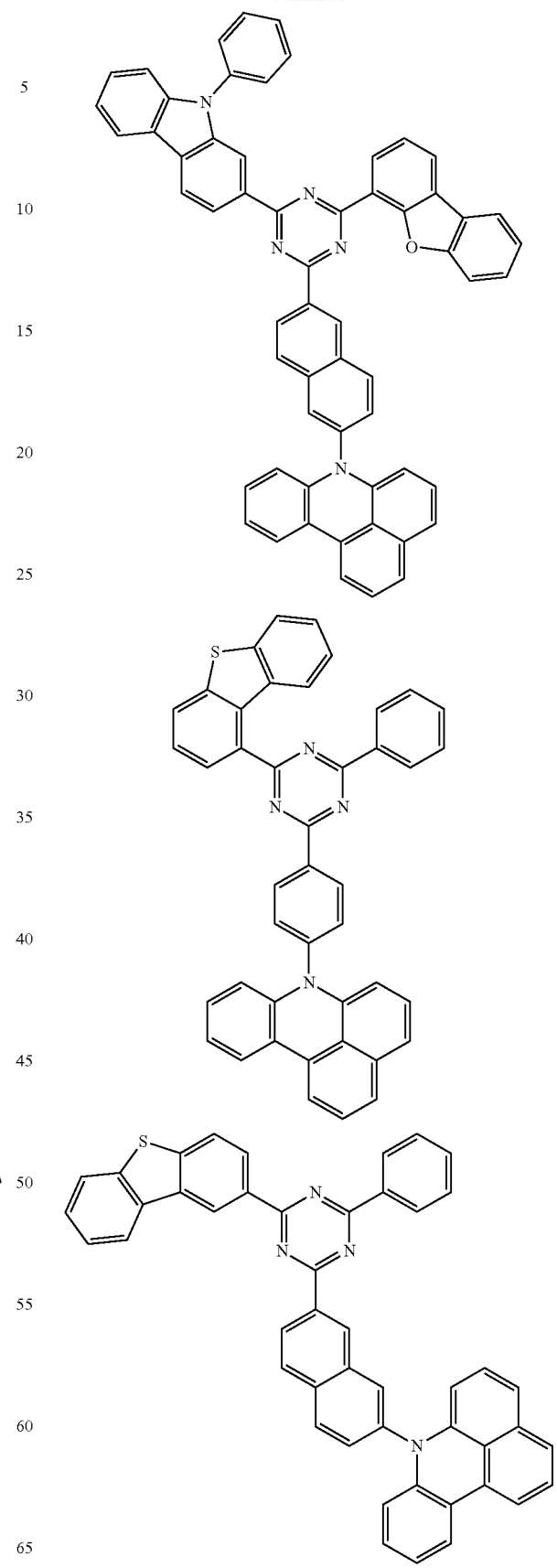

41
-continued
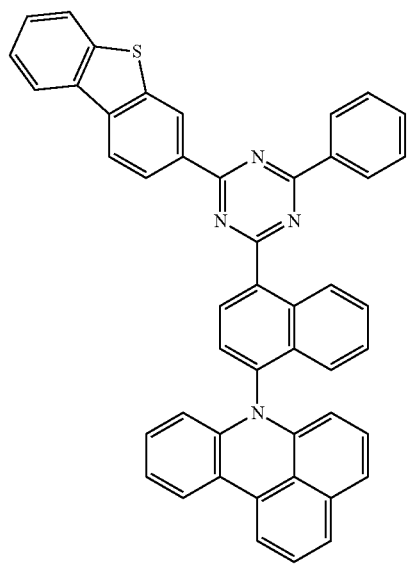
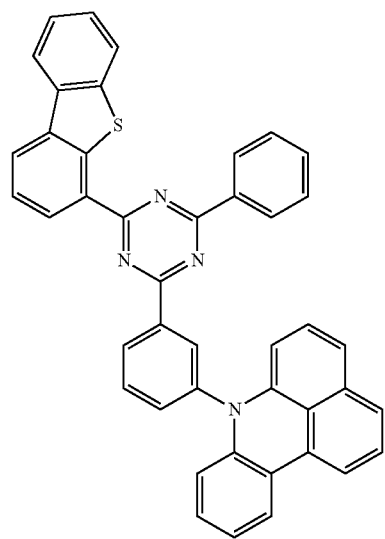
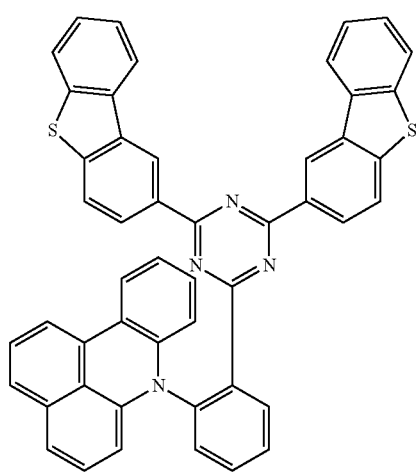
42
-continued
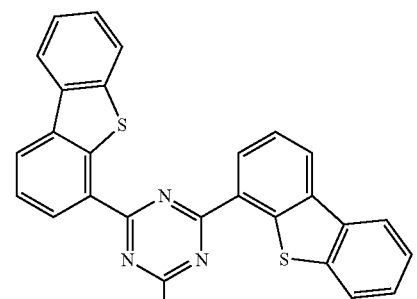
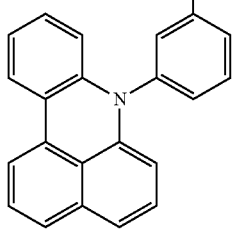
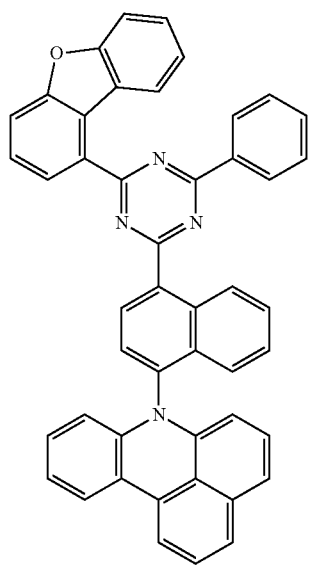
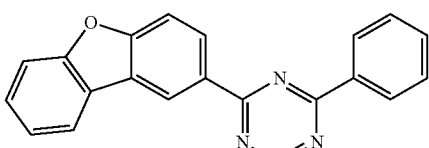
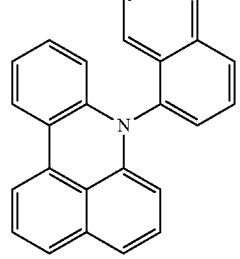

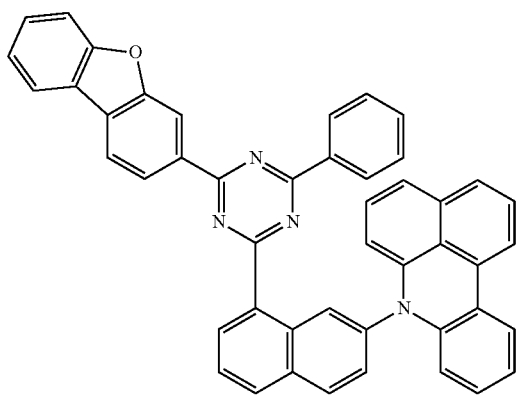
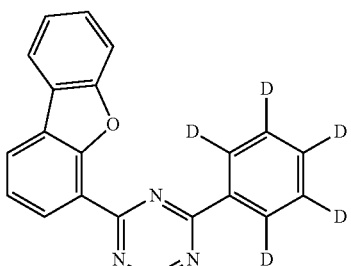
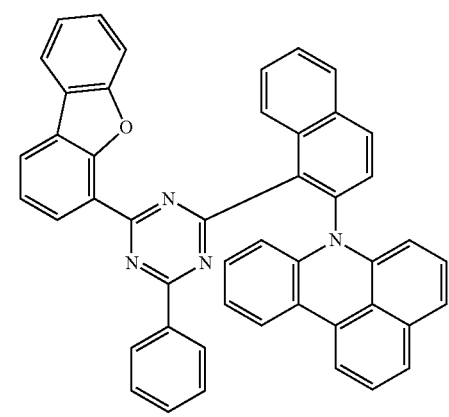
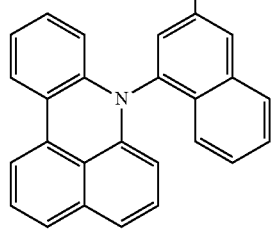
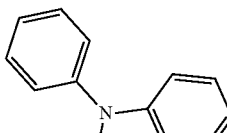
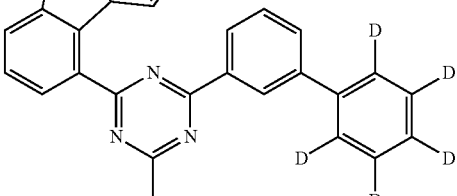
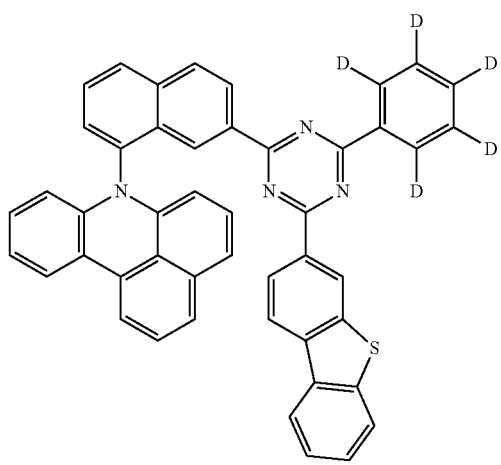
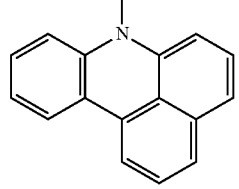
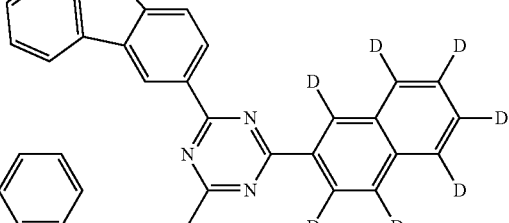
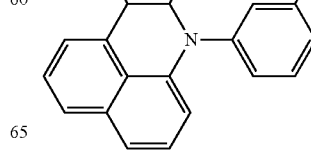

-continued
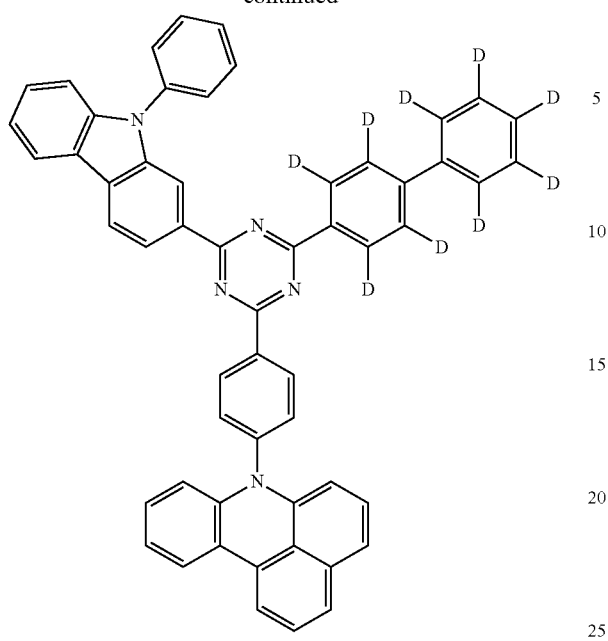
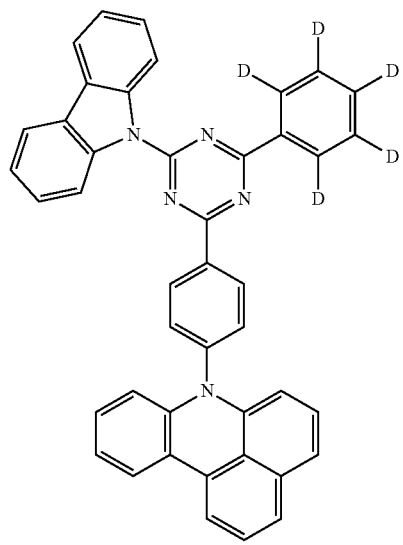
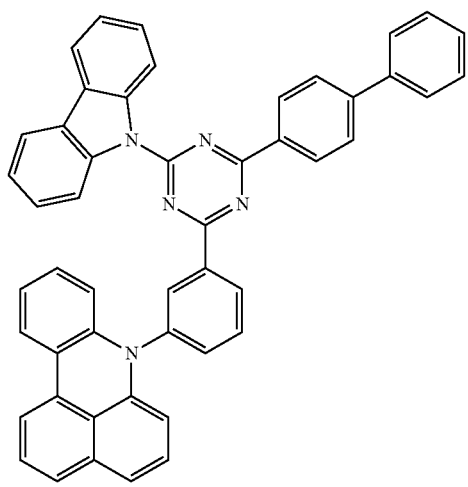
-continued
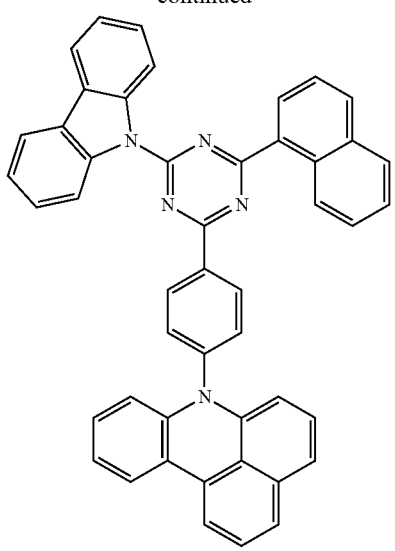
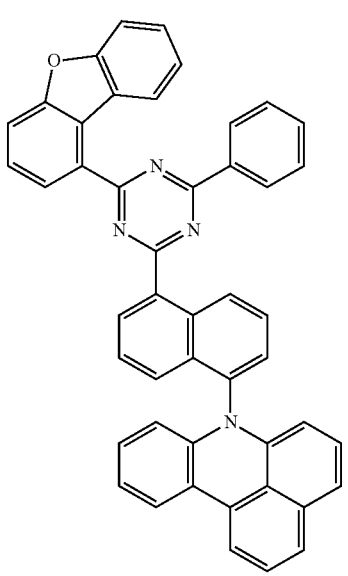
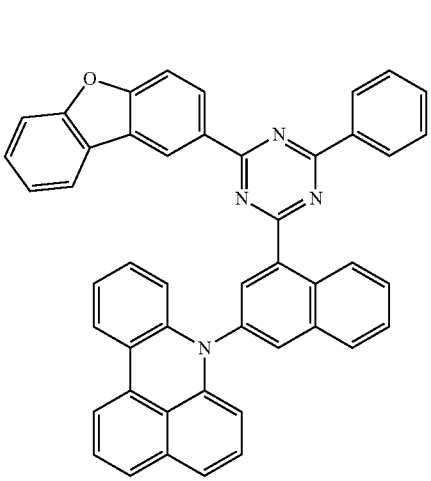

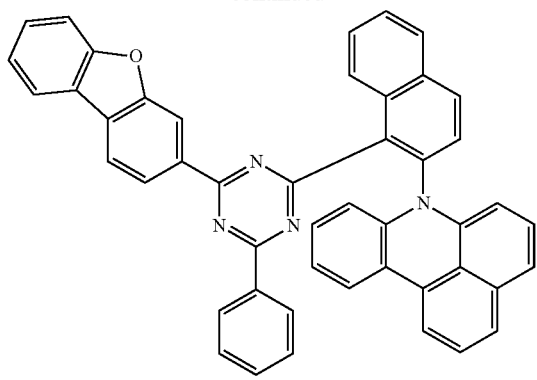
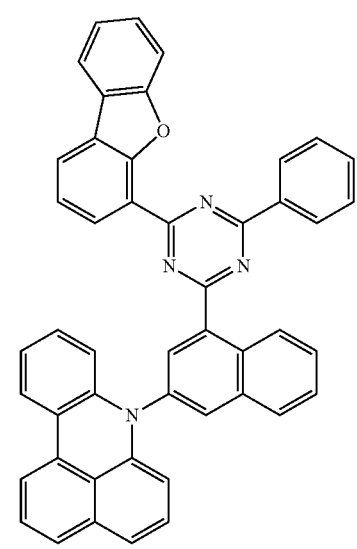
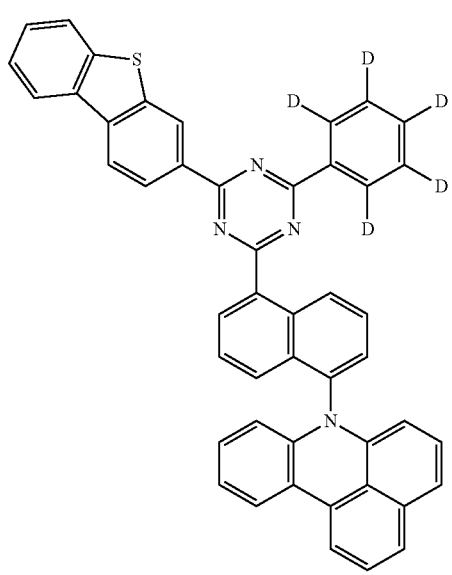
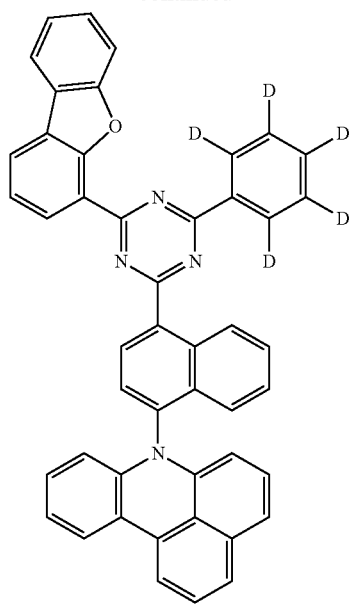
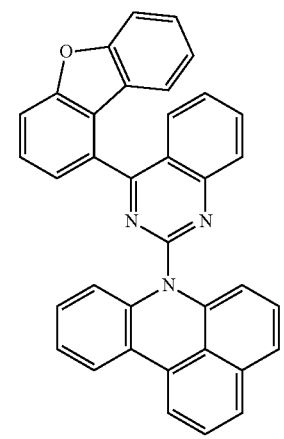
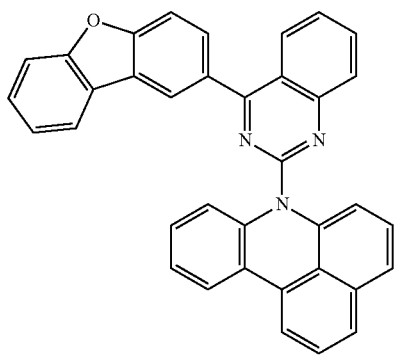

49
-continued
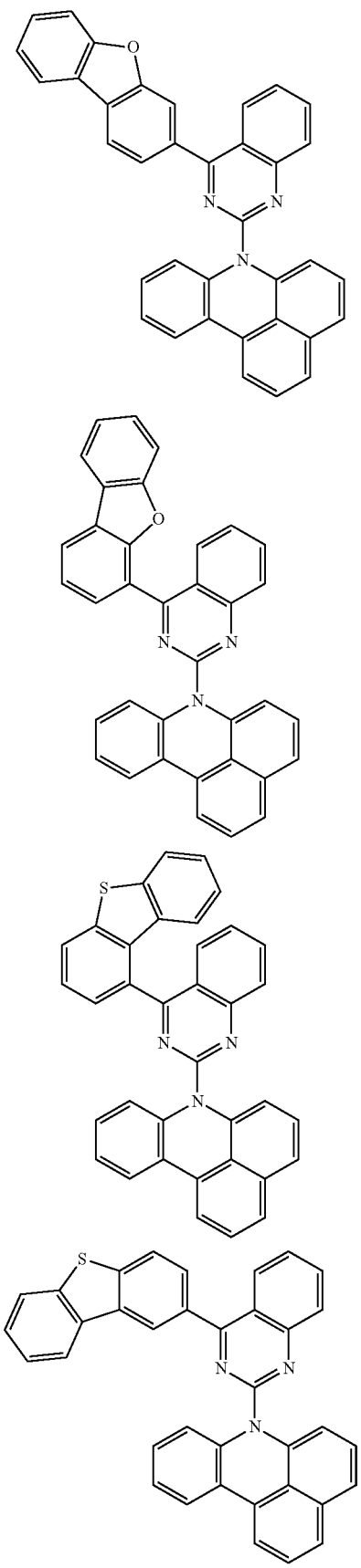
50
-continued
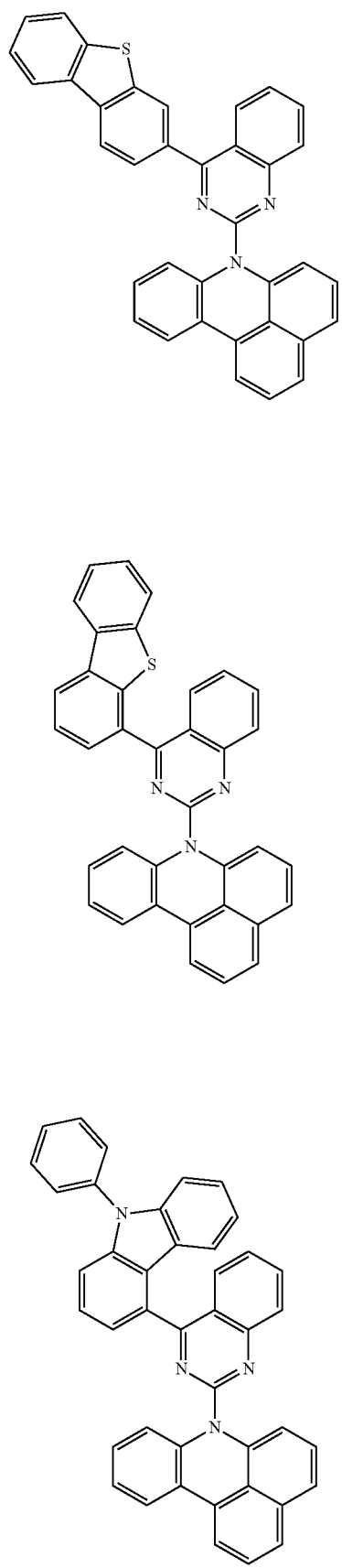

51
-continued
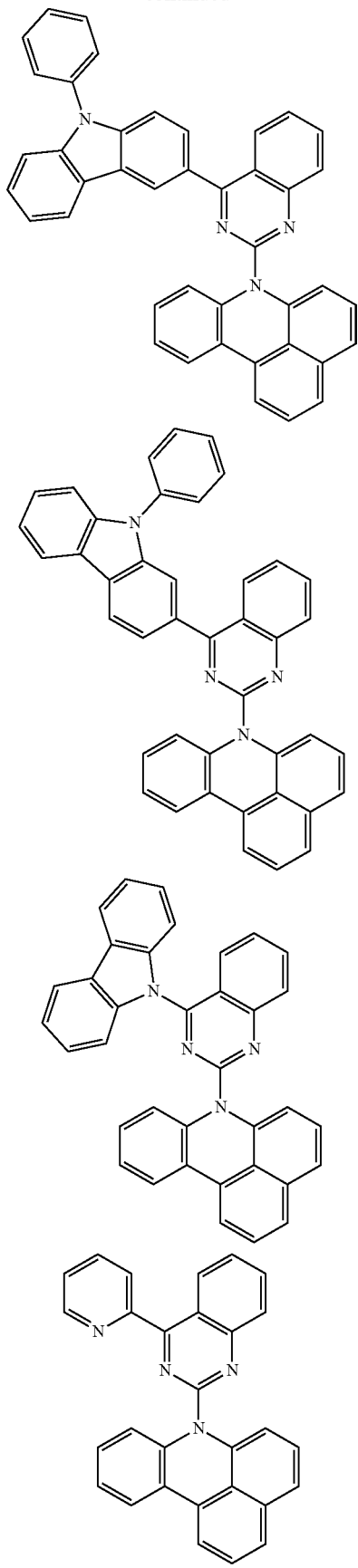
52
-continued
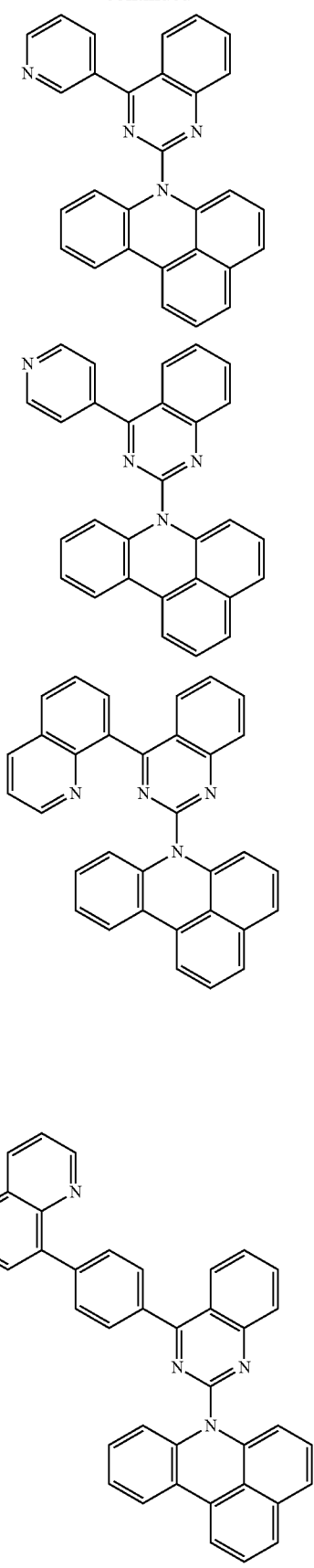

53
-continued
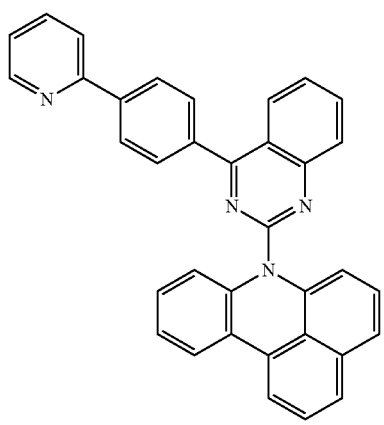
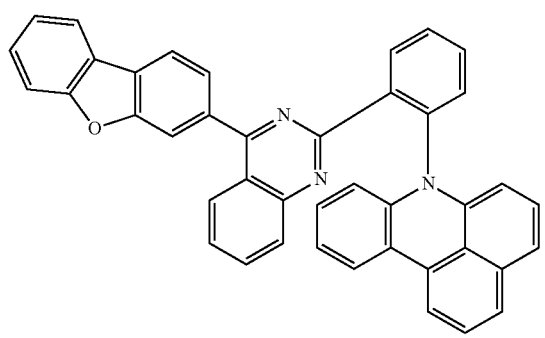
54
-continued
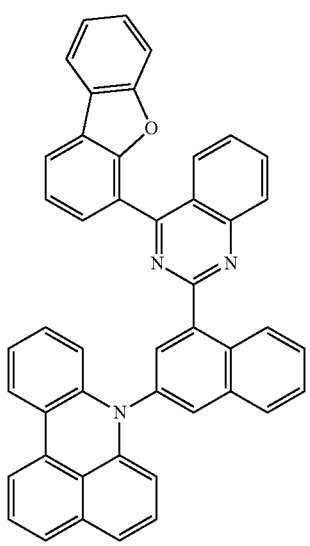
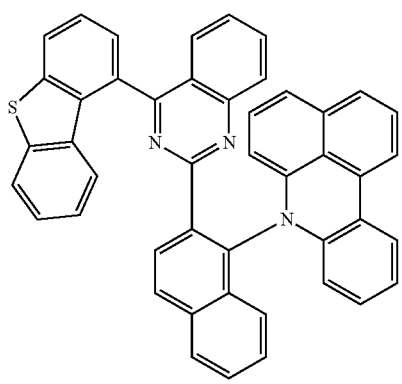
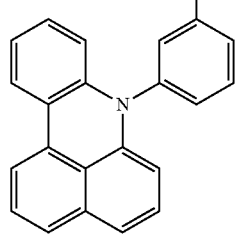

55
-continued
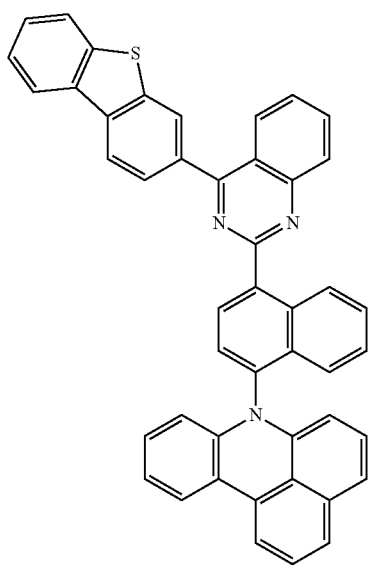
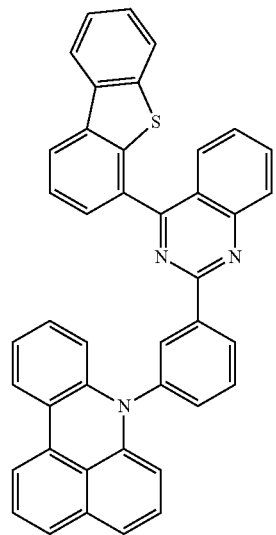
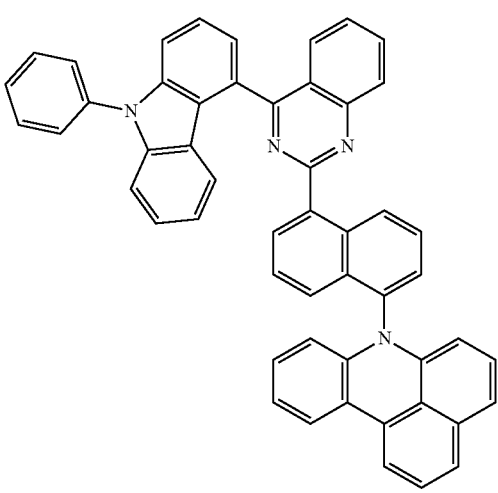
56
-continued
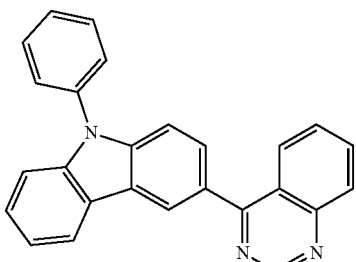
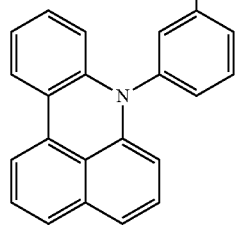
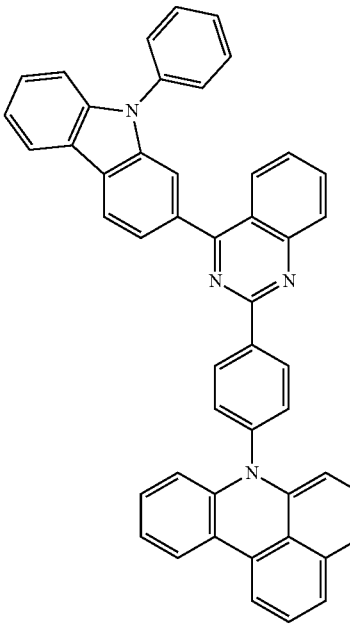
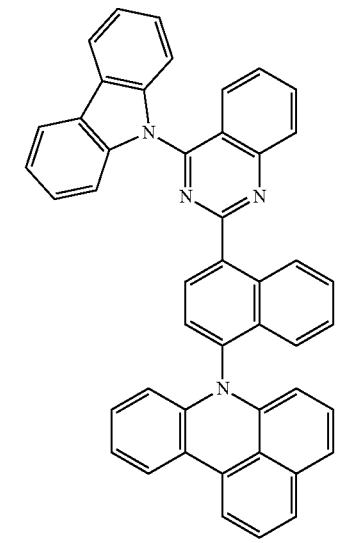

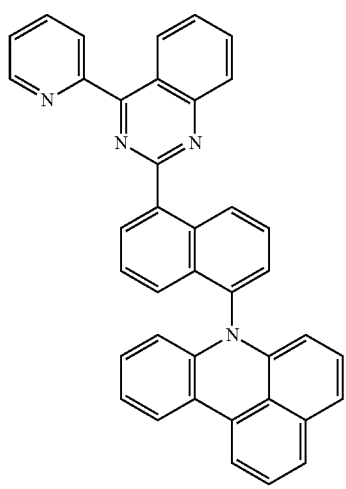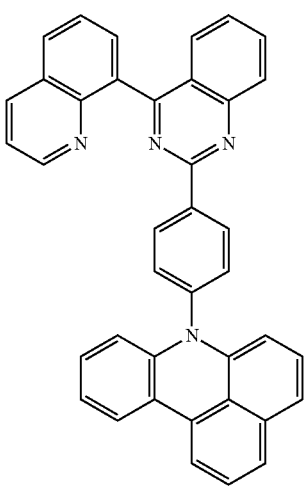

59
-continued
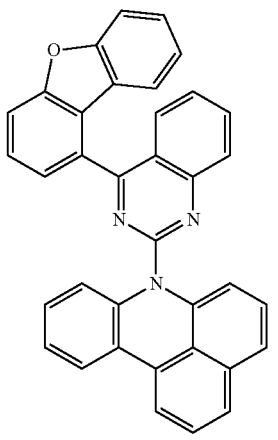
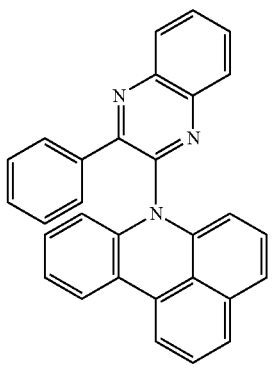
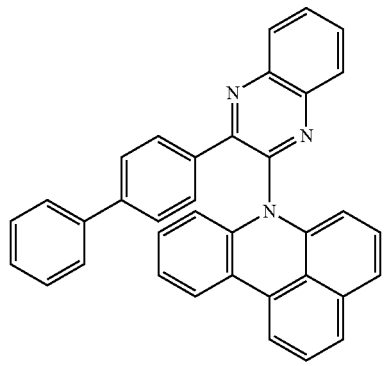
60
-continued
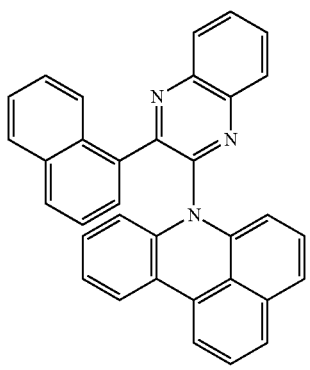
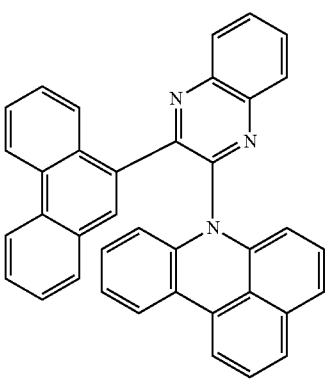
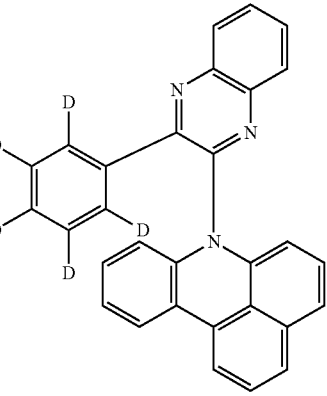
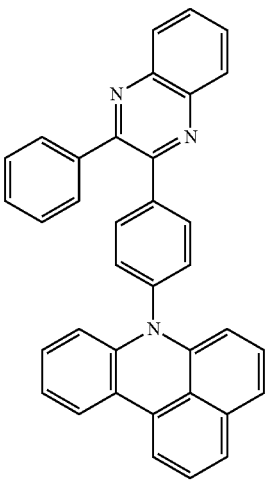

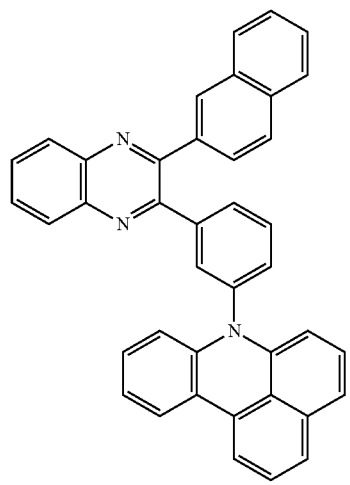
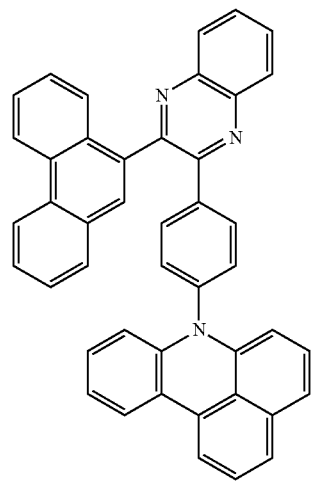
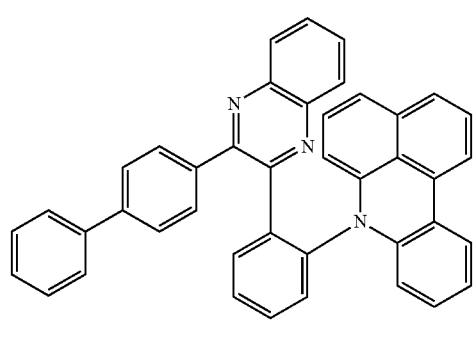
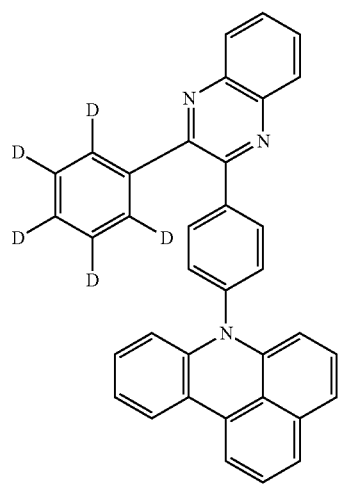
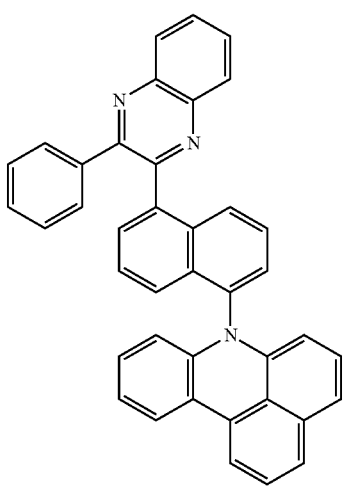

63
-continued
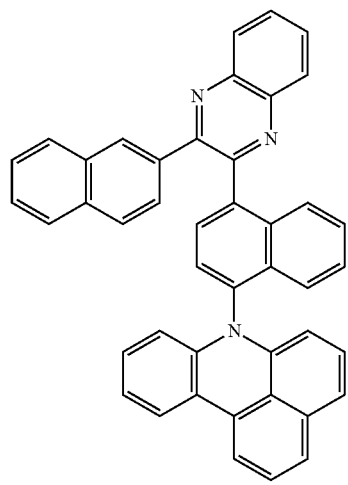
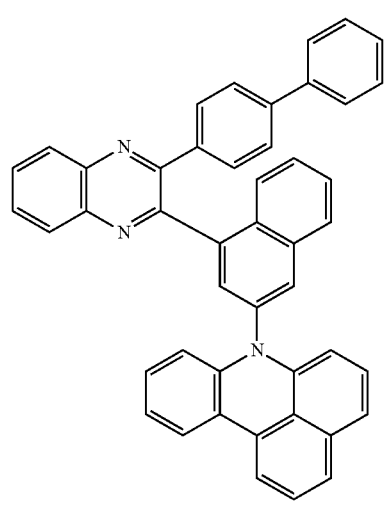
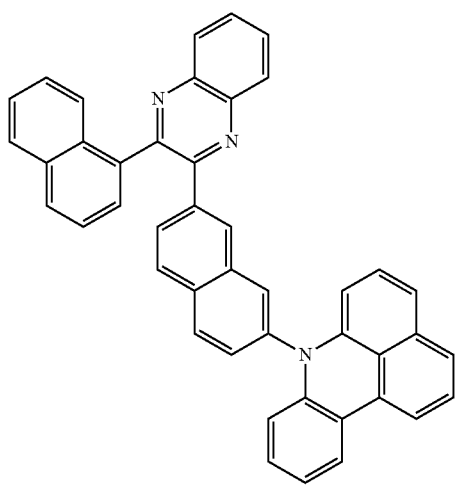
64
-continued
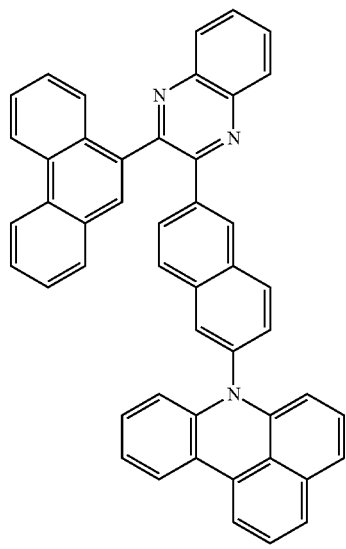
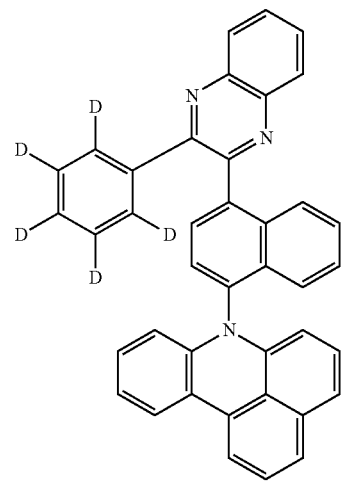
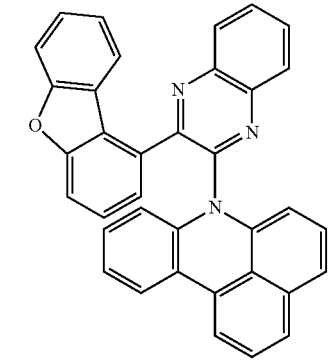

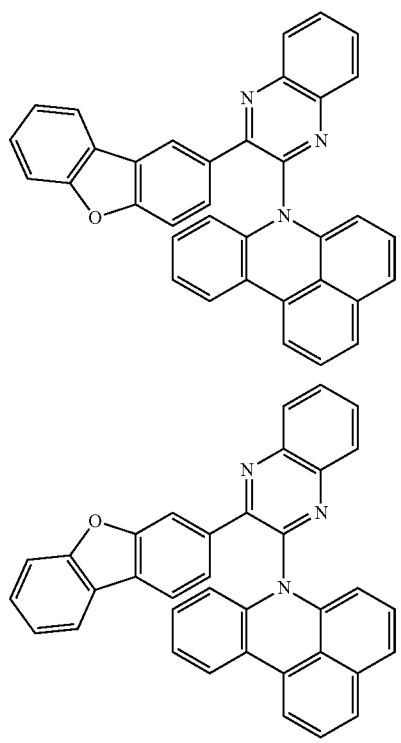
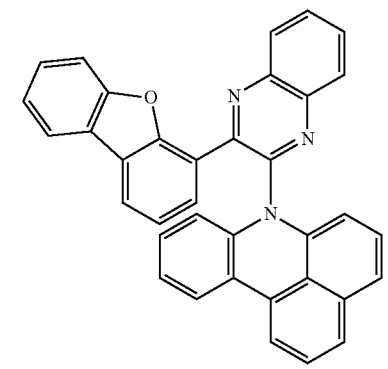
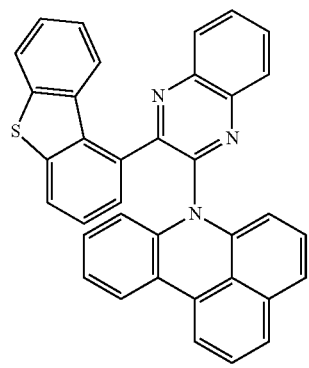
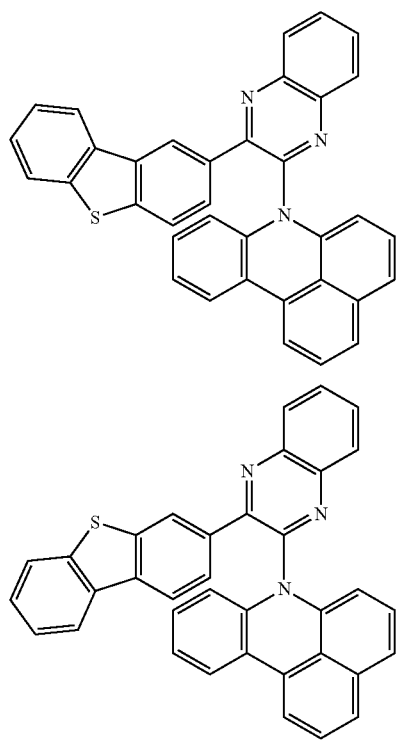
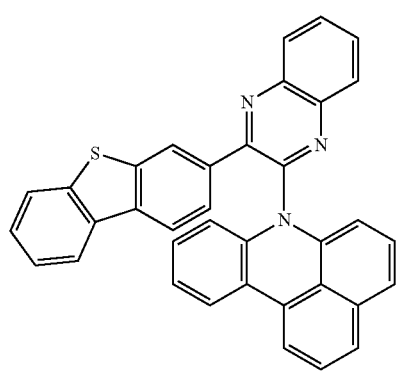
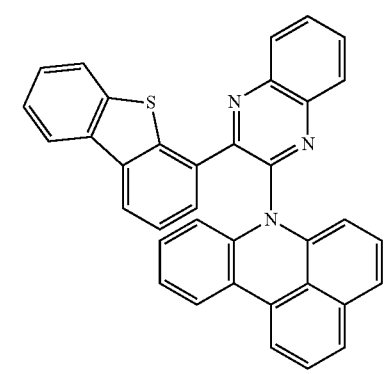
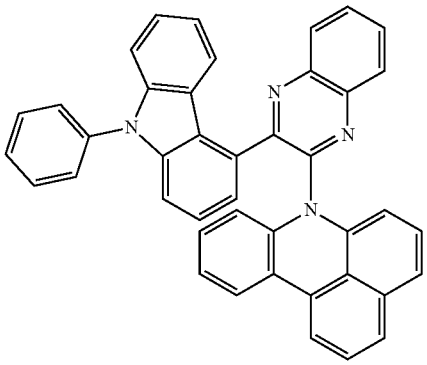

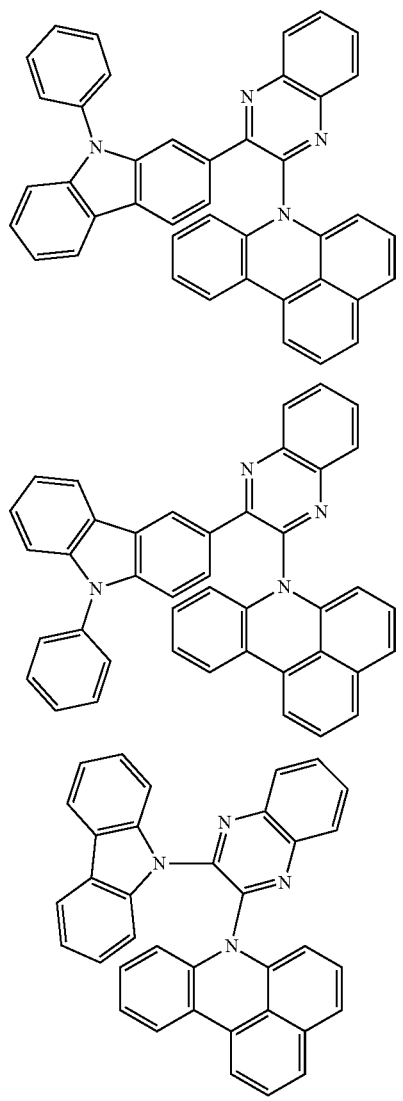
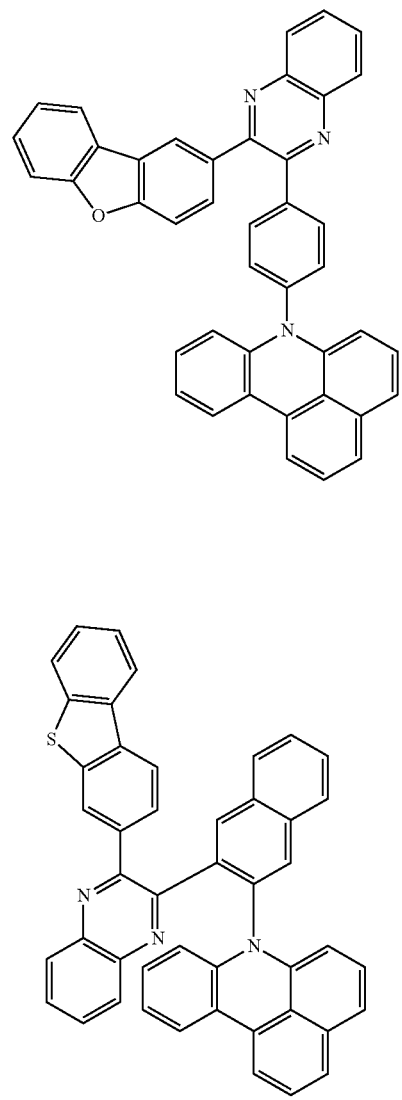
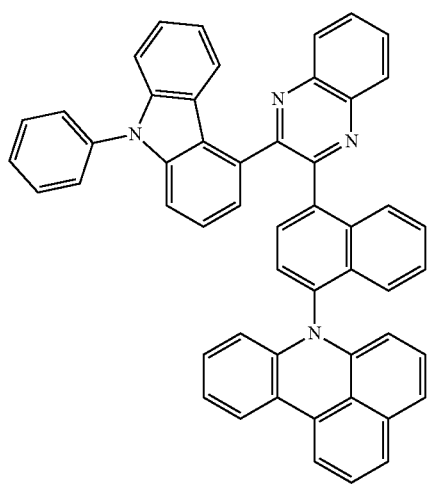
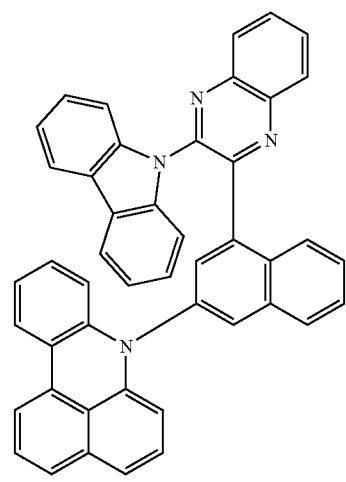

69
-continued
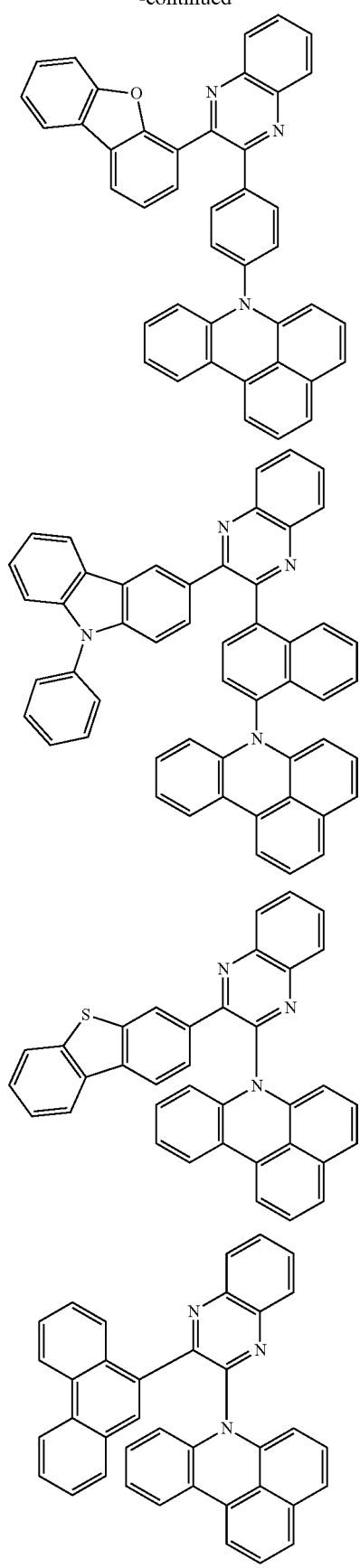
70
-continued
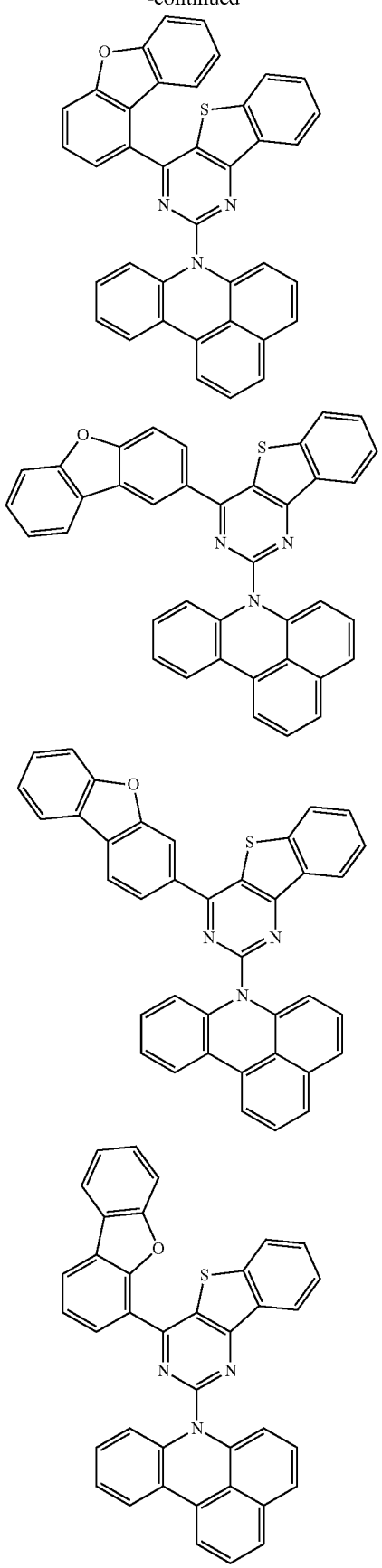

-continued
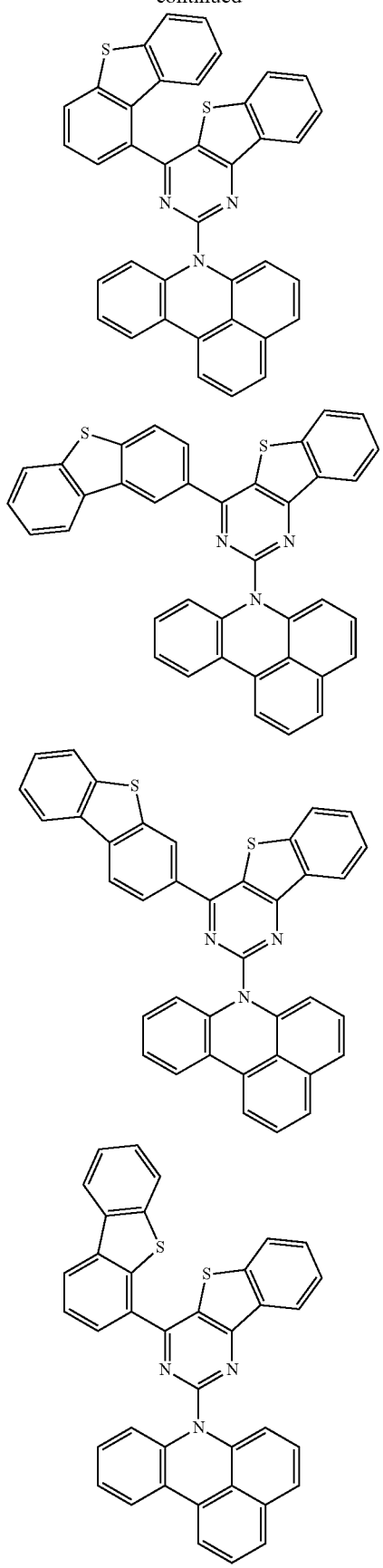
-continued
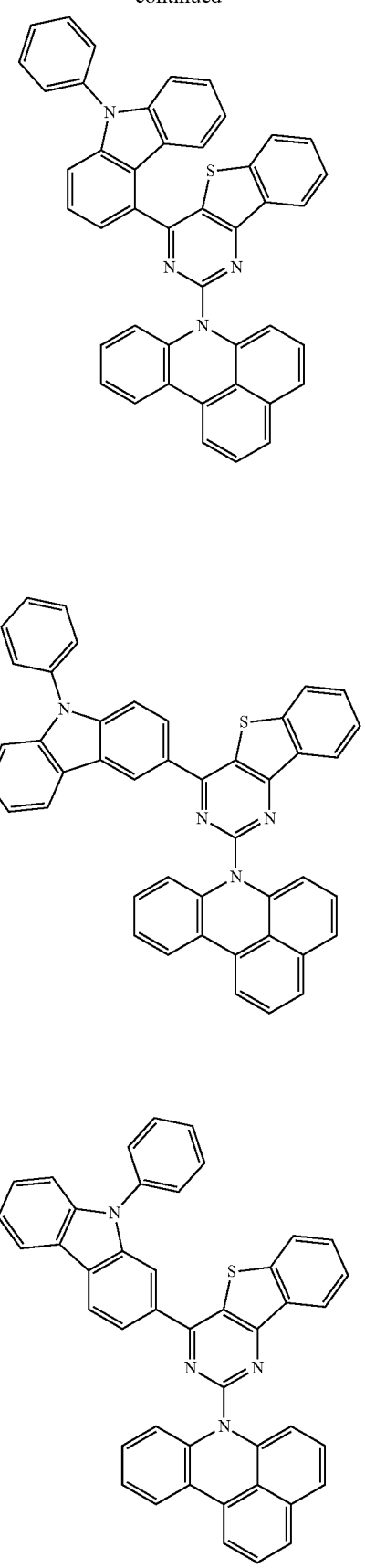

73
-continued
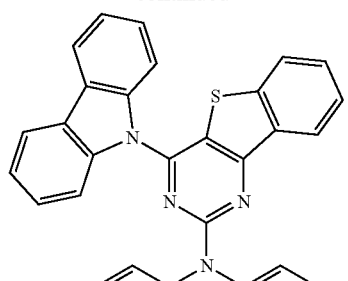
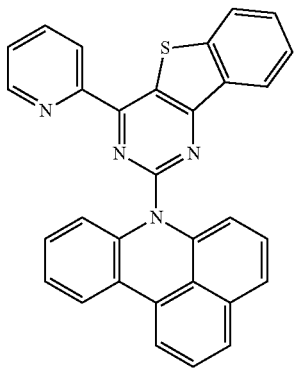
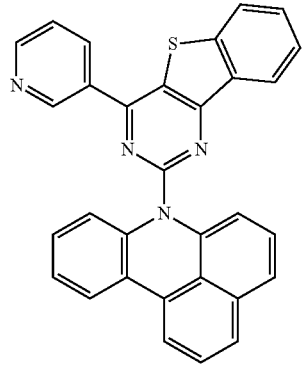
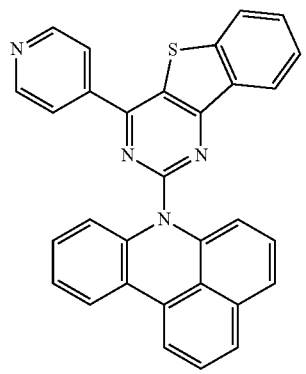
74
-continued
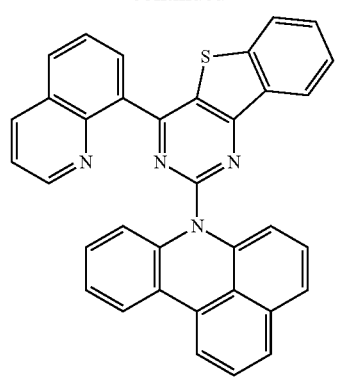
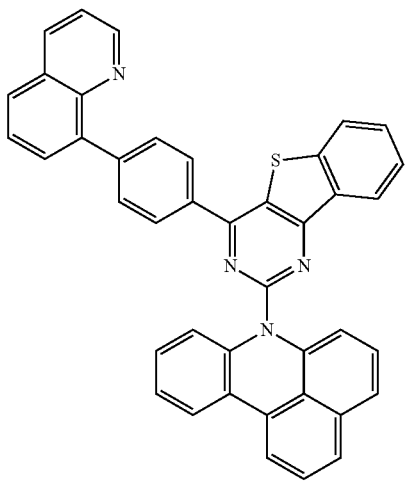
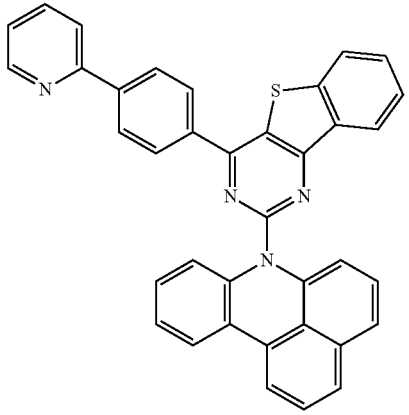

75
-continued
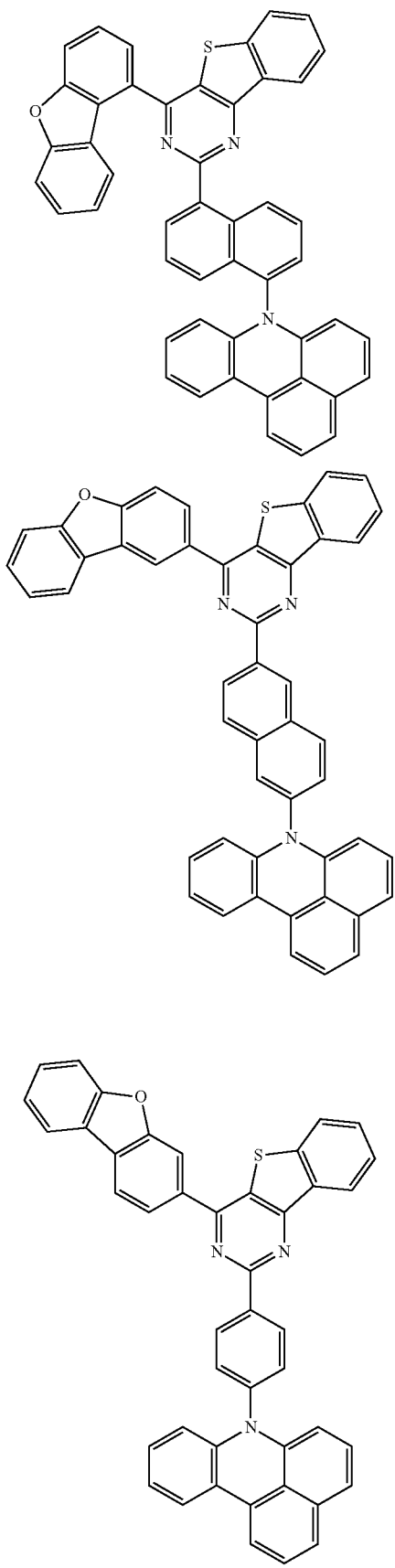
76
-continued
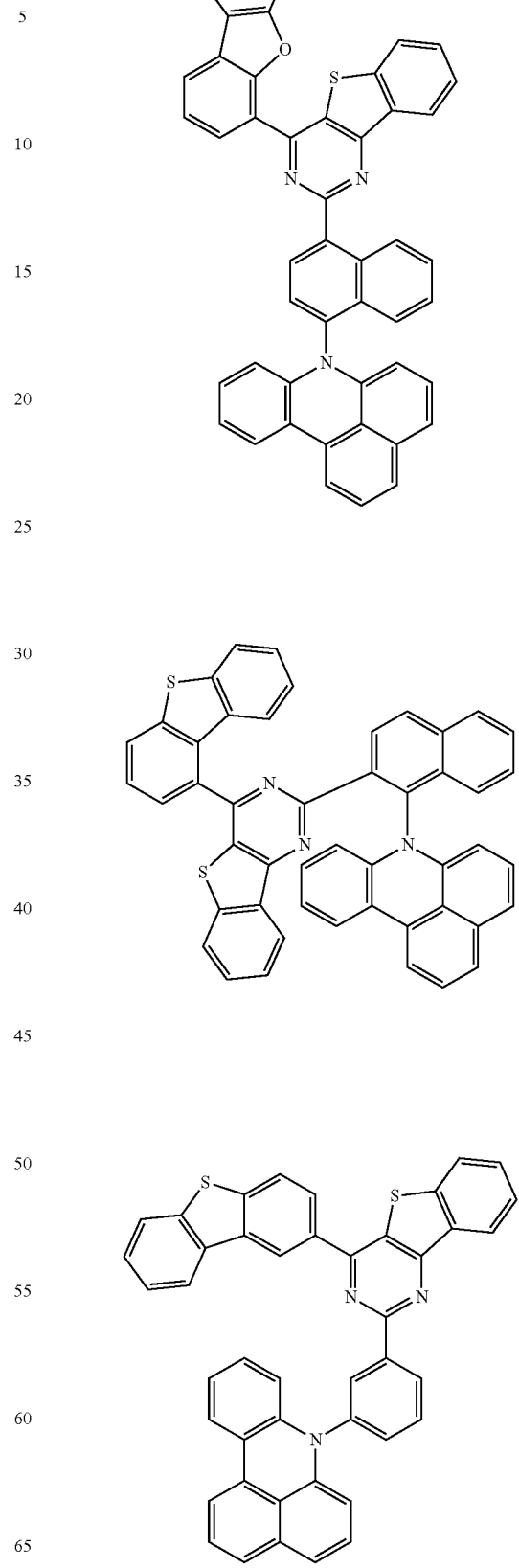

77
-continued
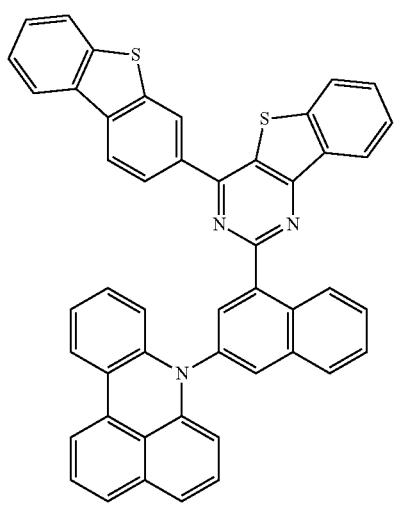
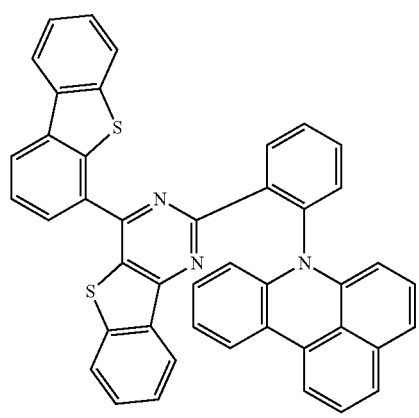
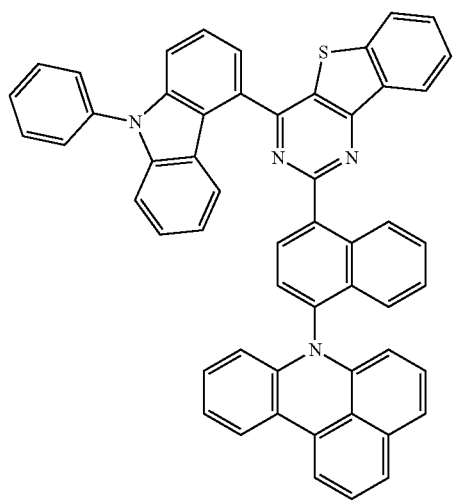
78
-continued
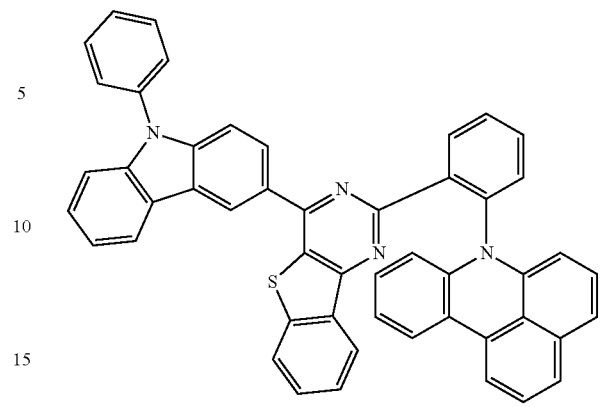
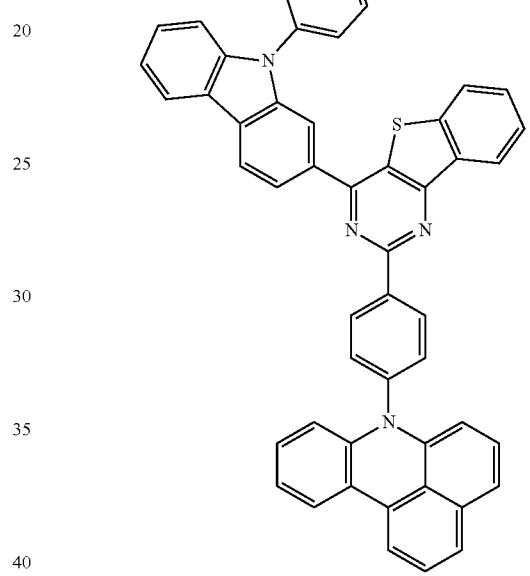
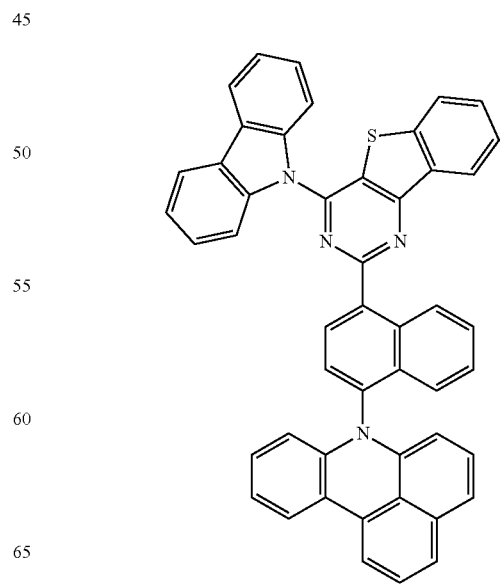

79
-continued
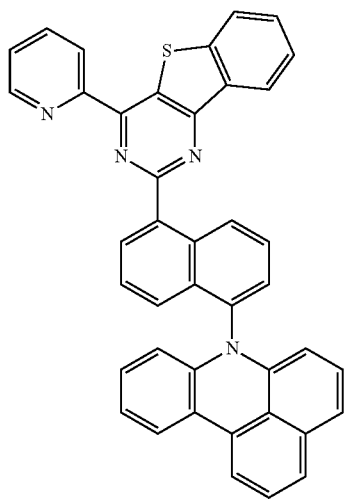
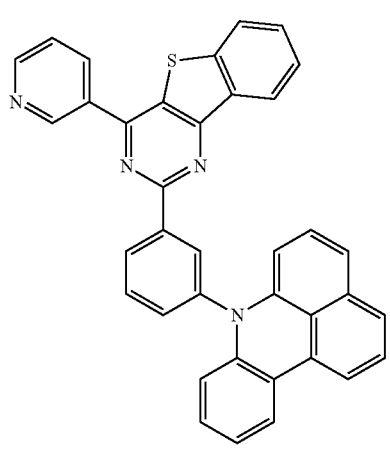
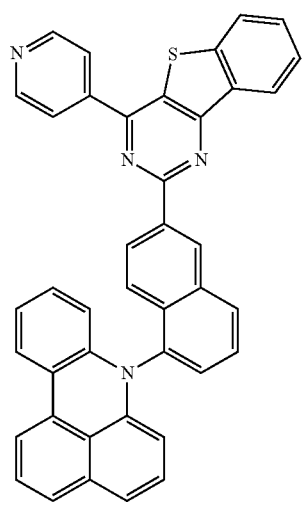
80
-continued
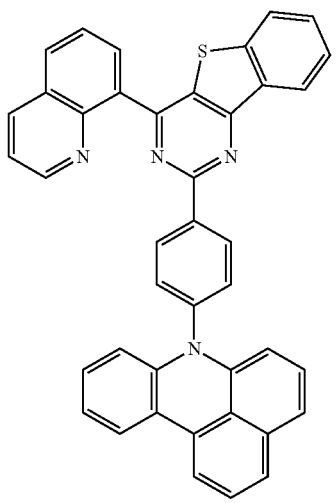
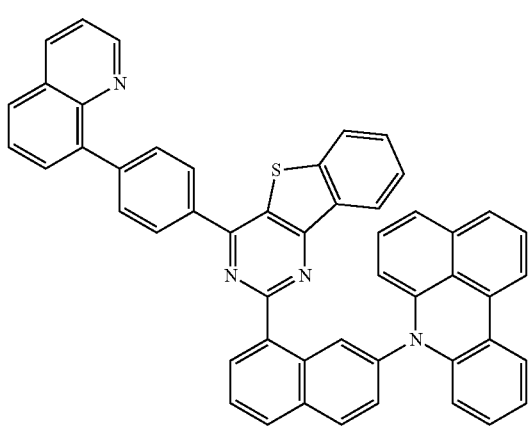
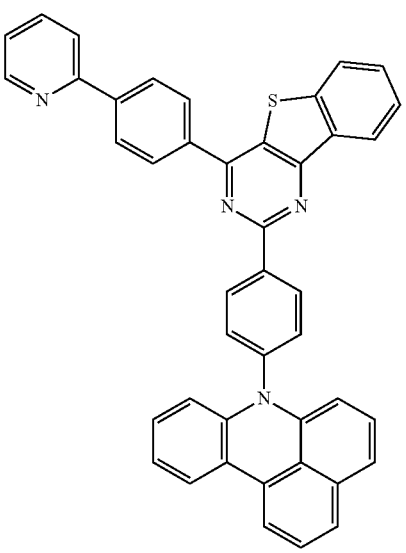

81
-continued
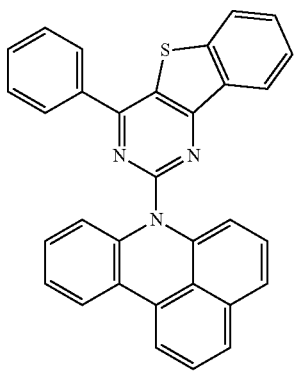
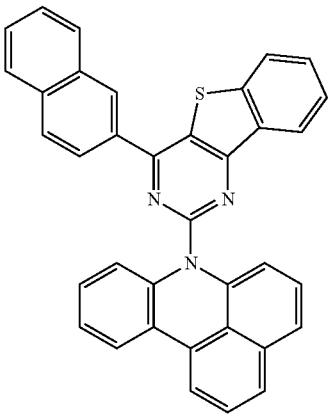
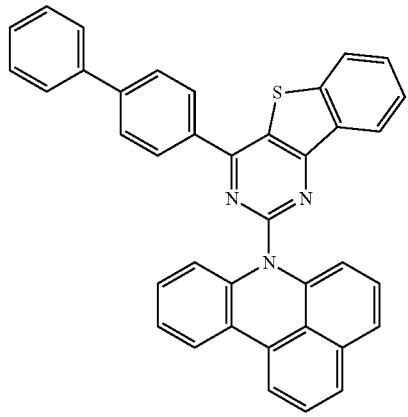
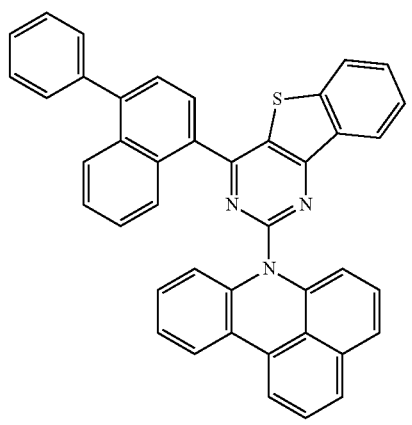
82
-continued
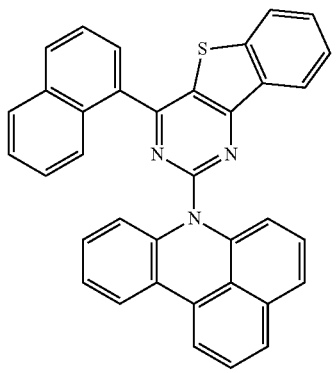
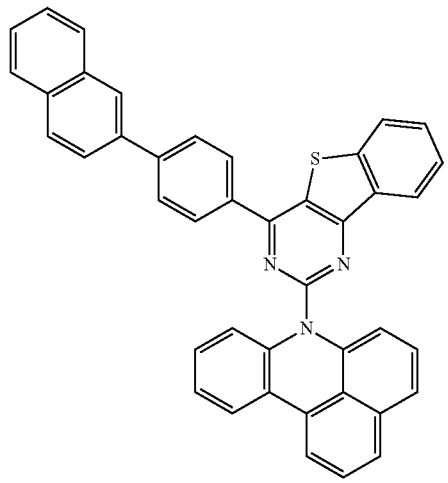
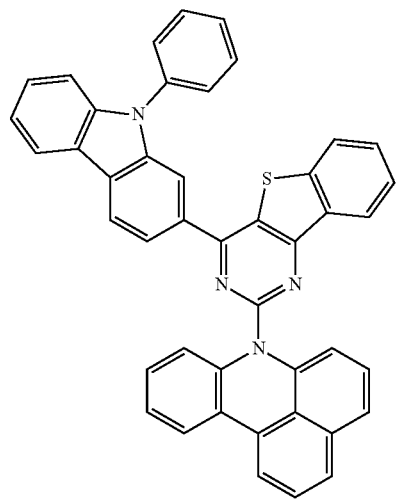

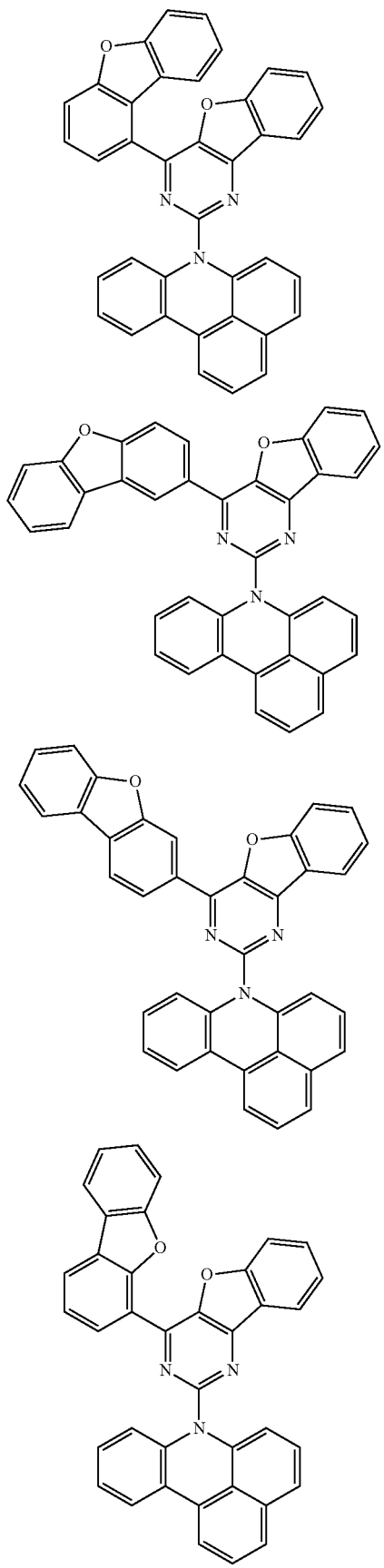
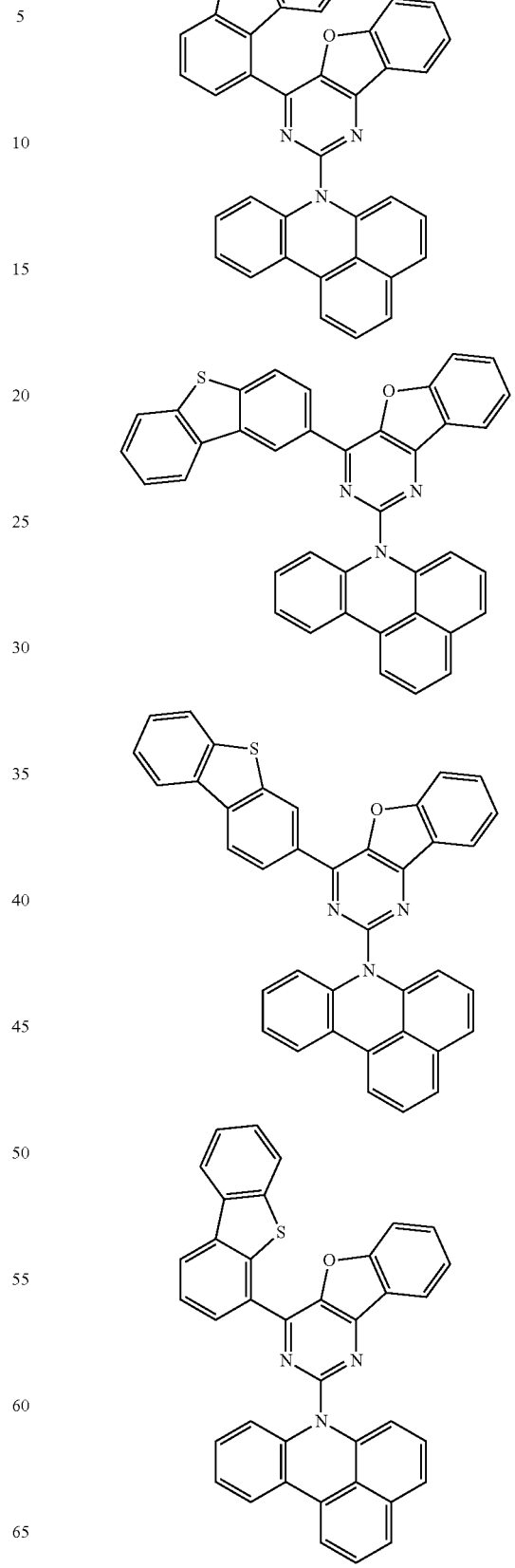

85
-continued
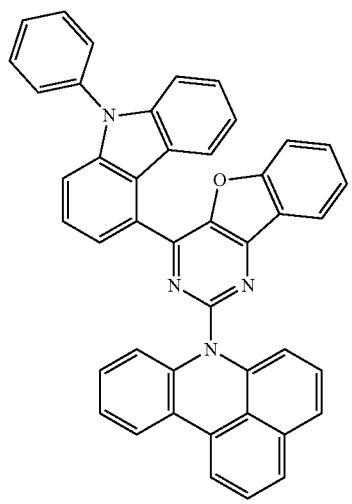
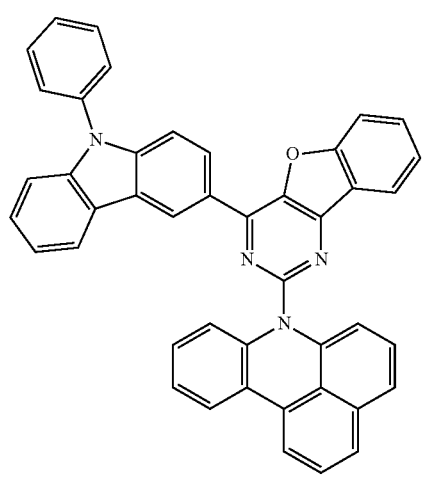
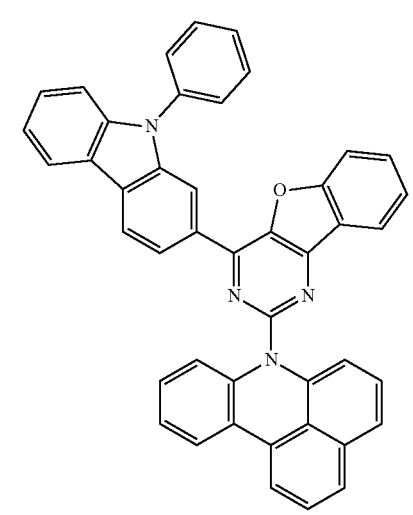
86
-continued
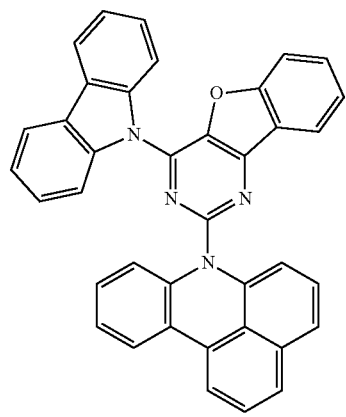
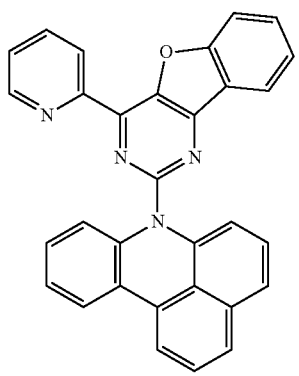
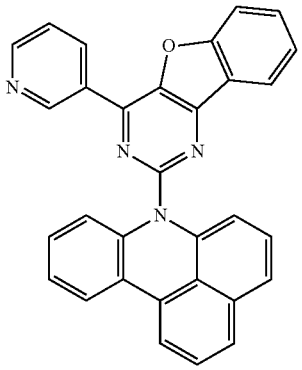
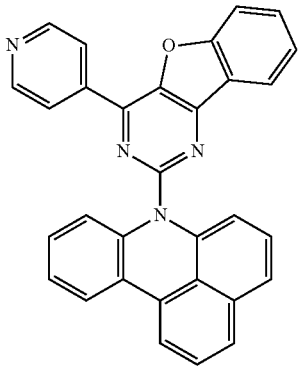

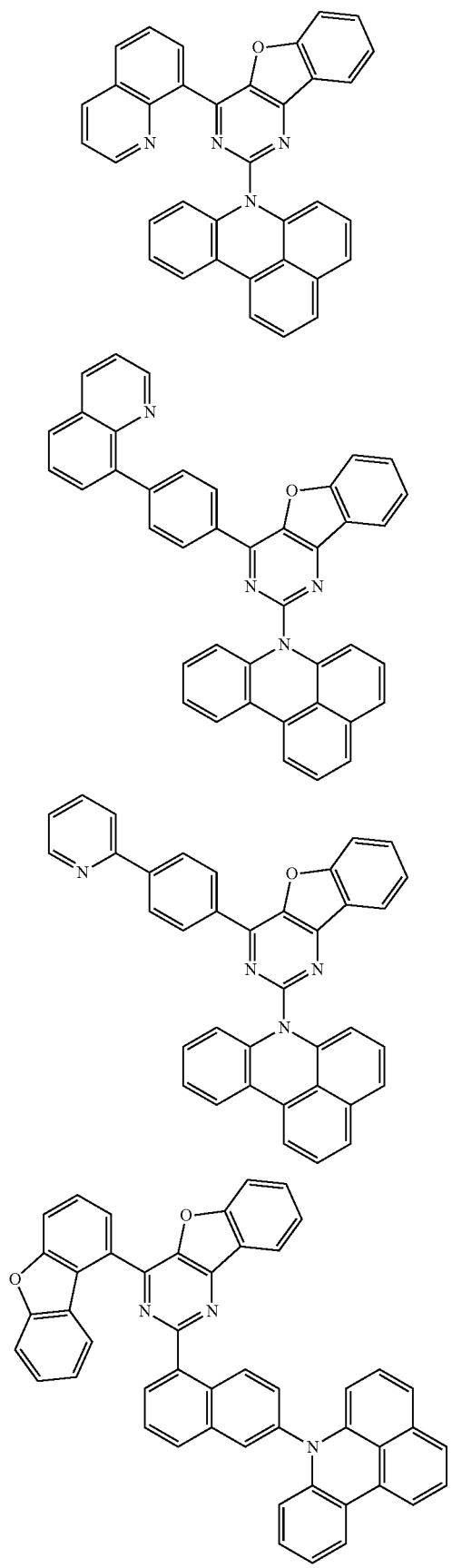
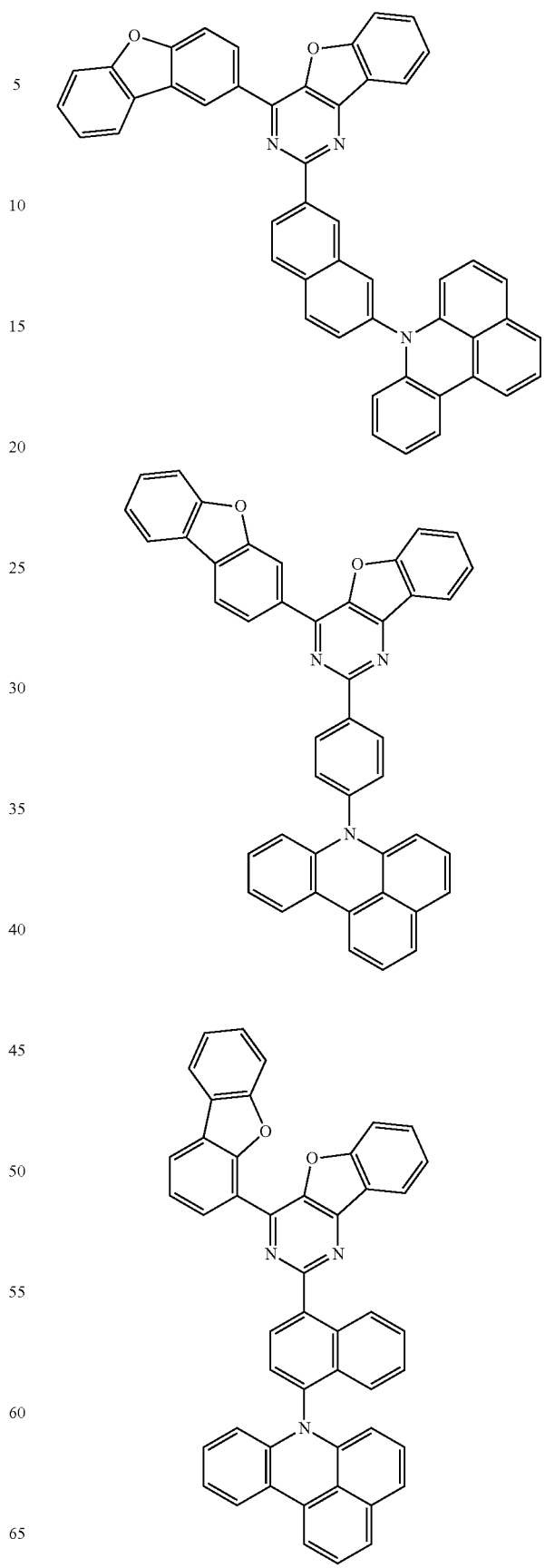

89
-continued
90
-continued
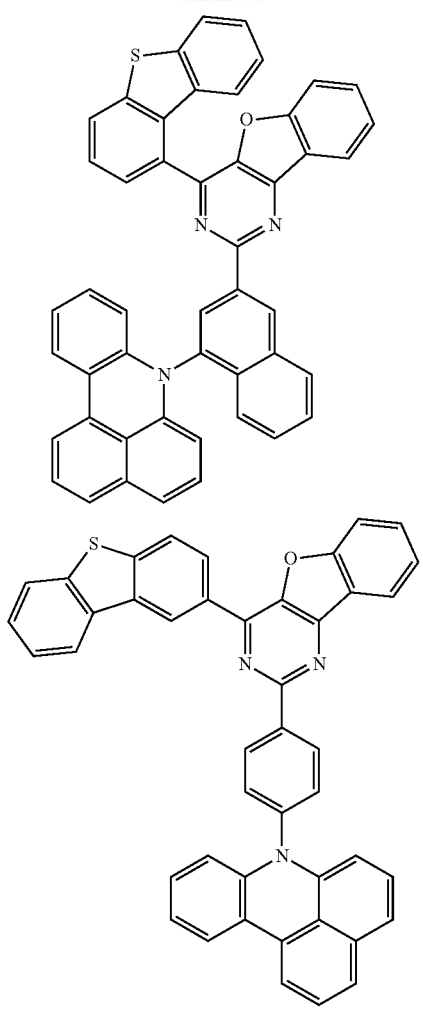
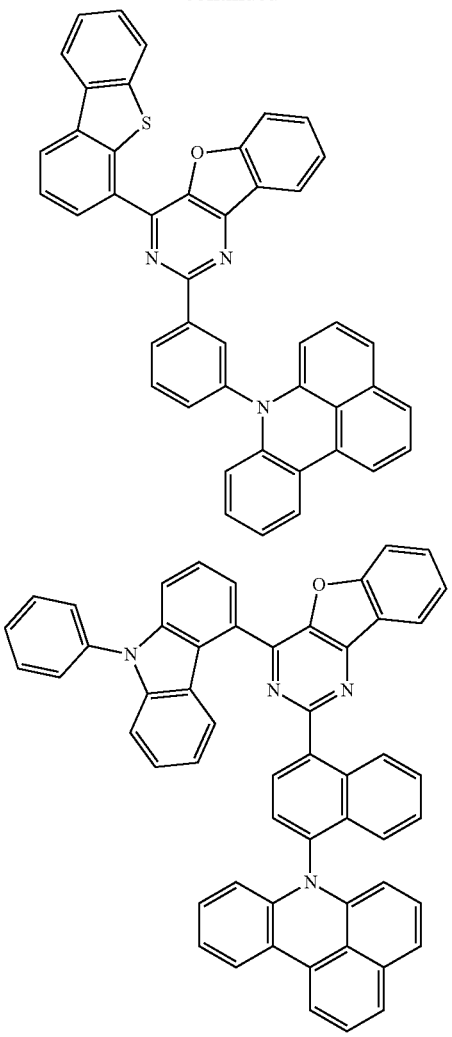
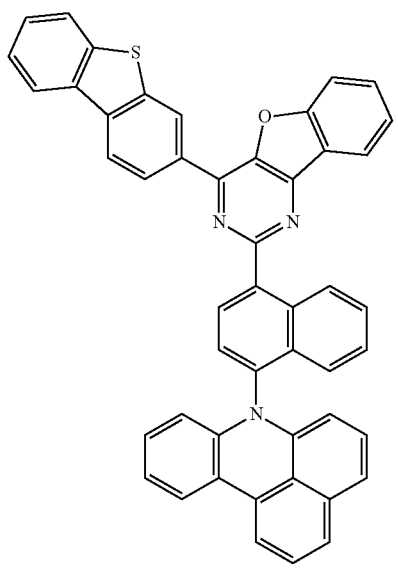

91
-continued
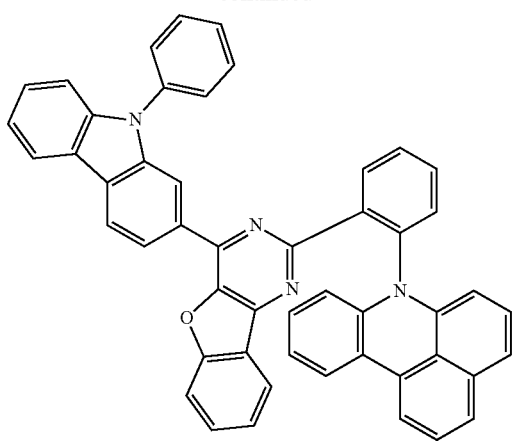
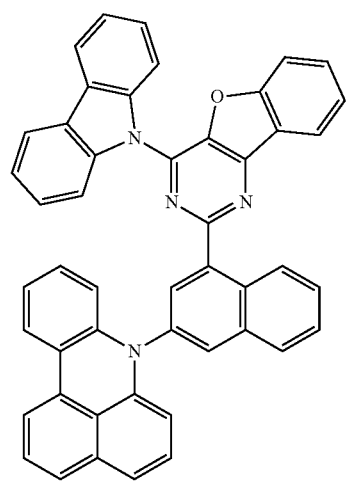
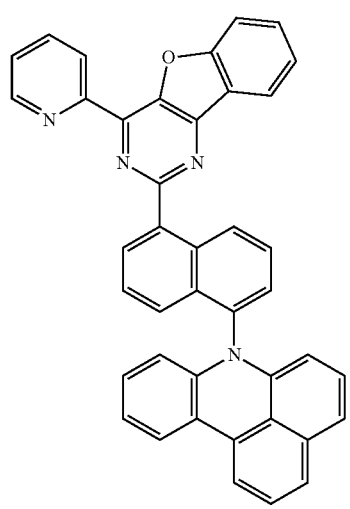
92
-continued
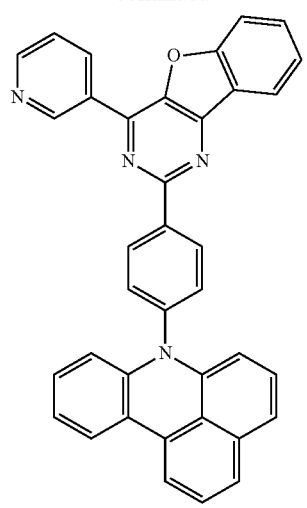
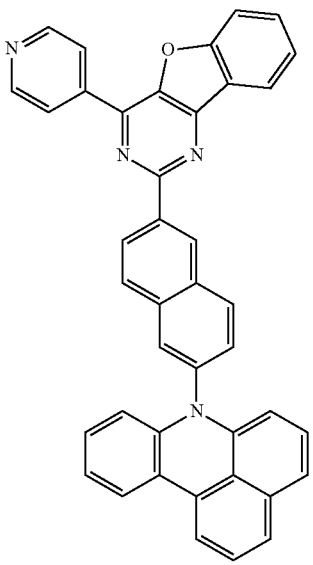
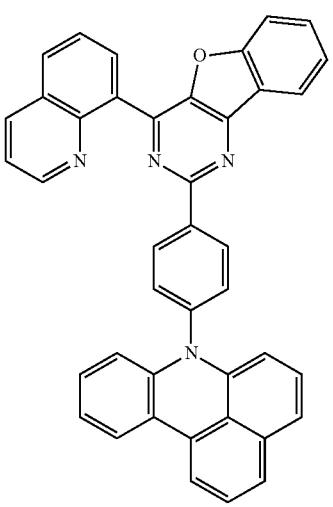

93
-continued
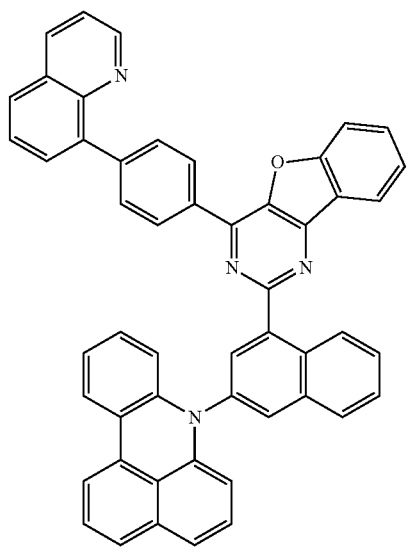
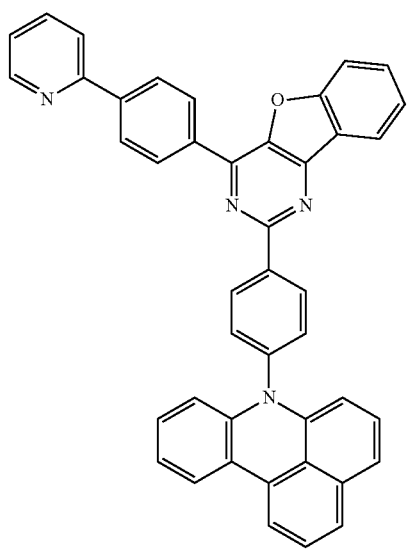
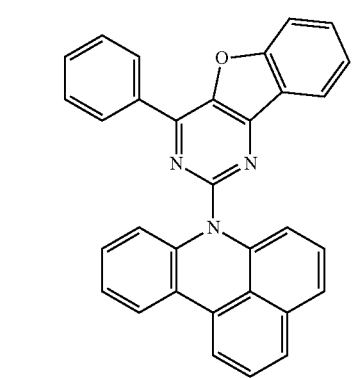
94
-continued
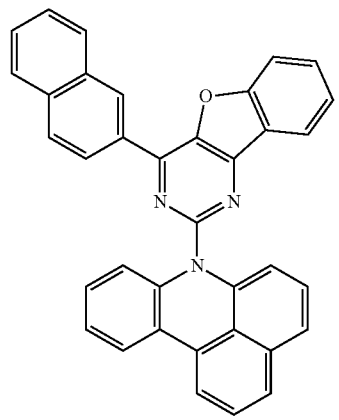
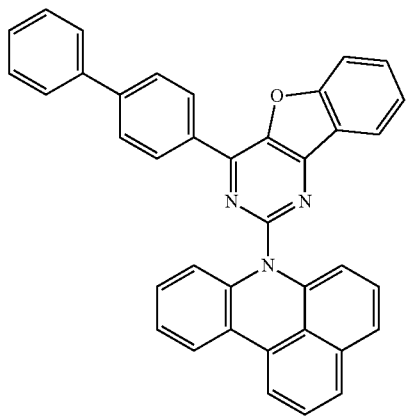
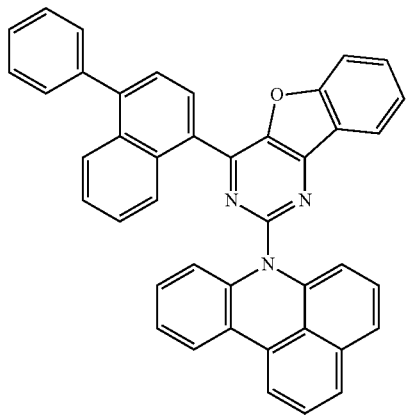
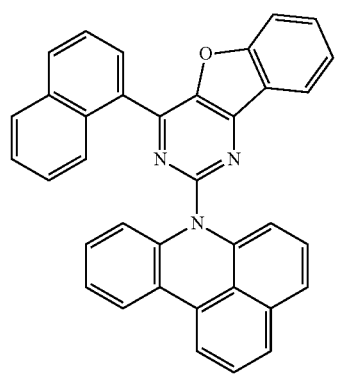

95
-continued
96
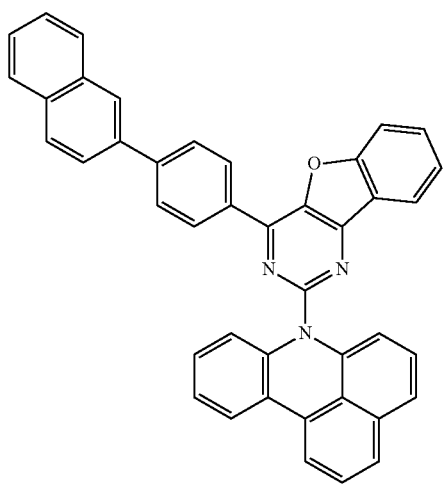
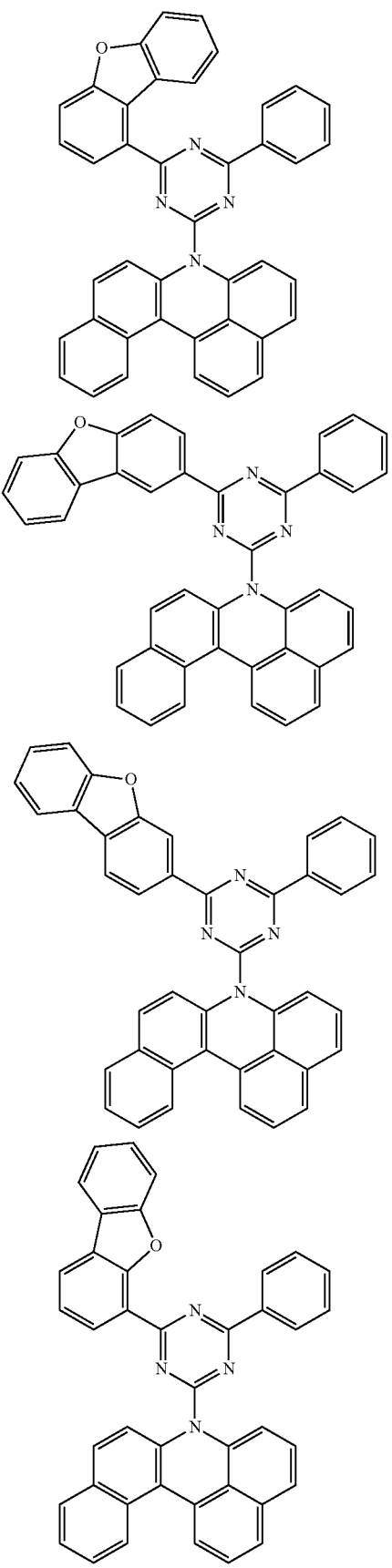

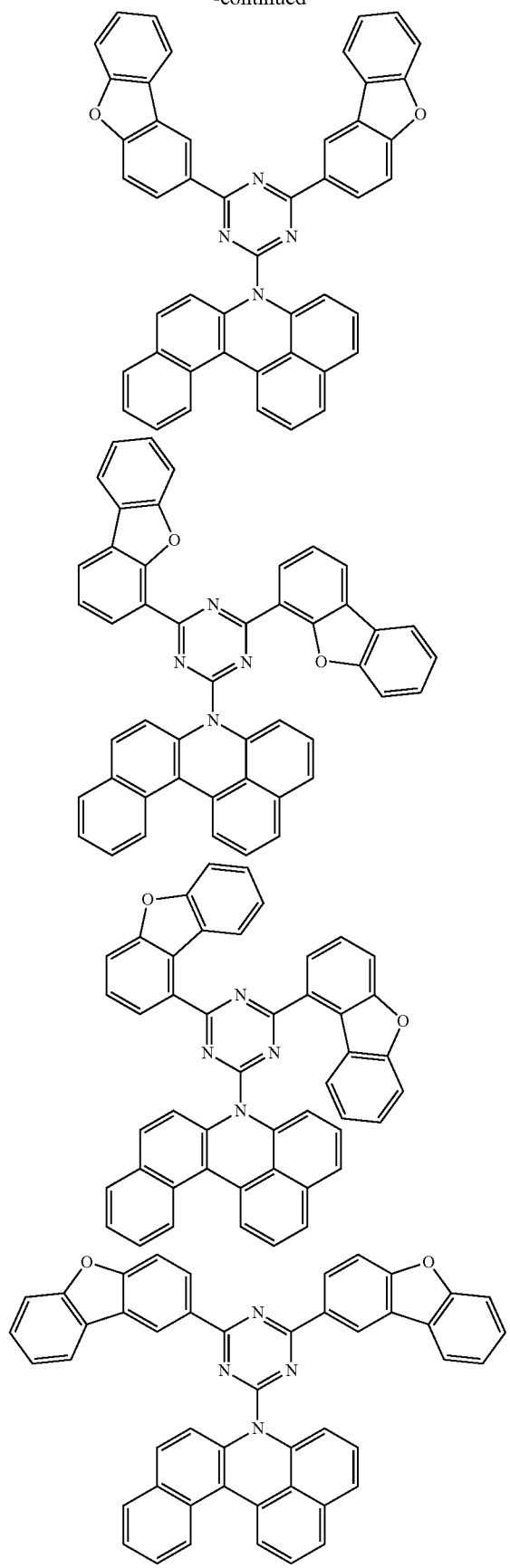
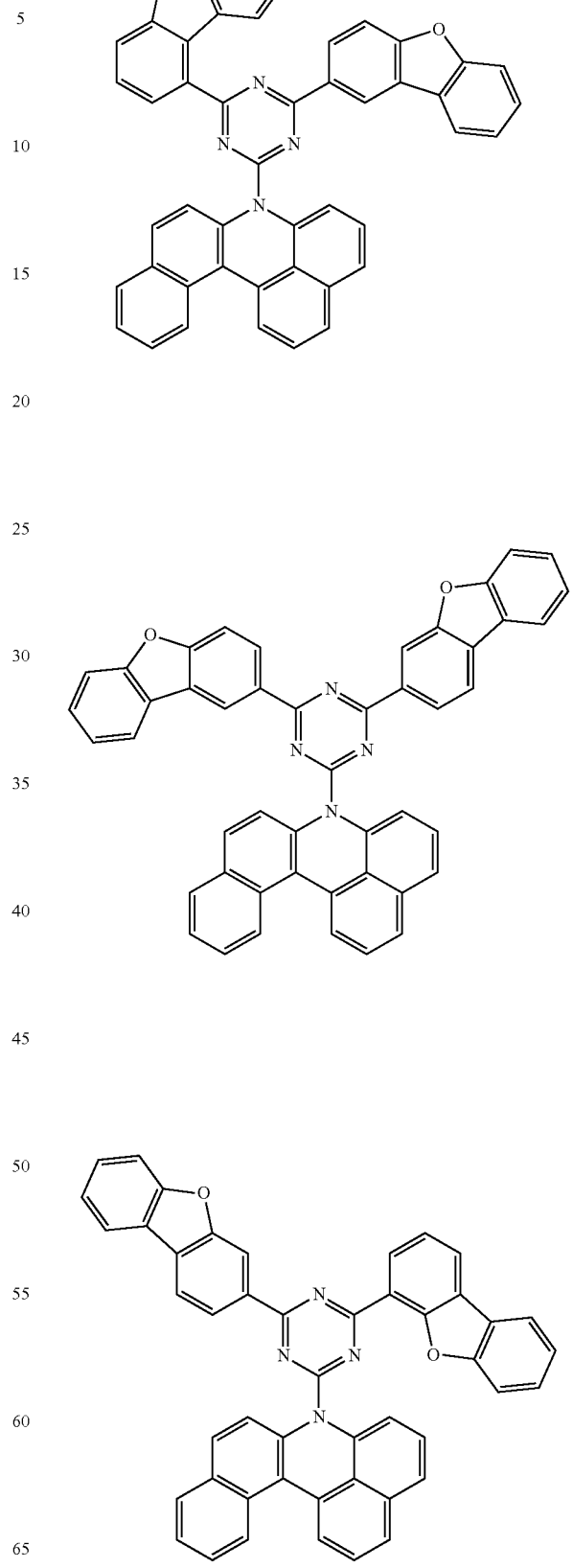

99
-continued
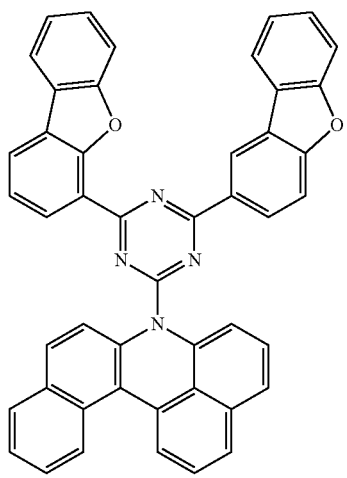
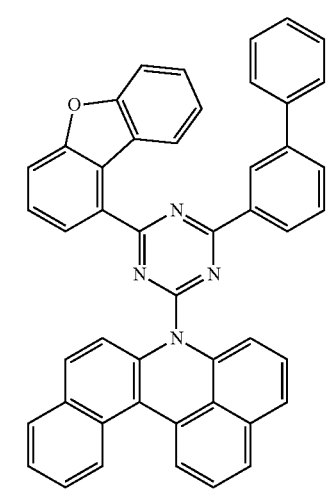
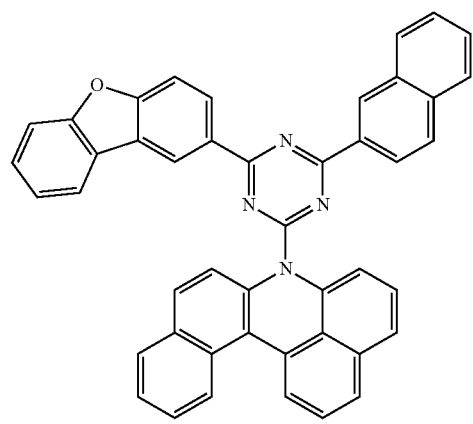 [SMILES: c1ccc2cc(-c3nc(-c4ccc5sc6ccccc6c5c4)nc(N4c5ccc6ccccc6c5-c5cccc6cccc4c56)n3)ccc2c1]
100
-continued
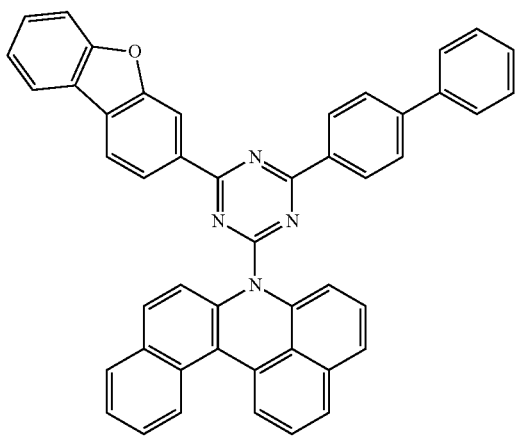
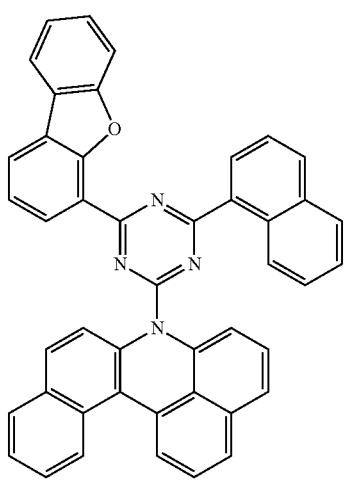
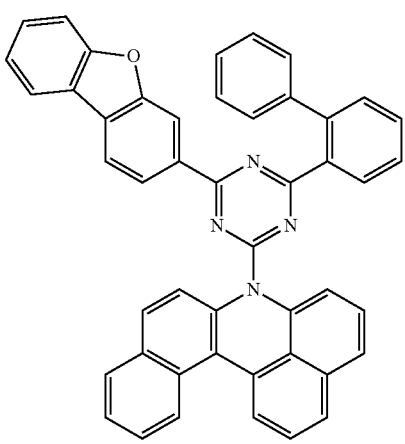

101
-continued
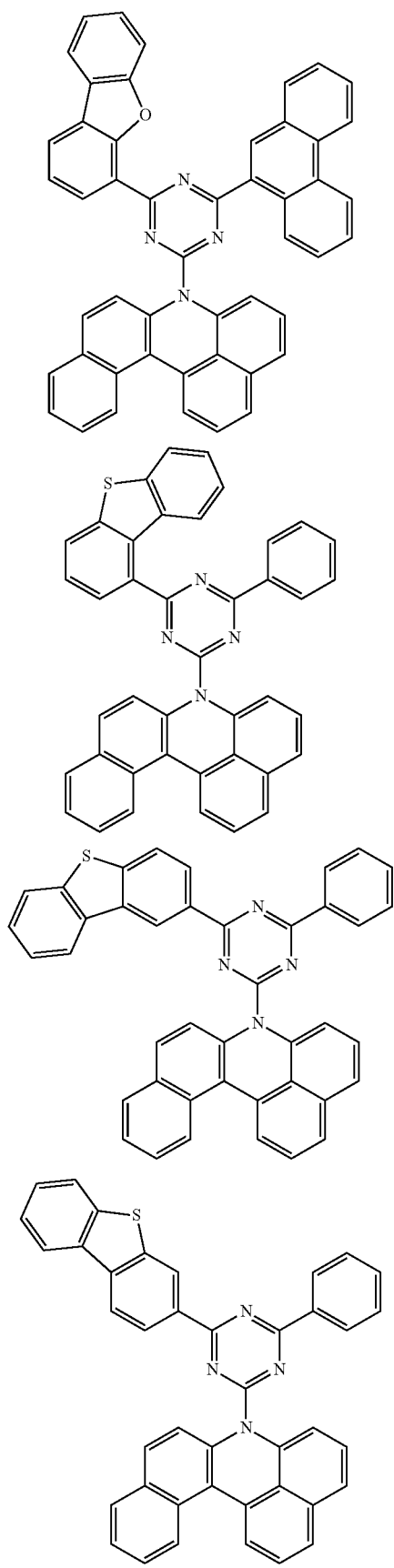
102
-continued
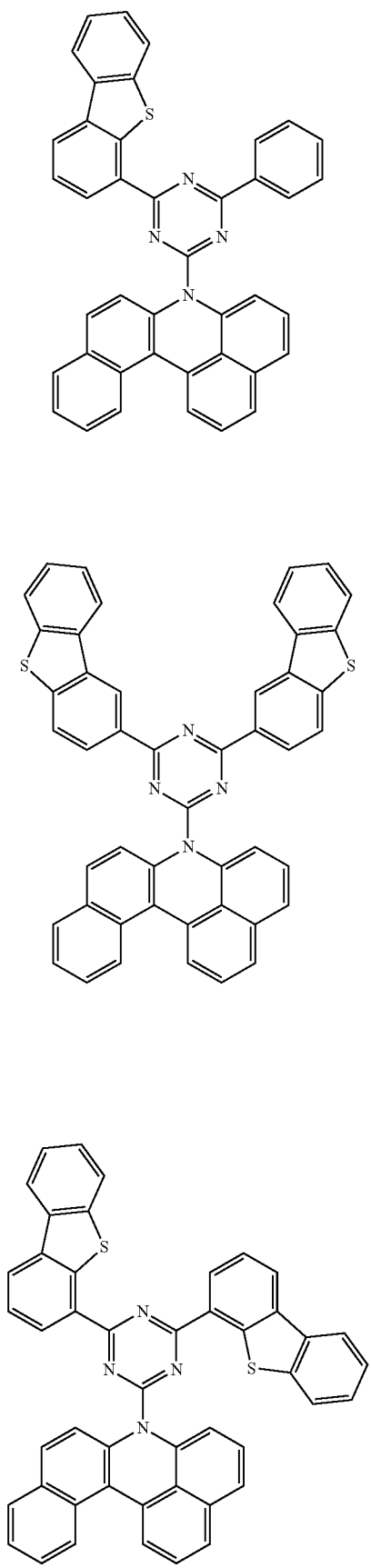

103
-continued
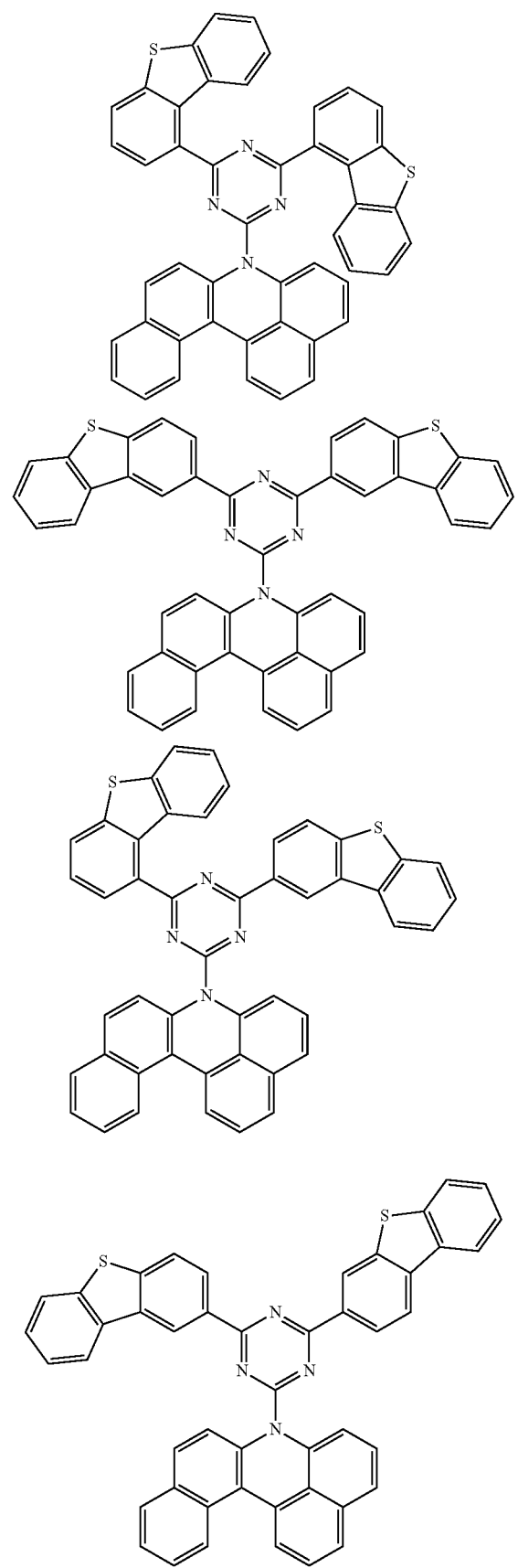
104
-continued
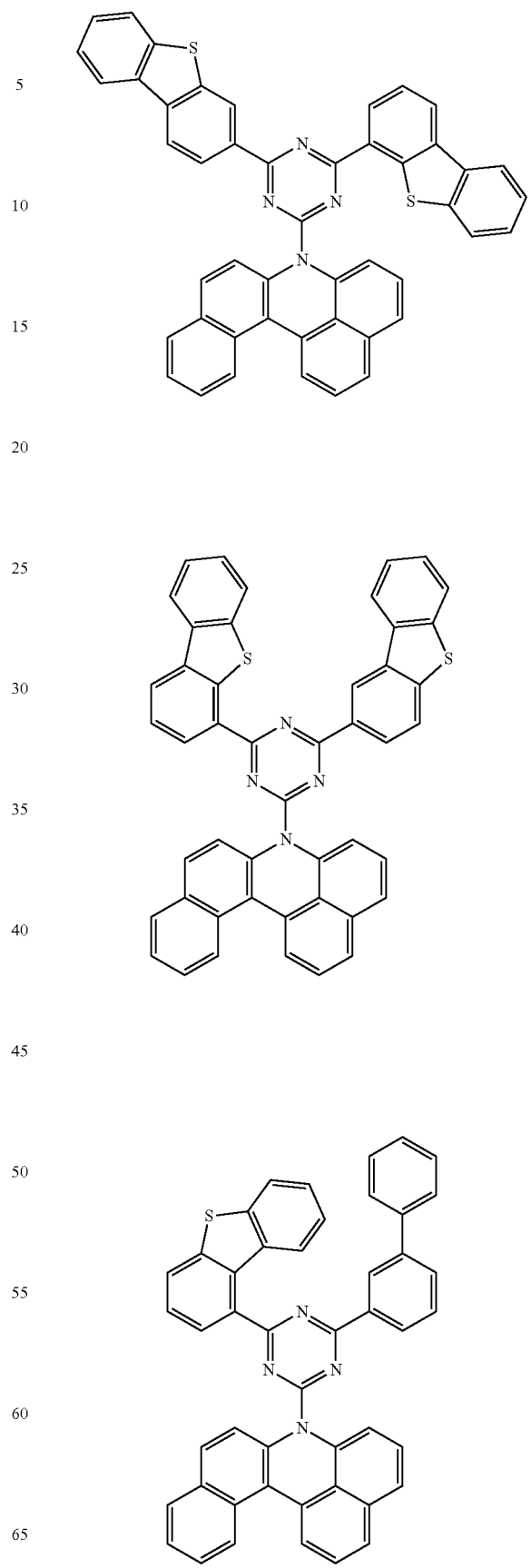

105
-continued
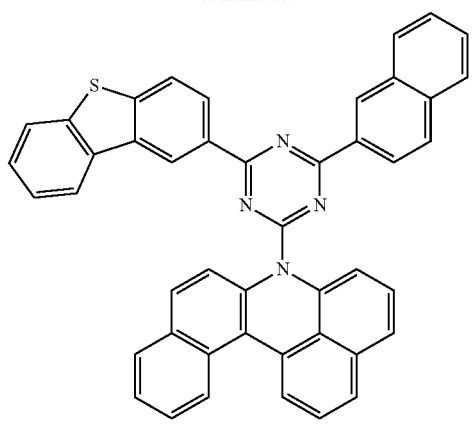
106
-continued
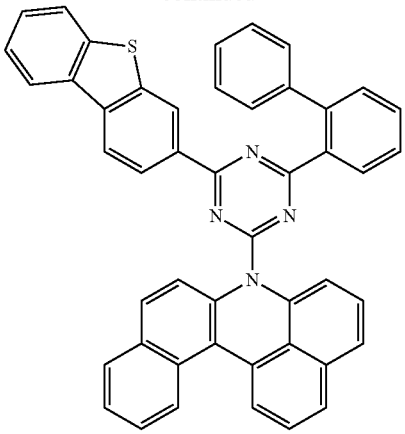
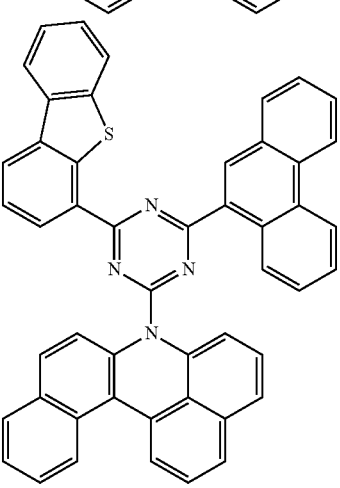
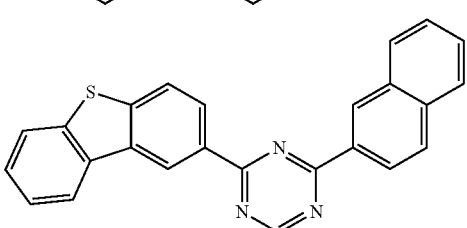
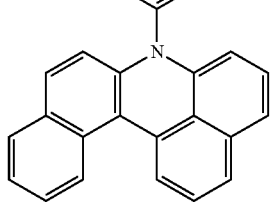
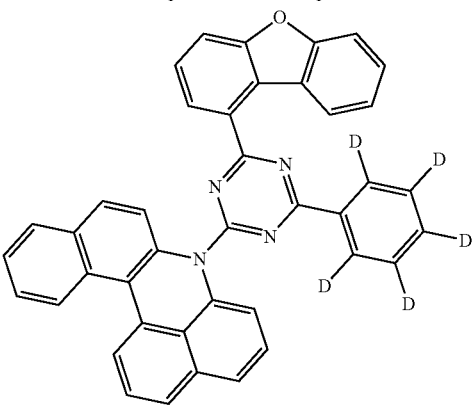

107
-continued
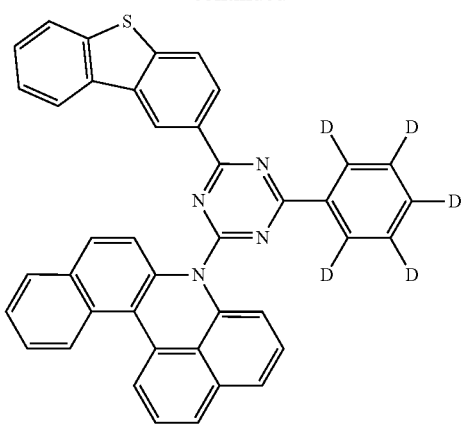
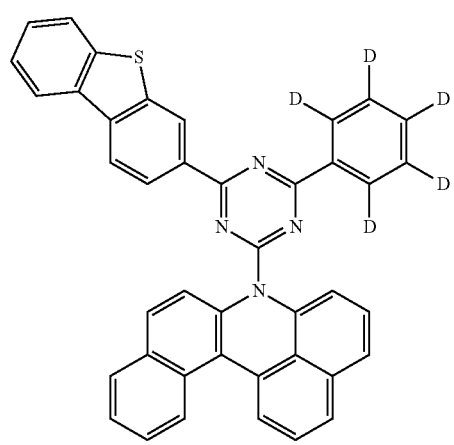
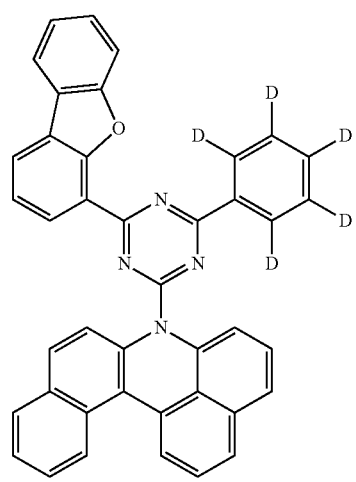
108
-continued
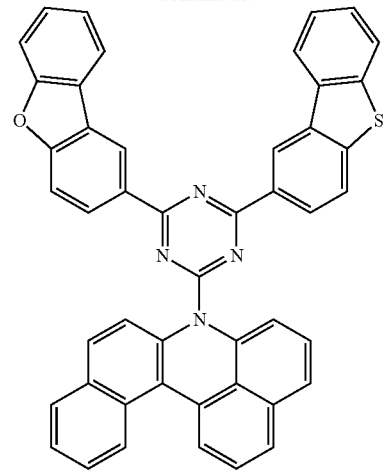
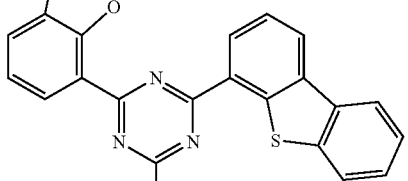
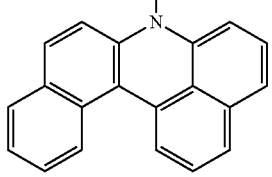
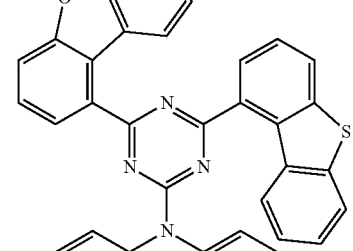
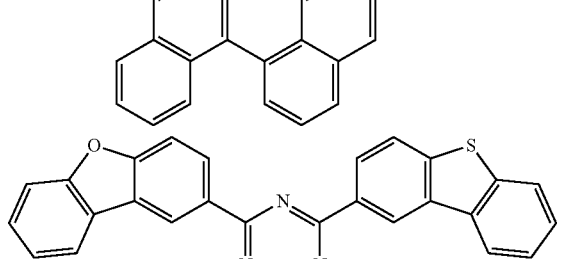
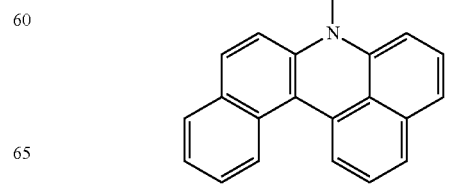

109
-continued
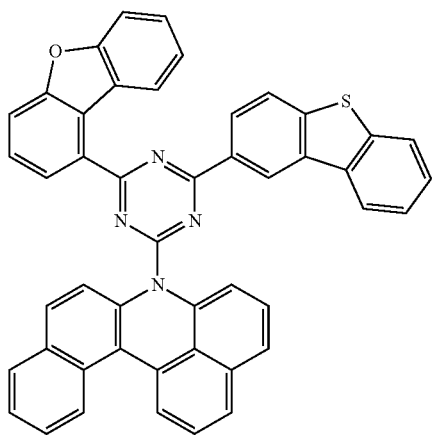
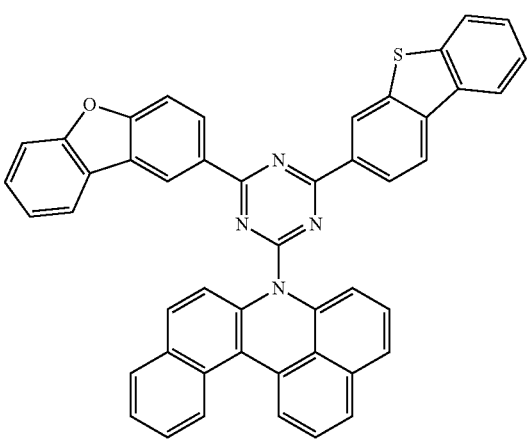
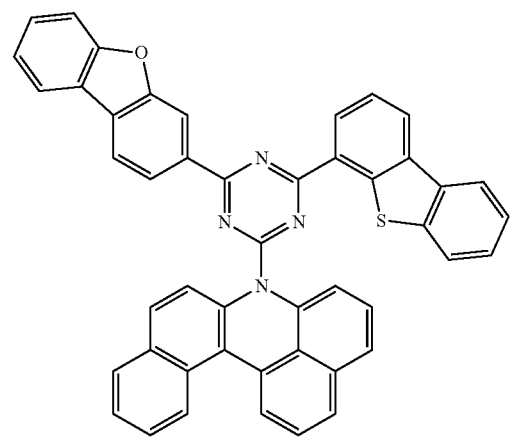
110
-continued
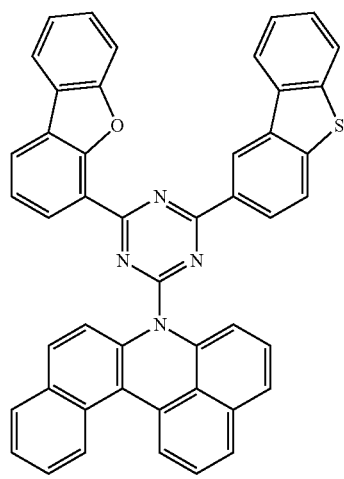

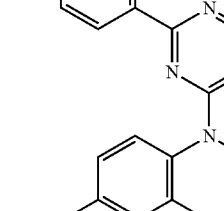

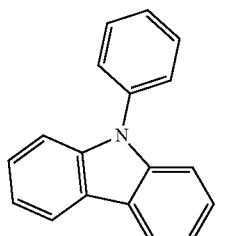
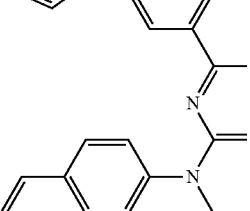

111
-continued
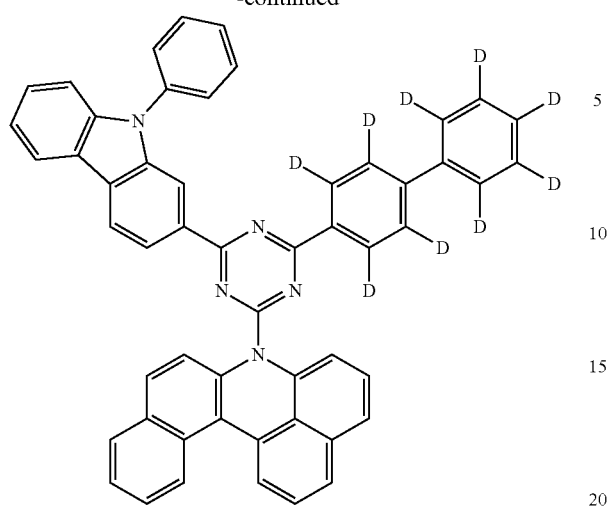
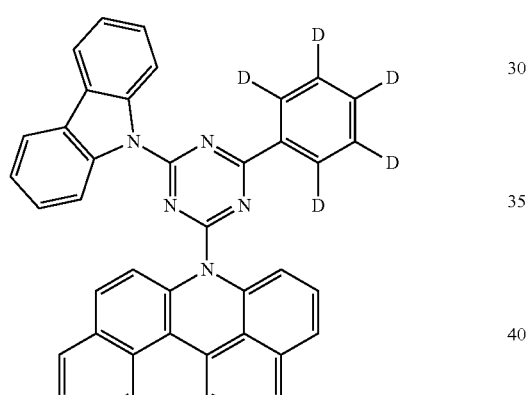
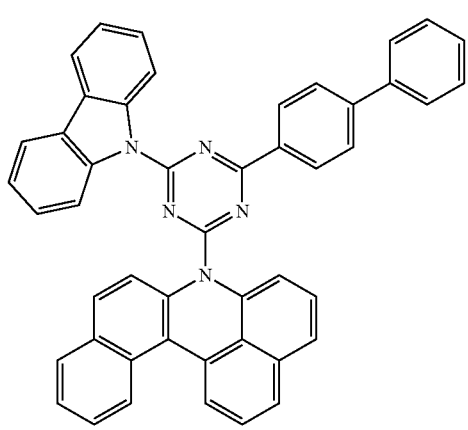
112
-continued
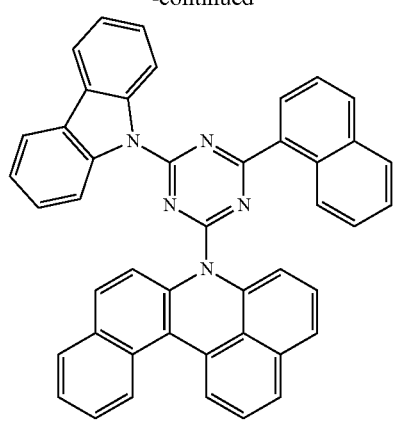
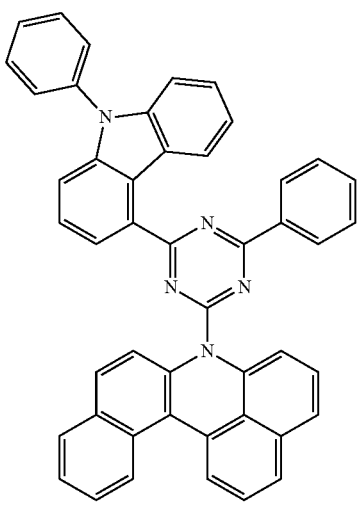
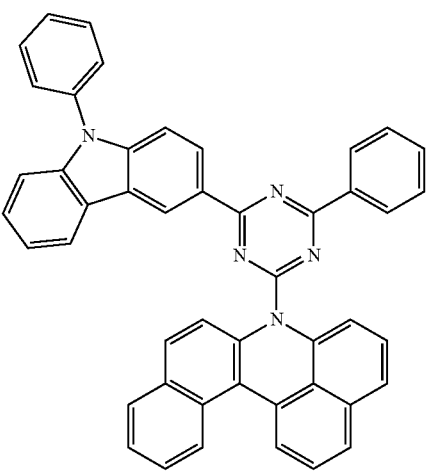

113
-continued
114
-continued
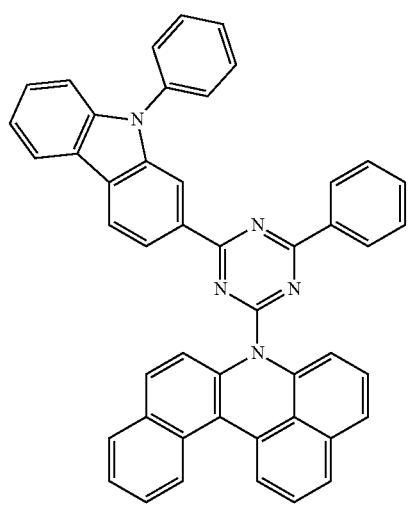
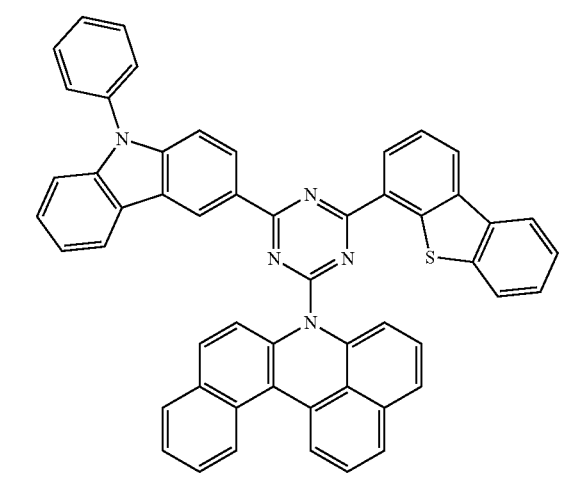
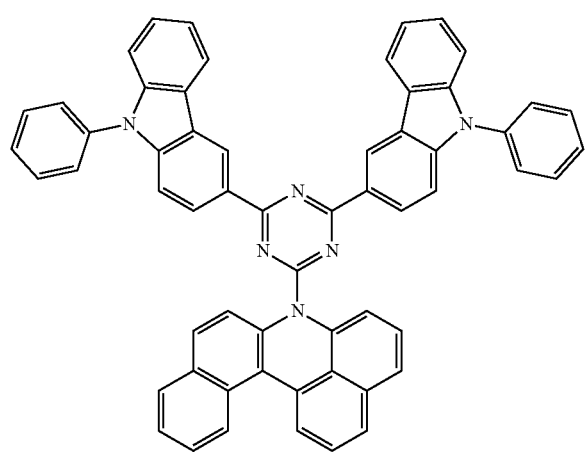
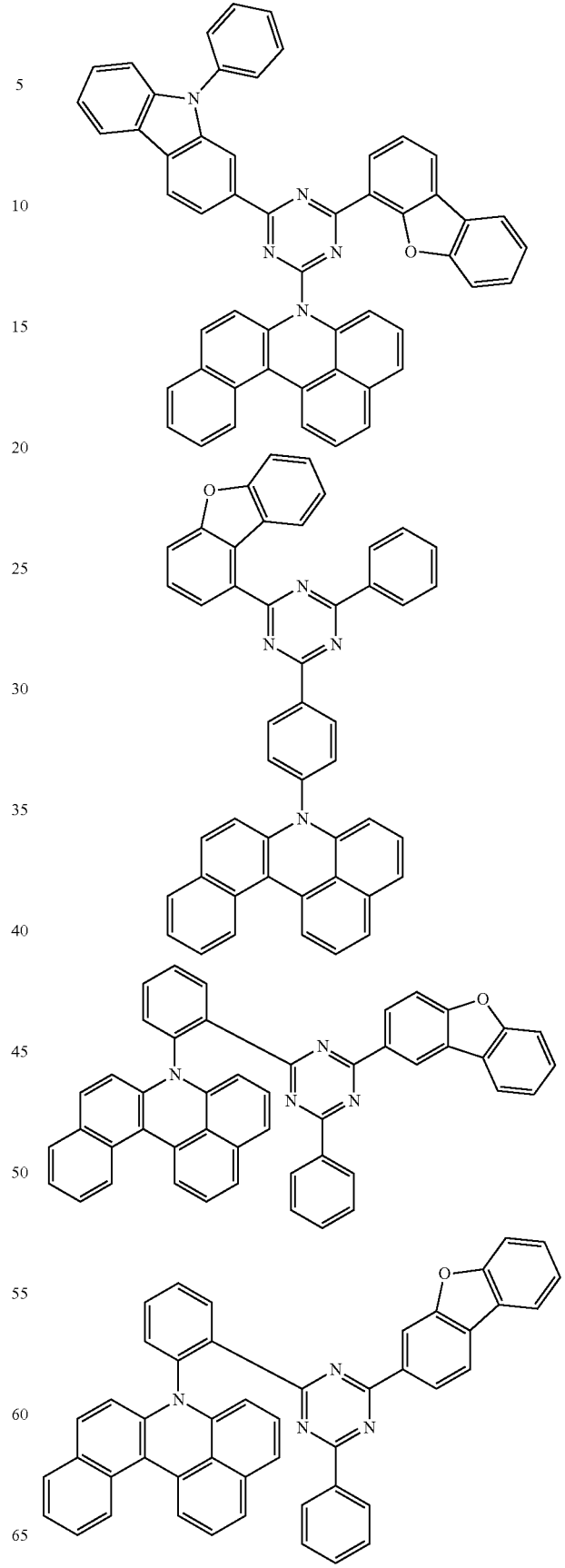

115
-continued
116
-continued
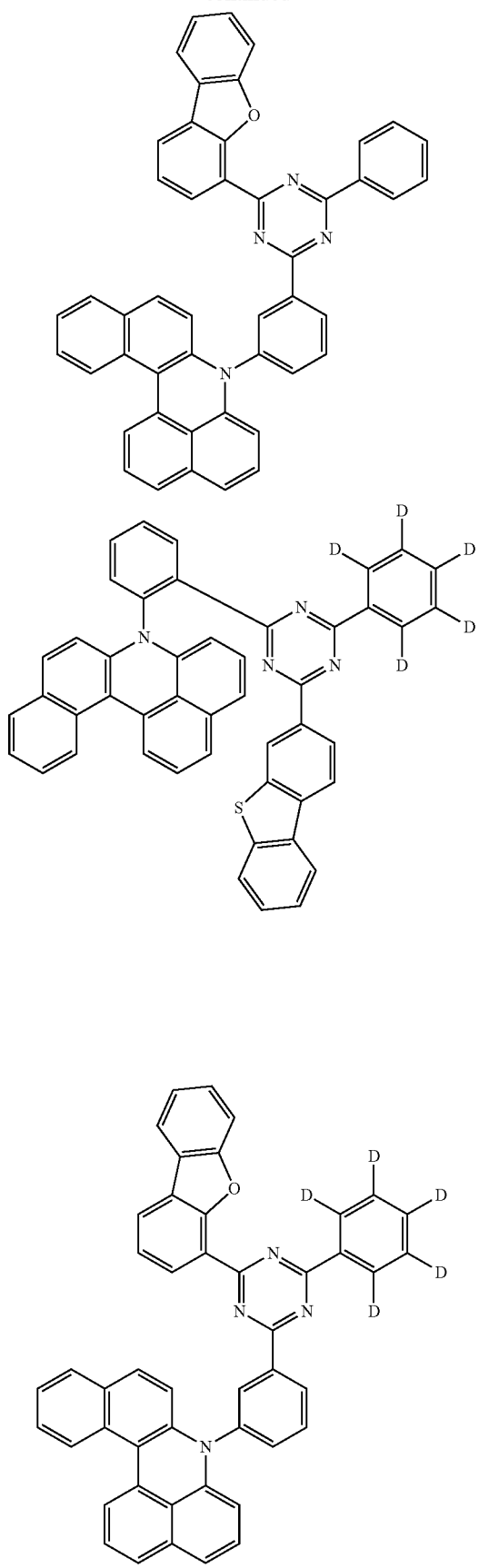
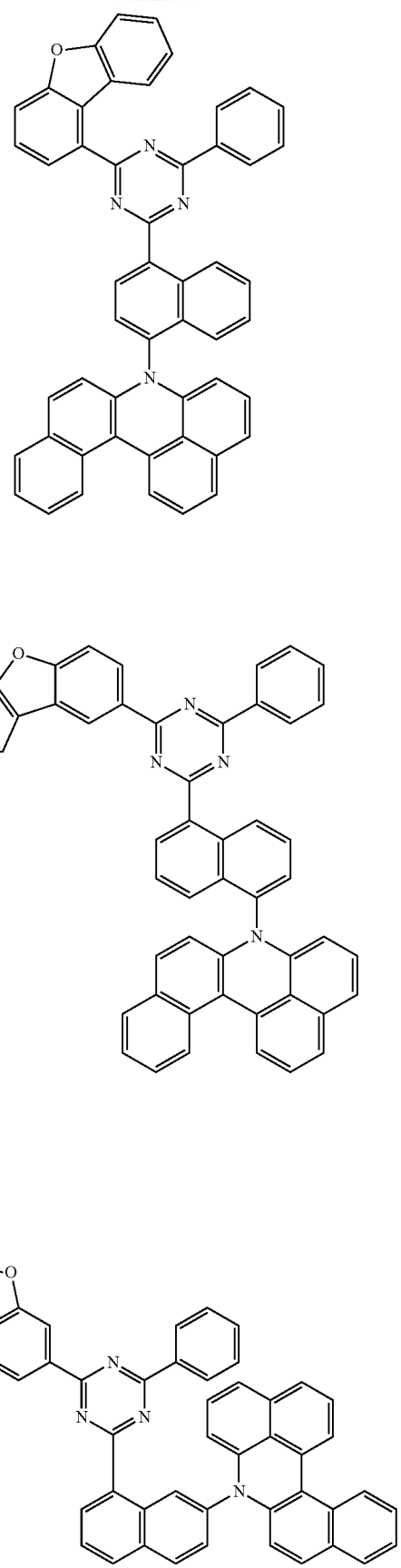

117
-continued
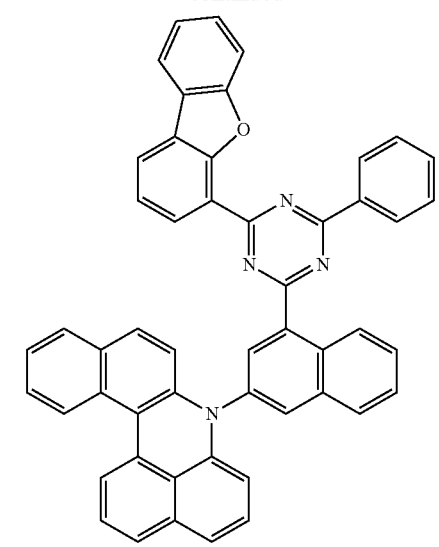
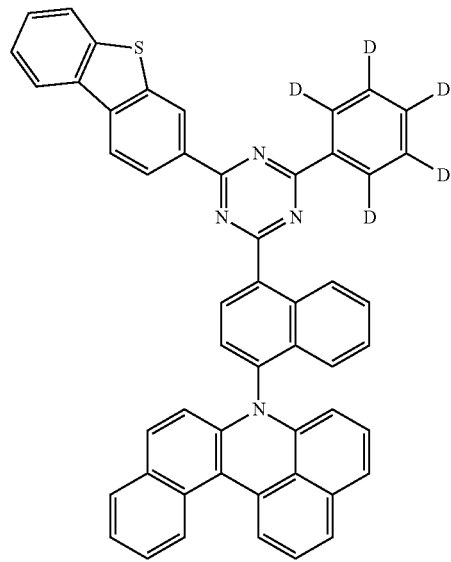
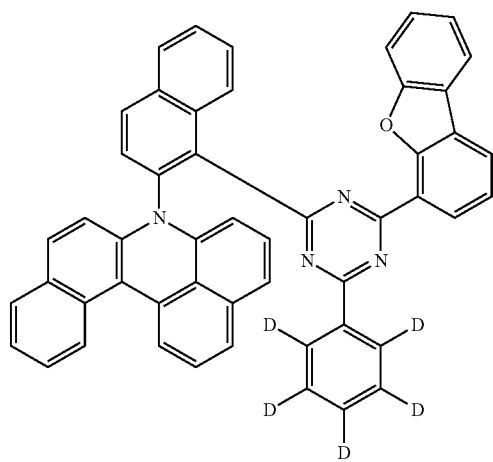
118
-continued
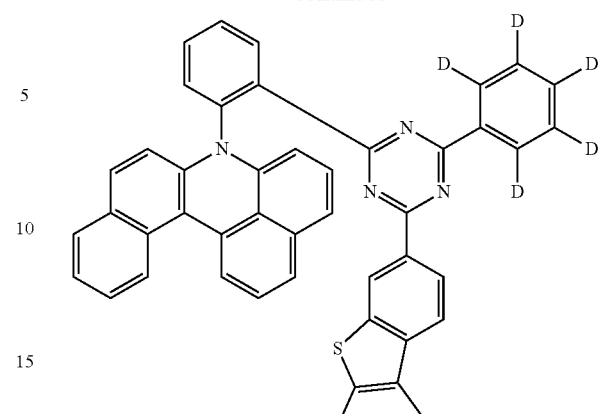
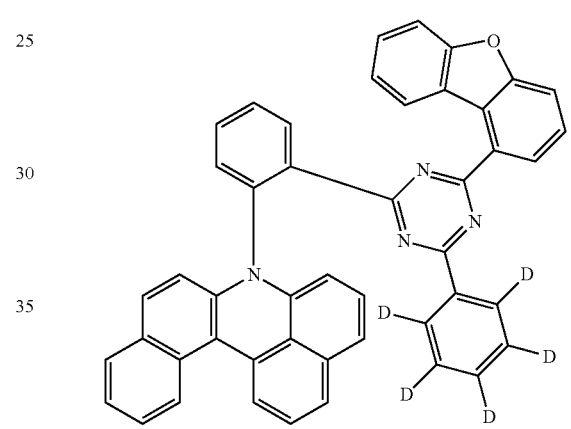
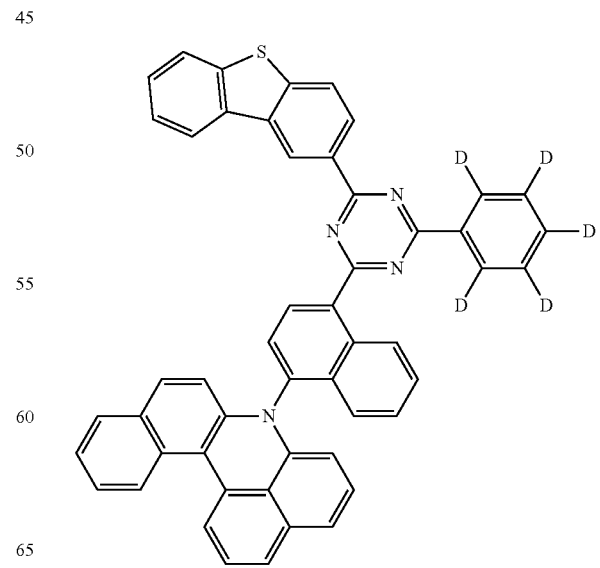

119
-continued
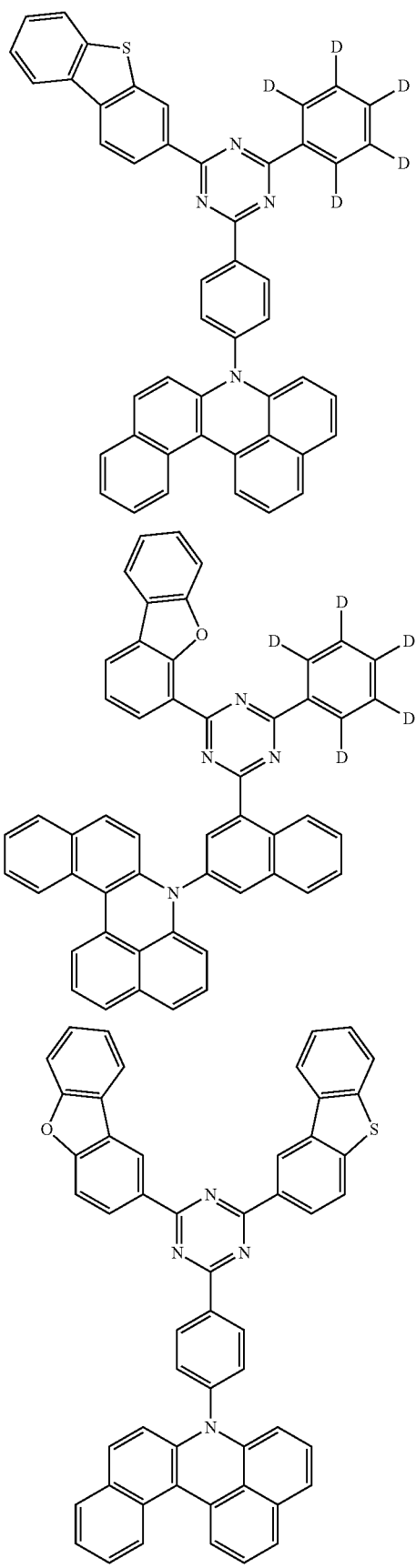
120
-continued
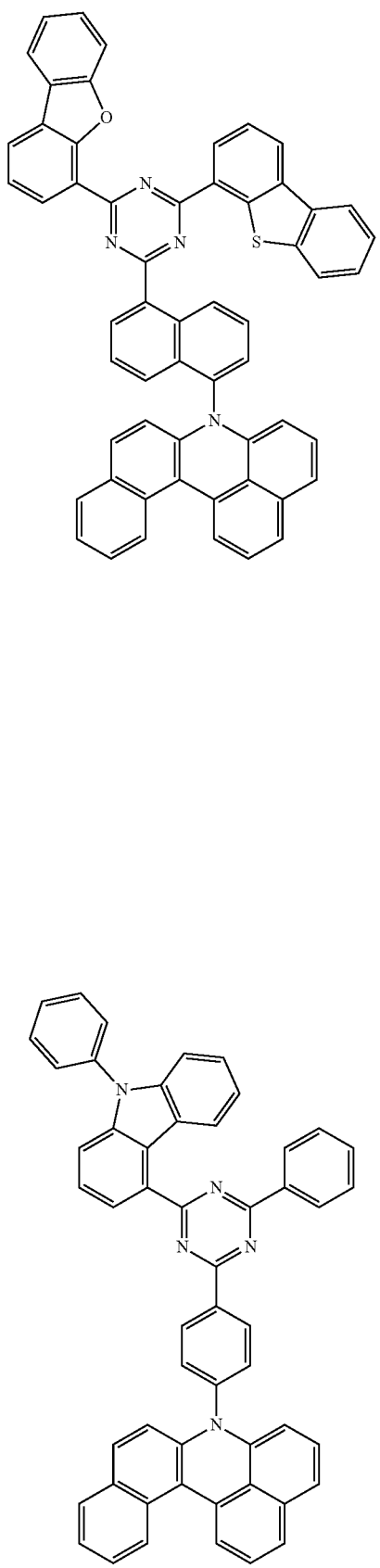

121
-continued
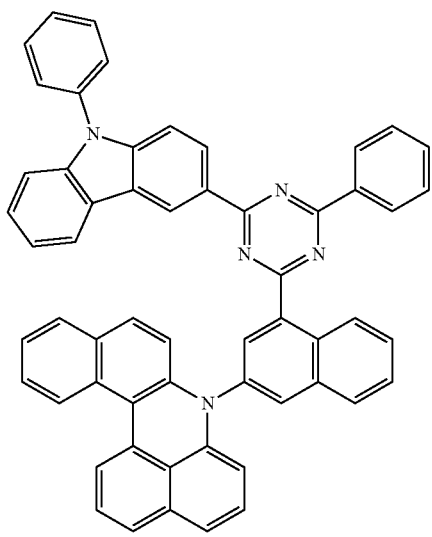
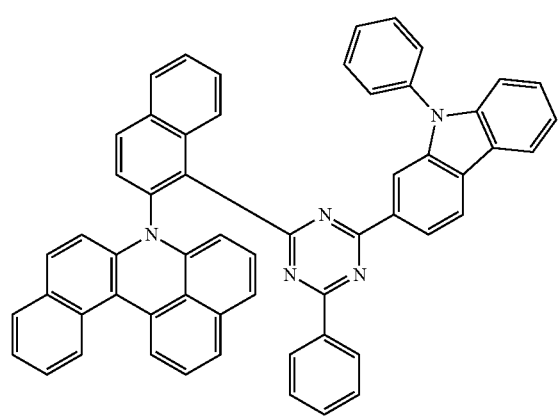
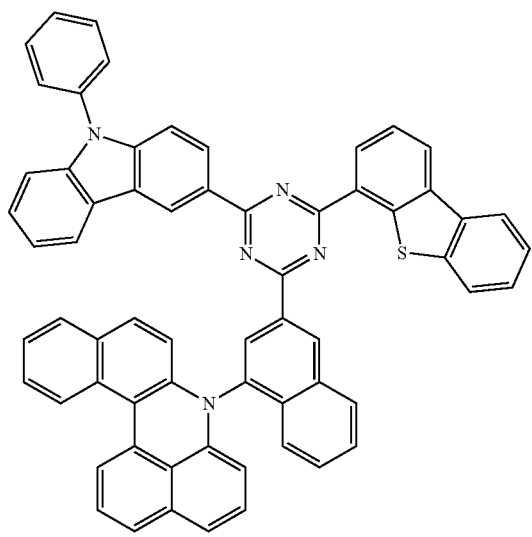 [SMILES: c1ccc(-n2c3ccccc3c3cc(-c4nc(-c5cc(N6c7ccc8ccccc8c7-c7cccc8cccc6c78)c6ccccc6c5)nc(-c5cccc6c5sc5ccccc56)n4)ccc32)cc1]
122
-continued
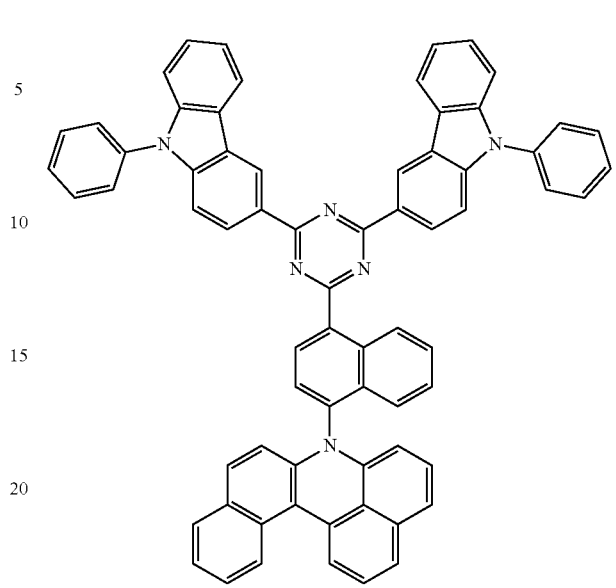
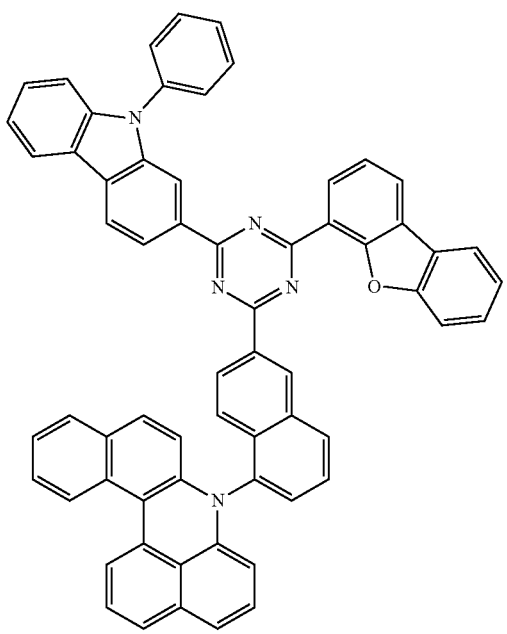

123
-continued
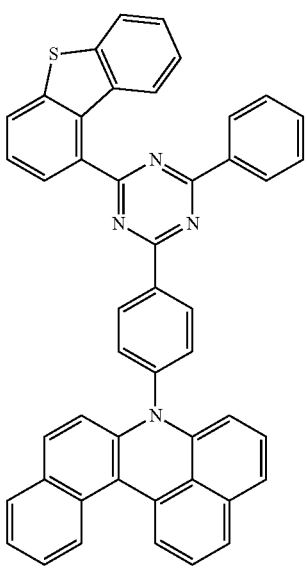
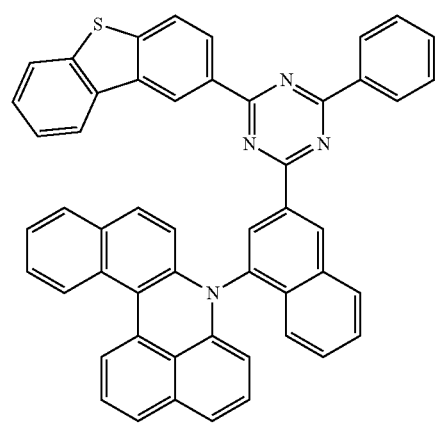
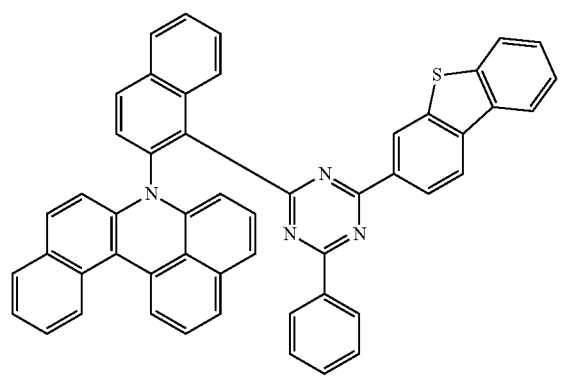
124
-continued
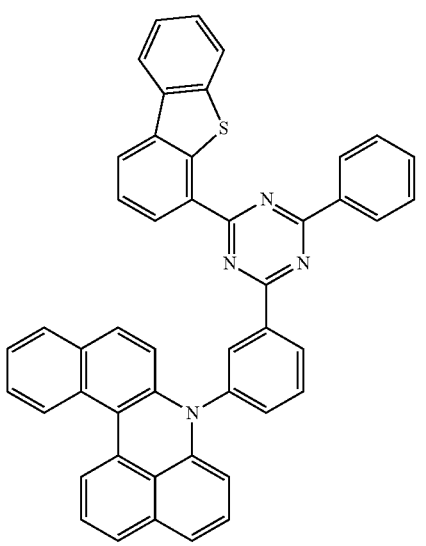
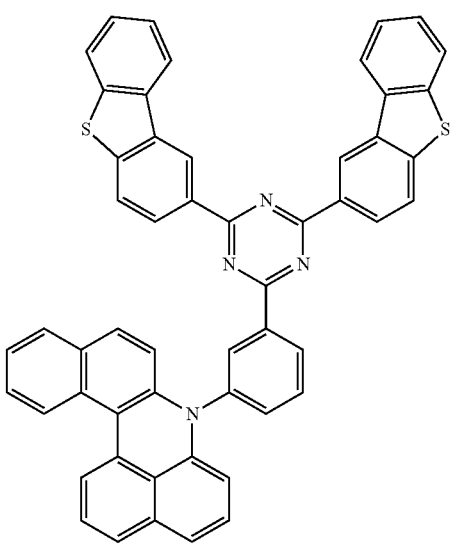
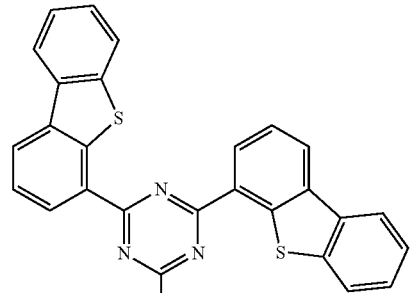

125
-continued
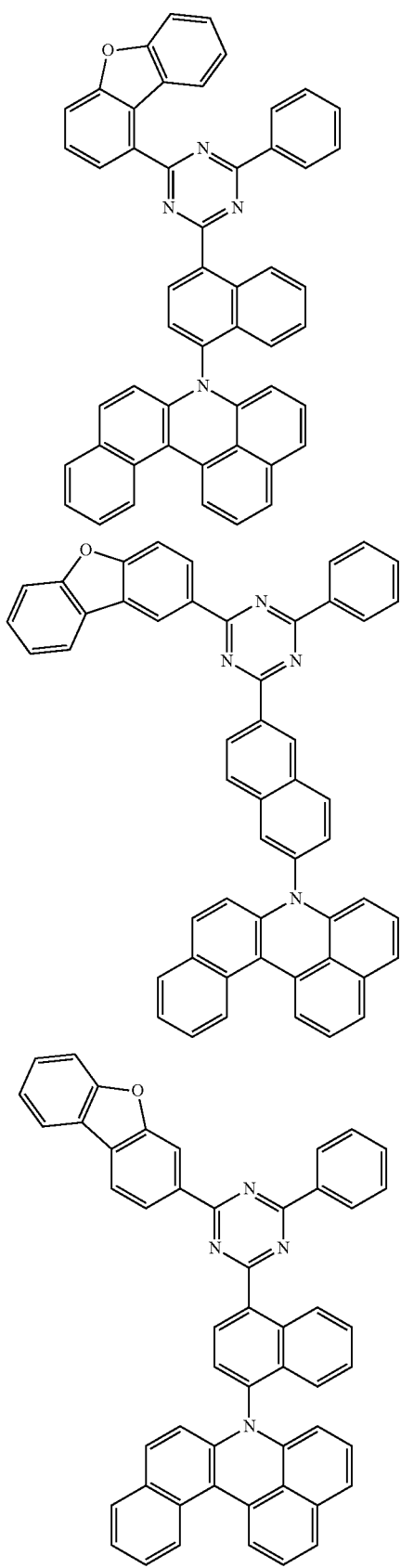
126
-continued
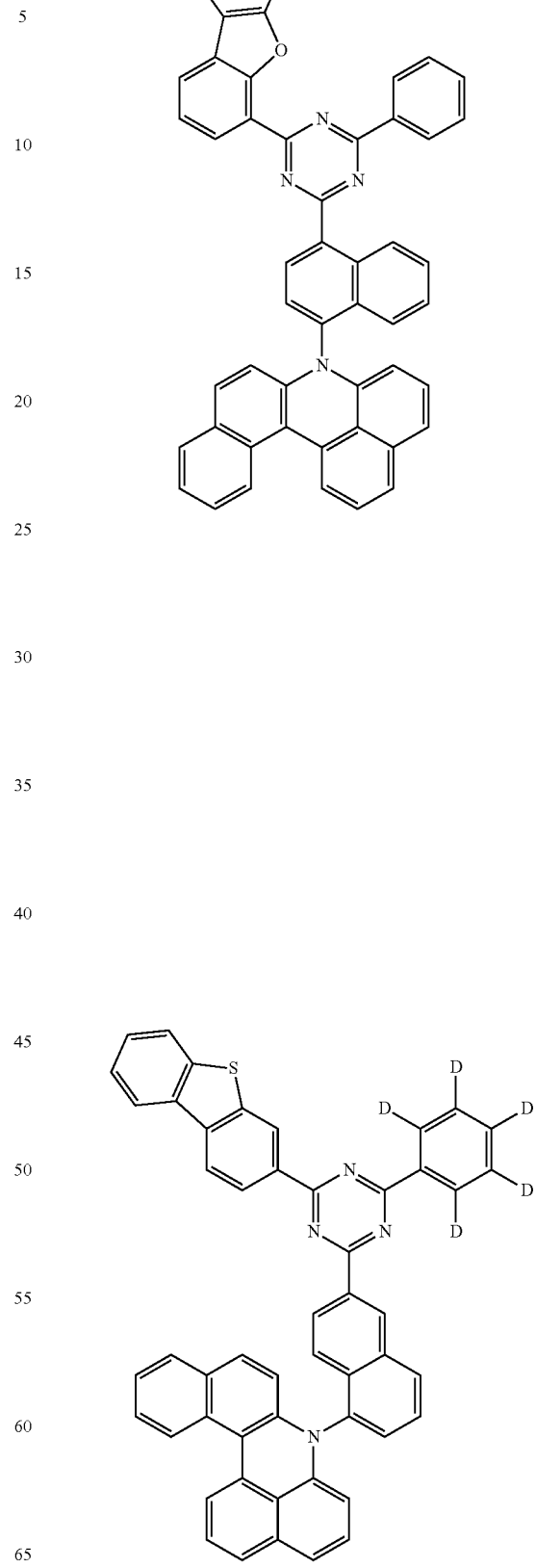

127
-continued
128
-continued
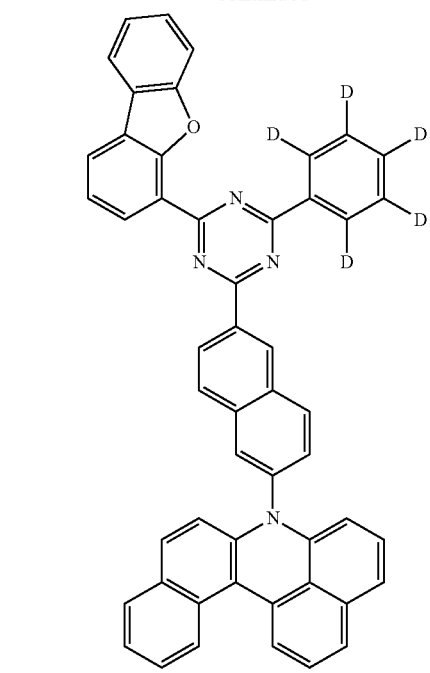
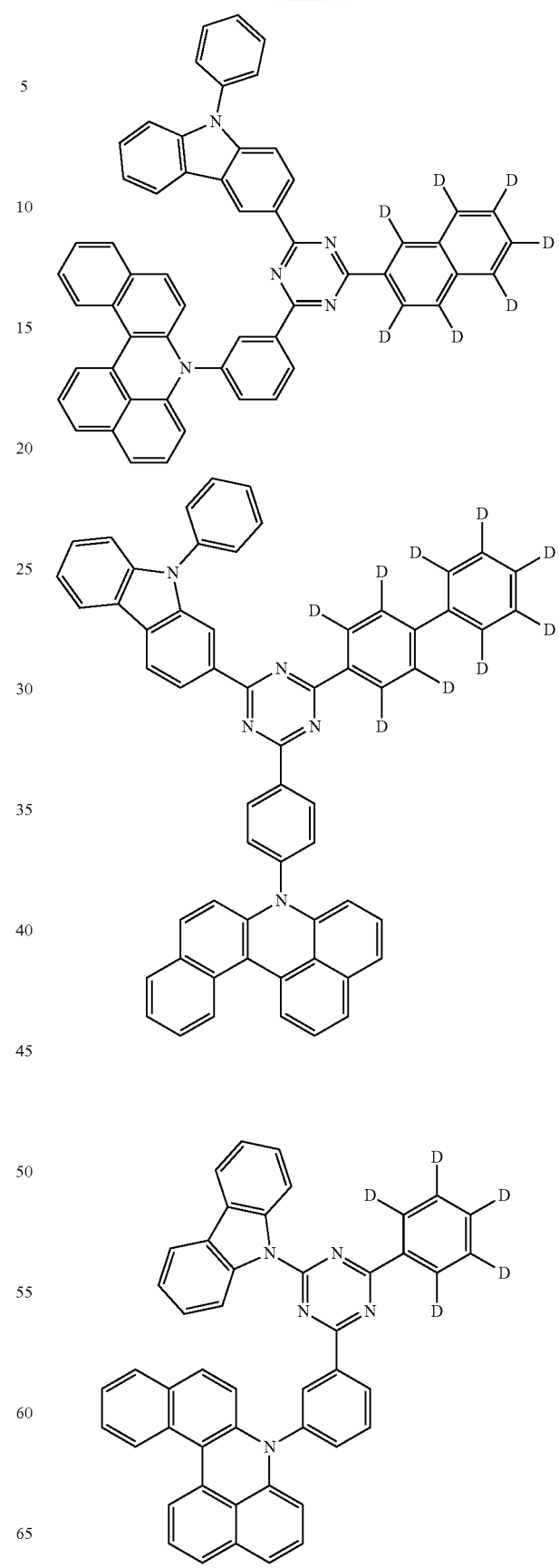

129
-continued
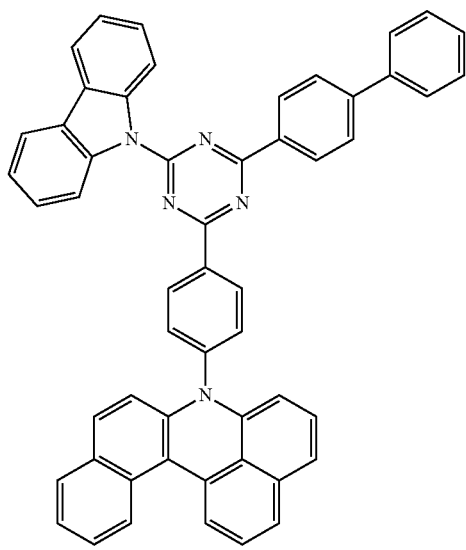
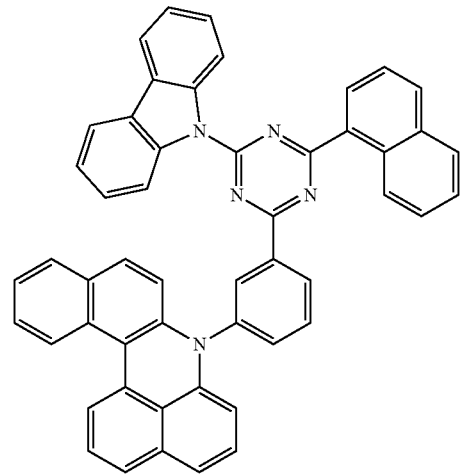
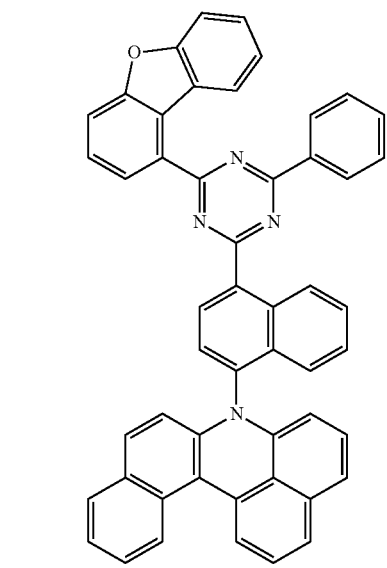
130
-continued
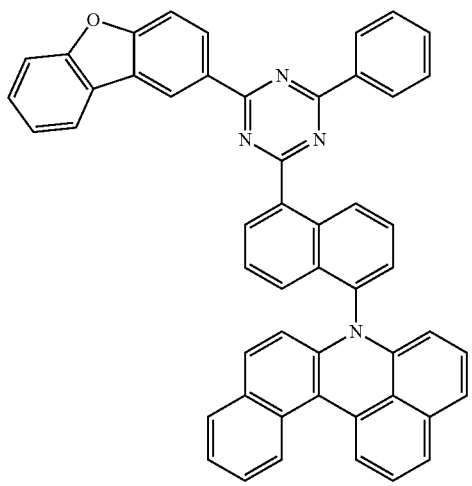
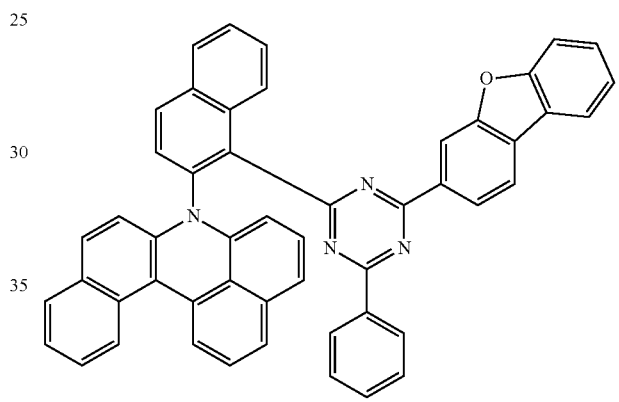
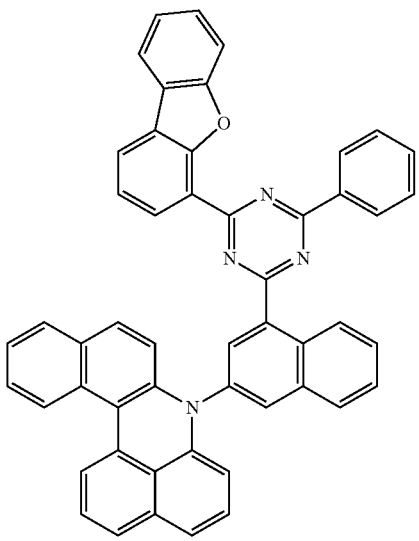

131
-continued
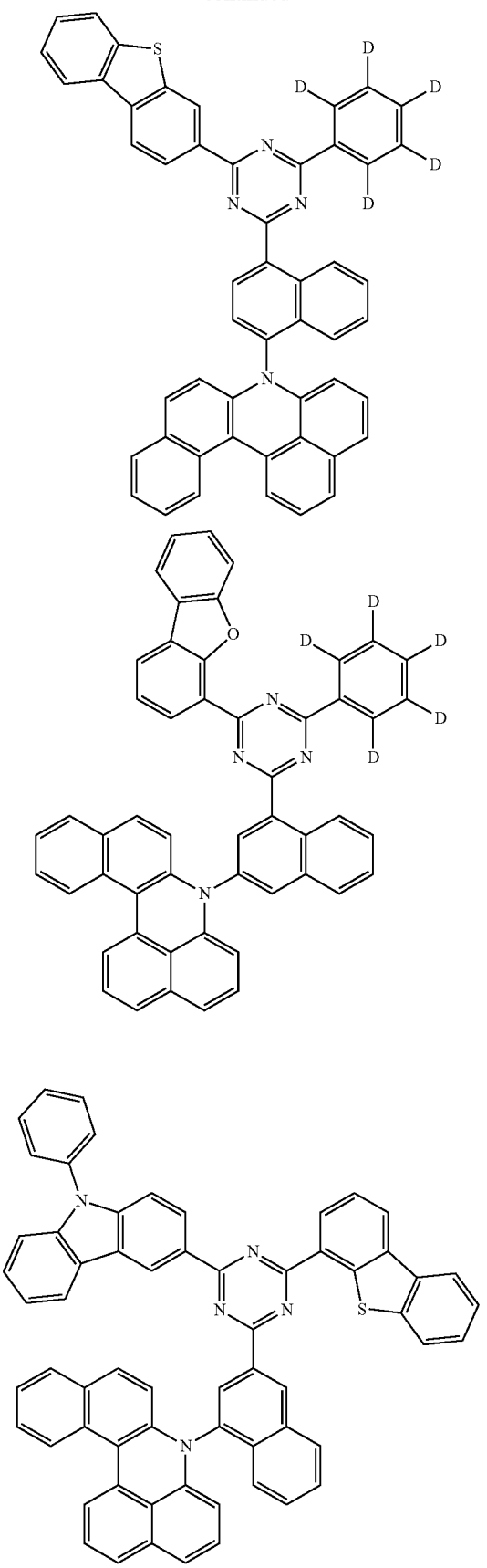
132
-continued
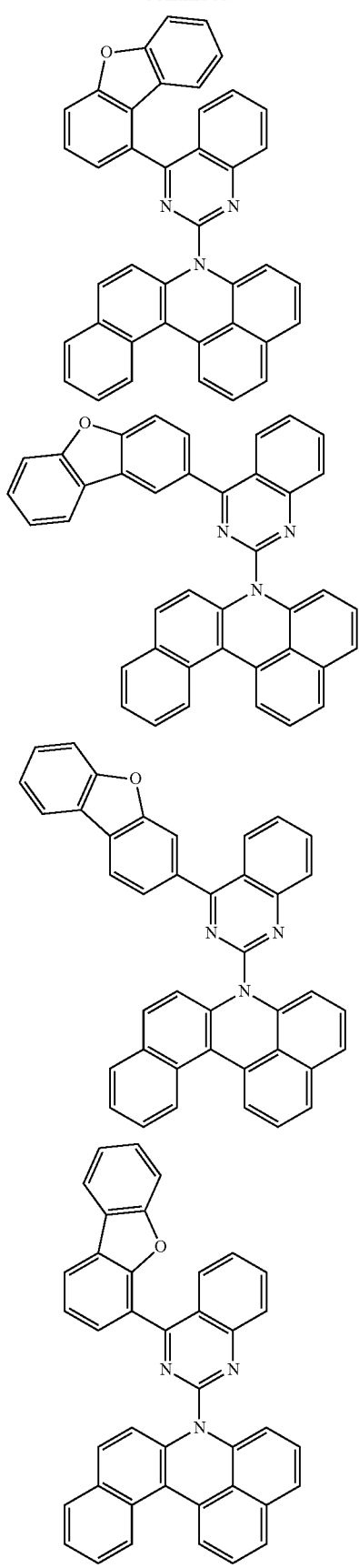

133
-continued
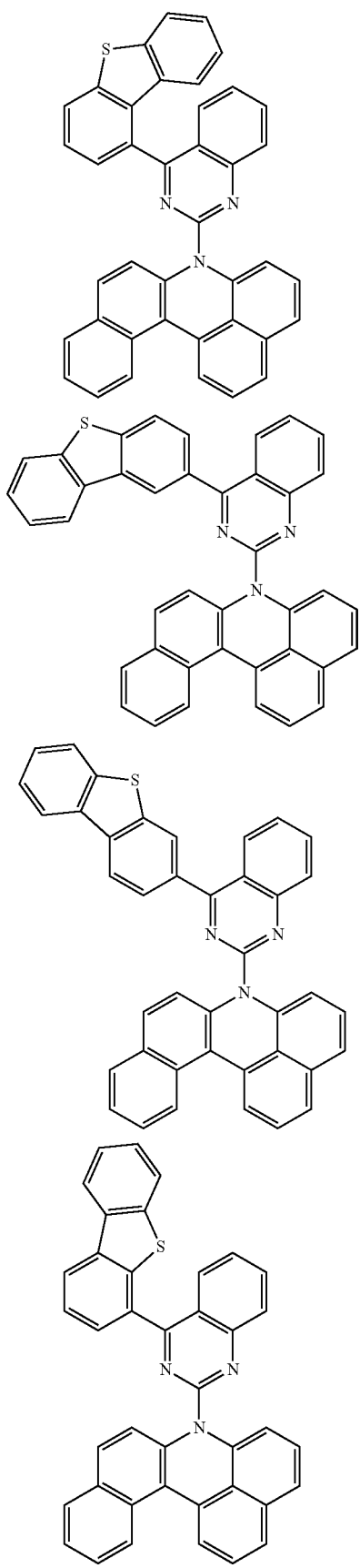
134
-continued
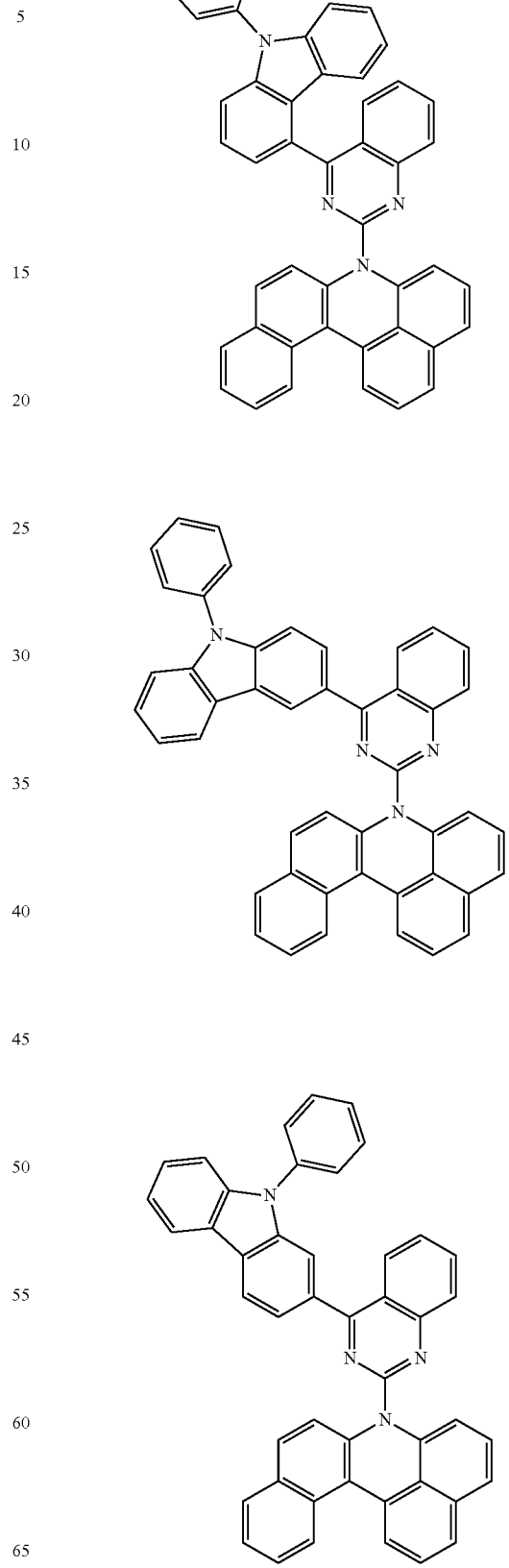

US 11,812,658 B2
135
-continued
136
-continued
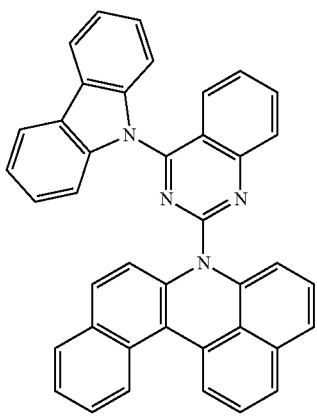
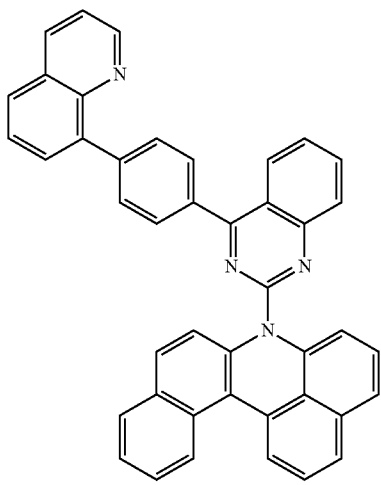
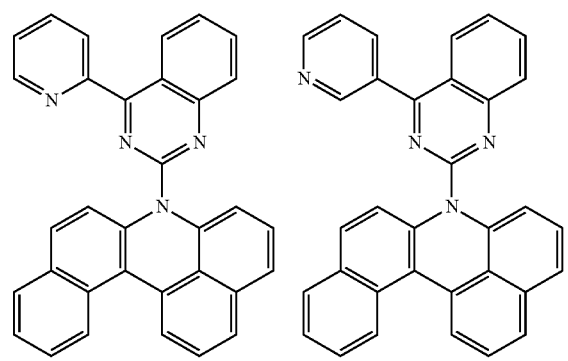
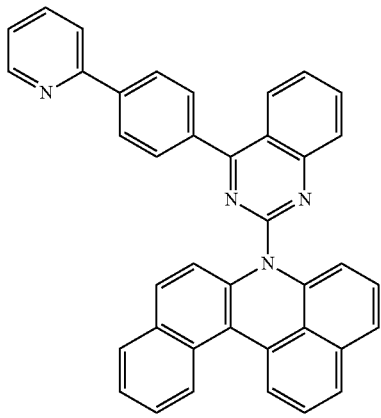
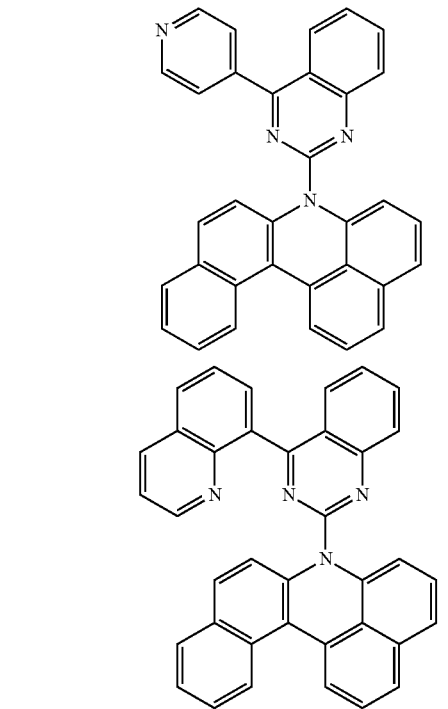
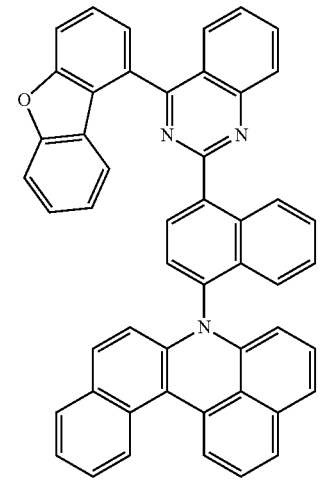

137
-continued
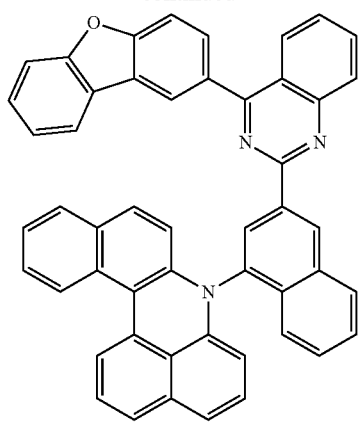
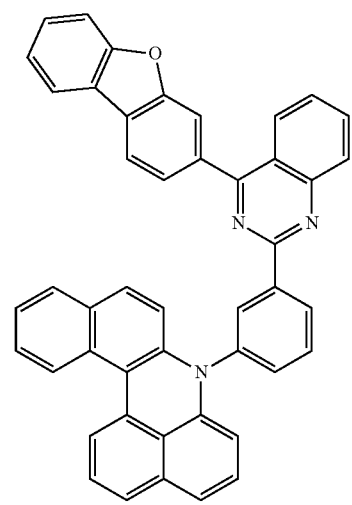
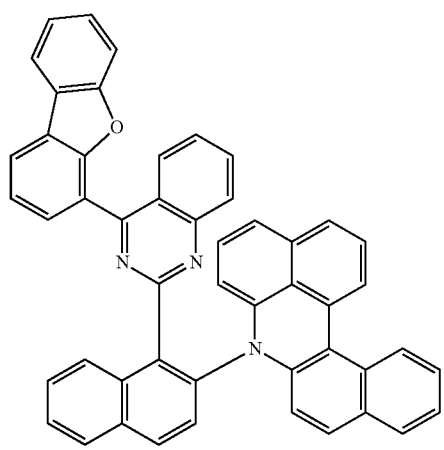
138
-continued
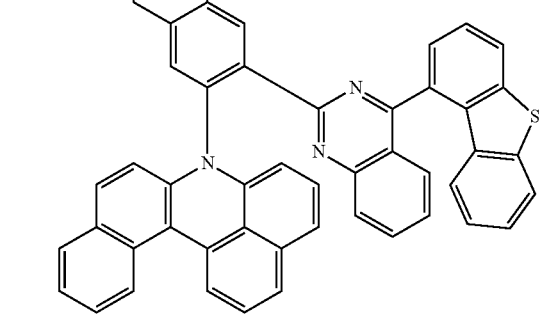
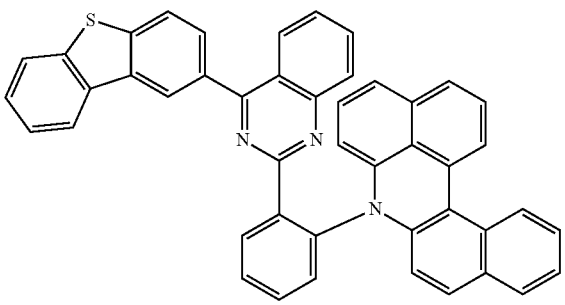
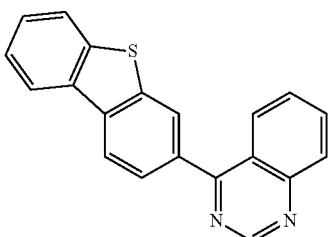
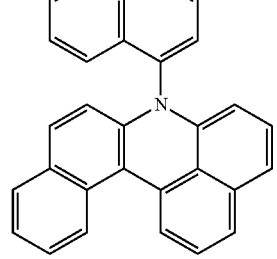

139
-continued
140
-continued
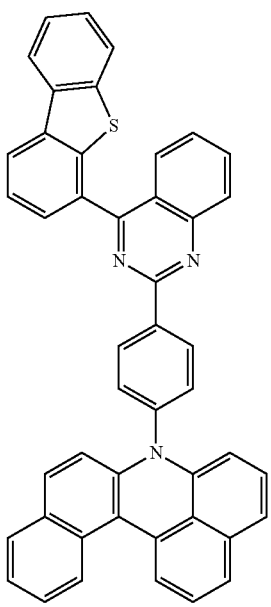
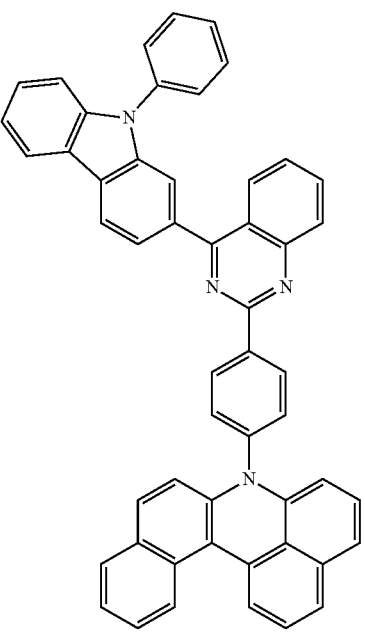

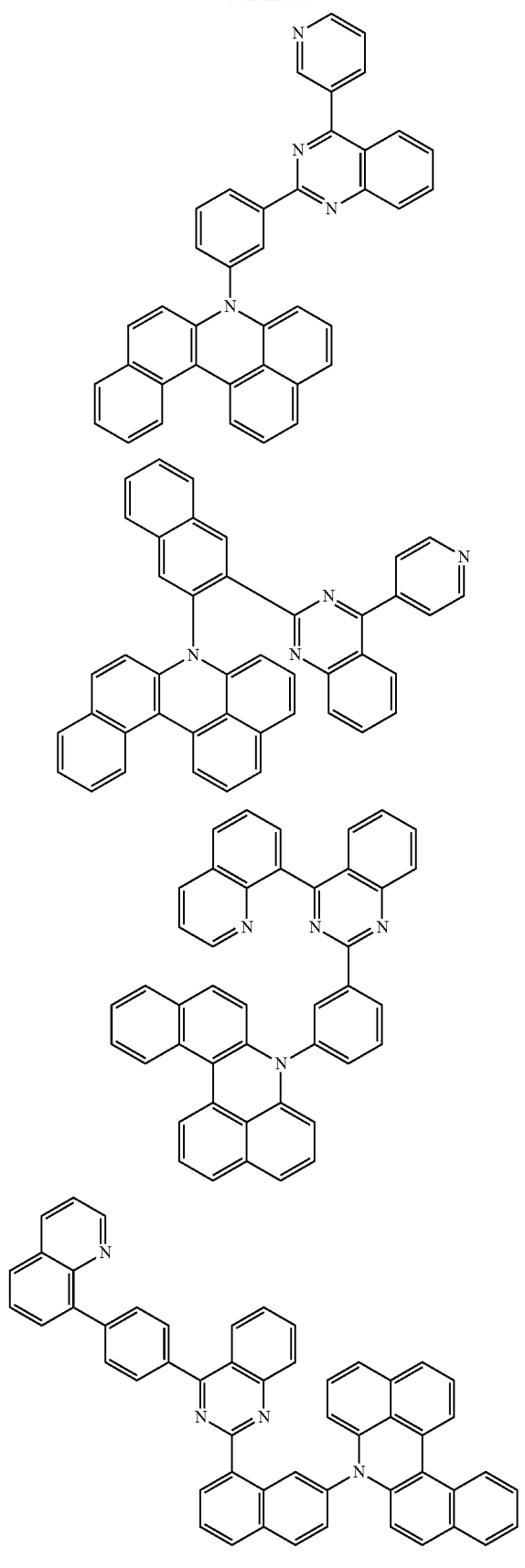
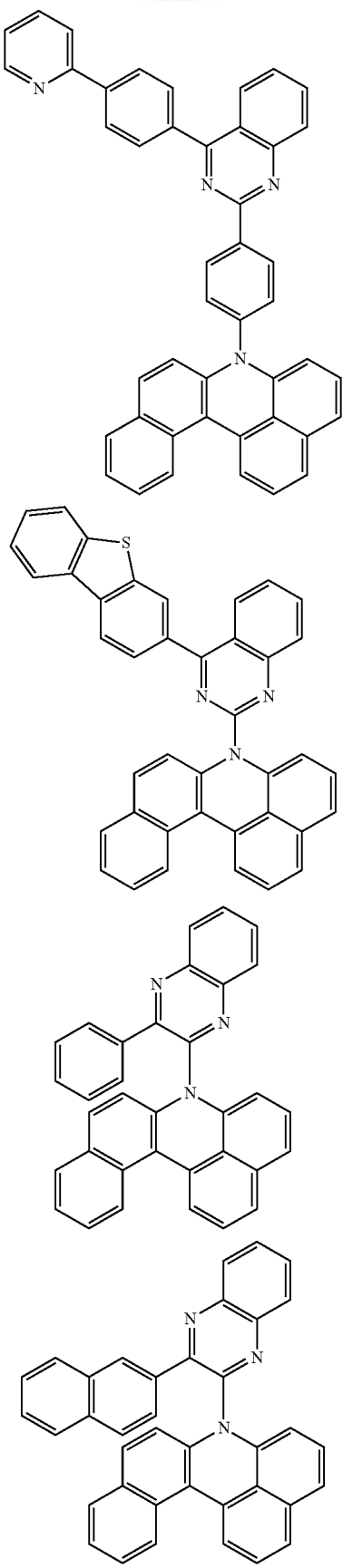

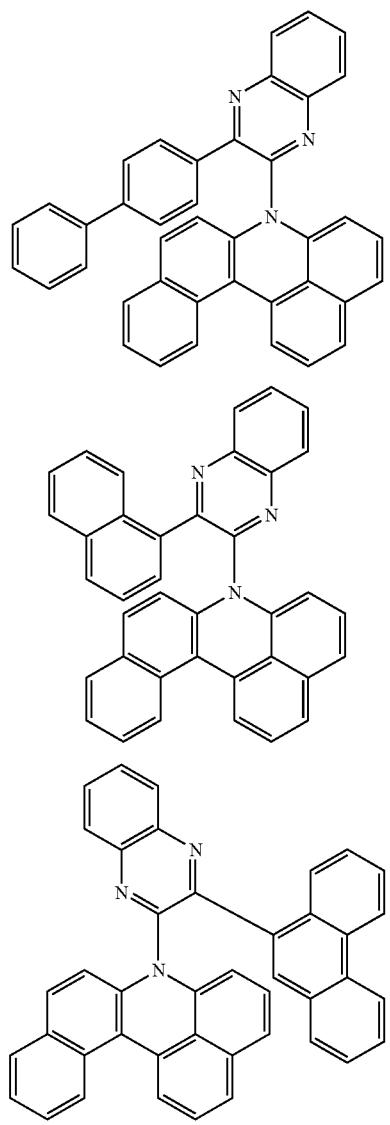
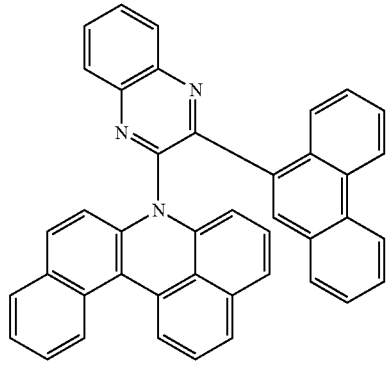
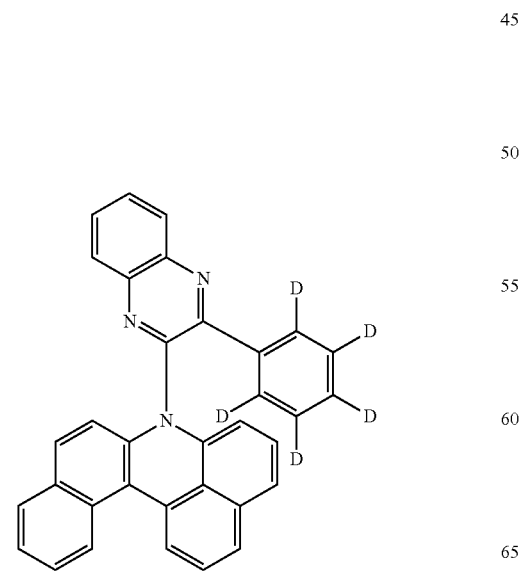
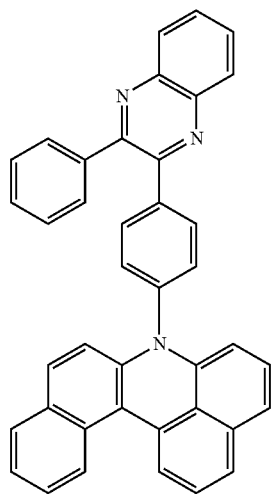
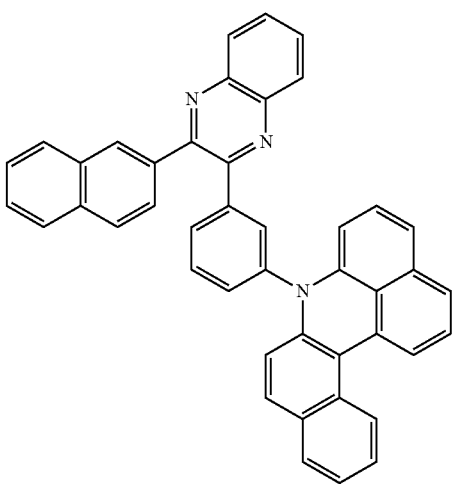
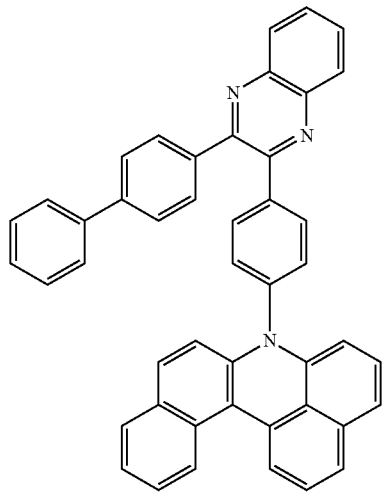

145
-continued
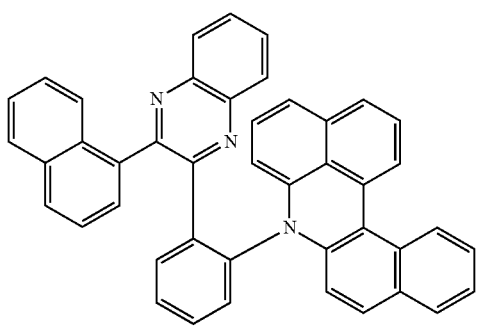
146
-continued
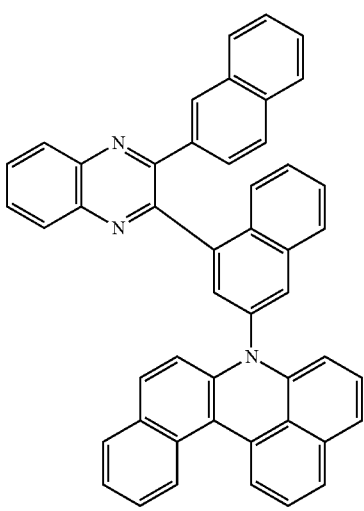
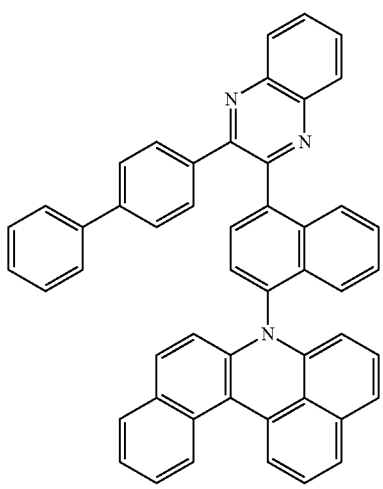
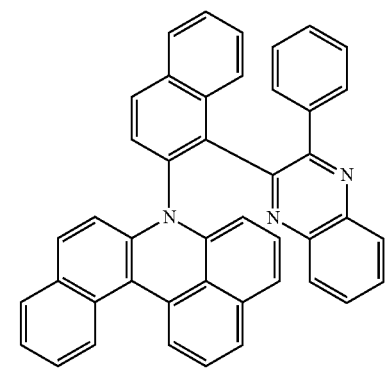
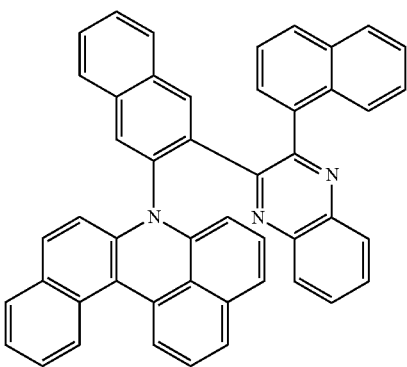

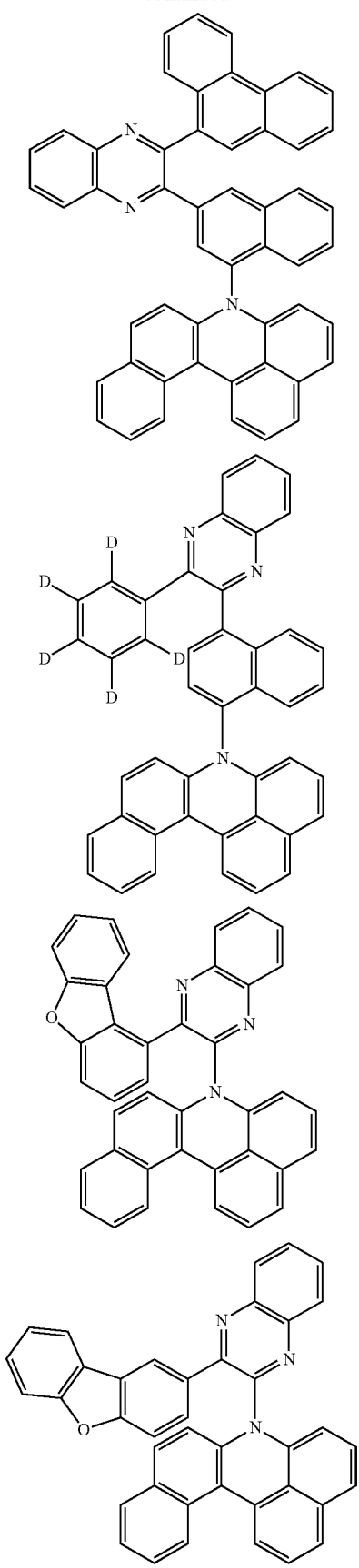
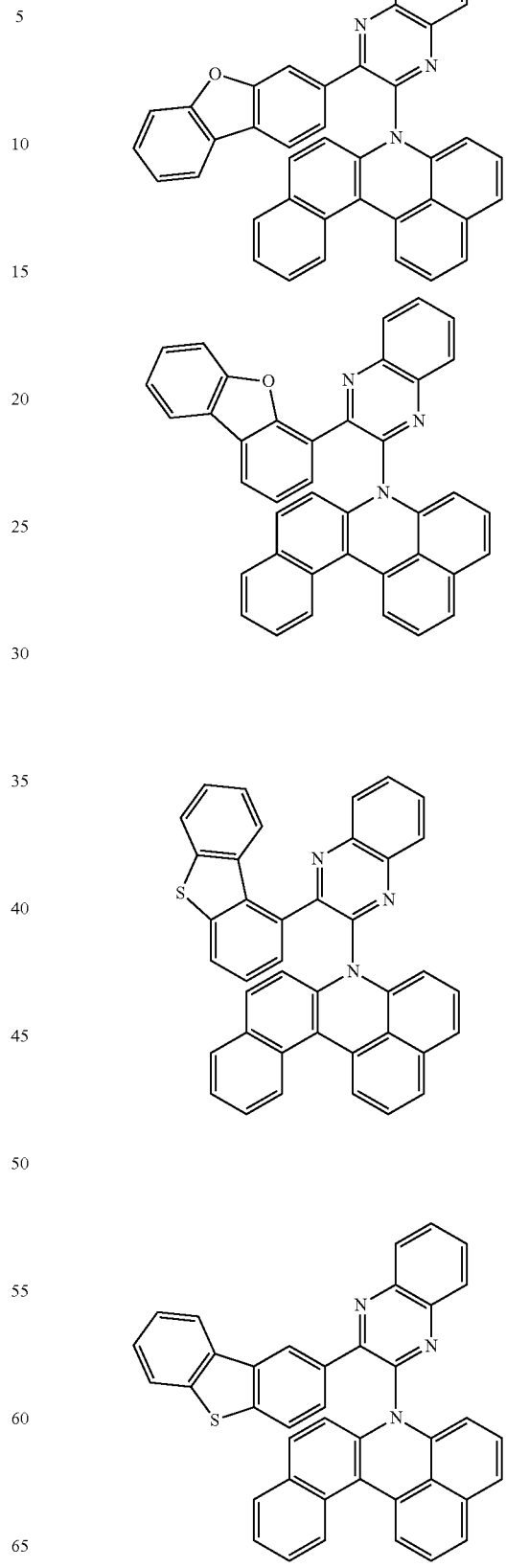

149
-continued
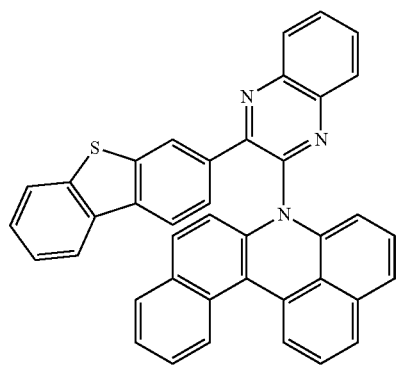
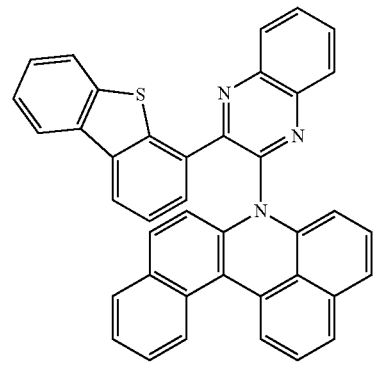
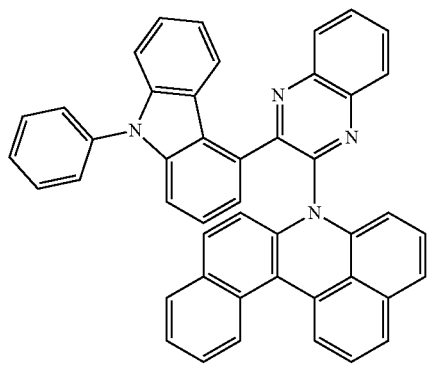
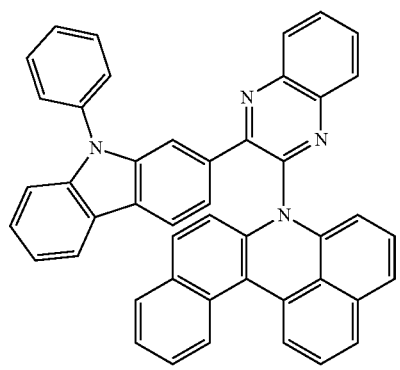
150
-continued
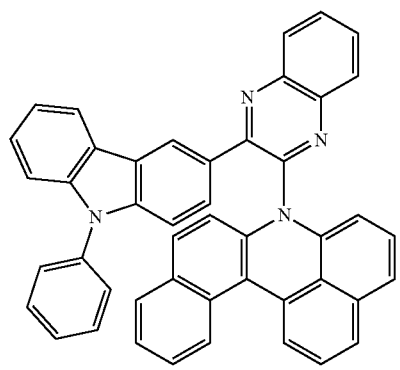
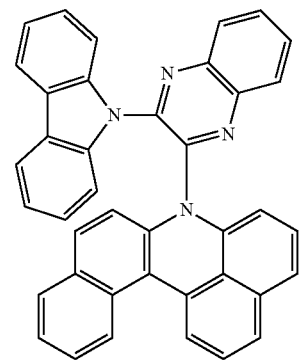
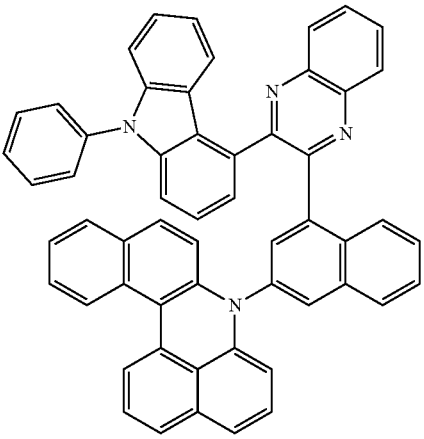
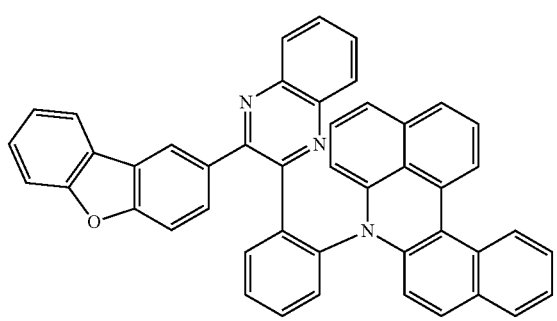

151
-continued
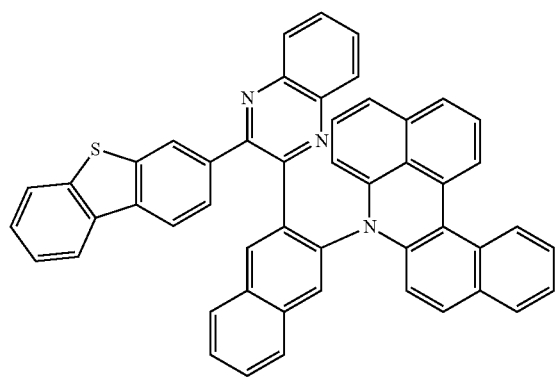
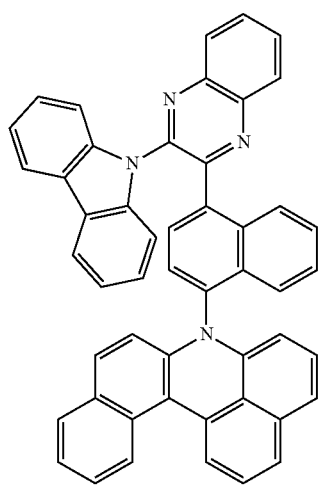
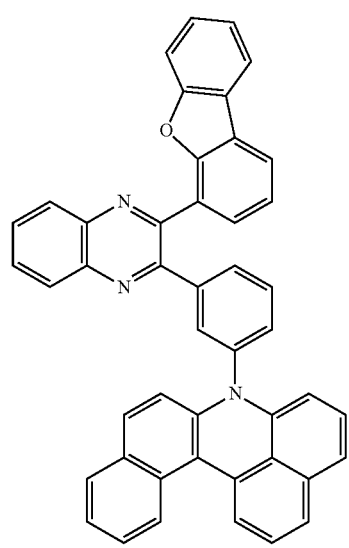
152
-continued
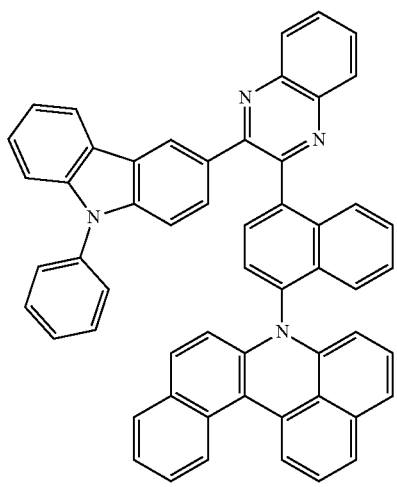
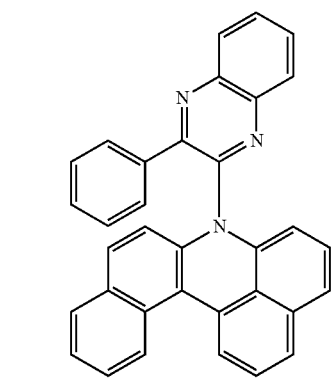
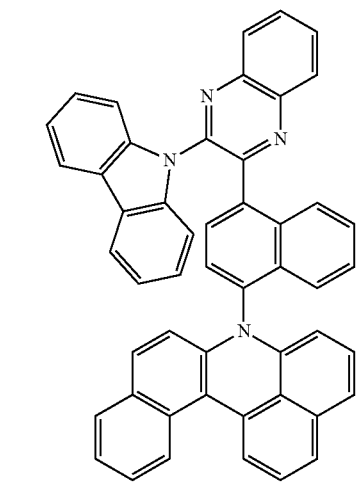

153
-continued
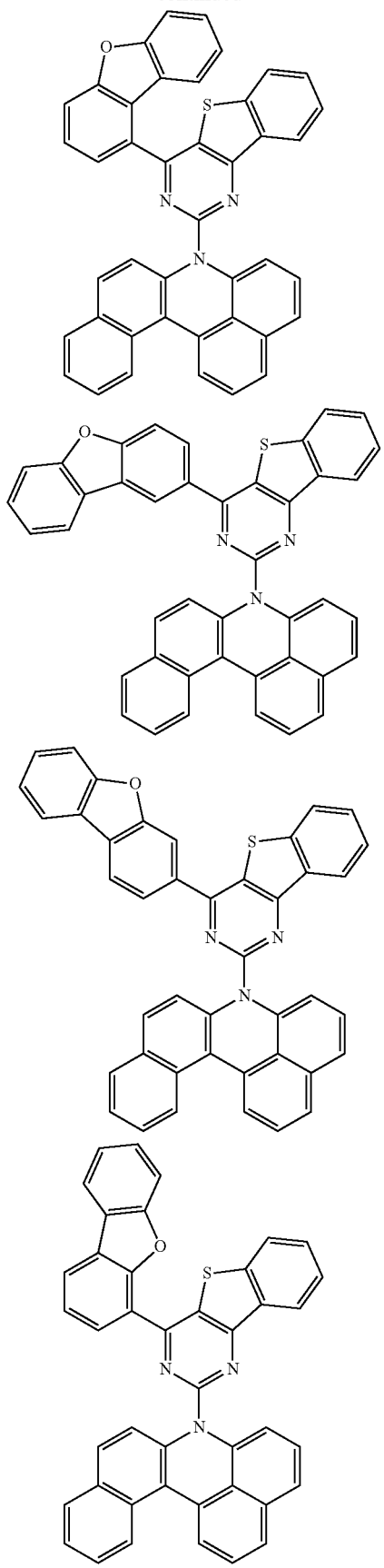
154
-continued
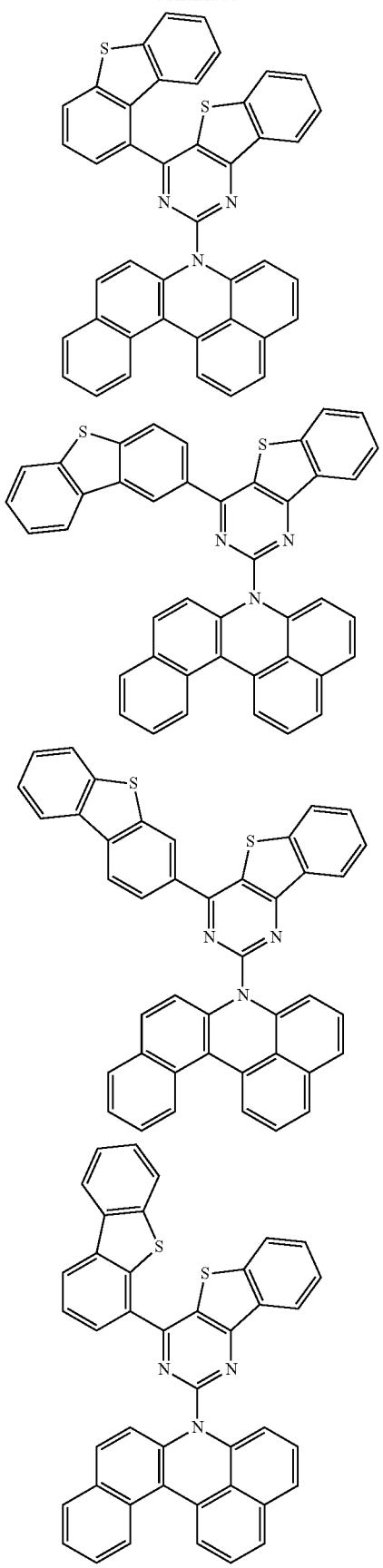

155
-continued

156
-continued

157
-continued
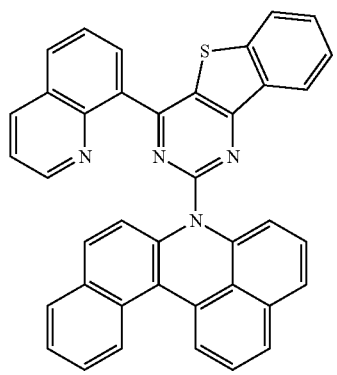
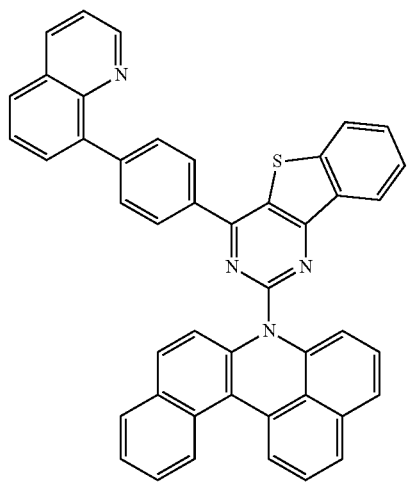
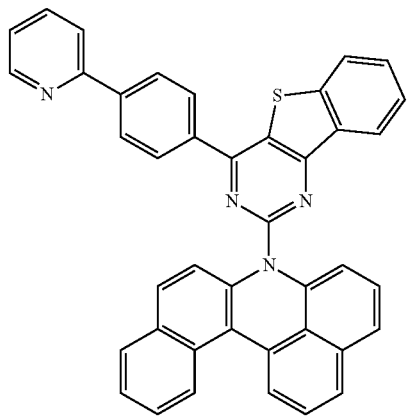
158
-continued
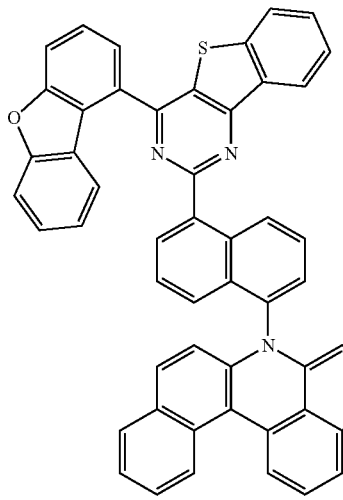
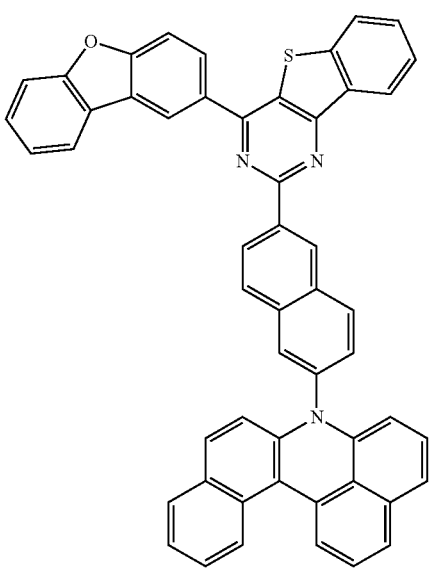
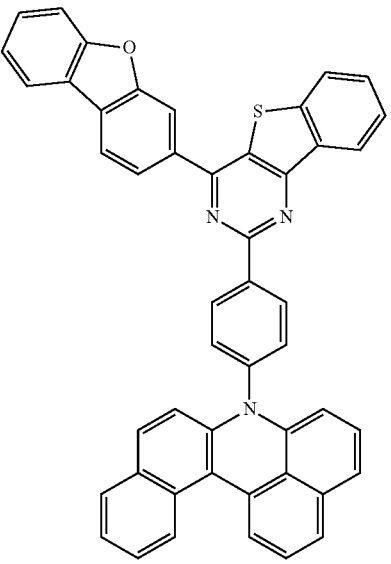

159
-continued
160
-continued
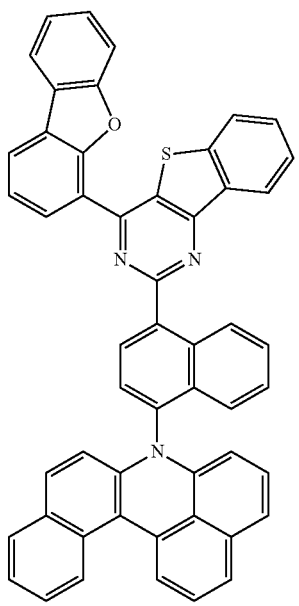
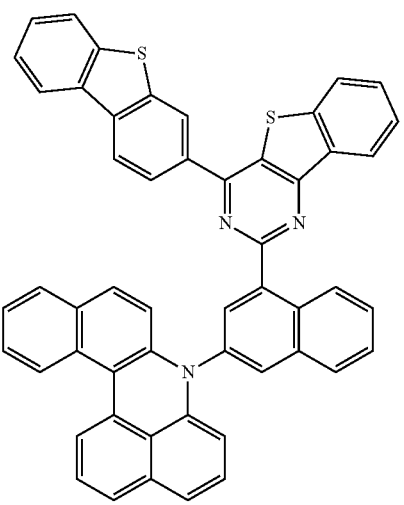 [SMILES: c1ccc2c(-c3nc(-c4ccc5c(c4)sc4ccccc45)c4sc5ccccc5c4n3)cc(N3c4ccc5ccccc5c4-c4cccc5cccc3c45)cc2c1]
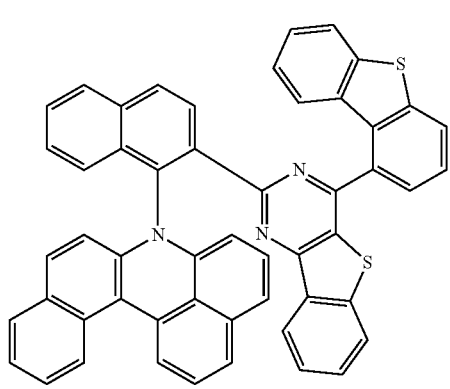
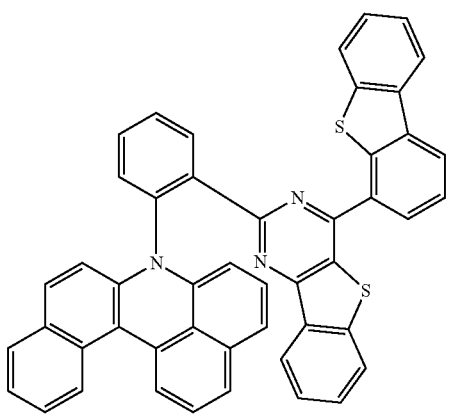
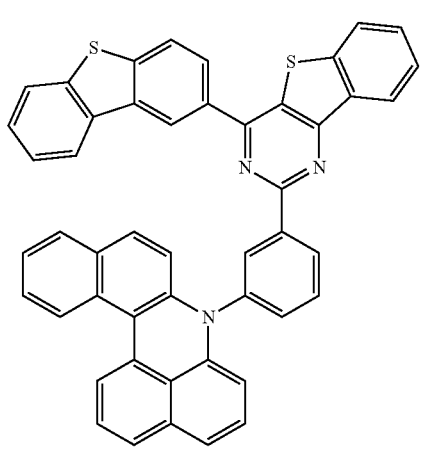
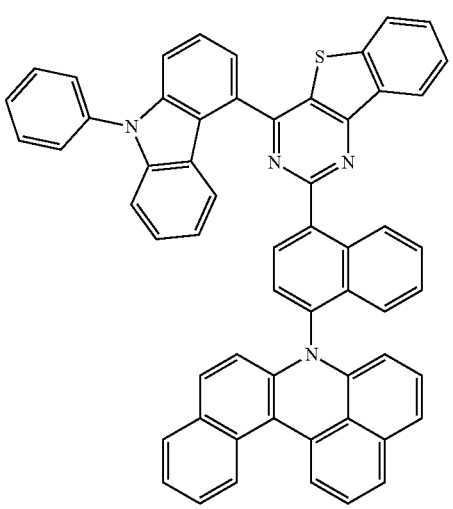

161
-continued
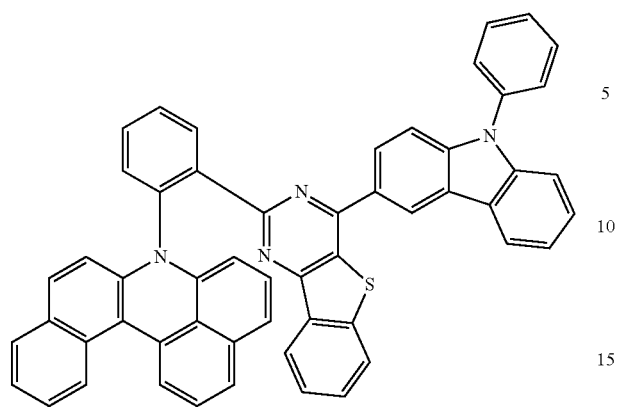
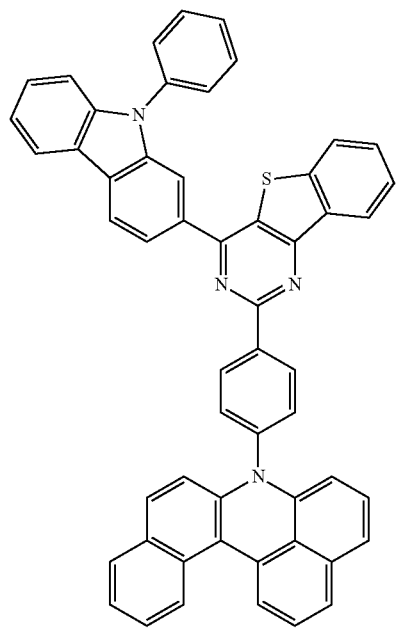
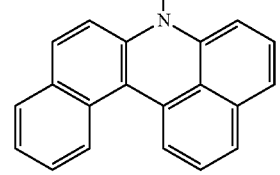
162
-continued
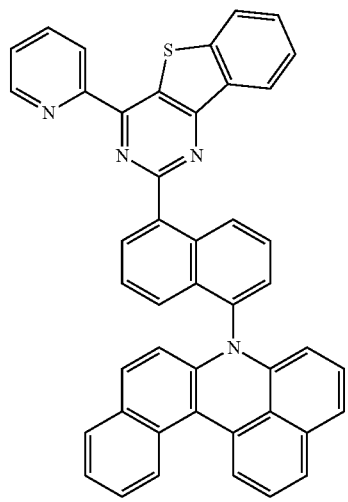
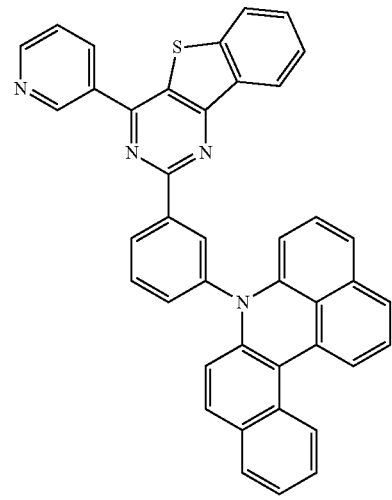
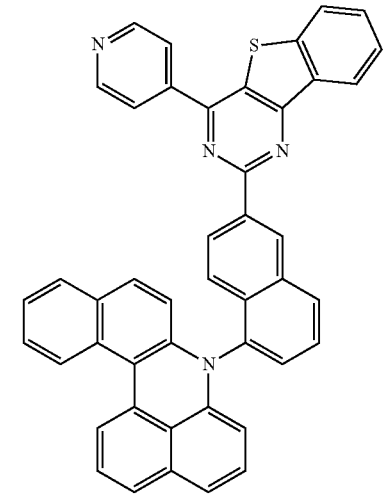

163
-continued
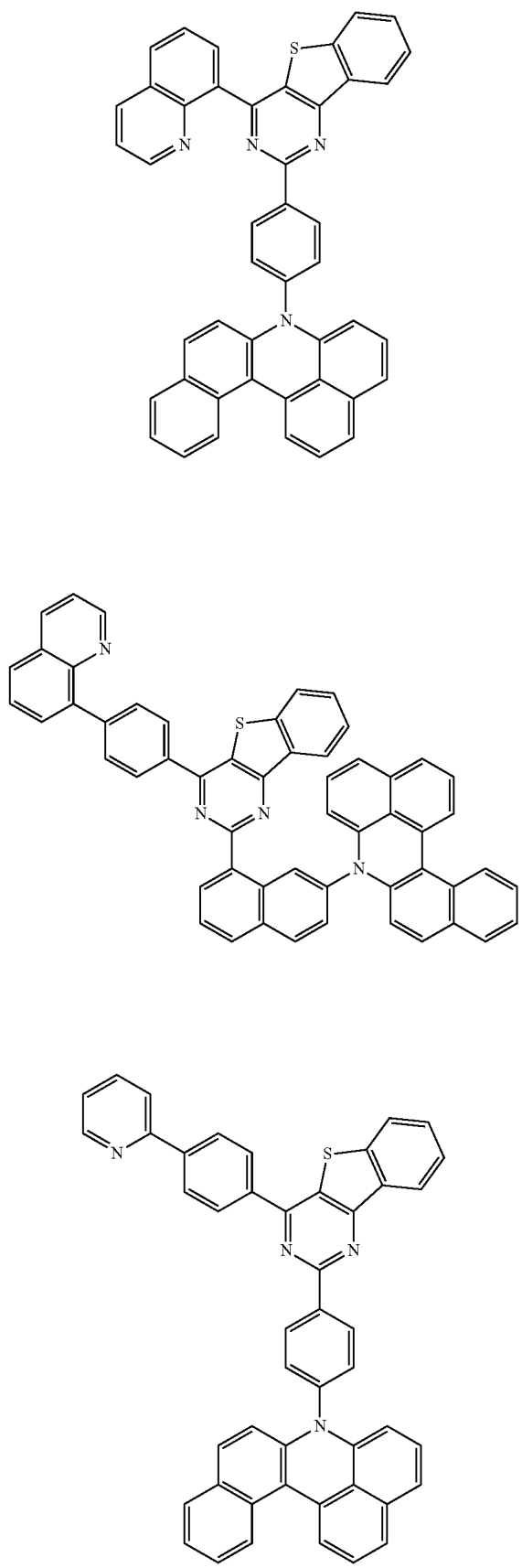
164
-continued
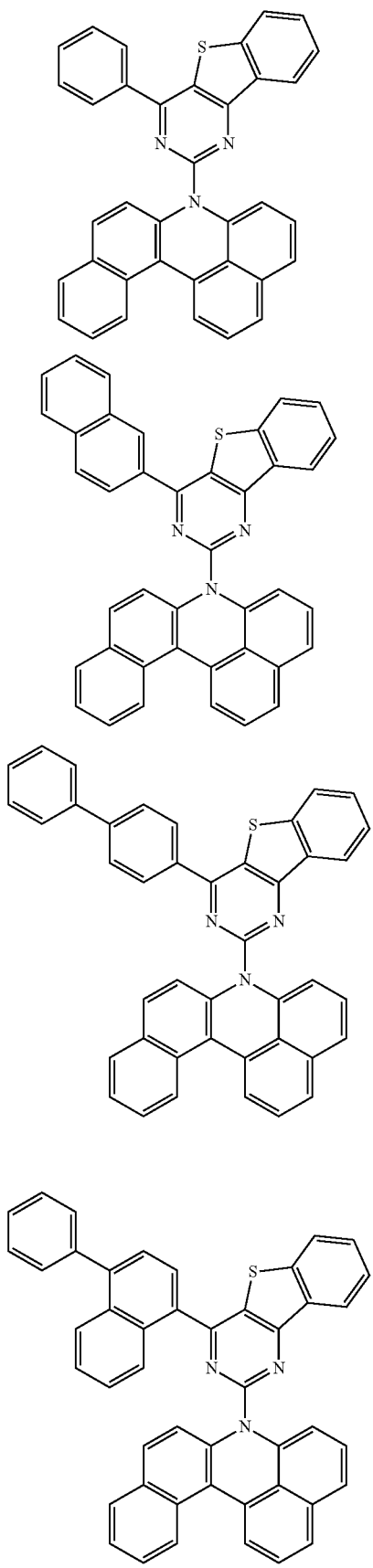

165
-continued
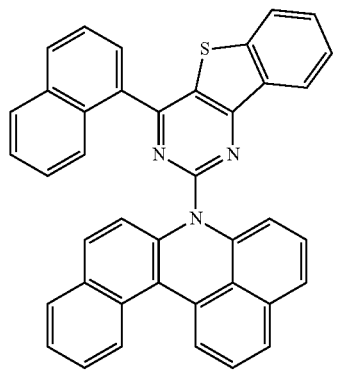
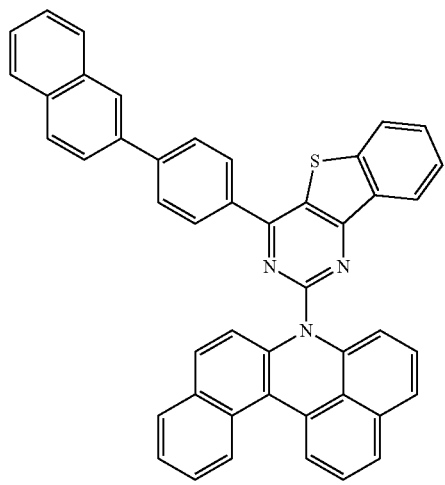
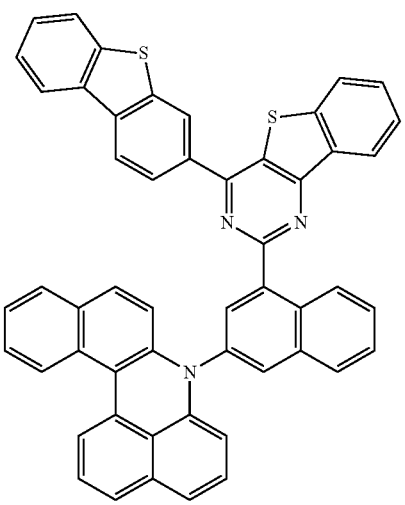
166
-continued
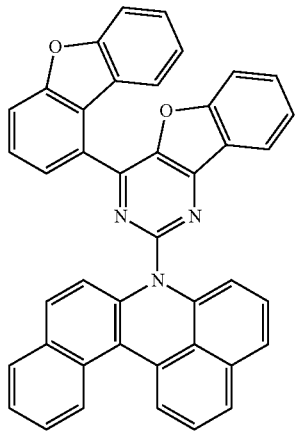
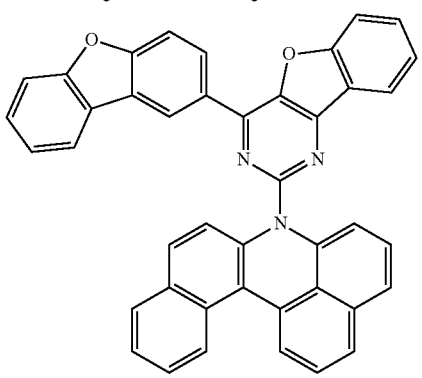
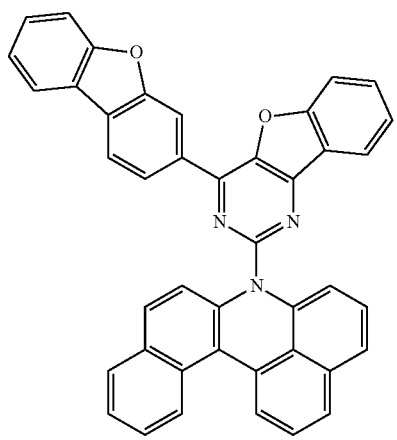
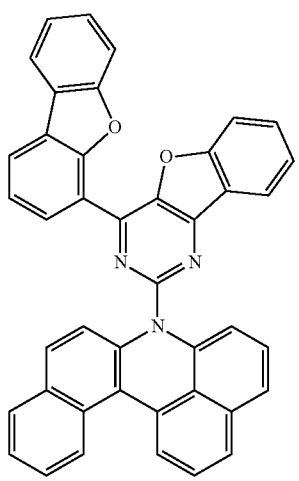

167
-continued
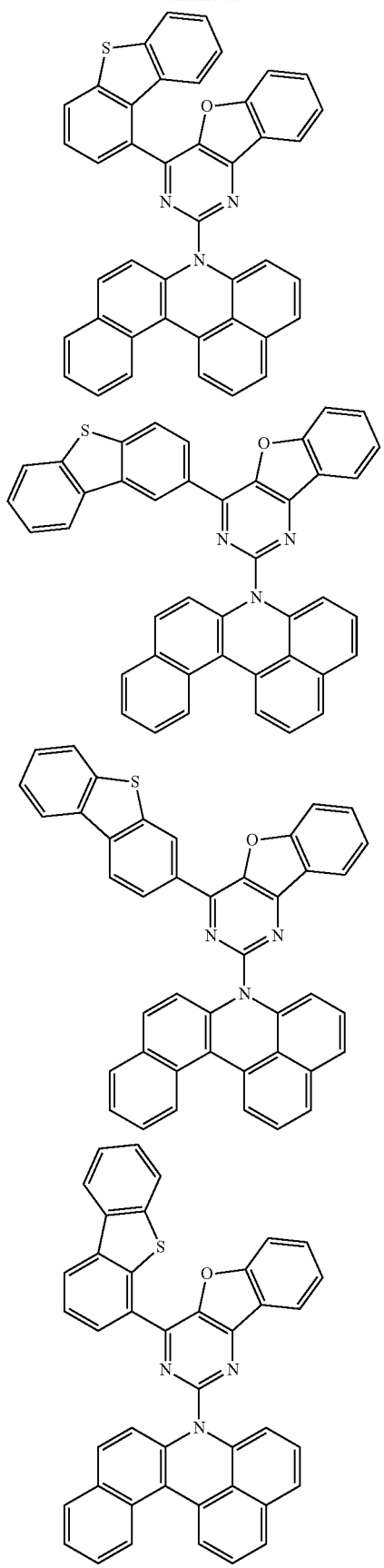
168
-continued
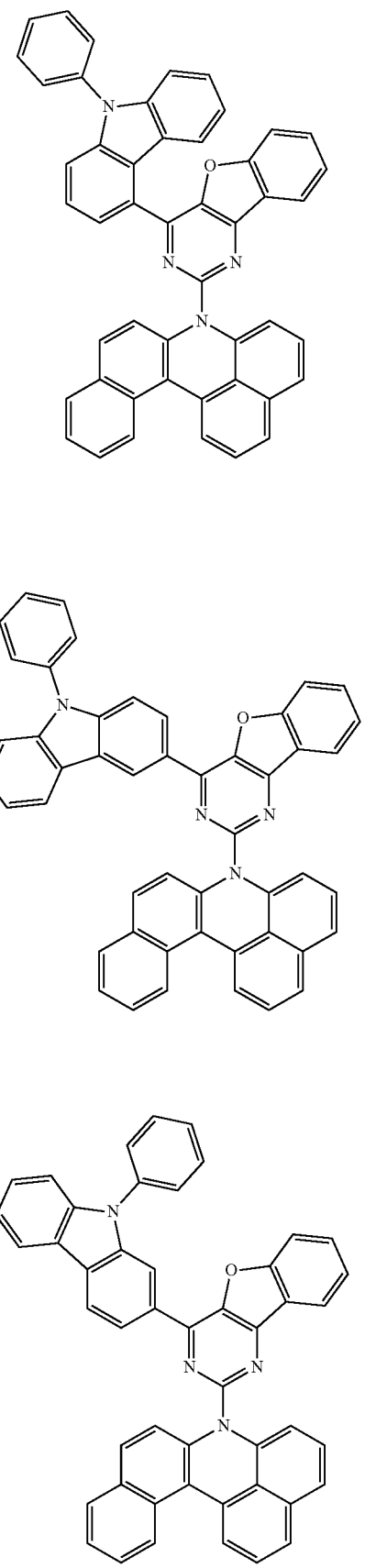

169
-continued
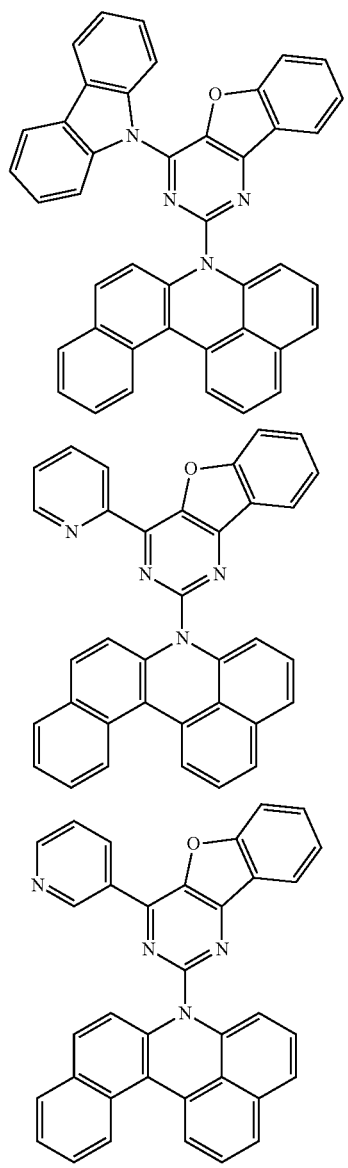
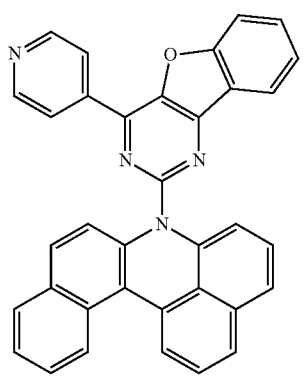
170
-continued
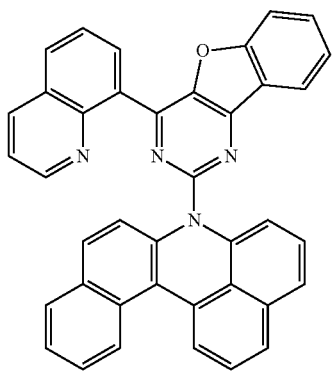
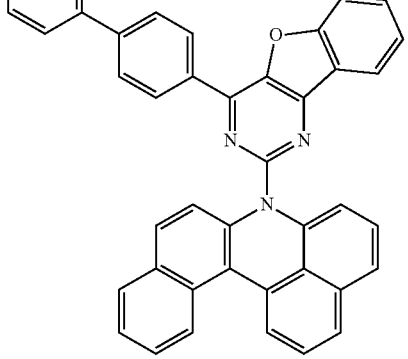
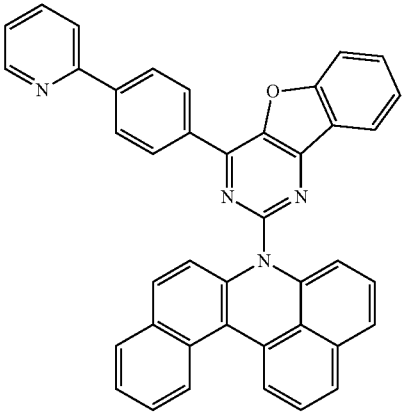

171
-continued
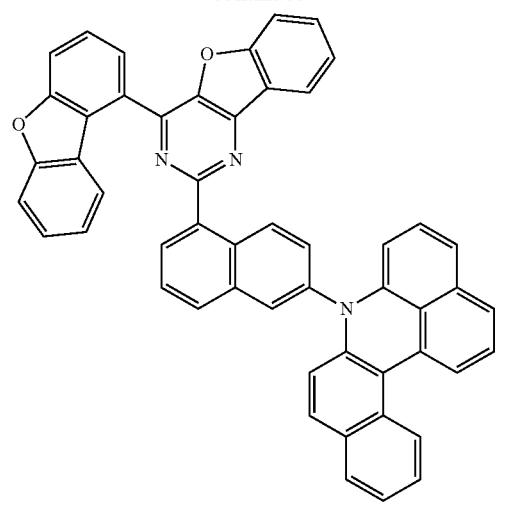
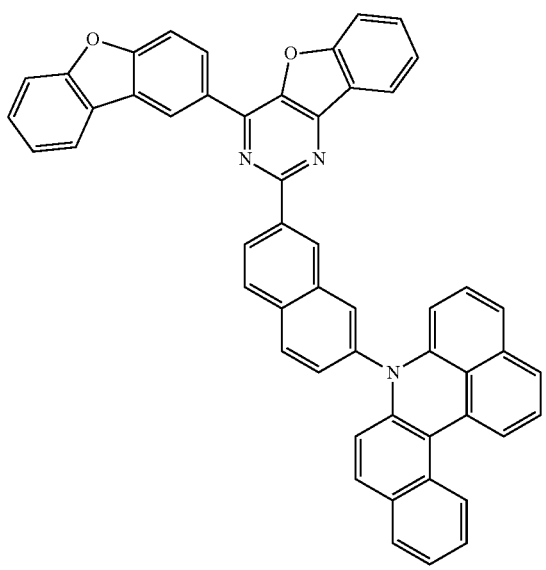
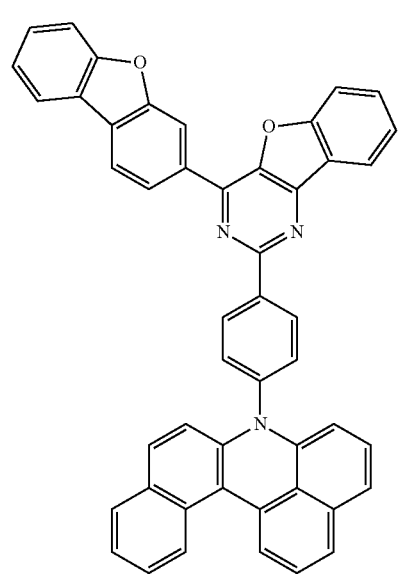
172
-continued
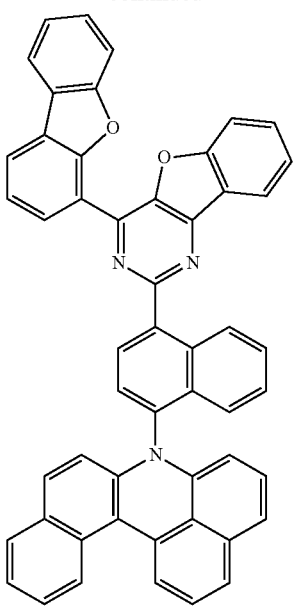
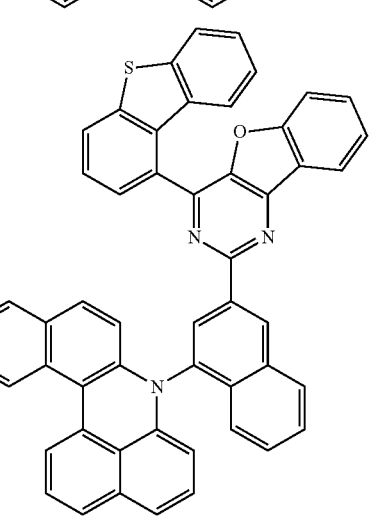
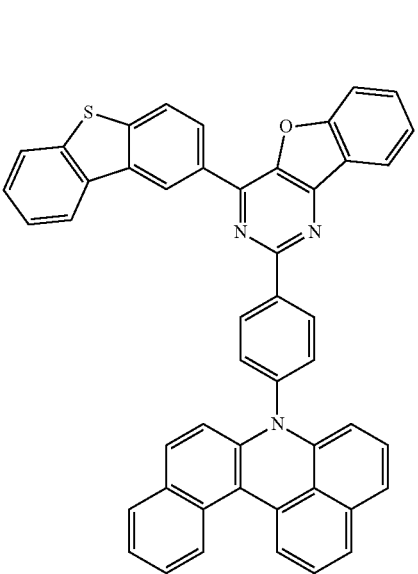
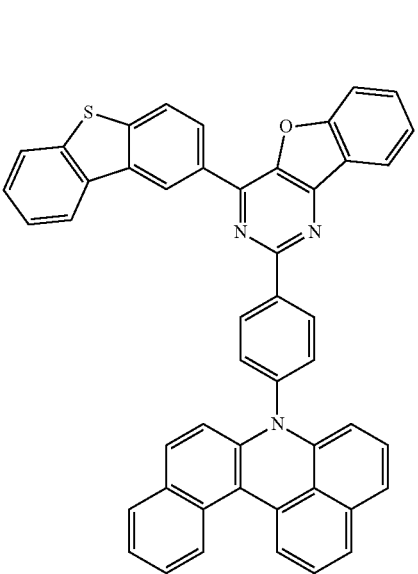

173
-continued
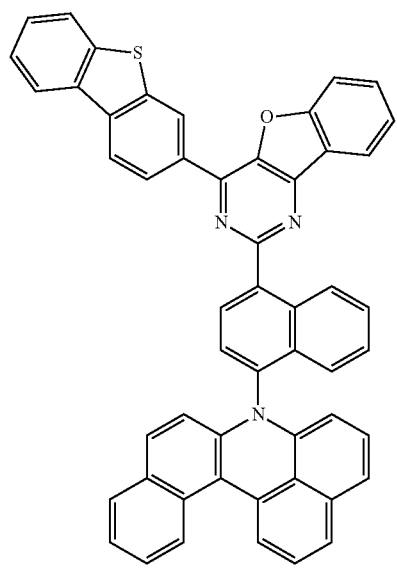
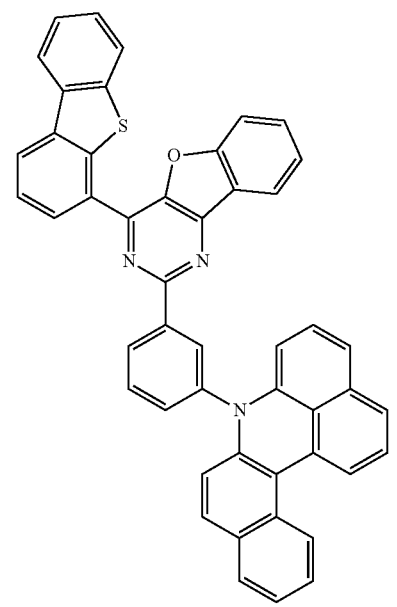
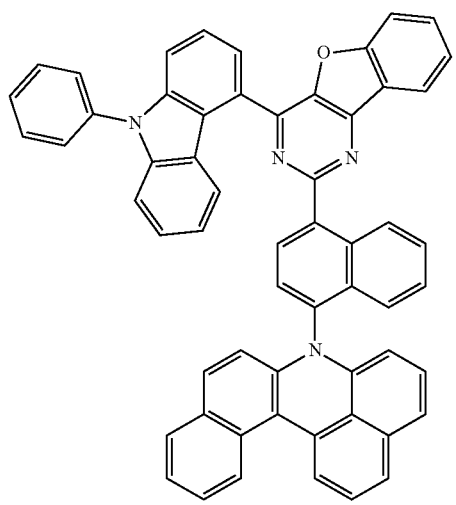
174
-continued
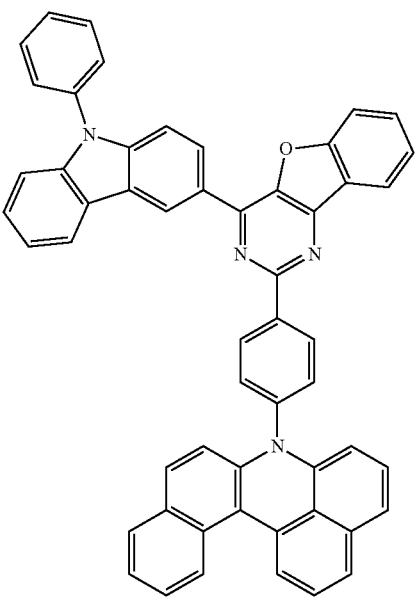
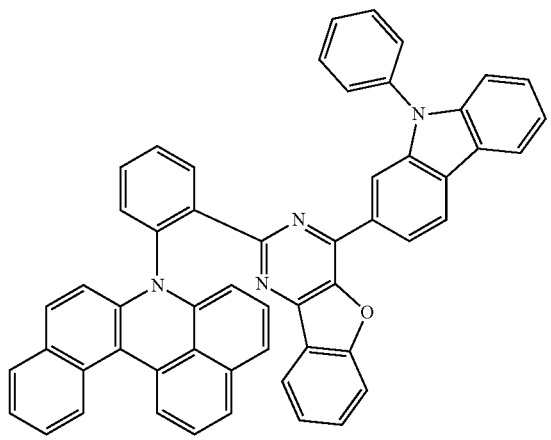
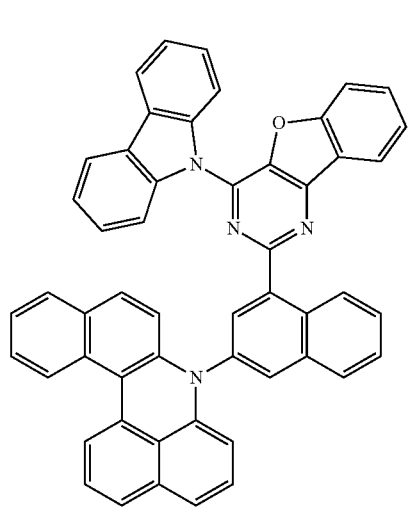

175
-continued
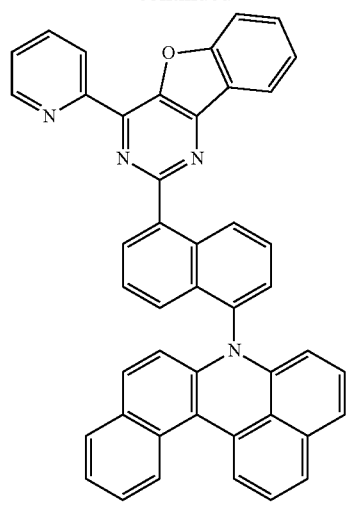
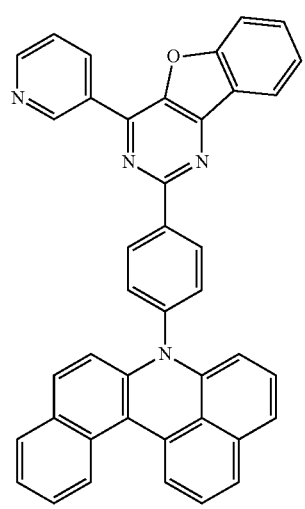
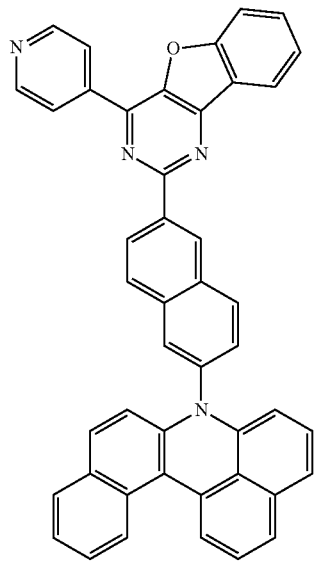
176
-continued
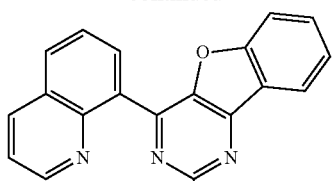
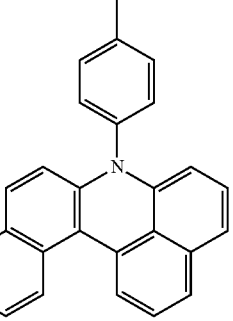
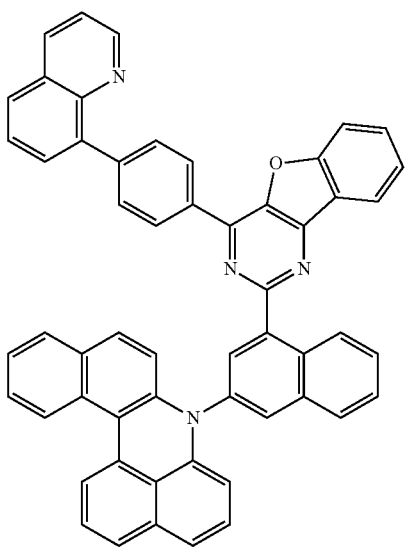
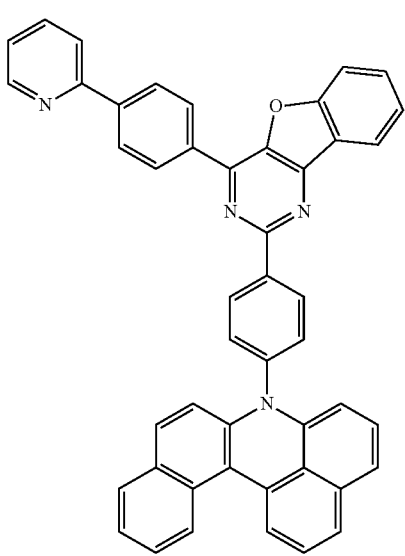

177
-continued
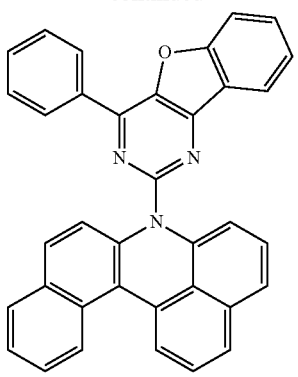
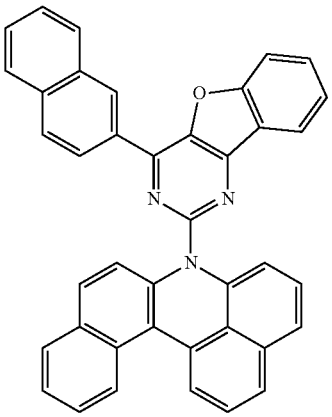
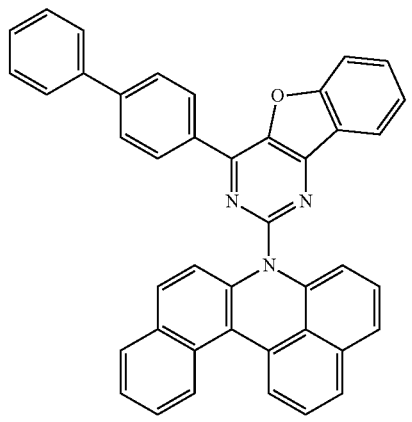
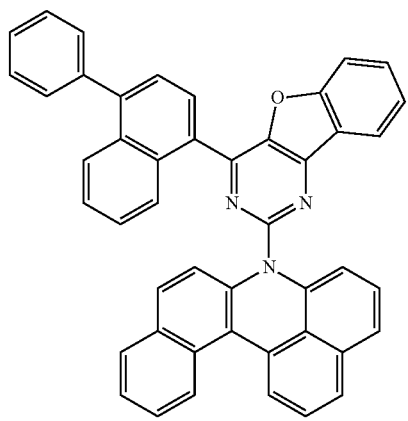
178
-continued
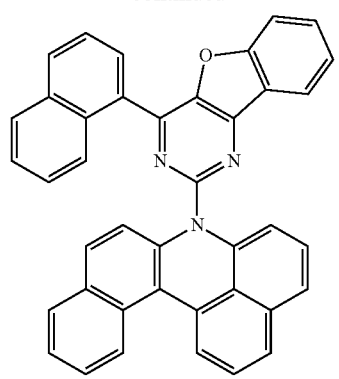
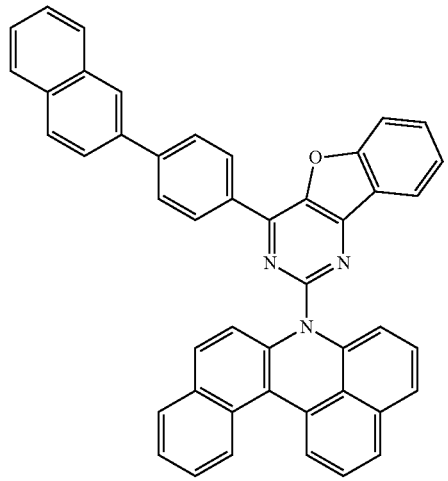
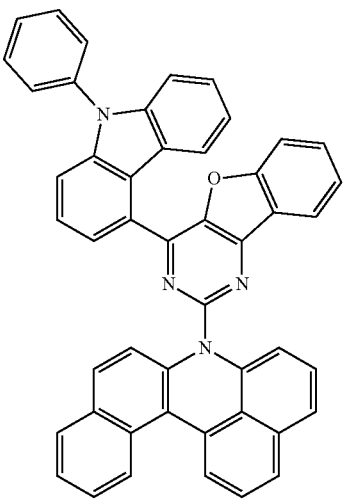

179
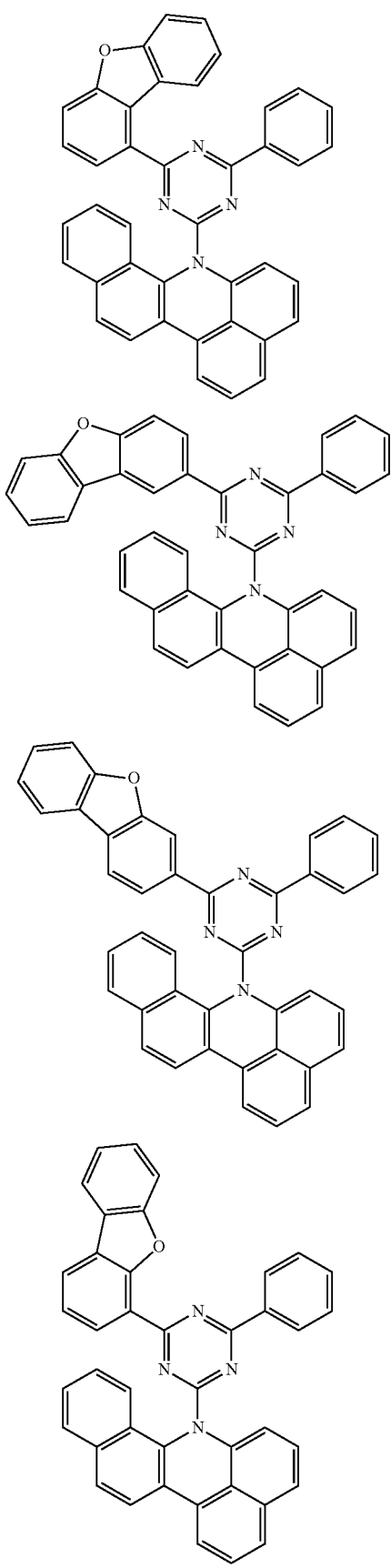 [SMILES: c1ccc(-c2nc(-c3cccc4oc5ccccc5c34)nc(N3c4c(ccc5ccccc45)-c4cccc5cccc3c45)n2)cc1 ; c1ccc(-c2nc(-c3ccc4oc5ccccc5c4c3)nc(N3c4c(ccc5ccccc45)-c4cccc5cccc3c45)n2)cc1 ; c1ccc(-c2nc(-c3ccc4c(c3)oc3ccccc34)nc(N3c4c(ccc5ccccc45)-c4cccc5cccc3c45)n2)cc1 ; c1ccc(-c2nc(-c3cccc4c3oc3ccccc34)nc(N3c4c(ccc5ccccc45)-c4cccc5cccc3c45)n2)cc1]
180
-continued
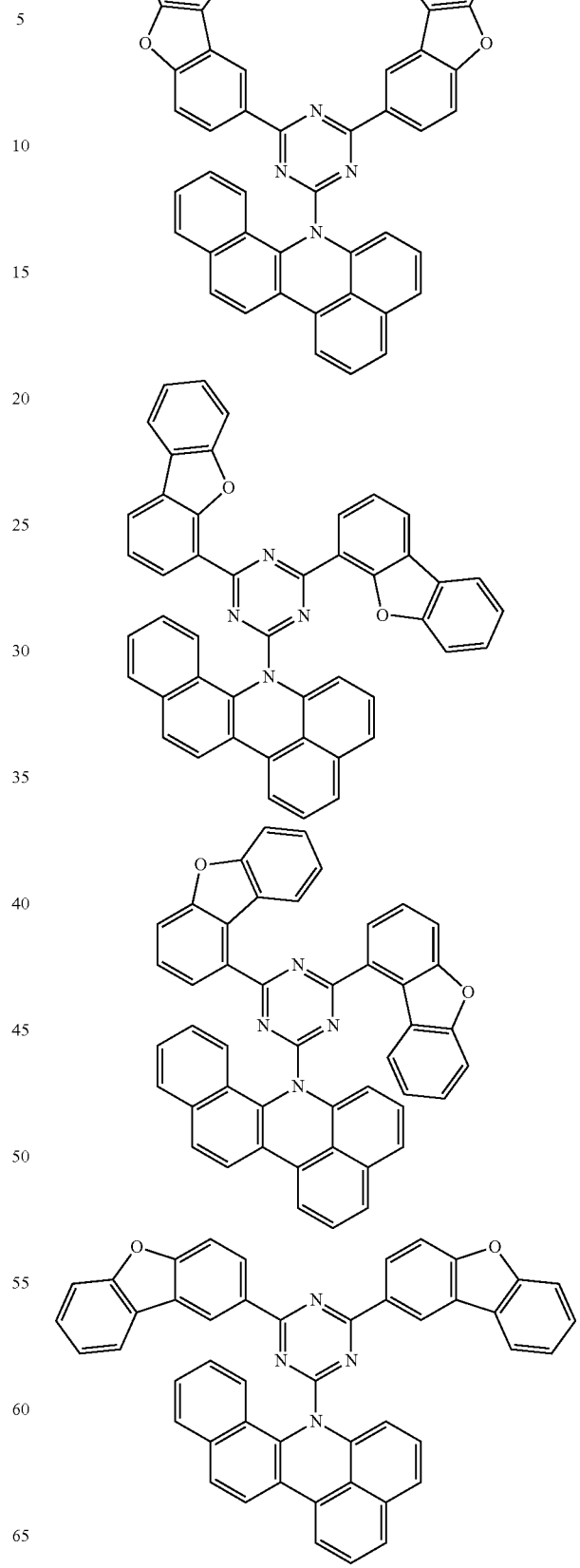

181
-continued
182
-continued
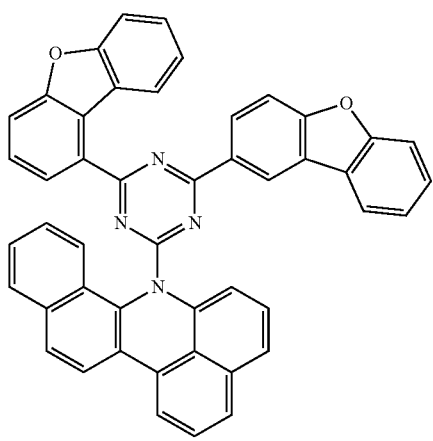
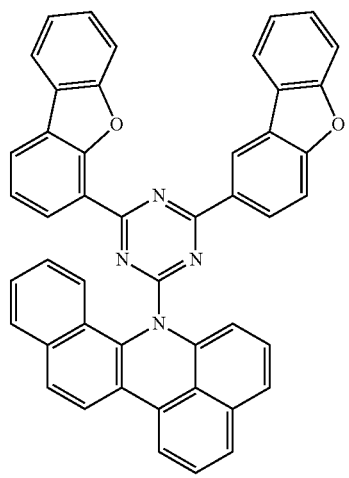
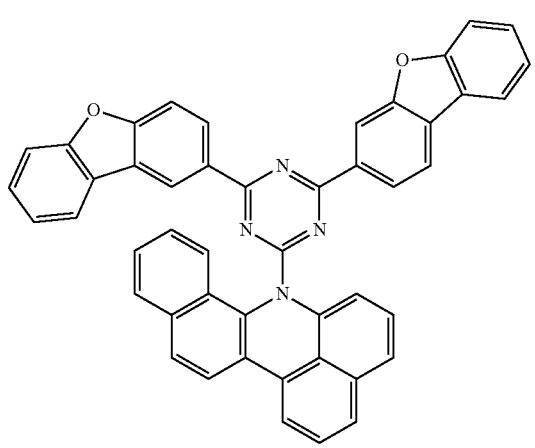
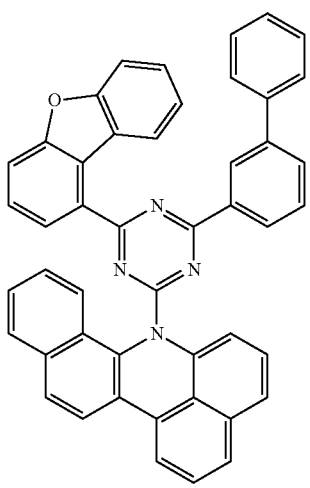
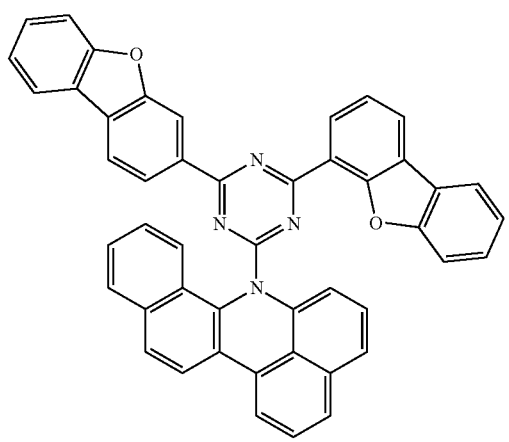
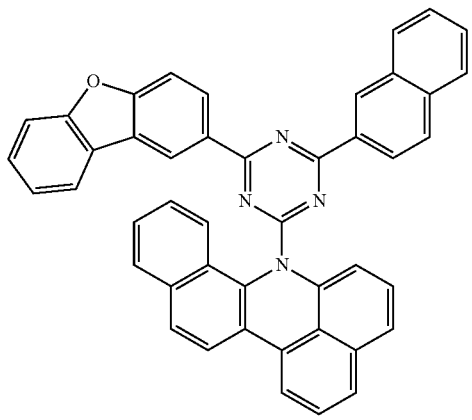

183
-continued
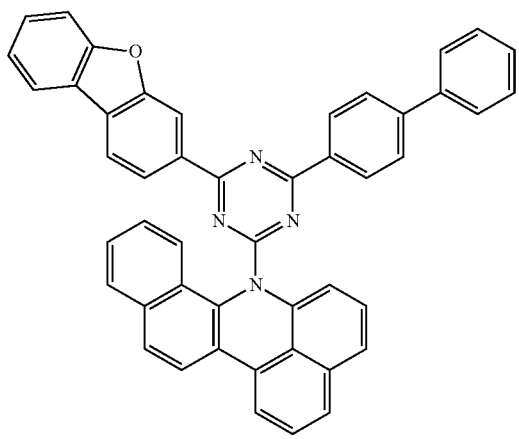
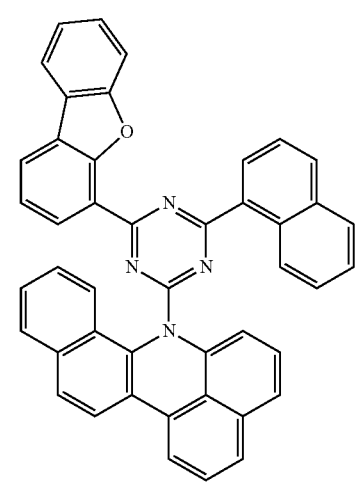
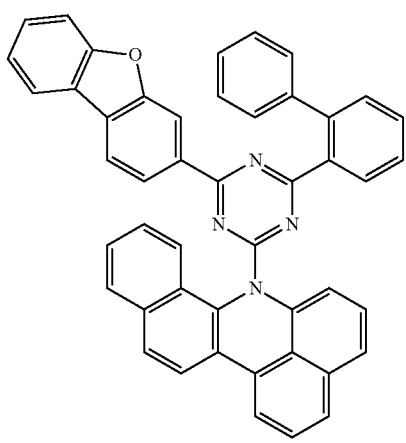
184
-continued
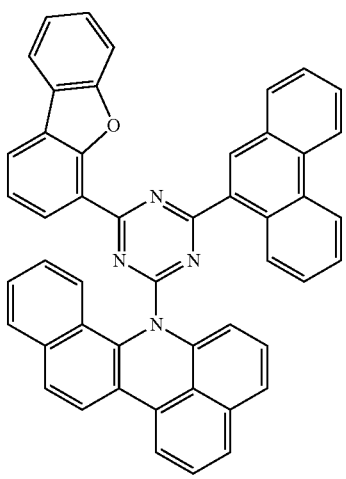
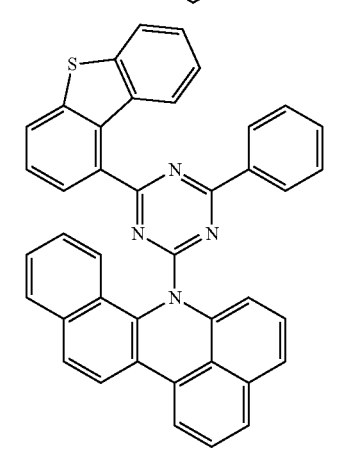

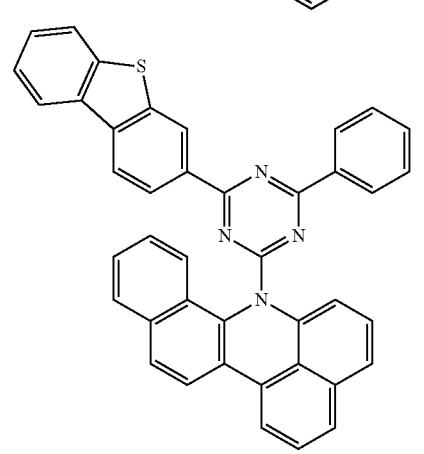

185
-continued
186
-continued
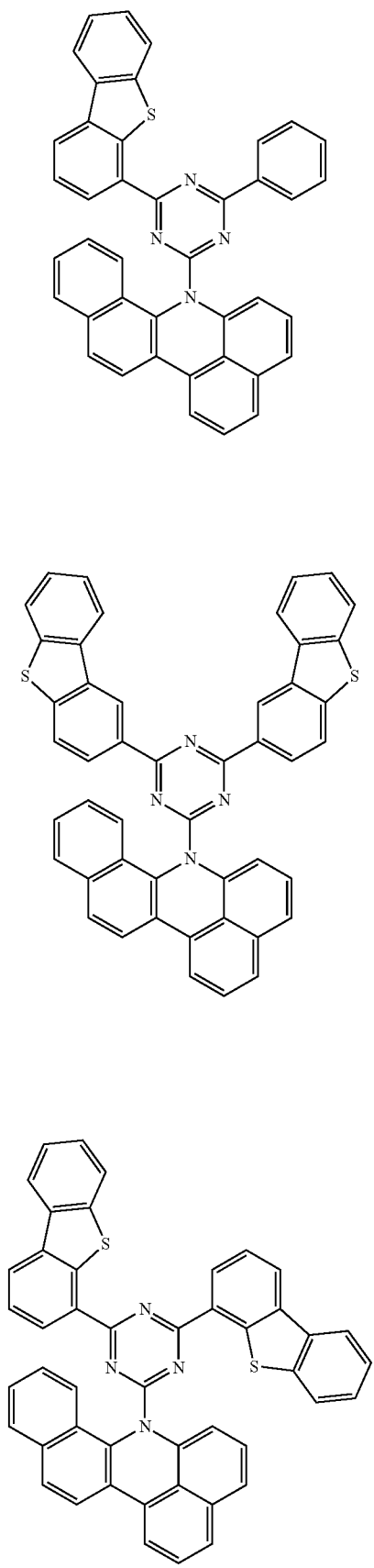
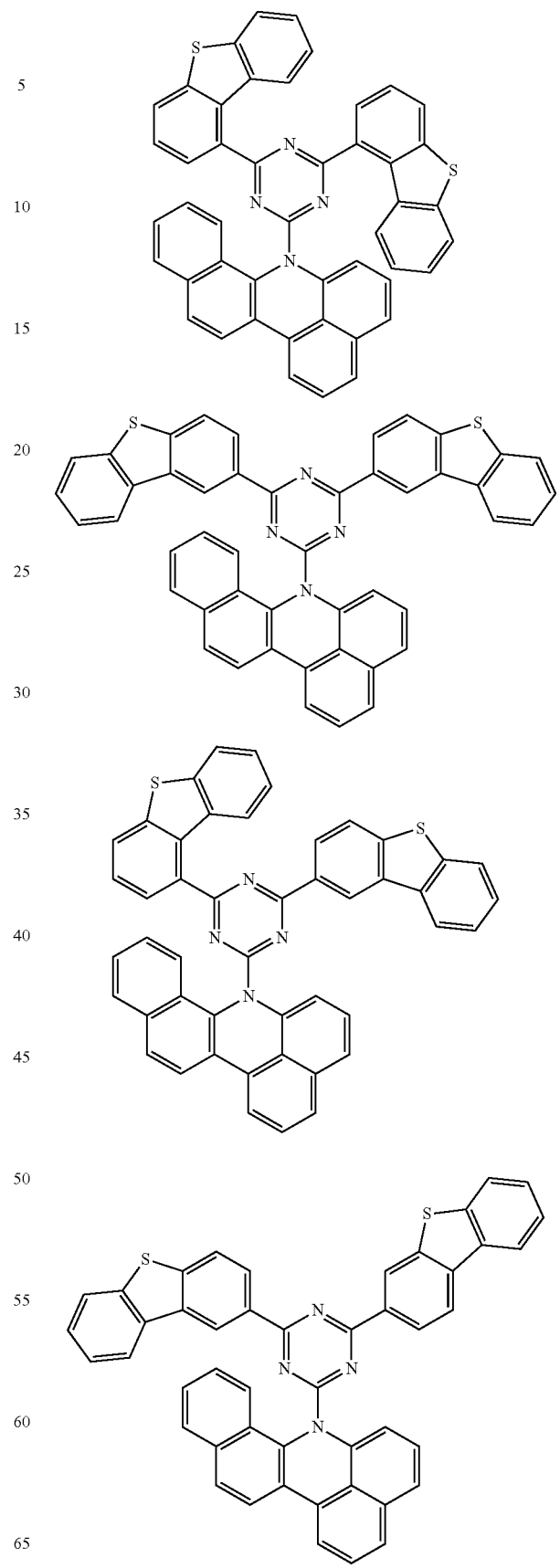

187
-continued
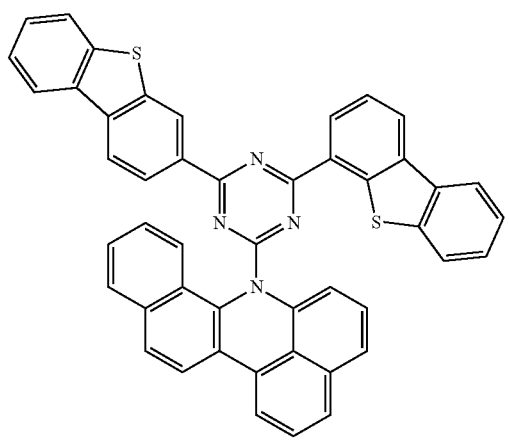
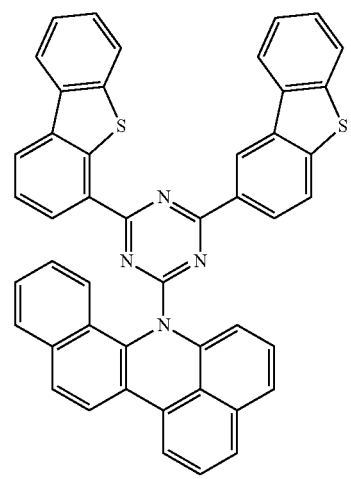
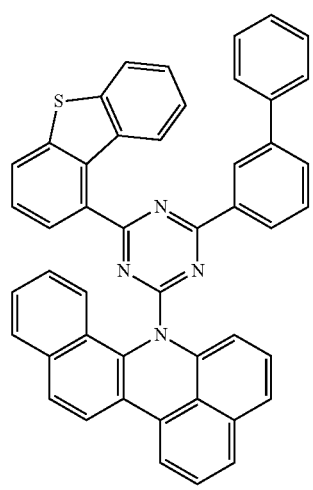
188
-continued
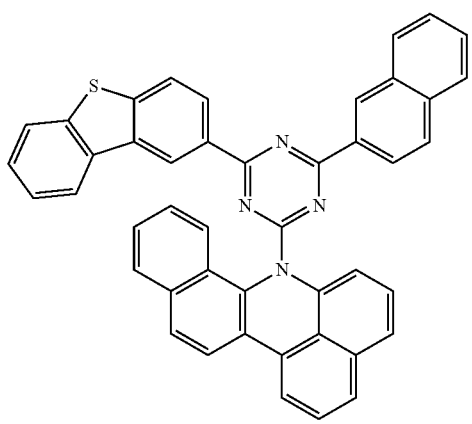
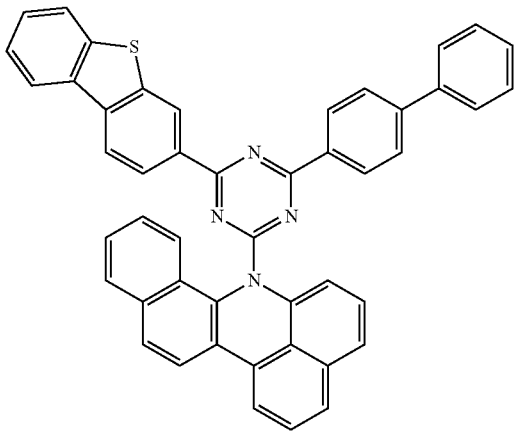
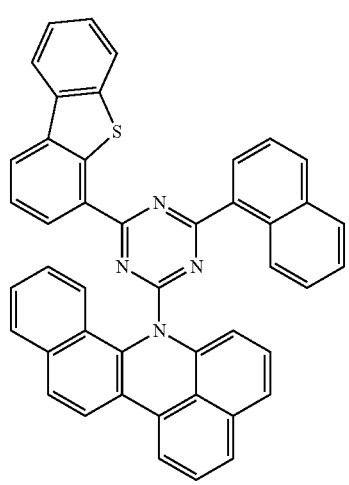

189
-continued
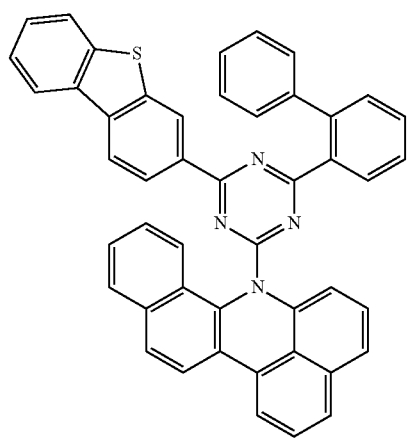
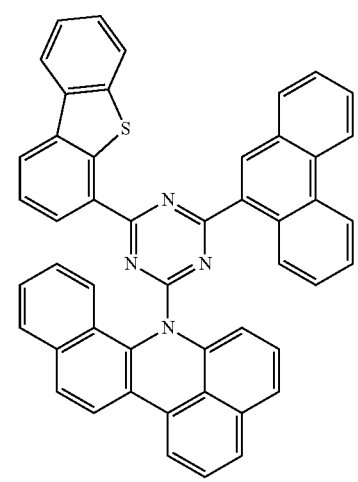
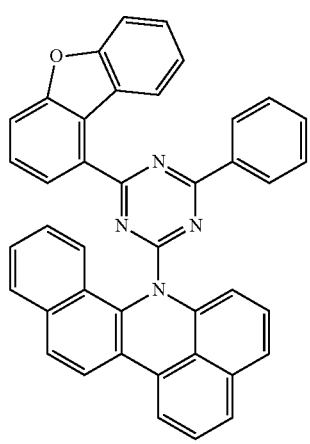
190
-continued
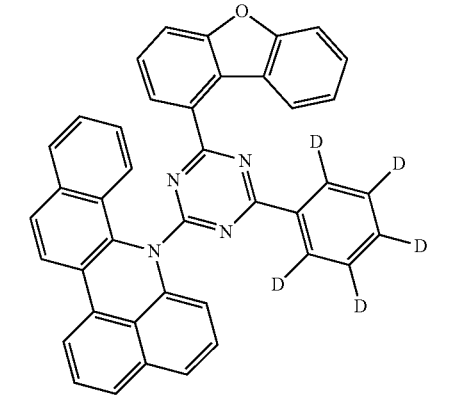
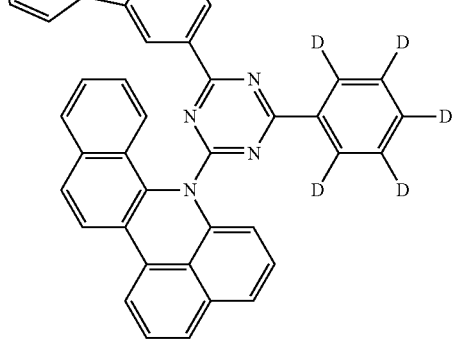
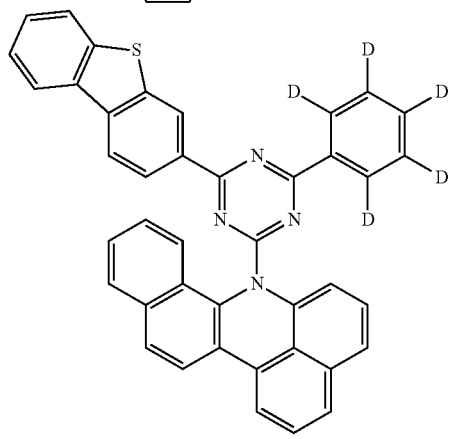
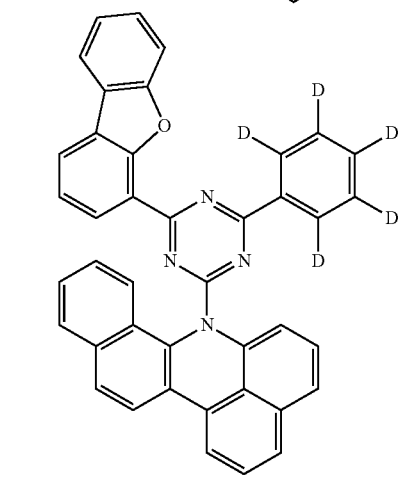

191
-continued
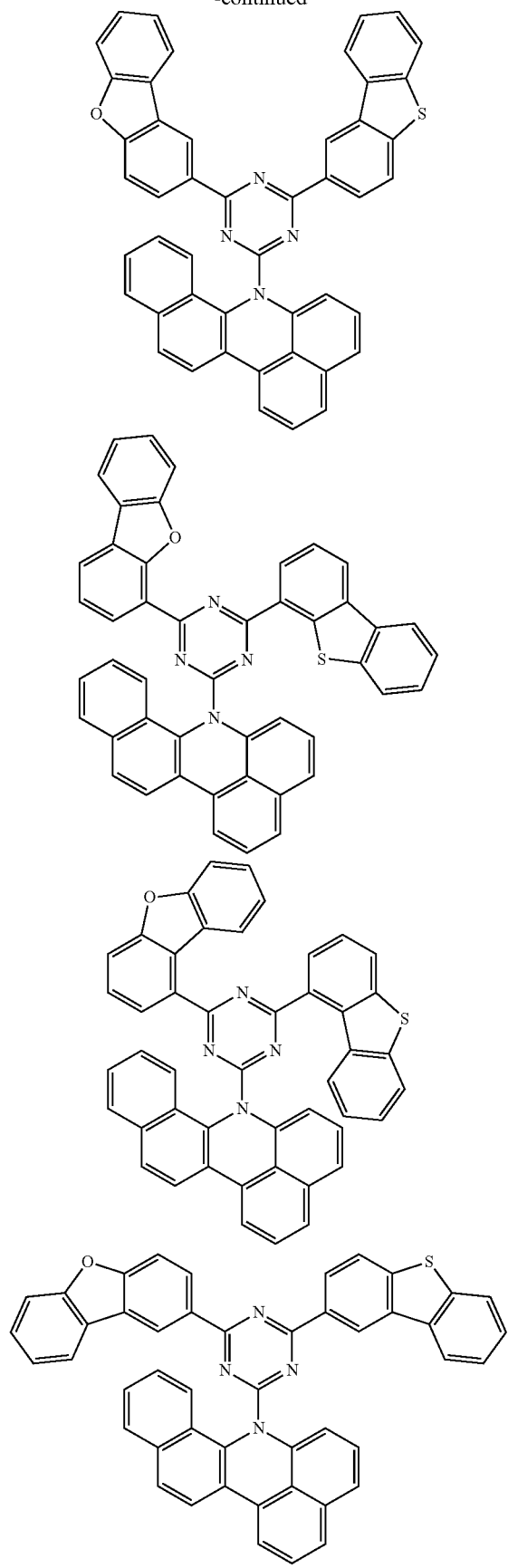
192
-continued
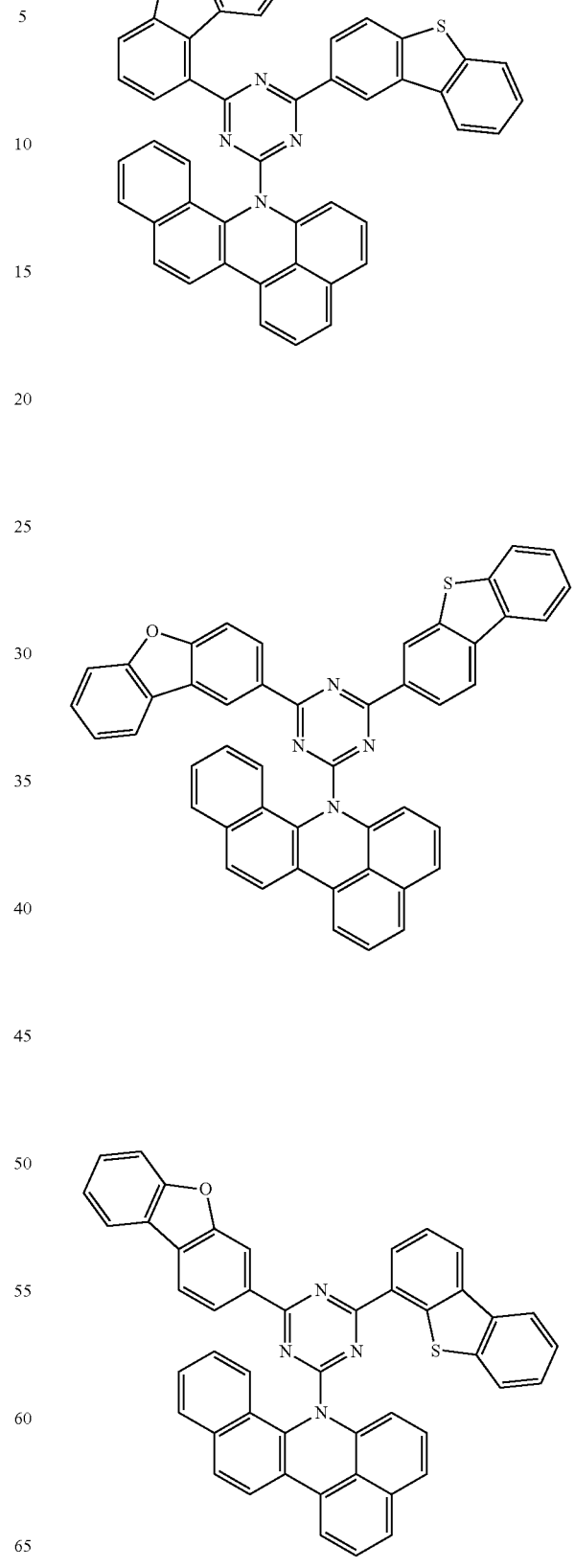

193
-continued
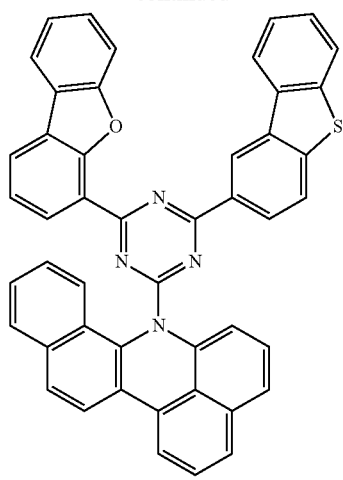
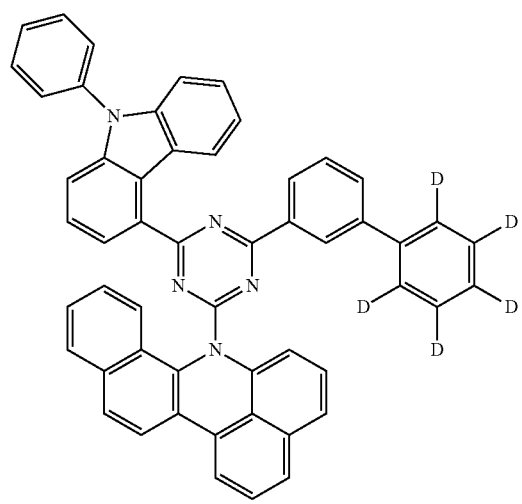
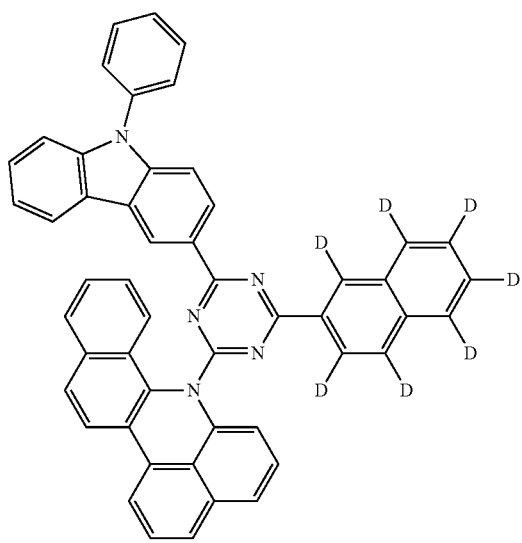
194
-continued
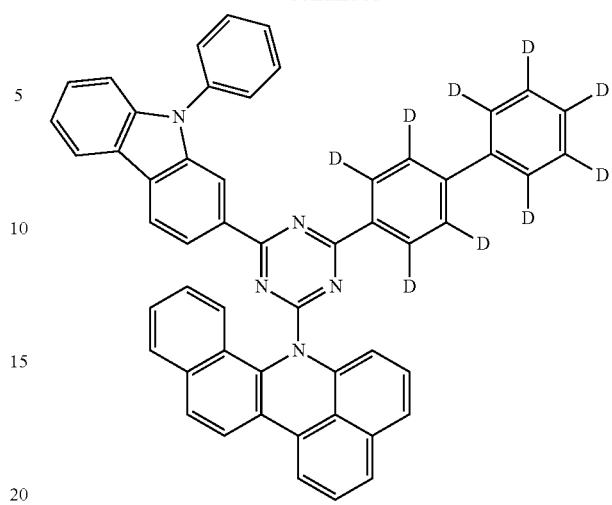
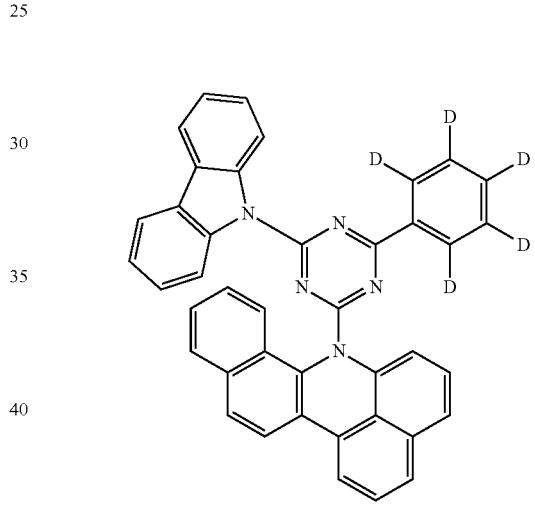
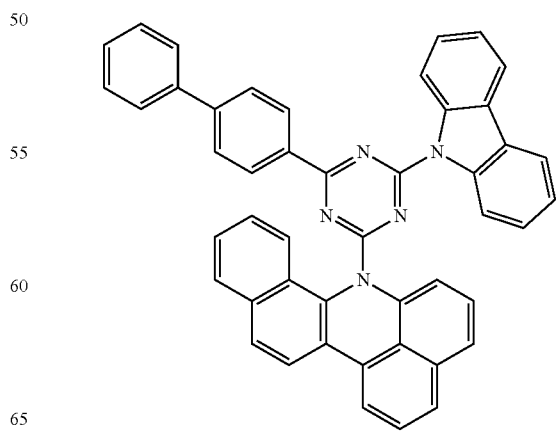

195
-continued
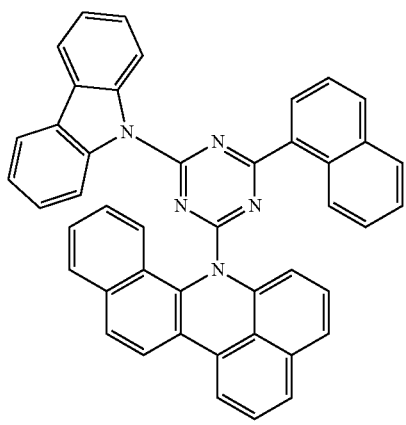
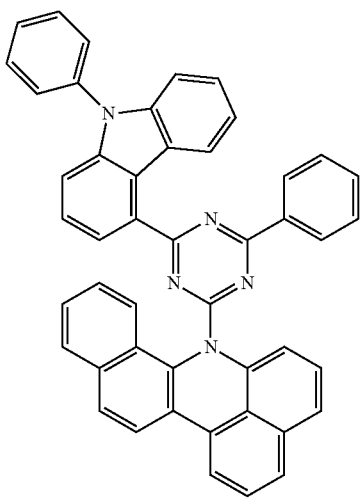
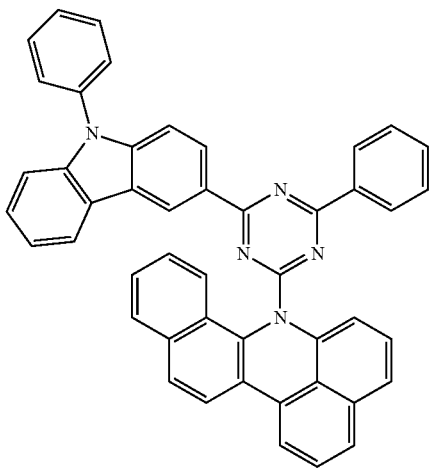
196
-continued
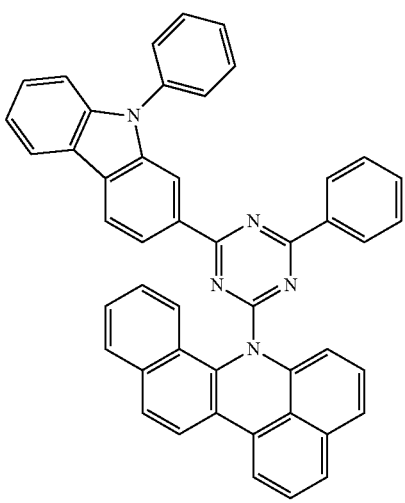
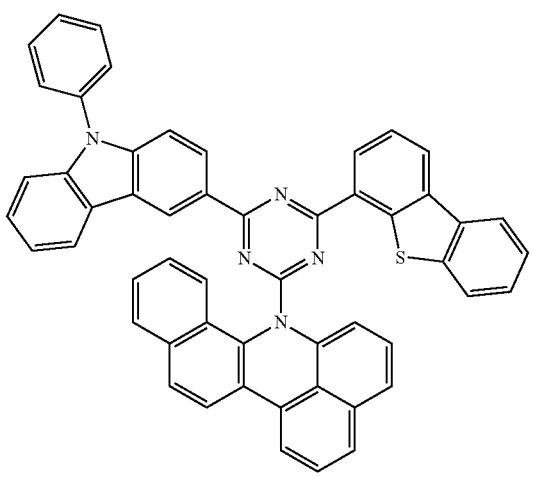
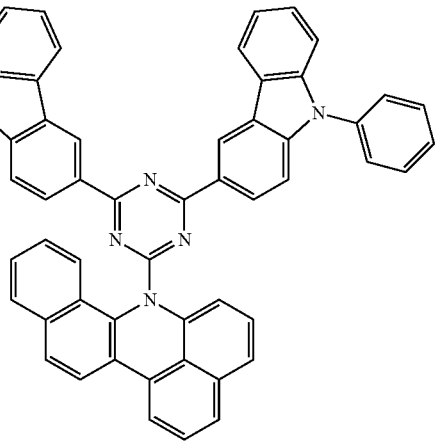

197
-continued
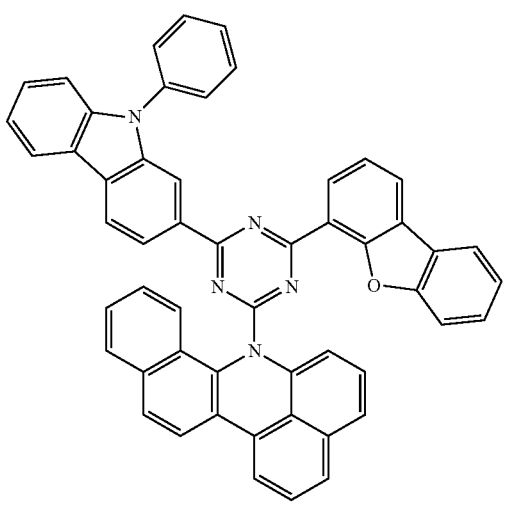
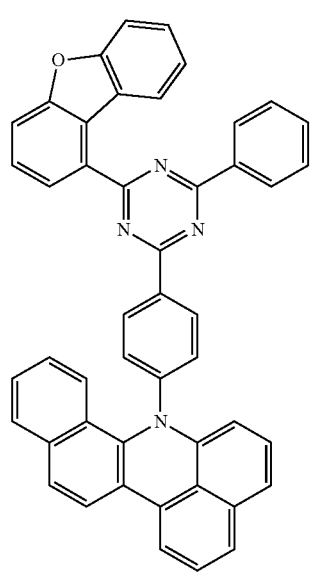
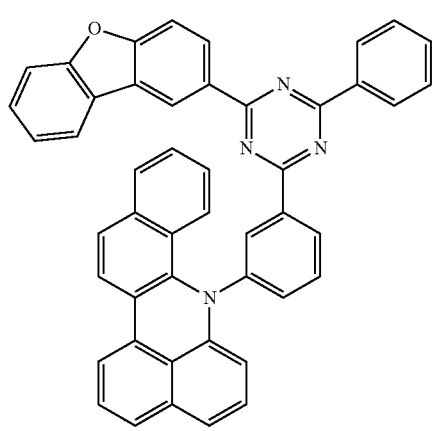
198
-continued
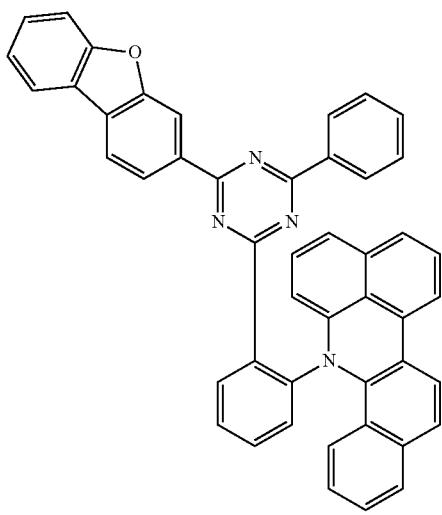
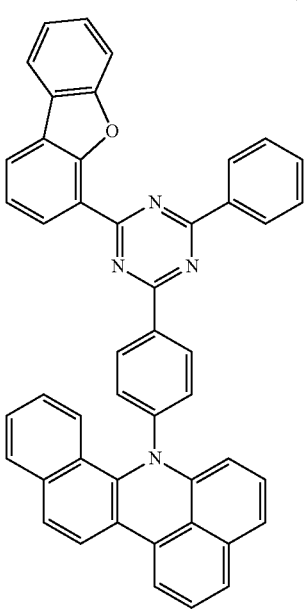
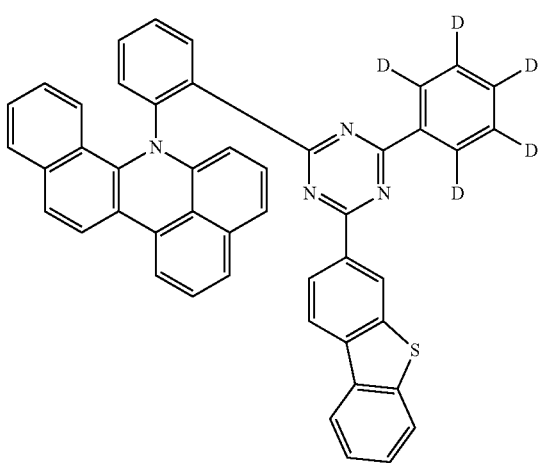

199
-continued
200
-continued
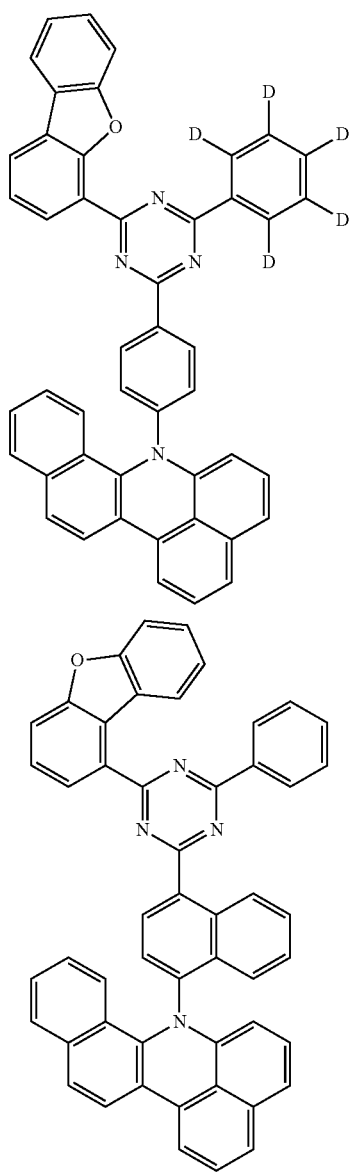
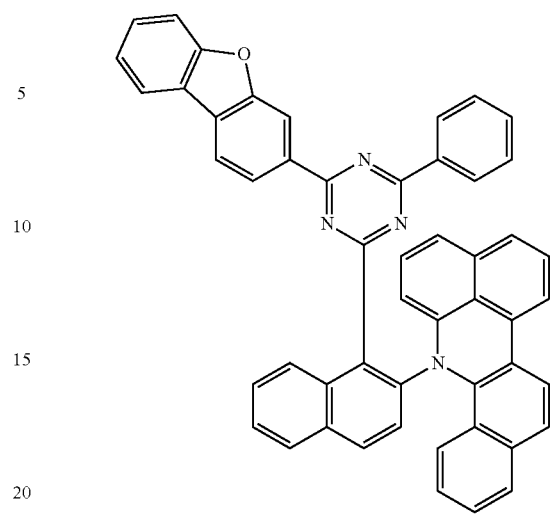
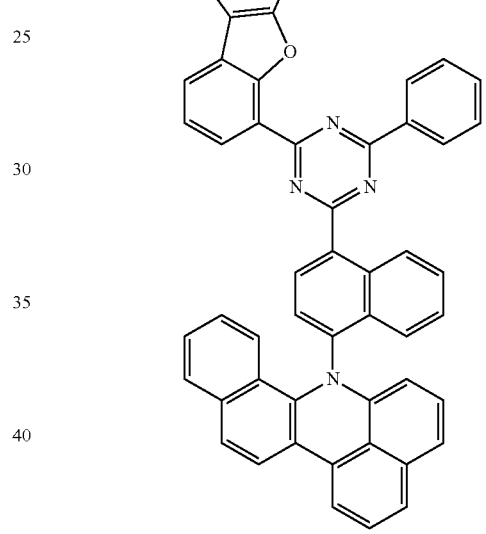
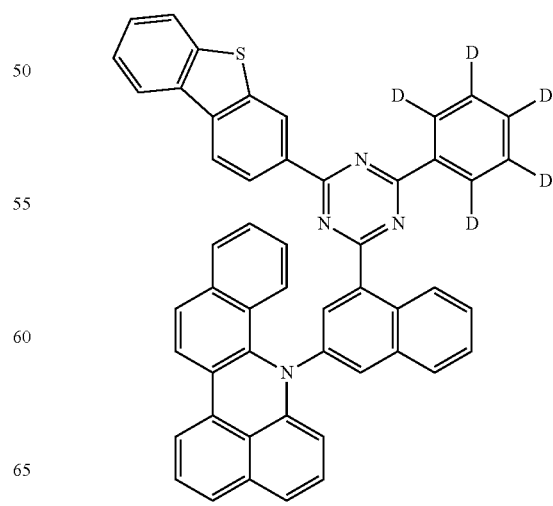

201
-continued
202
-continued
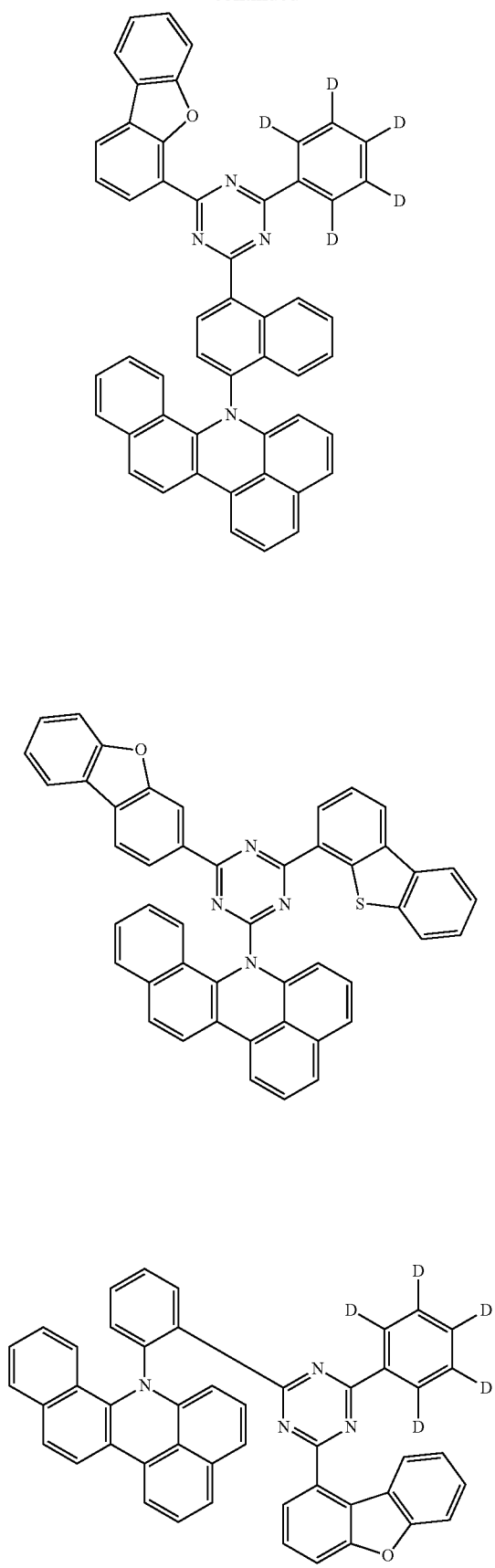
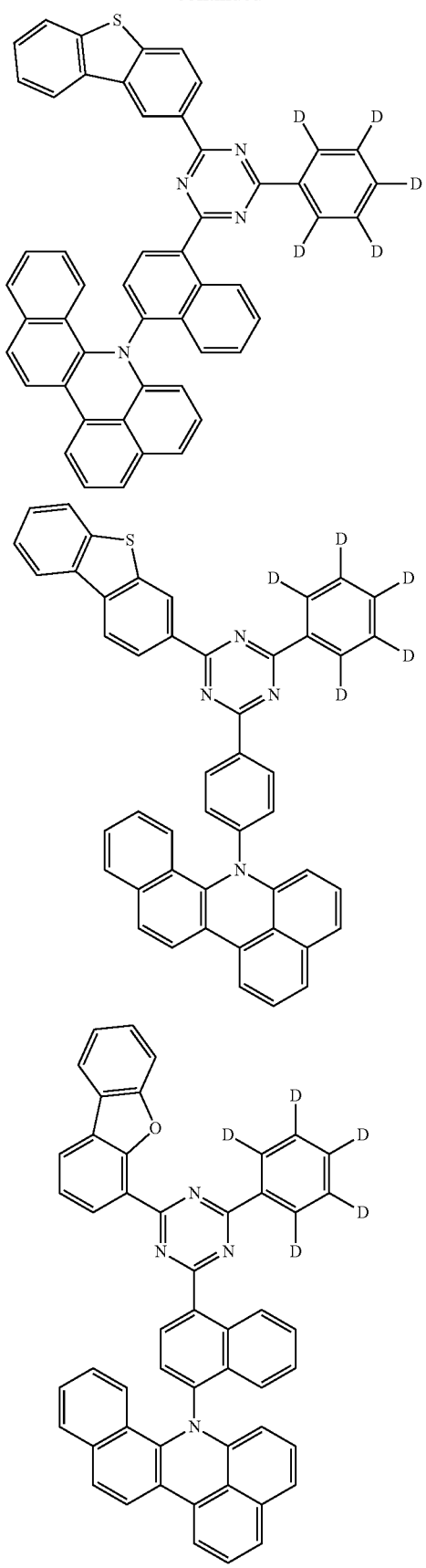

203
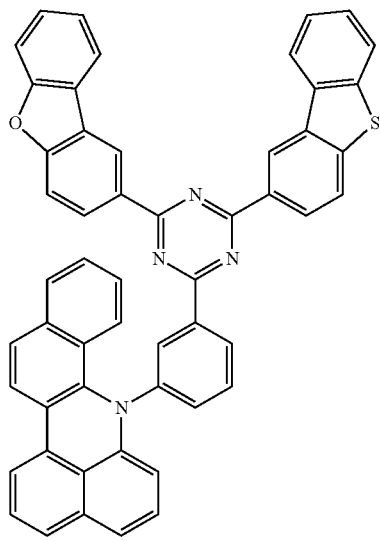
204
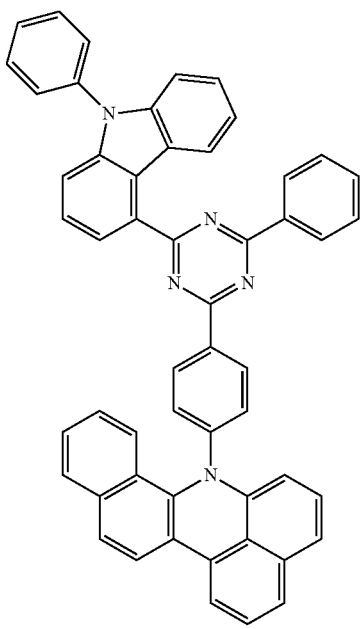
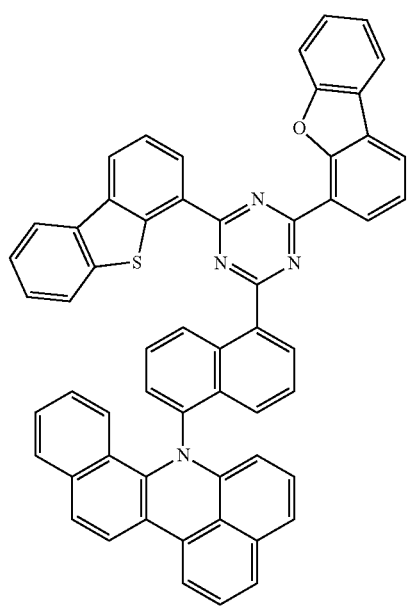
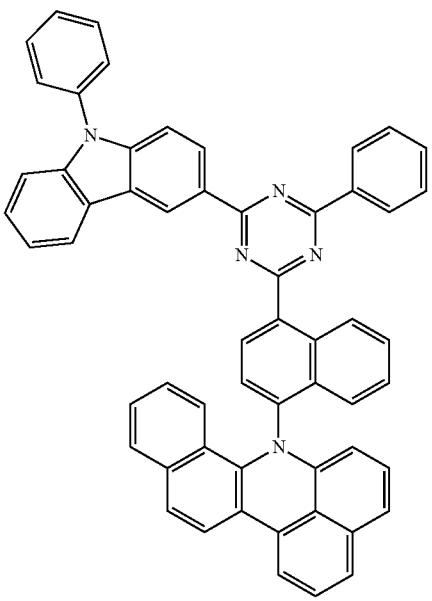

205
-continued
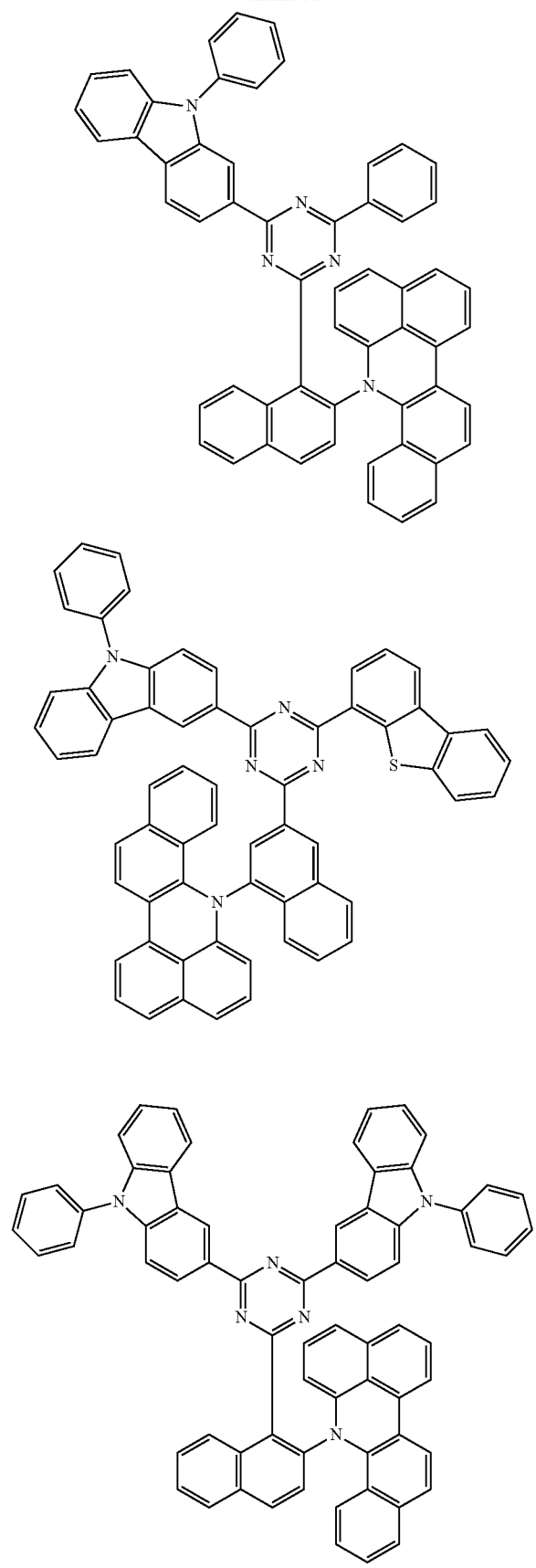
206
-continued
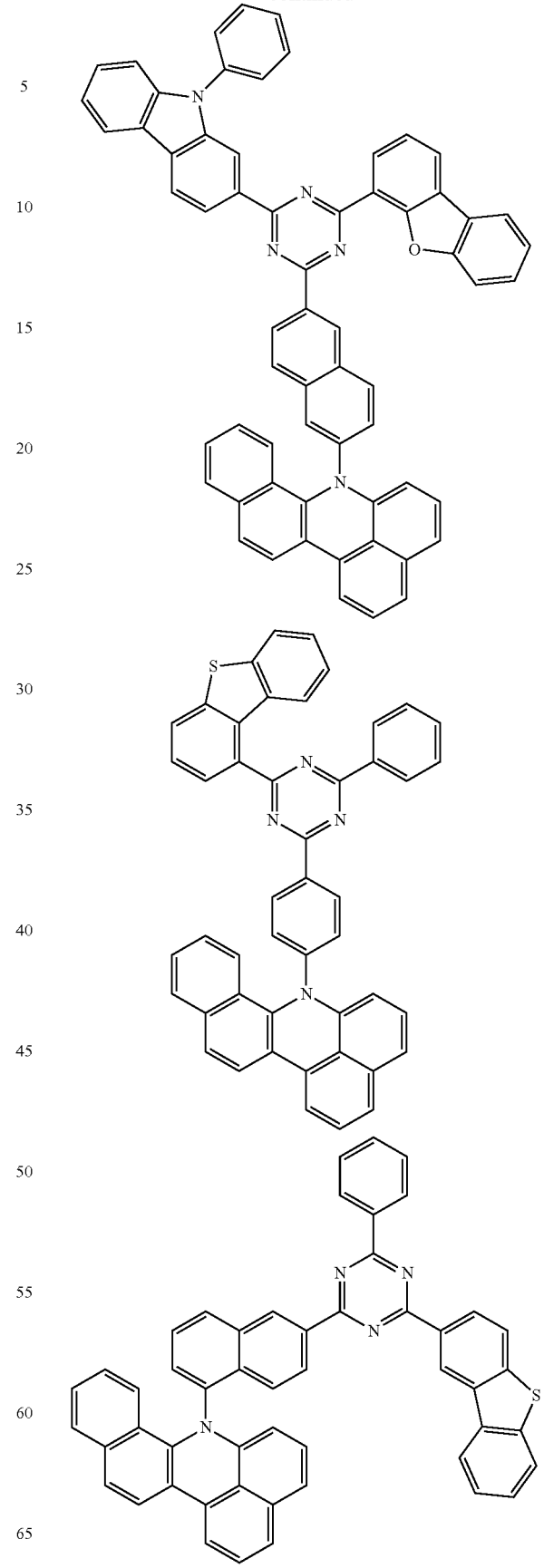

207
-continued
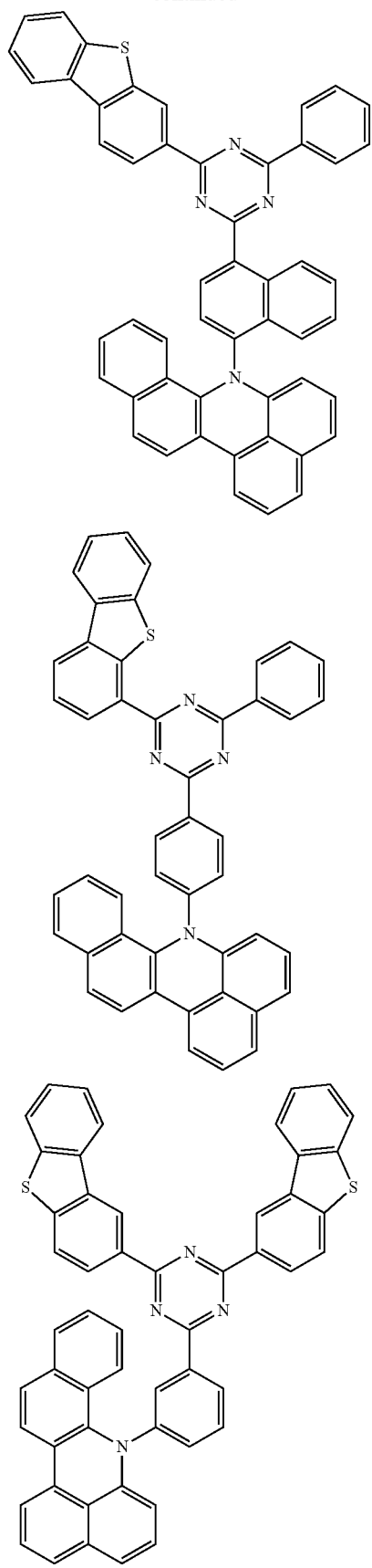
208
-continued
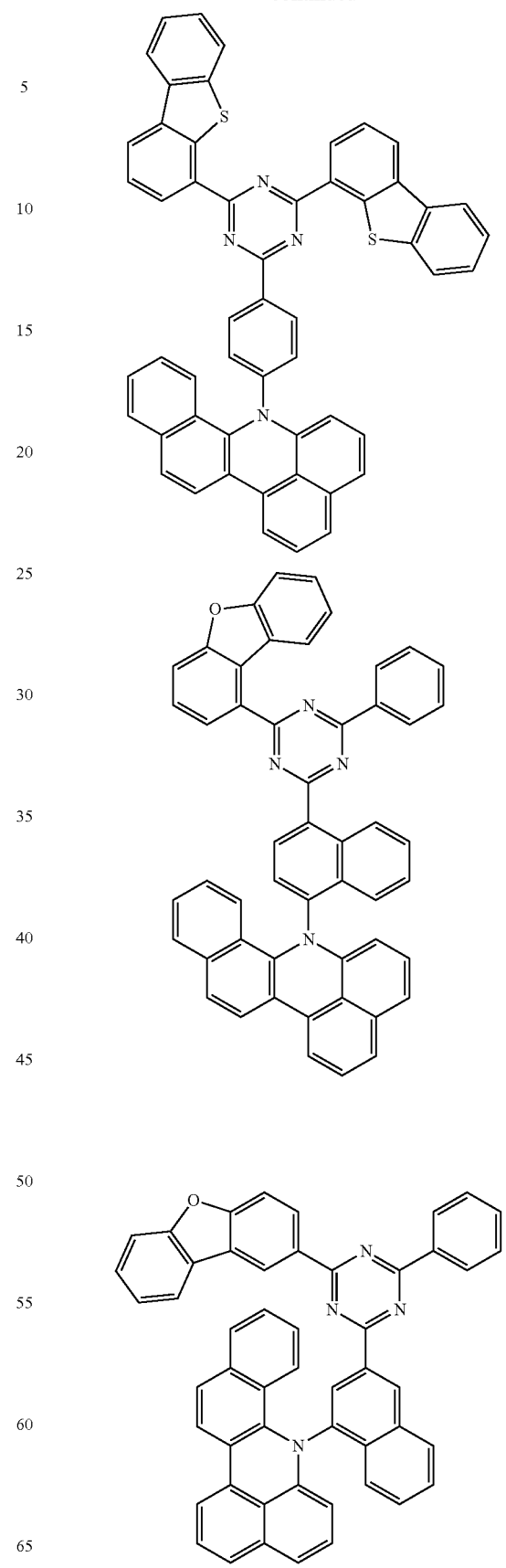

209
-continued
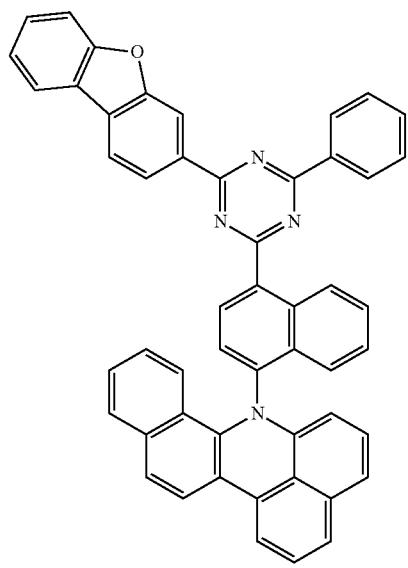
210
-continued
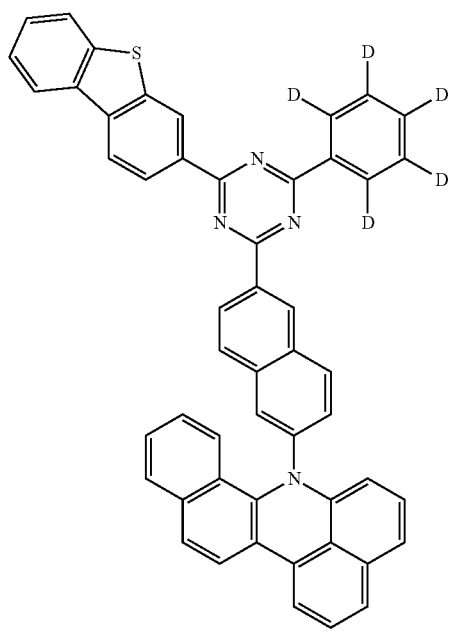
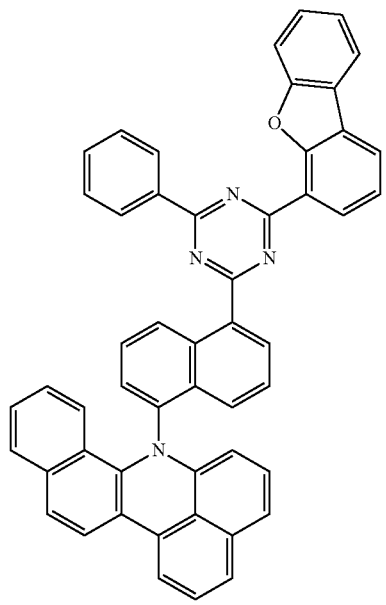

211
-continued
212
-continued
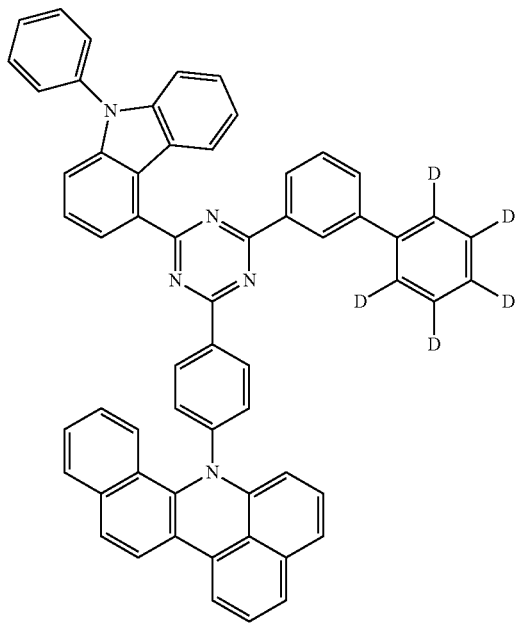
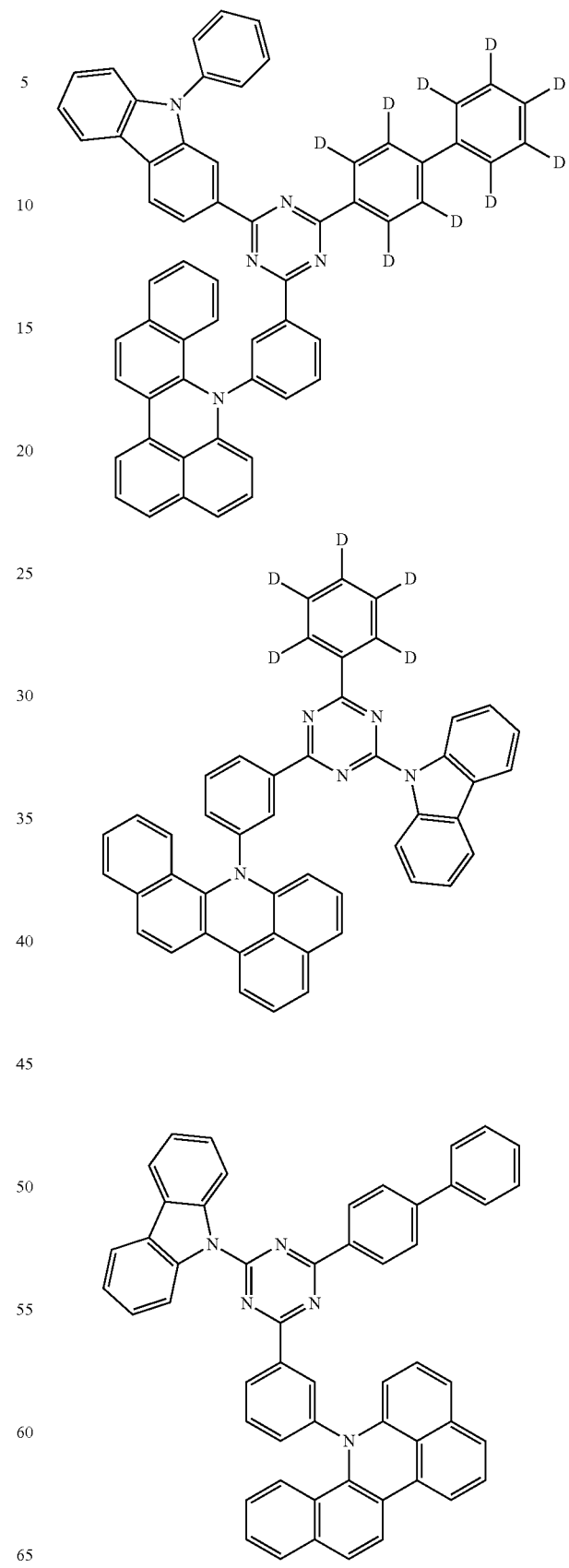

213
-continued
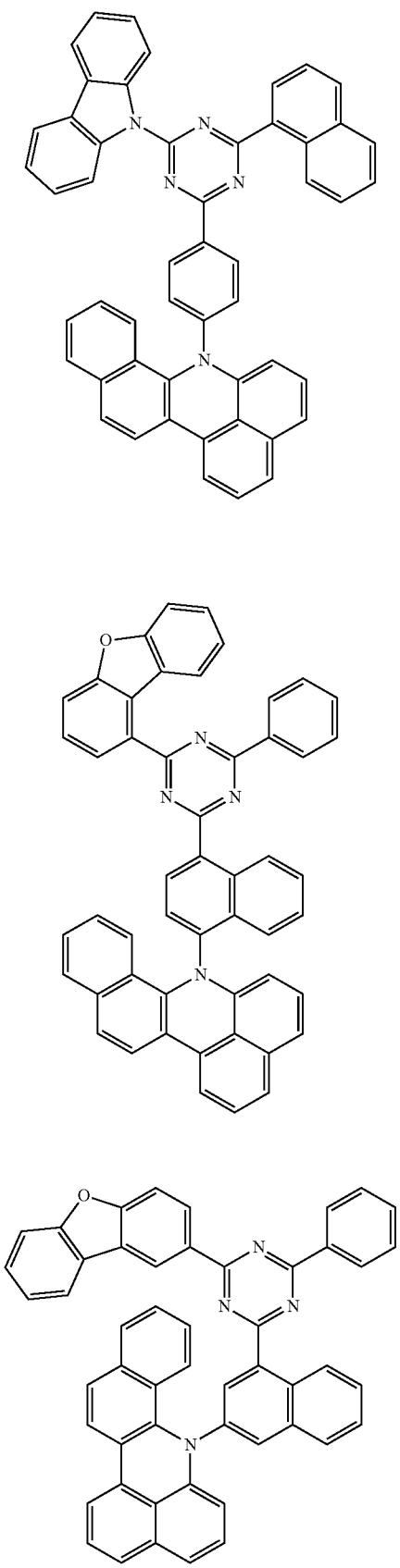
214
-continued
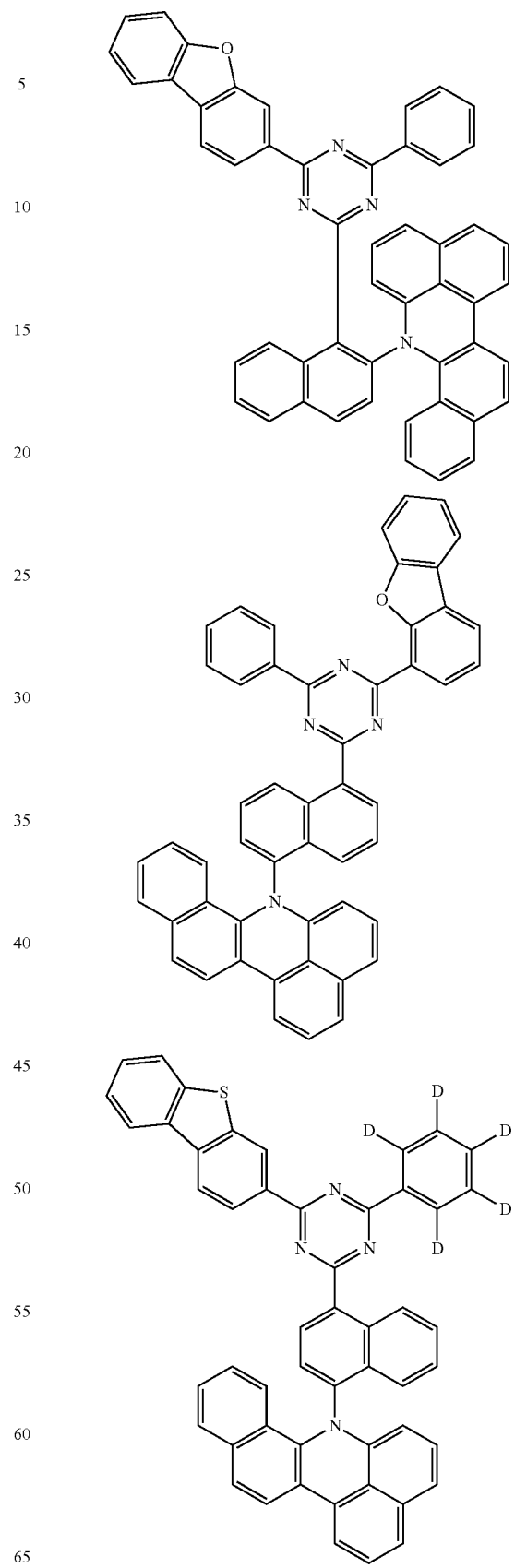

215
-continued
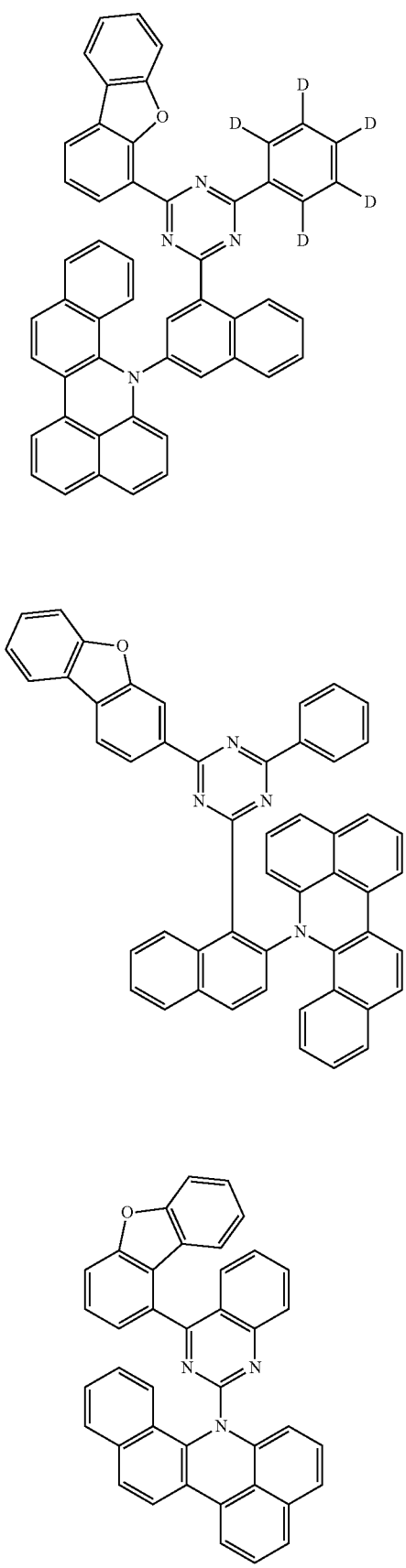
216
-continued
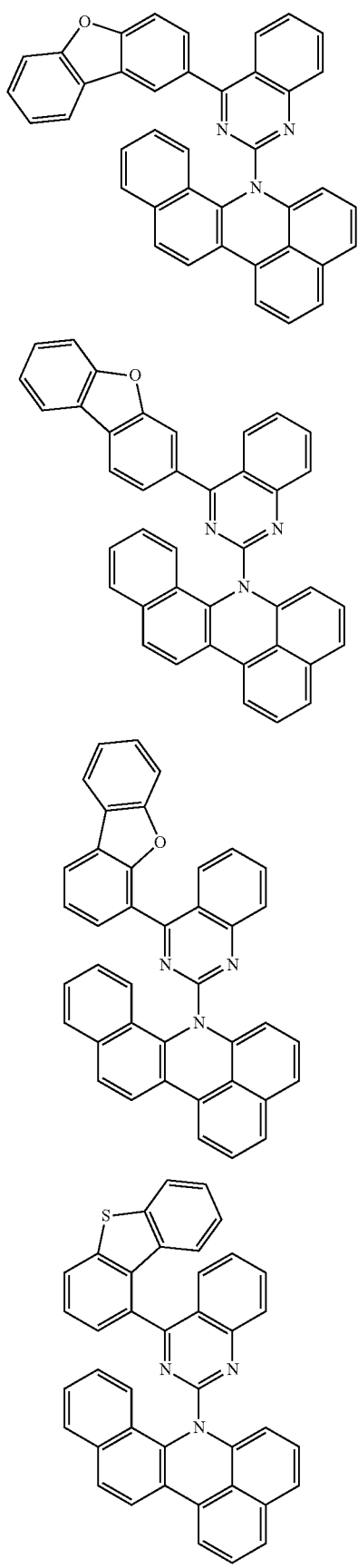

217
-continued
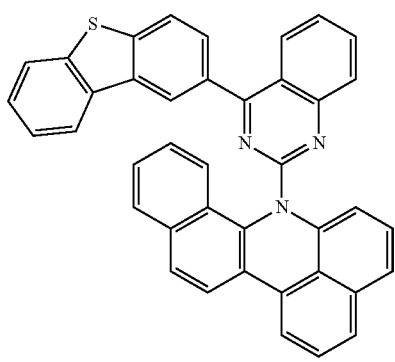
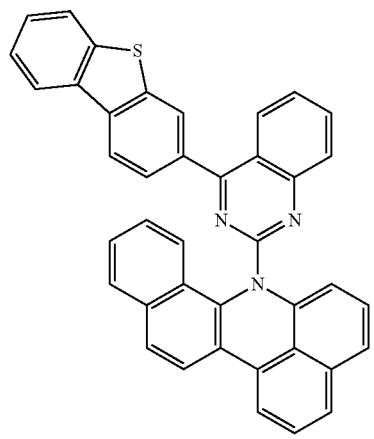
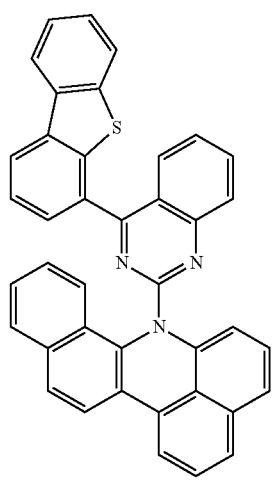
218
-continued
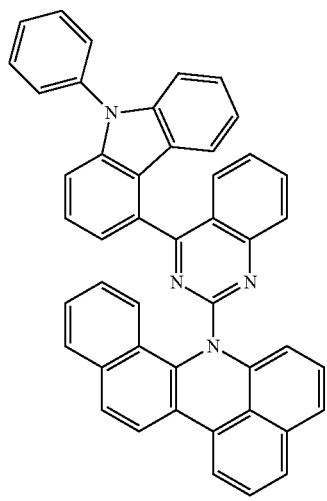
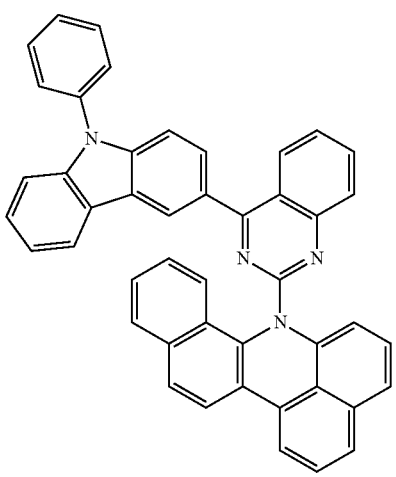
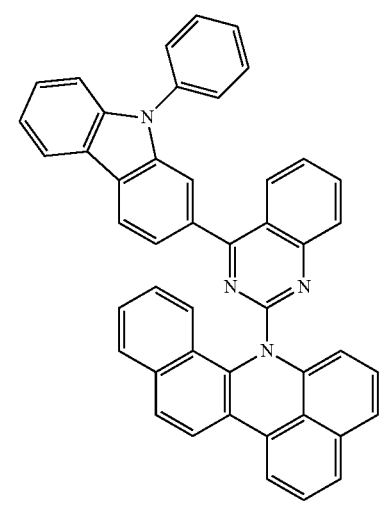

219
-continued
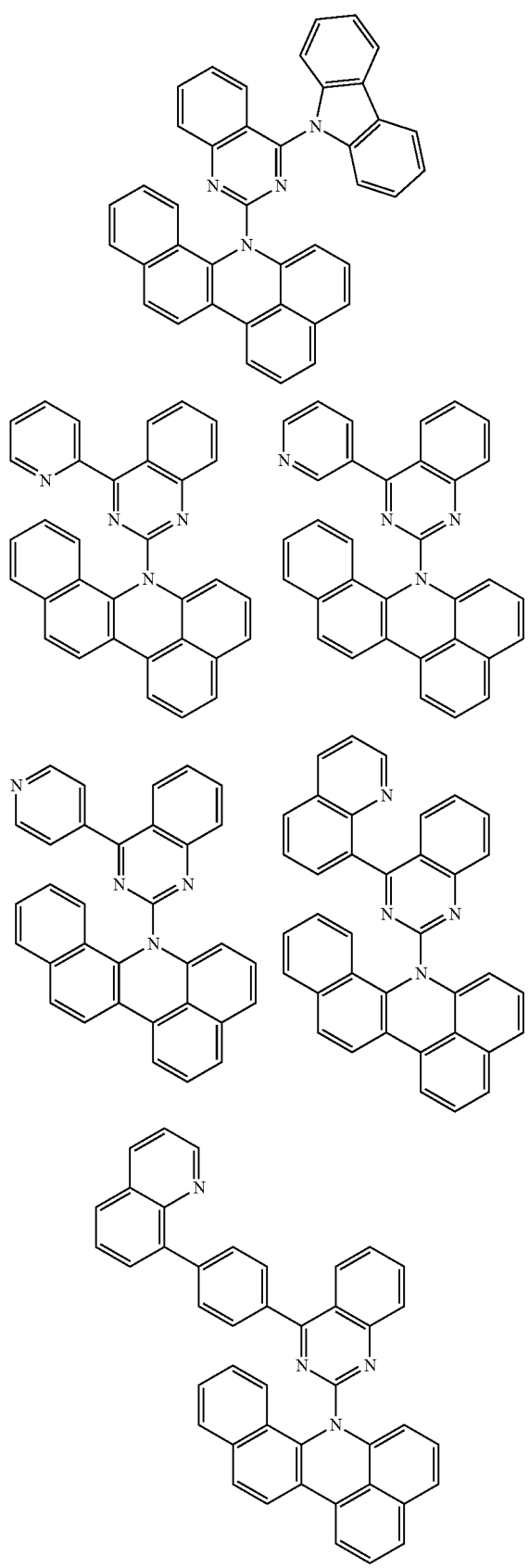
220
-continued
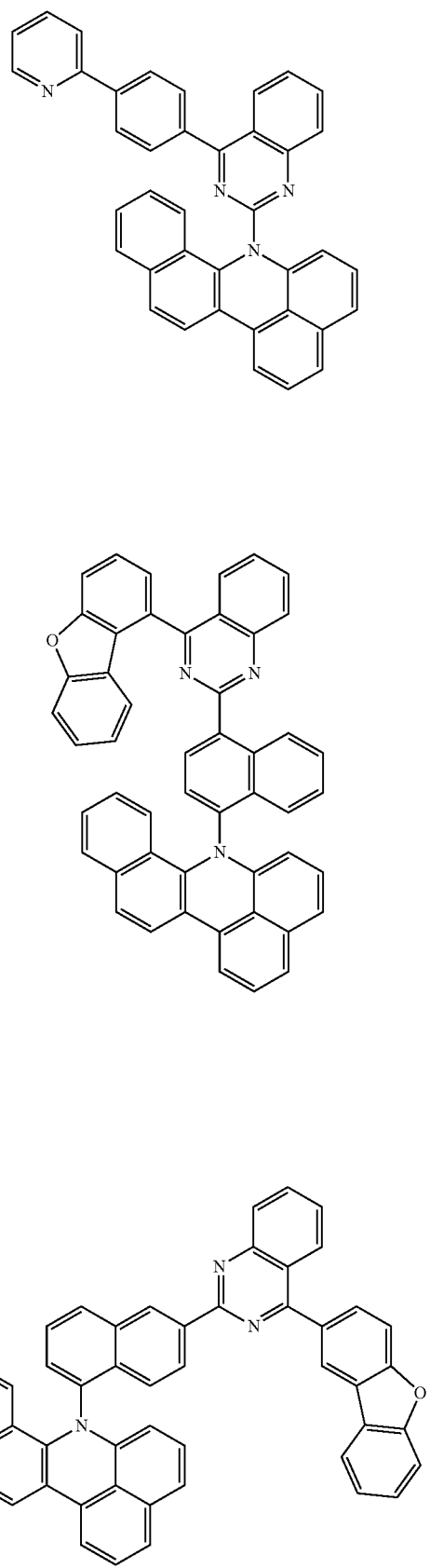

221
-continued
222
-continued
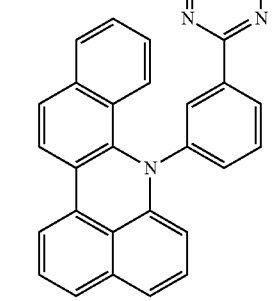
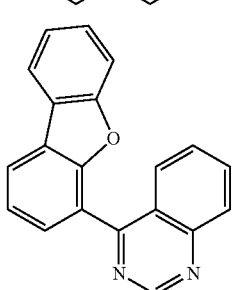
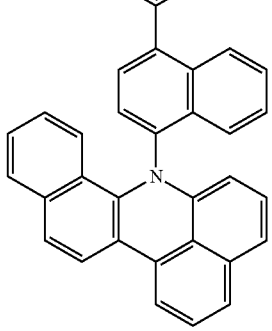
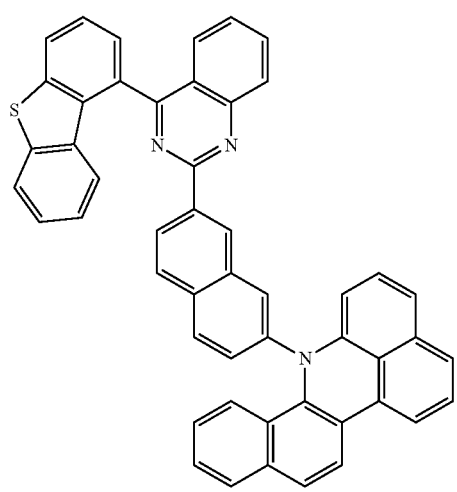
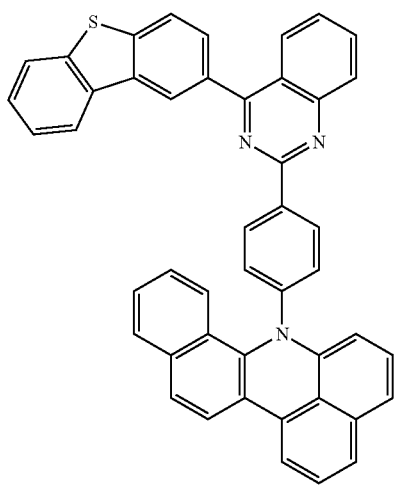
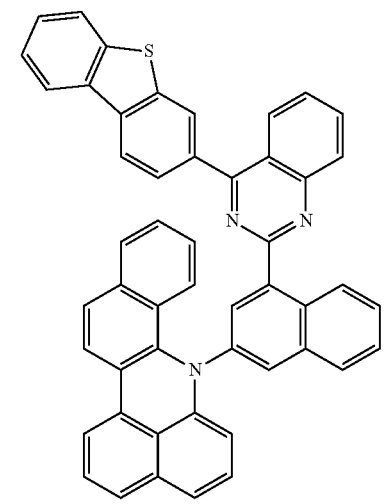
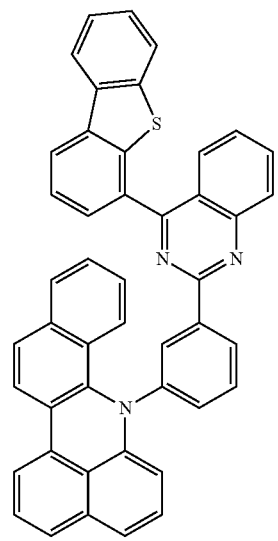

223
-continued
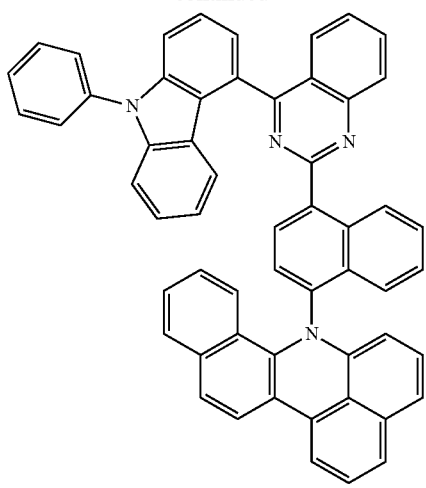
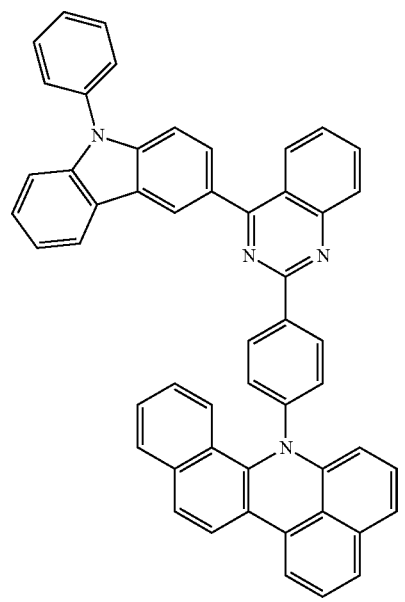
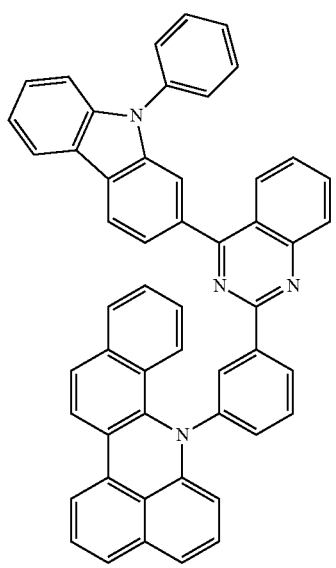
224
-continued
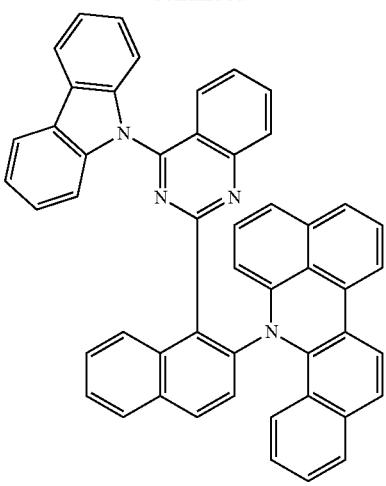
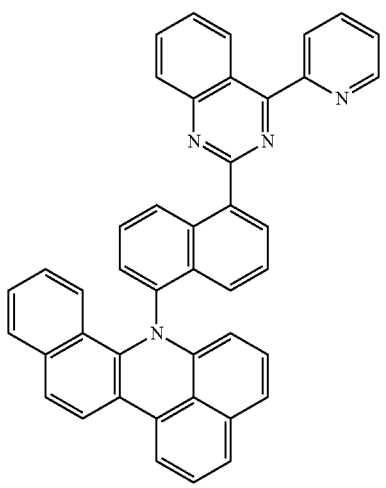
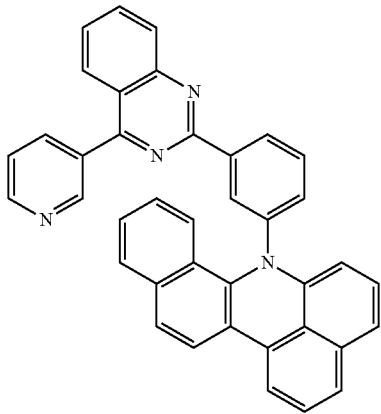

225
-continued
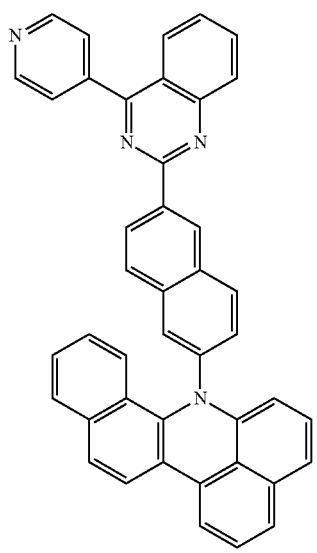
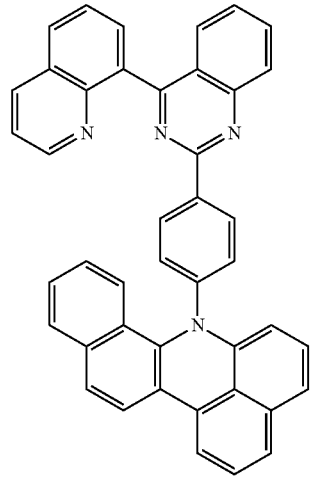
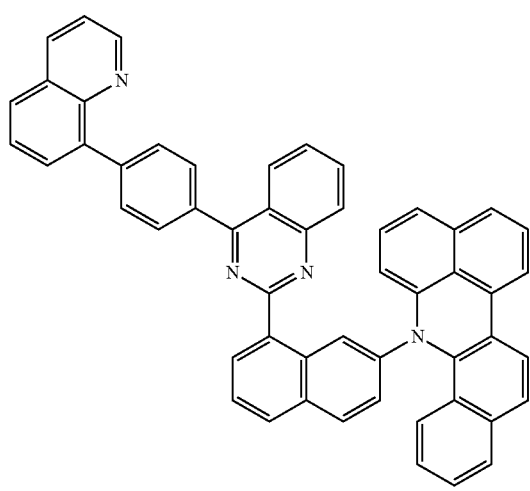
226
-continued
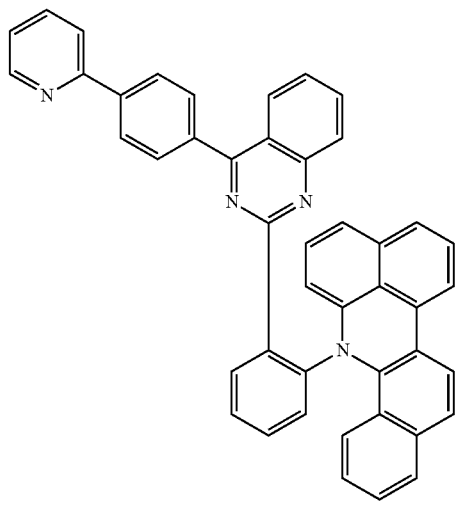
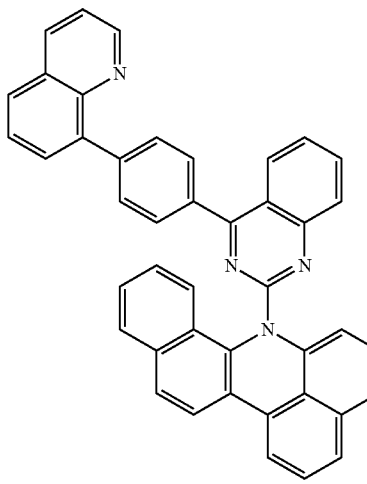
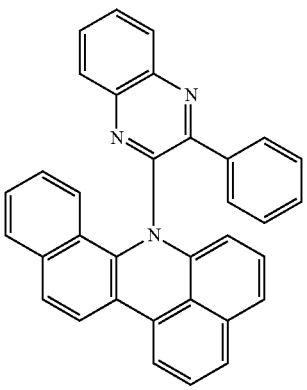

227
-continued
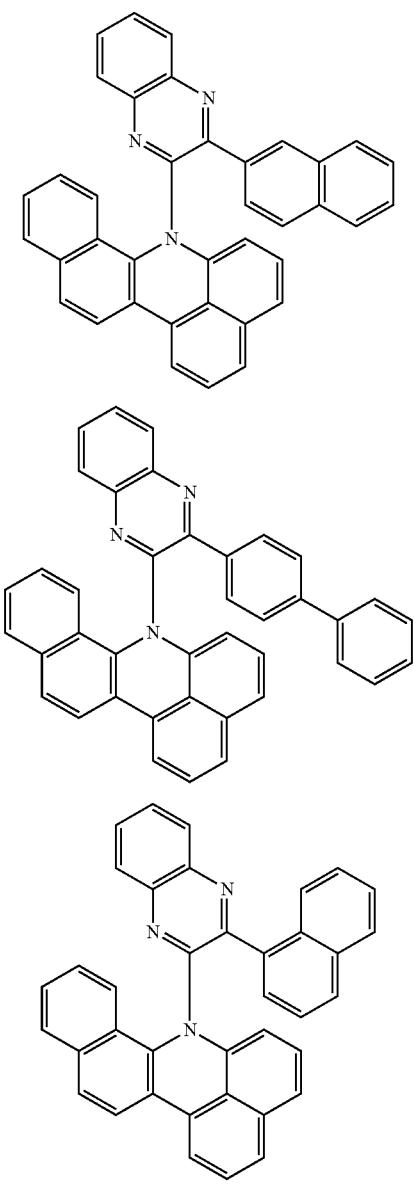
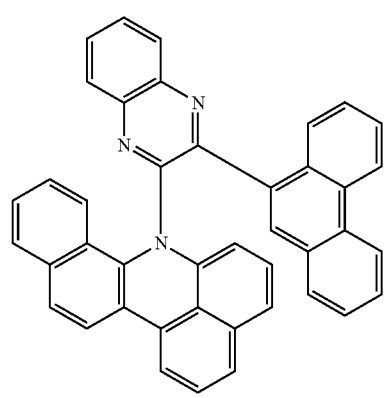
228
-continued
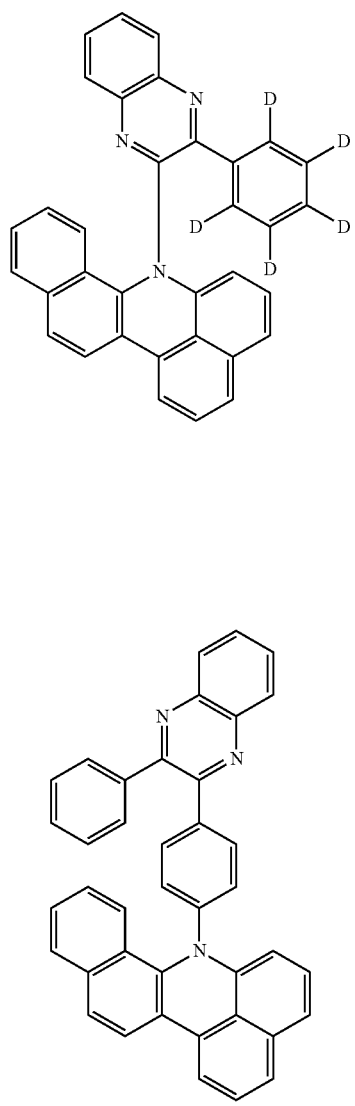
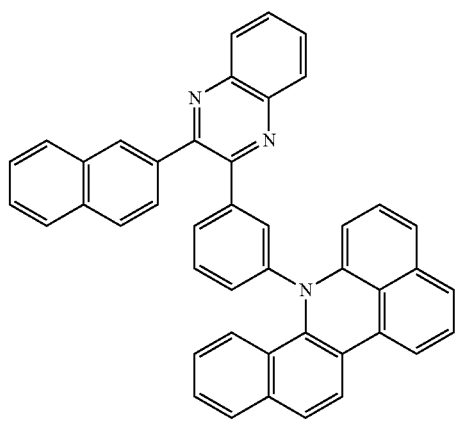

229
-continued
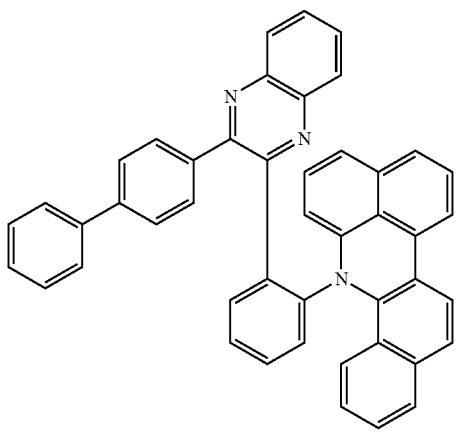
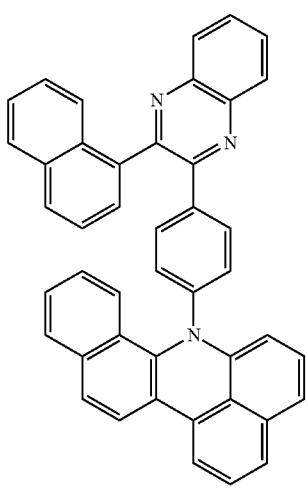
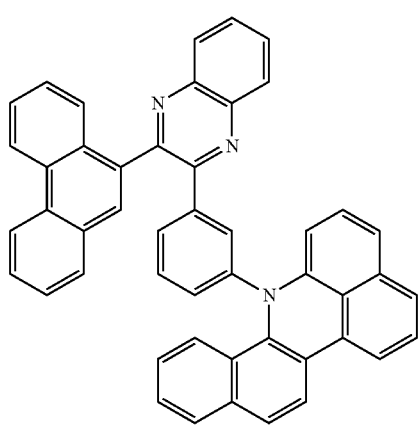
230
-continued
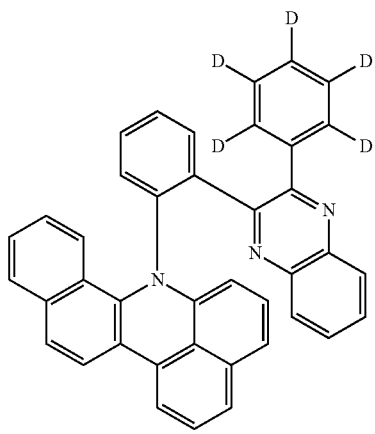
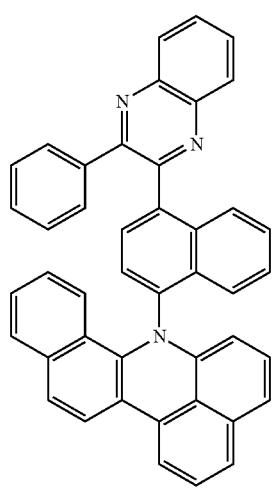
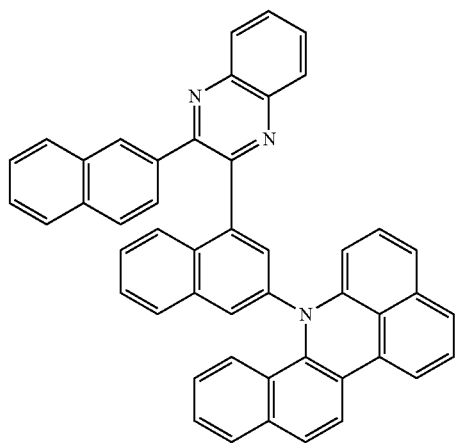

231
-continued
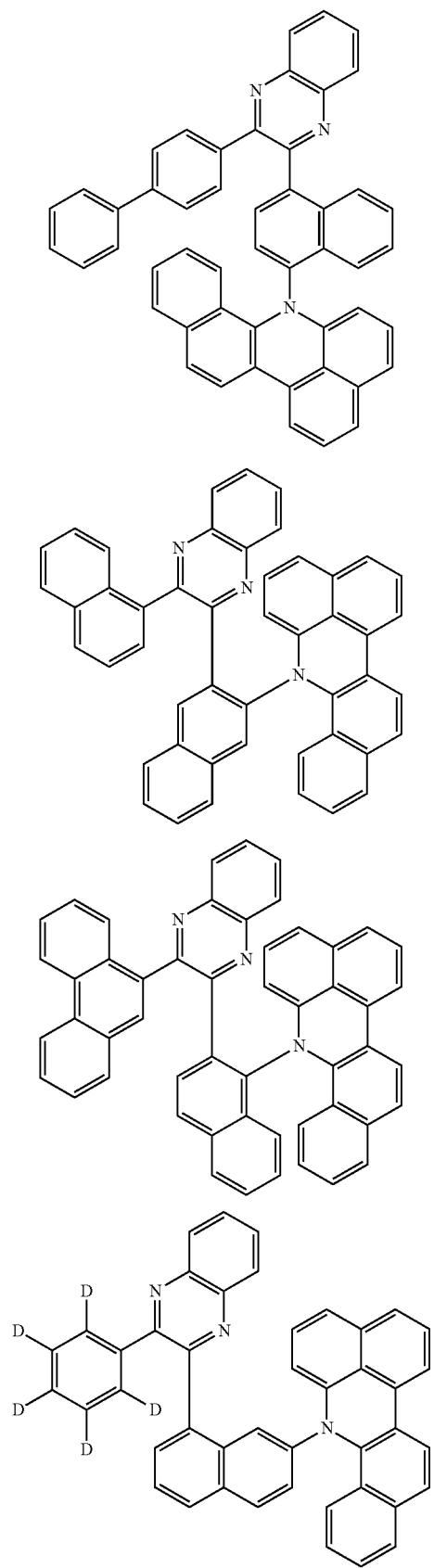
232
-continued
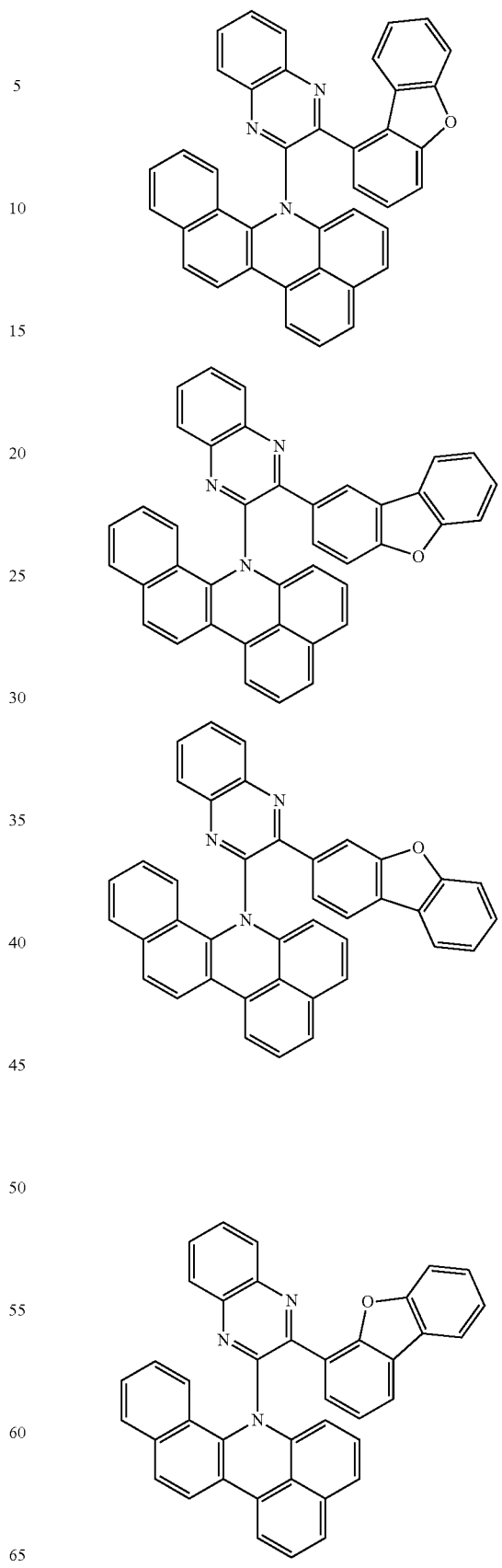

233
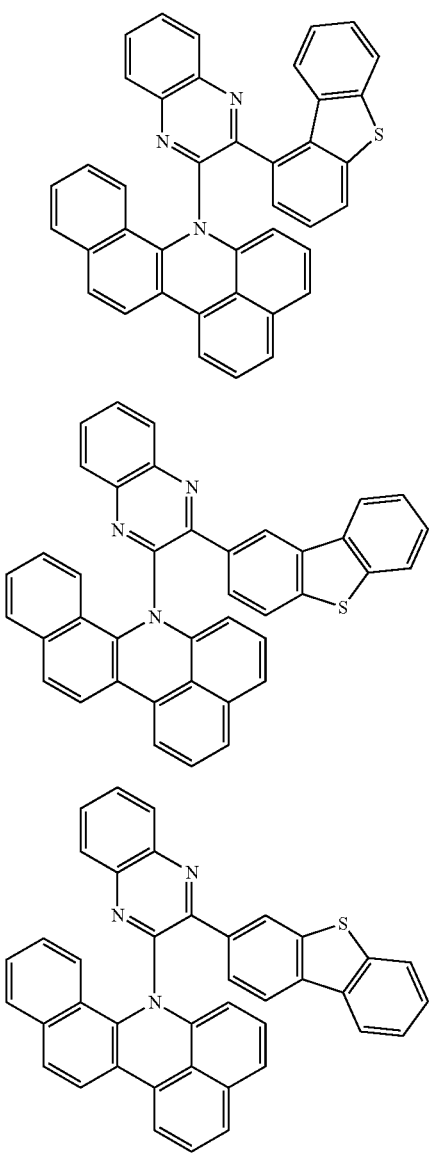
234
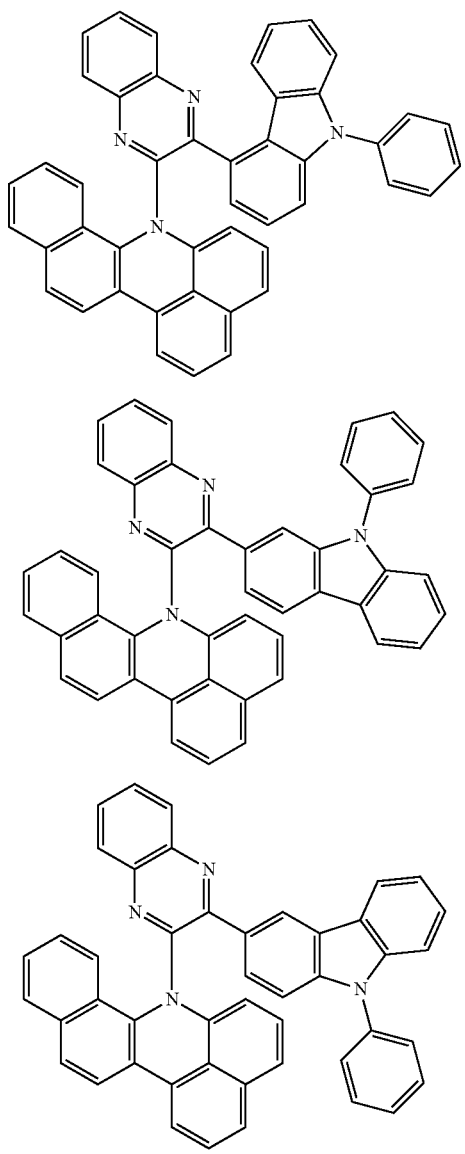
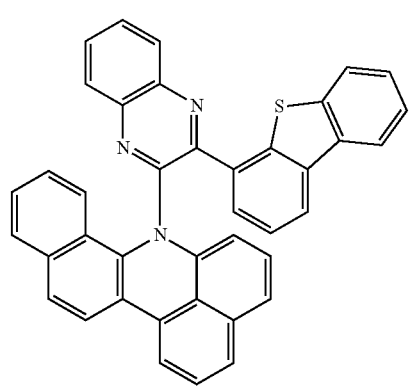

235
-continued
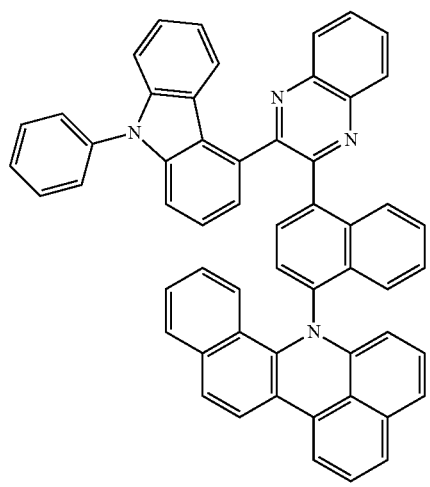
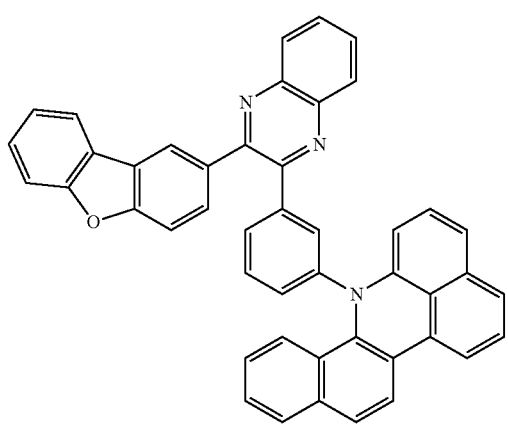
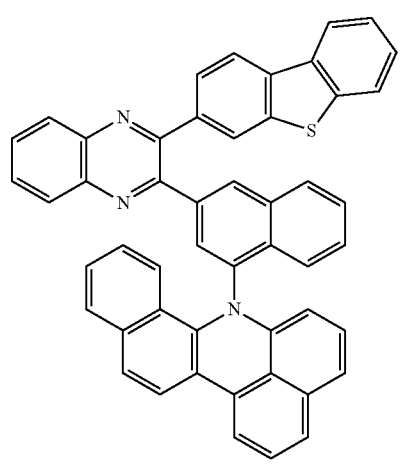
236
-continued
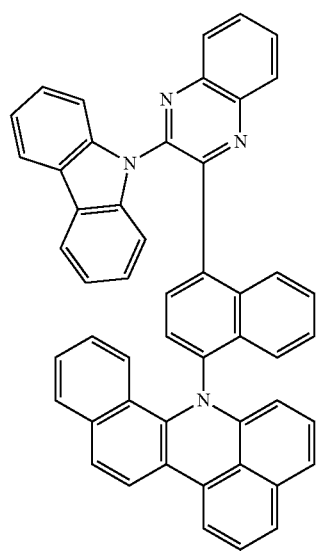
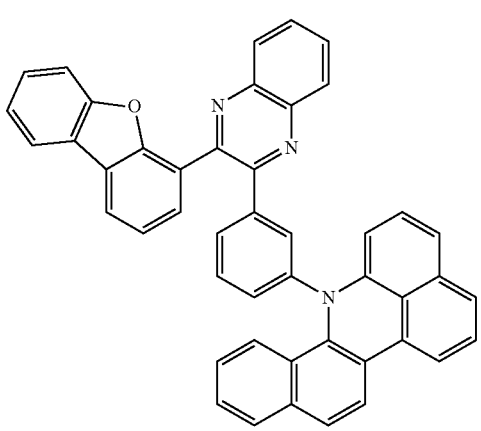
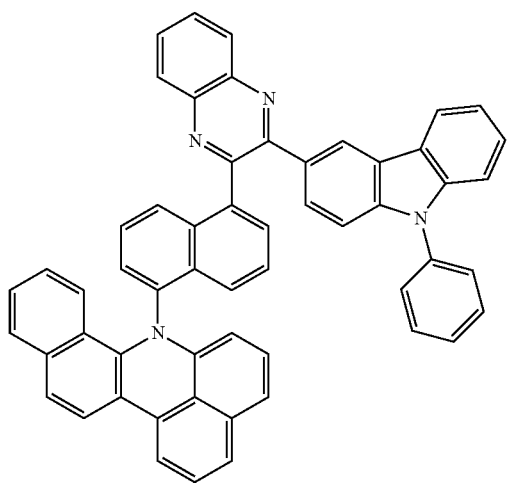

237
-continued
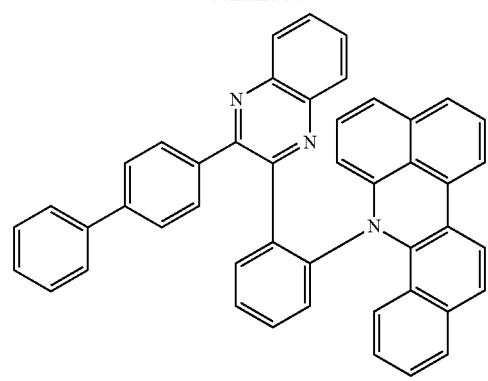
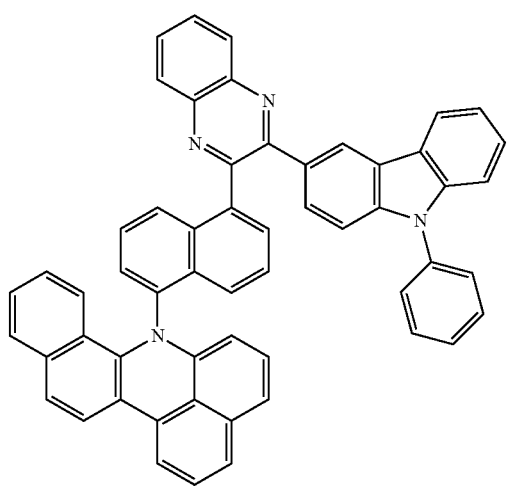
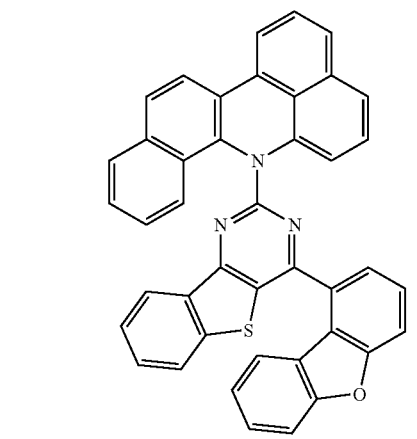
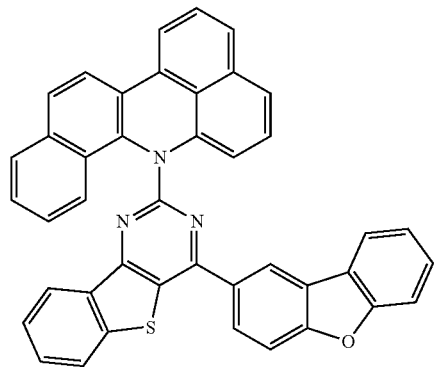
238
-continued
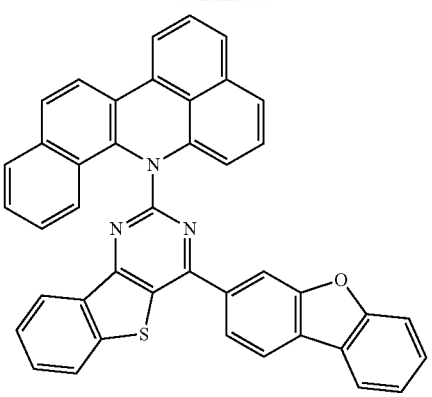
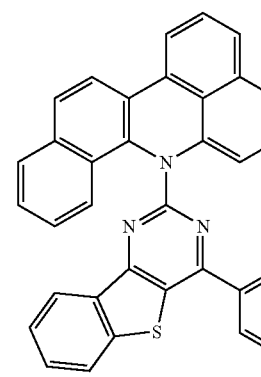
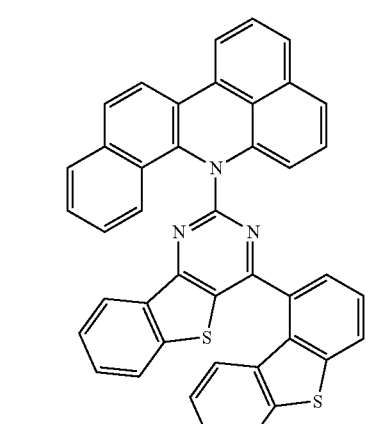
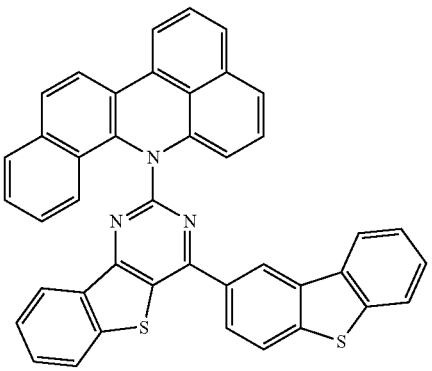

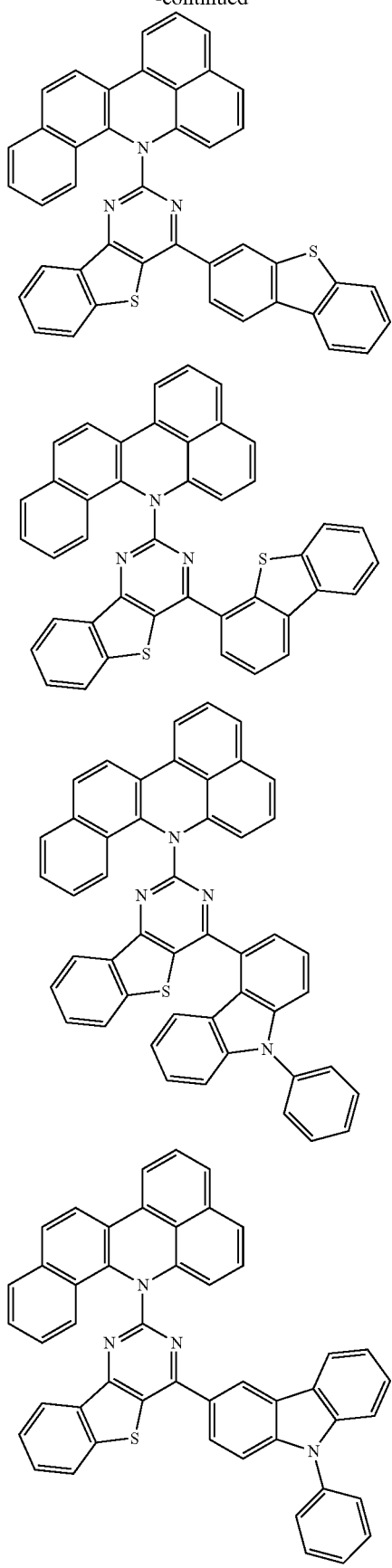
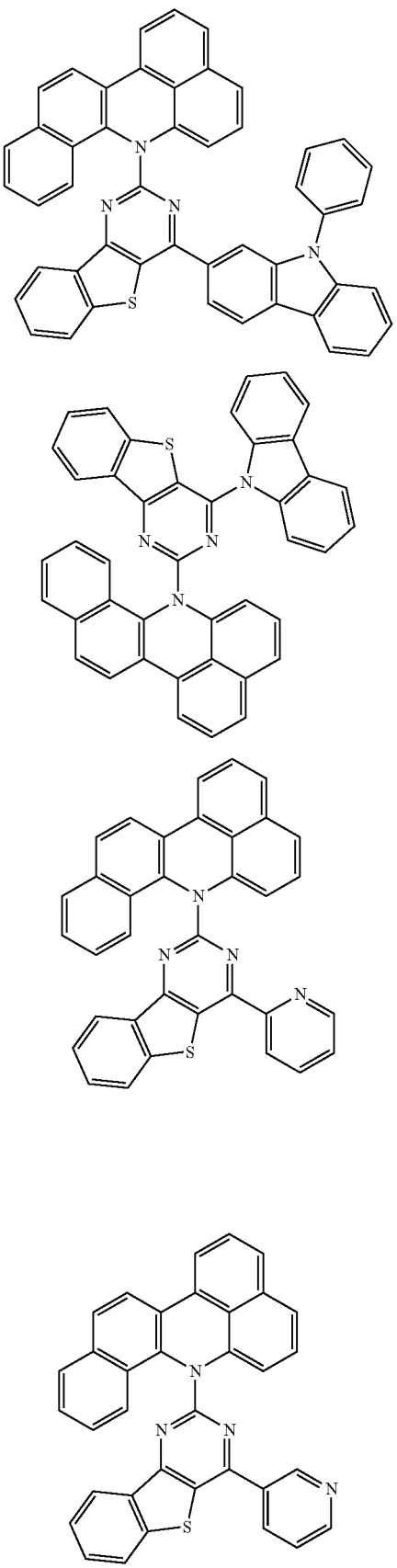

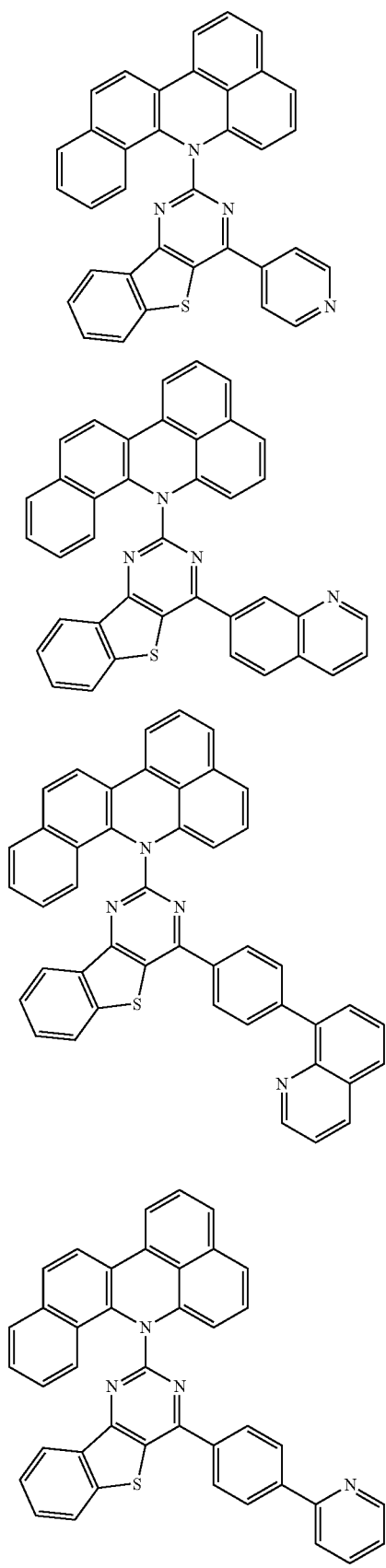
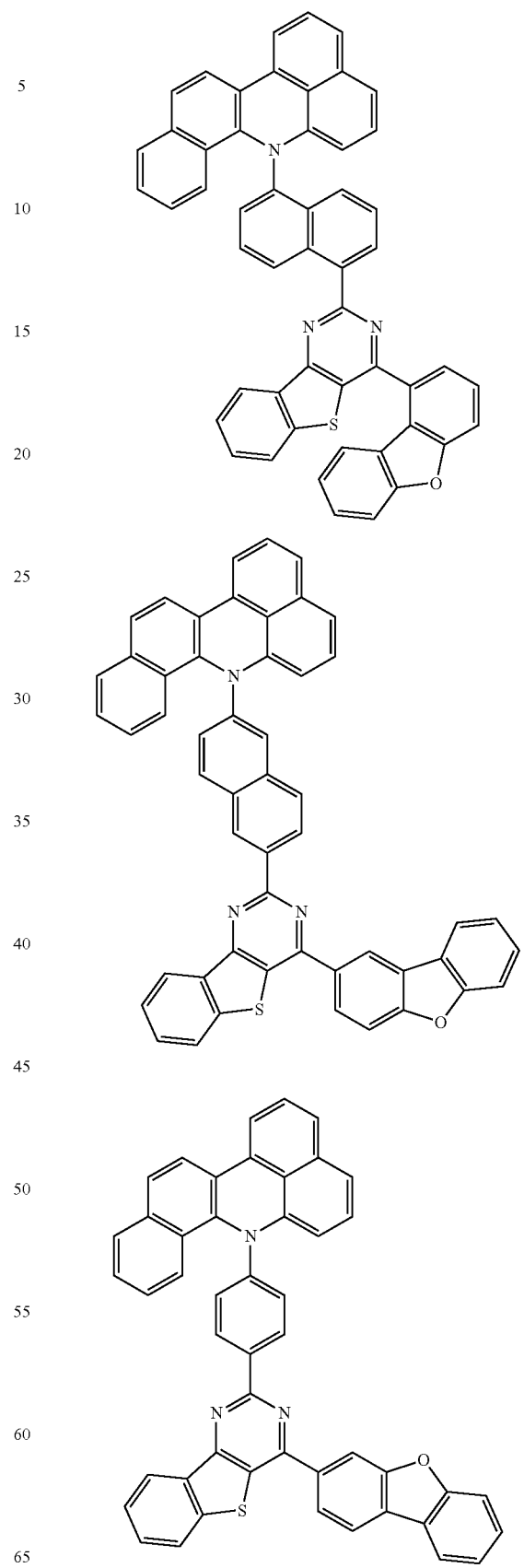

243
-continued
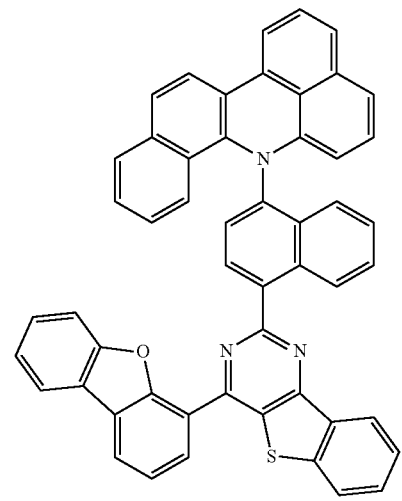
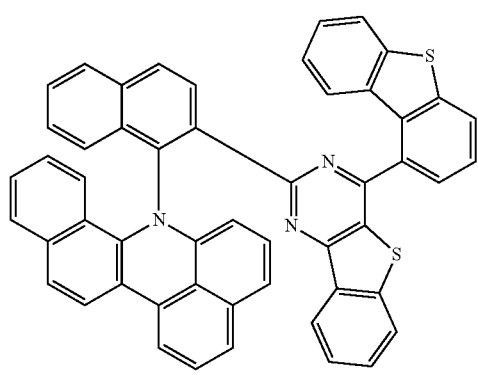
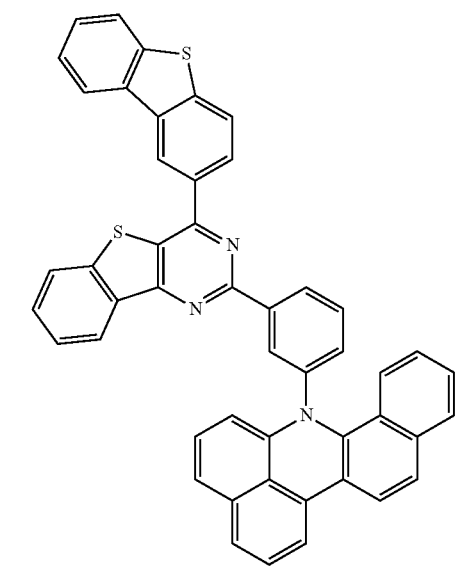
244
-continued
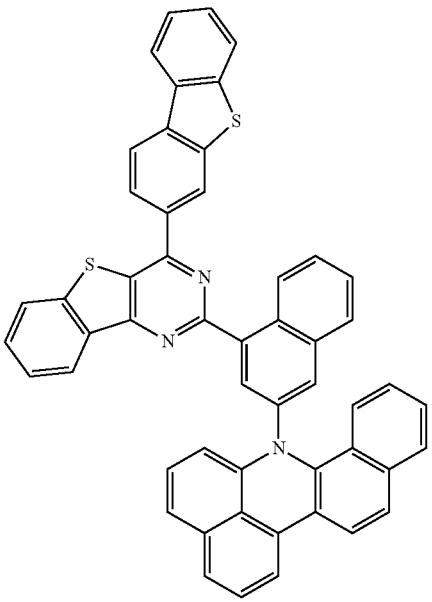
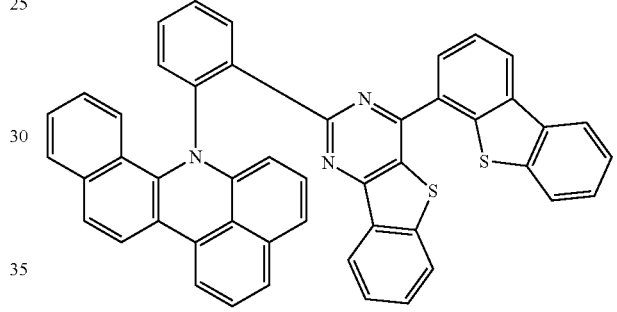
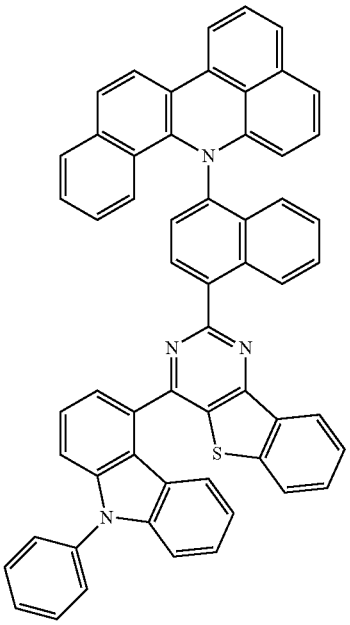

245
-continued
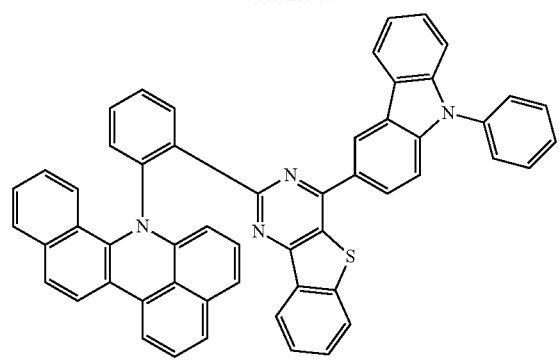
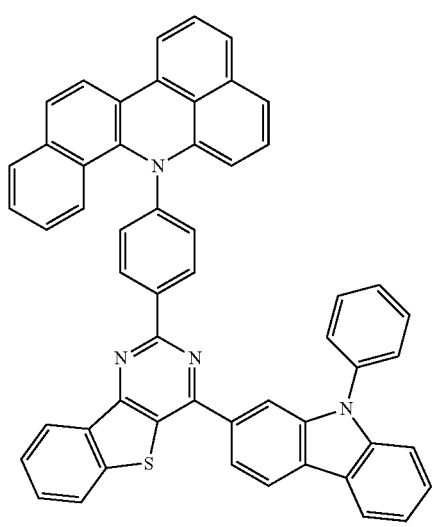
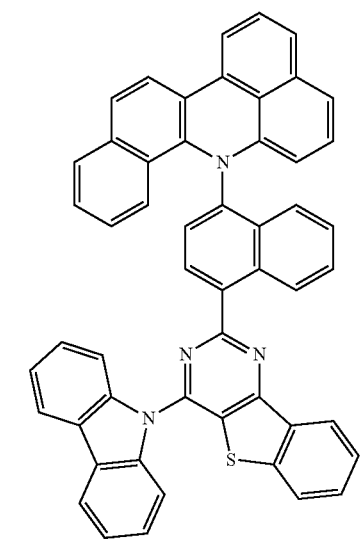
246
-continued
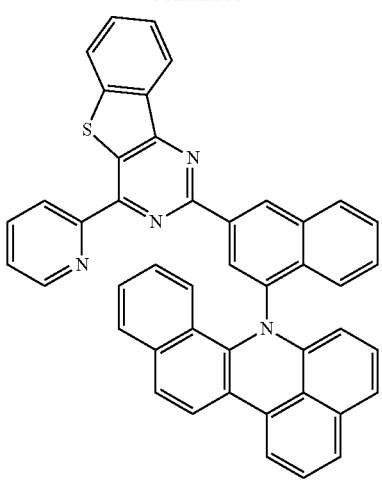
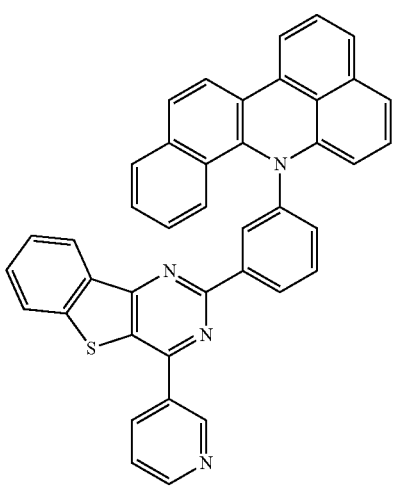
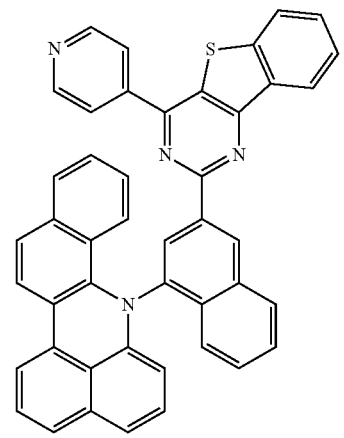

247
-continued
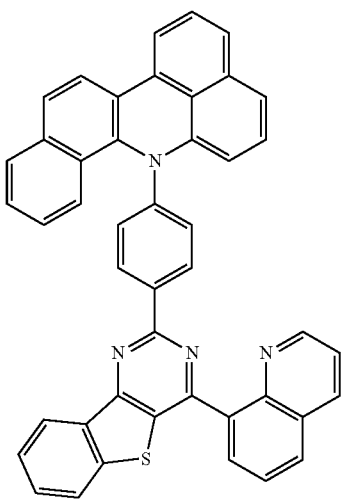
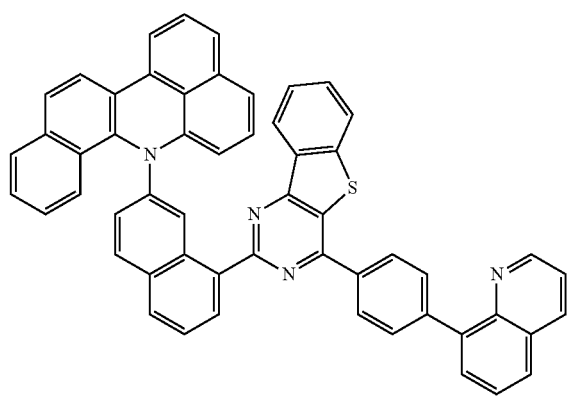
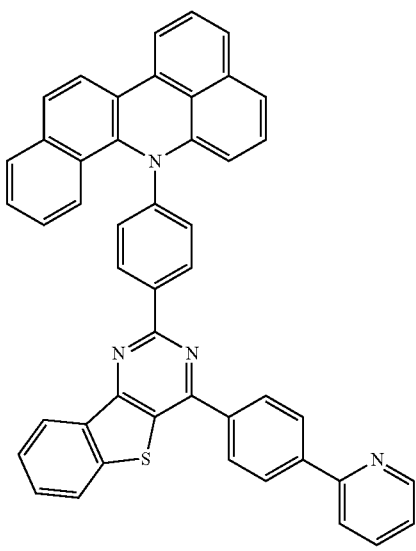
248
-continued
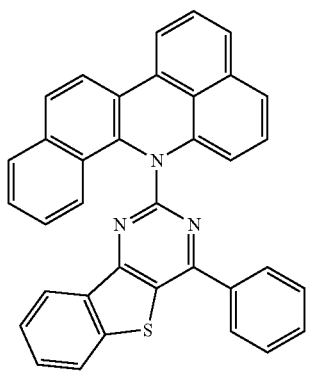
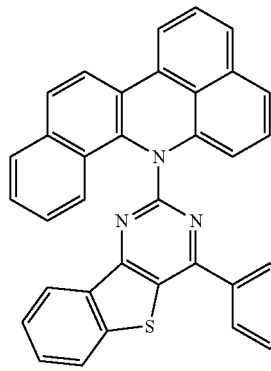
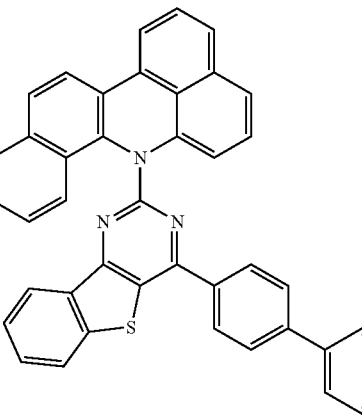
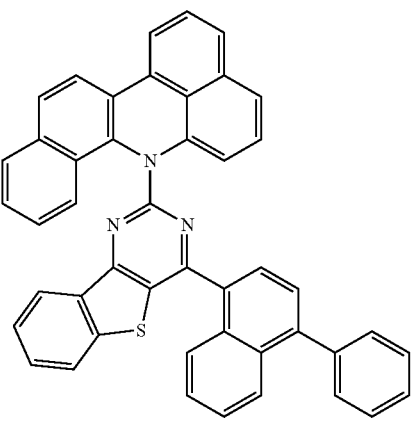

249
-continued
250
-continued
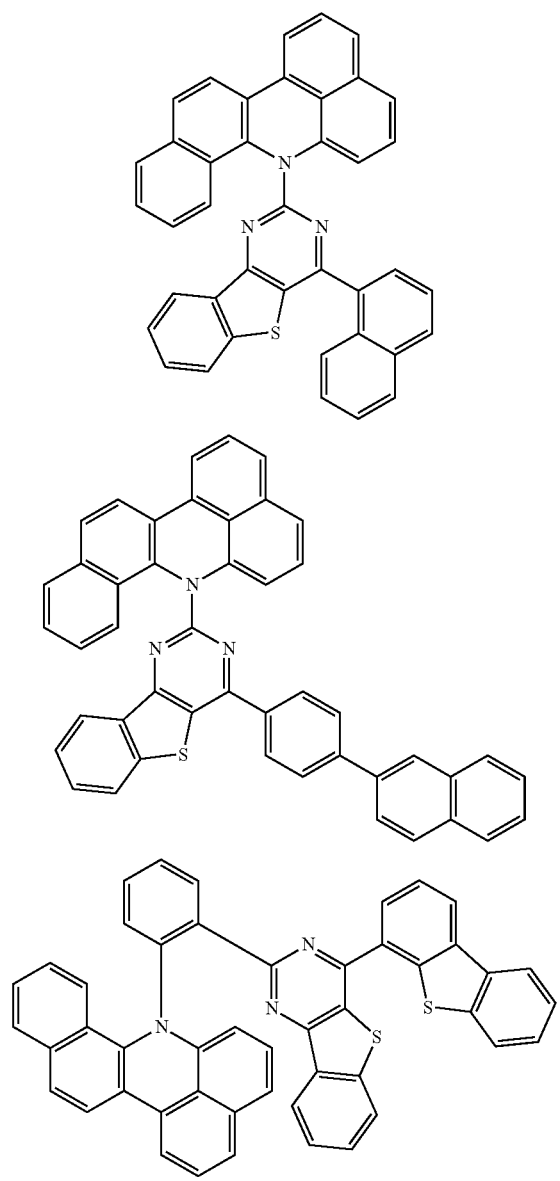
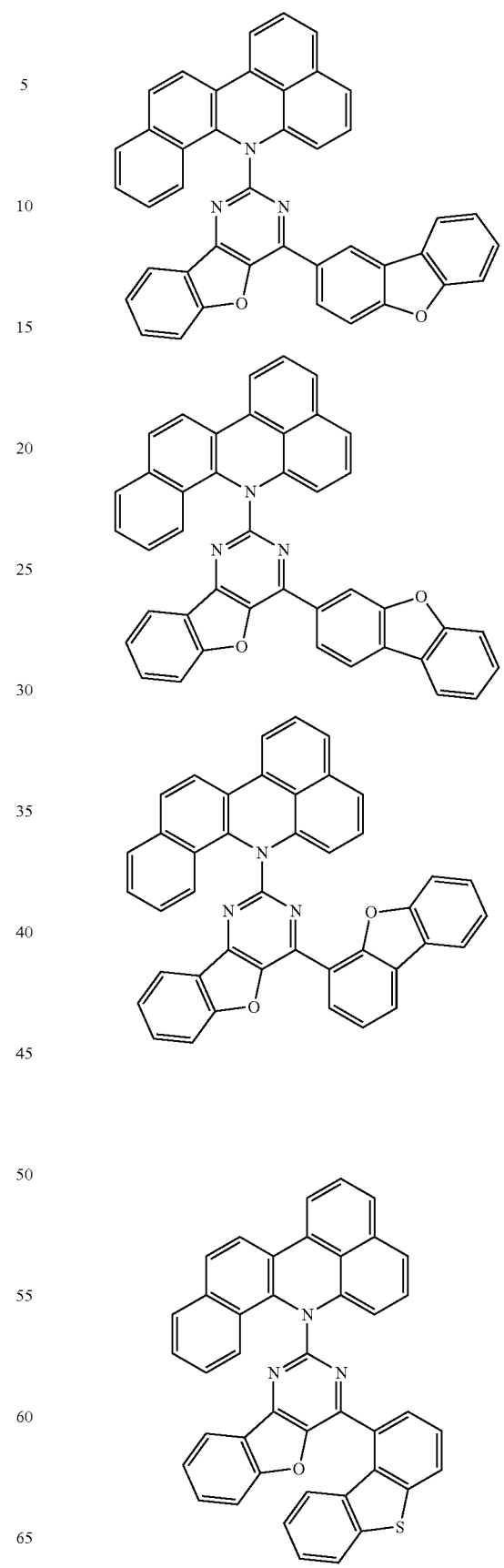

251
-continued
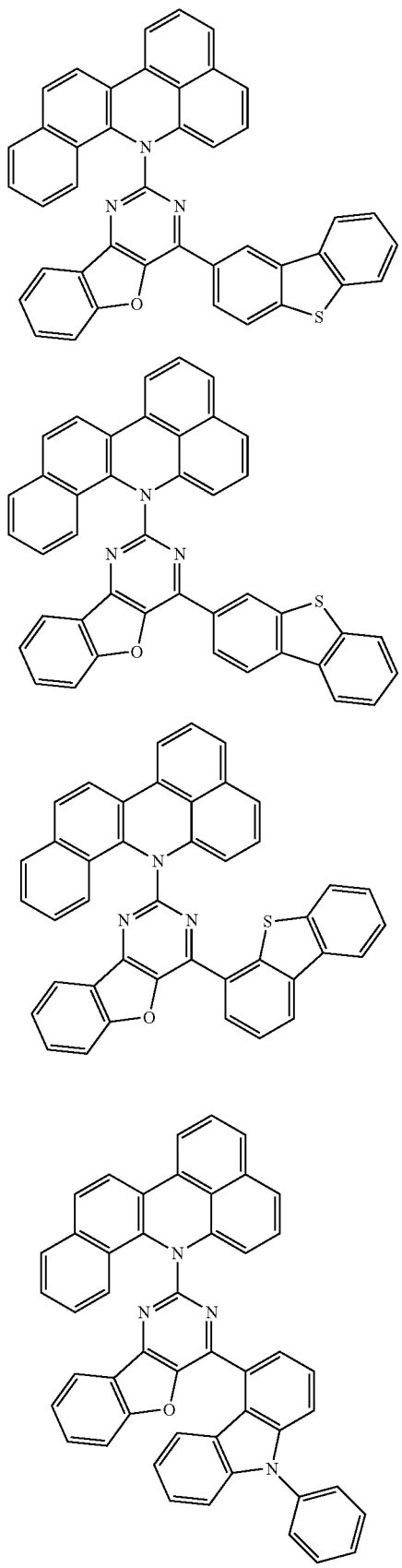
252
-continued
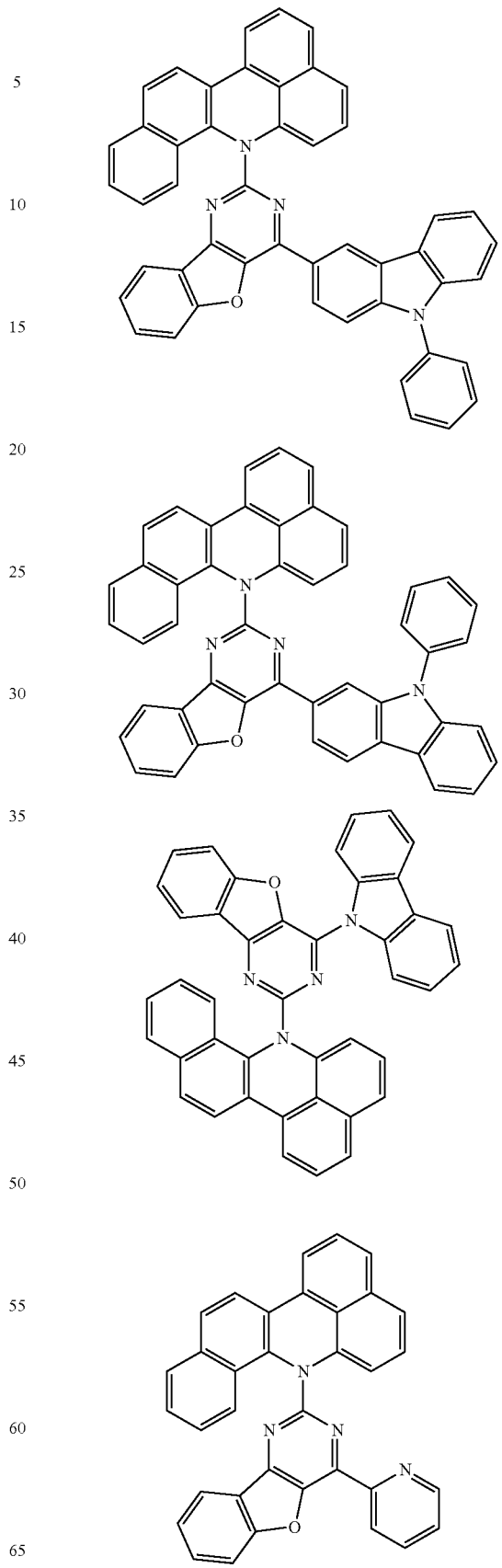

253
-continued
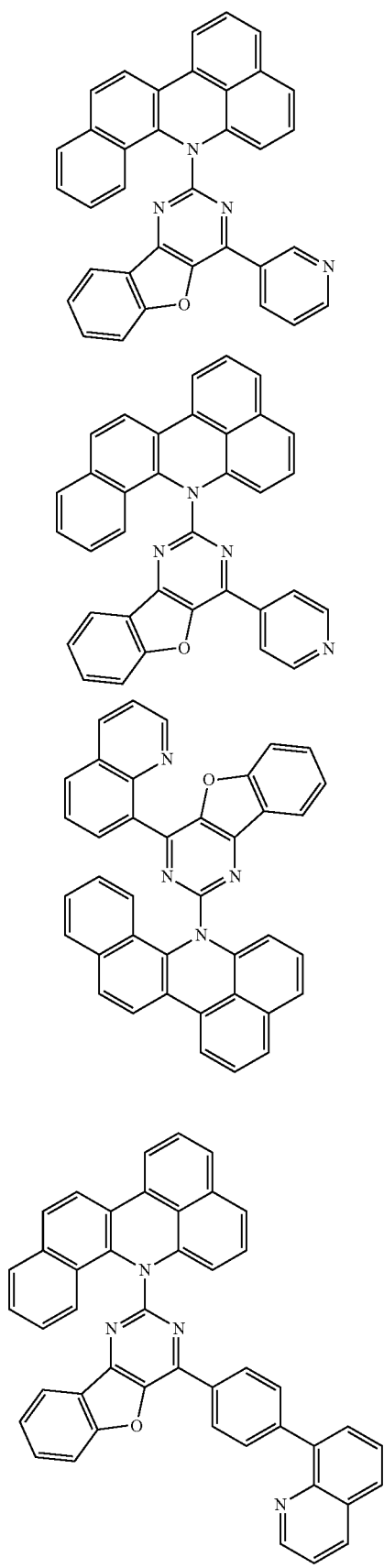
254
-continued
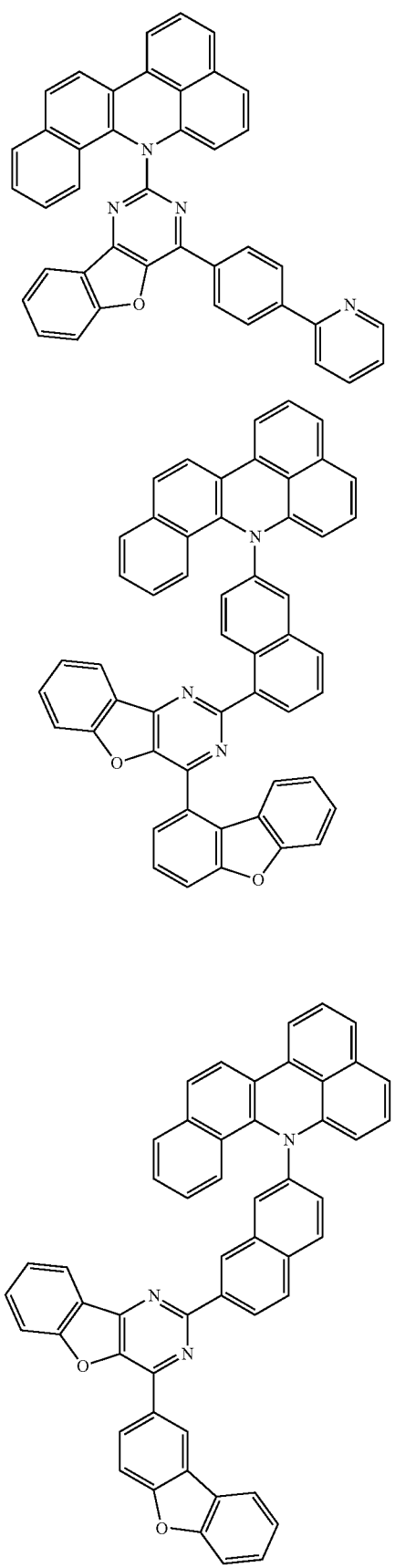

255
-continued
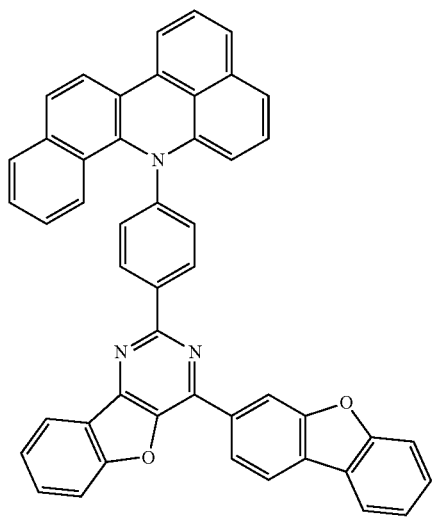
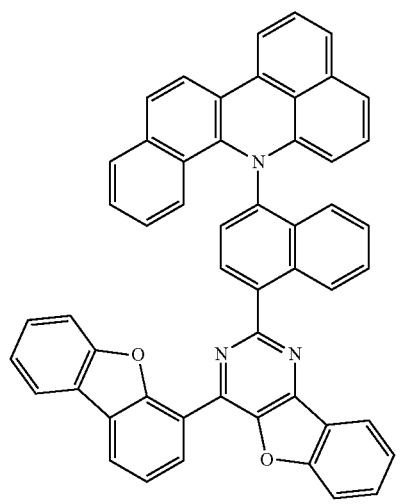
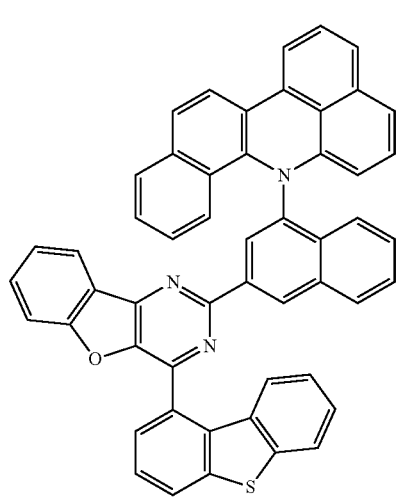
256
-continued
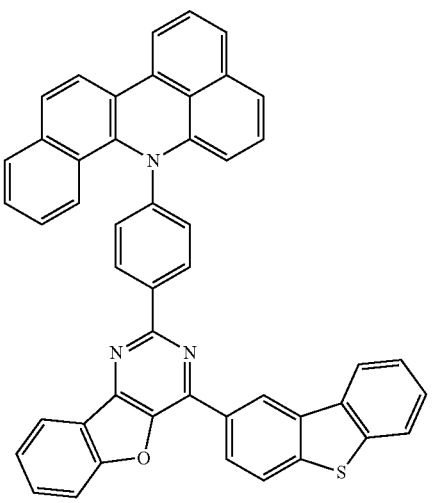
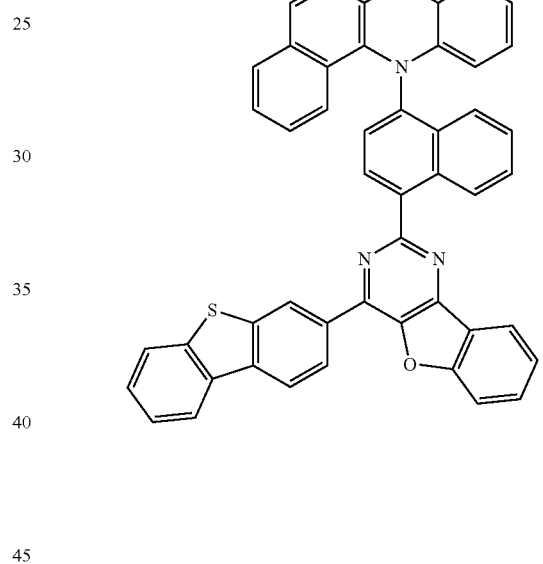
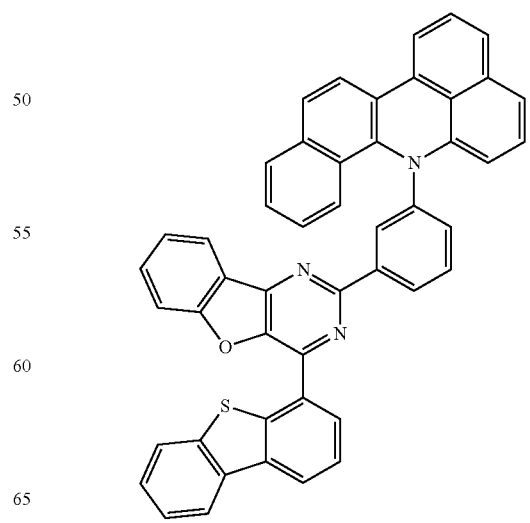

257
-continued
258
-continued
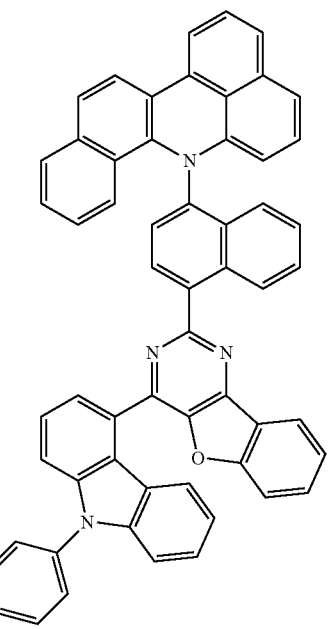
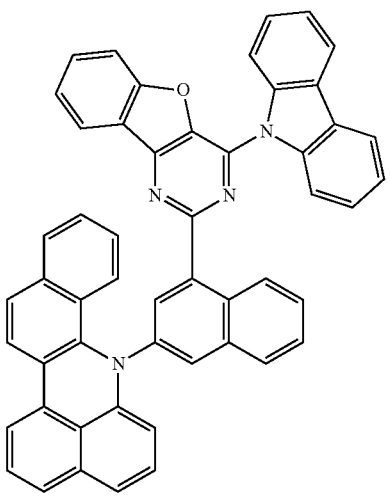
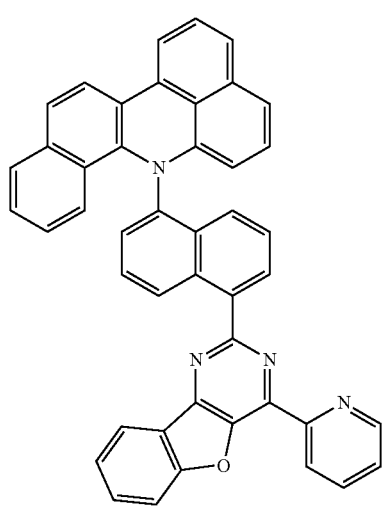
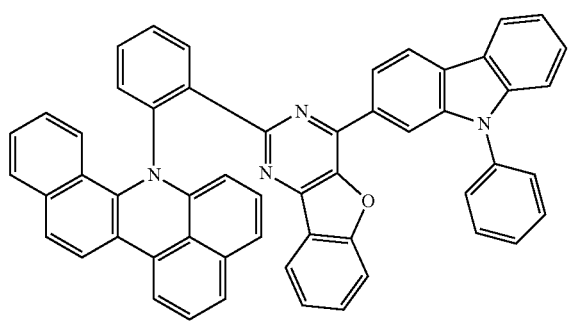
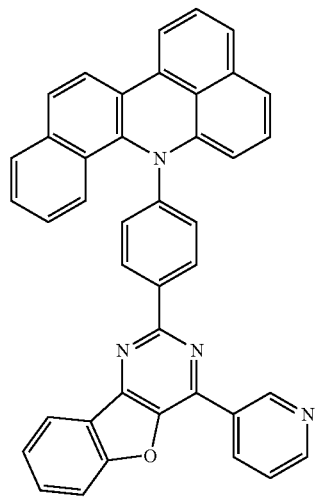

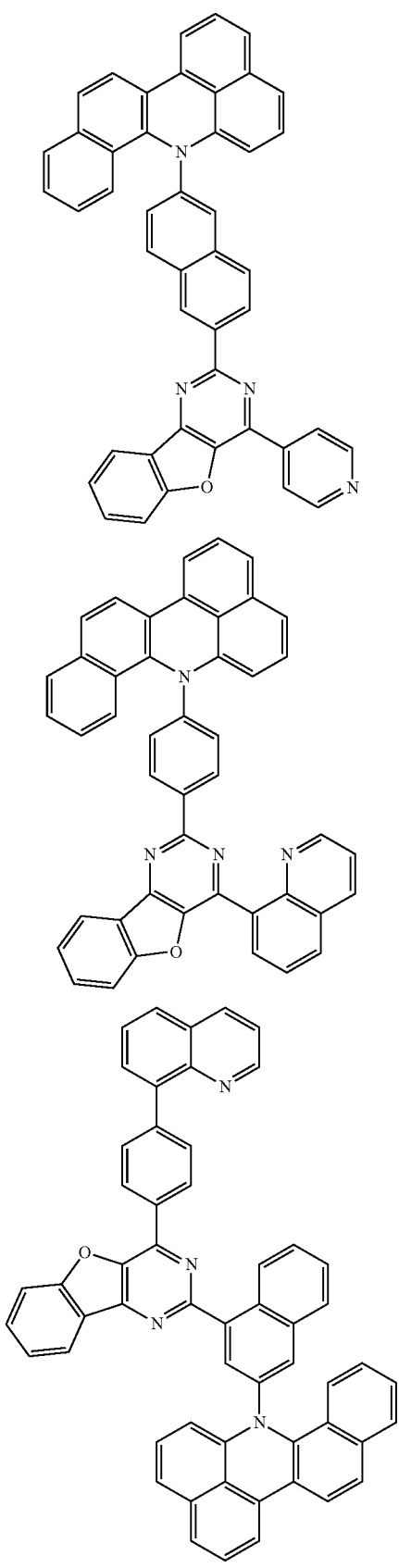
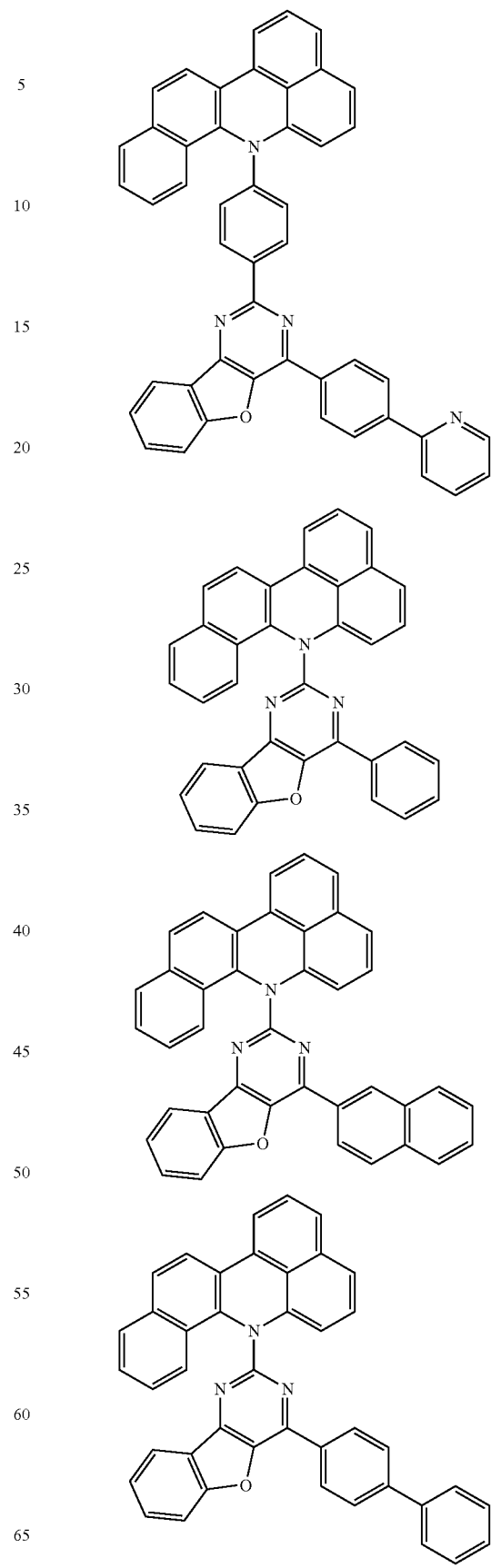

261
-continued
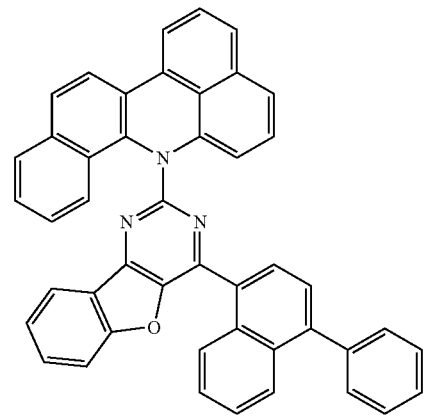
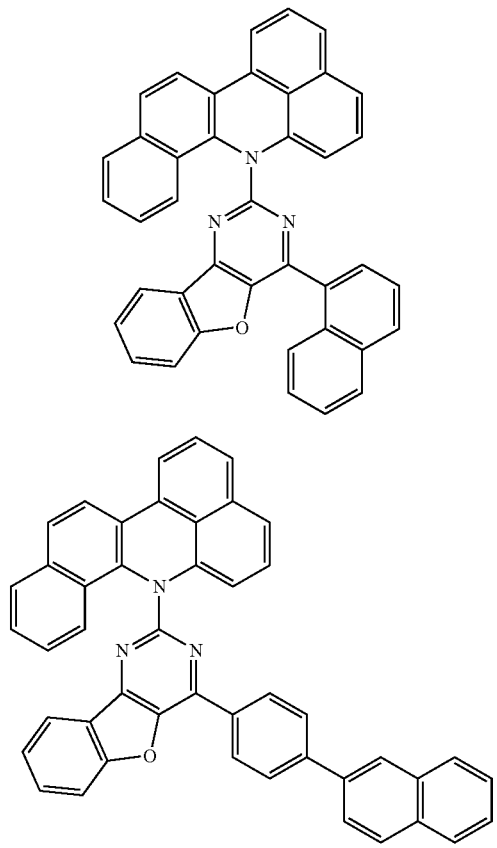
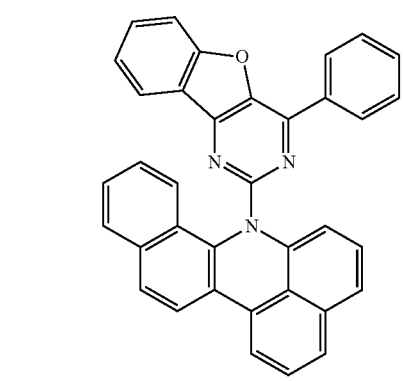
262
-continued
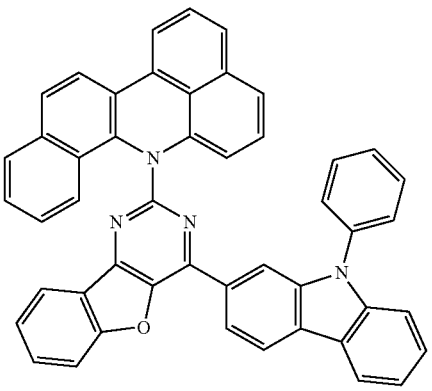
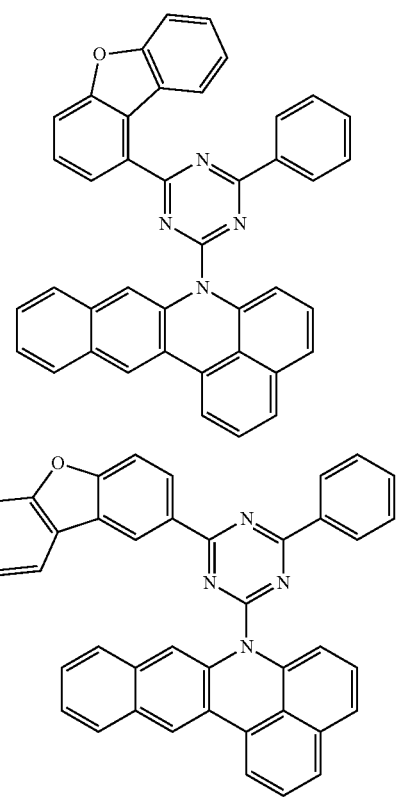
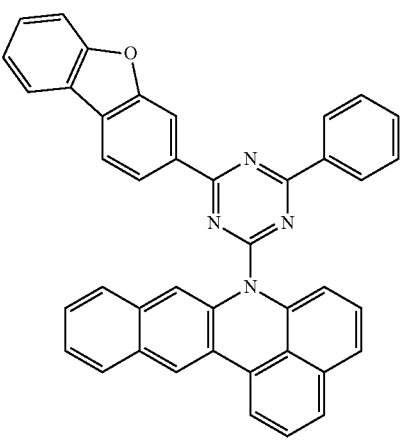

263
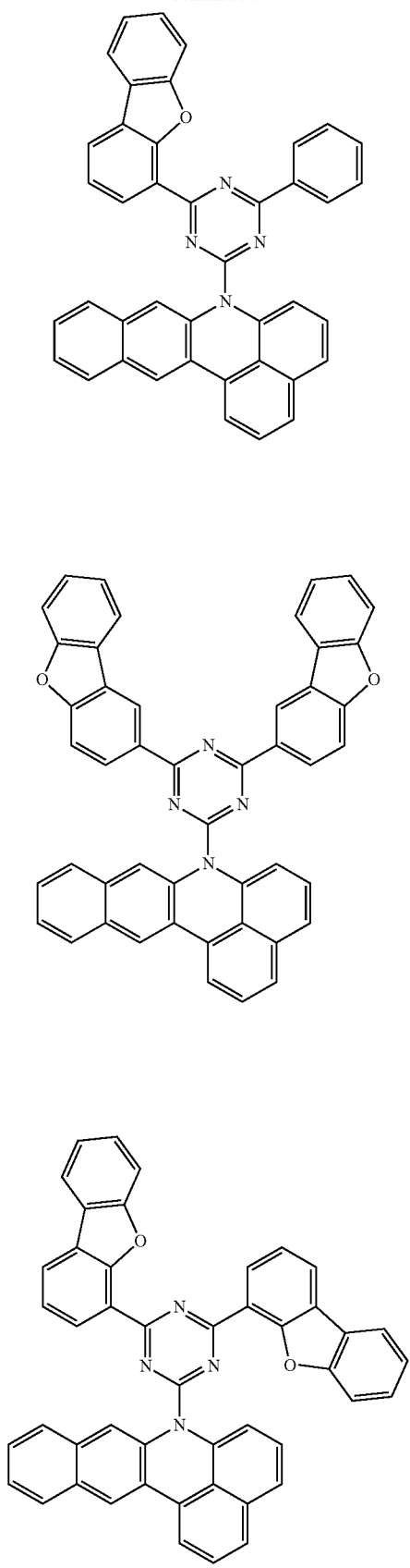
264
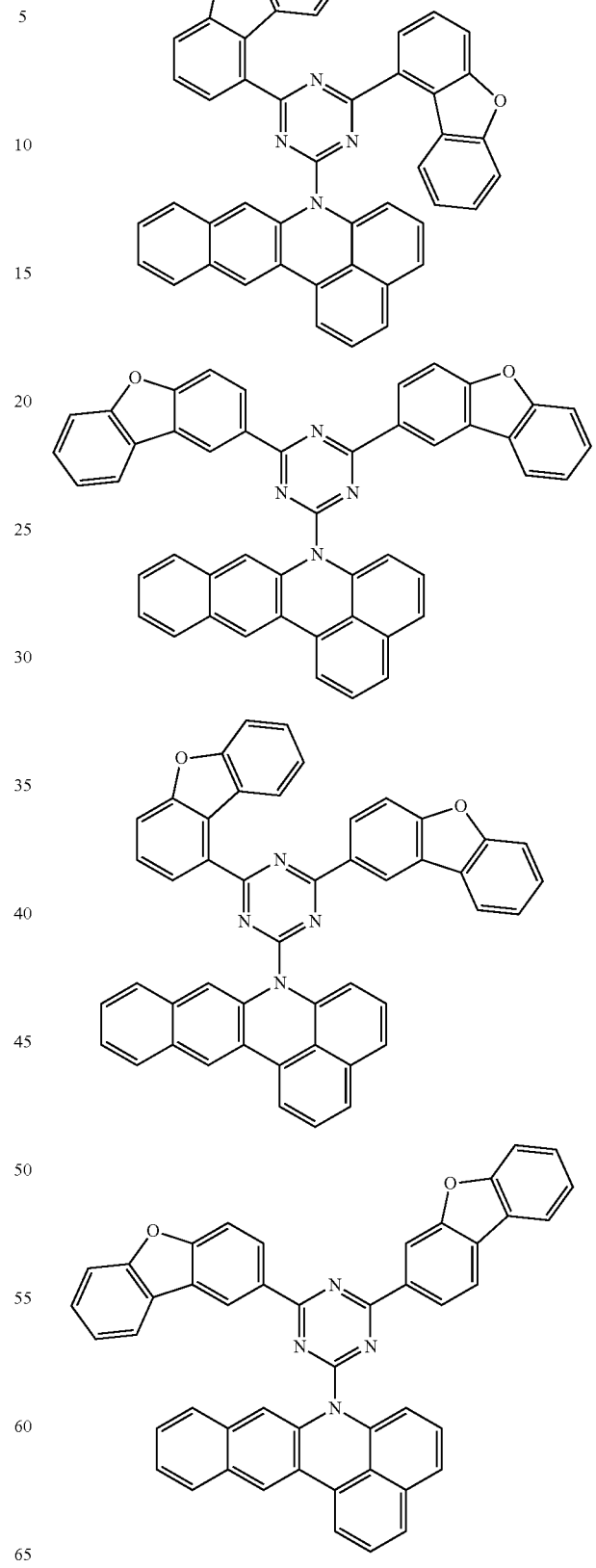

265
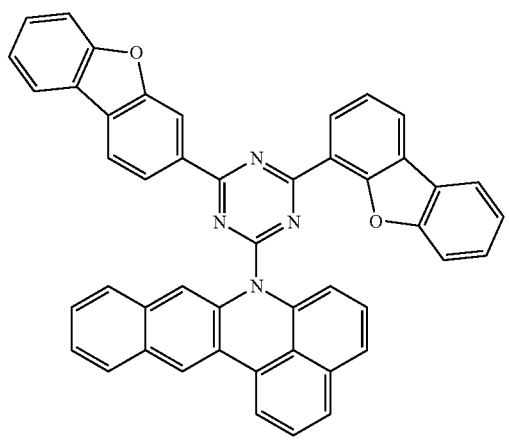
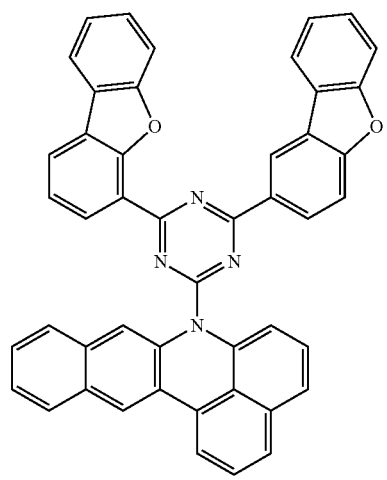
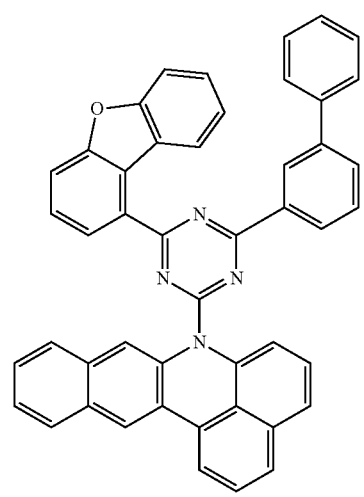
266
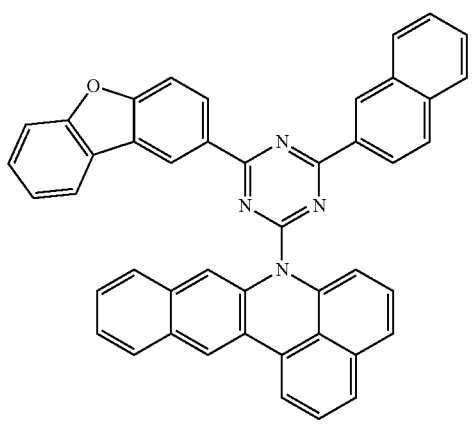
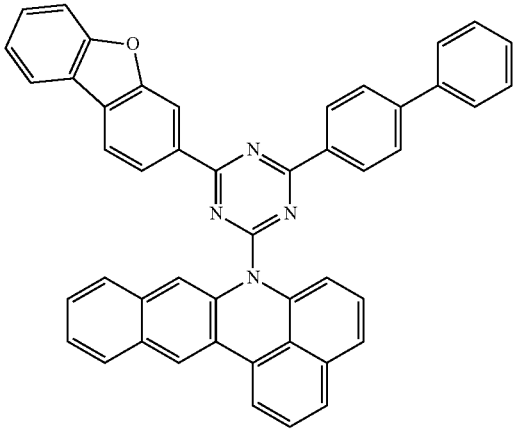
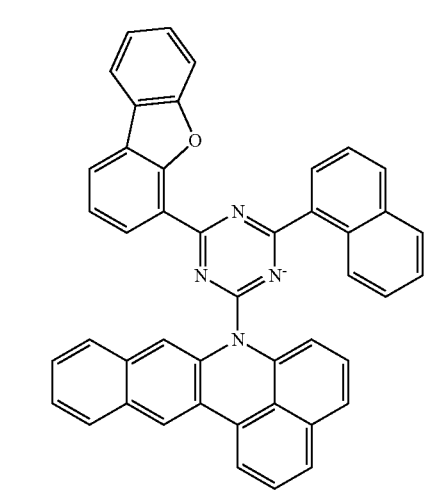

267
-continued
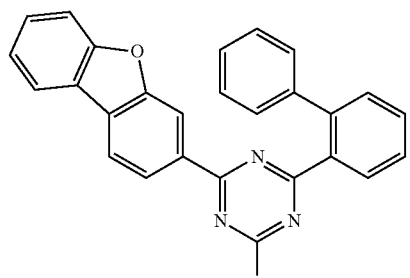
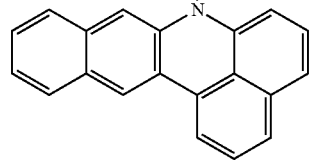
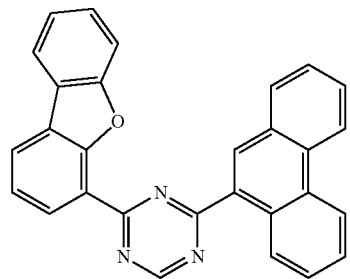
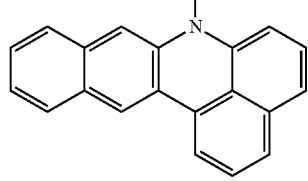
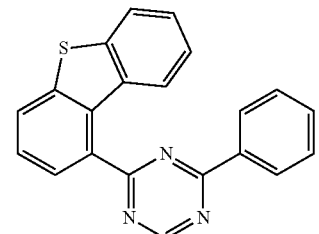
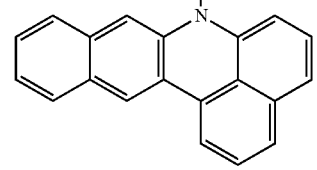
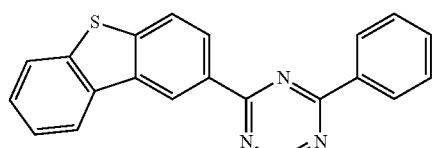
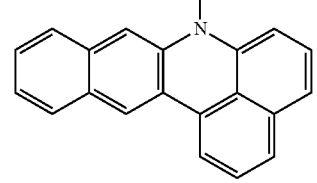
268
-continued
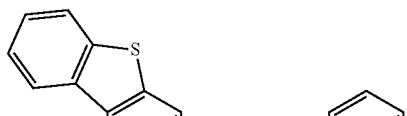
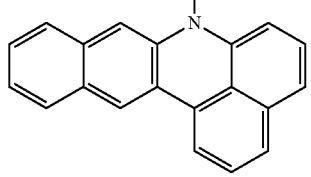
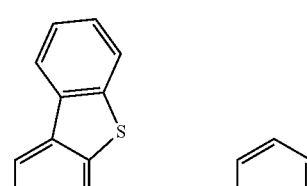
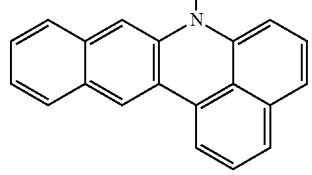
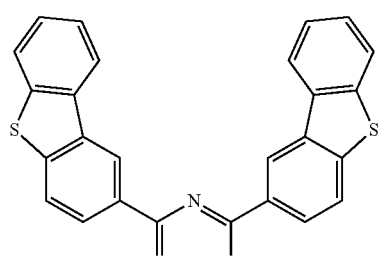
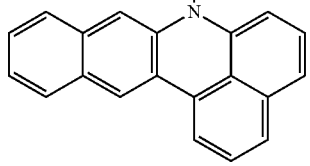

269
-continued
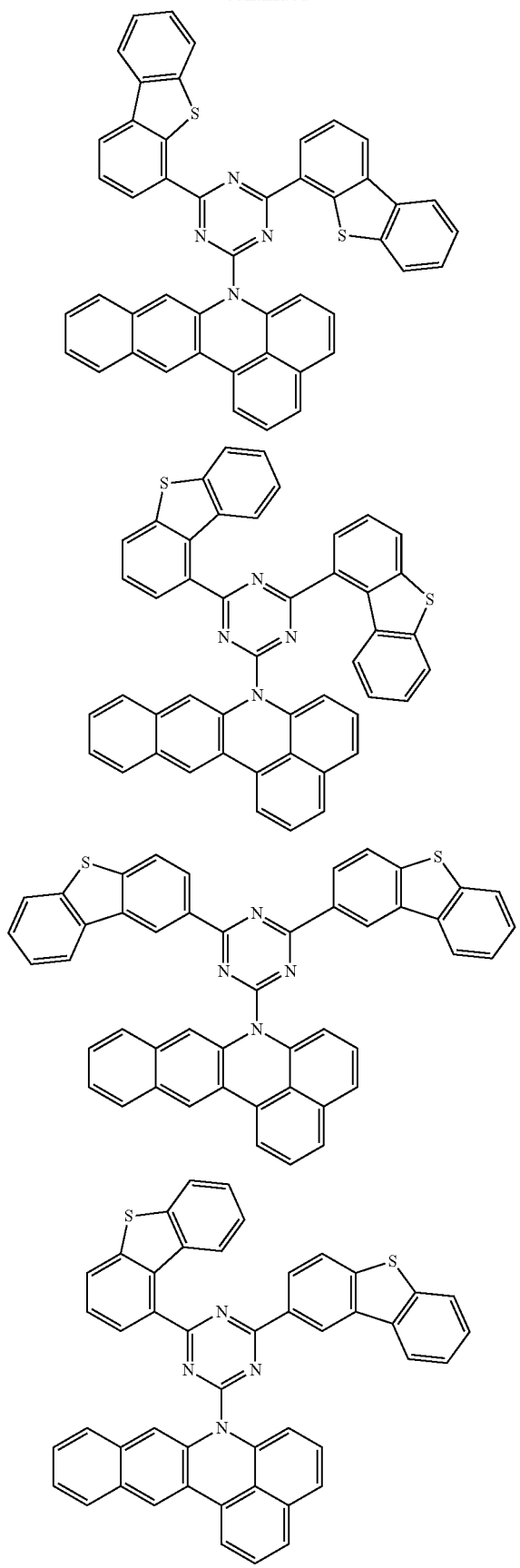
270
-continued

271
-continued
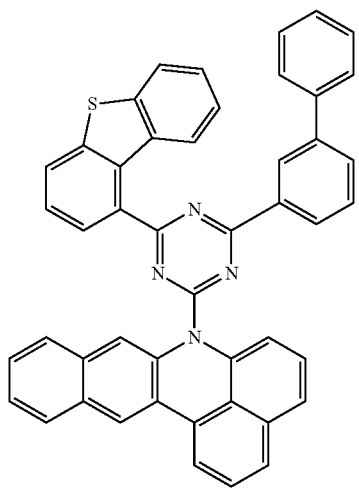
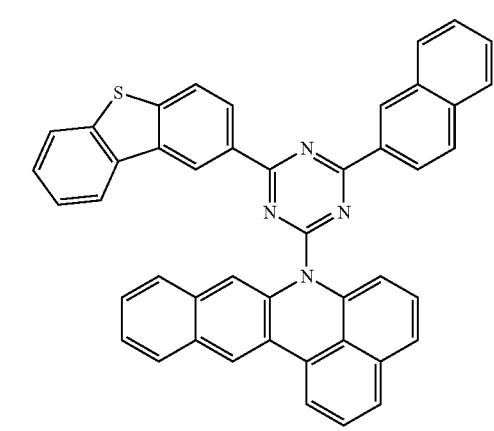
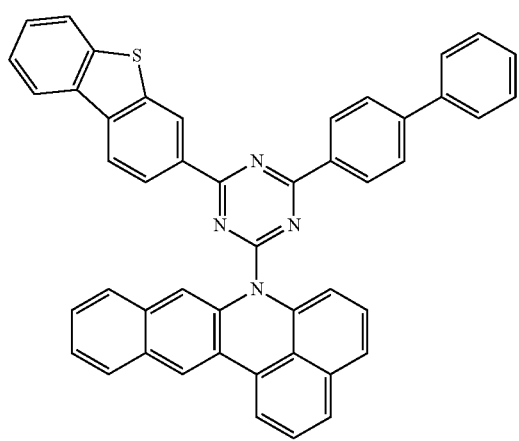
272
-continued
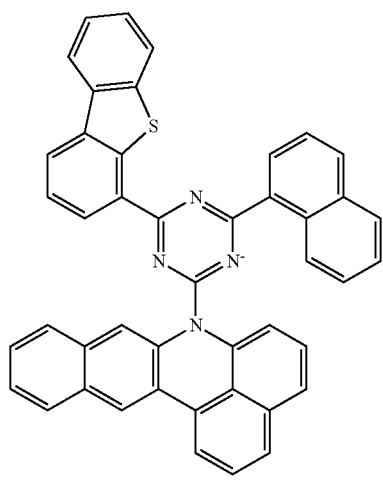
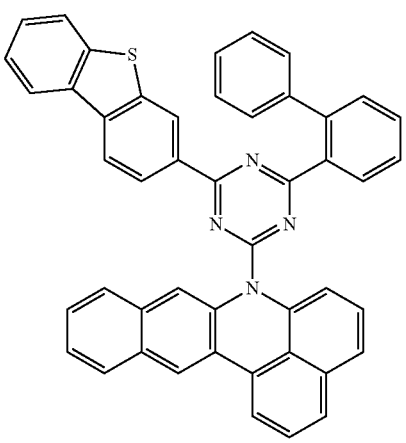
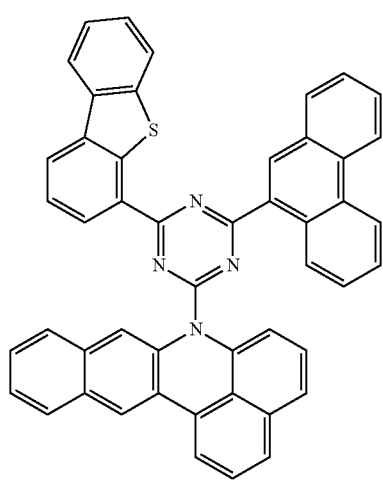

273
-continued
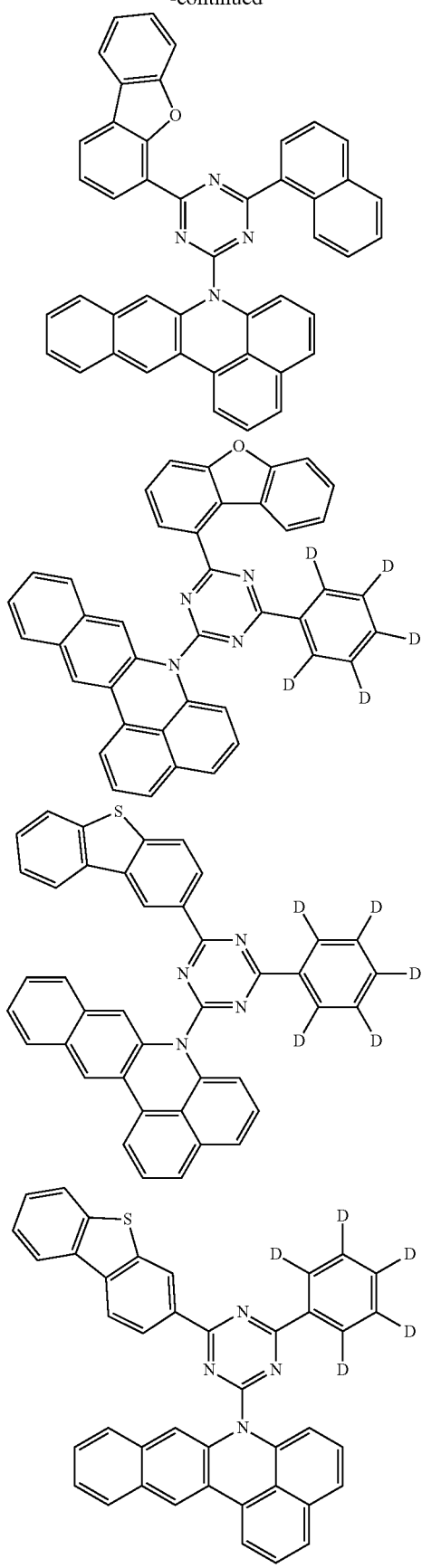
274
-continued
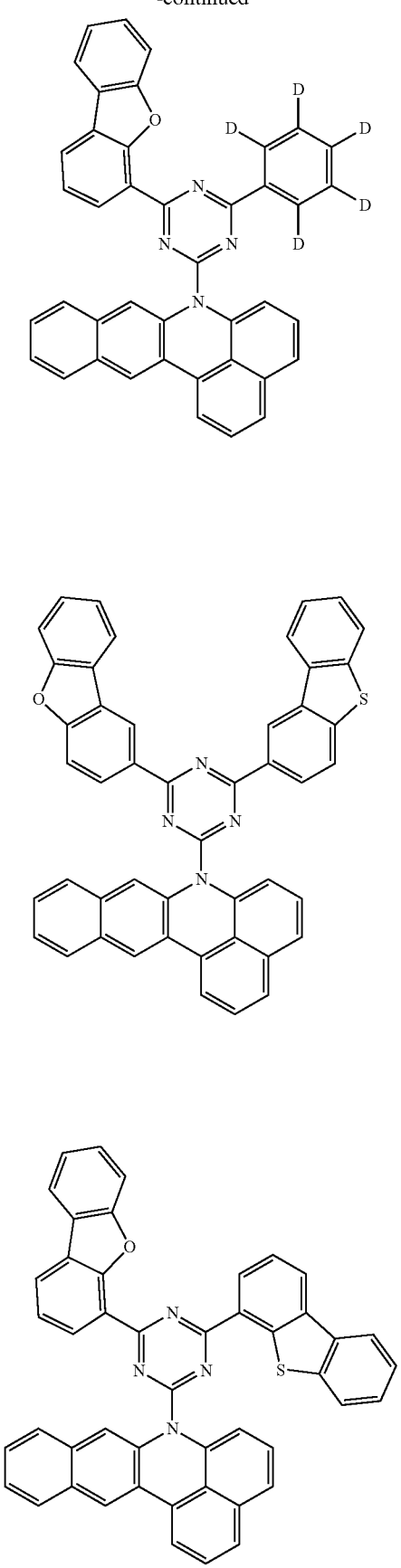

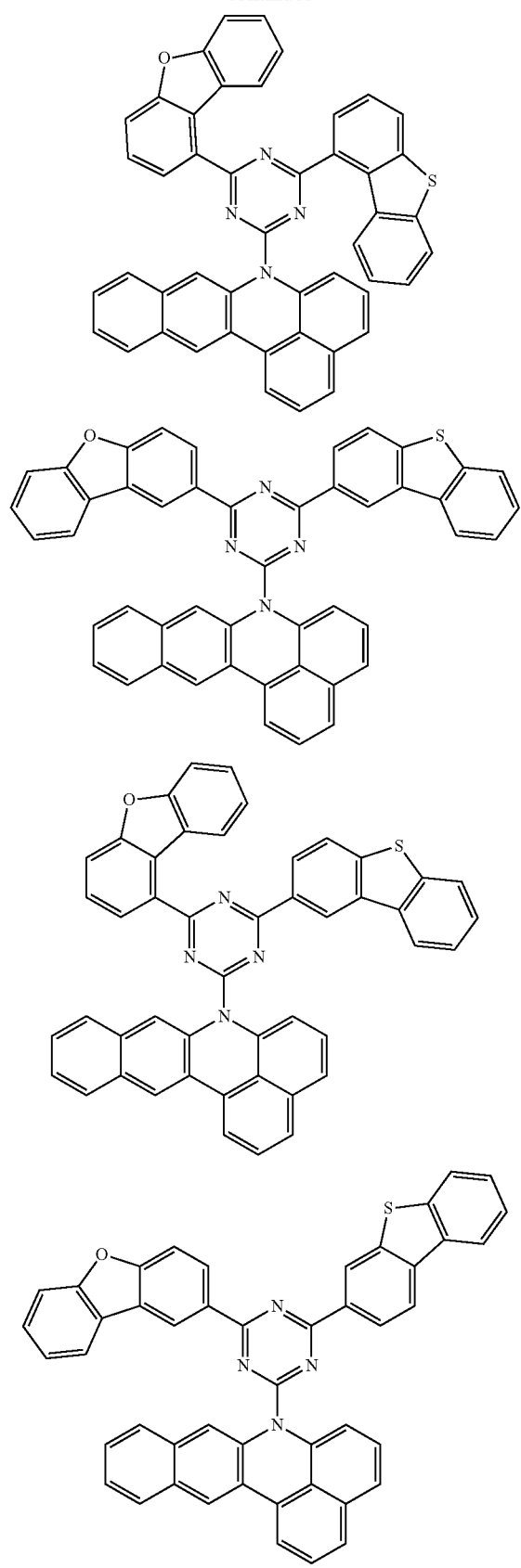
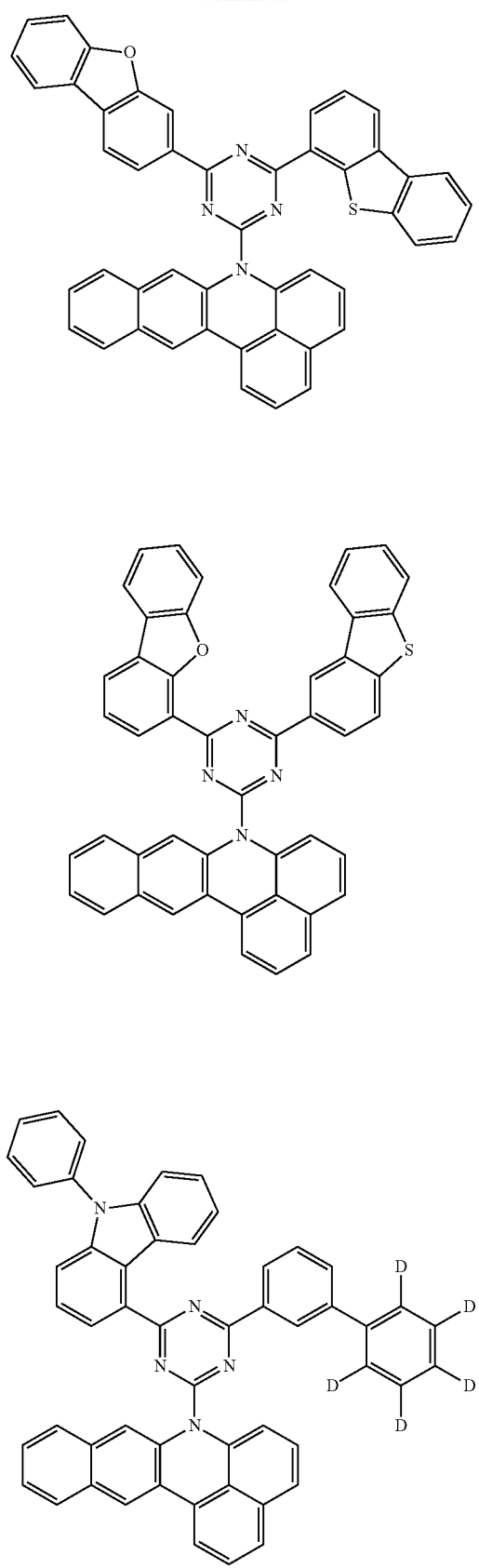

277
-continued
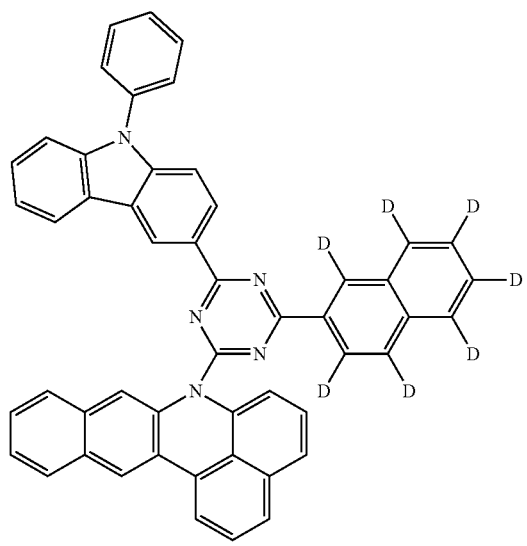
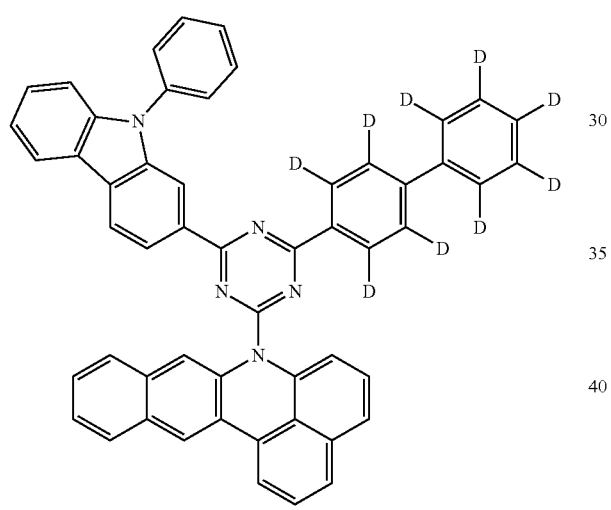
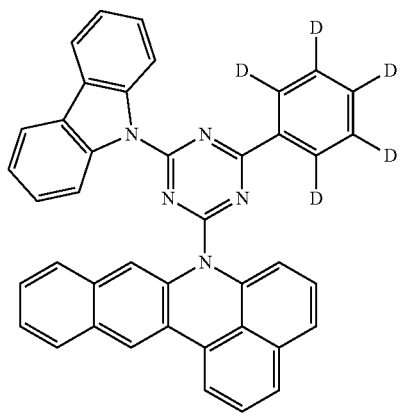
278
-continued
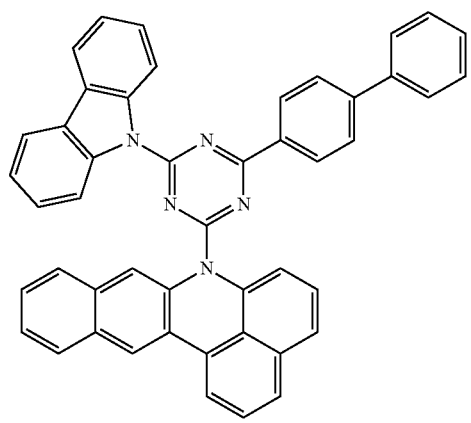
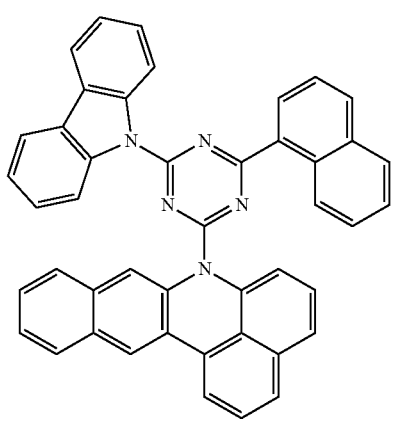
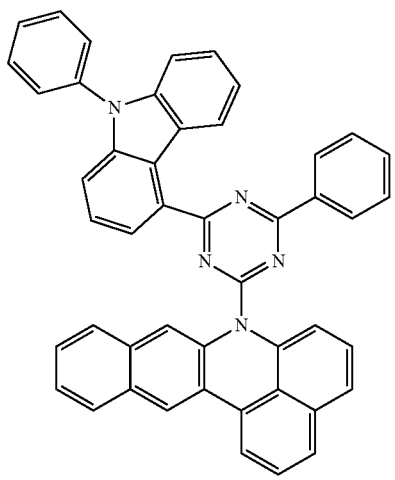

279
-continued
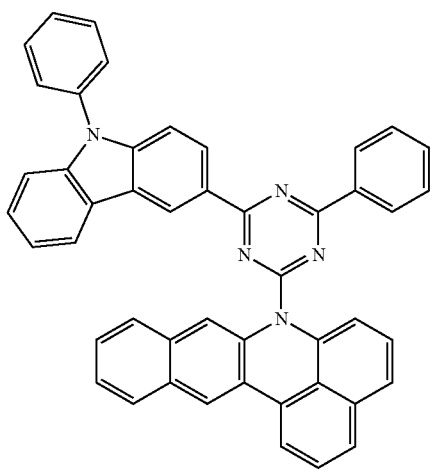
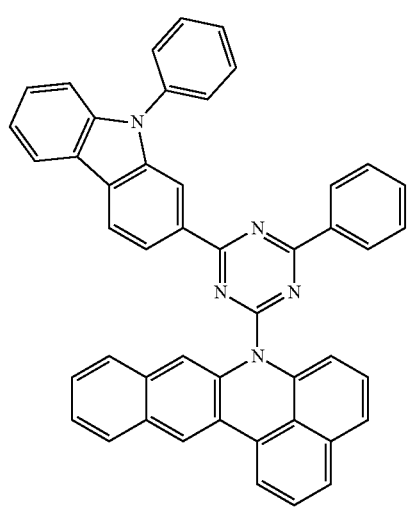
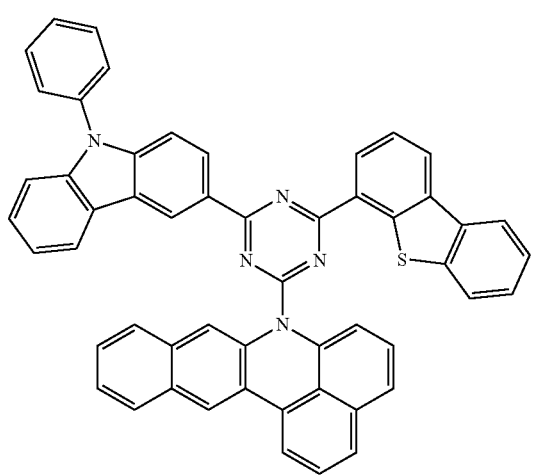
280
-continued
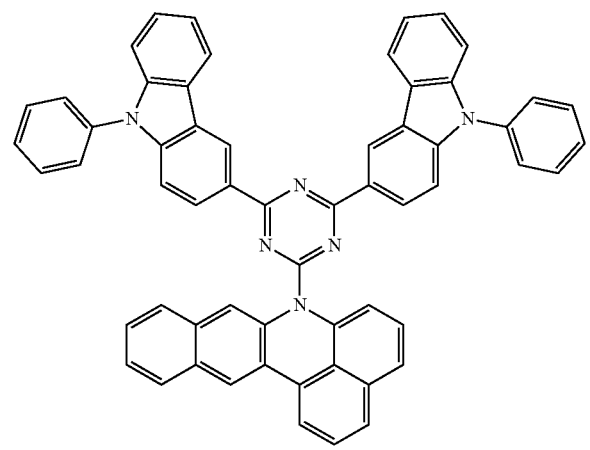
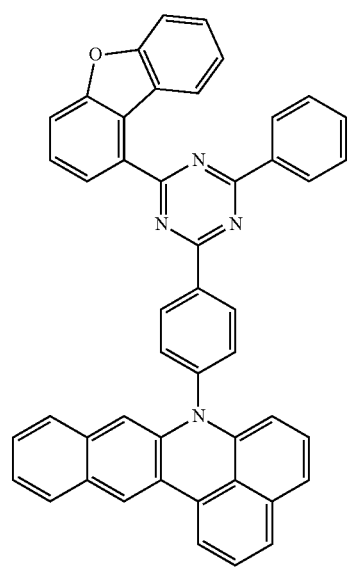

281
-continued
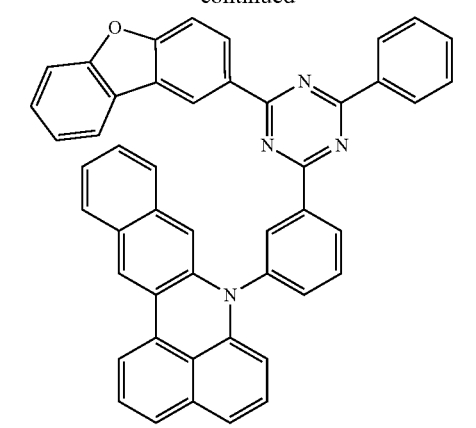
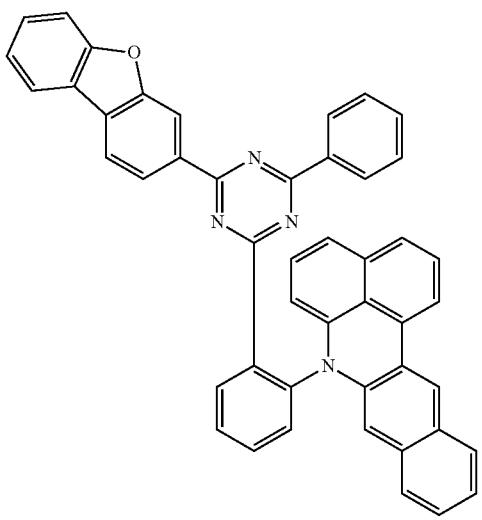
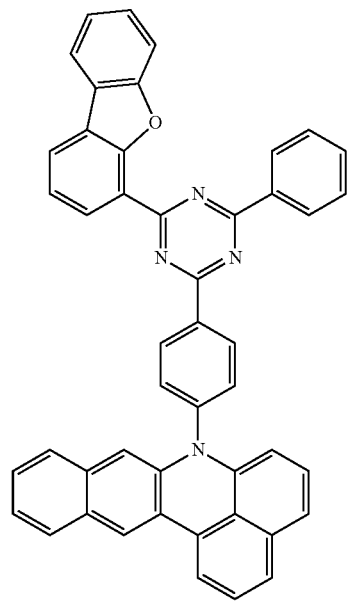
282
-continued
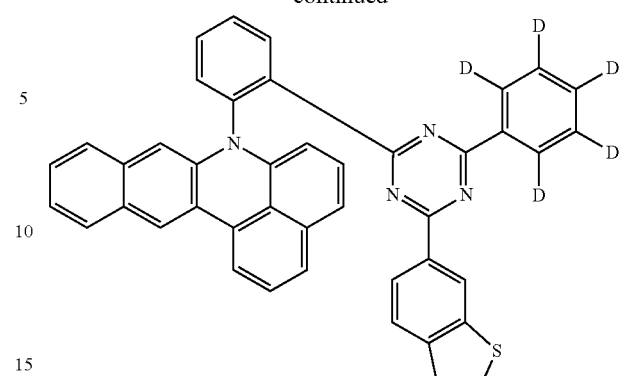
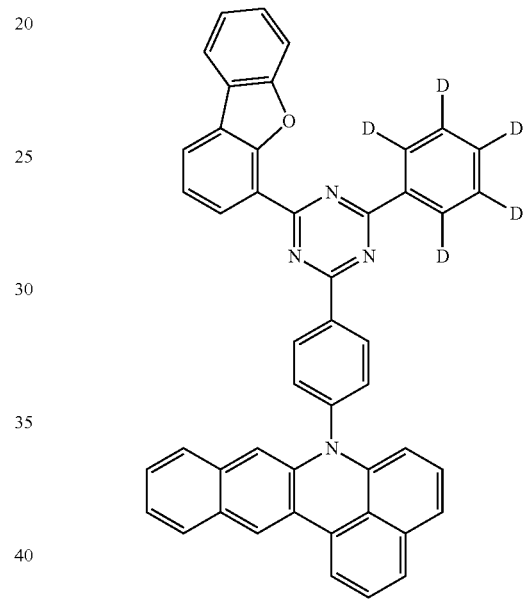
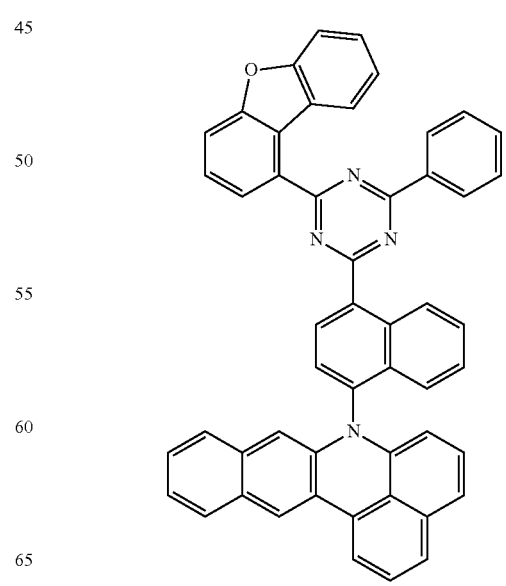

283
-continued
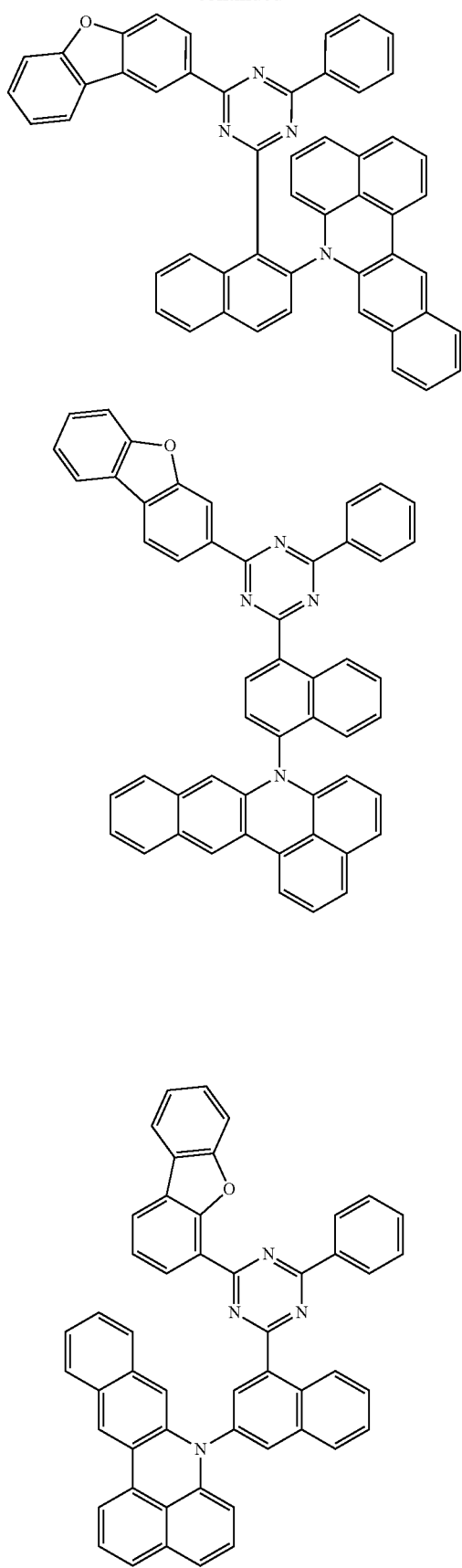
284
-continued
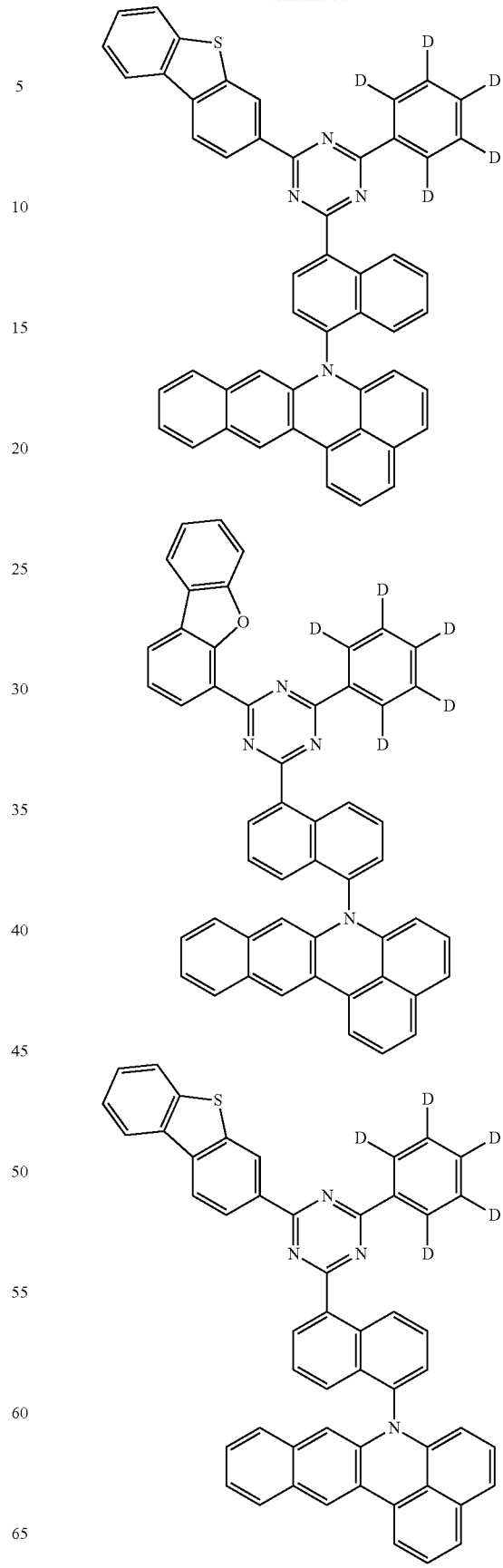

285
-continued
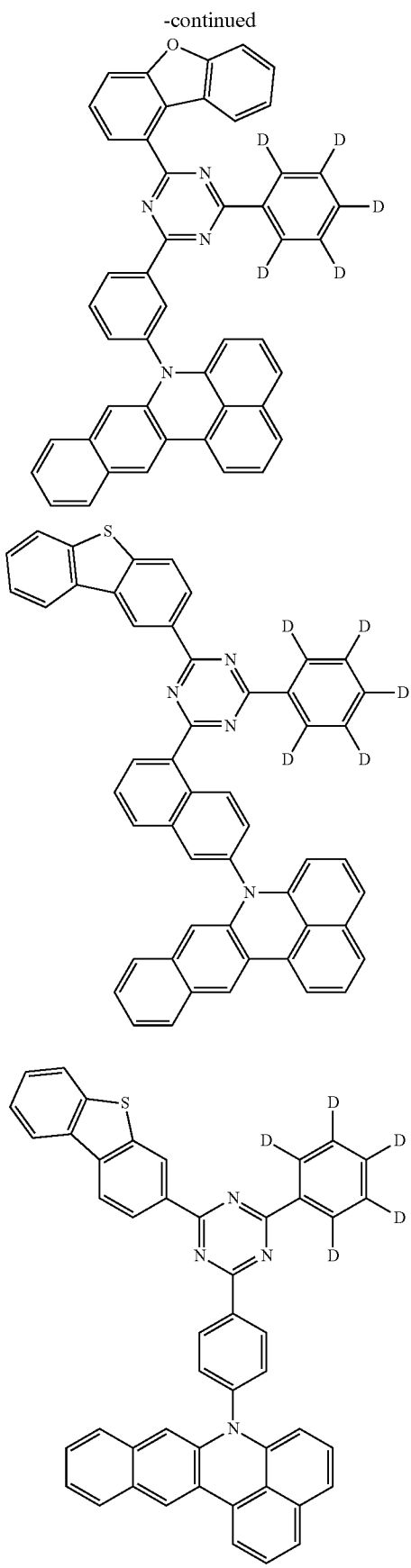
286
-continued
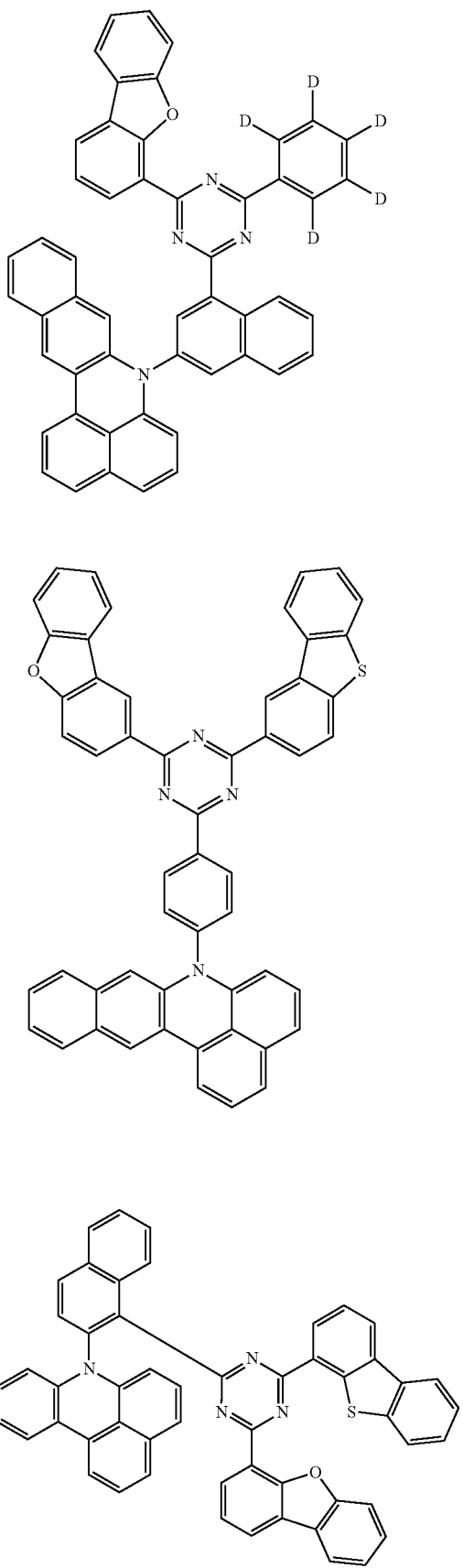

287
-continued
288
-continued
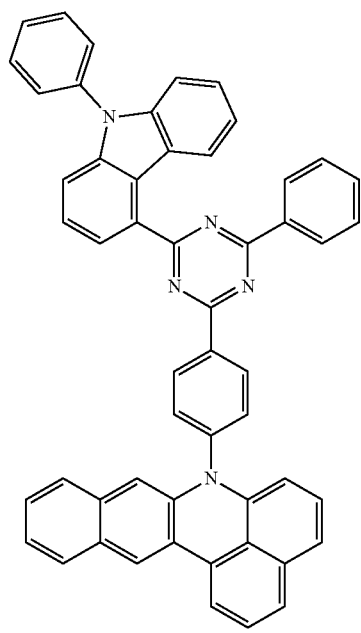
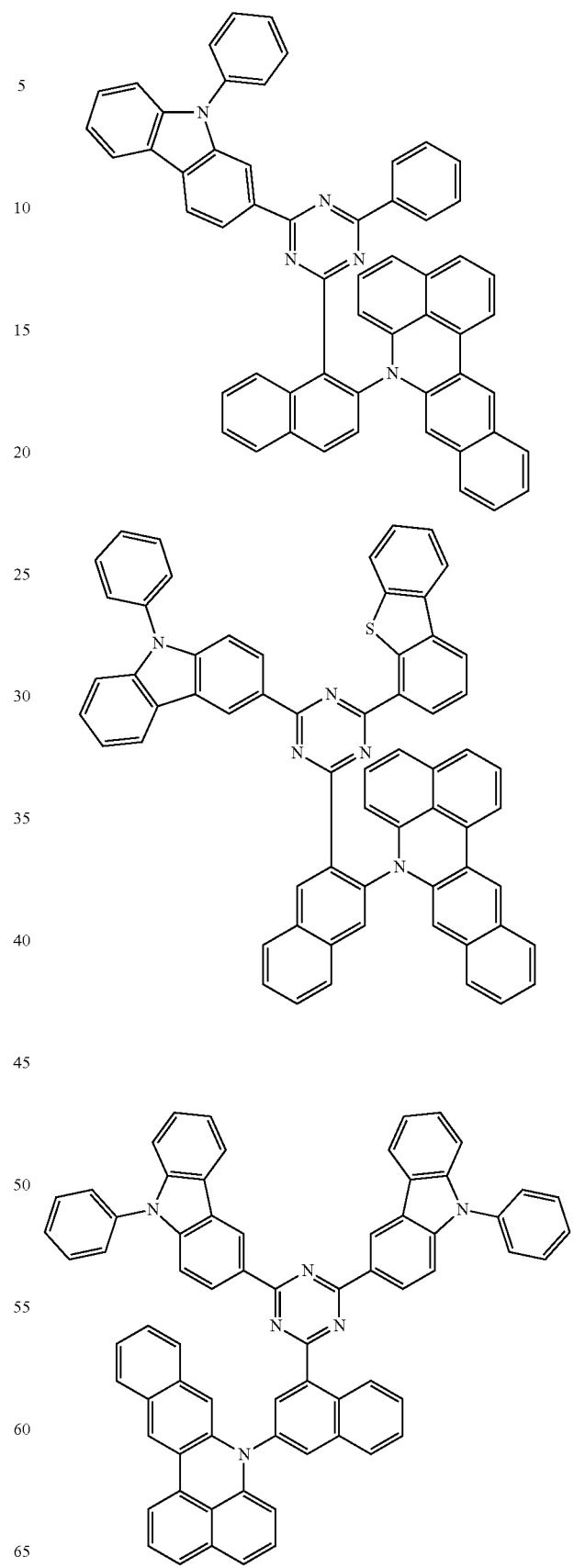

289
-continued
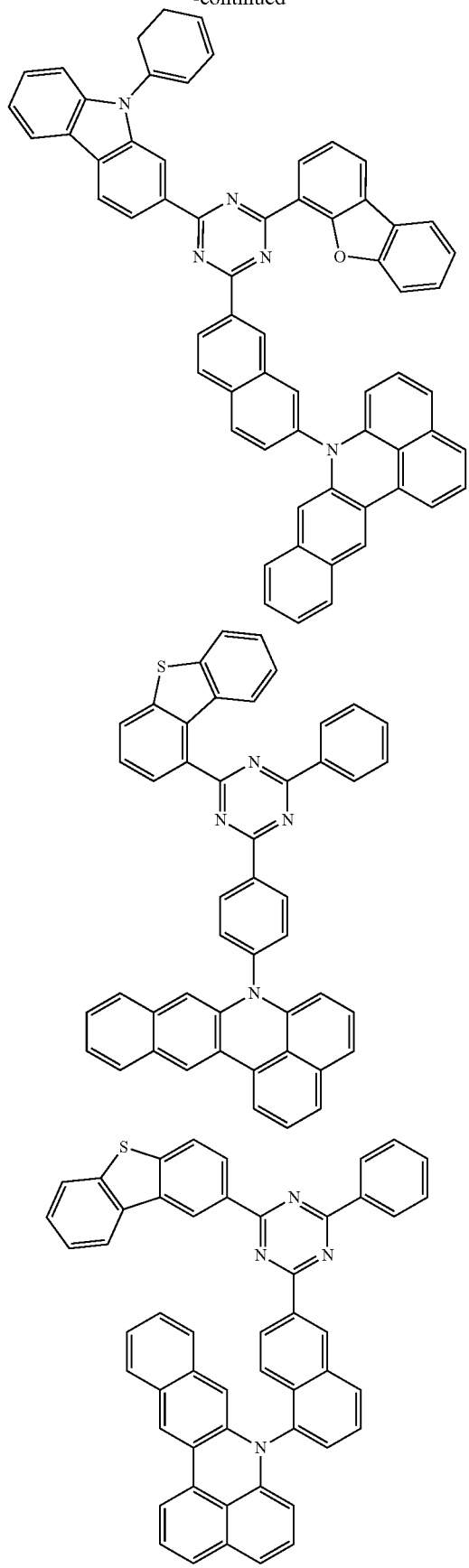
290
-continued
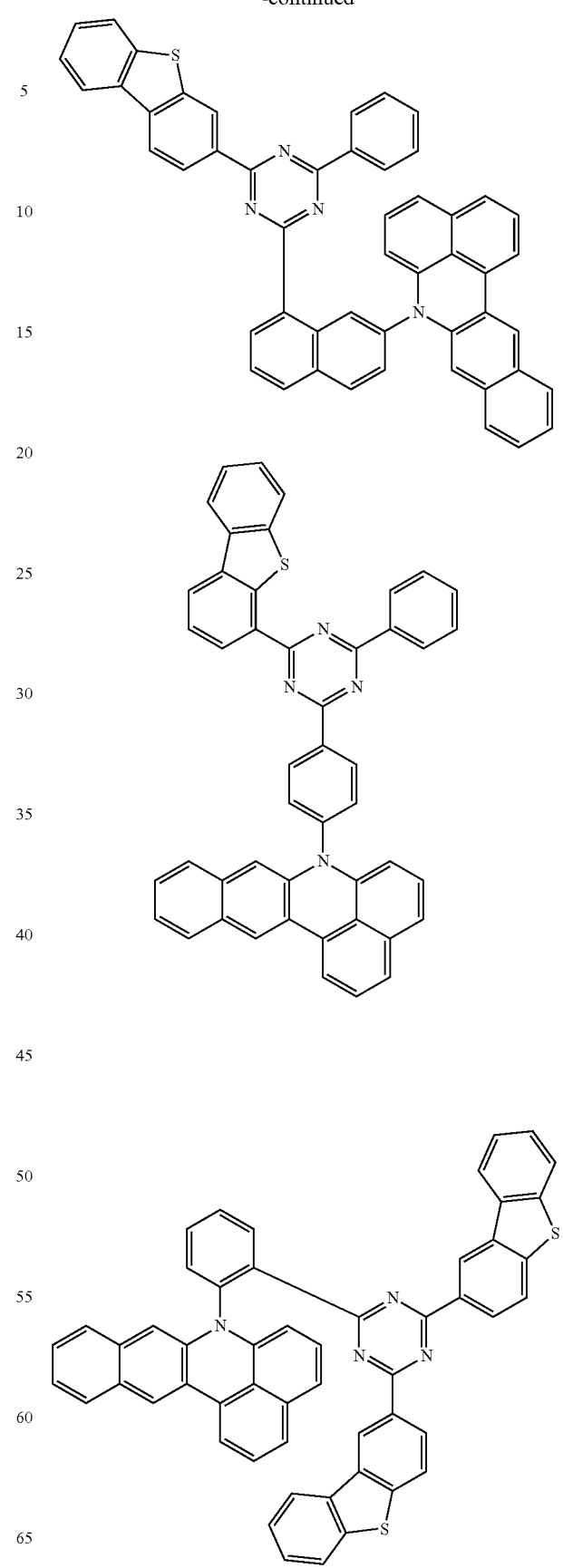

291
-continued
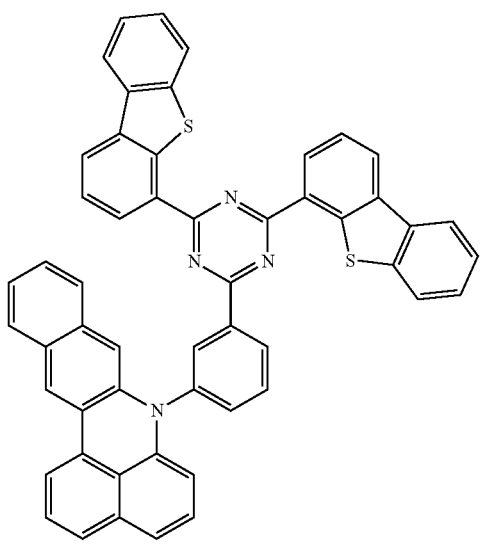
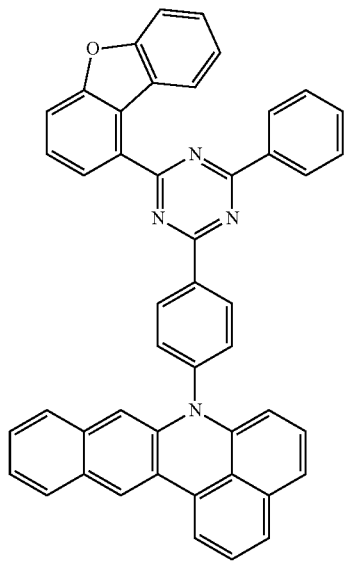
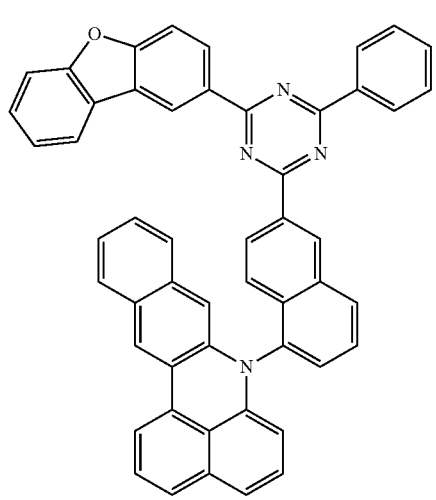
292
-continued
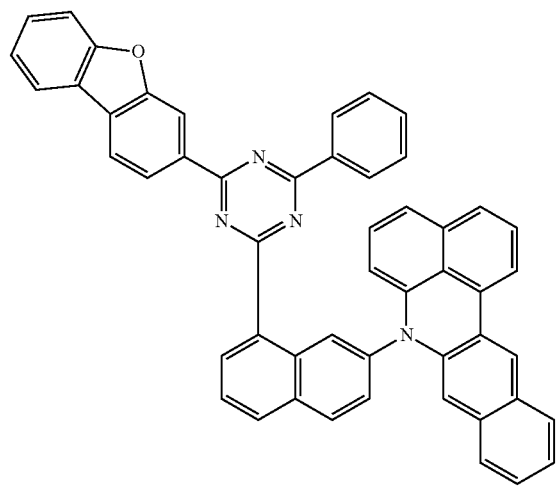
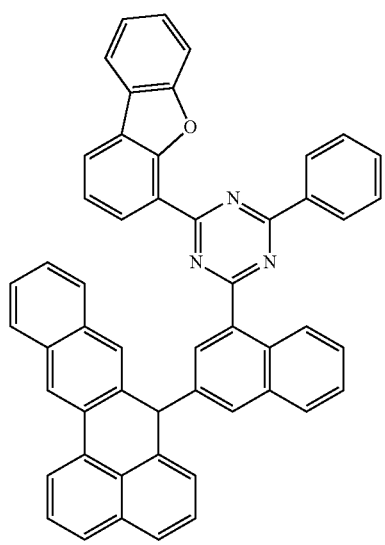
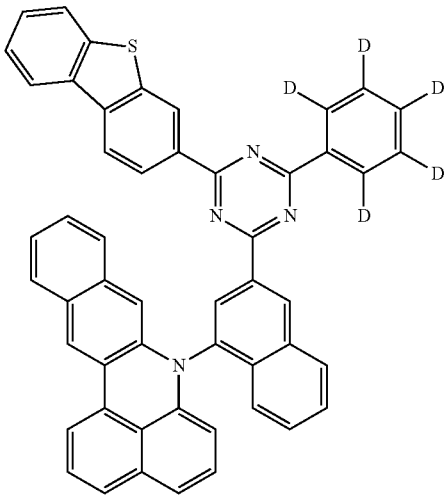

293
-continued
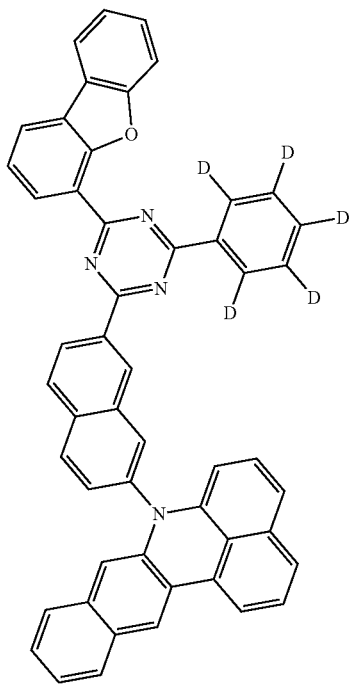
294
-continued
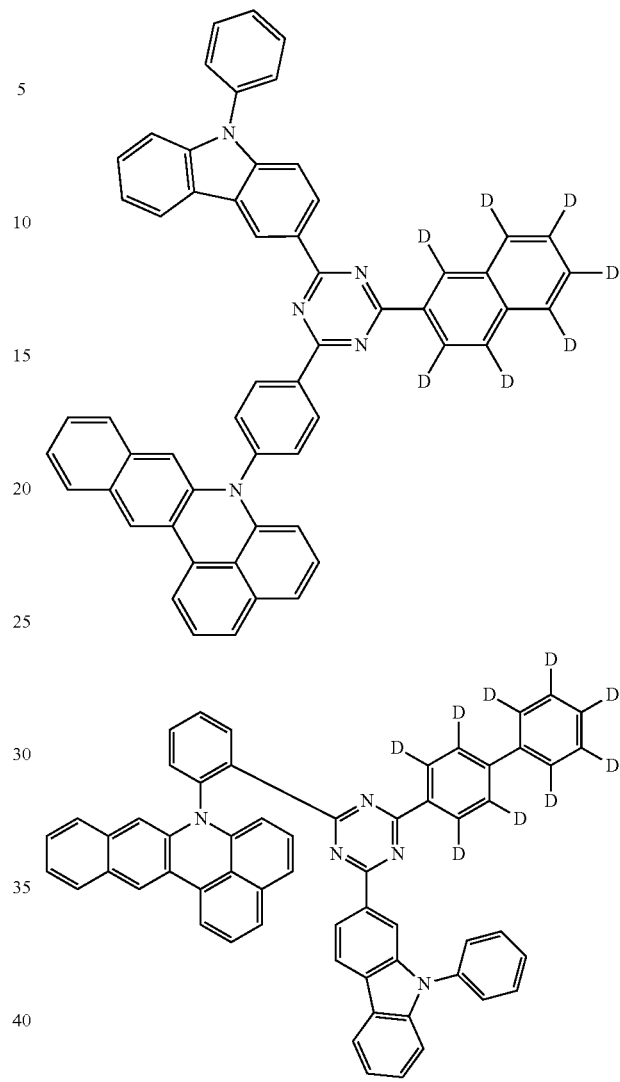
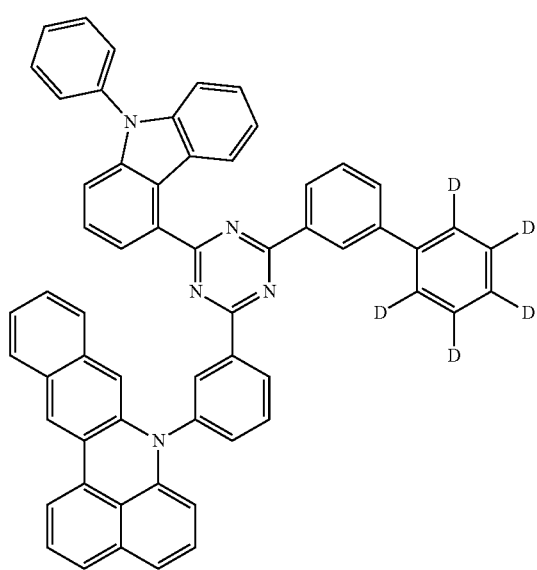
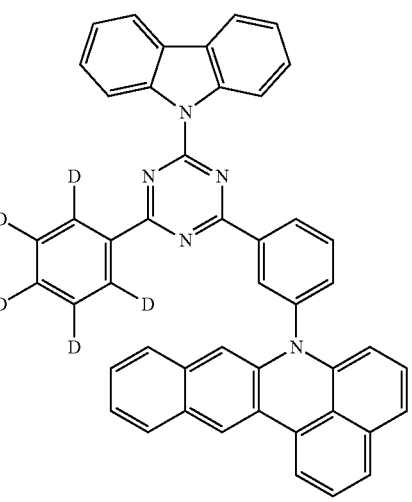

295
-continued
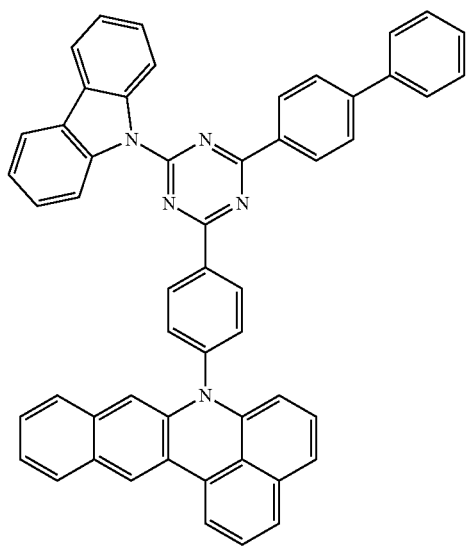
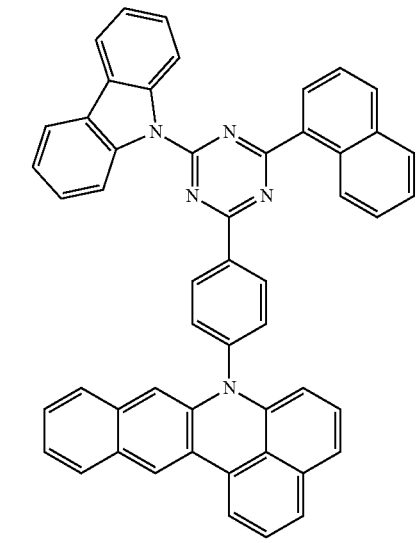
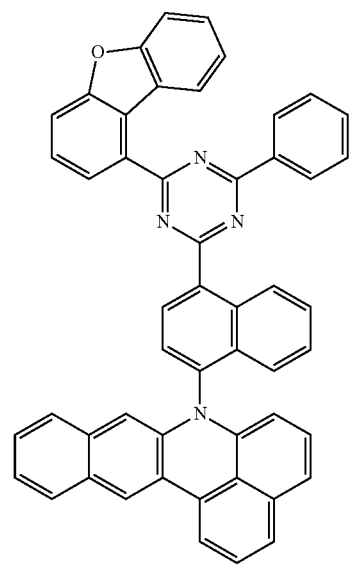
296
-continued
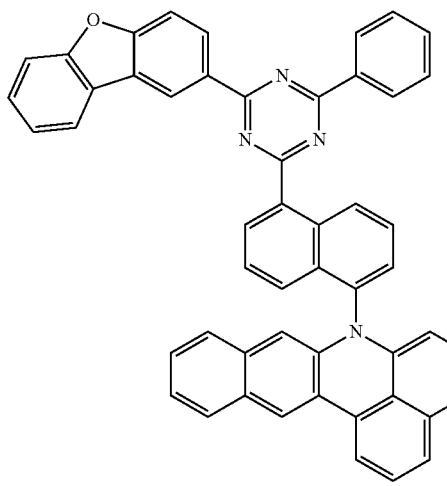
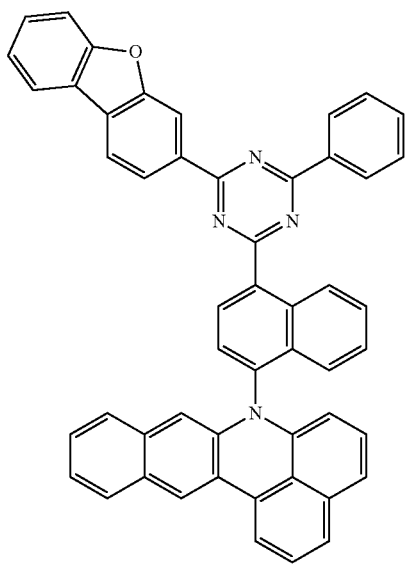
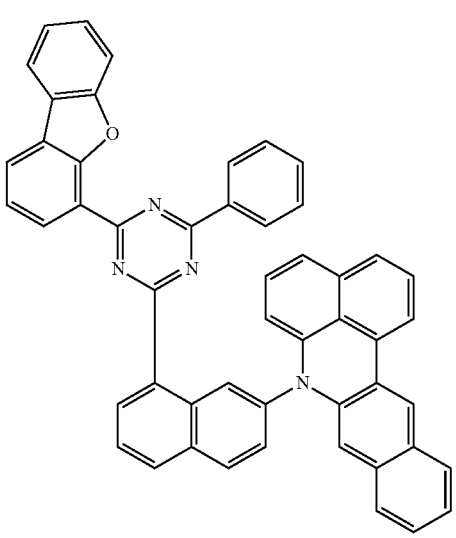

297
-continued
298
-continued
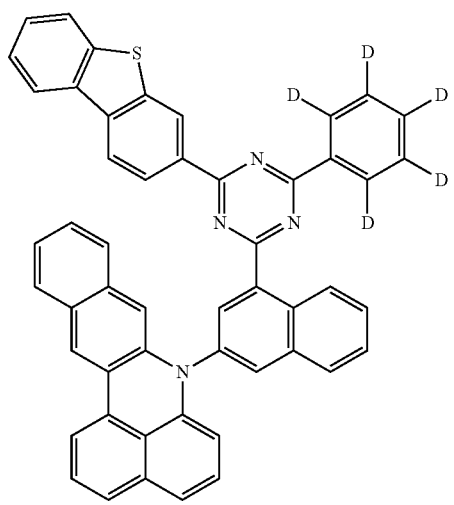
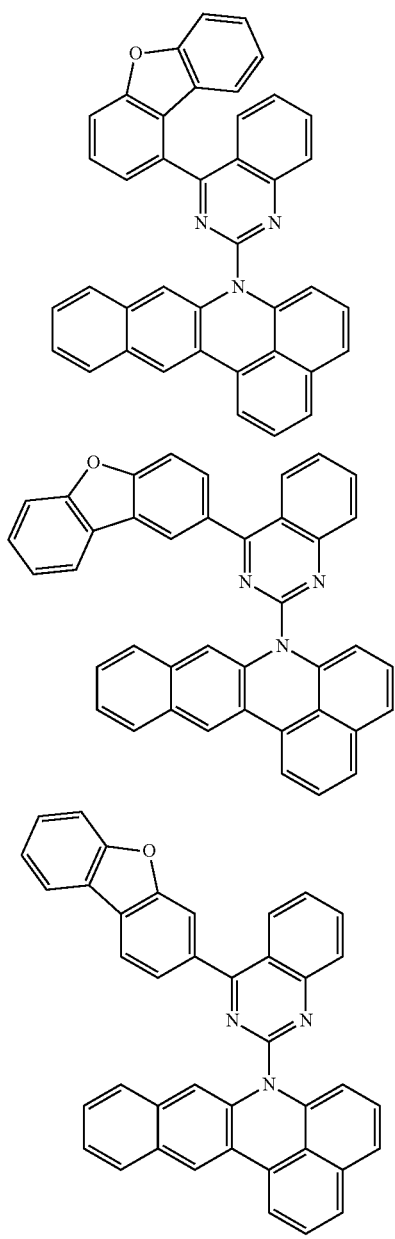
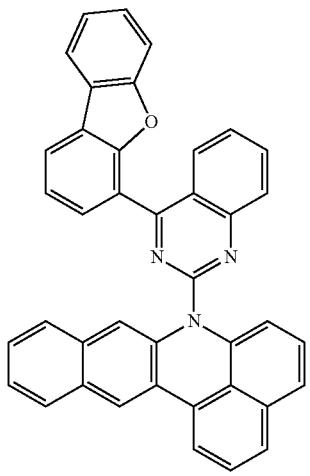

299
-continued
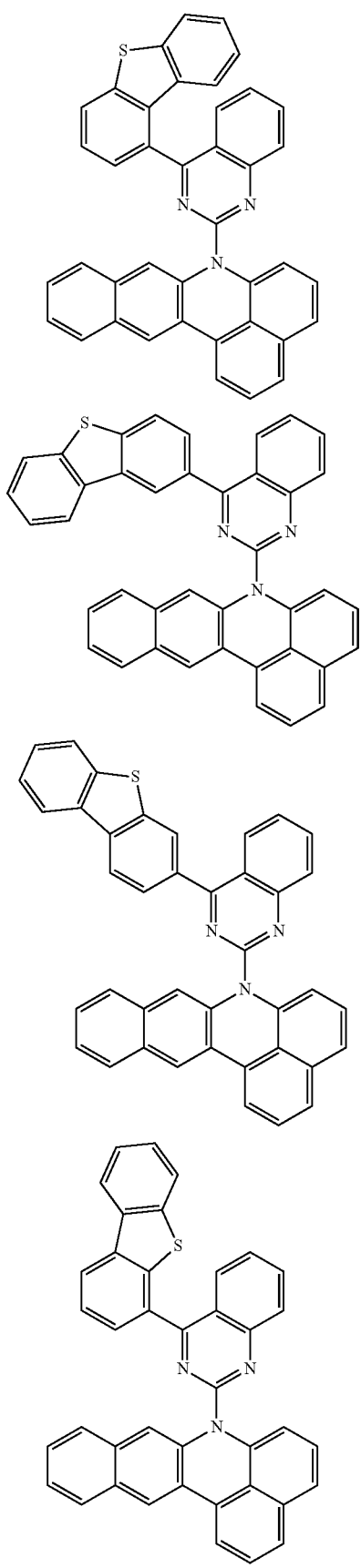
300
-continued
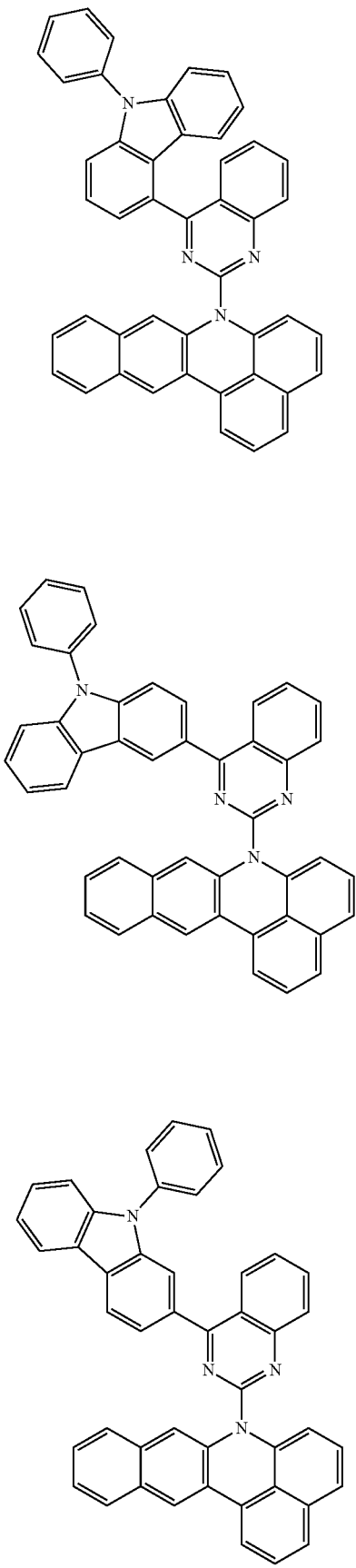

301
-continued
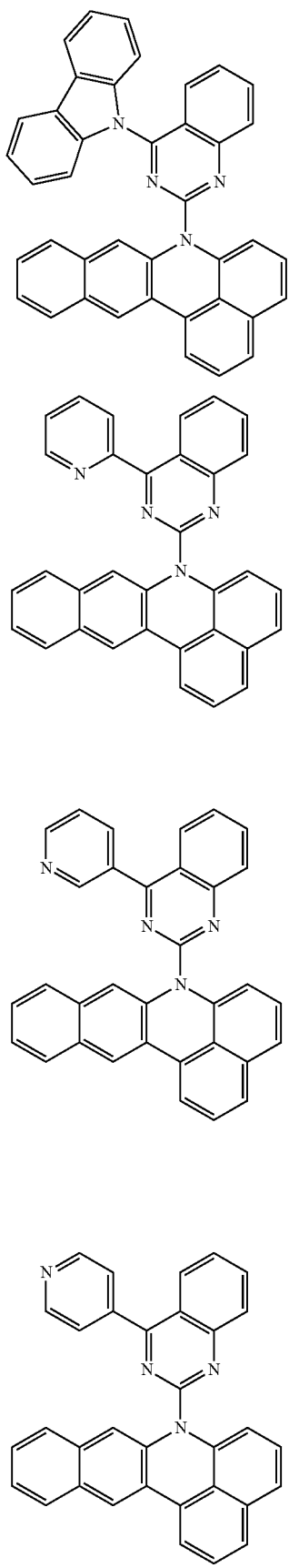
302
-continued
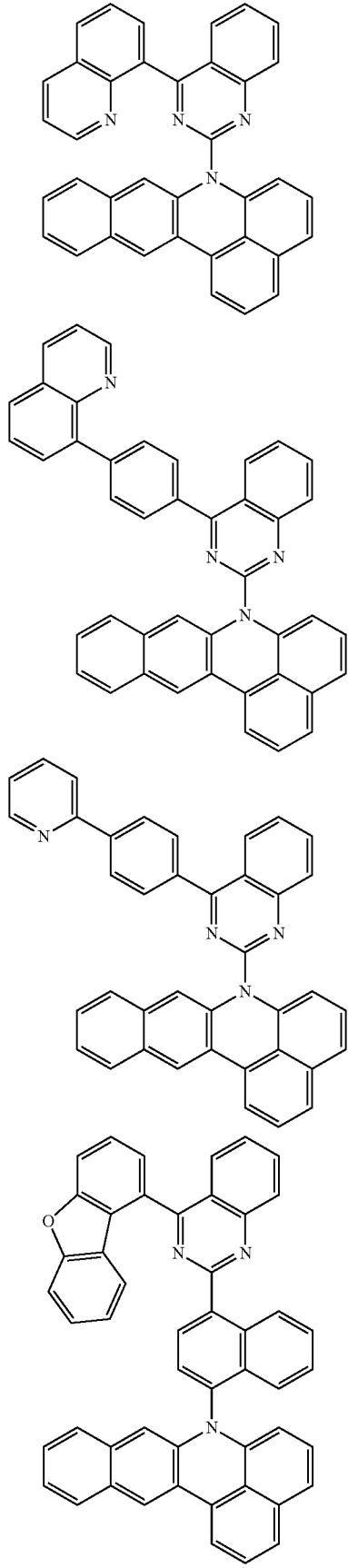

303
-continued
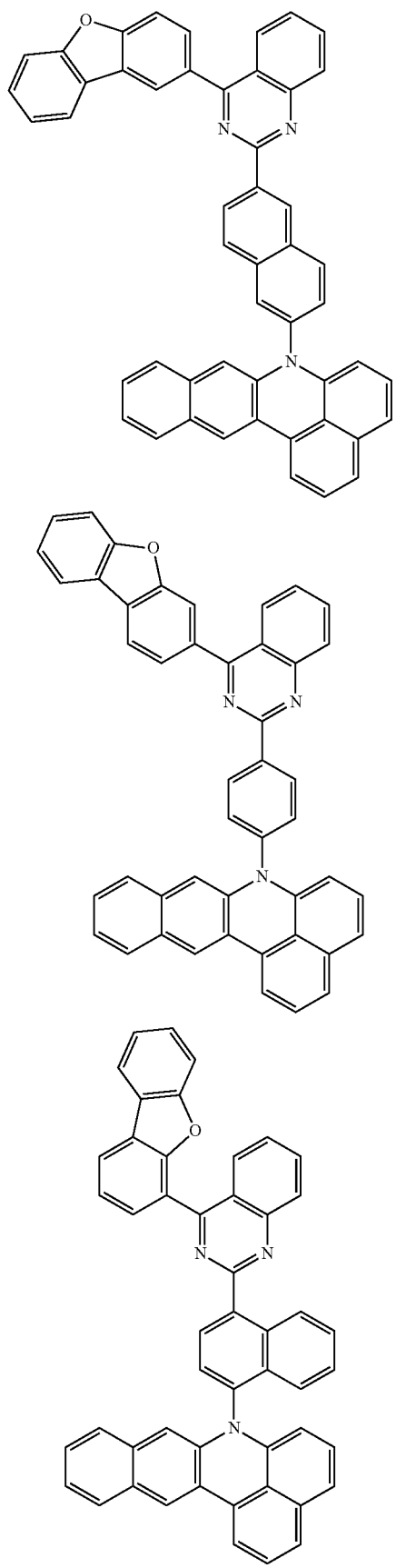
304
-continued
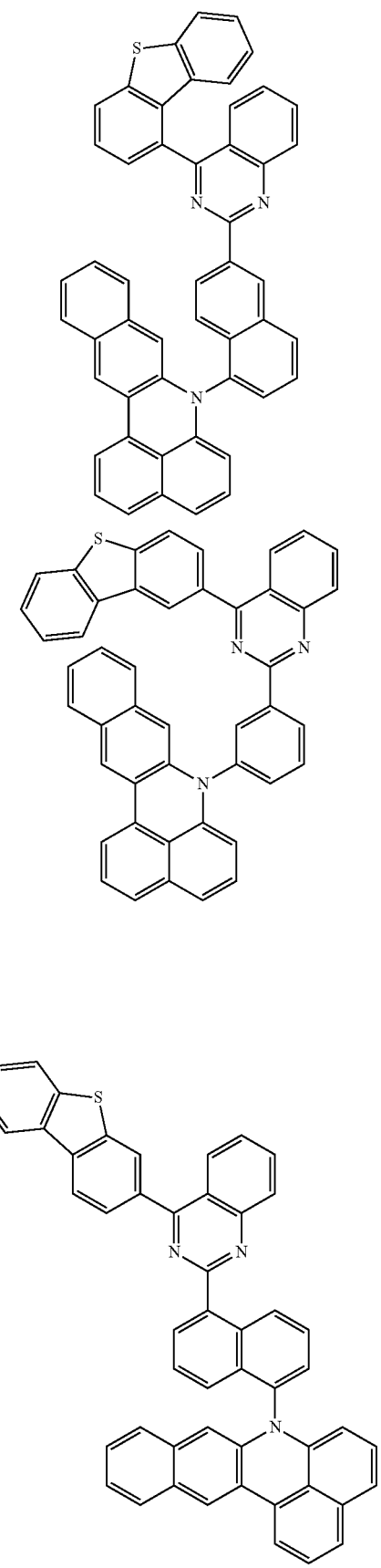

305
-continued
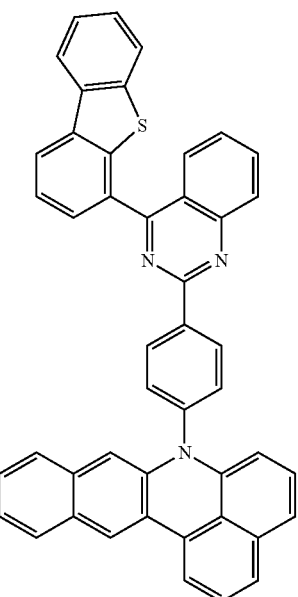
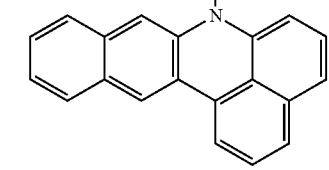
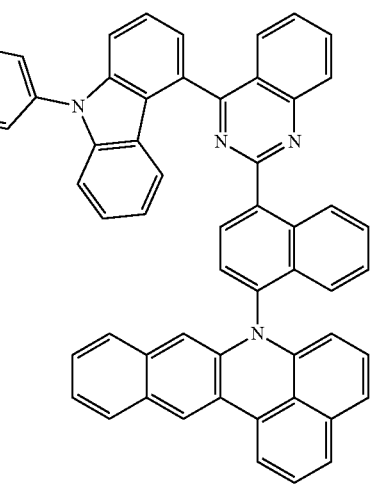
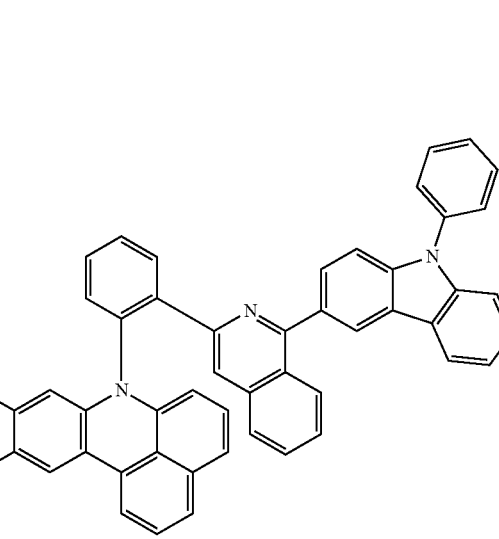
306
-continued
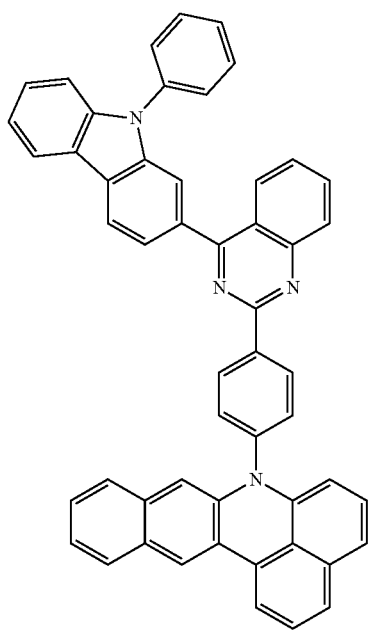
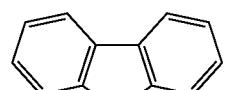
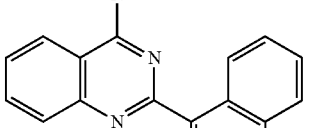
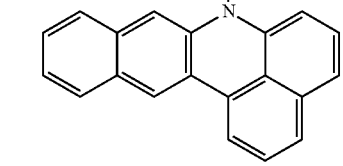
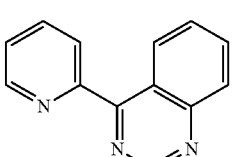
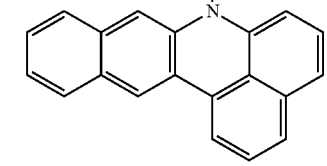

307
-continued
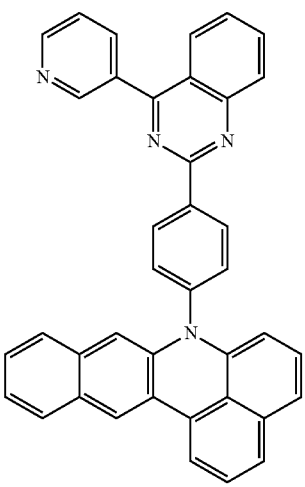
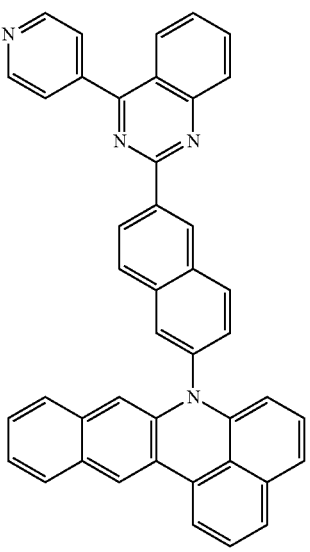
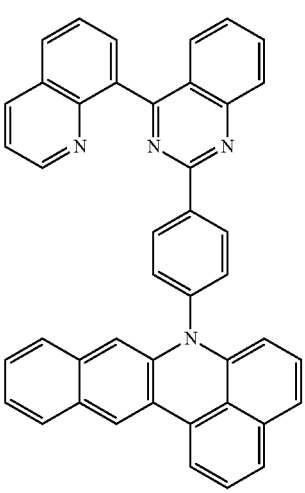
308
-continued
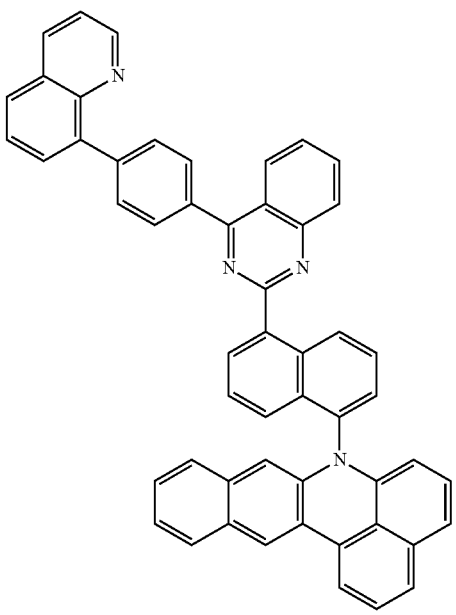
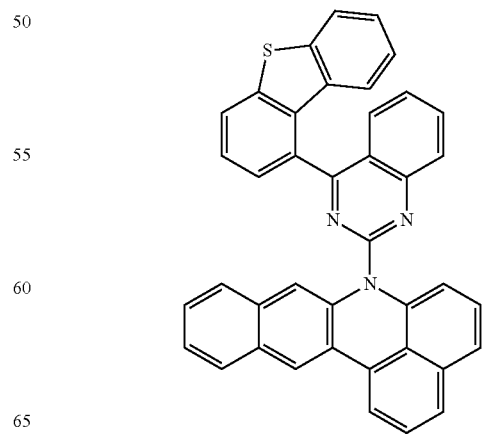

309
-continued
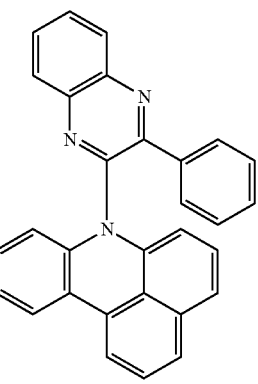
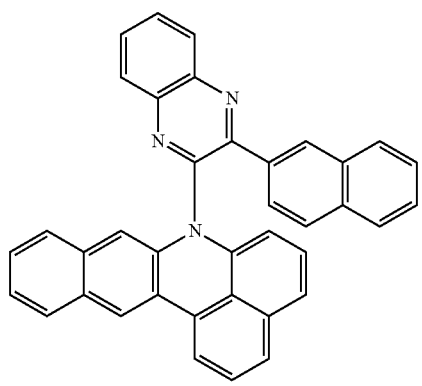
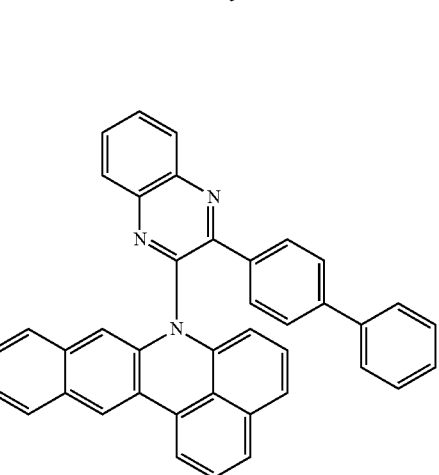
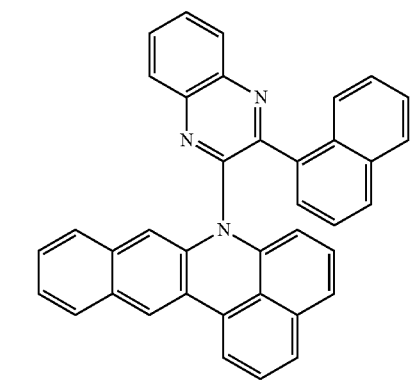
310
-continued
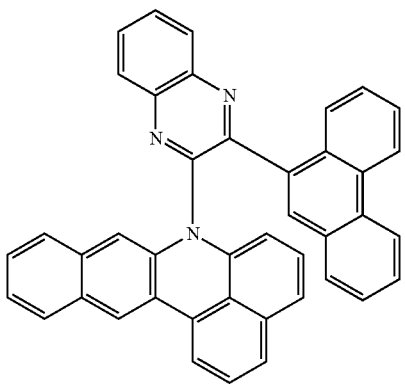
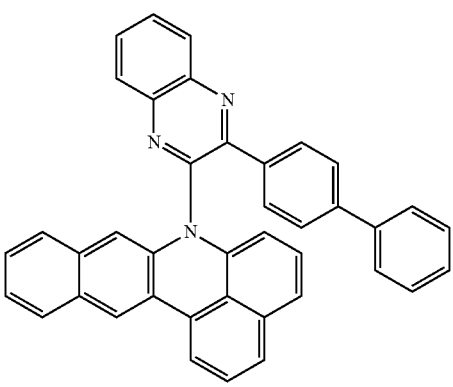
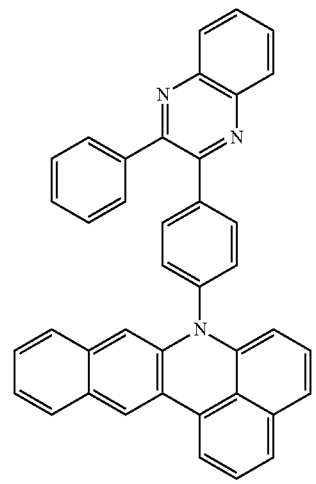

311
-continued
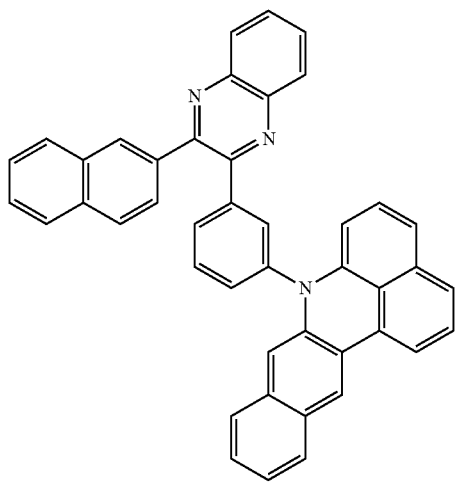
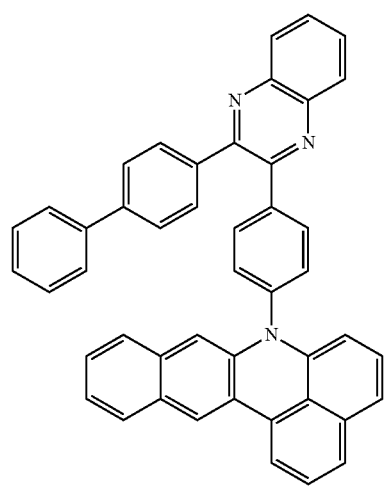
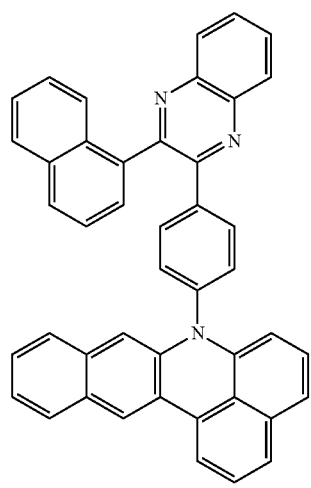
312
-continued
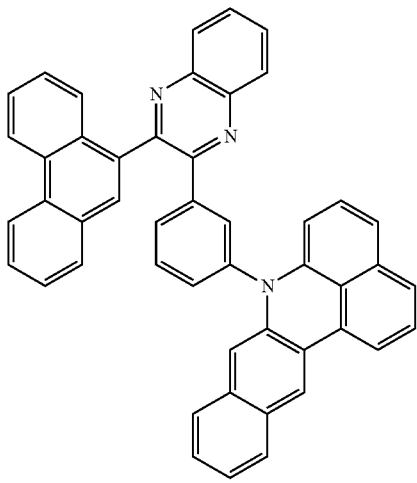
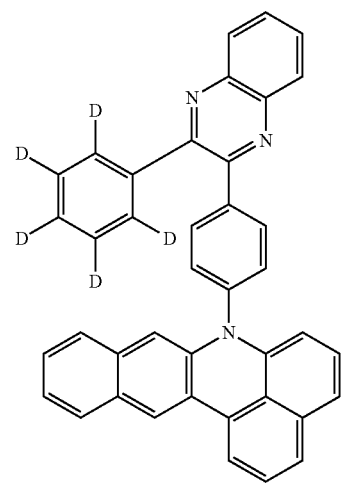
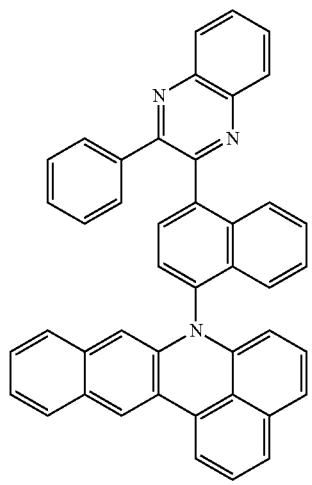

313
-continued
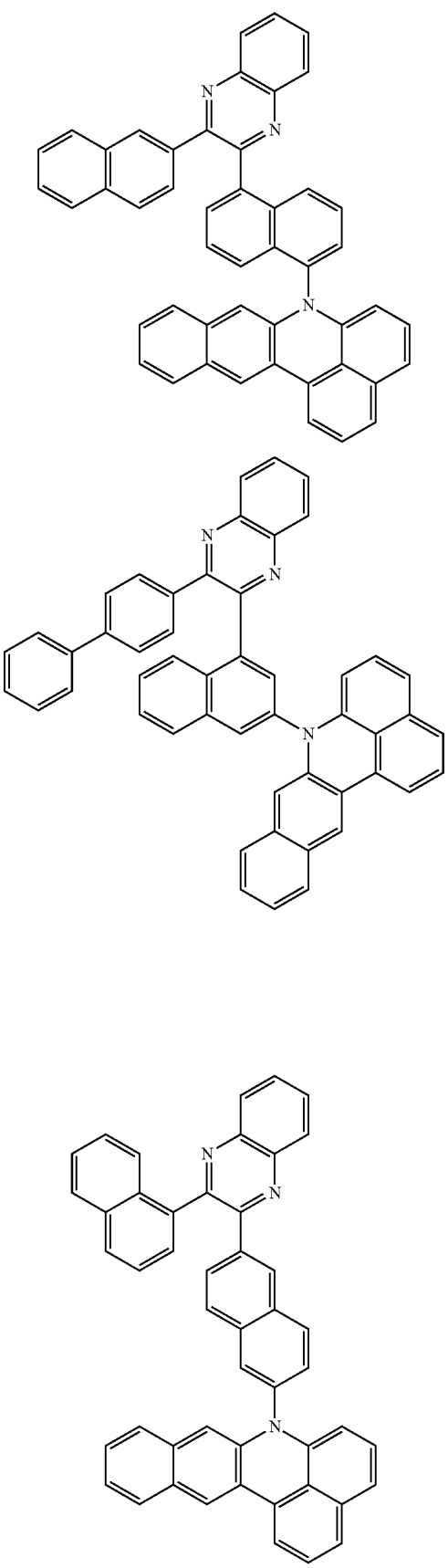
314
-continued
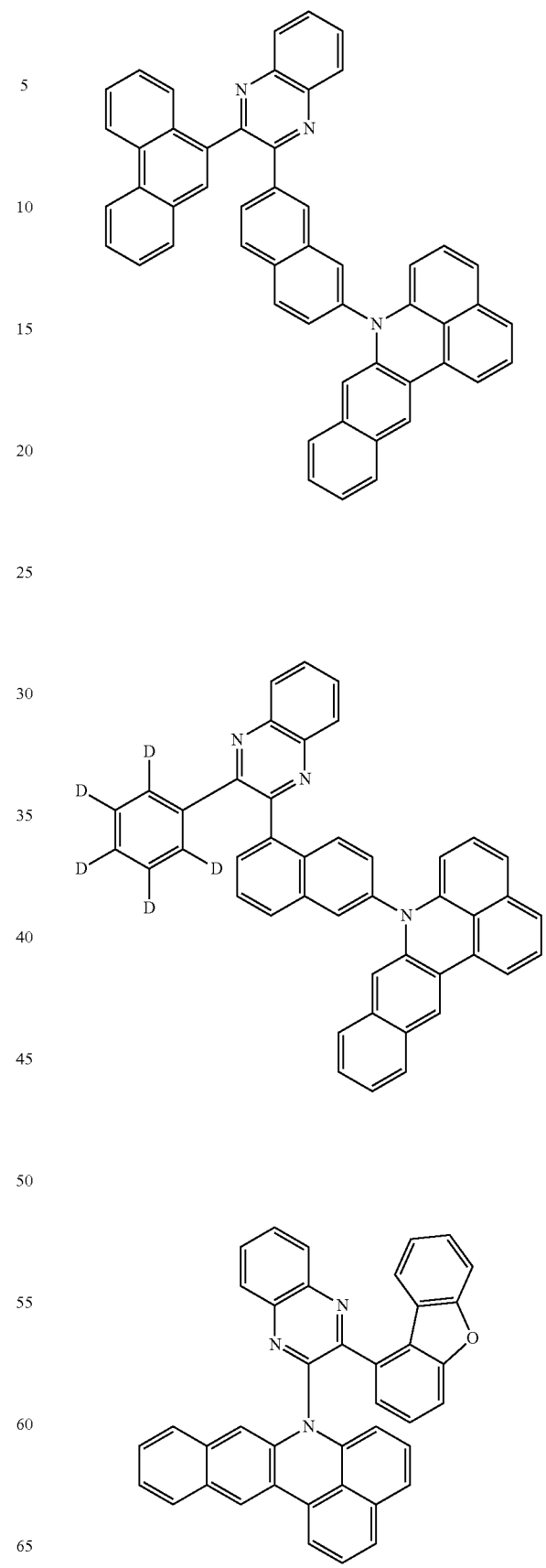

315
-continued
316
-continued
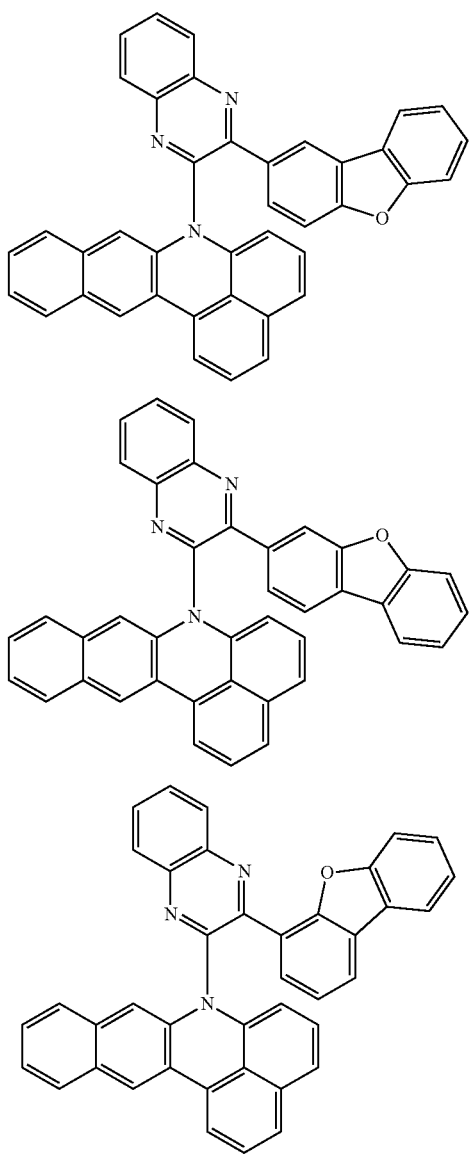
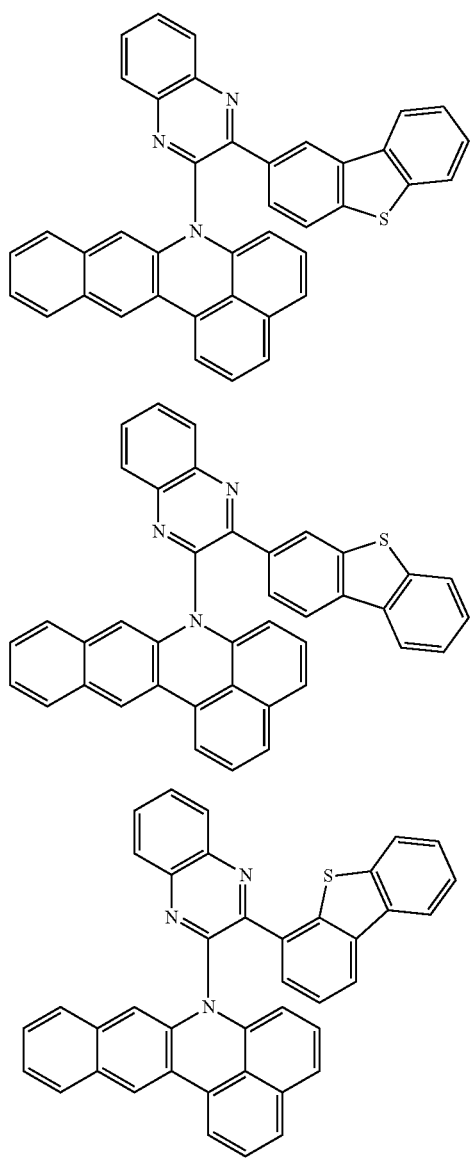
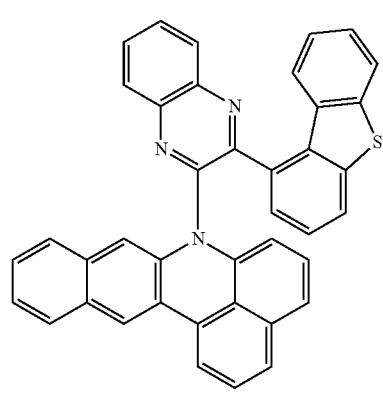
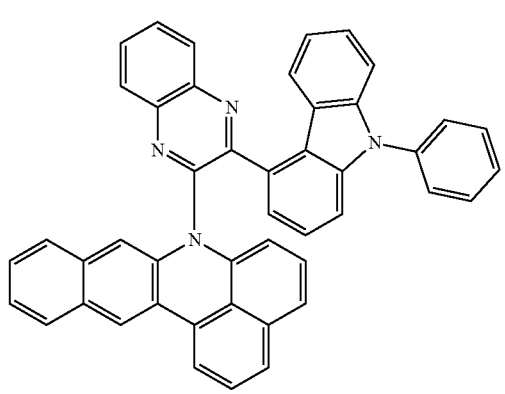

317
-continued
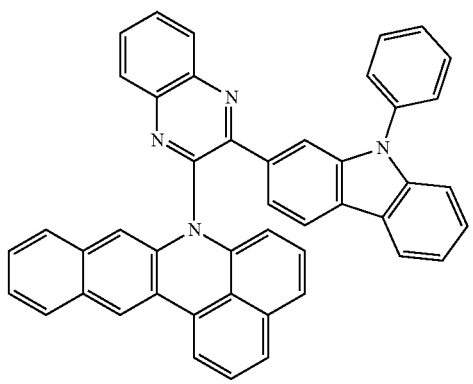
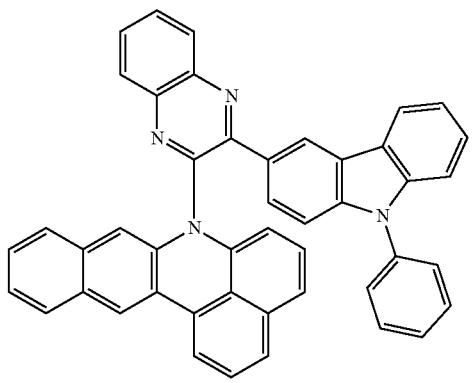
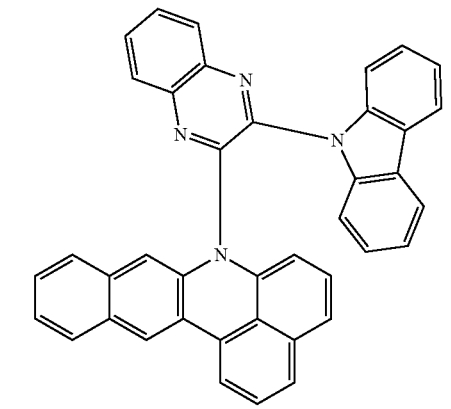
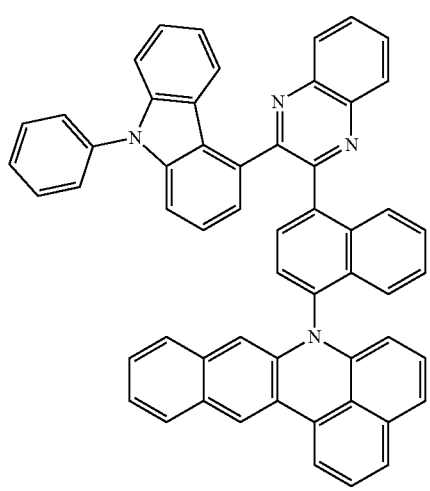
318
-continued
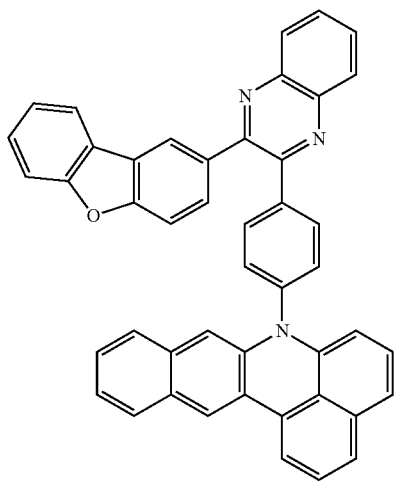
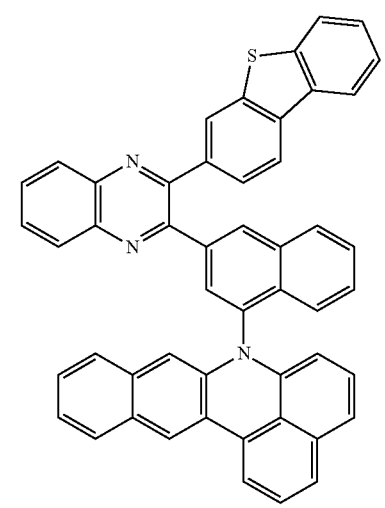
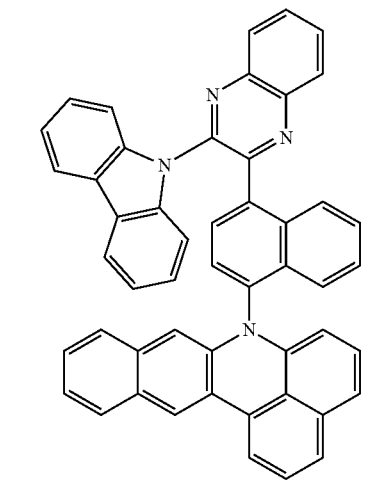

319
-continued
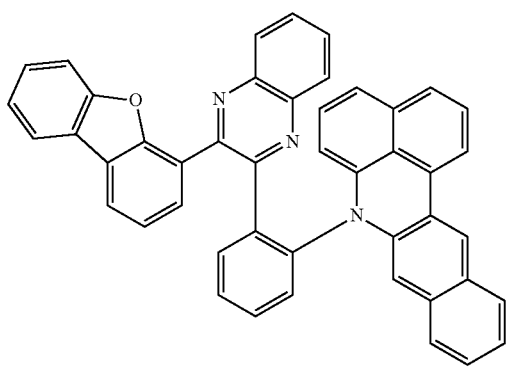
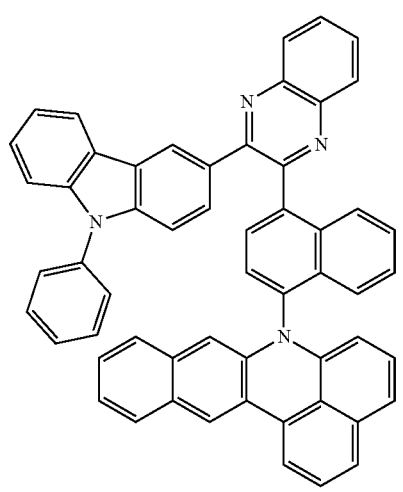
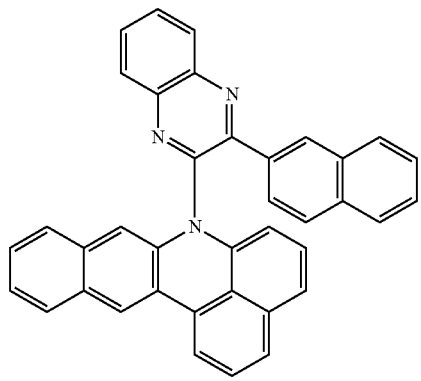
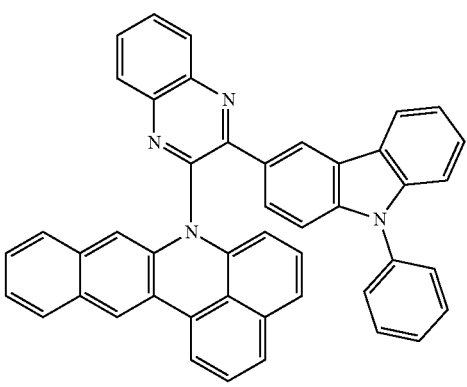
320
-continued
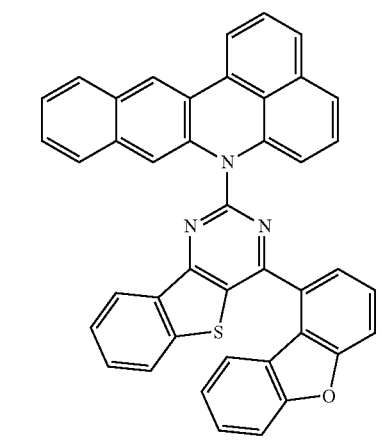
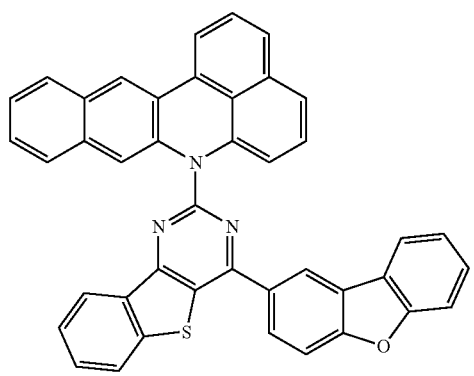
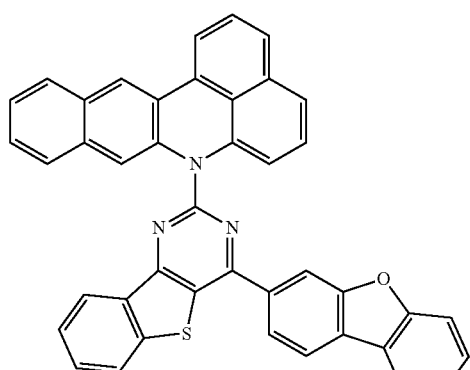
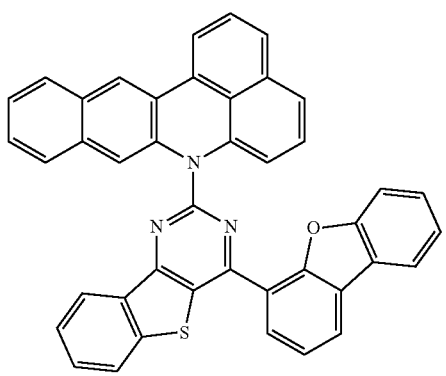

321
-continued
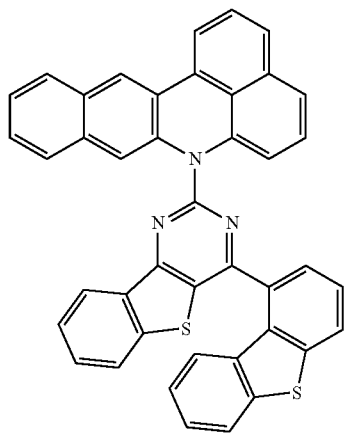
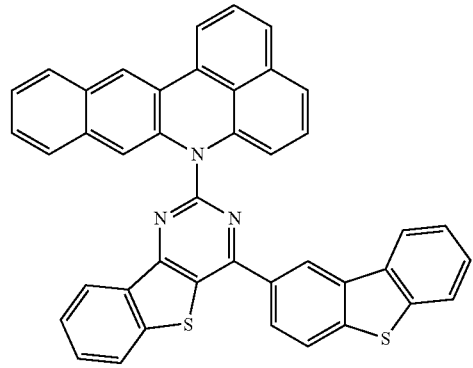
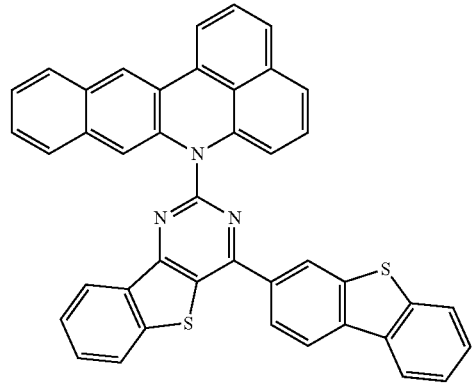
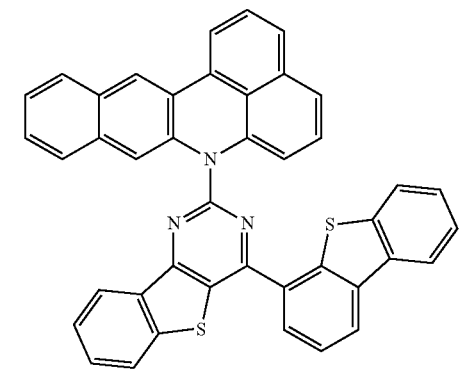
322
-continued
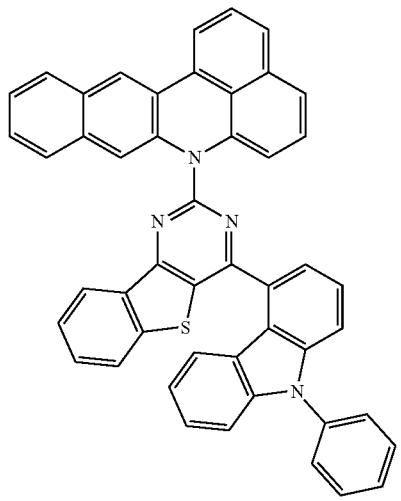
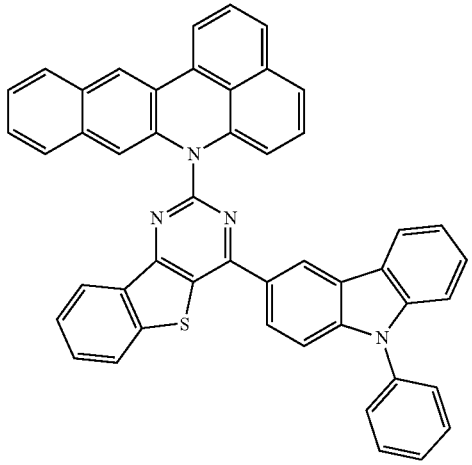
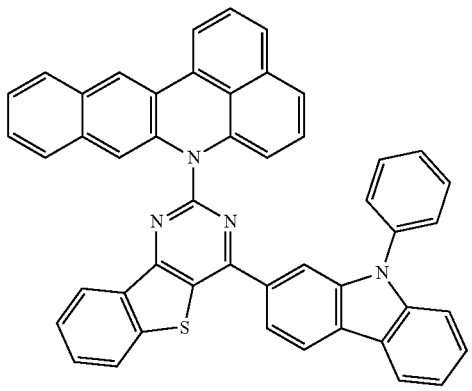

323
-continued
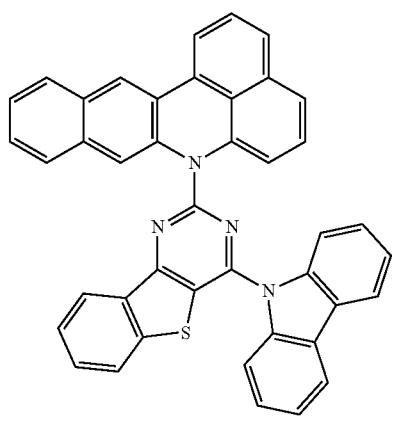
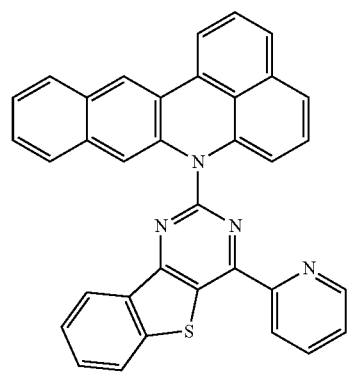
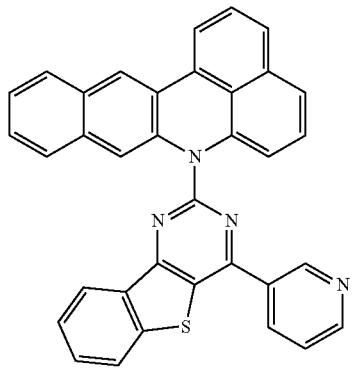
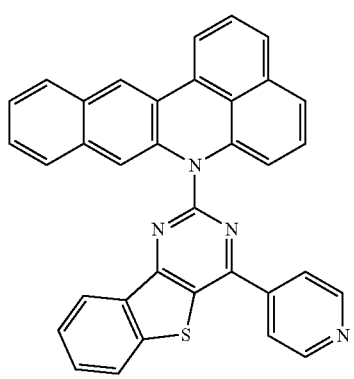
324
-continued
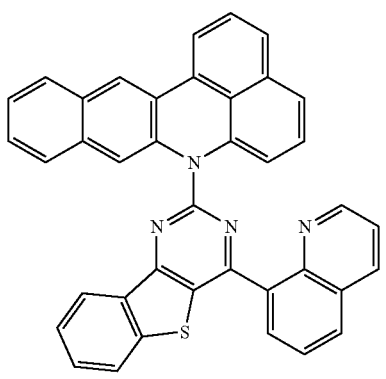
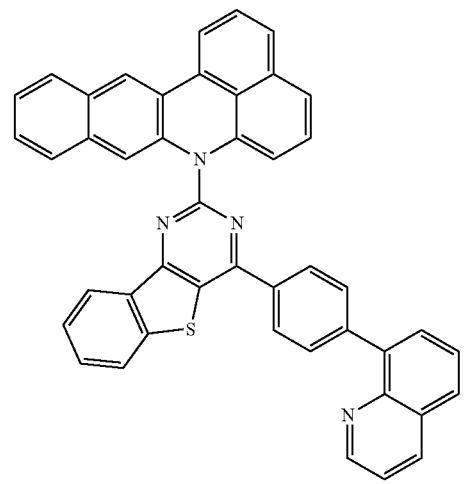
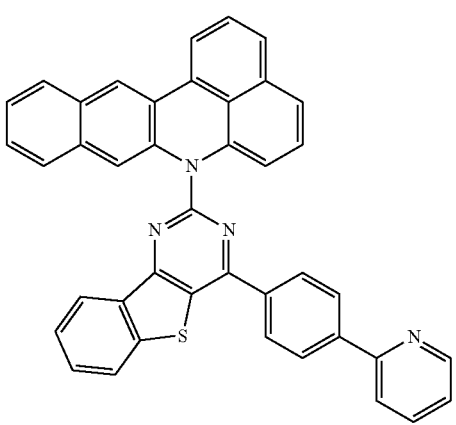

325
-continued
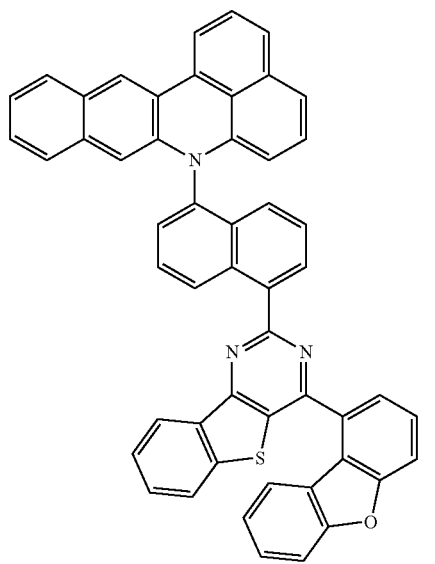
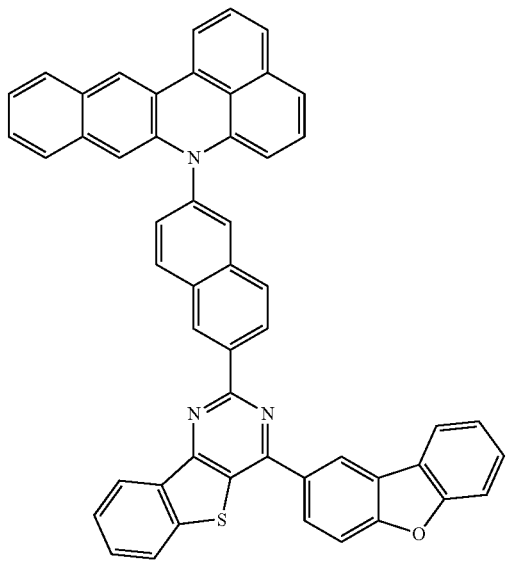
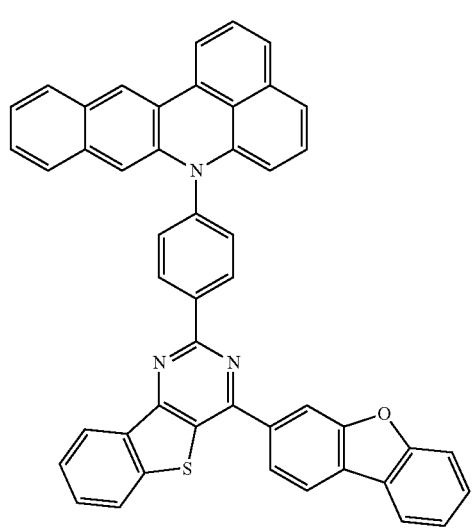
326
-continued
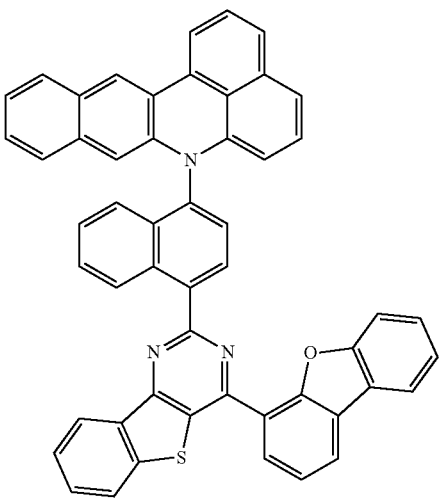
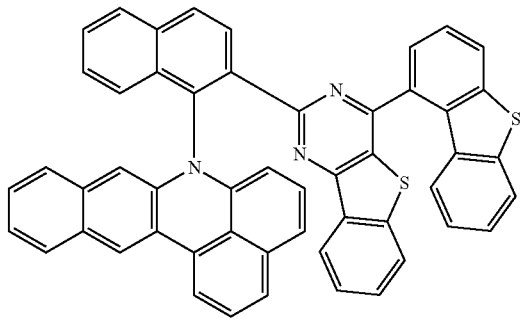
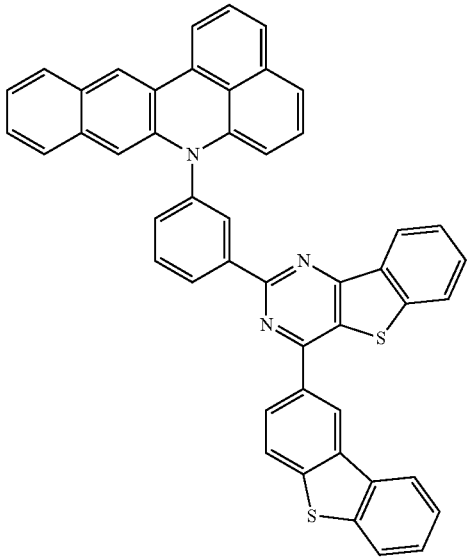

327
-continued
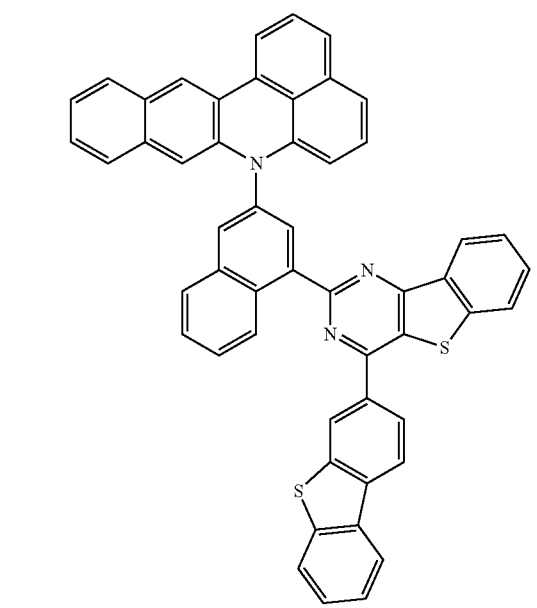
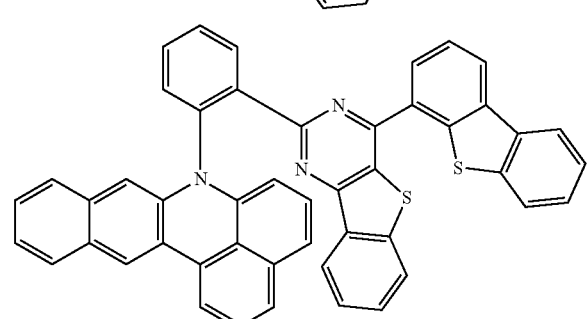
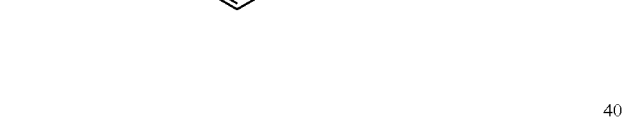
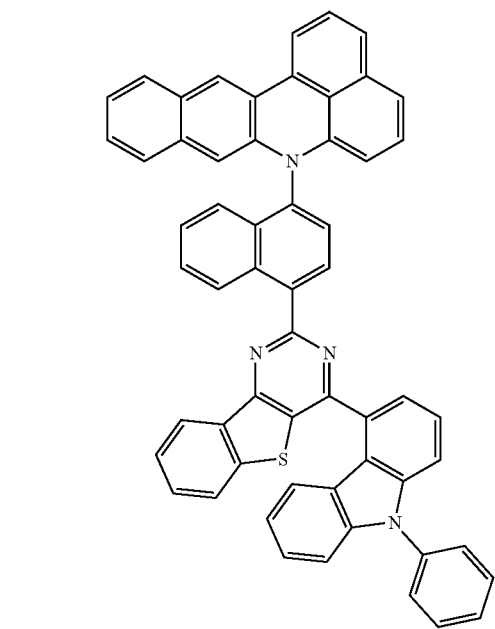
328
-continued
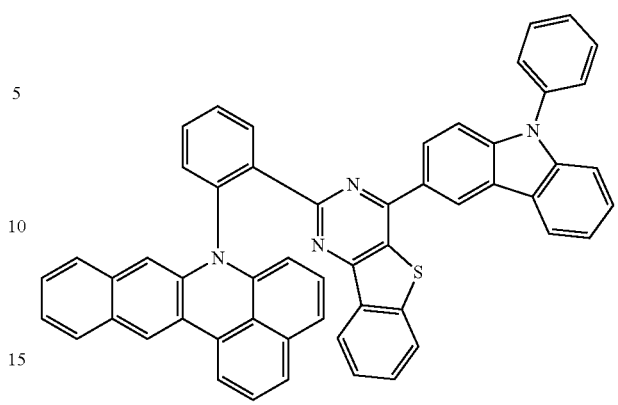
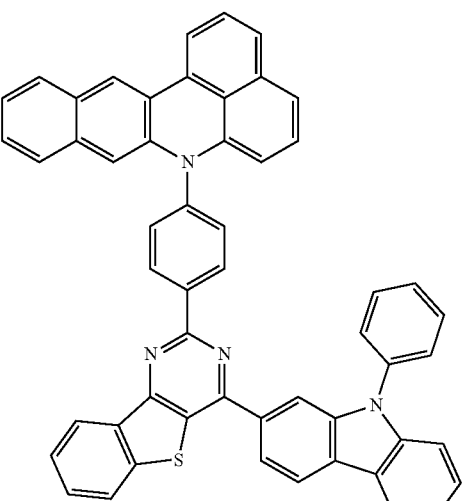
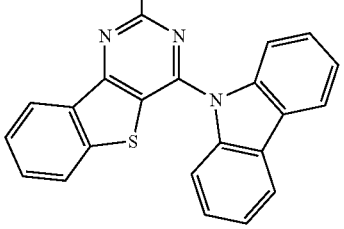

329
-continued
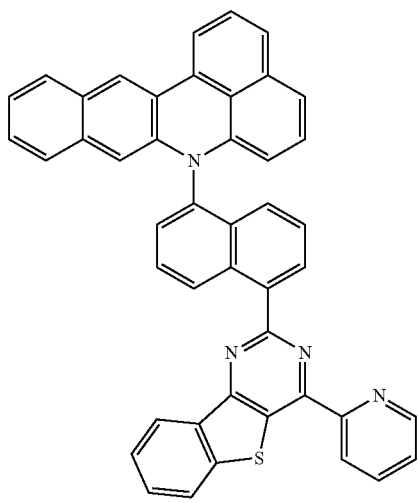
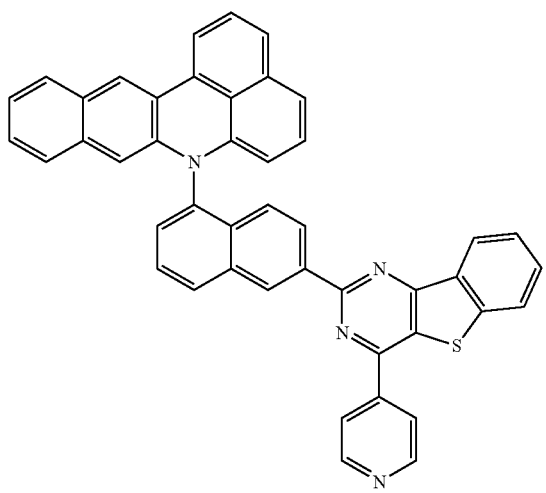
330
-continued
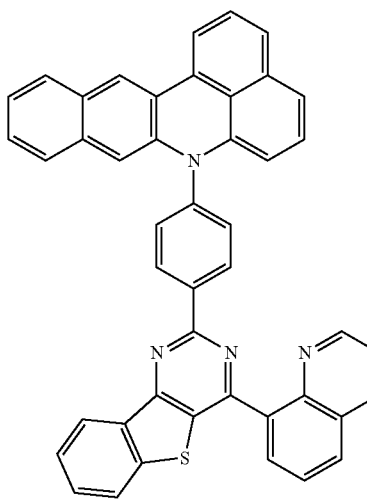
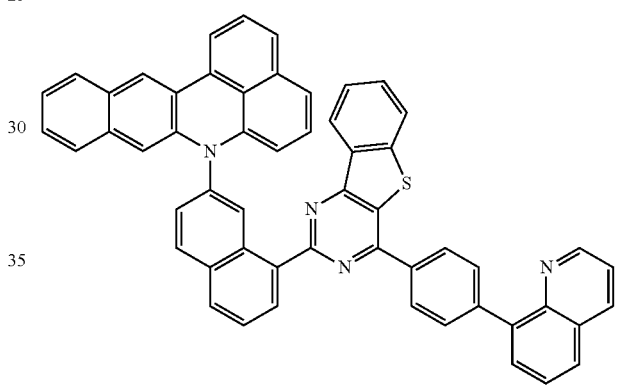
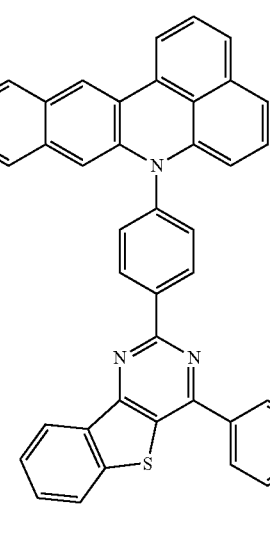

331
-continued
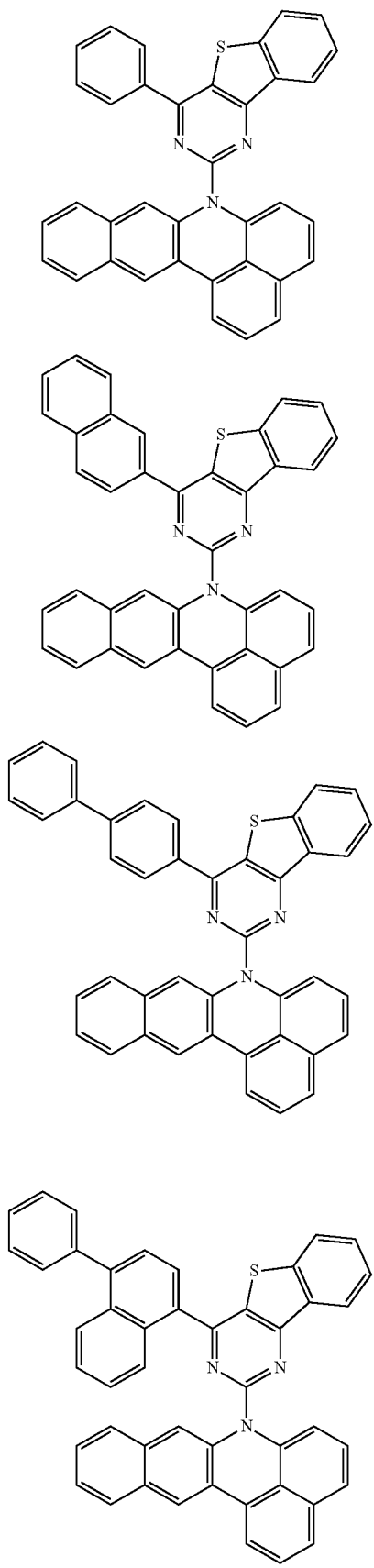
332
-continued
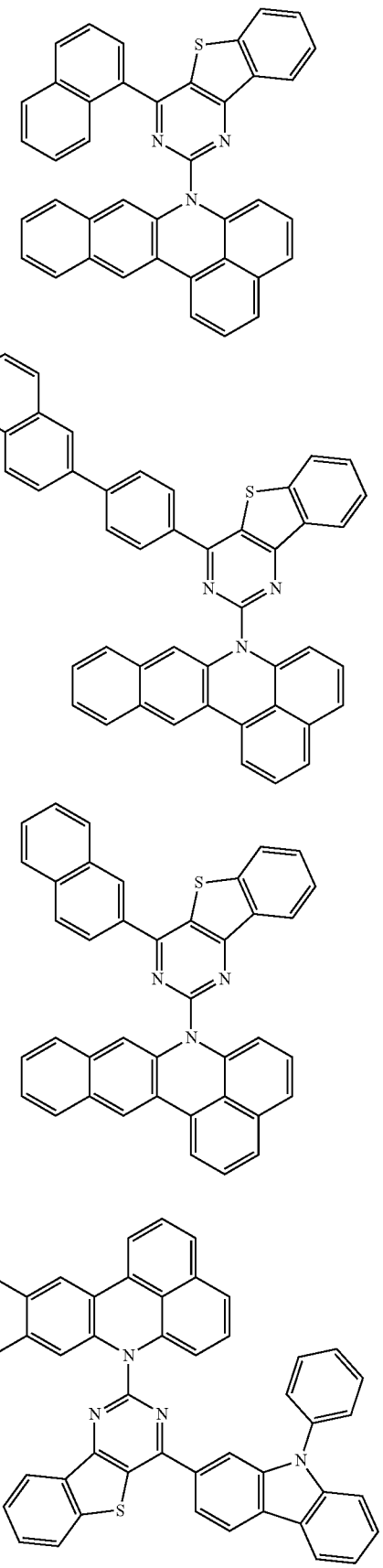

333
-continued
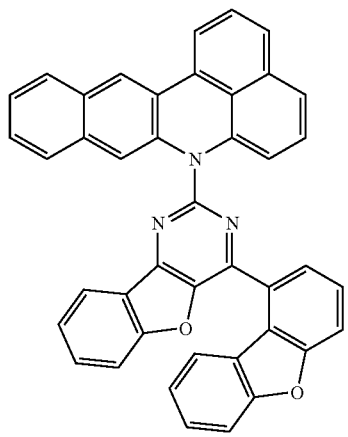
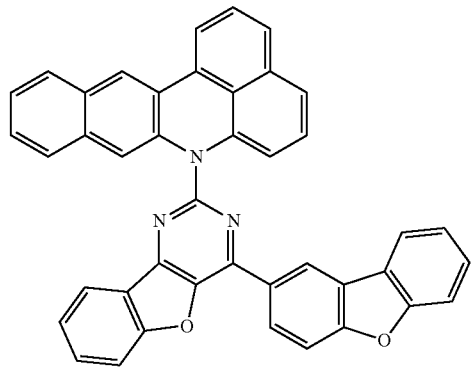
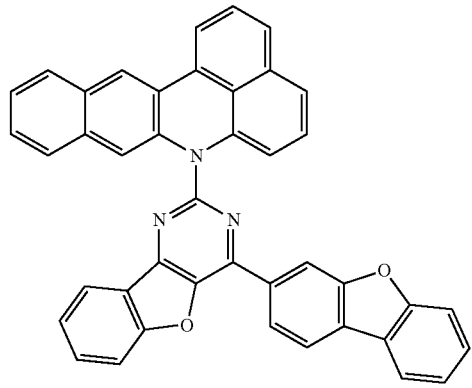
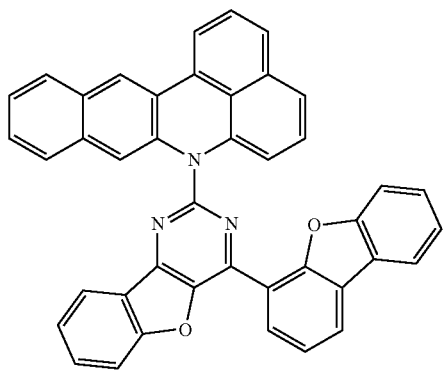
334
-continued
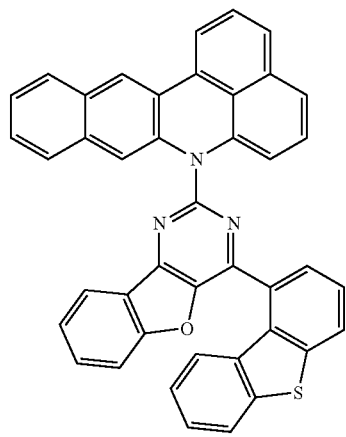
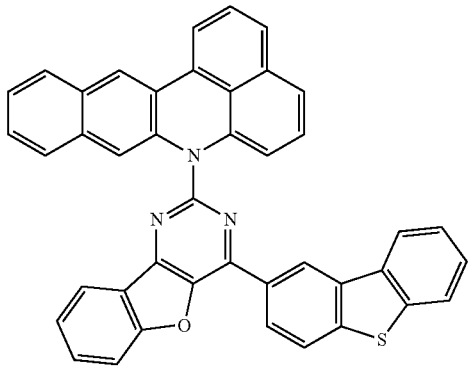
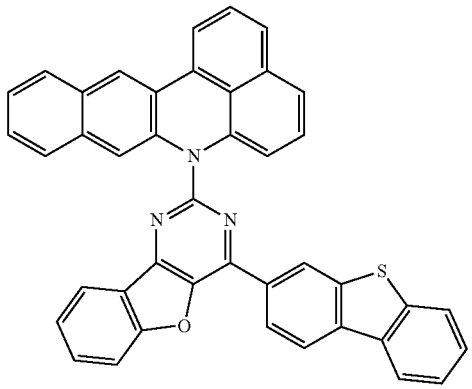
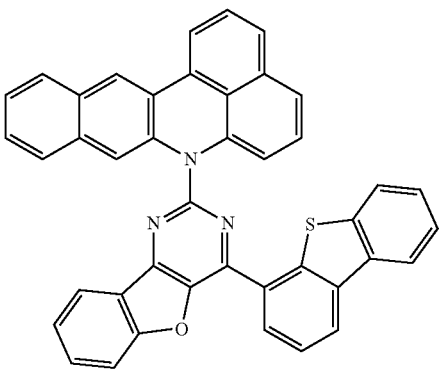

335
-continued
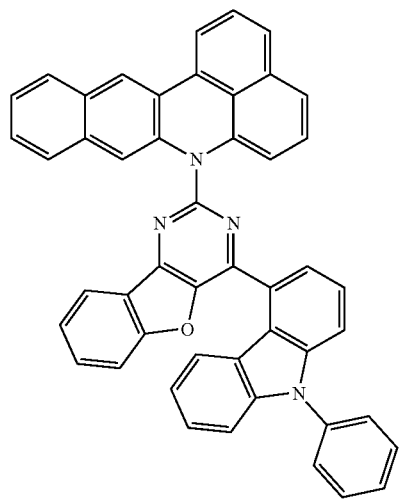
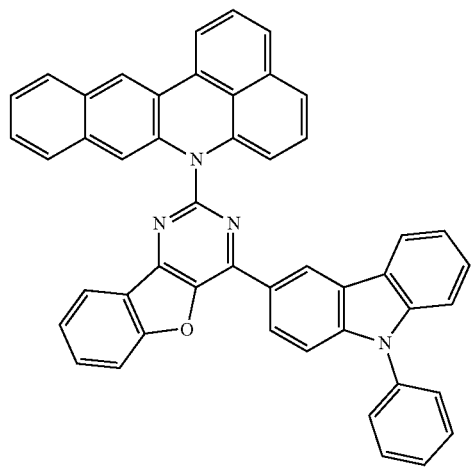
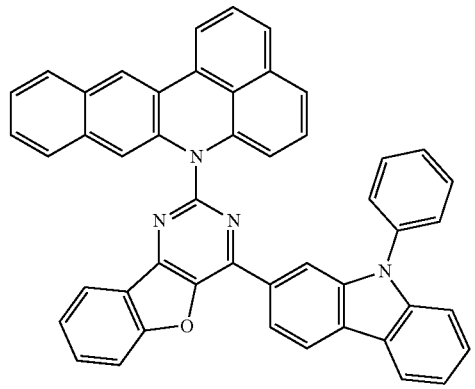
336
-continued
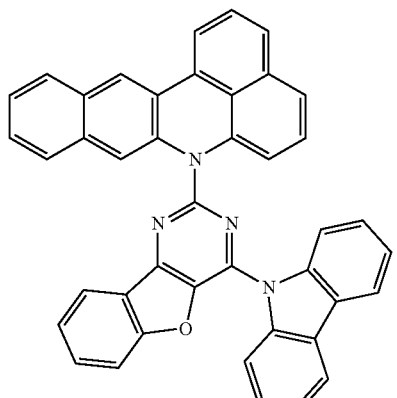
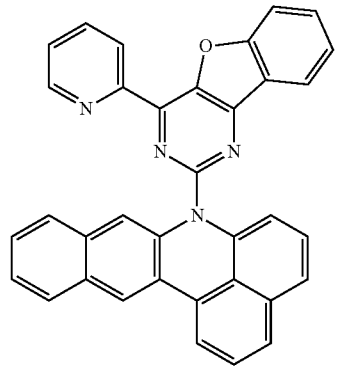
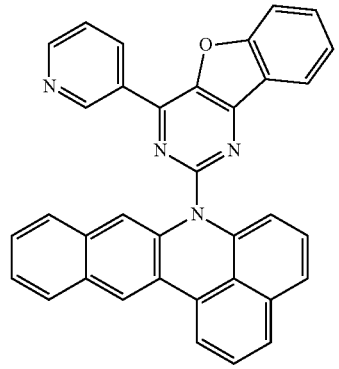
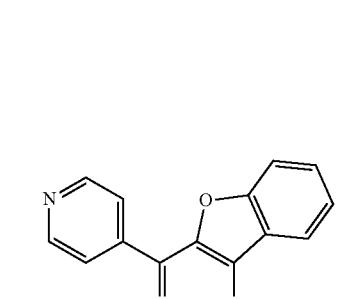

337
-continued
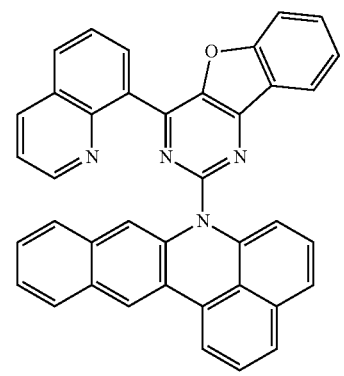
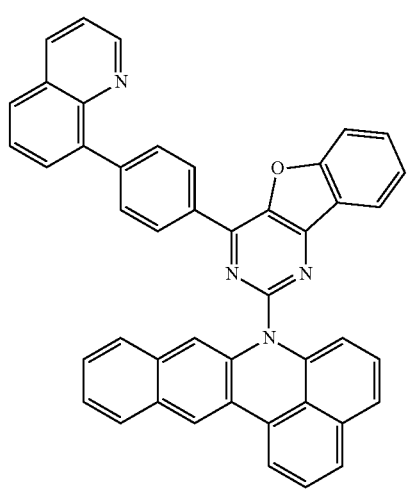
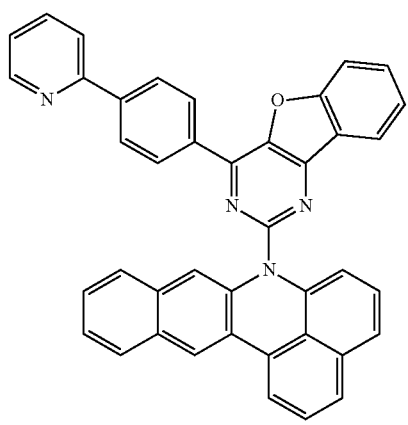
338
-continued
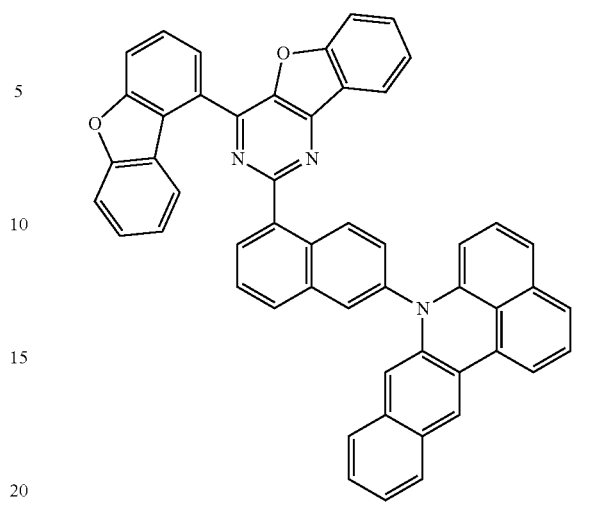
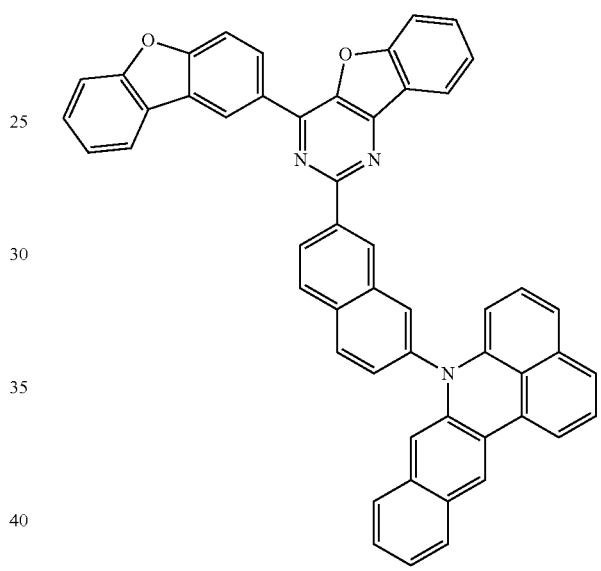
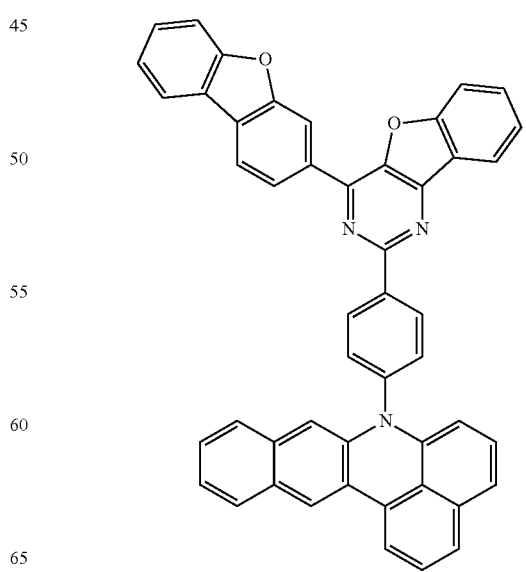

339
-continued
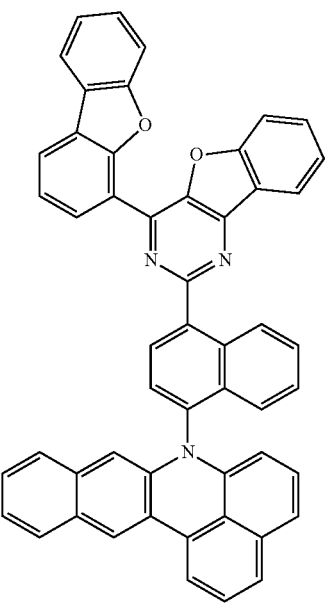
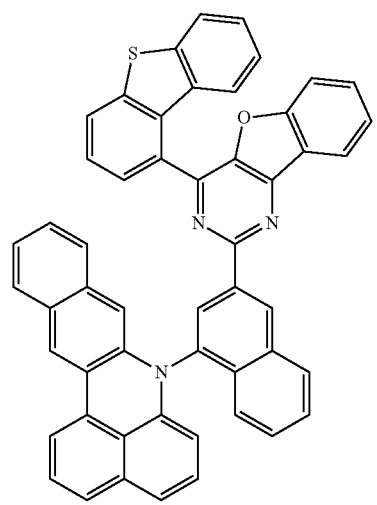
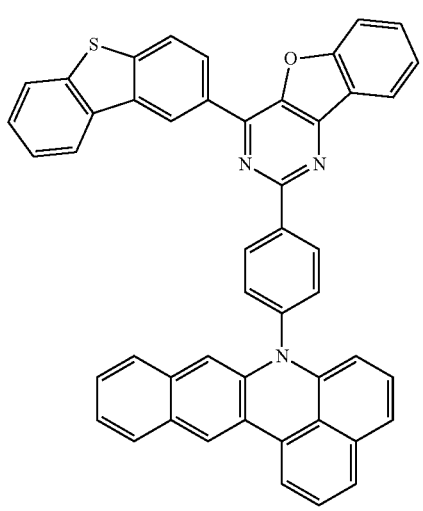
340
-continued
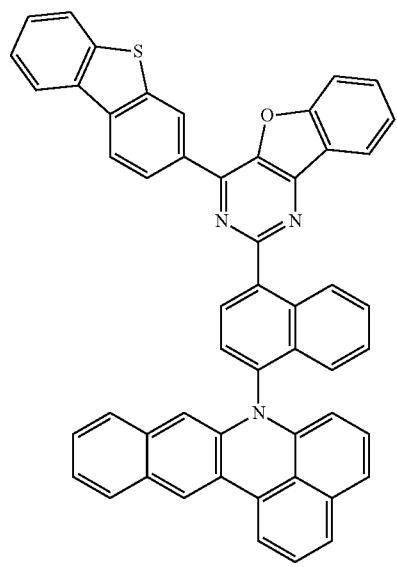
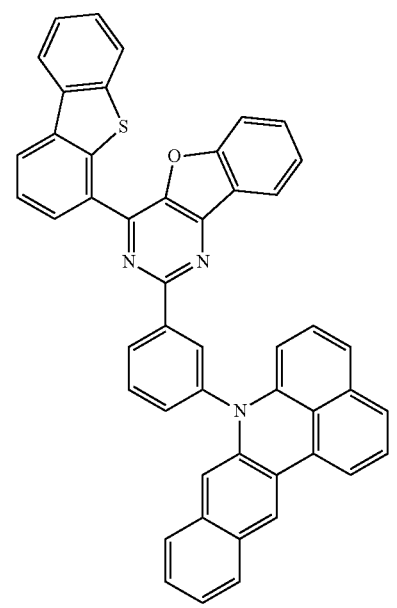
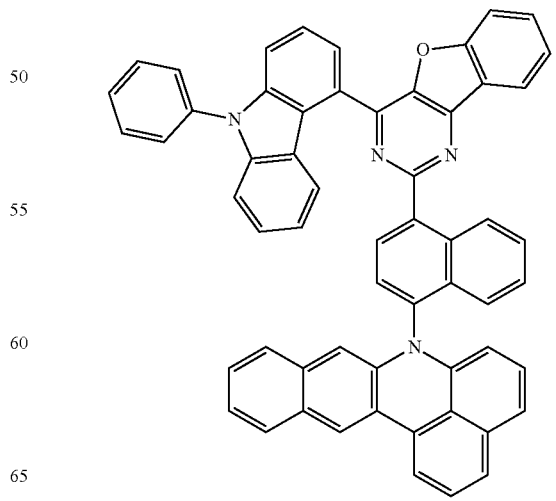

341
-continued
342
-continued
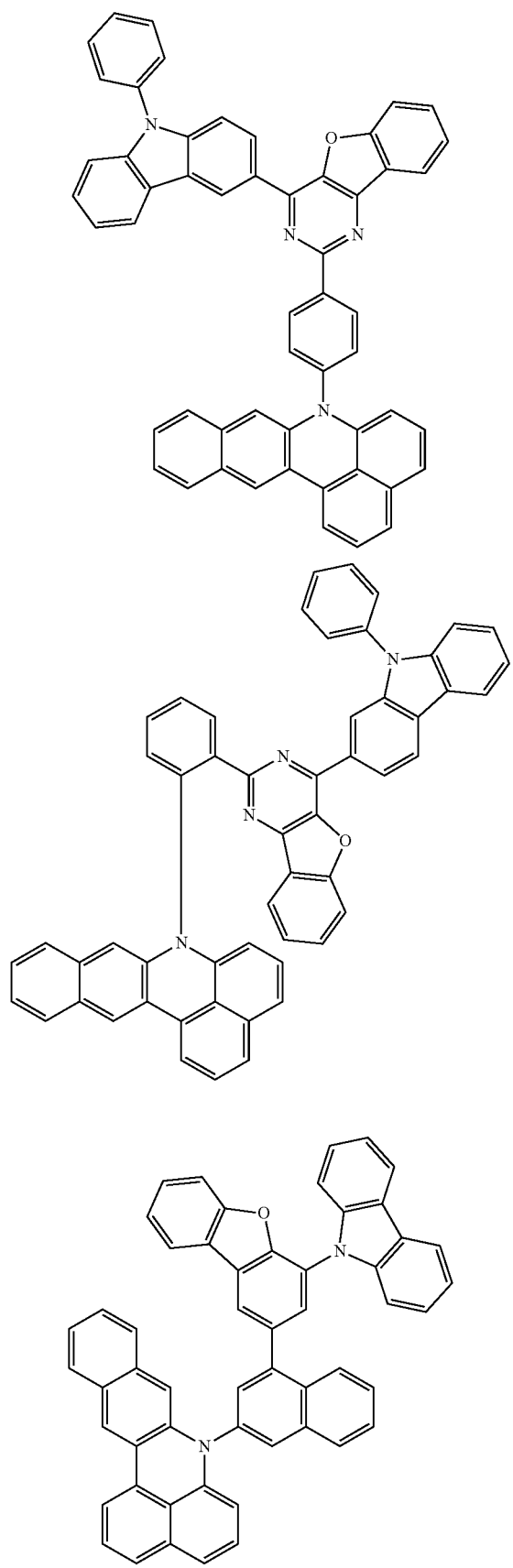
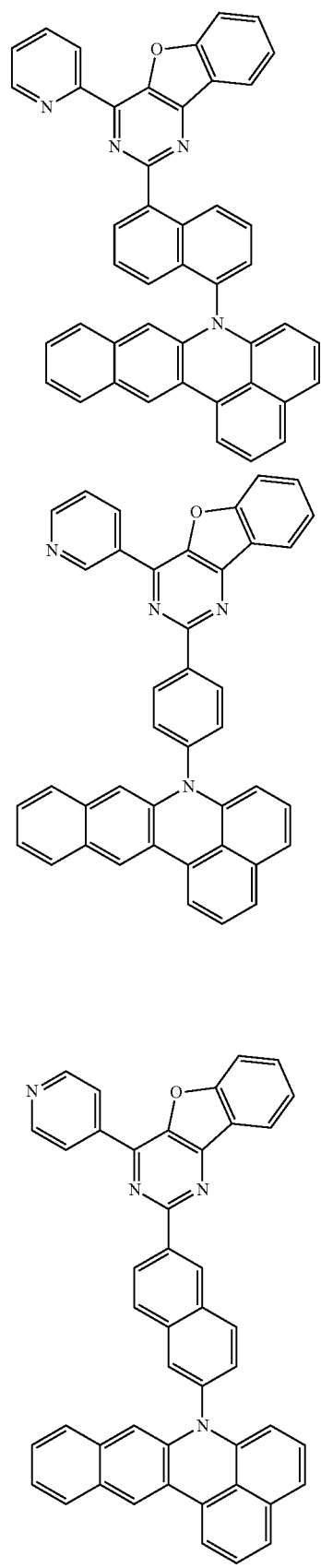

343
-continued
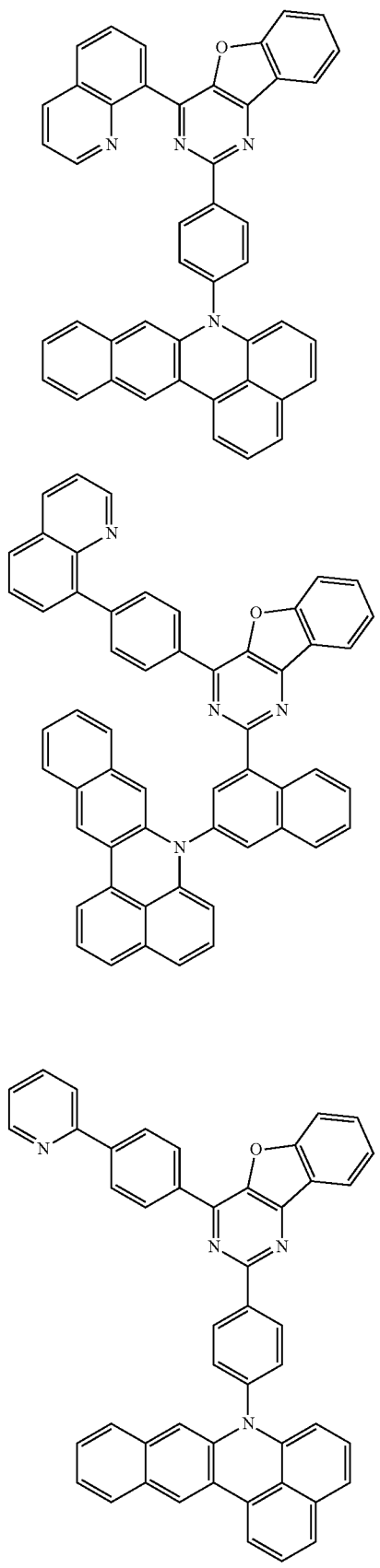
344
-continued
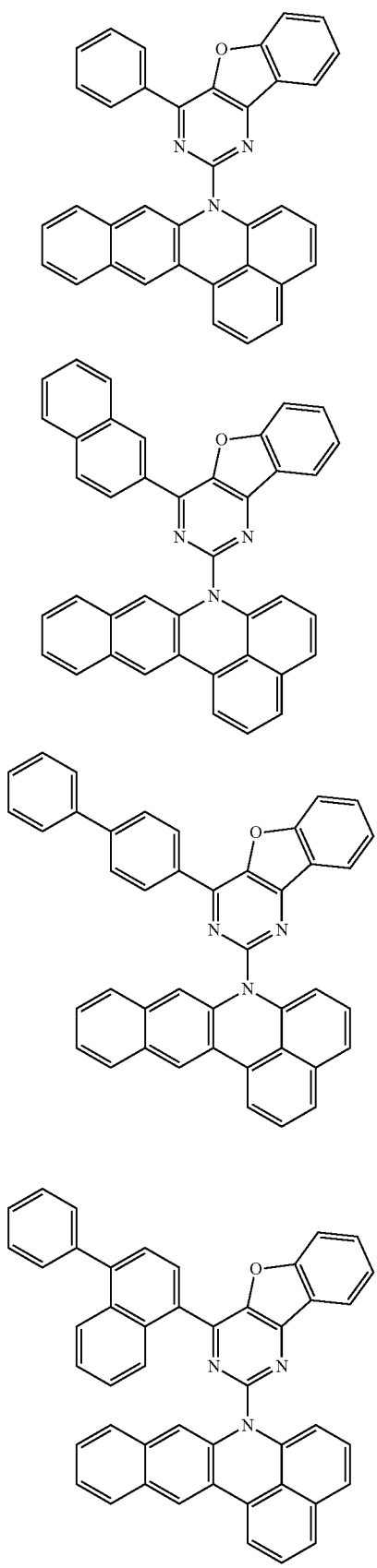

345
-continued
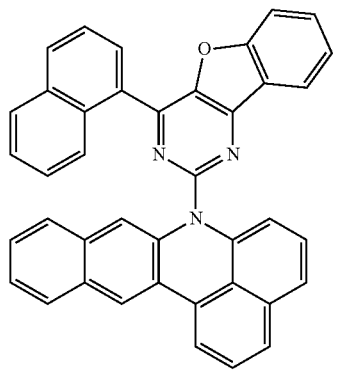
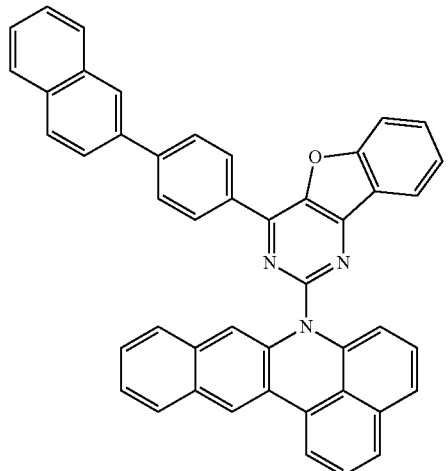
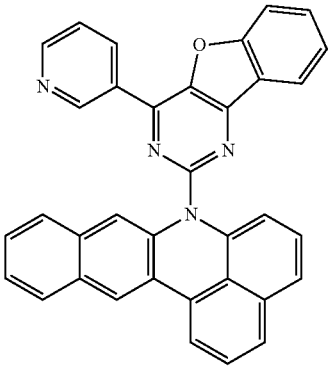
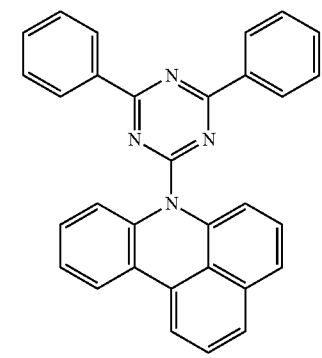
346
-continued
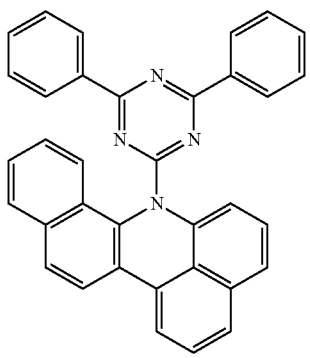
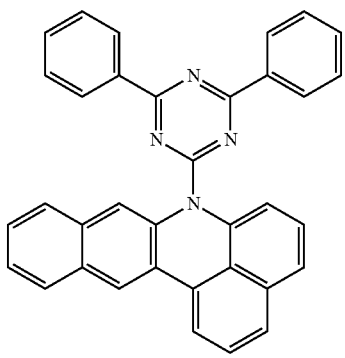
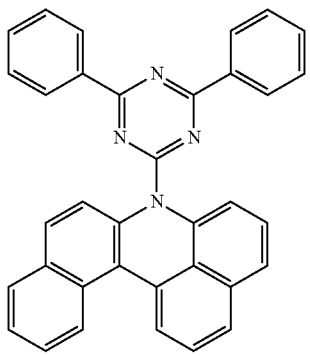
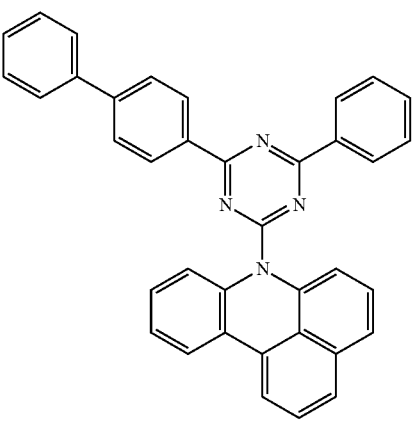

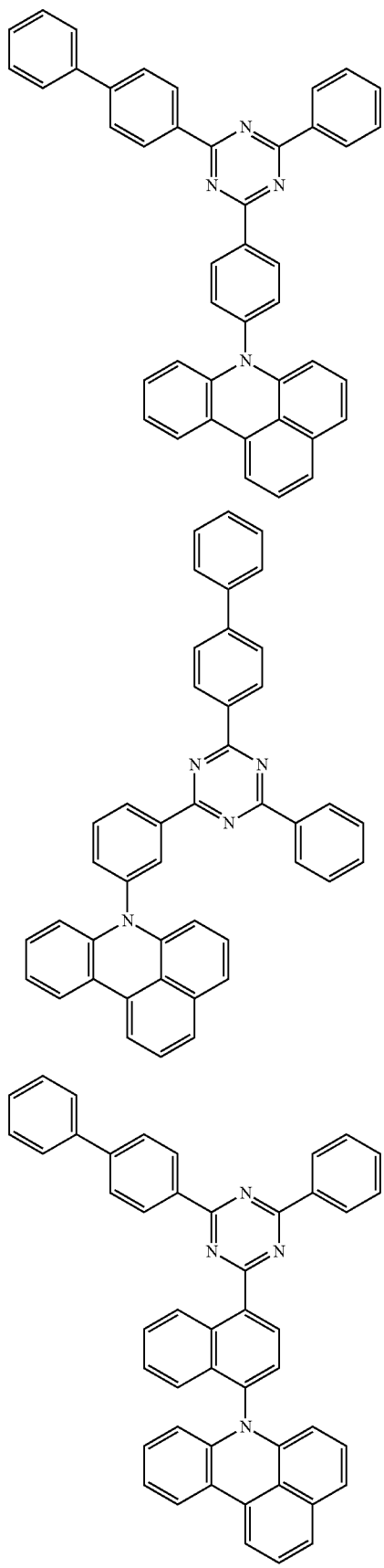

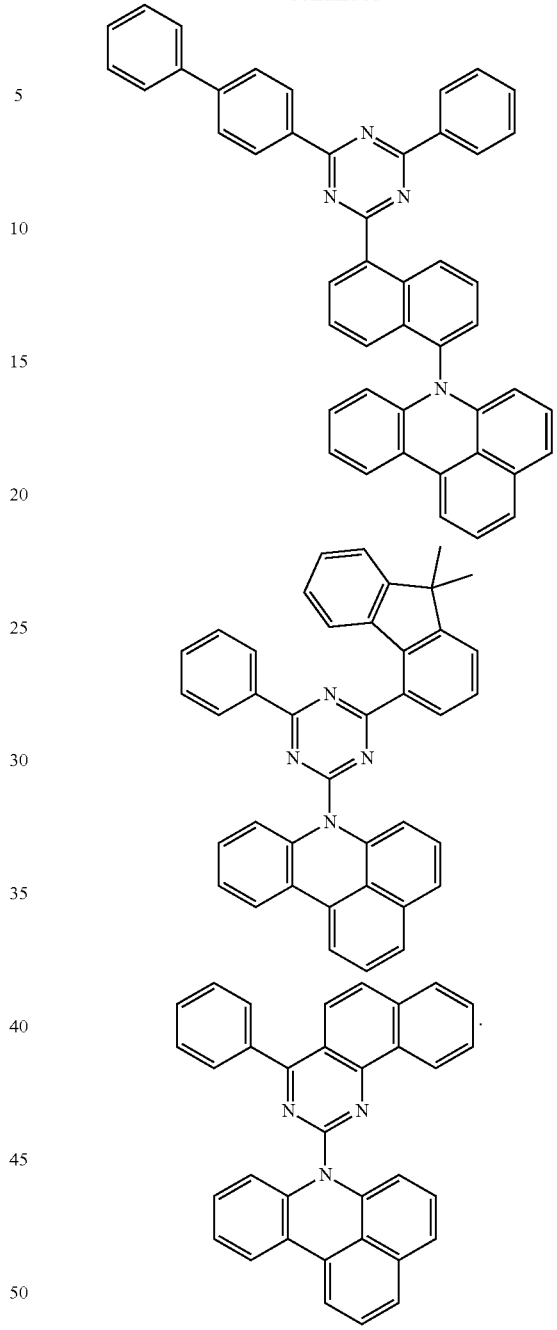

In addition, one embodiment of the present specification provides an organic light emitting device comprising the compound of Chemical Formula 1 described above.

In one embodiment of the present specification, the organic light emitting device comprises a first electrode; a second electrode provided opposite to the first electrode; and one or more organic material layers provided between the first electrode and the second electrode, wherein one or more layers of the organic material layers comprise the compound of Chemical Formula 1.

In the present specification, a description of one member being placed "on" another member comprises not only a case of the one member adjoining the another member but a case of still another member being present between the two members.

In the present specification, a description of a certain part "including" certain constituents means capable of further including other constituents, and does not exclude other constituents unless particularly stated on the contrary.

The organic material layer of the organic light emitting device of the present specification can be formed in a single layer structure, but can be formed in a multilayer structure in which two or more organic material layers are laminated. For example, the organic light emitting device of the present disclosure can have a structure including a hole injection layer, a hole transfer layer, a light emitting layer, an electron transfer layer, an electron injection layer and the like as the organic material layer. However, the structure of the organic light emitting device is not limited thereto, and can include a smaller or a larger number of organic material layers.

In one embodiment of the present specification, the organic material layer comprises a hole injection layer or a hole transfer layer, and the hole injection layer or the hole transfer layer comprises the compound of Chemical Formula 1.

In one embodiment of the present specification, the organic material layer comprises a light emitting layer, and the light emitting layer comprises the compound of Chemical Formula 1.

In one embodiment of the present specification, the organic material layer comprises an electron transfer layer or an electron injection layer, and the electron transfer layer or the electron injection layer comprises the compound of Chemical Formula 1.

In one embodiment of the present specification, the organic light emitting device further comprises one, two or more layers selected from the group consisting of a hole injection layer, a hole transfer layer, an electron transfer layer, an electron injection layer, an electron blocking layer and a hole blocking layer.

In one embodiment of the present application, the organic light emitting device comprises a first electrode; a second electrode provided opposite to the first electrode; a light emitting layer provided between the first electrode and the second electrode; and two or more organic material layers provided between the light emitting layer and the first electrode, or between the light emitting layer and the second electrode, and at least one of the two or more organic material layers comprises the compound of Chemical Formula 1. In one embodiment of the present application, two or more can be selected from the group consisting of an electron transfer layer, an electron injection layer, a layer carrying out electron transfer and electron injection at the same time, and a hole blocking layer as the two or more organic material layers.

In one embodiment of the present application, the organic material layer comprises two or more electron transfer layers, and at least one of the two or more electron transfer layers comprises the compound of Chemical Formula 1. Specifically, in one embodiment of the present specification, the compound can be included in one of the two or more electron transfer layers, or can be included in each of the two or more electron transfer layers.

In addition, when the compound is included in each of the two or more electron transfer layers in one embodiment of the present application, materials other than the compound can be the same as or different from each other.

In one embodiment of the present specification, the organic material layer further comprises, in addition to the organic material layer comprising the compound of Chemical Formula 1, a hole injection layer or a hole transfer layer comprising a compound comprising an arylamino group, a carbazole group or a benzocarbazole group.

In another embodiment, the organic light emitting device can be an organic light emitting device having a normal direction structure in which a first electrode, one or more organic material layers and a second electrode are consecutively laminated on a substrate (normal type).

In another embodiment, the organic light emitting device can be an organic light emitting device having a reversed direction structure in which a second electrode, one or more organic material layers and a first electrode are consecutively laminated on a substrate (inverted type).

For example, the organic light emitting device according to one embodiment of the present specification can have structures as illustrated in FIGS. 1 to 3.

FIG. 1 illustrates a structure of the organic light emitting device in which a substrate (1), a first electrode (2), a light emitting layer (3) and a second electrode (4) are consecutively laminated. In such a structure, the compound of Chemical Formula 1 can be included in the light emitting layer (3).

FIG. 2 illustrates a structure of the organic light emitting device in which a substrate (1), a first electrode (2), a hole injection layer (5), a hole transfer layer (6), a light emitting layer (3), an electron transfer layer (7) and a second electrode (4) are consecutively laminated. In such a structure, the compound of Chemical Formula 1 can be included in one or more of the hole injection layer (5), the hole transfer layer (6), the light emitting layer (3) and the electron transfer layer (7).

FIG. 3 illustrates a structure of the organic light emitting device in which a substrate (1), a first electrode (2), a hole injection layer (5), a hole transfer layer (6), an electron blocking layer (8), a light emitting layer (3), a hole blocking layer (9), a layer carrying out electron transfer and electron injection at the same time (10) and a second electrode (4) are consecutively laminated. In such a structure, the compound of Chemical Formula 1 can be included in the light emitting layer (3).

The organic light emitting device of the present specification can be manufactured using materials and methods known in the art, except that one or more layers of the organic material layers include the compound of the present specification, that is, the compound of Chemical Formula 1.

When the organic light emitting device includes a plurality of organic material layers, the organic material layers can be formed with the same material or different materials.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device can also be manufactured by consecutively depositing a second electrode material, an organic material layer and a first electrode material on a substrate.

In addition, the compound of Chemical Formula 1 can be formed into an organic material layer using a solution coating method as well as a vacuum deposition method when manufacturing the organic light emitting device.

Herein, the solution coating method means spin coating, dip coating, doctor blading, inkjet printing, screen printing, a spray method, roll coating and the like, but is not limited thereto.

In addition to such a method, the organic light emitting device can also be manufactured by consecutively depositing a second electrode material, an organic material layer and a first electrode material on a substrate (International Patent Application Laid-Open Publication No. WO 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in a first electrode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of a first electrode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer receiving holes from a hole injection layer and transferring the holes to a light emitting layer, and as the hole transfer material, materials capable of receiving holes from a first electrode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The electron blocking layer is a layer preventing excess electrons passing through a light emitting layer from moving toward a hole transfer layer. As the electron blocking material, materials having a lower lowest unoccupied molecular orbital (LUMO) level than the hole transfer layer are preferred, and proper materials can be selected considering energy levels of surrounding layers. In one embodiment, arylamine-based organic materials can be used as the electron blocking layer, however, the electron blocking layer is not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, compounds, dibenzofuran derivatives, ladder-type furan compounds, pyrimidine derivatives and the like can be included, however, the host material is not limited thereto.

In the present specification, the organic material layer including the compound of Chemical Formula 1 further includes a dopant.

In one embodiment of the present specification, the light emitting layer comprising the compound of Chemical Formula 1 further comprises a dopant.

In one embodiment of the present specification, the dopant can be selected from among the following compounds, but is not limited thereto:

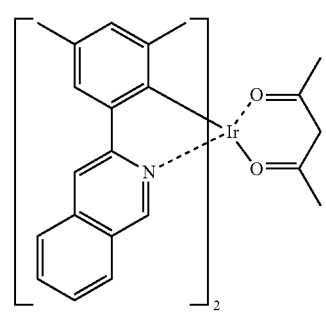

Dp-1

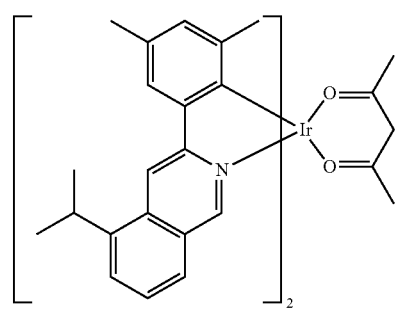

Dp-2

Dp-3
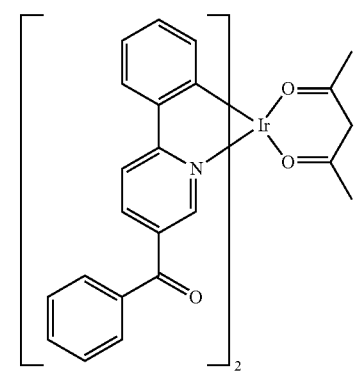
Dp-4
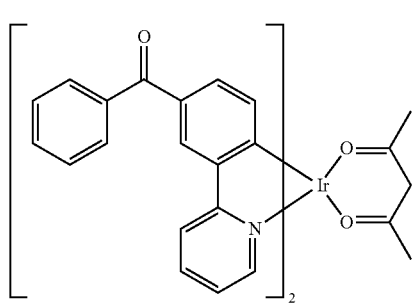
Dp-5
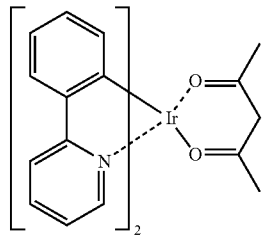
Dp-6
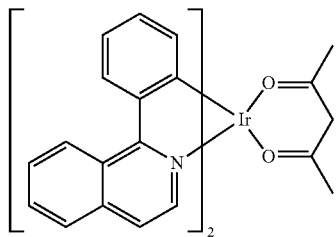
Dp-7
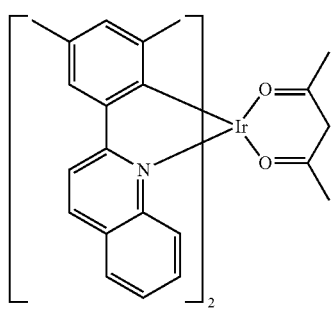
Dp-8
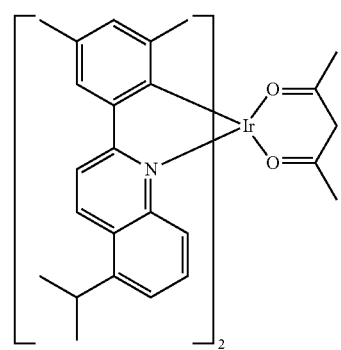
Dp-9
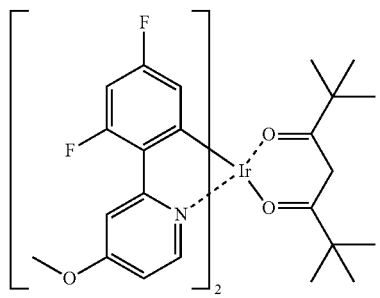
Dp-10
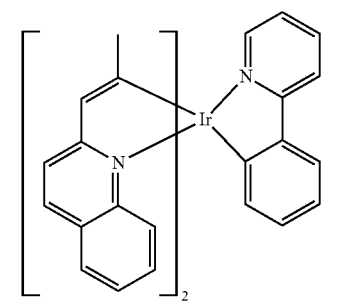
Dp-11
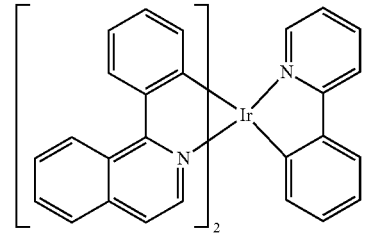
Dp-12
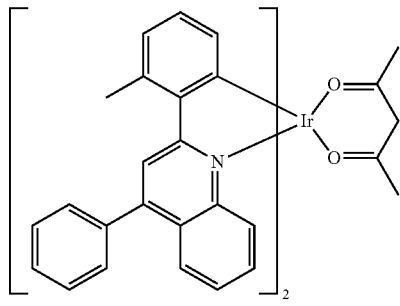

Dp-13
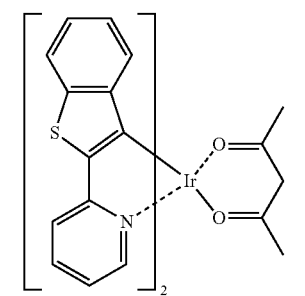
Dp-14
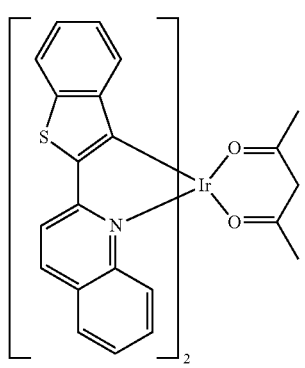
Dp-15
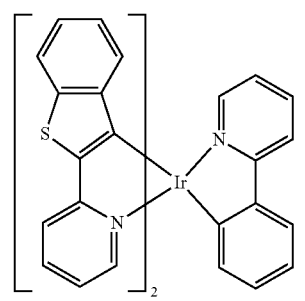
Dp-16
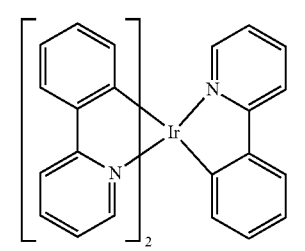
Dp-17
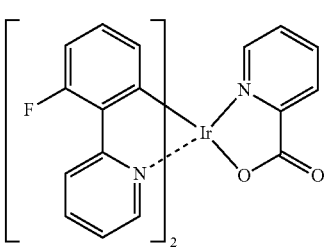
Dp-18
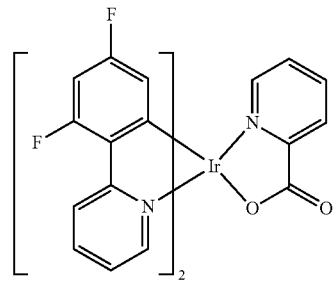
Dp-19
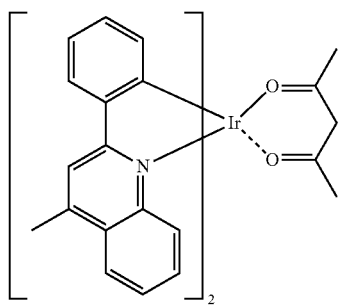
Dp-20
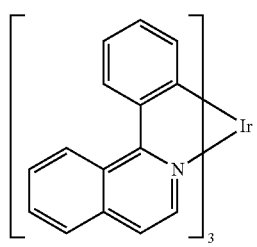
Dp-21
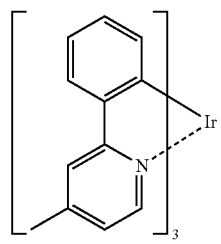
DP-22
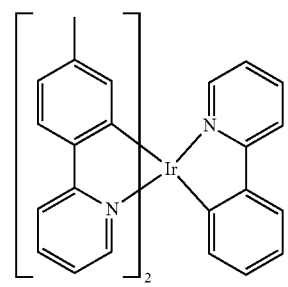
Dp-23
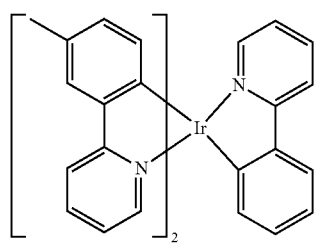

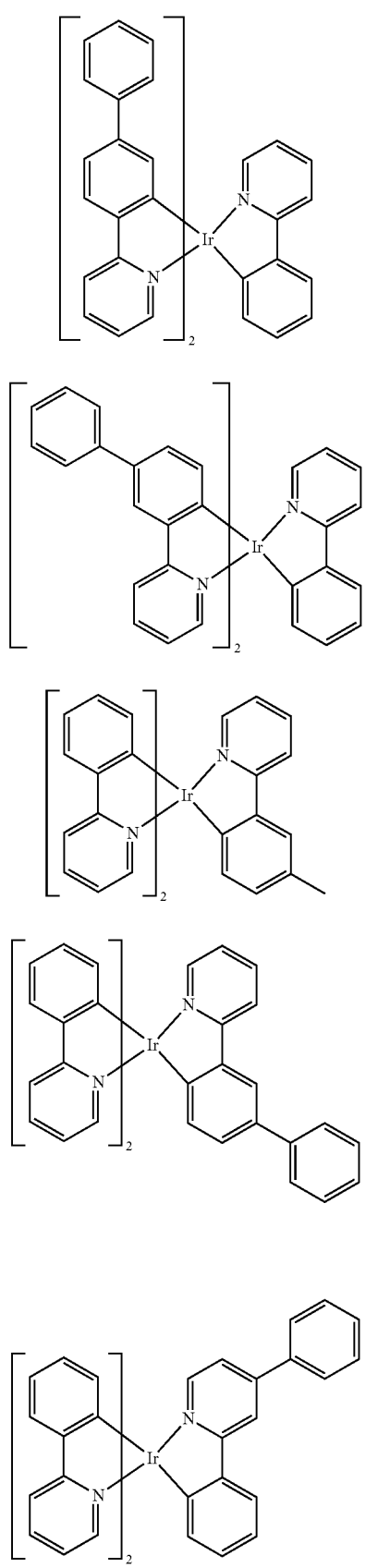
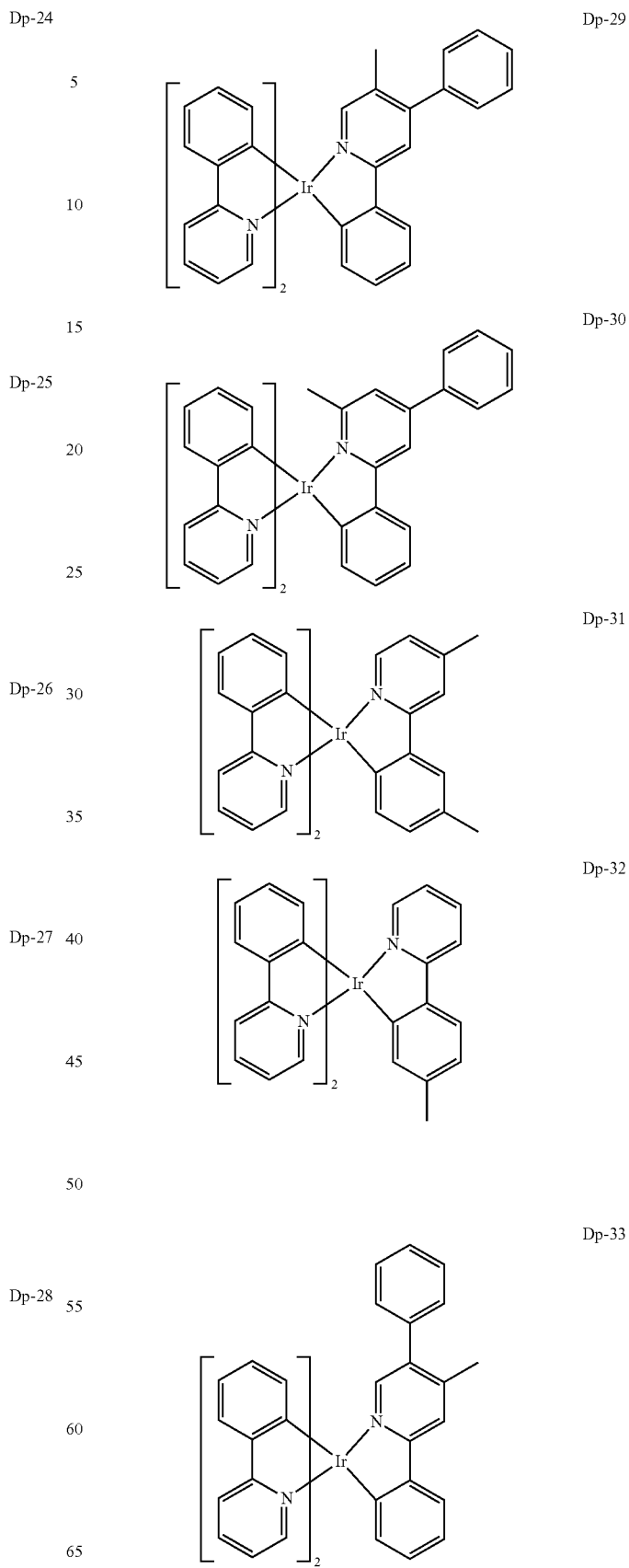

Dp-34 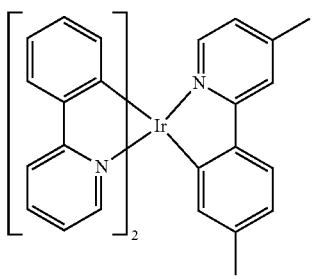

Dp-35 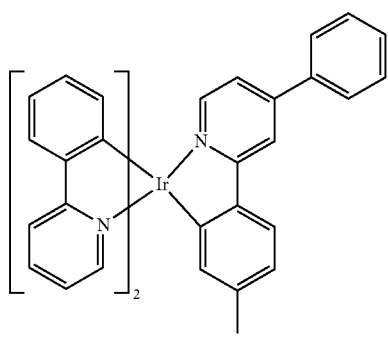

Dp-36 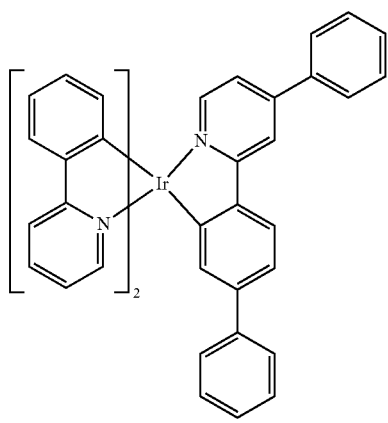

Dp-37 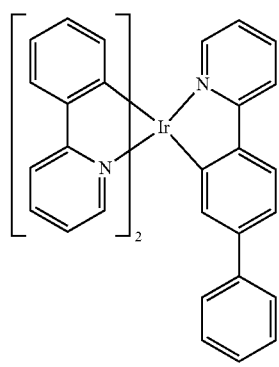

Dp-38 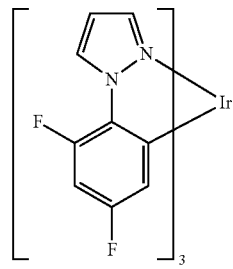

Dp-39 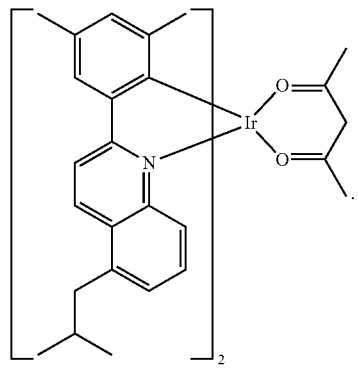

The hole blocking layer performs a role of preventing holes from passing through a light emitting layer and entering a cathode while driving an organic light emitting device. As the hole blocking material, materials having a very low highest occupied molecular orbital (HOMO) level are preferably used. Specific examples of the hole blocking material can include oxadiazole derivatives, triazole derivatives, phenanthroline derivatives, BCP, aluminum complexes, TPBi, BCP, CBP, PBD, PTCBI, BPhen and the like, but are not limited thereto.

The electron transfer layer is a layer receiving electrons from an electron injection layer and transferring the electrons to a light emitting layer, and as the electron transfer material, materials capable of favorably receiving electrons from a second electrode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material can include common materials having low work function and having an aluminum layer or a silver layer following. Specifically, cesium, barium, calcium, ytterbium and samarium are included, and in each case, an aluminum layer or a silver layer follows.

The electron injection layer is a layer injecting electrons from an electrode. As the electron injection material, compounds having an electron transferring ability, having an electron injection effect from a second electrode, having an excellent electron injection effect for a light emitting layer or light emitting material, and preventing excitons generated in the light emitting layer from moving to a hole injection layer, and in addition thereto, having an excellent thin film forming ability are preferred. Examples of the electron injection material include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)-chlorogallium, bis(2-methyl-8-quinolinato) (o-cresolato)-gallium, bis(2-methyl-8-quinolinato)(1-naphtholato)aluminum, bis(2-methyl-8-quinolinato) (2-naphtholato)gallium and the like, but is not limited thereto.

The organic light emitting device according to the present specification can be a top-emission type, a bottom-emission type or a dual-emission type depending on the materials used.

A method for preparing the compound of Chemical Formula 1 and a method for manufacturing an organic light emitting device including the same will be specifically described in the following examples. However, the following examples are for illustrative purposes only, and the scope of the present disclosure is not limited thereto.

The compound of the present disclosure can be prepared using a Buchwald-Hartwig coupling reaction, a Suzuki coupling reaction or the like.

Preparation Example 1

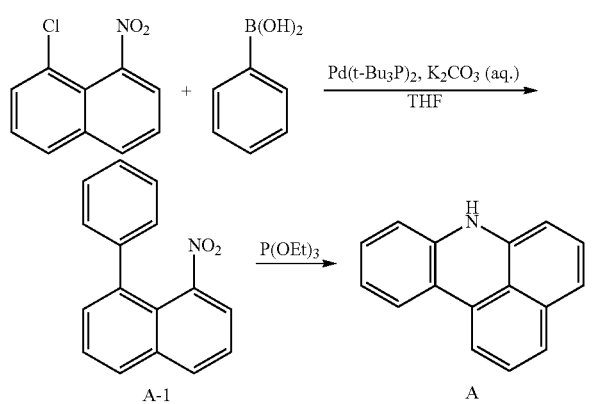

After dissolving 1-chloro-8-nitronaphthalene (100 g, 1 eq.) and phenylboronic acid (64.58 g, 1.1 eq.) in tetrahydrofuran (THF) (1000 ml), potassium carbonate ($K_2CO_3$) (133.1 g, 2 eq.) dissolved in water (300 ml) was introduced thereto. Bis(tri-tert-butylphosphine)palladium(0) (Pd(t-$Bu_3P)_2$) (1.23 g, 0.005 eq.) was introduced thereto, and the result was stirred under reflux. When the reaction was finished, the solvent was removed under vacuum. After that, the result was completely dissolved in chloroform ($CHCl_3$), washed with water, treated with anhydrous magnesium sulfate, then vacuumed to remove the solvent, and column chromatographed to obtain Compound A-1 (97.22 g, yield 81%). ($MH^+$=250)

Chemical Formula A-1 (97.22 g, 1 eq.) was introduced to triethyl phosphite (200 mL), and the result was stirred under reflux. After 2 hours, the reaction was terminated, and the reaction material was poured into ethanol (2 L) to precipitate solids. The solids were completely dissolved in chloroform ($CHCl_3$), and the result was washed with water and treated with anhydrous magnesium sulfate, and the solution was vacuum concentrated and purified using column chromatography to obtain Compound A (61.86 g, yield 73%). ($MH^+$=218)

Preparation Example 2

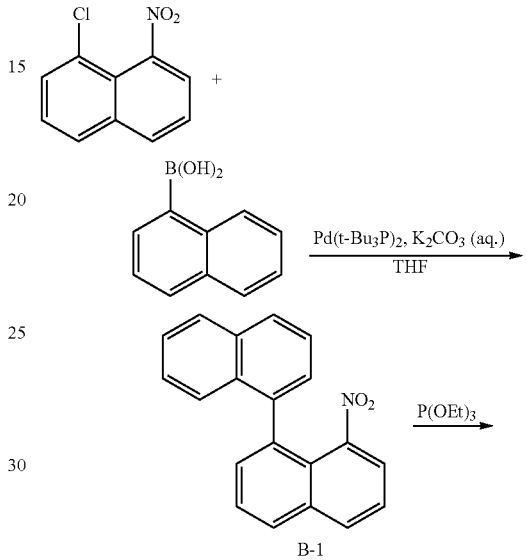

Compound B was synthesized in the same manner as in the method for preparing Compound A of Preparation Example 1 except that naphthalen-1-ylboronic acid was used instead of phenylboronic acid.

Preparation Example 3

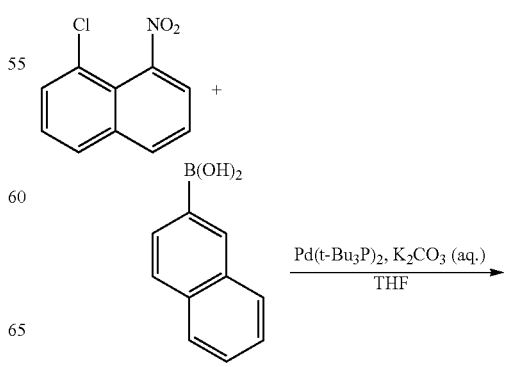

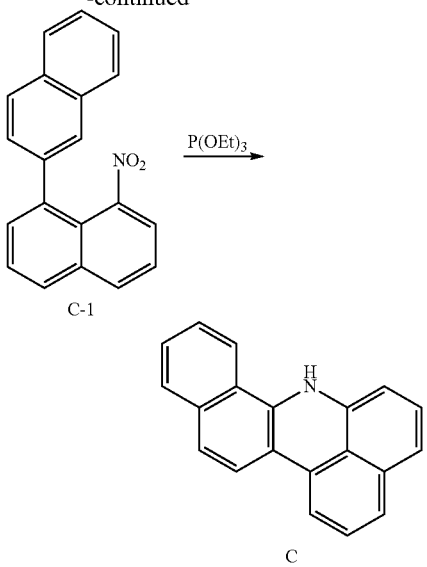

Compound C was synthesized in the same manner as in the method for preparing Compound A of Preparation Example 1 except that naphthalen-2-ylboronic acid was used instead of phenylboronic acid.

Preparation Example 4

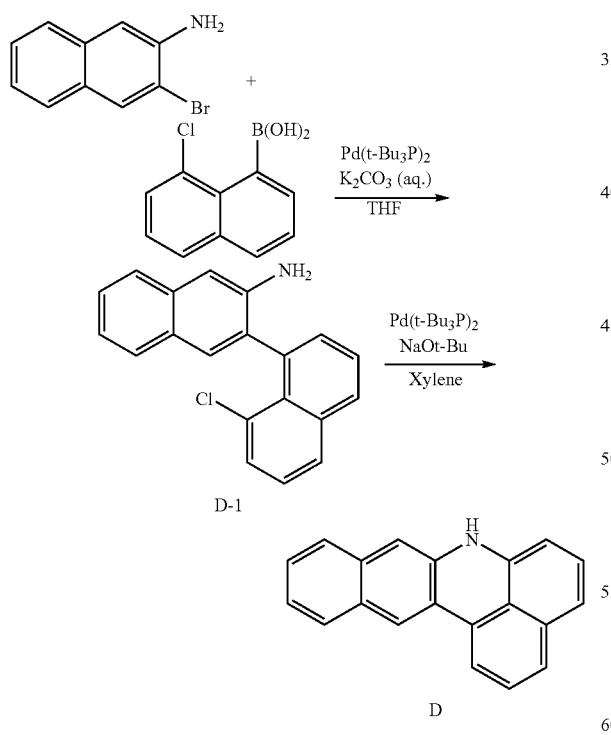

After dissolving 3-bromonaphthalene-2-amine (100 g, 1 eq.) and (8-chloronaphthalen-1-yl)boronic acid (102.24 g, 1.1 eq.) in tetrahydrofuran (THF) (1000 ml), potassium carbonate ($K_2CO_3$) (124.46 g, 2 eq.) dissolved in water (300 ml) was introduced thereto. Bis(tri-tert-butylphosphine)palladium(0) (Pd(t-Bu$_3$P)$_2$) (1.15 g, 0.005 eq.) was introduced thereto, and the result was stirred under reflux. When the reaction was finished, the solvent was removed under vacuum. After that, the result was completely dissolved in chloroform (CHCl$_3$), washed with water, treated with anhydrous magnesium sulfate, then vacuumed to remove the solvent, and column chromatographed to obtain Compound D-1 (101.22 g, yield 74%). (MH$^+$=304)

Compound D-1 (101.22 g, 1 eq.), bis(tri-tert-butylphosphine)palladium(0) (Pd(t-Bu$_3$P)$_2$) (0.85 g, 0.01 eq.) and sodium tert-butoxide (NaOt-Bu) (64.04 g, 2 eq.) were introduced to xylene (1000 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound D (59.67 g, yield 67%). (MH$^+$=268)

SYNTHESIS EXAMPLE

Synthesis Example 1

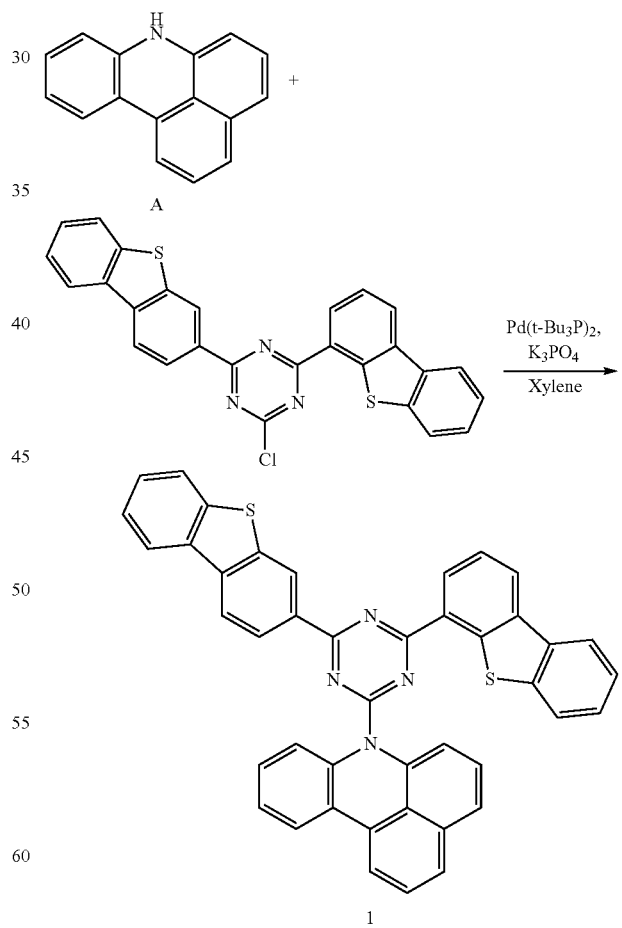

Compound A (10 g, 1 eq.), 2-chloro-4-(dibenzo[b,d]-thiophen-3-yl)-6-(dibenzo[b,d]thiophen-4-yl)-1,3,5-triazine (24.3 g, 1.1 eq.), bis(tri-tert-butylphosphine)-palladium(0)

(Pd(t-Bu₃P)₂) (0.23 g, 0.01 eq.) and potassium phosphate tribasic (K₃PO₄) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 1 (22.2 g, yield 73%). (MH⁺=661)

Synthesis Example 2

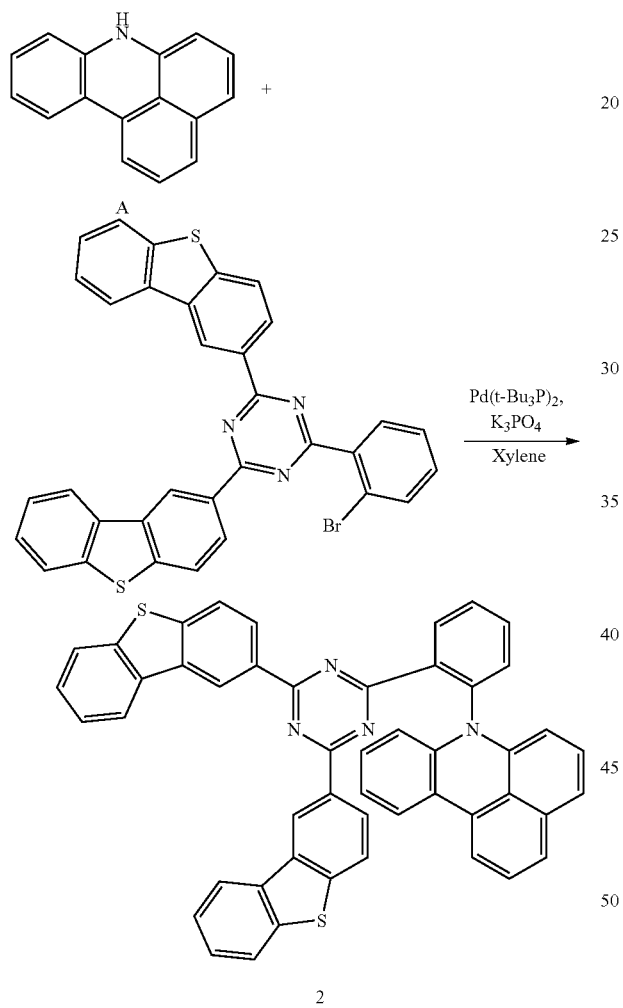

2

Compound A (10 g, 1 eq.), 2-(2-bromophenyl)-4,6-bis(dibenzo[b,d]thiophen-2-yl)-1,3,5-triazine (30.4 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 2 (24.75 g, yield 61%). (MH⁺=737)

Synthesis Example 3

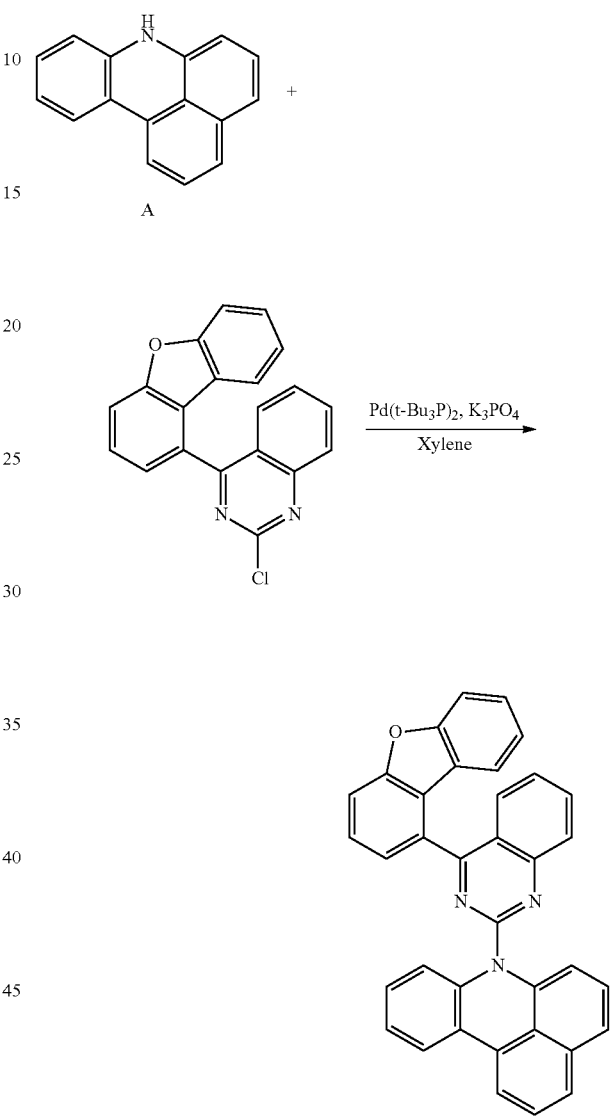

Compound A (10 g, 1 eq.), 2-chloro-4-(dibenzo[b,d]furan-1-yl)quinazoline (16.74 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.54 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 3 (16.95 g, yield 72%). (MH⁺=512)

Synthesis Example 4

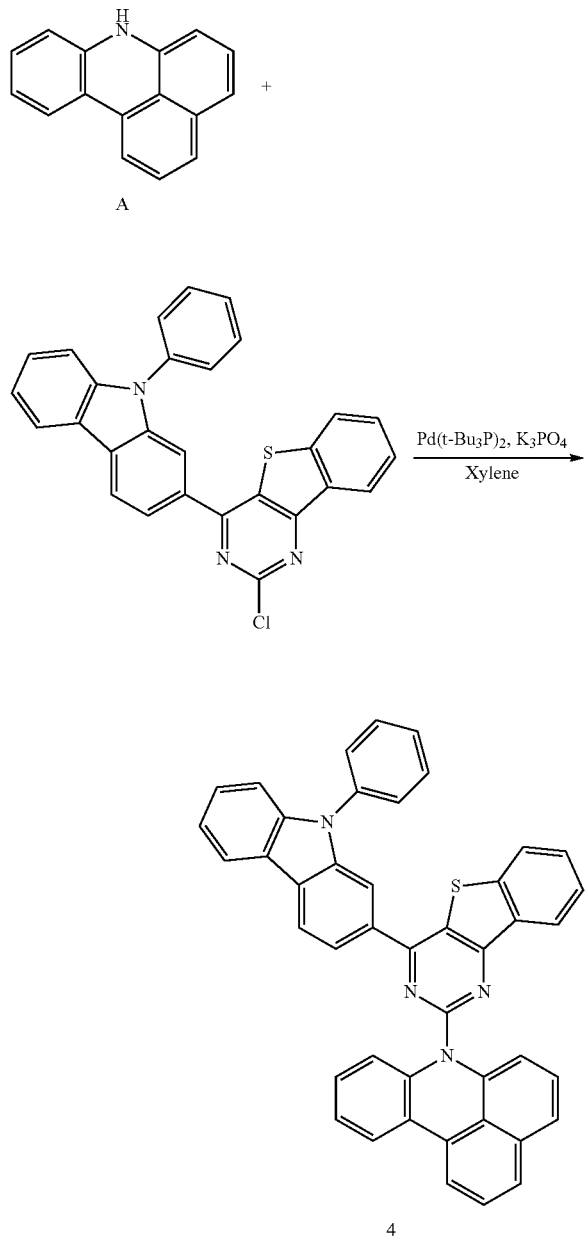

4

Compound A (10 g, 1 eq.), 2-chloro-4-(9-phenyl-9H-carbazol-2-yl)benzo[4,5]thieno[3,2-d]pyrimidine (23.38 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 4 (20.11 g, yield 68%). (MH⁺=643)

Synthesis Example 5

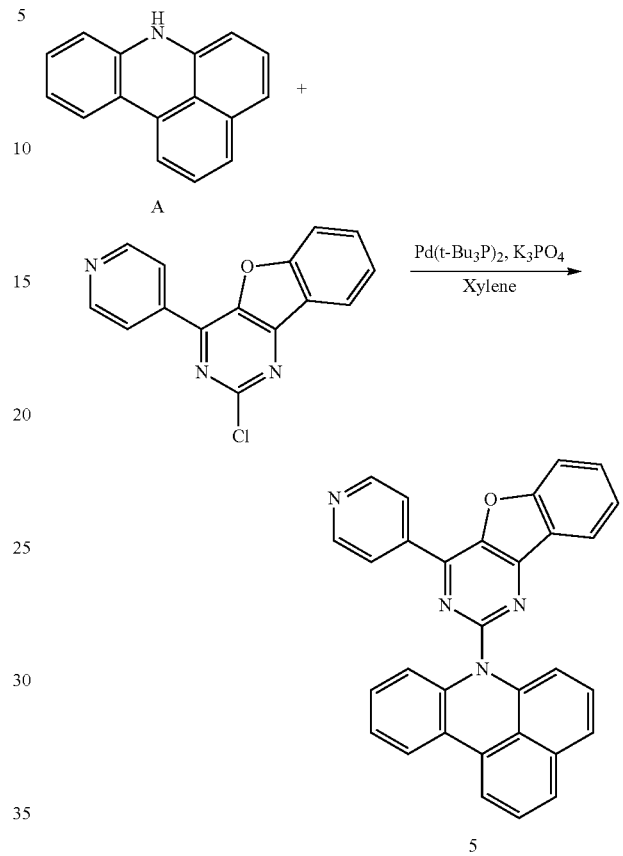

5

Compound A (10 g, 1 eq.), 2-chloro-4-(pyridin-4-yl)benzofuro[3,2-d]pyrimidine (14.26 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 5 (13.83 g, yield 65%). (MH⁺=463)

Synthesis Example 6

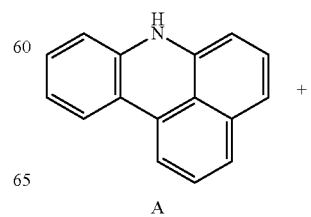

-continued

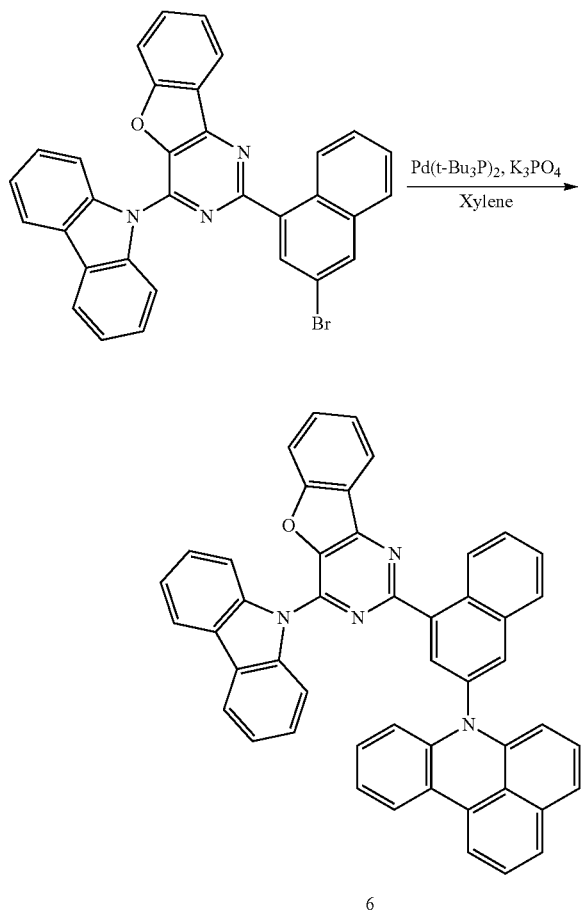

Compound A (10 g, 1 eq.), 2-(3-bromonaphthalen-1-yl)-4-(9H-carbazol-9-yl)benzofuro[3,2-d]pyrimidine (27.36 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 6 (20.24 g, yield 67%). (MH⁺=677)

Synthesis Example 7

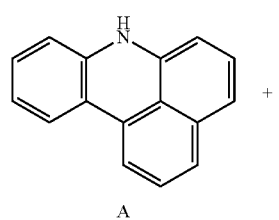

-continued

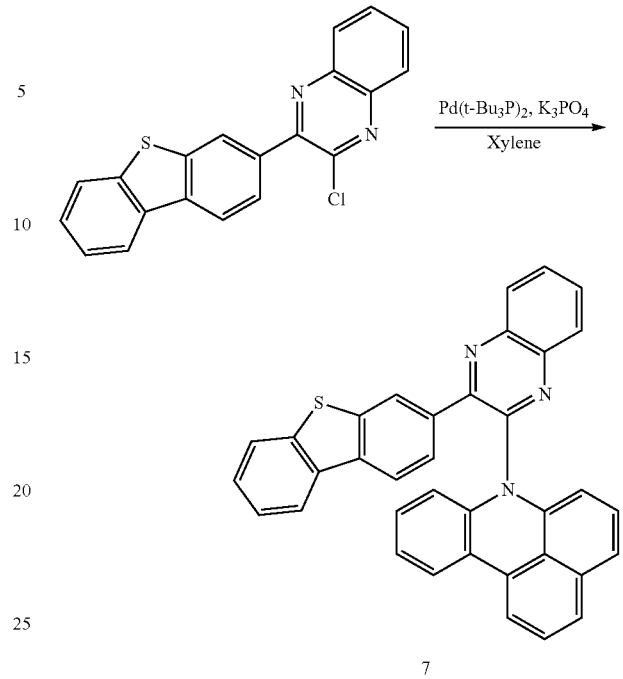

Compound A (10 g, 1 eq.), 2-chloro-3-(dibenzo[b,d]-thiophen-3-yl)quinoxaline (17.56 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.54 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 7 (16.75 g, yield 69%). (MH⁺=528)

Synthesis Example 8

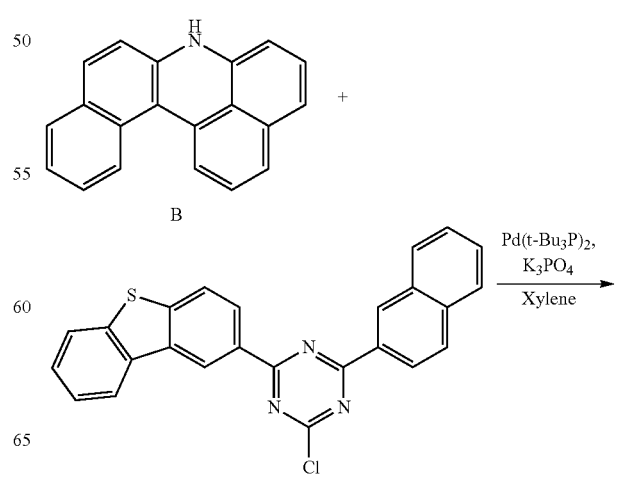

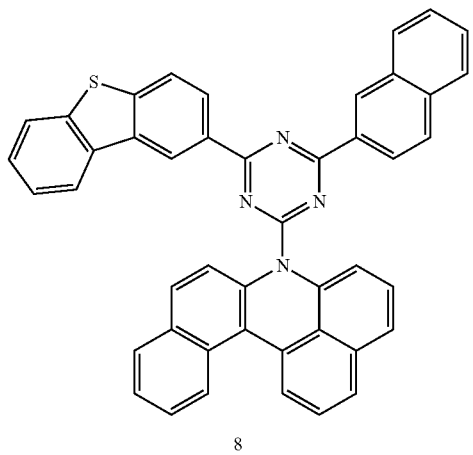

8

Compound B (10 g, 1 eq.), 2-chloro-4-(dibenzo-[b,d]thiophen-2-yl)-6-(naphthalen-2-yl)-1,3,5-triazine (17.44 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 8 (16.41 g, yield 67%). (MH⁺=655)

Synthesis Example 9

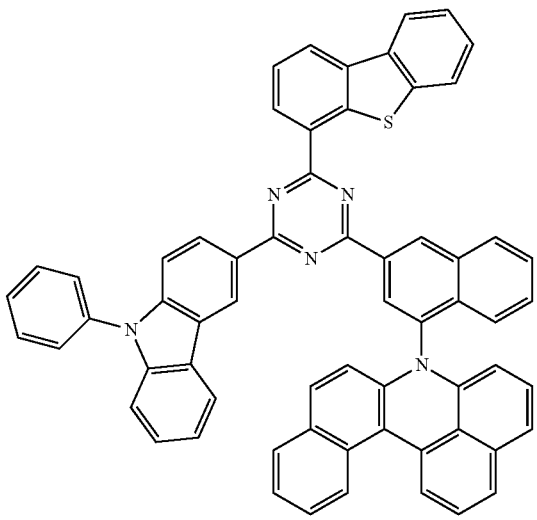

9

Compound B (10 g, 1 eq.), 3-(4-(4-bromonaphthalen-2-yl)-6-(dibenzo[b,d]thiophen-4-yl)-1,3,5-triazin-2-yl)-9-phenyl-9H-carbazole (29.2 g, 1.1 eq.), bis(tri-tert-butyl-phosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 9 (20.44 g, yield 61%). (MH⁺=897)

Synthesis Example 10

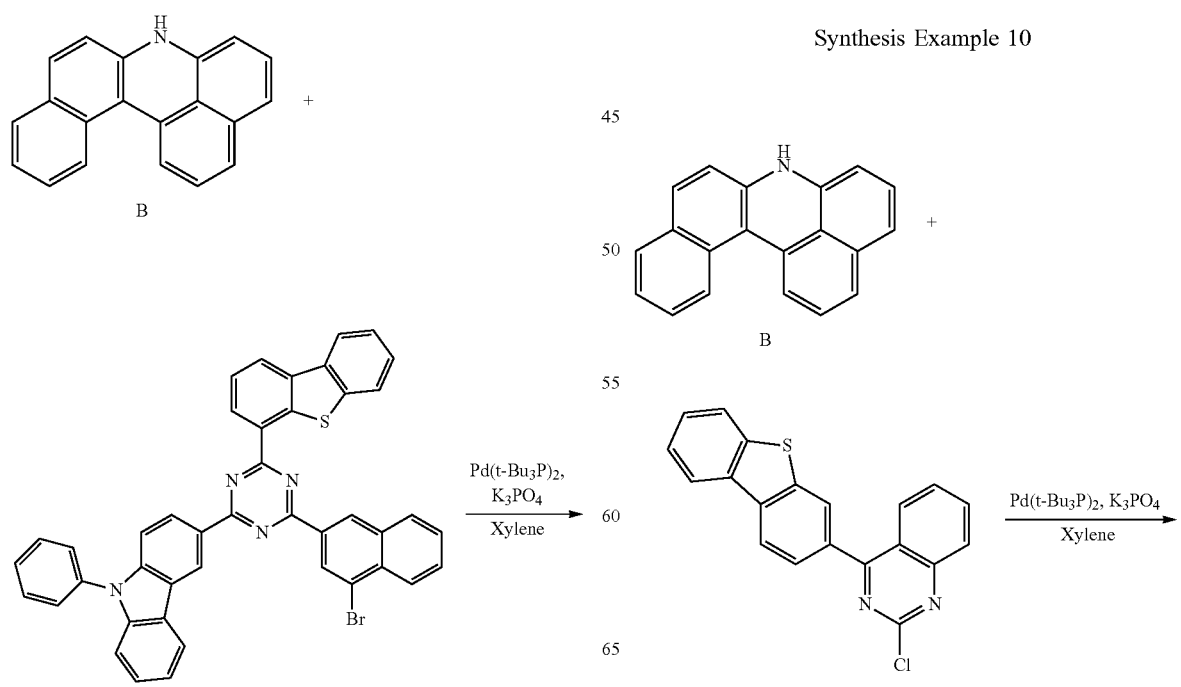

373

-continued

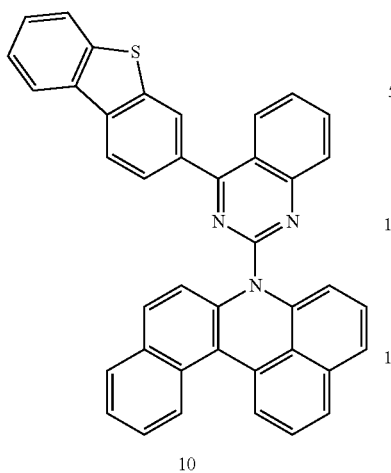

10

Compound B (10 g, 1 eq.), 2-chloro-4-(dibenzo-[b,d]thiophen-3-yl)quinazoline (26.49 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 10 (15.99 g, yield 74%). (MH+=578)

Synthesis Example 11

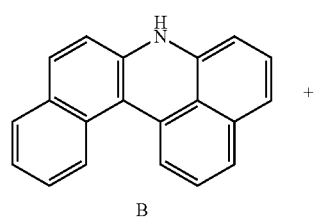

B

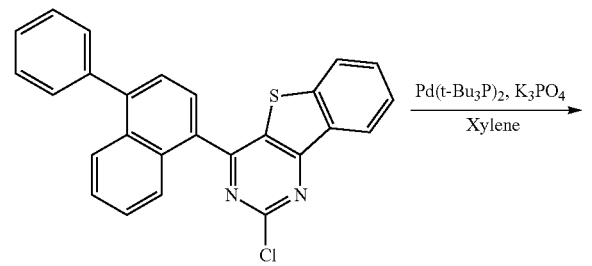

374

-continued

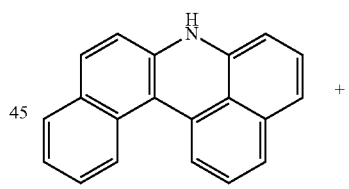

11

Compound B (10 g, 1 eq.), 2-chloro-4-(4-phenylnaphthalen-1-yl)benzo[4,5]thieno[3,2-d]pyrimidine (17.4 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 11 (17.36 g, yield 71%). (MH⁺=654)

Synthesis Example 12

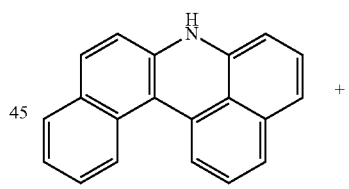

B

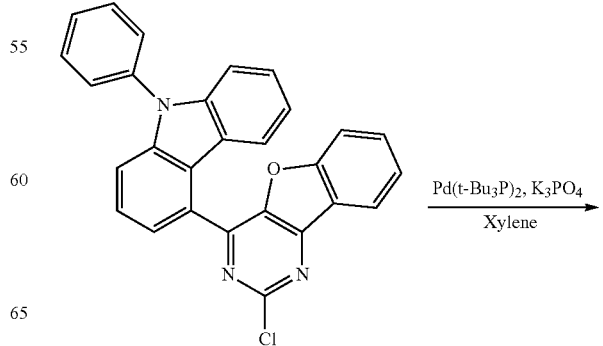

-continued

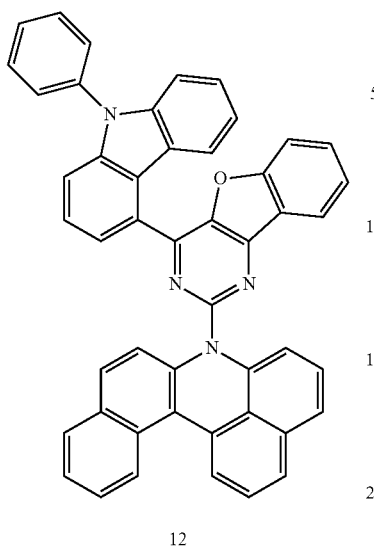

12

Compound B (10 g, 1 eq.), 2-chloro-4-(9-phenyl-9H-carbazol-4-yl)benzofuro[3,2-d]pyrimidine (18.34 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl3), washed with water, and then vacuumed again to remove approximately 50% of the solvent. Crystals were precipitated while introducing ethyl acetate thereto under reflux again, and the result was cooled and then filtered. This was column chromatographed to obtain Compound 12 (18.73 g, yield 74%). (MH⁺=677)

Synthesis Example 13

-continued

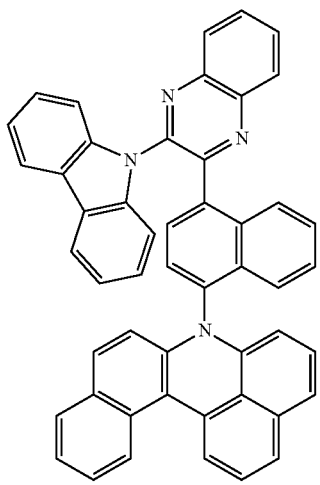

13

Compound B (10 g, 1 eq.), 9-(3-(4-bromonaphthalen-1-yl)quinoxalin-2-yl)-9H-carbazole (20.59 g, 1.1 eq.), bis(tri-tert-butylphosphine)palladium(0) (Pd(t-Bu₃P)₂) (0.19 g, 0.01 eq.) and K₃PO₄ (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 13 (19.01 g, yield 74%). (MH⁺=687)

Synthesis Example 14

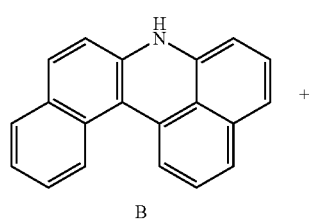

B

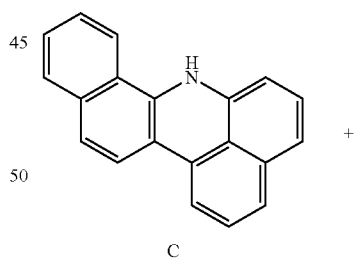

C

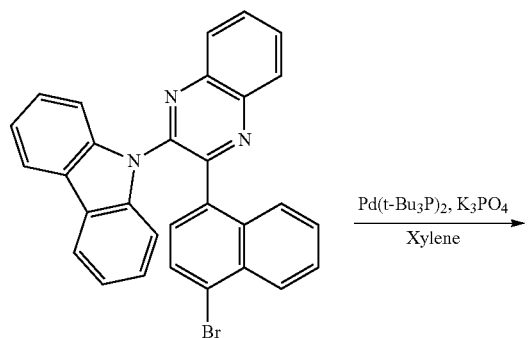

$\xrightarrow{\text{Pd(t-Bu}_3\text{P)}_2, \text{K}_3\text{PO}_4}{\text{Xylene}}$

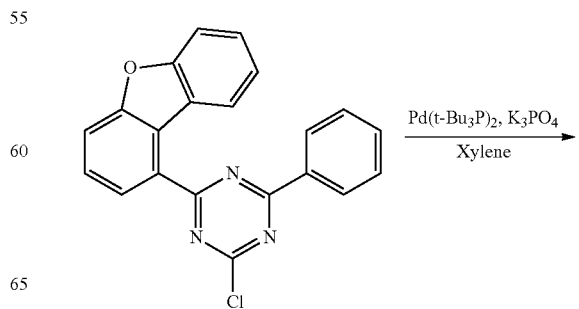

$\xrightarrow{\text{Pd(t-Bu}_3\text{P)}_2, \text{K}_3\text{PO}_4}{\text{Xylene}}$

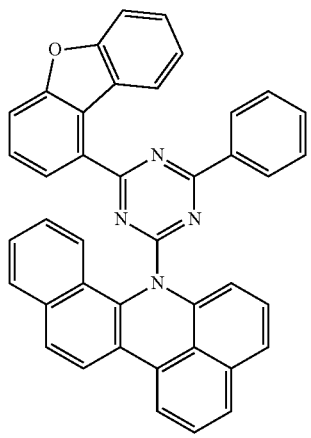

14

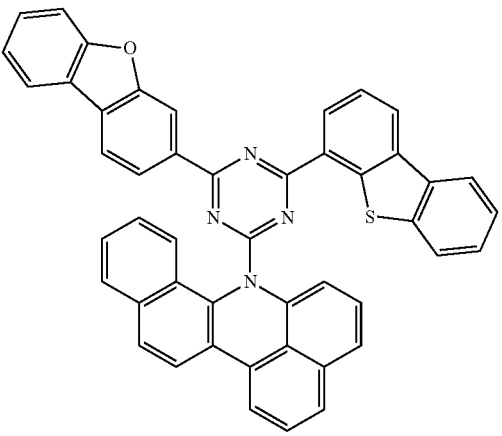

15

Compound C (10 g, 1 eq.), 2-chloro-4-(dibenzo[b,d]furan-1-yl)-6-phenyl-1,3,5-triazine (14.72 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 14 (15.41 g, yield 70%). (MH⁺=589)

Compound C (10 g, 1 eq.), 2-chloro-4-(dibenzo[b,d]furan-3-yl)-6-(dibenzo[b,d]thiophen-4-yl)-1,3,5-triazine (19.09 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 15 (18.97 g, yield 73%). (MH⁺=695)

Synthesis Example 15

Synthesis Example 16

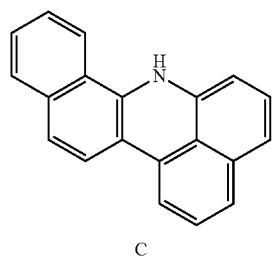

C

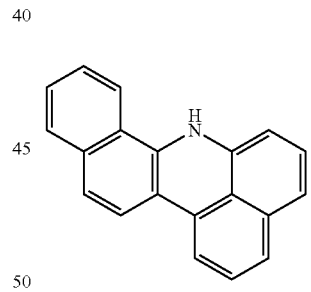

C

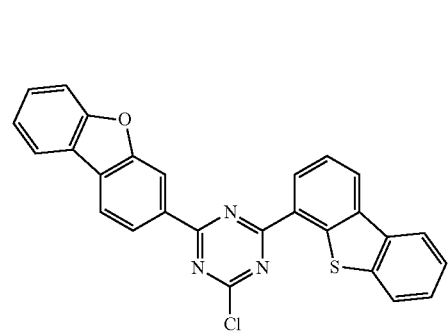

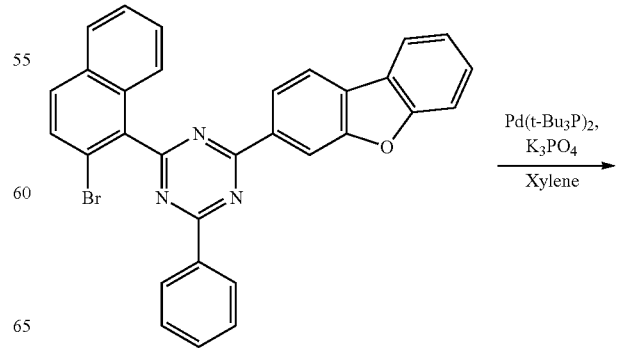

-continued

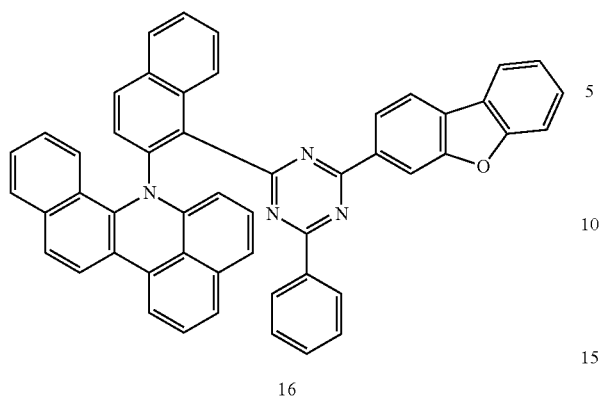

16

Compound C (10 g, 1 eq.), 2-(2-bromonaphthalen-1-yl)-4-(dibenzo[b,d]furan-3-yl)-6-phenyl-1,3,5-triazine (21.74 g, 1.1 eq.), bis(tri-tert-butylphosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 16 (19.51 g, yield 73%). (MH$^+$=714)

Synthesis Example 17

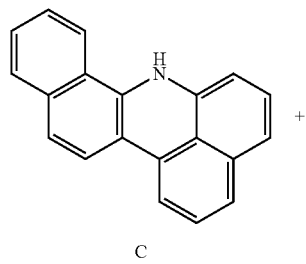

C

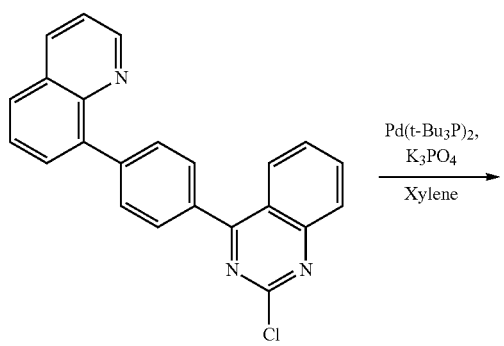

-continued

17

Compound C (10 g, 1 eq.), 2-chloro-4-(4-(quinolin-8-yl)phenyl)quinazoline (15.13 g, 1.1 eq.), bis(tri-tert-butylphosphine)palladium(0) (Pd(t-Bu$_3$P)$_2$) (0.19 g, 0.01 eq.), and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 17 (15.9 g, yield 71%). (MH$^+$=599)

Synthesis Example 18

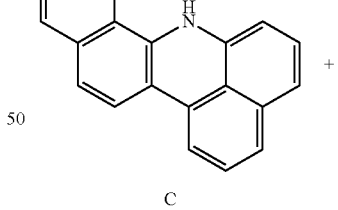

C

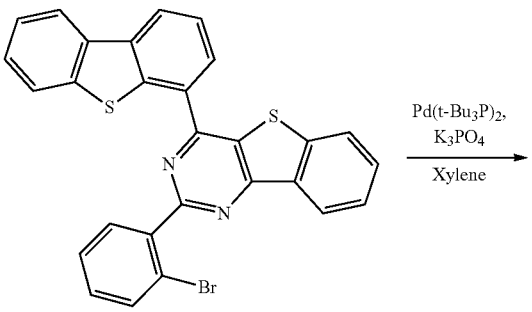

381

-continued

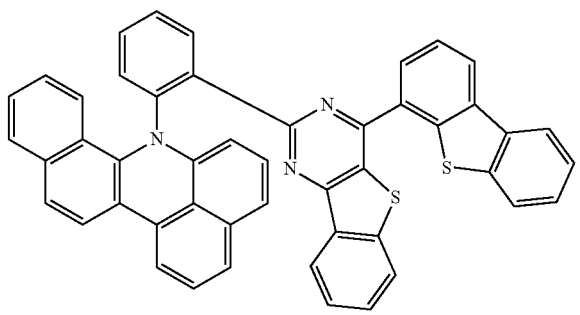

18

Compound C (10 g, 1 eq.), 2-(2-bromophenyl)-4-(dibenzo-[b,d]thiophen-4-yl)benzo[4,5]thieno[3,2-d]pyrimidine (21.53 g, 1.1 eq.), bis(tri-tert-butylphosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 18 (16.46 g, yield 62%). (MH$^+$=710)

Synthesis Example 19

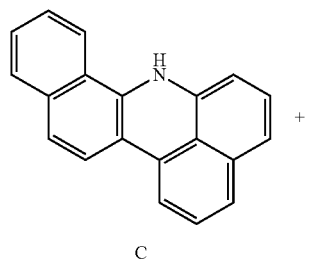

C

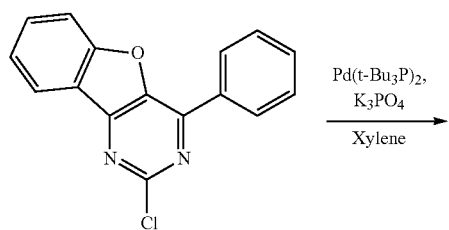

382

-continued

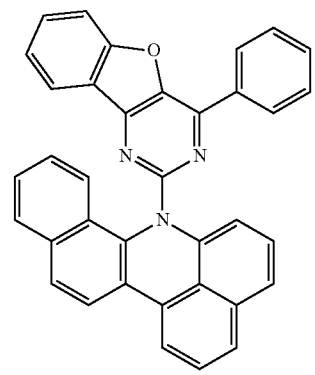

19

Compound C (10 g, 1 eq.), 2-chloro-4-phenylbenzofuro[3,2-d]pyrimidine (11.55 g, 1.1 eq.), bis(tri-tert-butyl-phosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 19 (13.96 g, yield 73%). (MH$^+$=512)

Synthesis Example 20

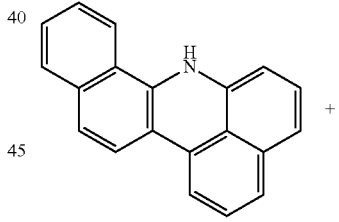

C

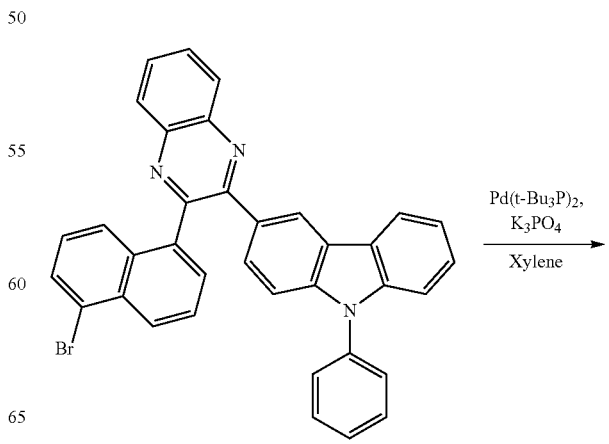

383
-continued

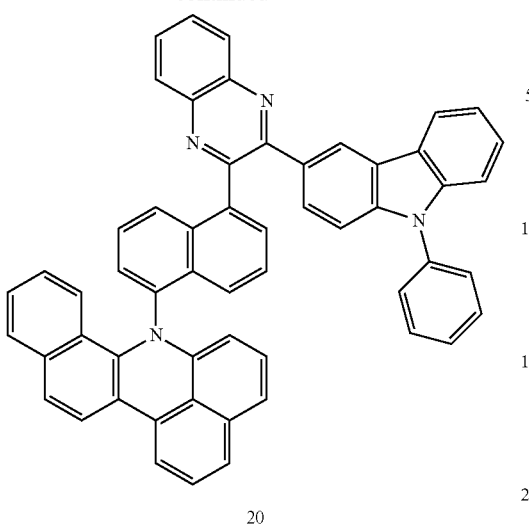

20

Compound C (10 g, 1 eq.), 3-(3-(5-bromonaphthalen-1-yl)quinoxalin-2-yl)-9-phenyl-9H-carbazole (23.72 g, 1.1 eq.), bis(tri-tert-butylphosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 20 (19.98 g, yield 70%). (MH$^+$=763)

Synthesis Example 21

384
-continued

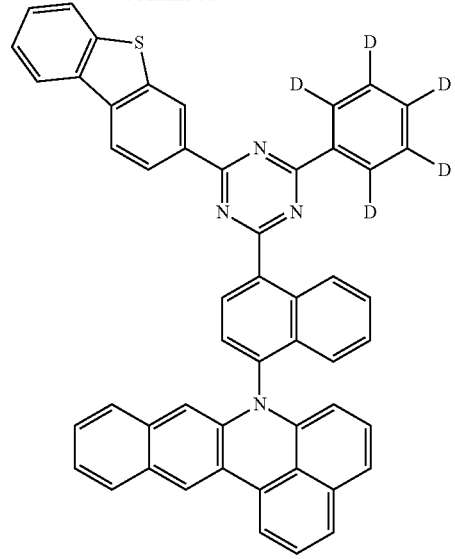

21

Compound D (10 g, 1 eq.), 2-(4-bromonaphthalen-1-yl)-4-(dibenzo[b,d]thiophen-3-yl)-6-(phenyl-d5)-1,3,5-triazine (22.61 g, 1.1 eq.), bis(tri-tert-butylphosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 21 (18.99 g, yield 69%). (MH$^+$=736)

Synthesis Example 22

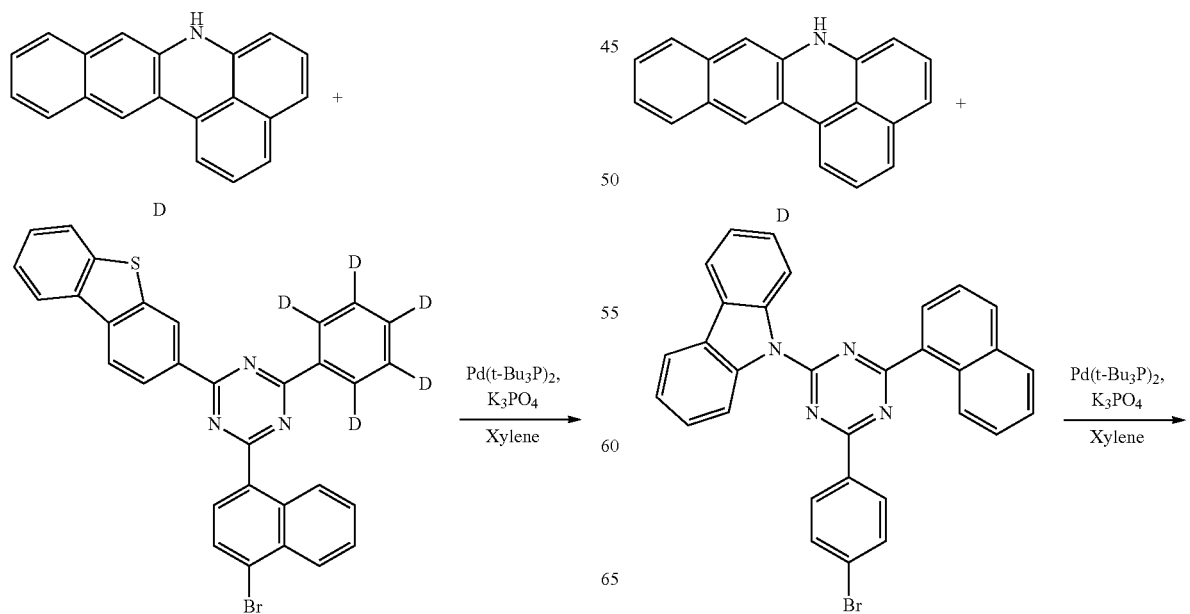

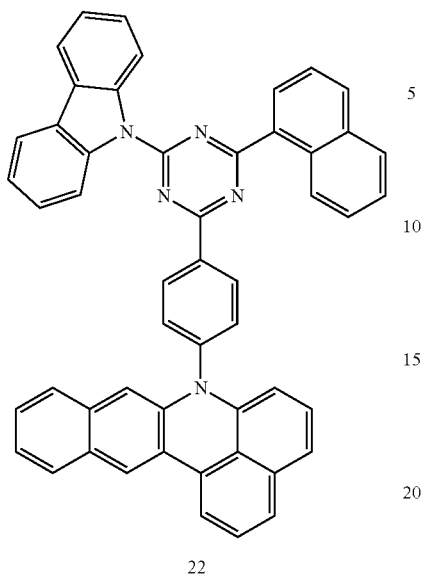

22

Compound D (10 g, 1 eq.), 9-(4-(4-bromophenyl)-6-(naphthalen-1-yl)-1,3,5-triazin-2-yl)-9H-carbazole (21.7 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 22 (20.02 g, yield 75%). (MH⁺=714)

Synthesis Example 23

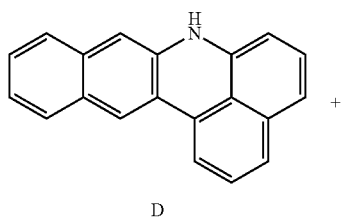

D

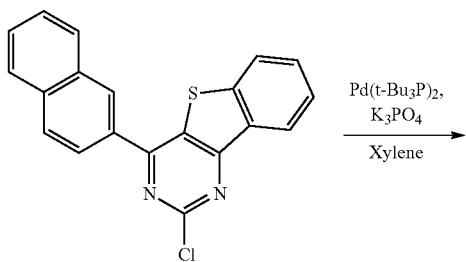

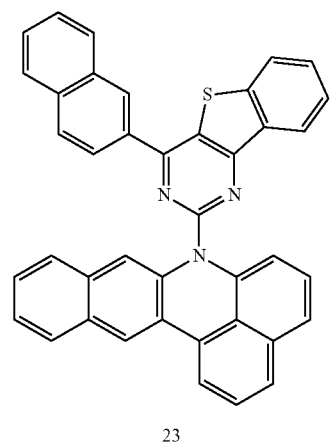

23

Compound D (10 g, 1 eq.), 2-chloro-4-(naphthalen-2-yl)benzo[4,5]thieno[3,2-d]pyrimidine (14.27 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 23 (15.34 g, yield 71%). (MH⁺=578)

Synthesis Example 24

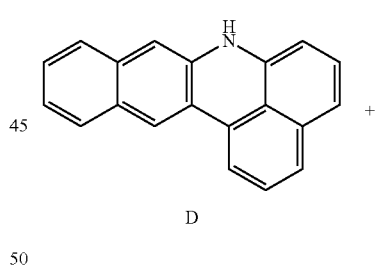

D

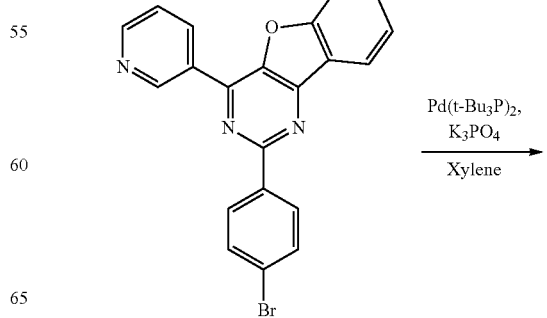

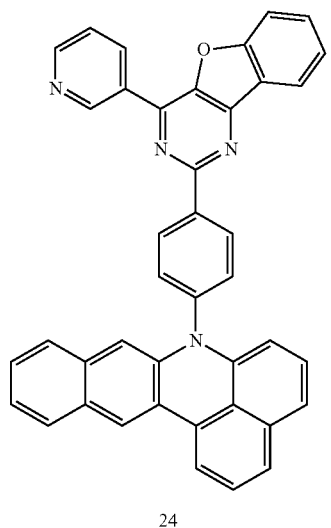

24

Compound D (10 g, 1 eq.), 2-(4-bromophenyl)-4-(pyridin-3-yl)benzofuro[3,2-d]pyrimidine (16.55 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 24 (16.29 g, yield 74%). (MH⁺=589)

Synthesis Example 25

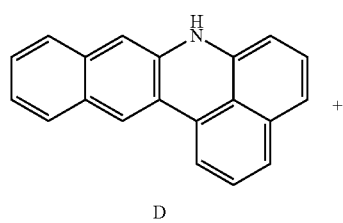

D

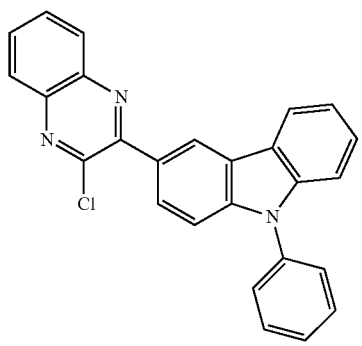

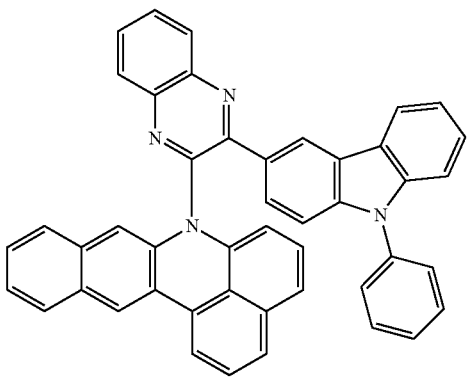

25

Compound D (10 g, 1 eq.), 3-(3-chloroquinoxalin-2-yl)-9-phenyl-9H-carbazole (16.70 g, 1.1 eq.), bis(tri-tert-butylphosphine)palladium(0) (Pd(t-Bu₃P)) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 25 (14.76 g, yield 62%). (MH⁺=637)

Synthesis Example 26

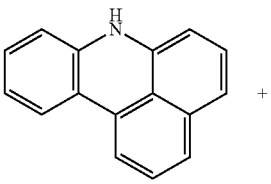

A

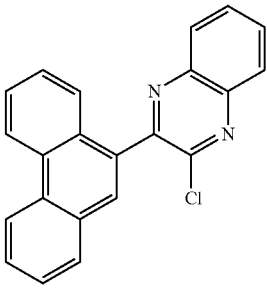

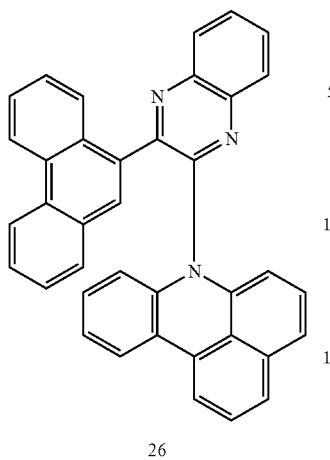

26

Compound A (10 g, 1 eq.), 2-chloro-3-(phenanthren-9-yl) quinoxaline (17.25 g, 1.1 eq.), bis(tri-tert-butylphosphine) palladium(0) (Pd(t-Bu$_3$P)$_2$) (0.23 g, 0.01 eq.) and potassium phosphate tribasic (K$_3$PO$_4$) (19.53 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 26 (15.6 g, yield 65%). (MH$^+$=522)

Synthesis Example 27

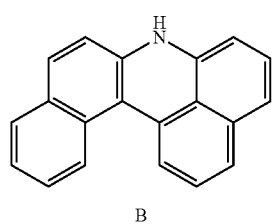

B

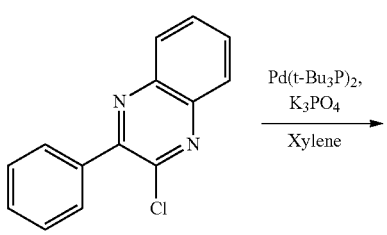

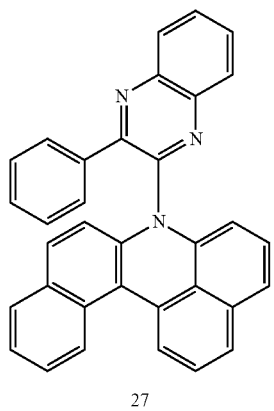

27

Compound B (10 g, 1 eq.), 2-chloro-3-phenylquinoxaline (9.9 g, 1.1 eq.), bis(tri-tert-butylphosphine)palladium(0) (Pd(t-Bu$_3$P)$_2$) (0.19 g, 0.01 eq.) and potassium phosphate tribasic (K$_3$PO$_4$) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 27 (11.99 g, yield 68%). (MH$^+$=472)

Synthesis Example 28

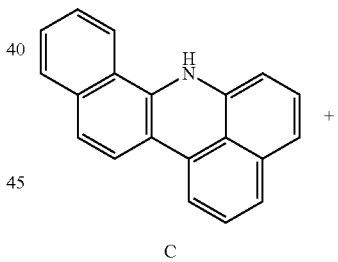

C

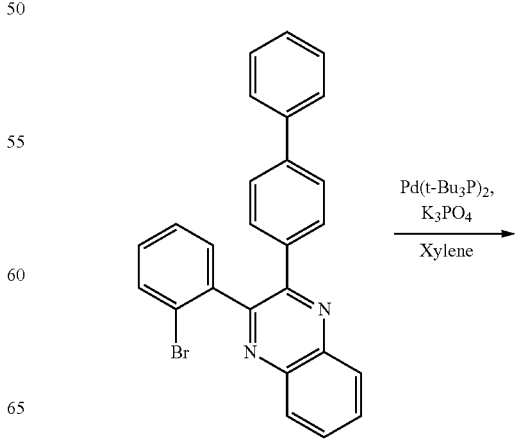

-continued

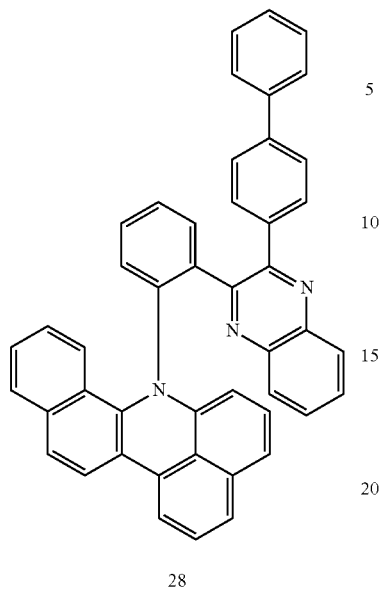

28

Compound C (10 g, 1 eq.), 2-([1,1'-biphenyl]-4-yl)-3-(2-bromophenyl)quinoxaline (17.99 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 28 (14.46 g, yield 62%). (MH⁺=624)

Synthesis Example 29

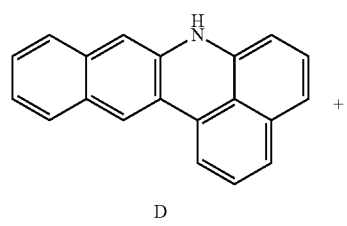

D

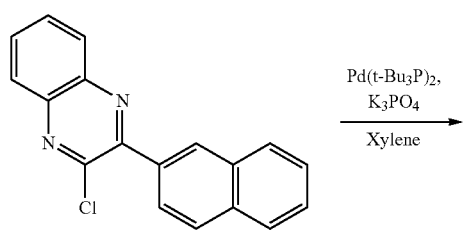

-continued

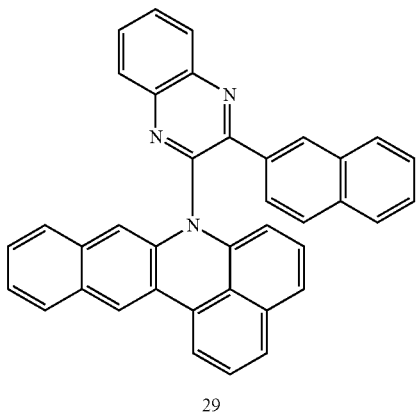

29

Compound D (10 g, 1 eq.), 2-chloro-3-(naphthalen-2-yl)quinoxaline (11.96 g, 1.1 eq.), bis(tri-tert-butylphosphine)palladium(0) (Pd(t-Bu₃P)₂) (0.19 g, 0.01 eq.) and potassium phosphate tribasic (K₃PO₄) (15.88 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 29 (12.09 g, yield 65%). (MH⁺=522)

Synthesis Example 30

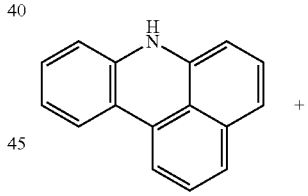

A

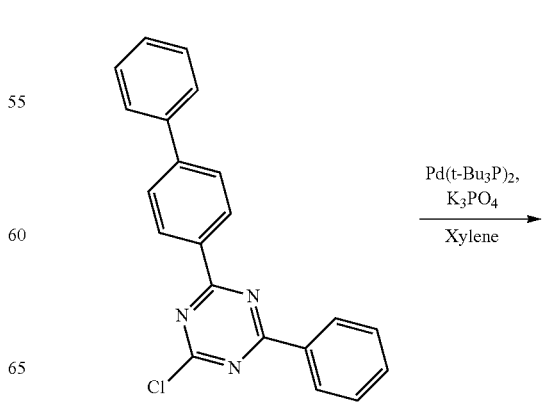

-continued

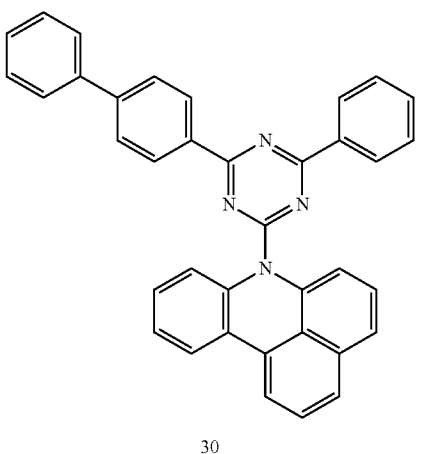

Compound A (10 g, 1 eq.), 2-([1,1'-biphenyl]-4-yl)-4-chloro-6-phenyl-1,3,5-triazine (17.4 g, 1.1 eq.), bis(tri-tert-butylphosphine)palladium(0) (Pd(t-Bu₃P)₂) (0.23 g, 0.01 eq.) and potassium phosphate tribasic (K₃PO₄) (19.54 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 30 (17.62 g, yield 73%). (MH⁺=525)

Synthesis Example 31

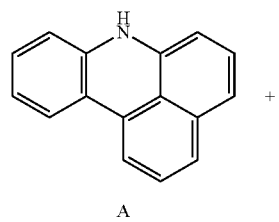

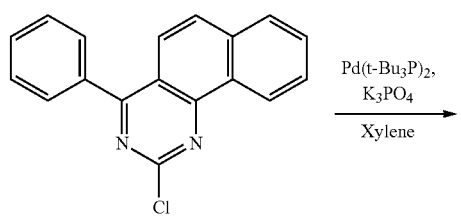

-continued

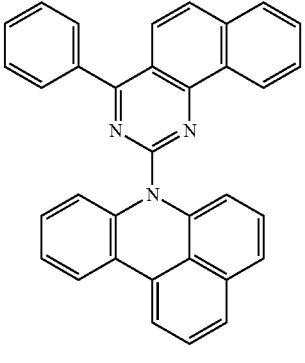

Compound A (10 g, 1 eq.), 2-chloro-4-phenylbenzo[h]quinazoline (14.72 g, 1.1 eq.), bis(tri-tert-butylphosphine) palladium(0) (Pd(t-Bu₃P)₂) (0.23 g, 0.01 eq.) and potassium phosphate tribasic (K₃PO₄) (19.54 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 31 (14.75 g, yield 68%). (MH⁺=472)

Example 1

A glass substrate on which indium tin oxide (ITO) was coated as a thin film to a thickness of 100 nm was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, the following Compound HI-1 was formed to a thickness of 115 nm as a hole injection layer while p-doping the following A-1 compound in a concentration of 1.5% weight. On the hole injection layer, a hole transfer layer having a film thickness of 80 nm was formed by vacuum depositing the following Compound HT-1. Subsequently, an electron blocking layer was formed on the hole transfer layer by vacuum depositing the following Compound EB-1 to a film thickness of 15 nm. Subsequently, a red light emitting layer having a thickness of 40 nm was formed on the EB-1 deposited film by vacuum depositing Compound 1 and the following Compound Dp-39 in a weight ratio of 98:2. On the light emitting layer, a hole blocking layer was formed by vacuum depositing the following Compound HB-1 to a film thickness of 3 nm. Subsequently, a layer carrying out electron injection and electron transfer at the same time was formed on the hole blocking layer to a thickness of 30 nm by vacuum depositing the following Compound ET-1 and the following Compound LiQ in a weight ratio of 2:1. On the layer carrying out electron injection and electron transfer at the same time, a cathode was formed by depositing lithium fluoride (LiF) to a thickness of 1.2 nm and aluminum to a thickness of 100 nm in consecutive order.

An organic light emitting device was manufactured by maintaining, in the above-mentioned process, the deposition rates of the organic materials at 0.04 nm/sec to 0.07 nm/sec, the deposition rates of the lithium fluoride and the aluminum at 0.03 nm/sec and 0.2 nm/sec, respectively, and the degree of vacuum during the deposition at $2 \times 10^{-7}$ torr to $5 \times 10^{-6}$ torr.

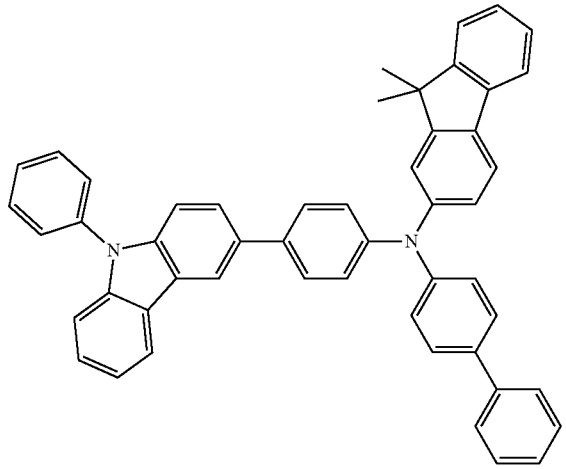

HI-1

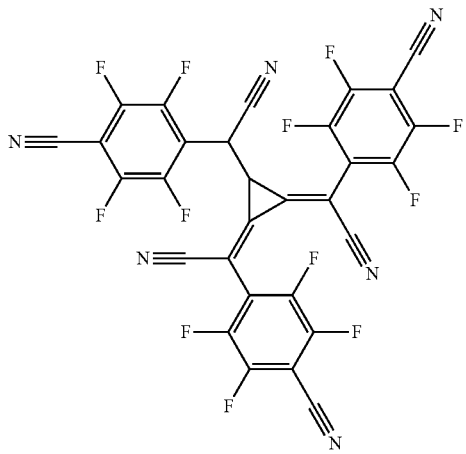

A-1

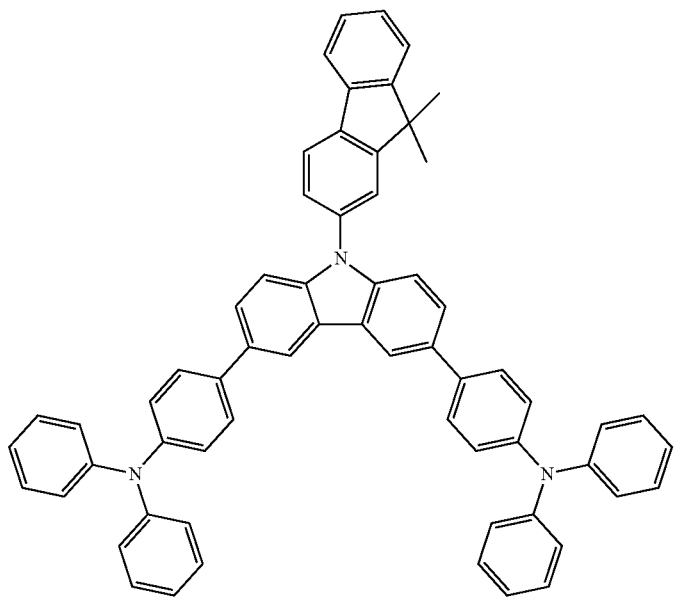

HT-1

EB-1
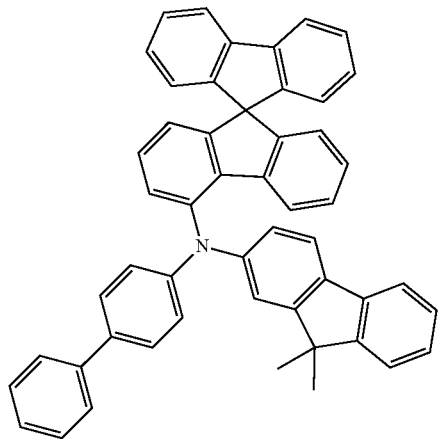
Dp-39
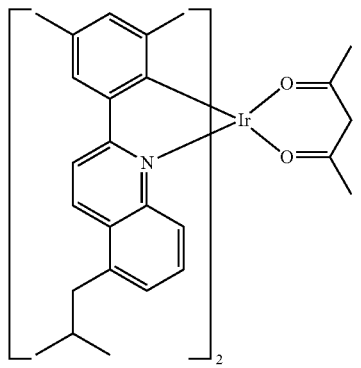
HB-1
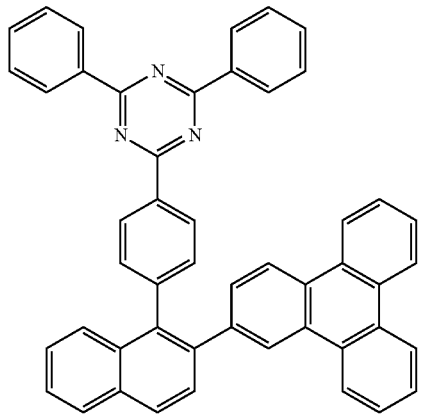
ET-1
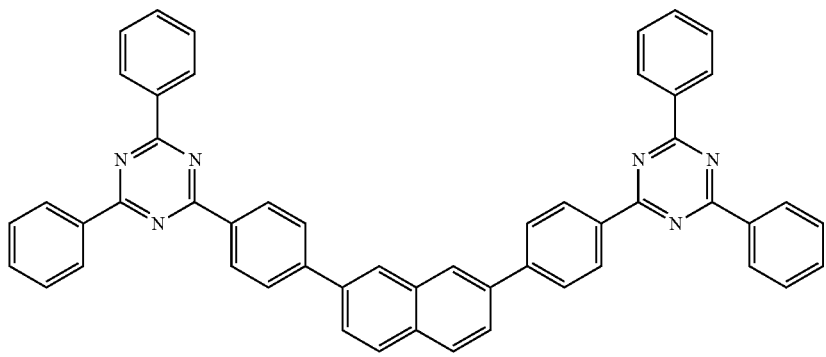

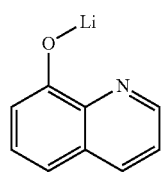

Example 2 to Example 31

Organic light emitting devices were manufactured in the same manner as in Example 1 except that compounds described in the following Table 1 were used instead of Compound 1.

Comparative Example 1 to Comparative Example 4

Organic light emitting devices were manufactured in the same manner as in Example 1 except that compounds described in the following Table 1 were used instead of Compound 1.

C-1

C-2

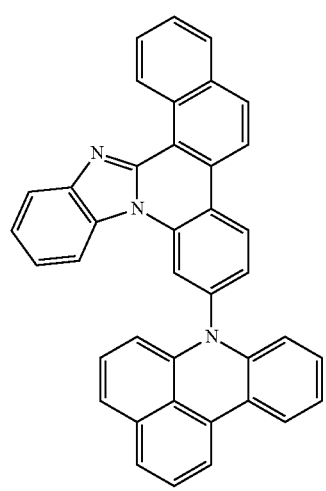

LiQ

-continued

C-3

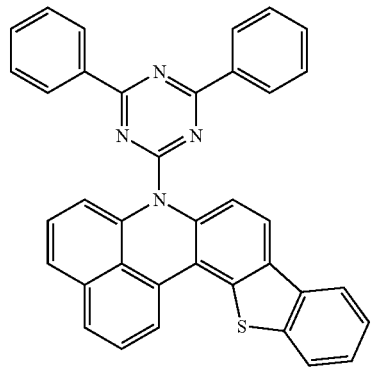

C-4

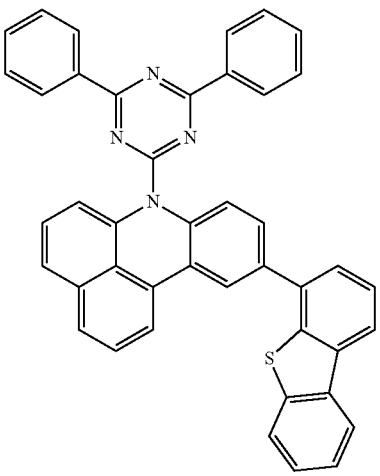

Voltage, efficiency and lifetime were measured by applying a current to each of the organic light emitting devices manufactured in Example 1 to Example 31 and Comparative Example 1 to Comparative Example 4, and the results are shown in the following Table 1. T95 means time taken for luminance decreasing to 95% from initial luminance (15000 nit).

TABLE 1

| Category | Compound | Driving Voltage (V) | Efficiency (cd/A) | T95 (hr) | Light Emission Color |
|---|---|---|---|---|---|
| Example 1 | 1 | 3.95 | 35.5 | 193 | Red |
| Example 2 | 2 | 3.93 | 36.1 | 191 | Red |
| Example 3 | 3 | 4.13 | 35.8 | 237 | Red |
| Example 4 | 4 | 4.10 | 34.7 | 205 | Red |
| Example 5 | 5 | 4.03 | 35.6 | 216 | Red |
| Example 6 | 6 | 4.05 | 34.9 | 203 | Red |
| Example 7 | 7 | 3.97 | 38.5 | 194 | Red |
| Example 8 | 8 | 4.17 | 40.1 | 223 | Red |
| Example 9 | 9 | 4.10 | 33.9 | 237 | Red |

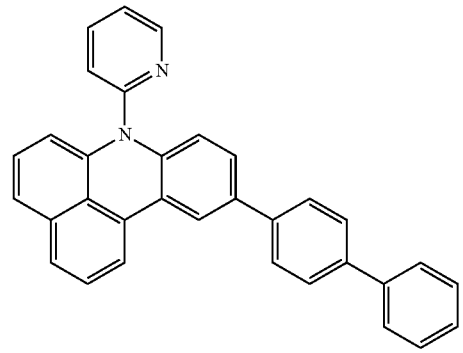

TABLE 1-continued

| Category | Compound | Driving Voltage (V) | Efficiency (cd/A) | T95 (hr) | Light Emission Color |
|---|---|---|---|---|---|
| Example 10 | 10 | 4.27 | 34.3 | 197 | Red |
| Example 11 | 11 | 4.15 | 38.0 | 210 | Red |
| Example 12 | 12 | 4.01 | 37.5 | 214 | Red |
| Example 13 | 13 | 3.91 | 38.4 | 199 | Red |
| Example 14 | 14 | 3.84 | 37.5 | 187 | Red |
| Example 15 | 15 | 4.13 | 34.1 | 239 | Red |
| Example 16 | 16 | 3.87 | 39.5 | 184 | Red |
| Example 17 | 17 | 4.21 | 36.3 | 229 | Red |
| Example 18 | 18 | 4.29 | 34.5 | 231 | Red |
| Example 19 | 19 | 3.83 | 36.7 | 198 | Red |
| Example 20 | 20 | 4.18 | 37.0 | 217 | Red |
| Example 21 | 21 | 3.91 | 36.8 | 224 | Red |
| Example 22 | 22 | 4.29 | 35.0 | 218 | Red |
| Example 23 | 23 | 4.20 | 36.3 | 229 | Red |
| Example 24 | 24 | 4.08 | 36.2 | 211 | Red |
| Example 25 | 25 | 3.87 | 37.0 | 228 | Red |
| Example 26 | 26 | 3.95 | 38.9 | 235 | Red |
| Example 27 | 27 | 3.89 | 39.9 | 230 | Red |
| Example 28 | 28 | 3.81 | 37.9 | 207 | Red |
| Example 29 | 29 | 3.88 | 40.9 | 241 | Red |
| Example 30 | 30 | 4.21 | 34.7 | 127 | Red |
| Example 31 | 31 | 4.43 | 33.5 | 159 | Red |
| Comparative Example 1 | C-1 | 4.80 | 17.5 | 17 | Red |
| Comparative Example 2 | C-2 | 4.77 | 19.7 | 26 | Red |
| Comparative Example 3 | C-3 | 4.30 | 29.1 | 104 | Red |
| Comparative Example 4 | C-4 | 4.35 | 30.5 | 109 | Red |

When applying a current to each of the organic light emitting devices manufactured in Examples 1 to 31 and Comparative Examples 1 to 4, results of Table 1 were obtained. In Comparative Examples 1 to 4, organic light emitting devices were manufactured using Compounds C-1 to C-4 instead of Compound 1.

Based on the data shown in Table 1, it was seen that, when using the compound of the present disclosure as a host of a red light emitting layer, energy is favorably transferred from the host to the red dopant based on the fact that lower driving voltage and enhanced efficiency were obtained compared to the devices of the comparative examples.

In addition, it was identified that the devices using the compound of the present disclosure had greatly improved lifetime properties. This is considered to be due to the fact that the compound of the present disclosure has a higher degree of stability for electrons and holes compared to the compounds of the comparative examples, which favorably balances electron and hole migration in the light emitting layer.

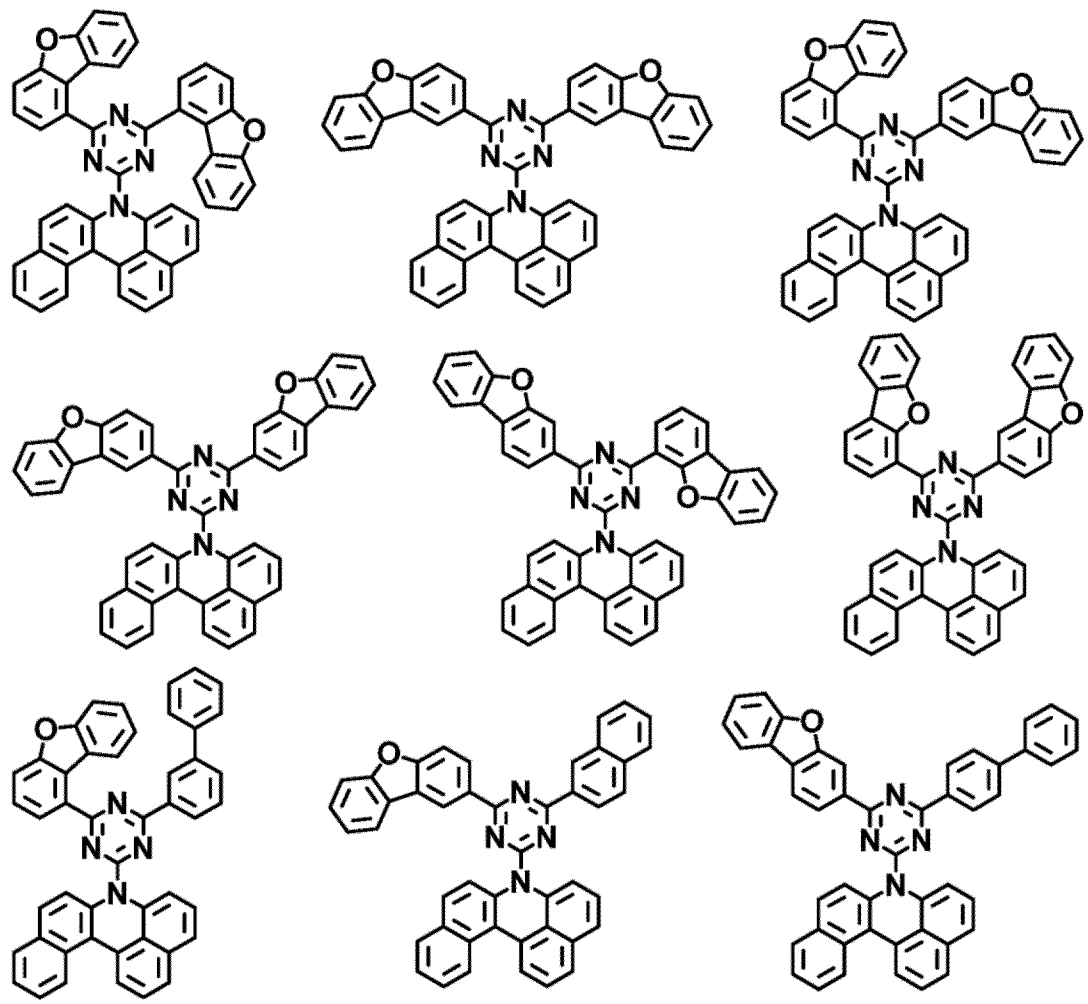

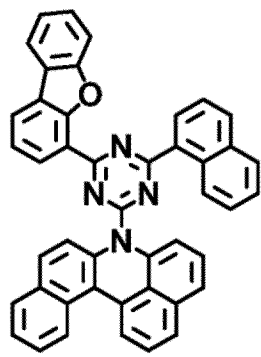 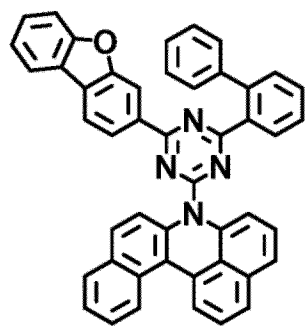 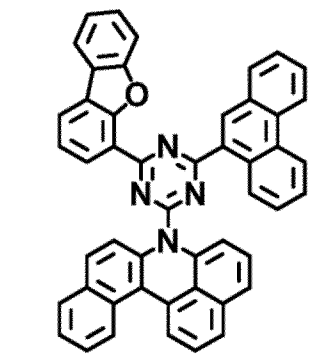
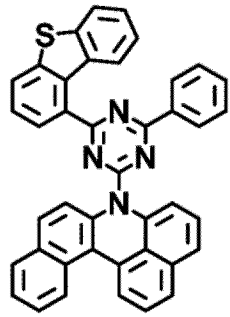 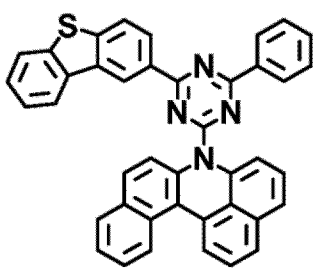 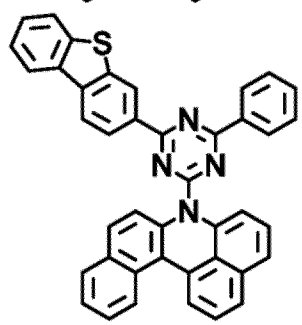
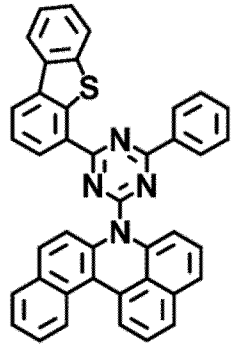 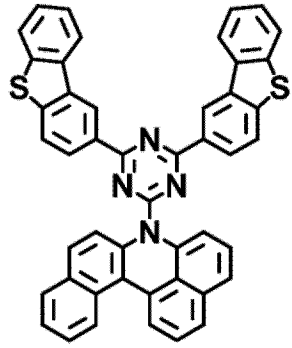 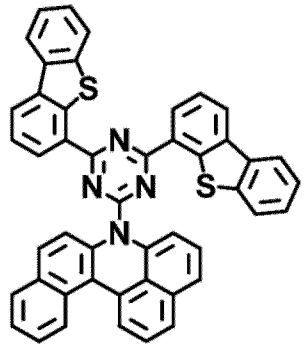

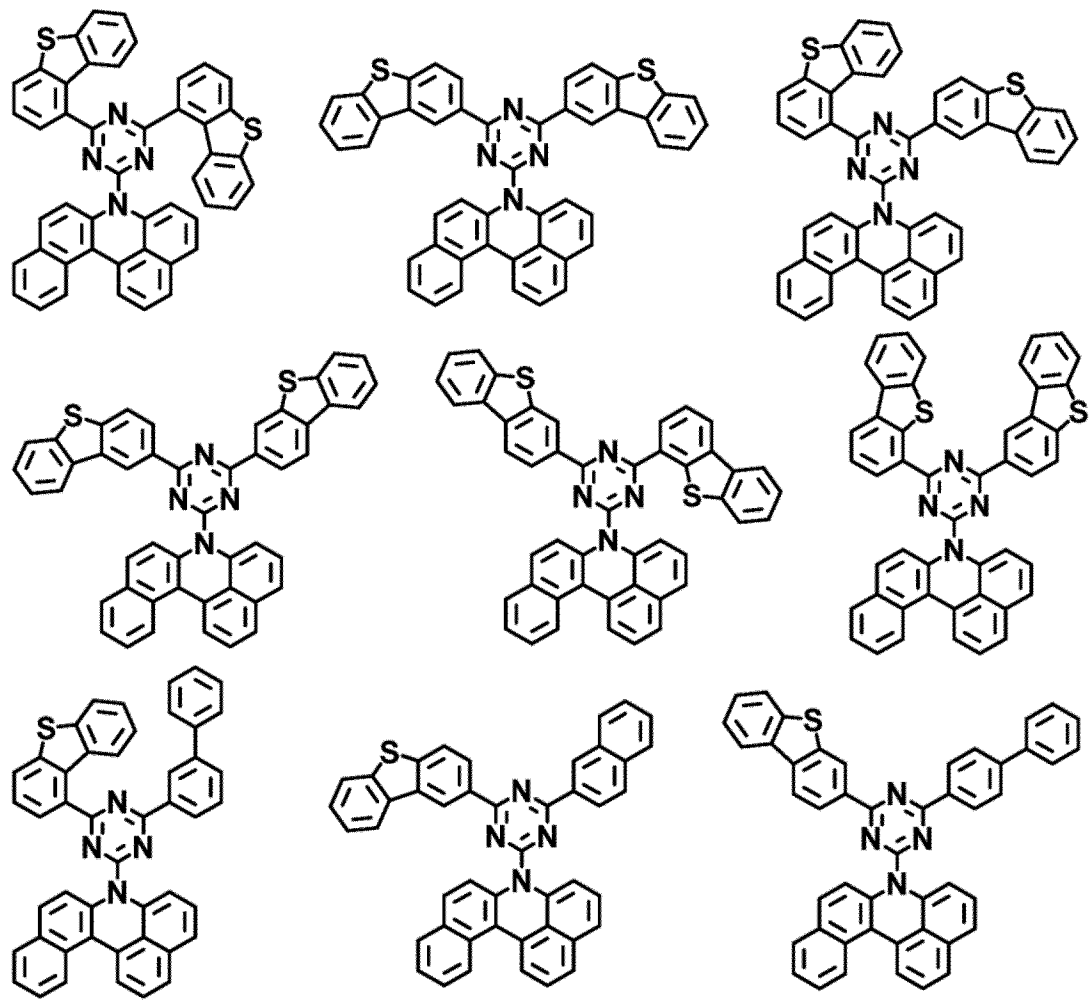

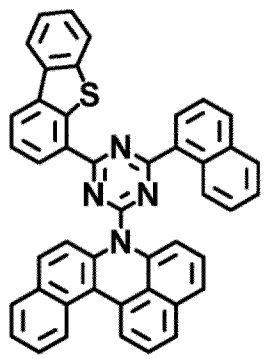
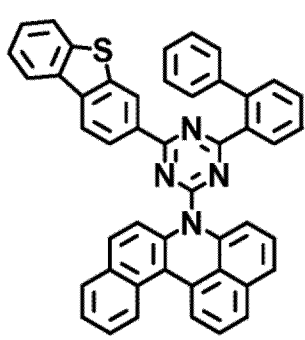
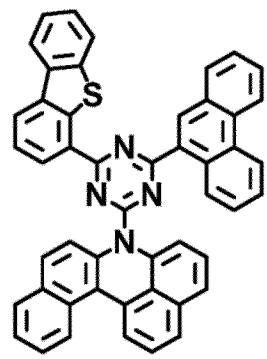
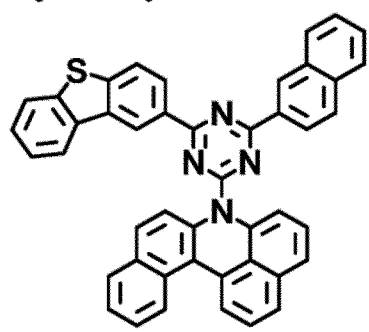
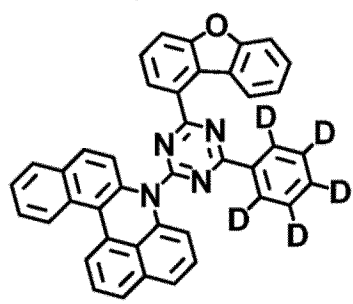
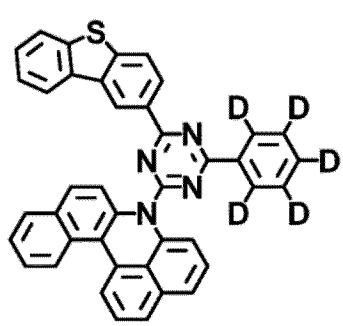
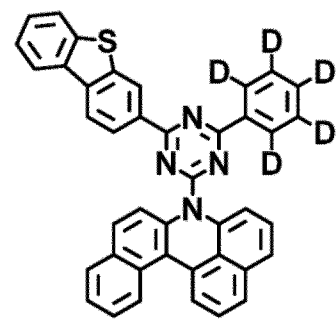

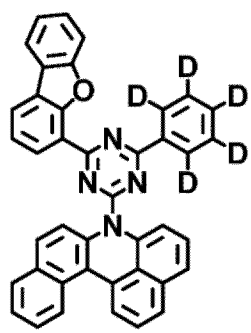 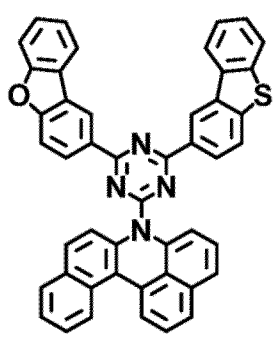 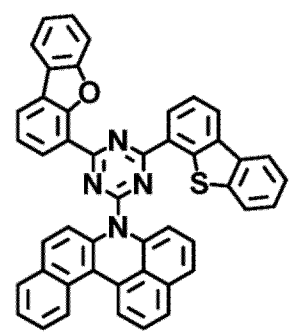
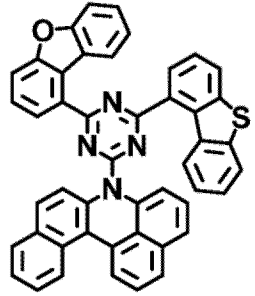 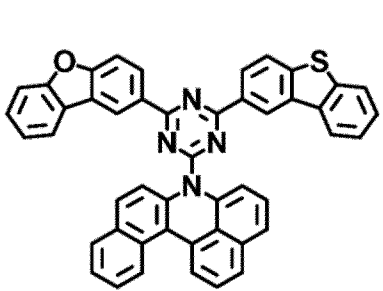 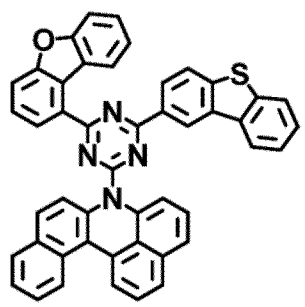
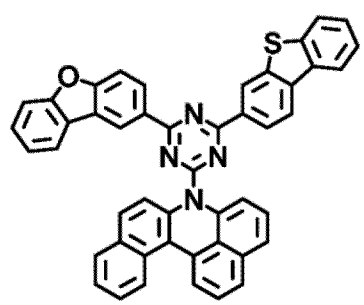 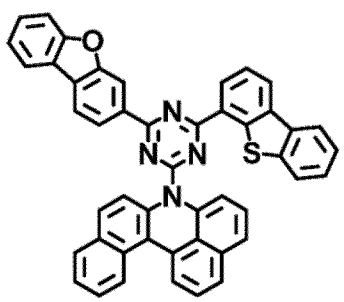 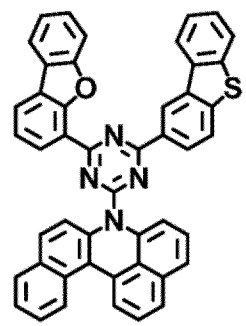

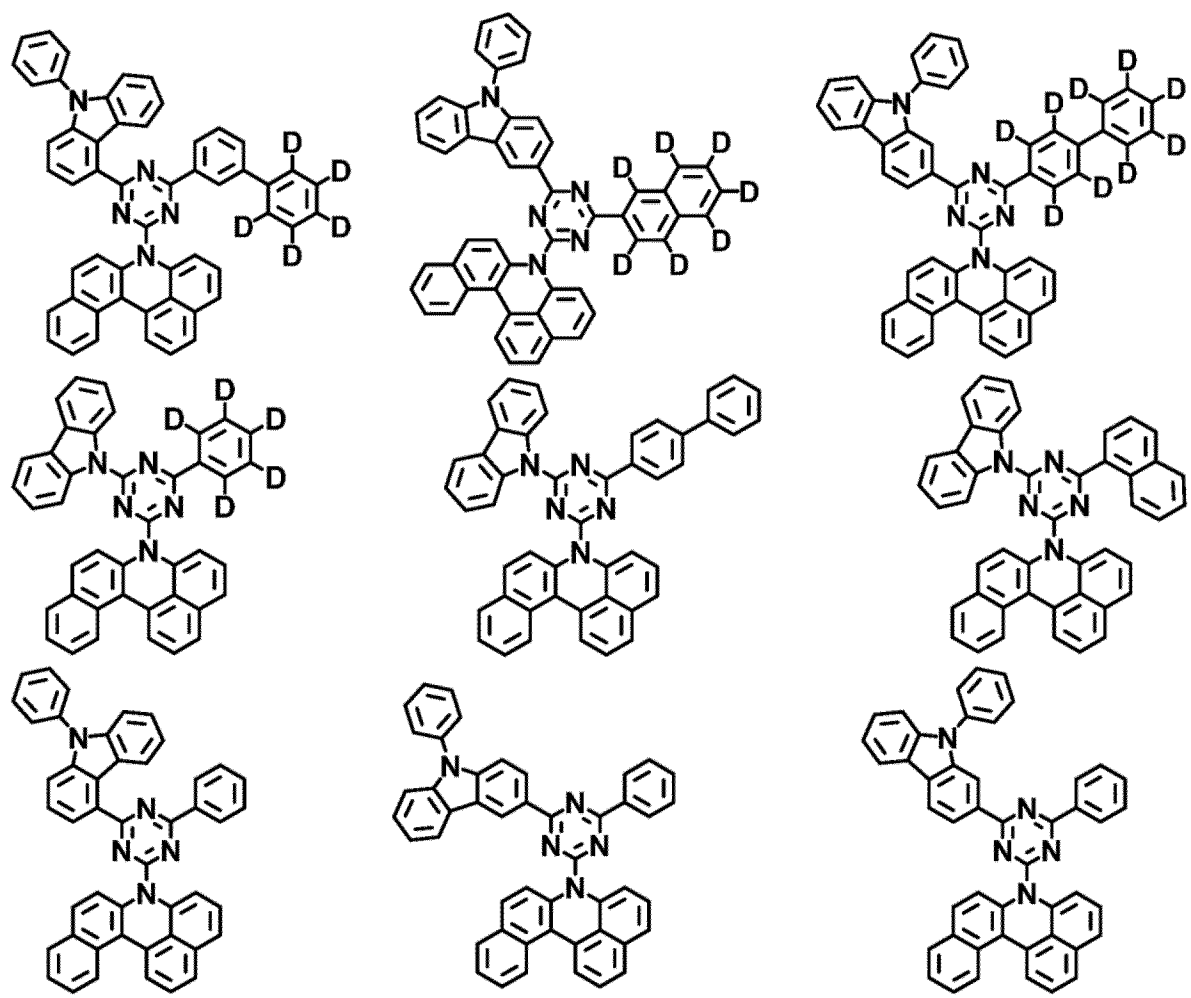

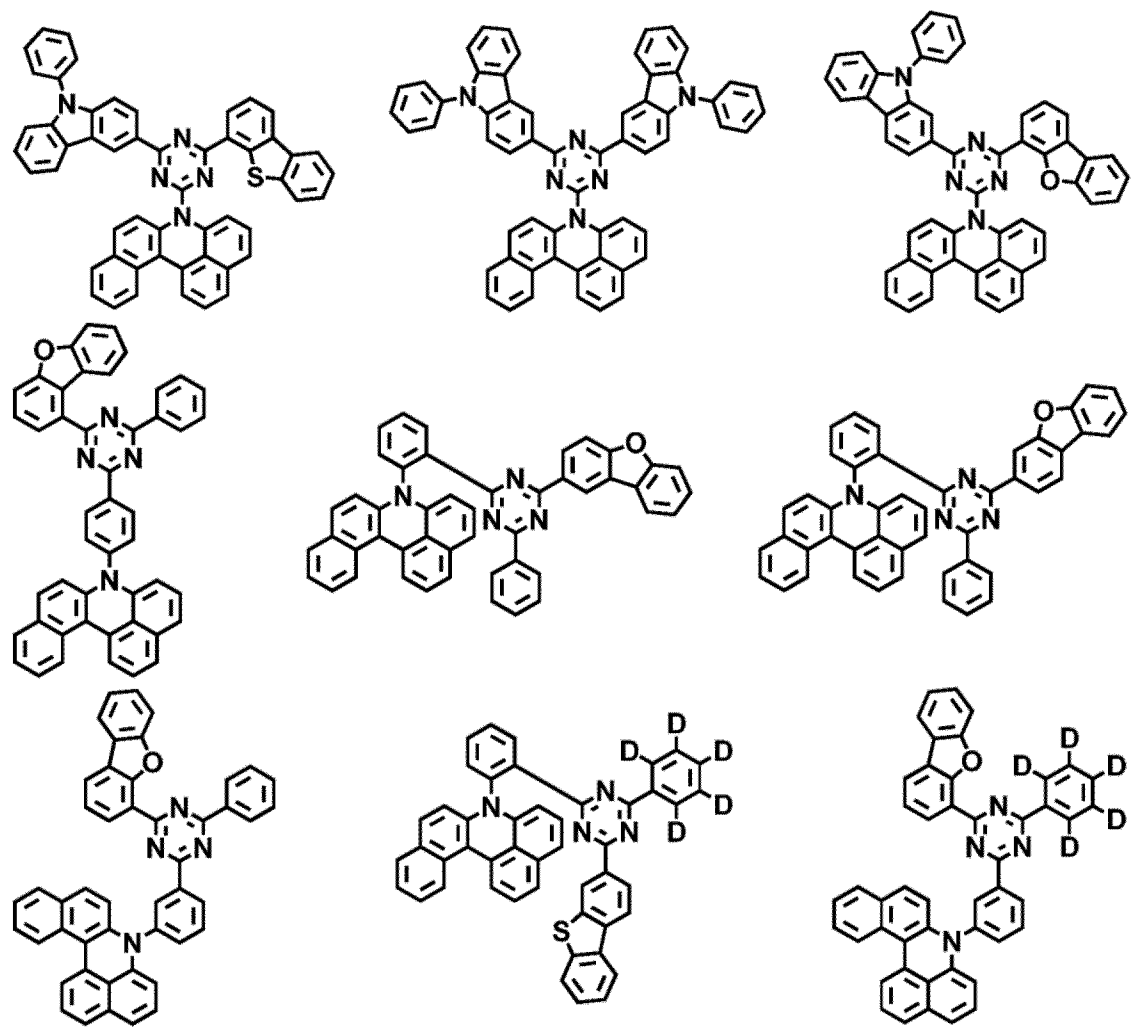

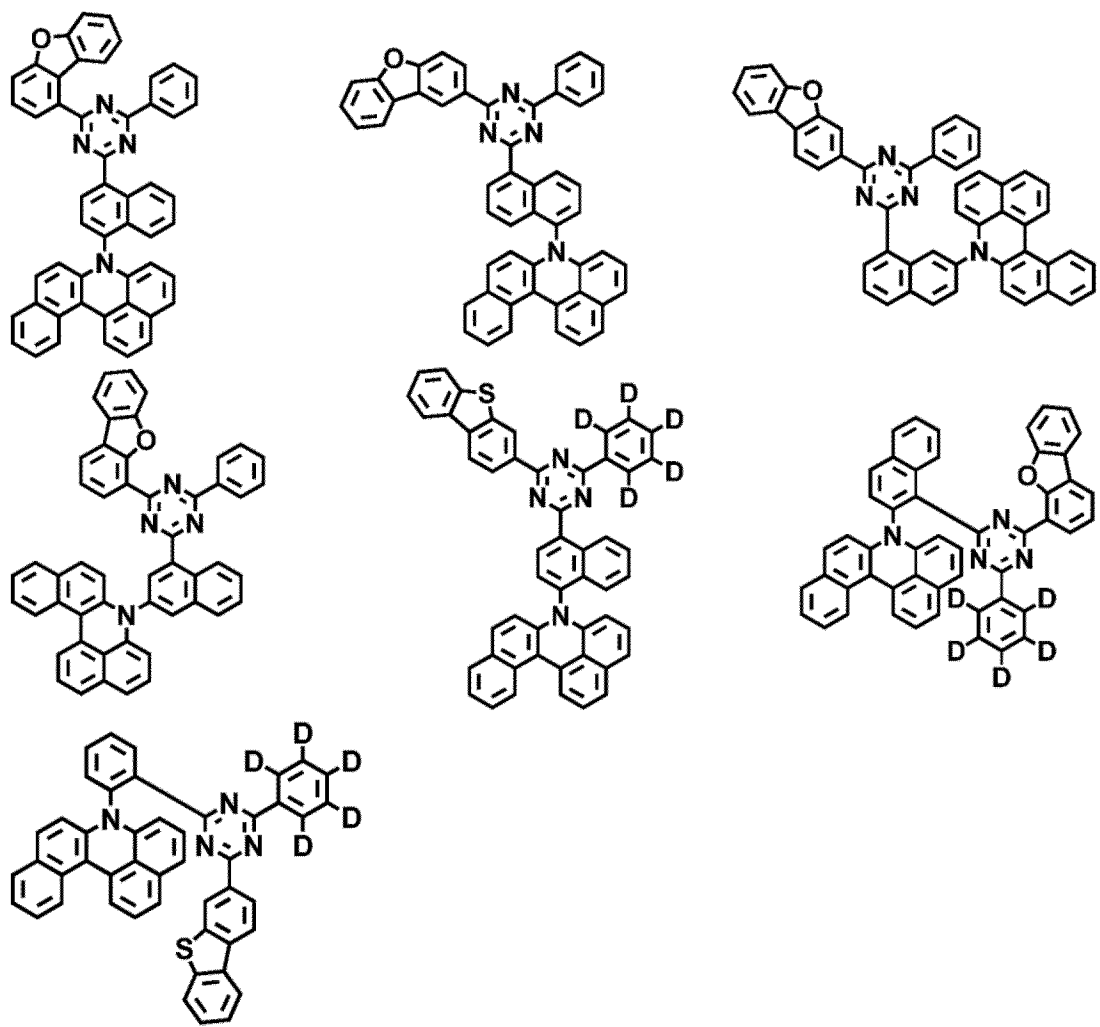

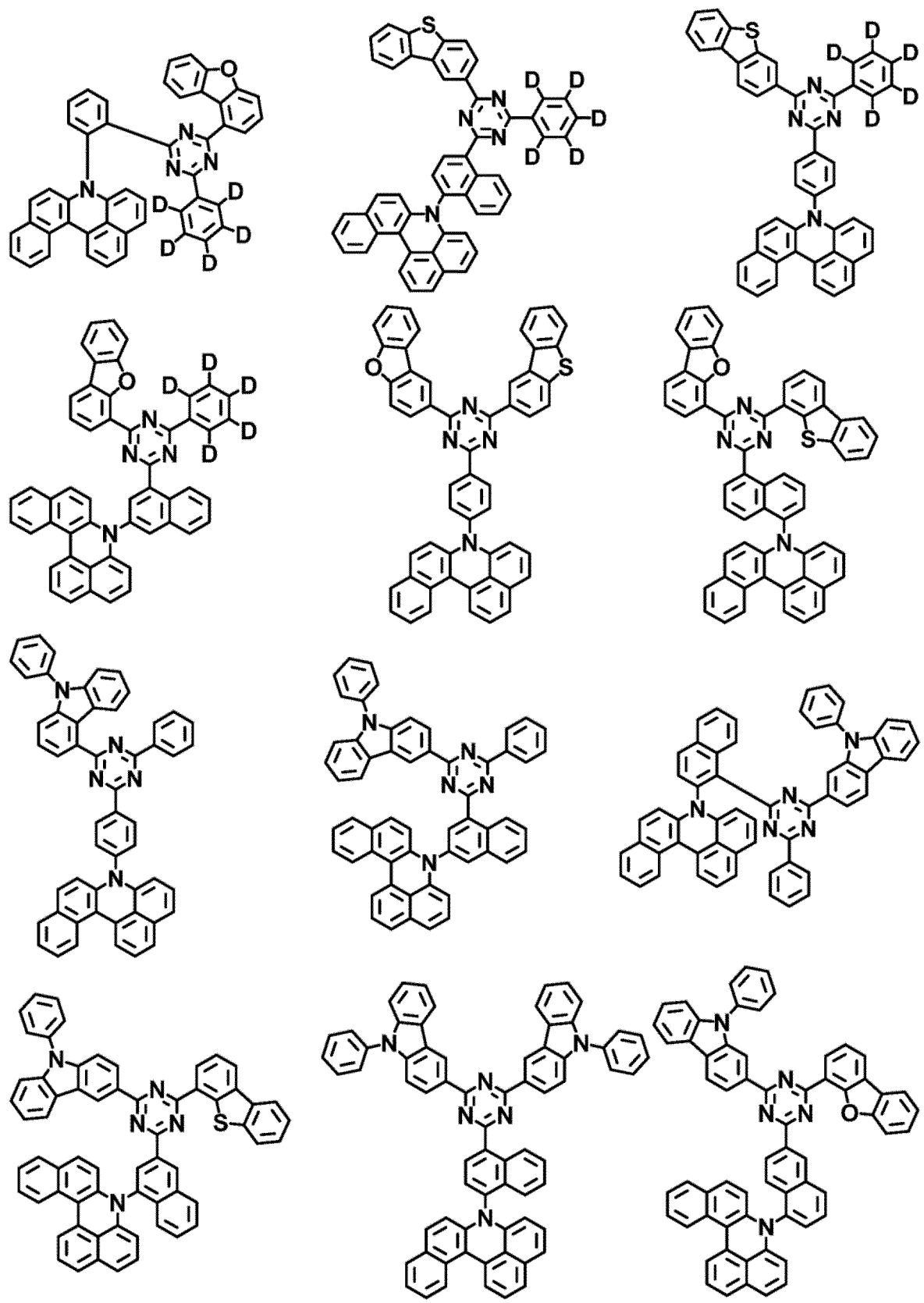

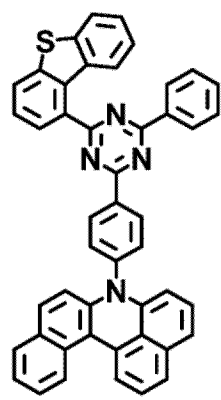
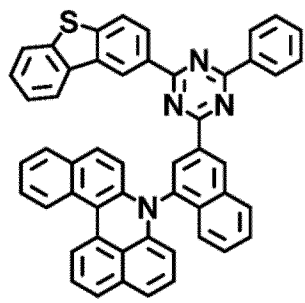
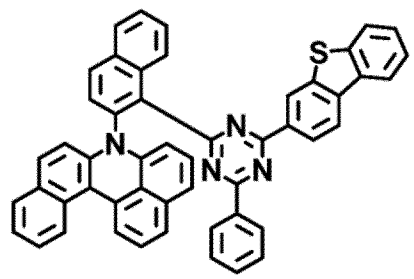
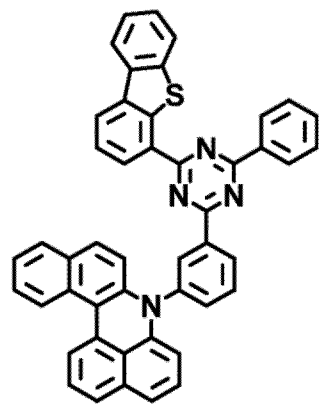
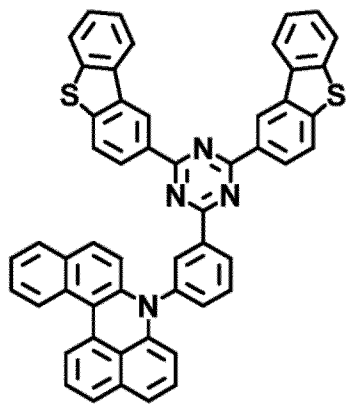
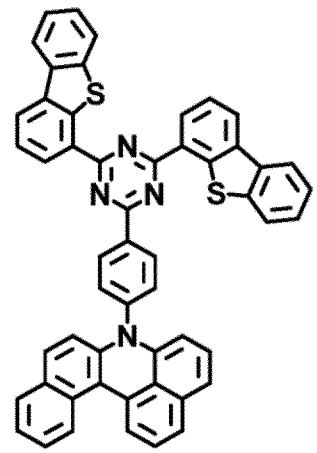

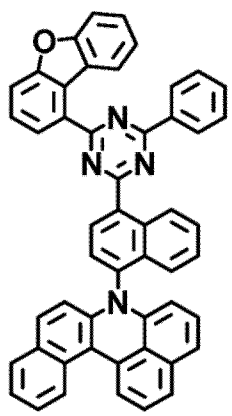
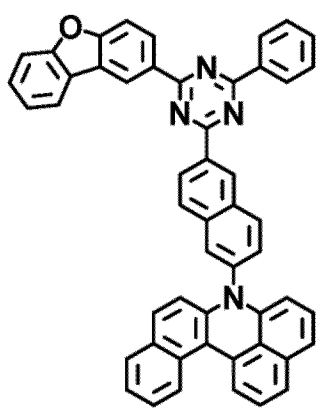
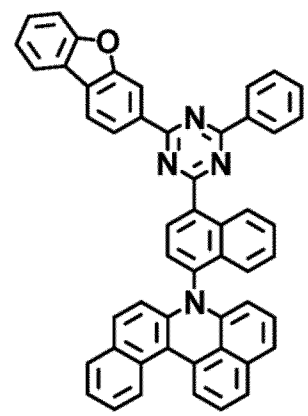
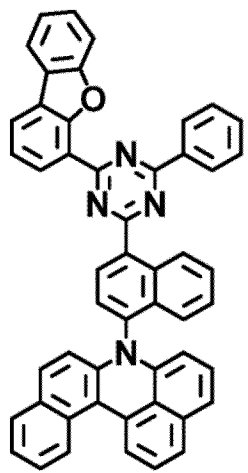
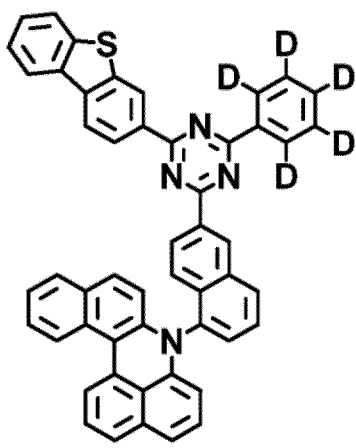
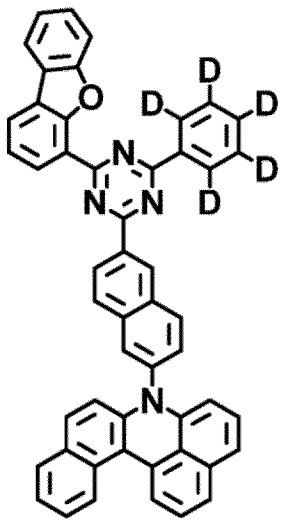

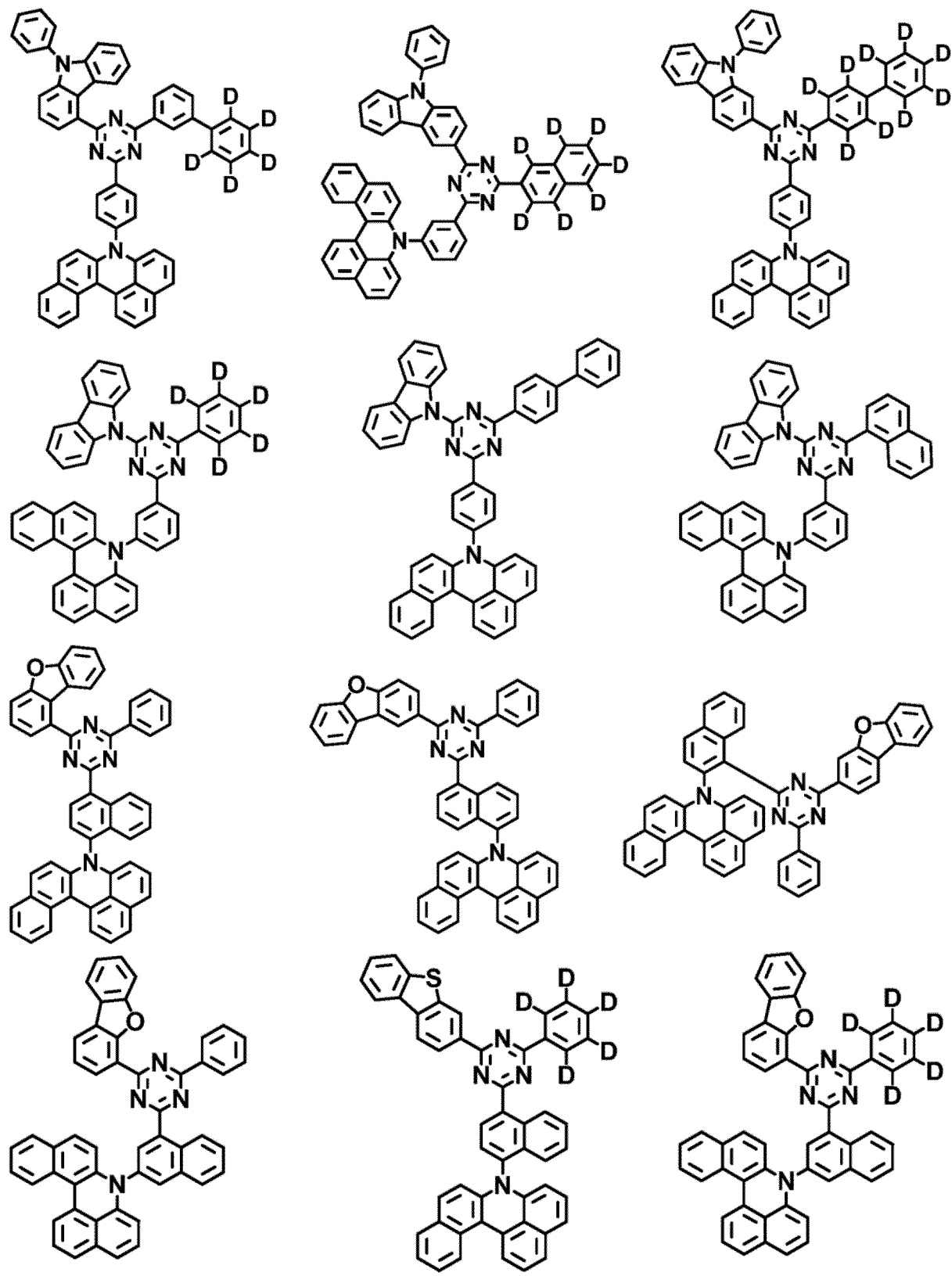

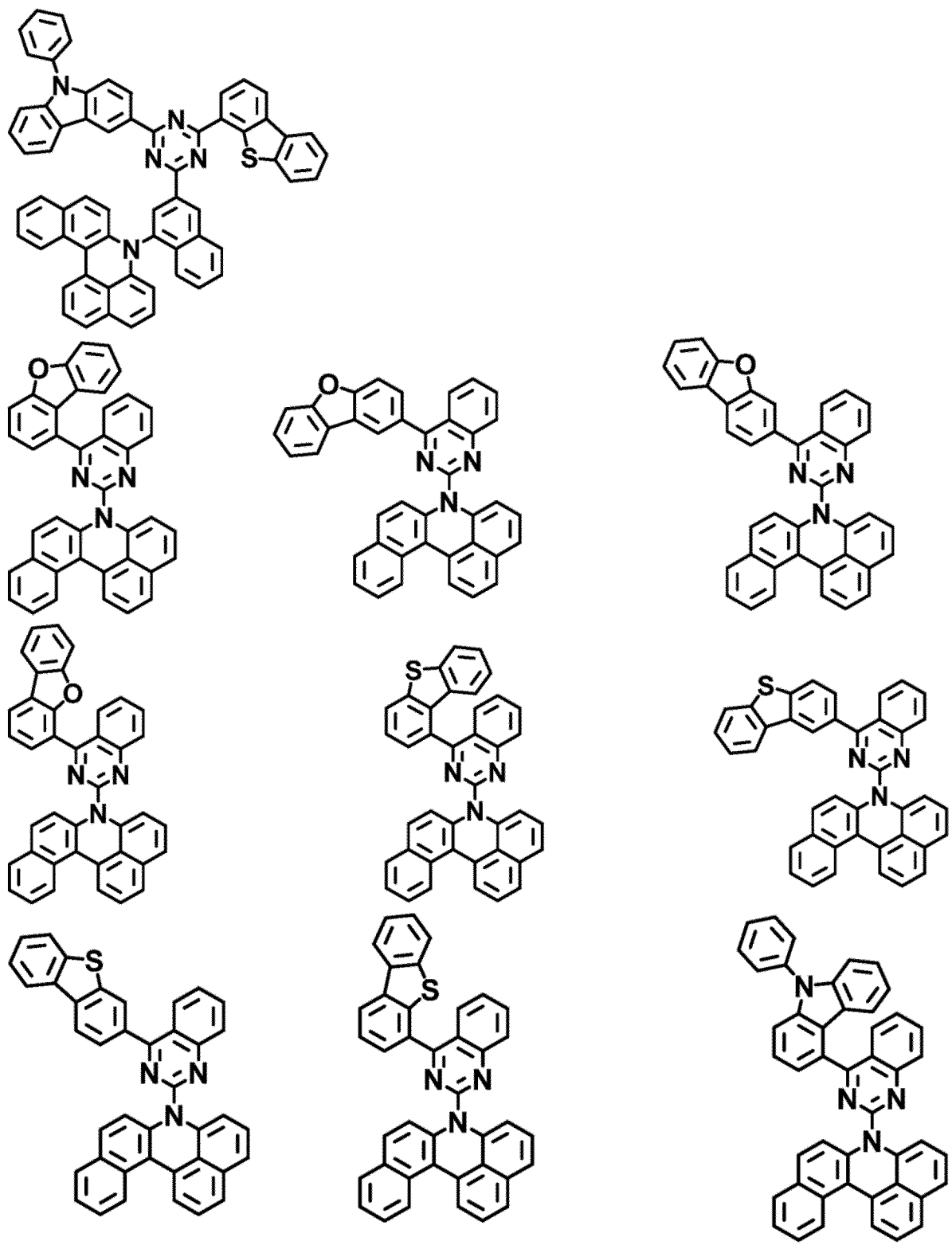

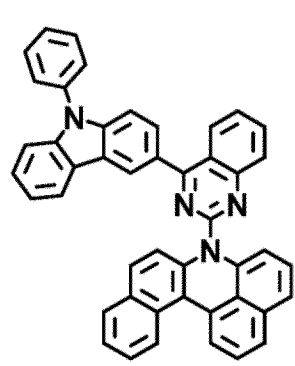 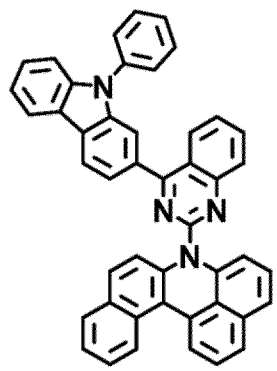 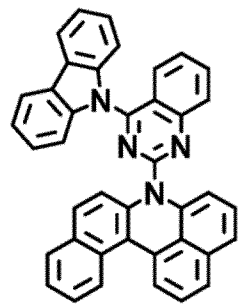
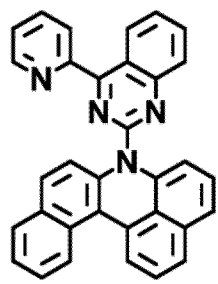 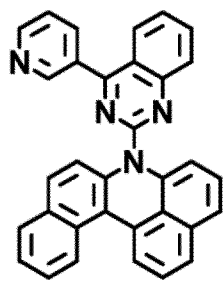 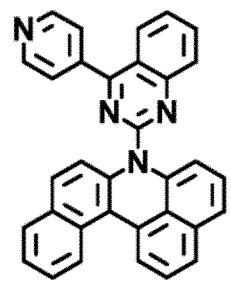
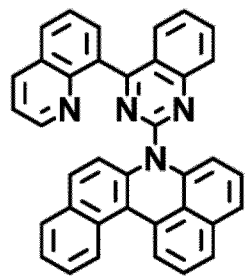 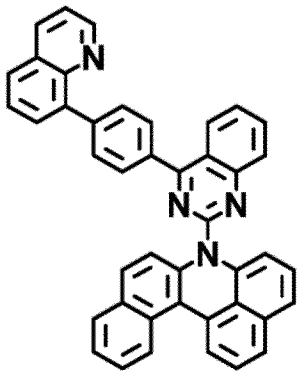 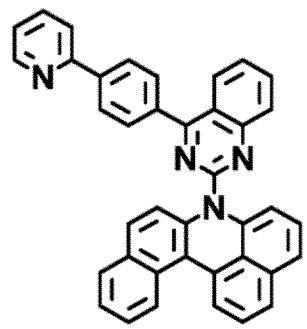

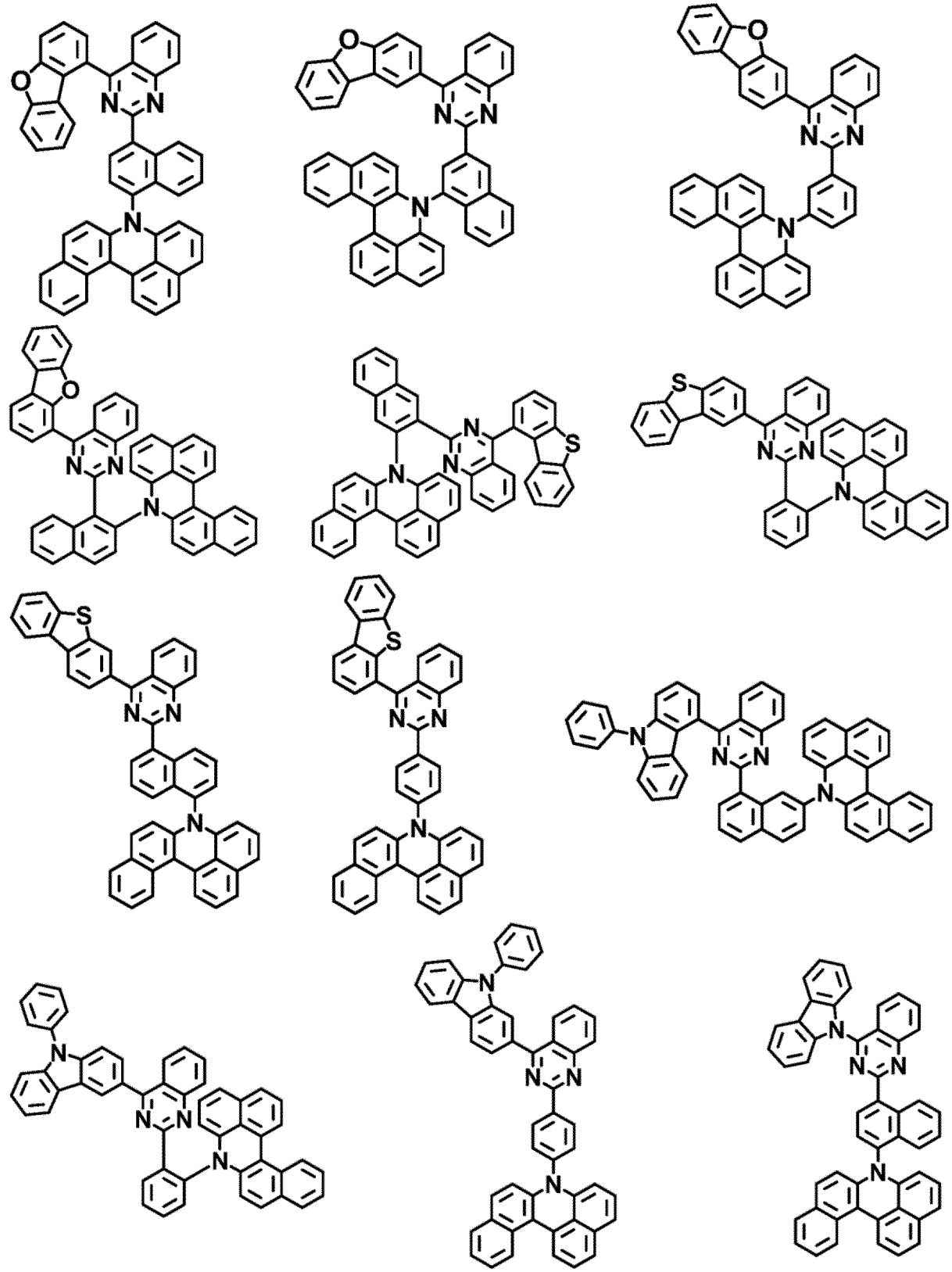

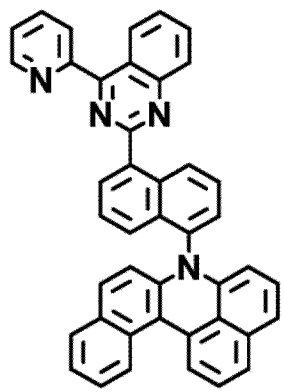 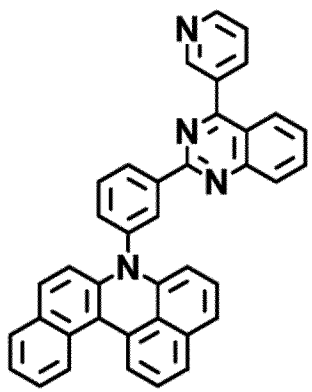 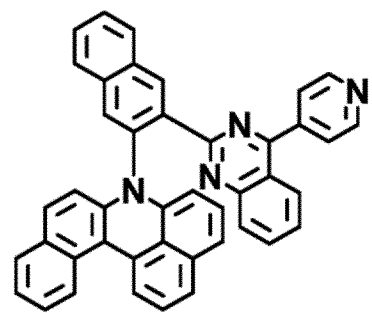
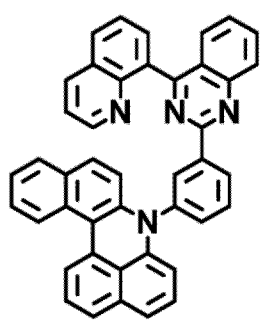 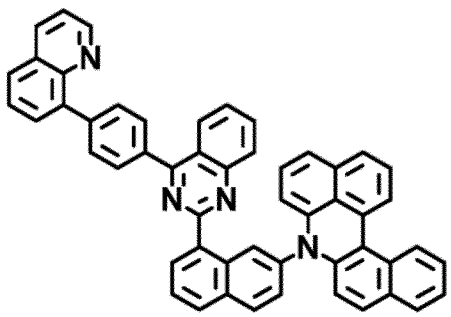 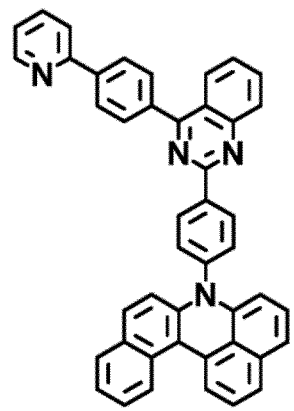

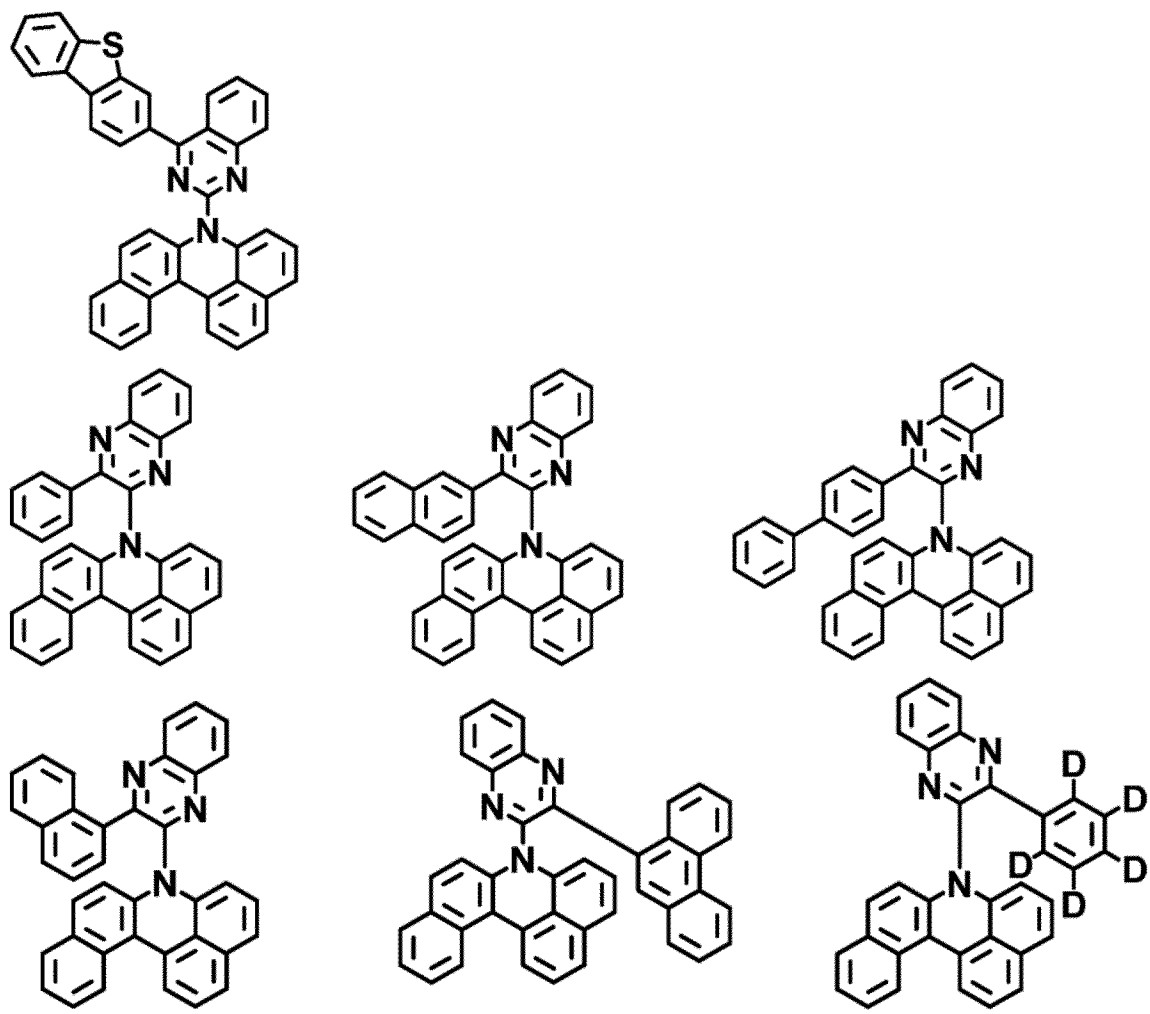

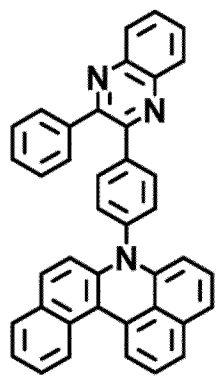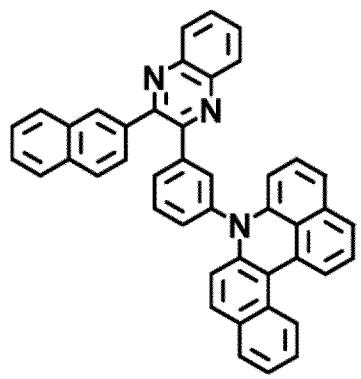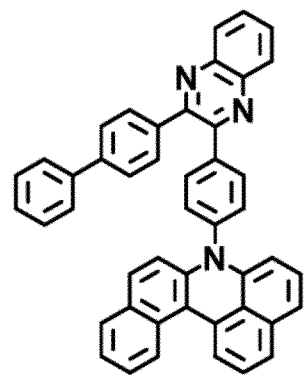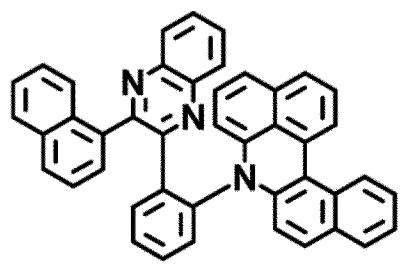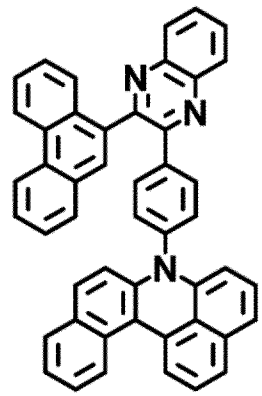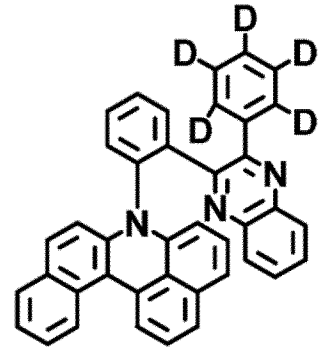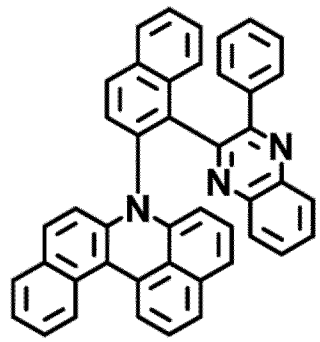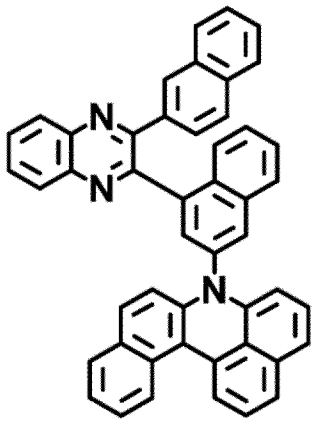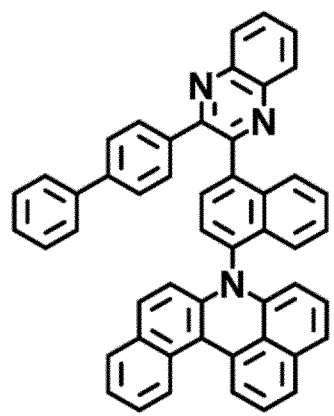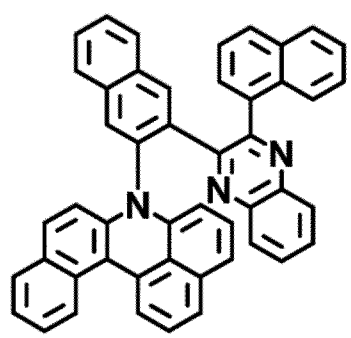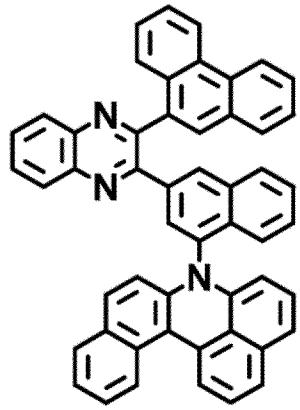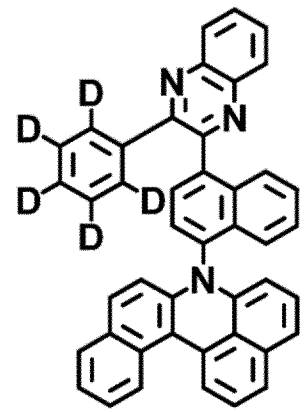

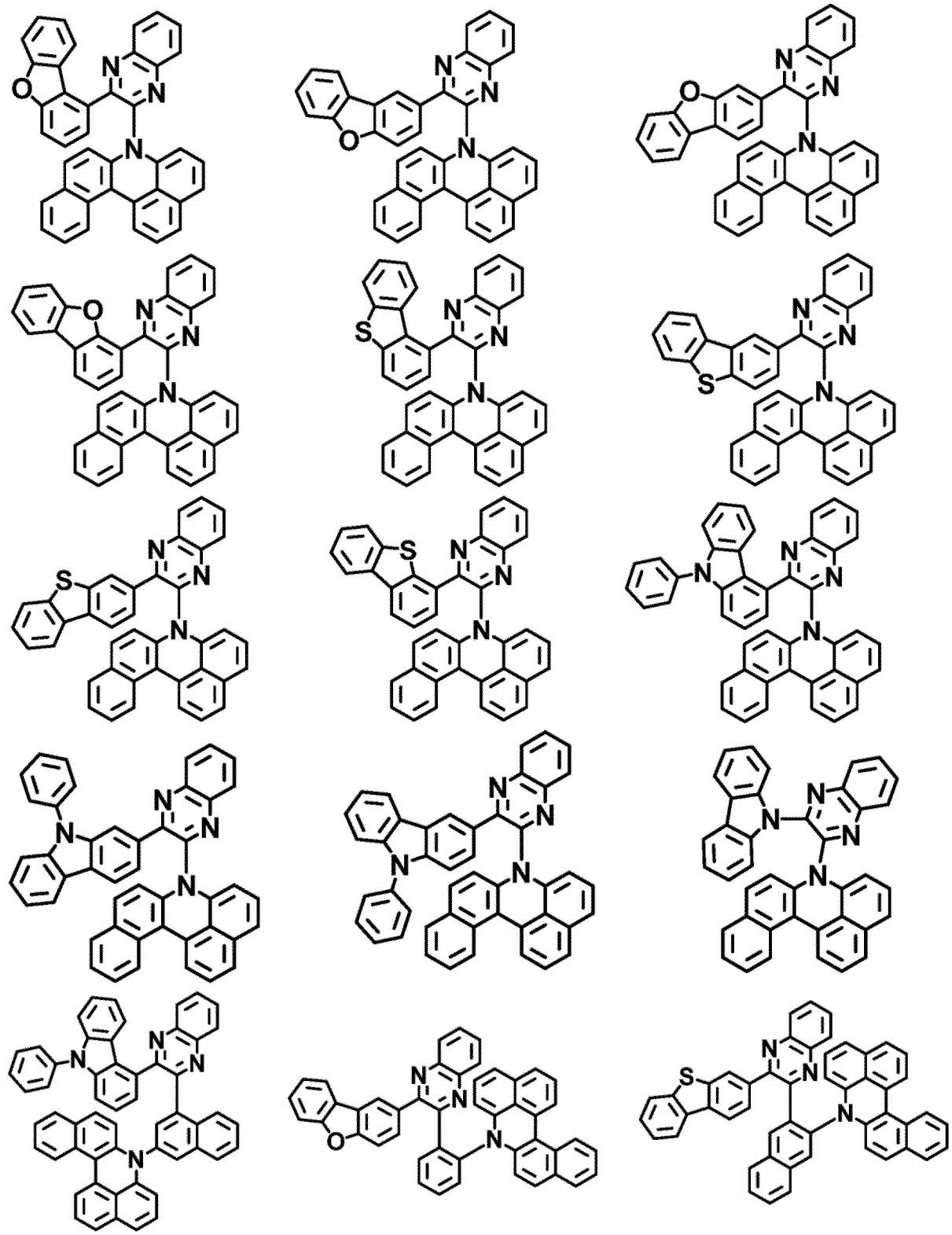

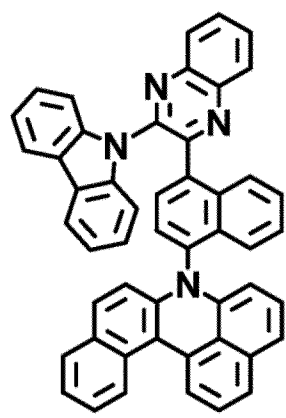 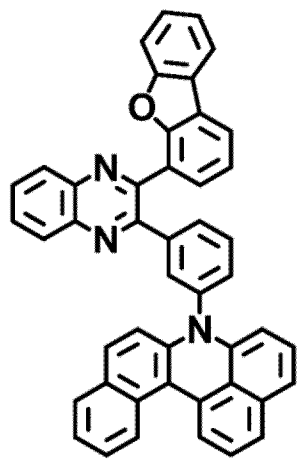 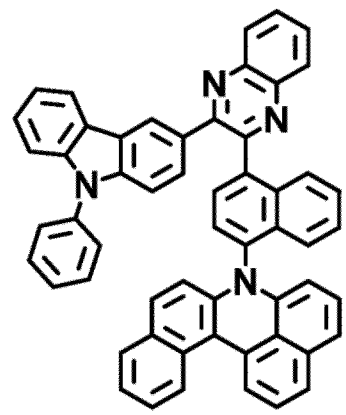
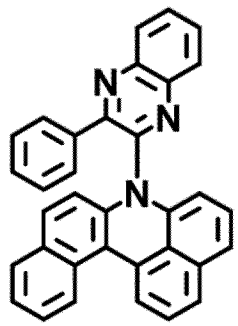 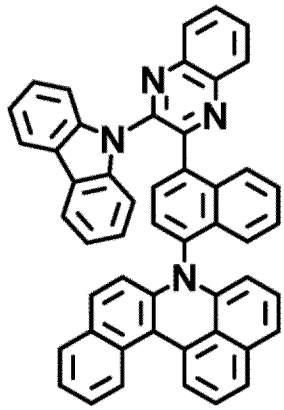
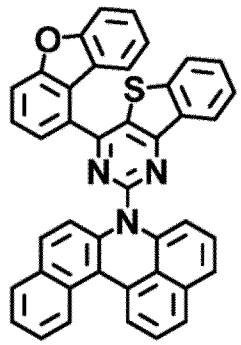 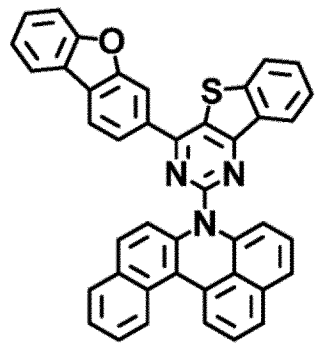
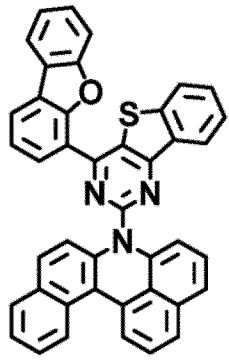 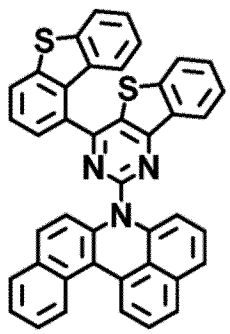 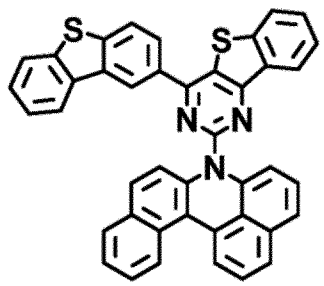

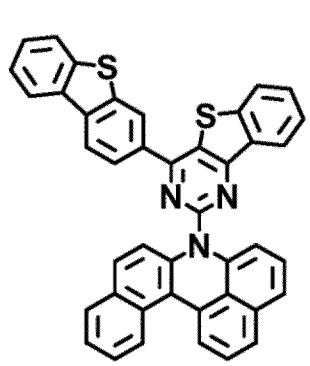 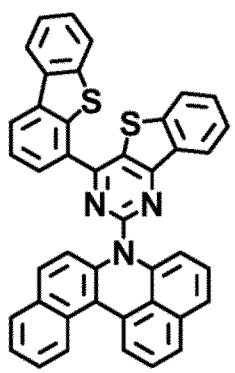 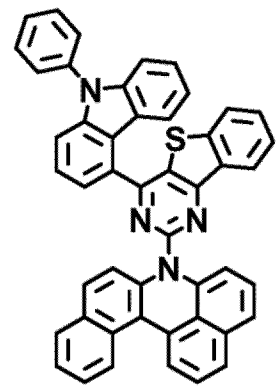
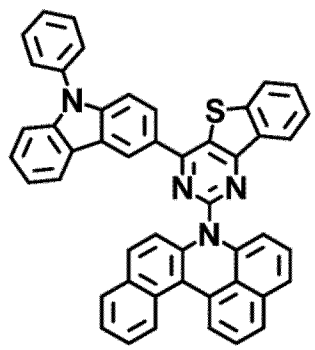 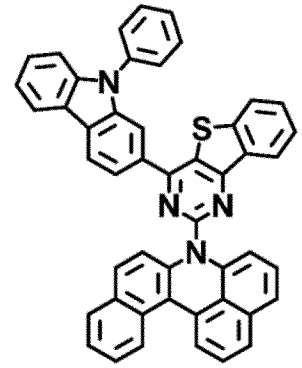 
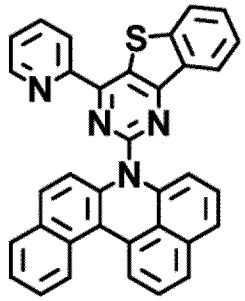 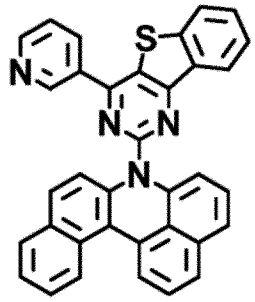 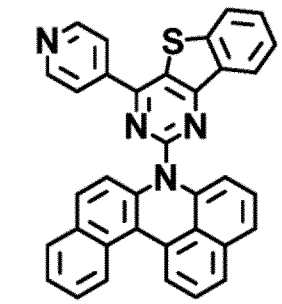
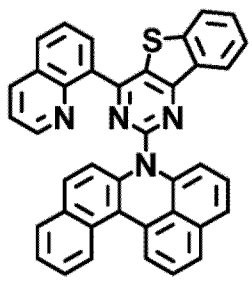 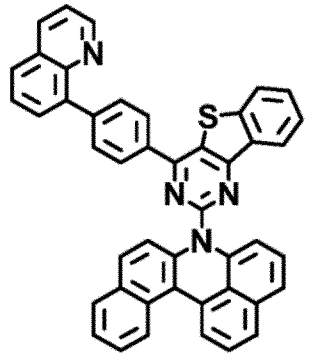 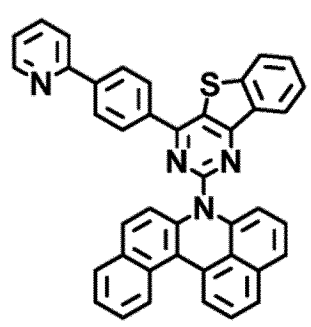

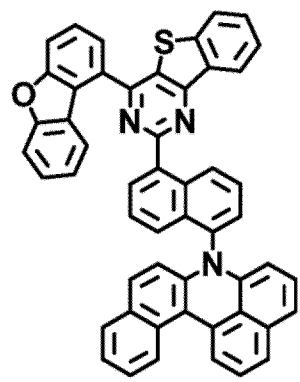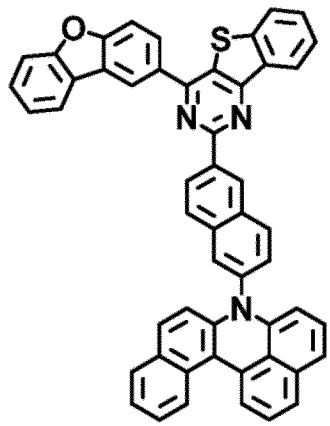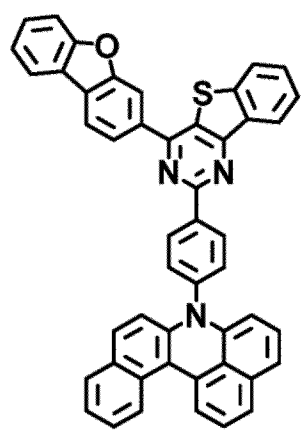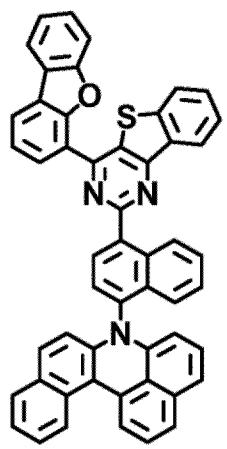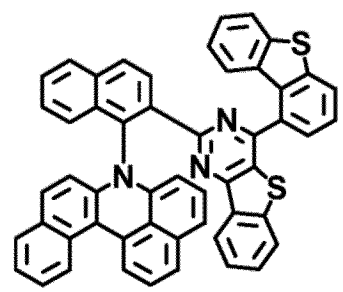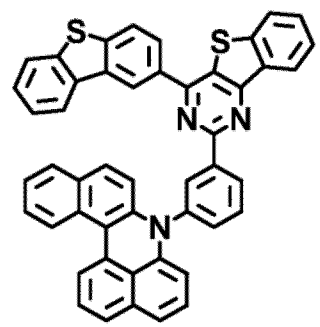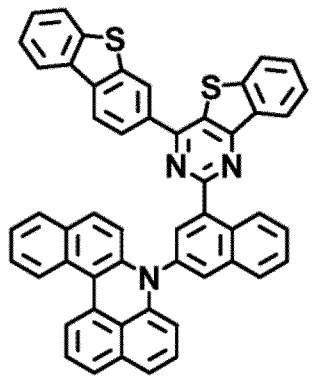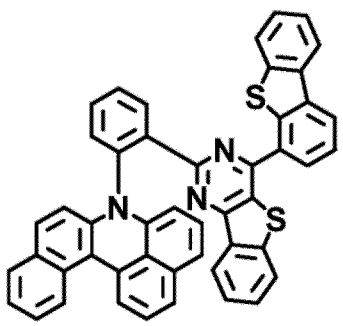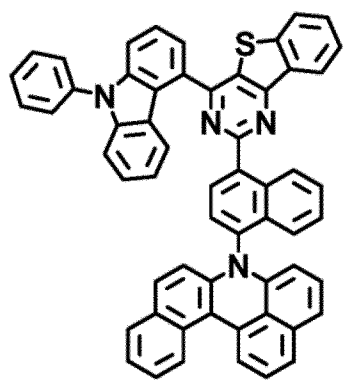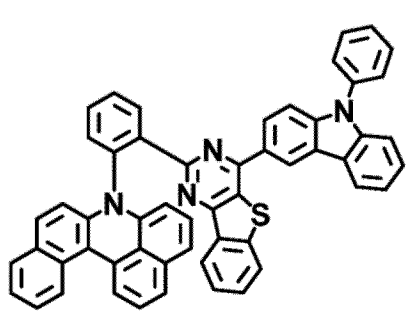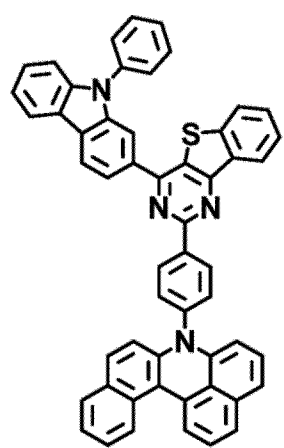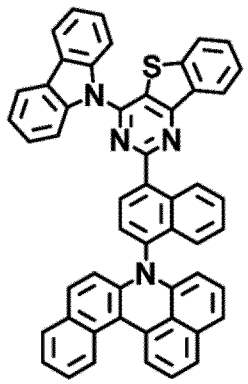

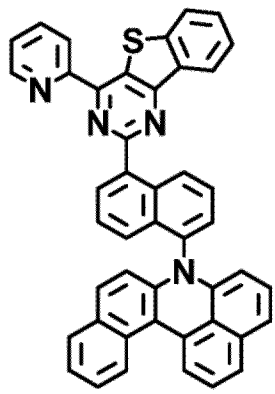 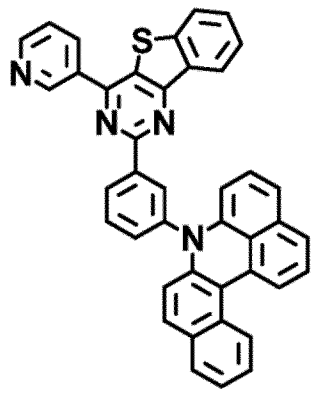 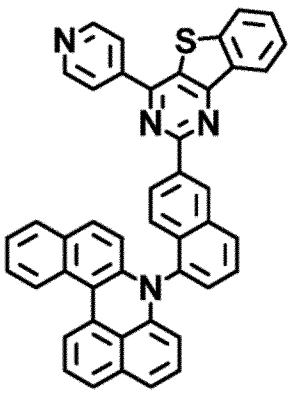
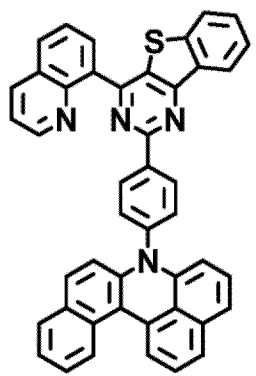 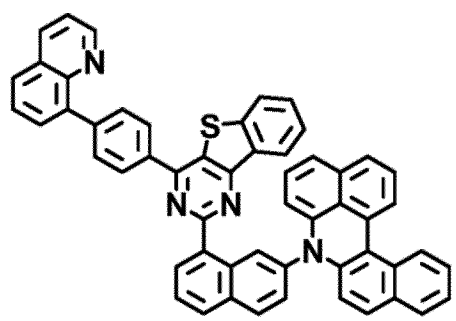 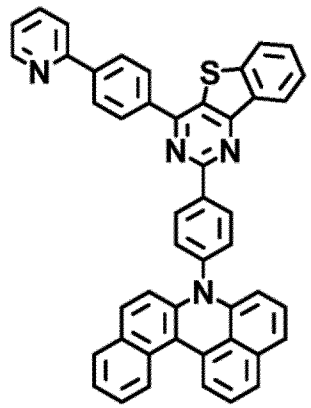
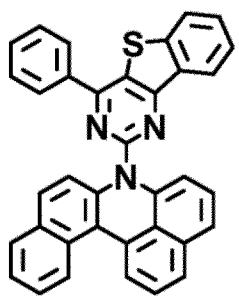 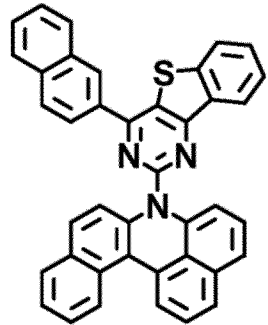 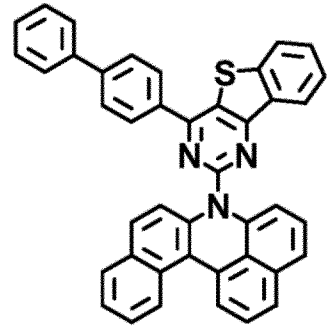
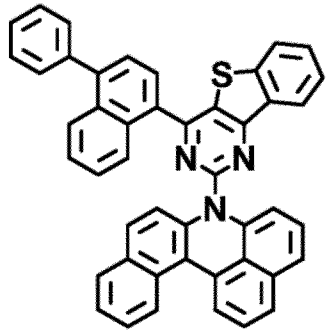 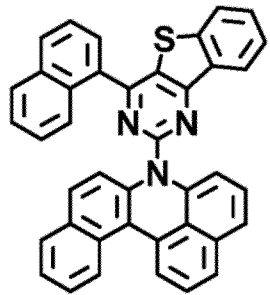 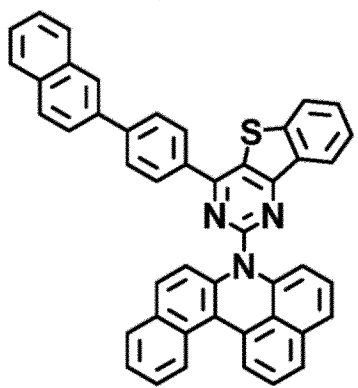

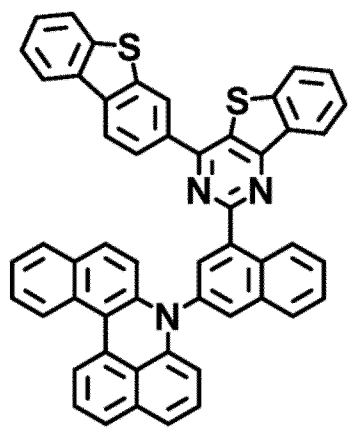
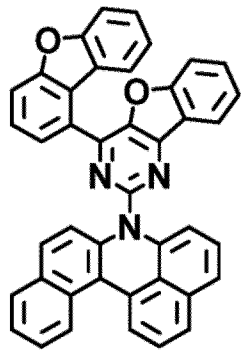
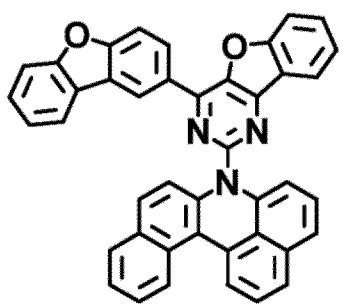
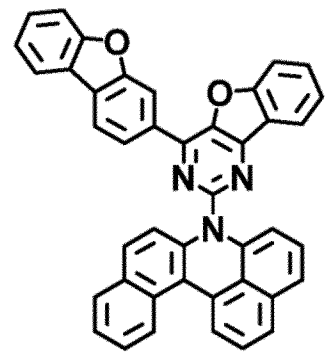
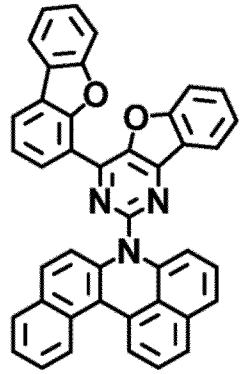
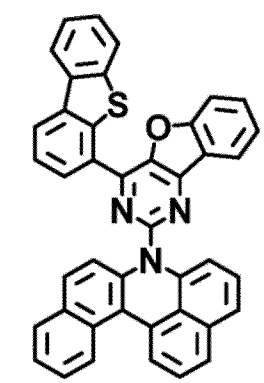
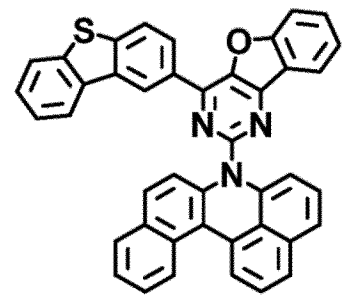
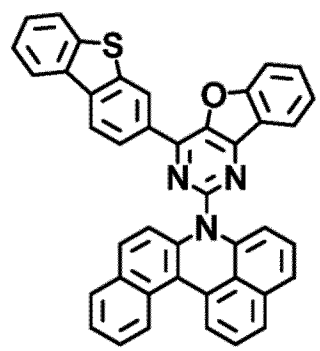
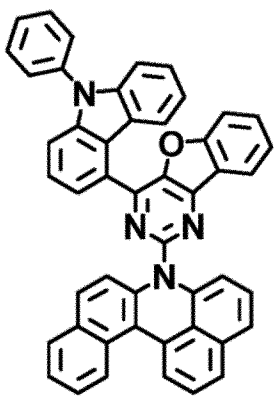

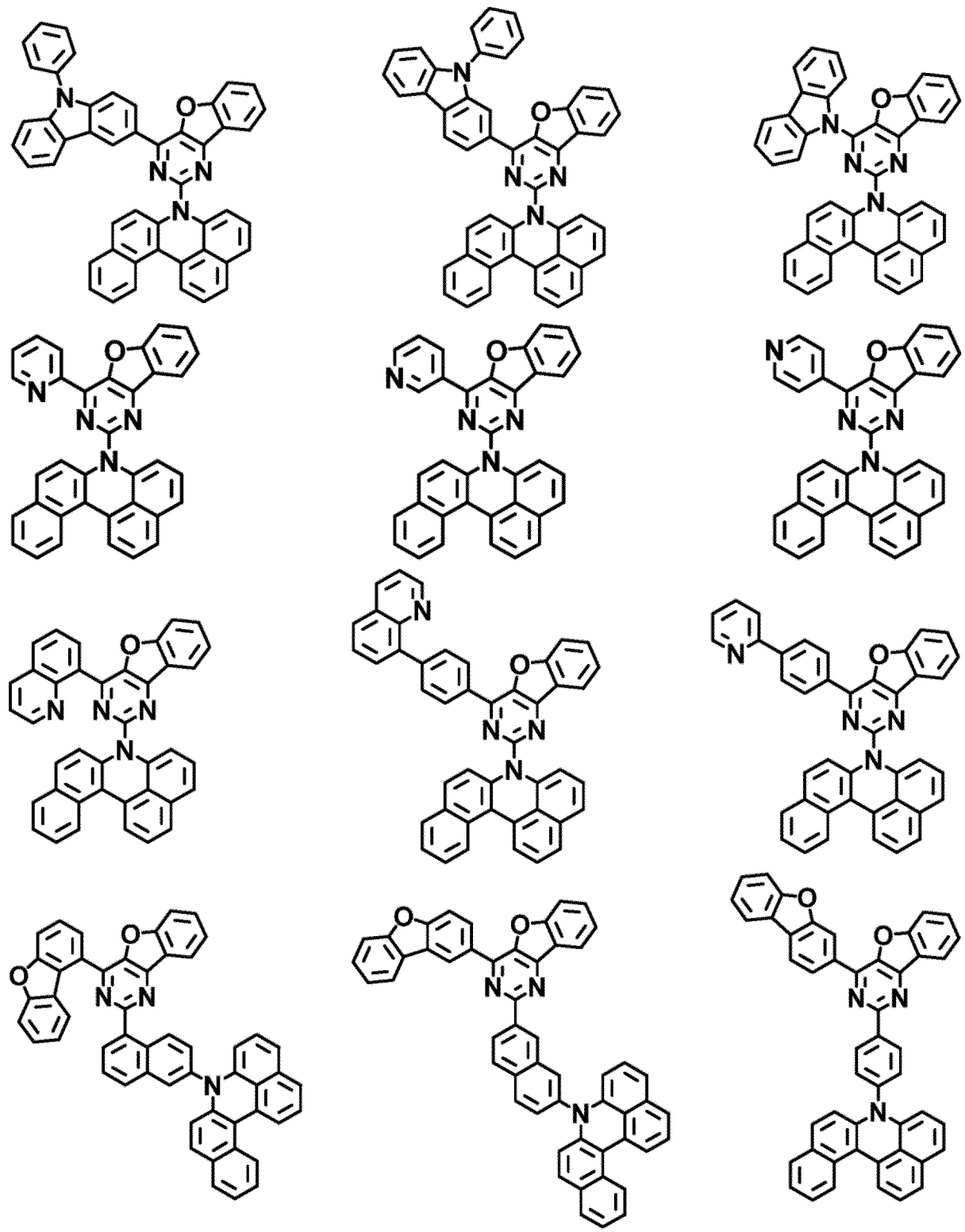

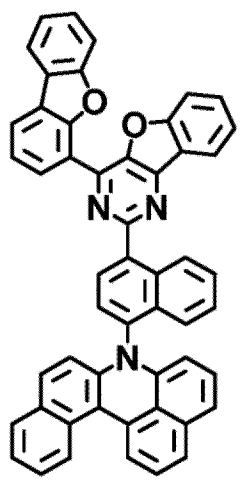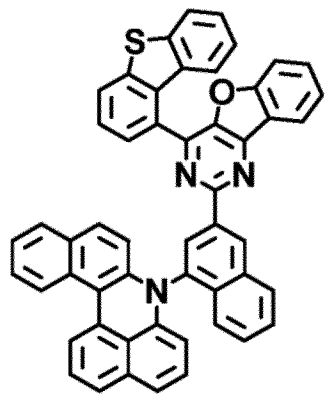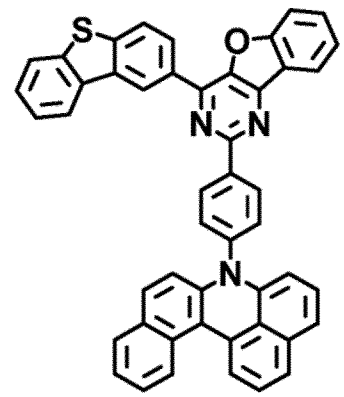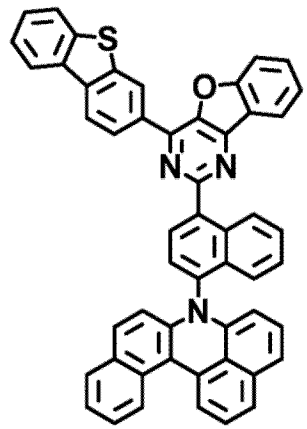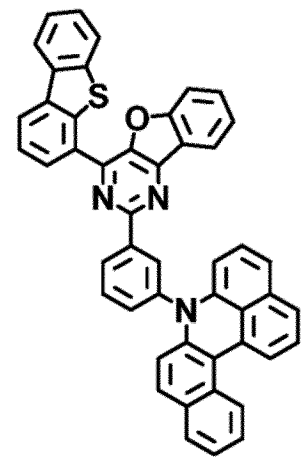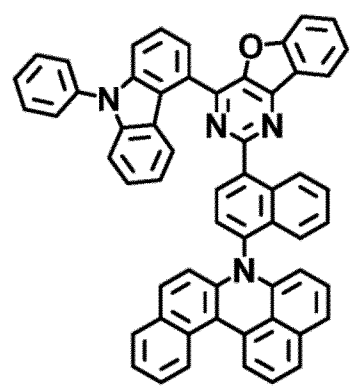

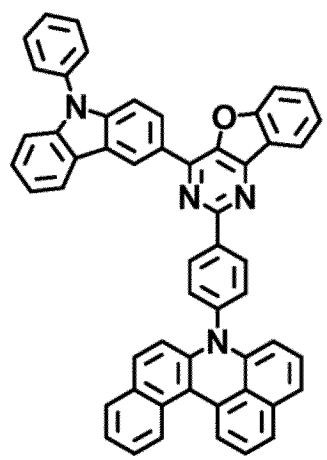
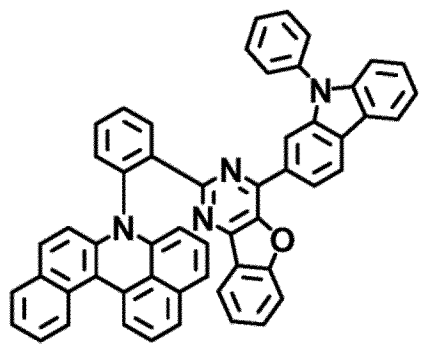
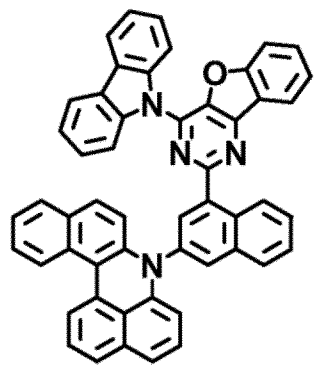
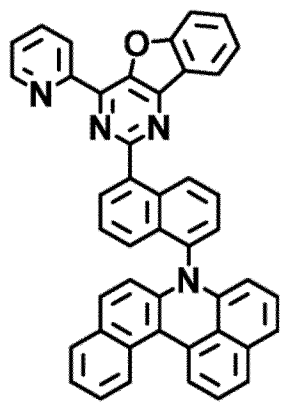
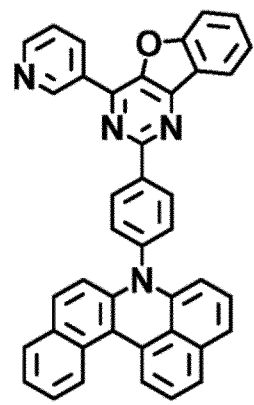
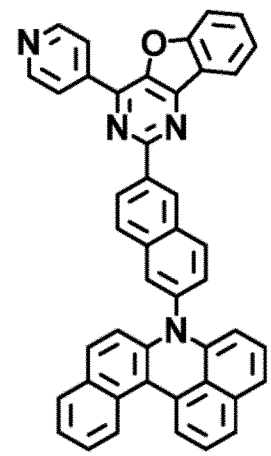
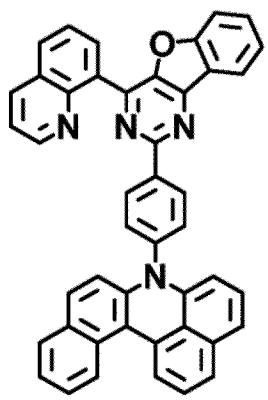
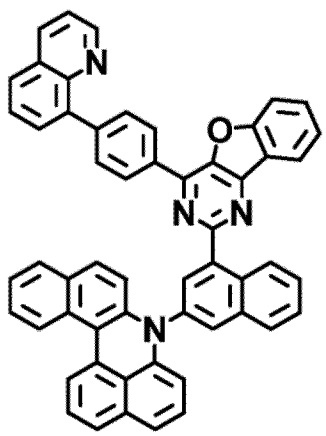
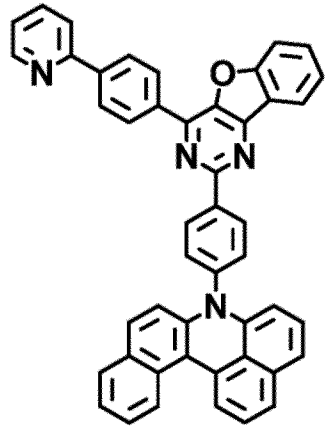
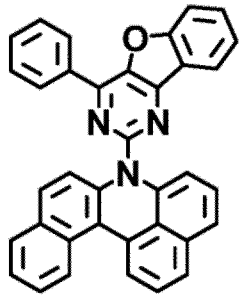
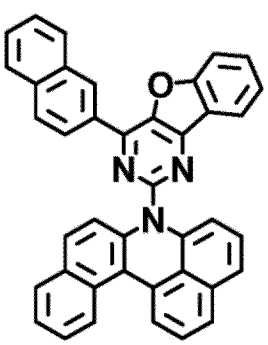
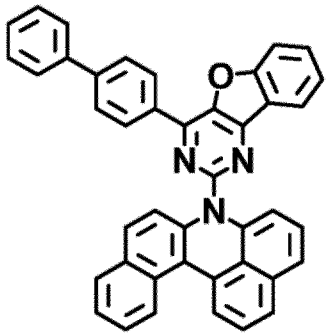

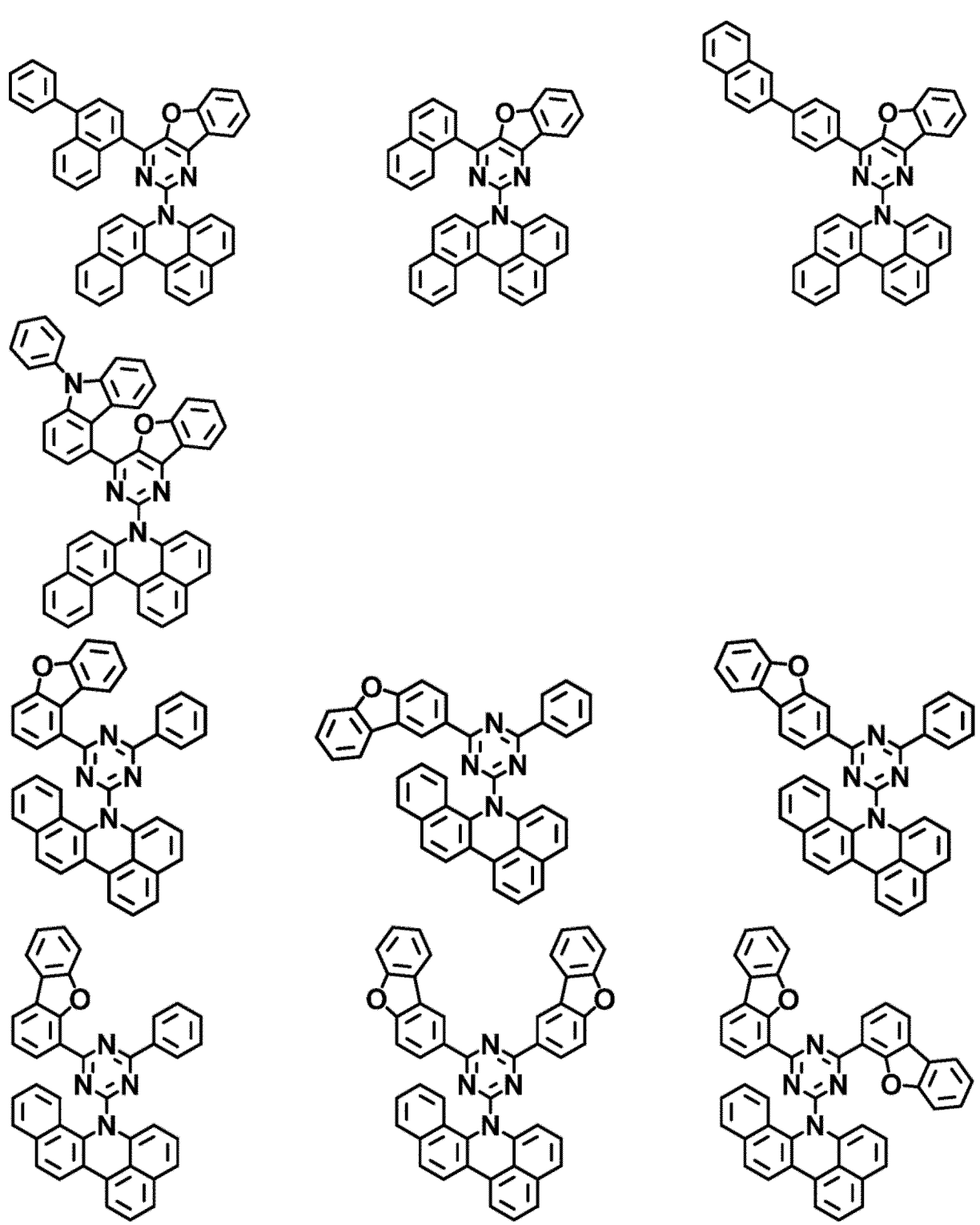

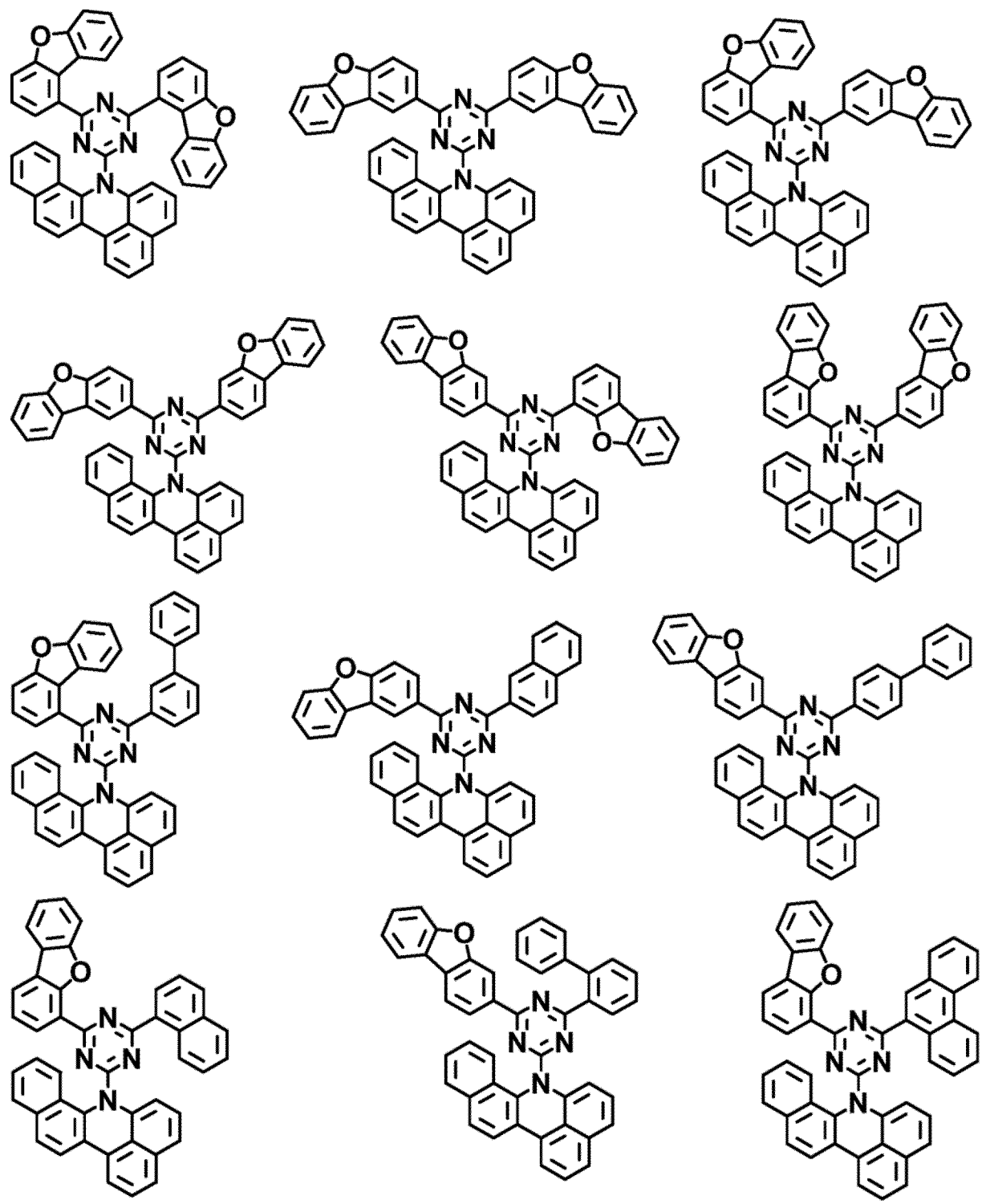

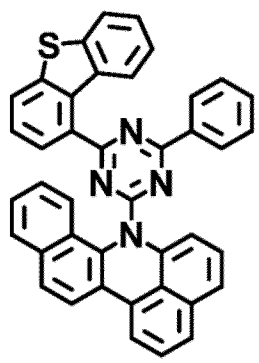
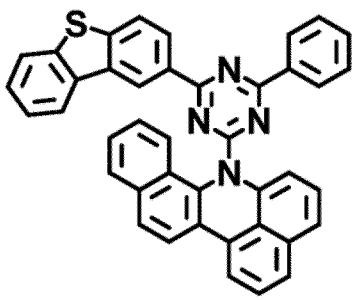
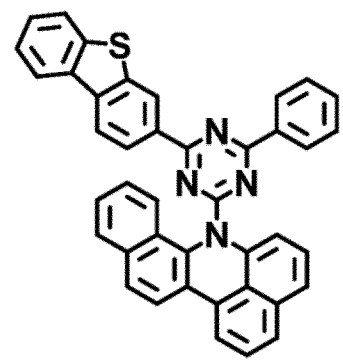
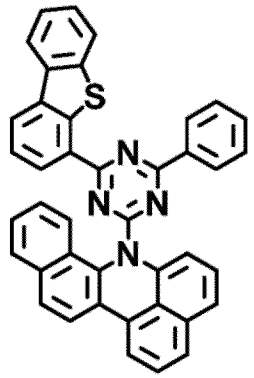
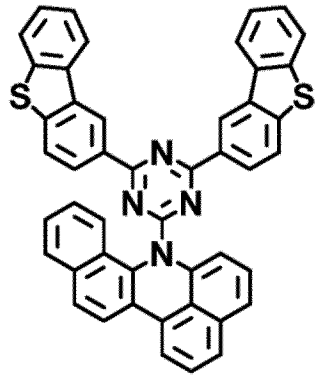
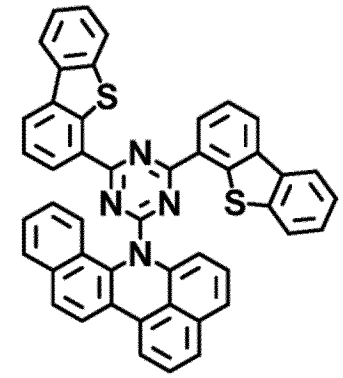
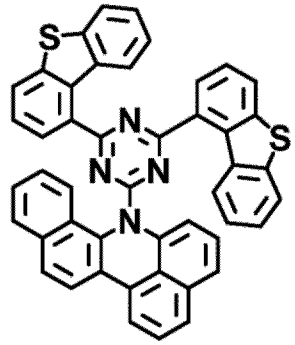
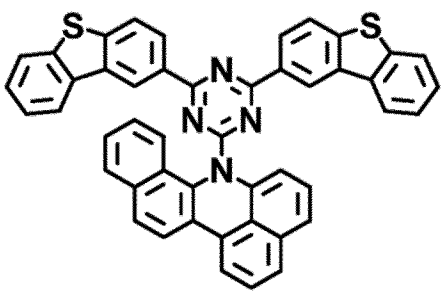
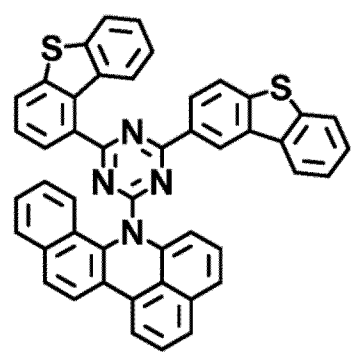
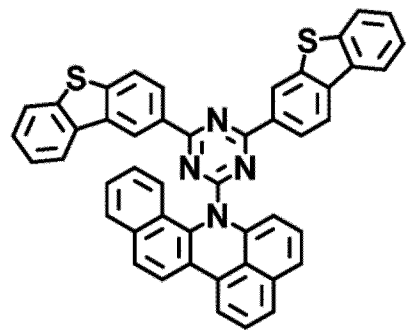
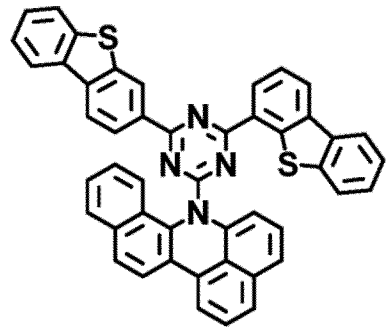
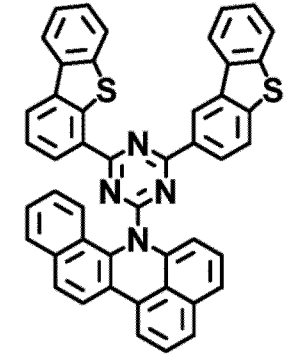

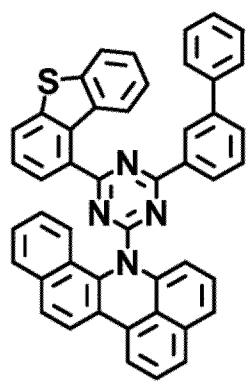
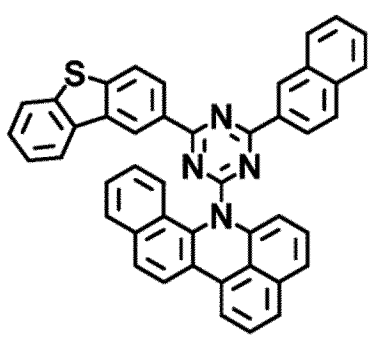
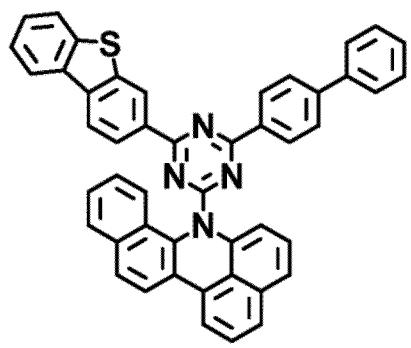
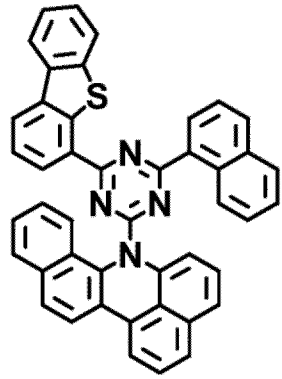
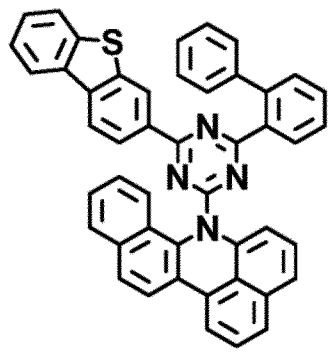
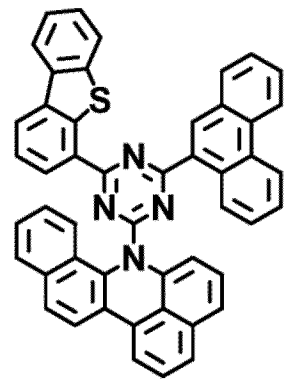
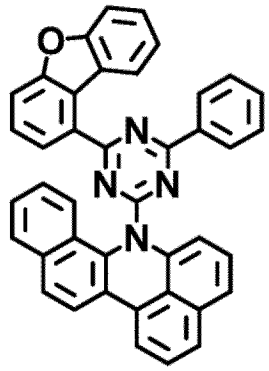
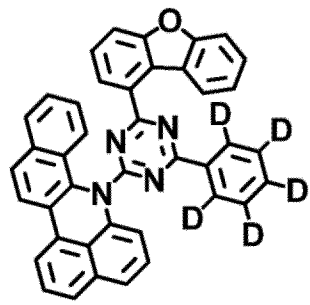
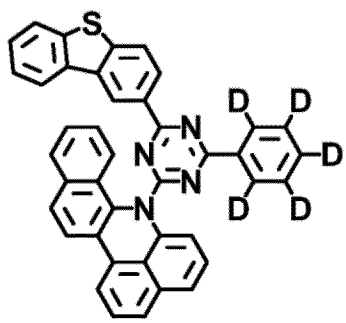
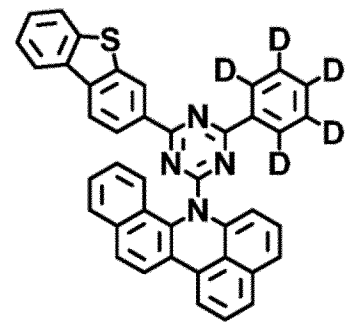

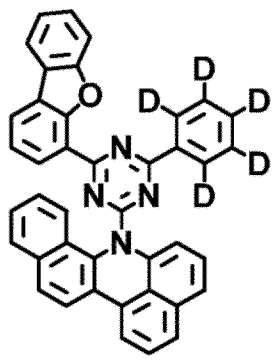
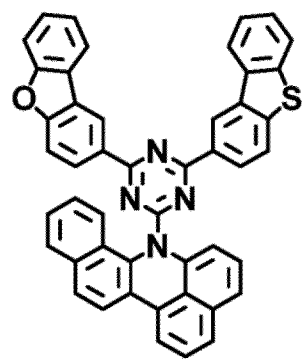
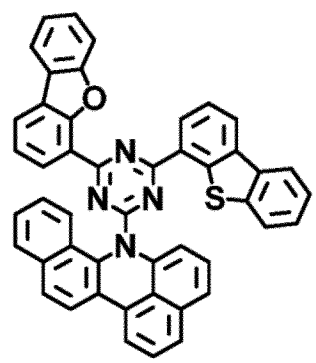
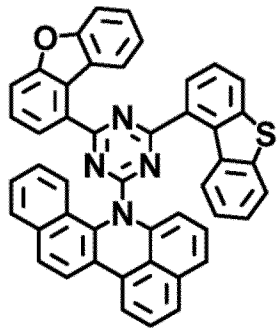
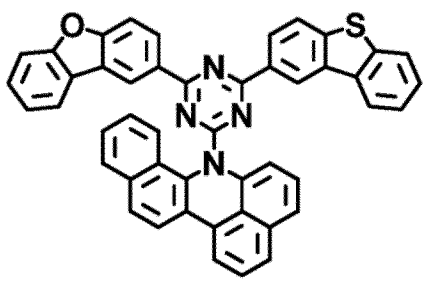
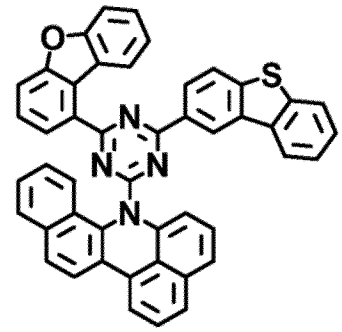
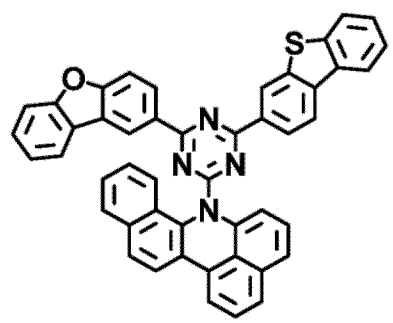
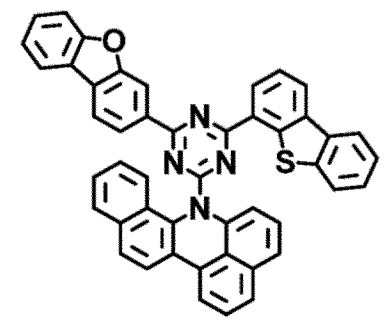
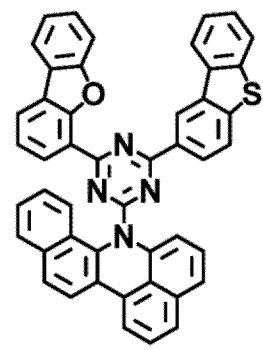
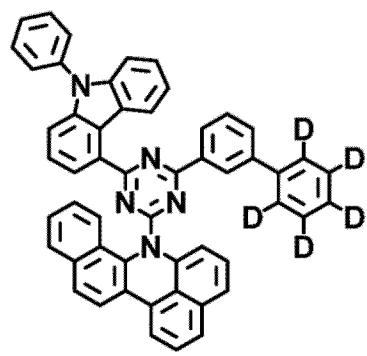
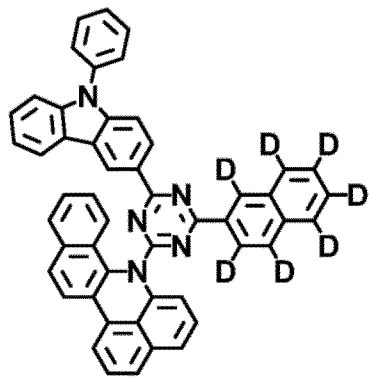
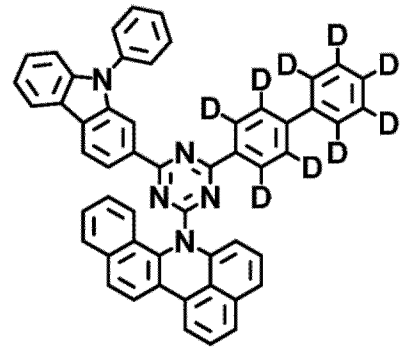

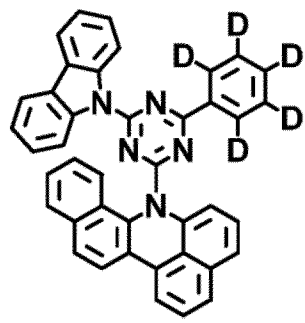
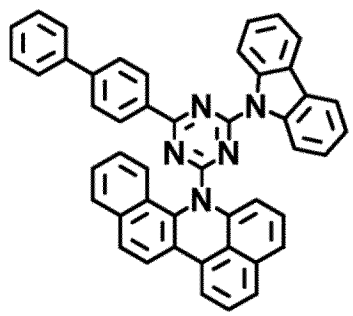
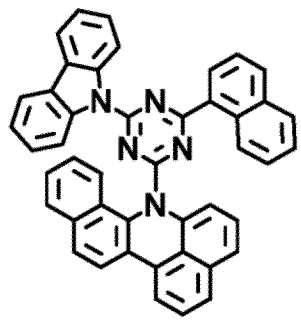
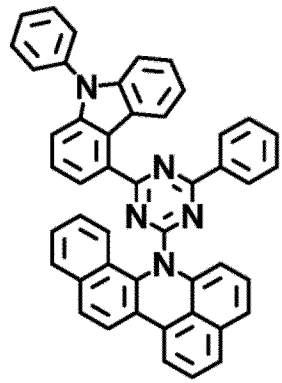
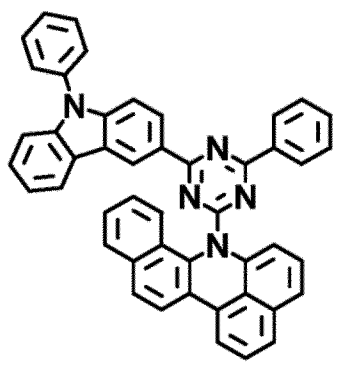
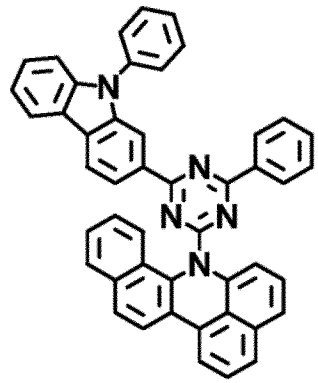
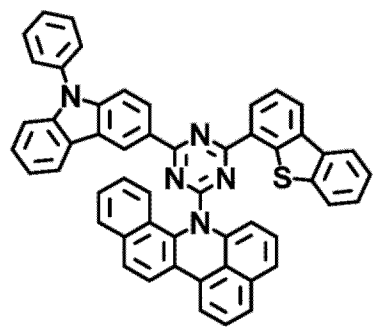
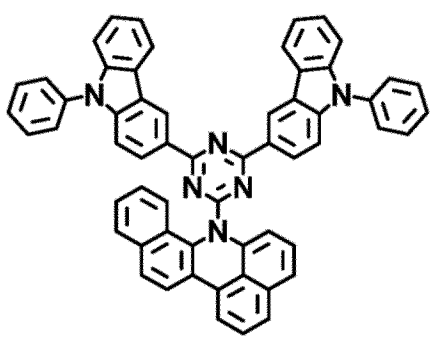
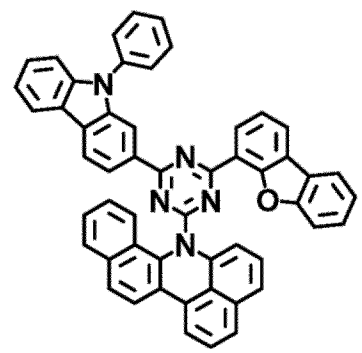
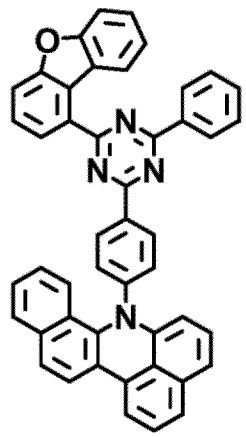
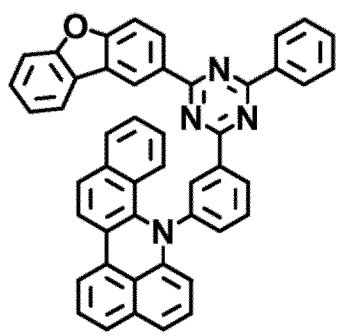
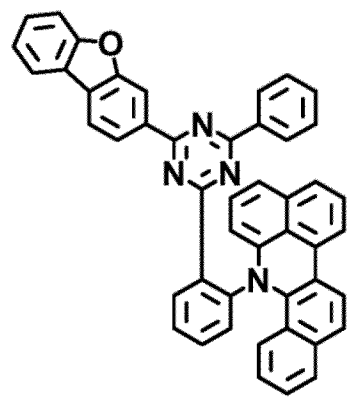

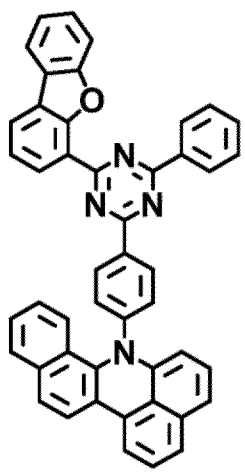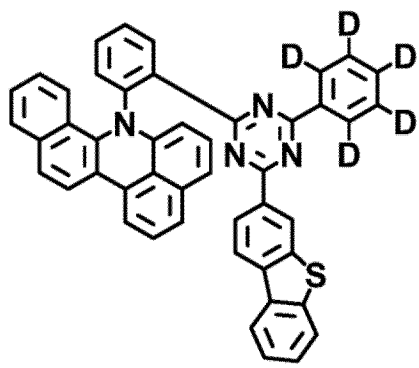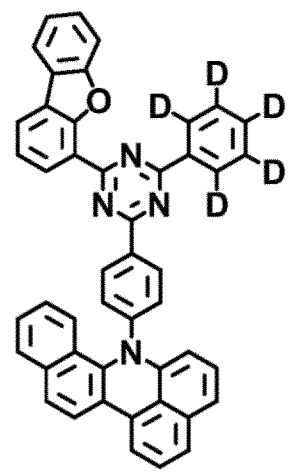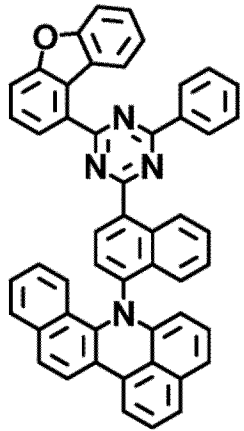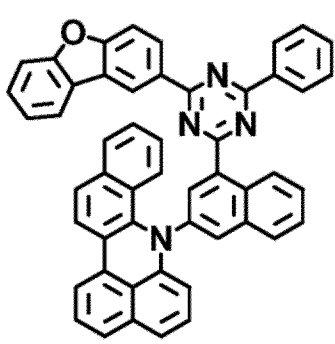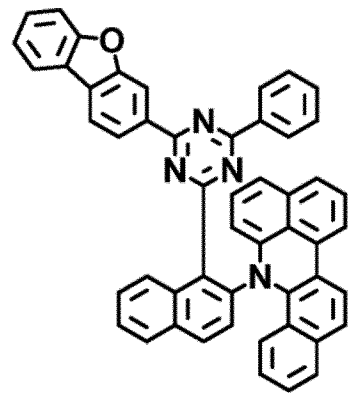

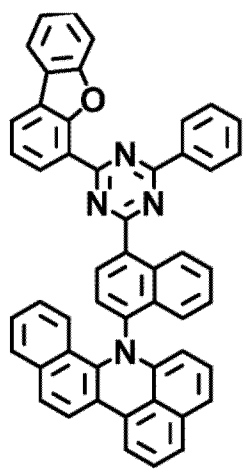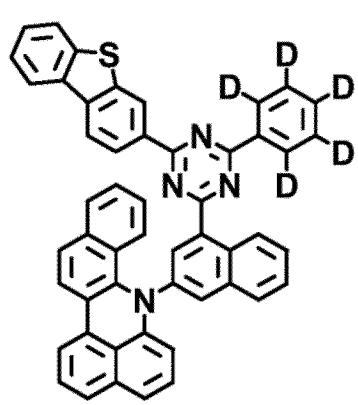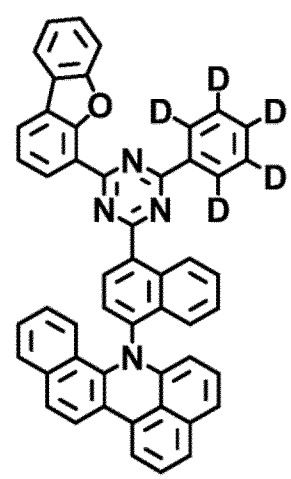
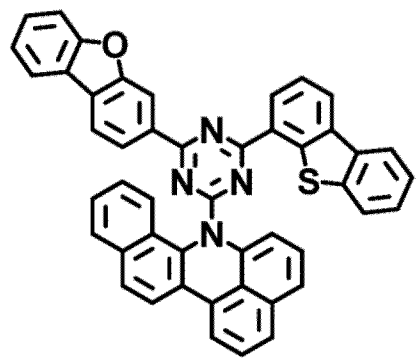

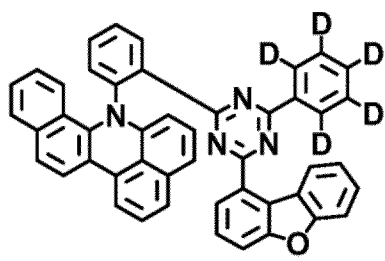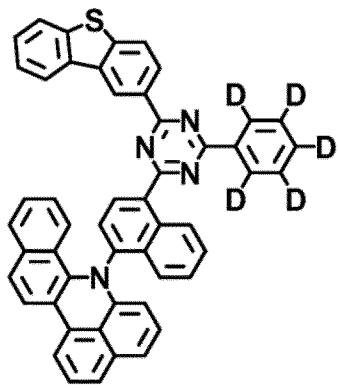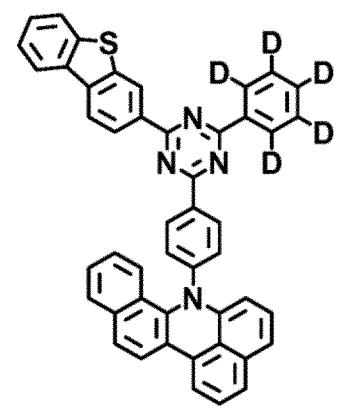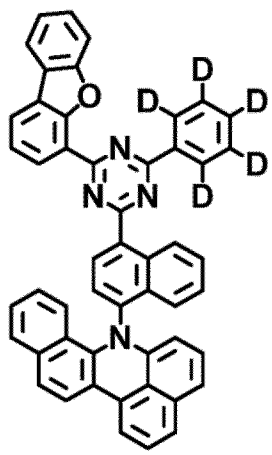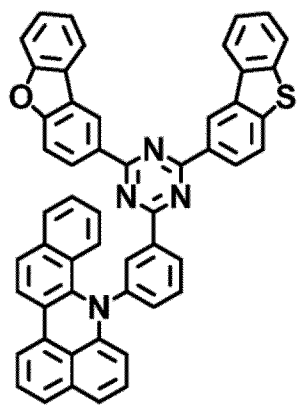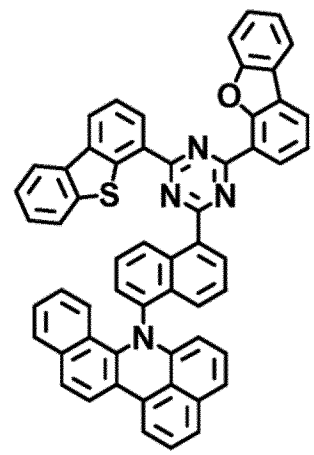

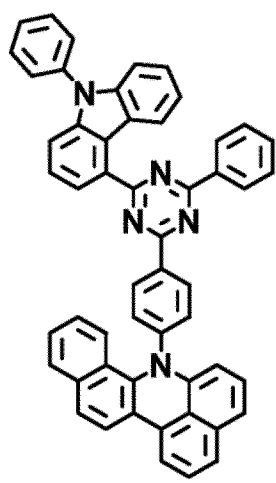 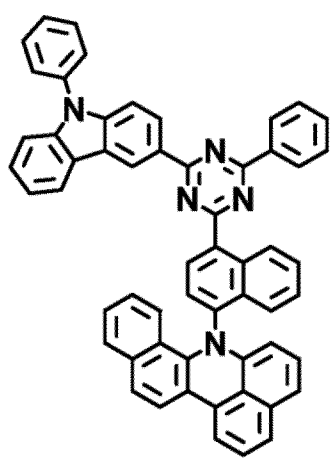 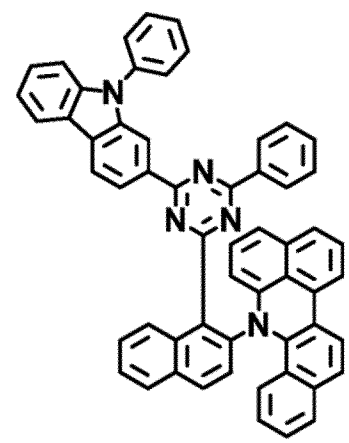
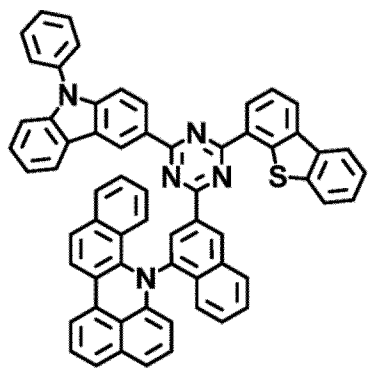 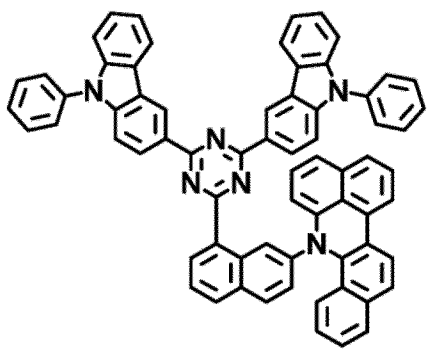 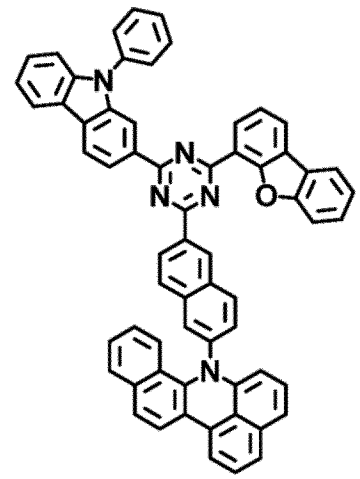

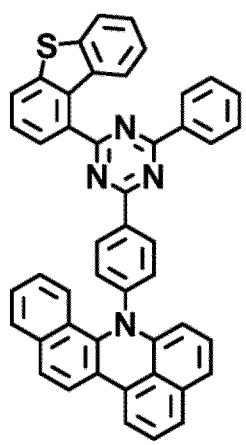 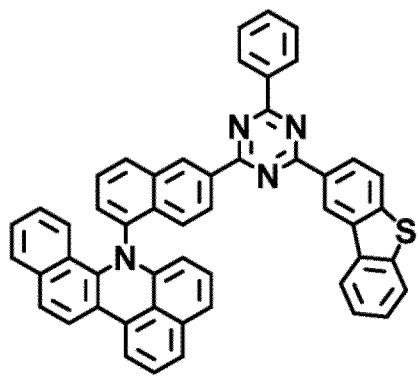 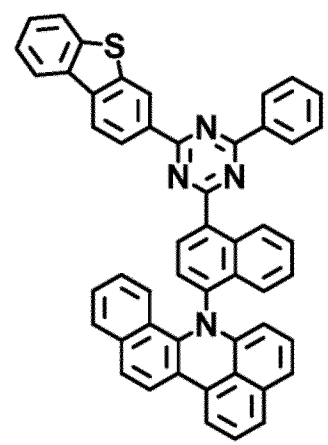
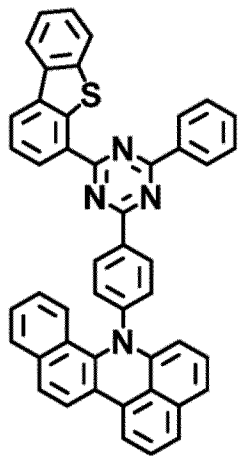 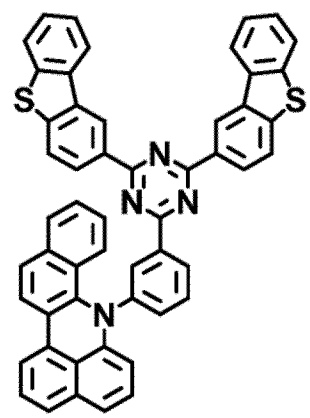 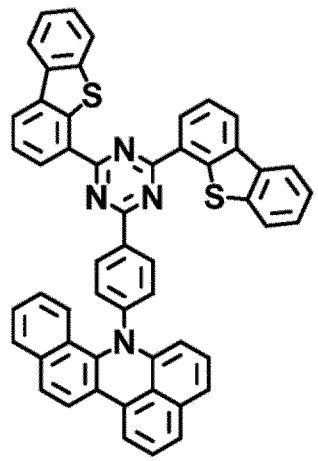

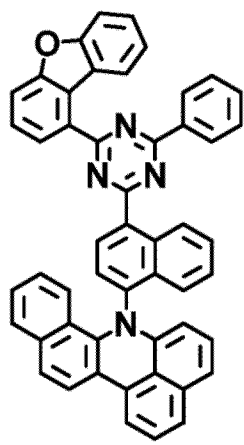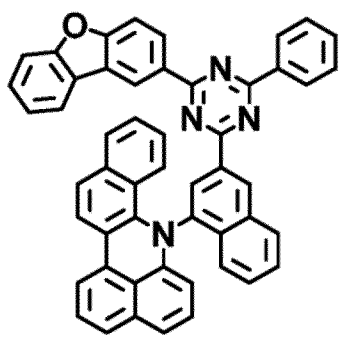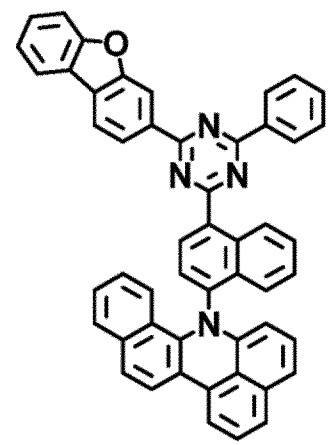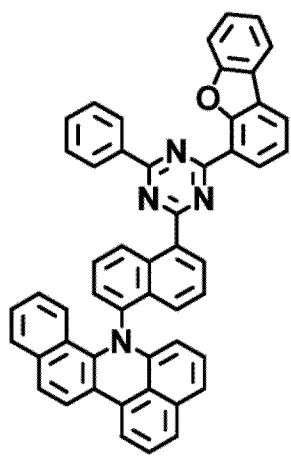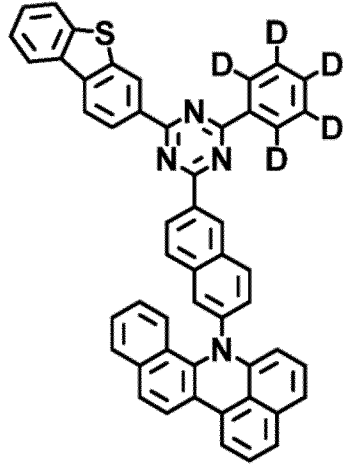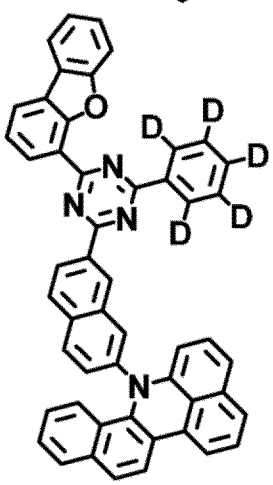

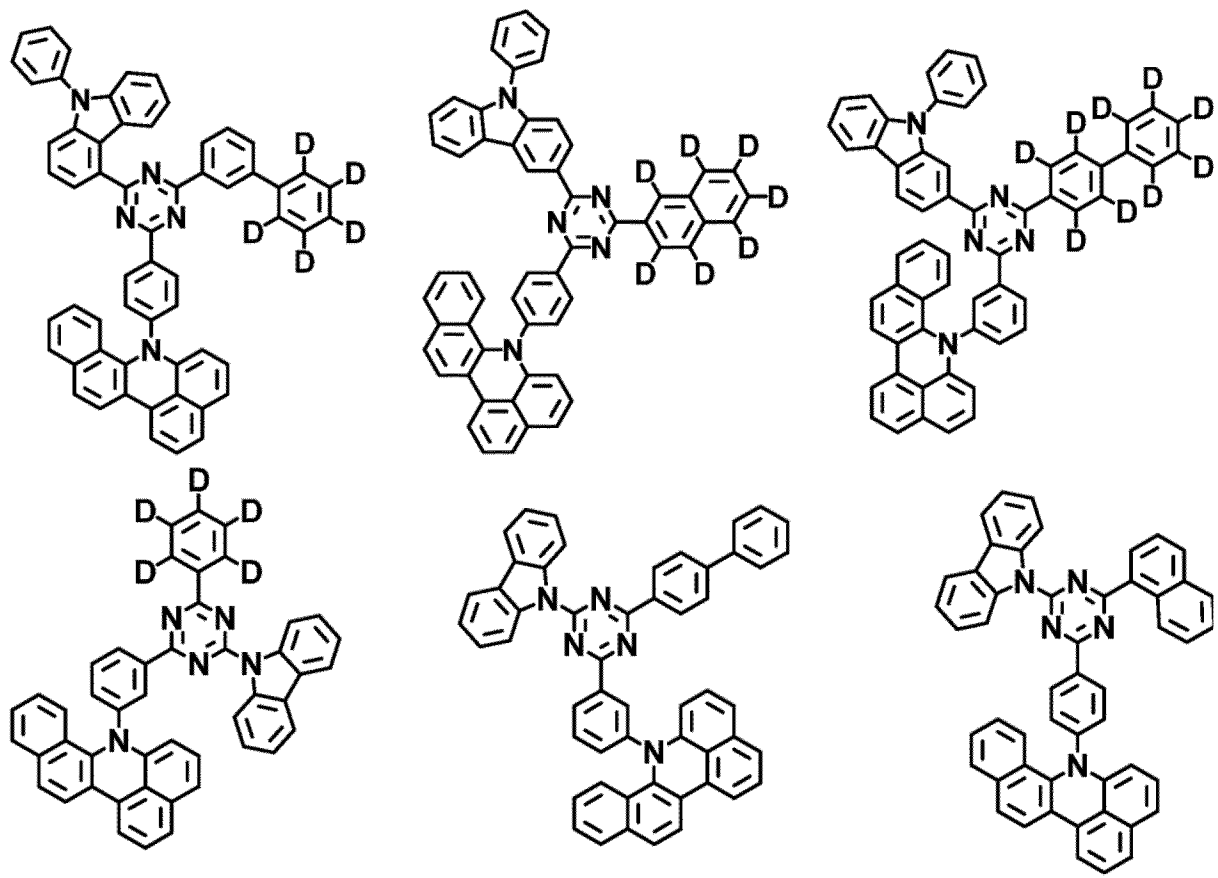

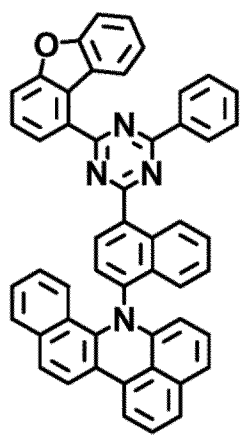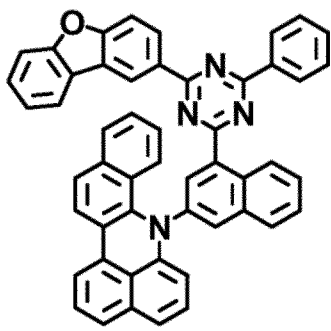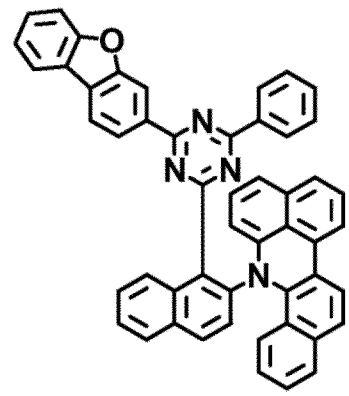
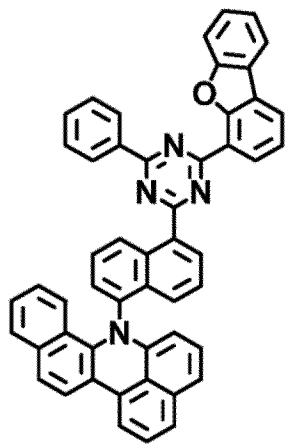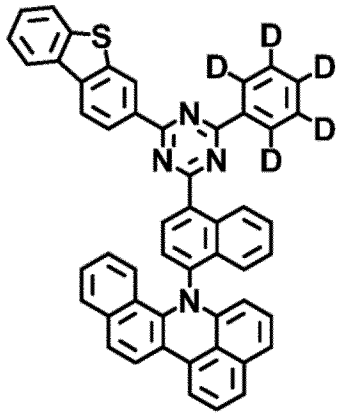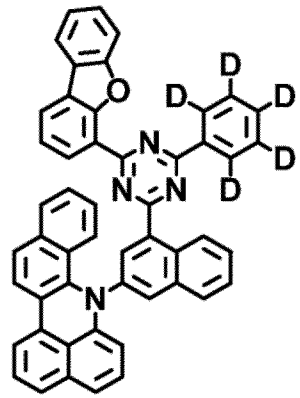
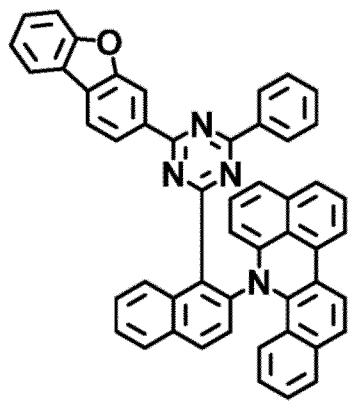
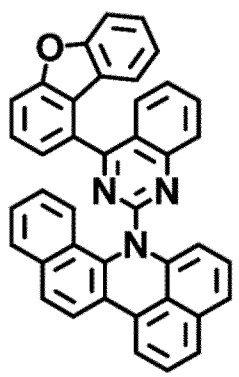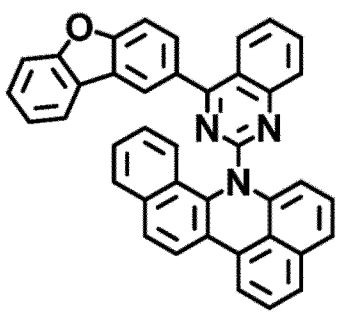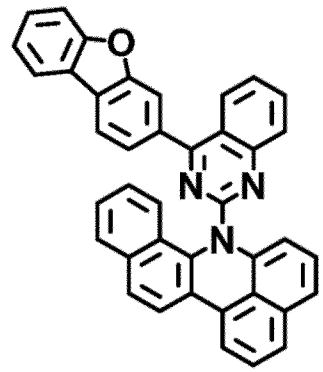

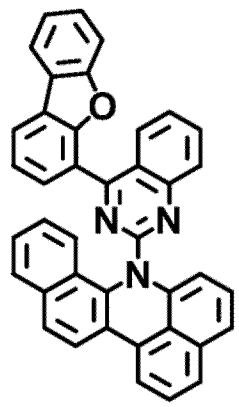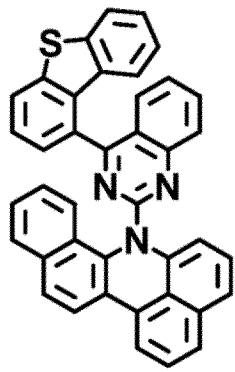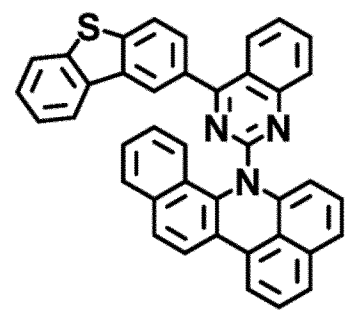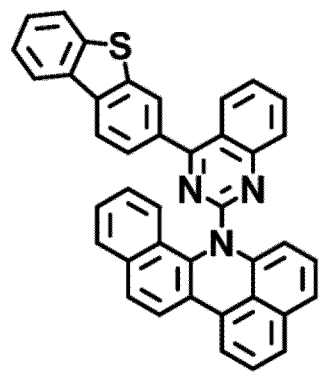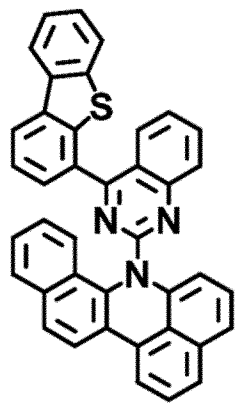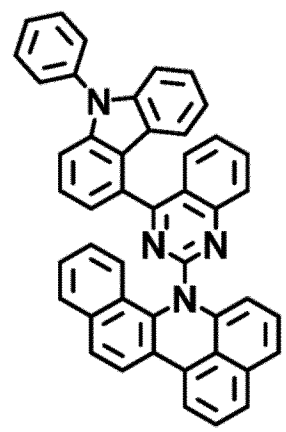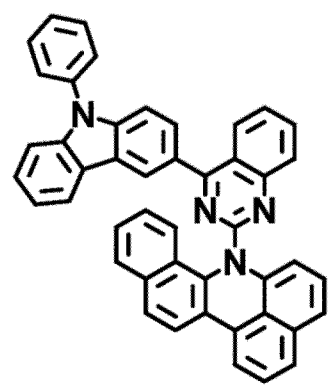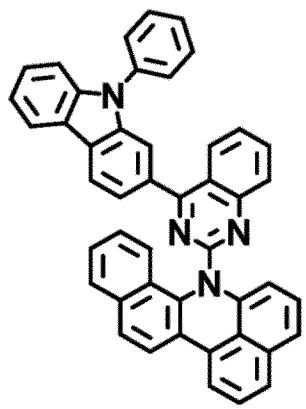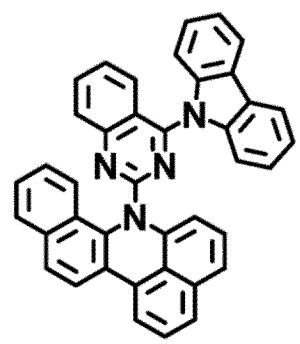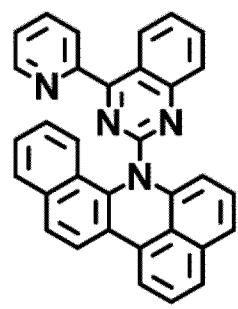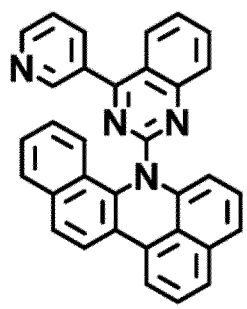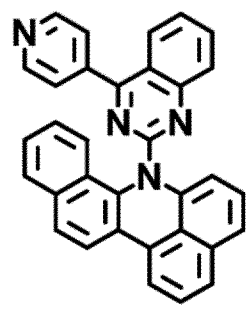

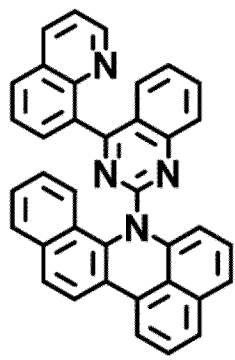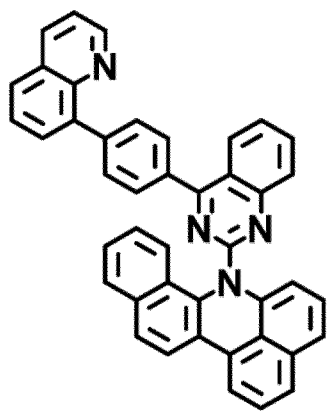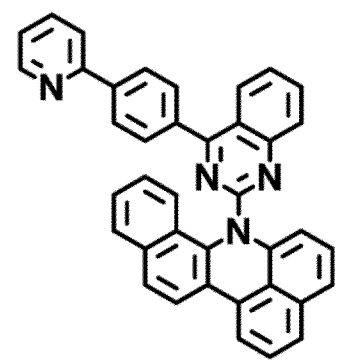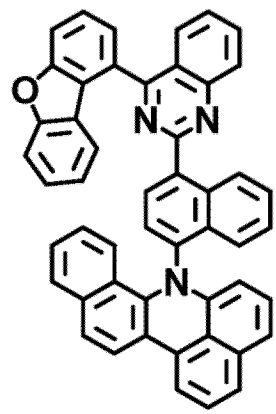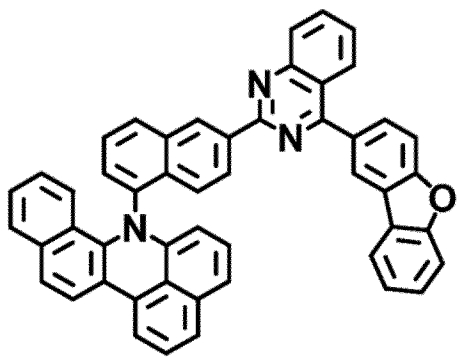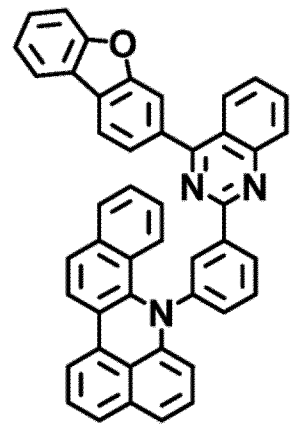

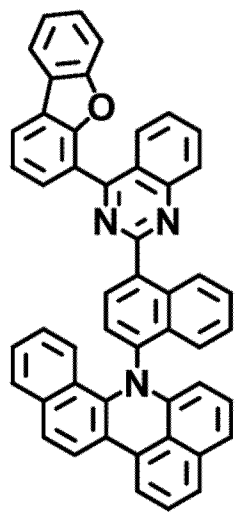
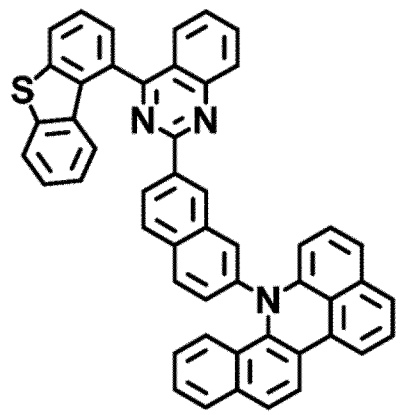
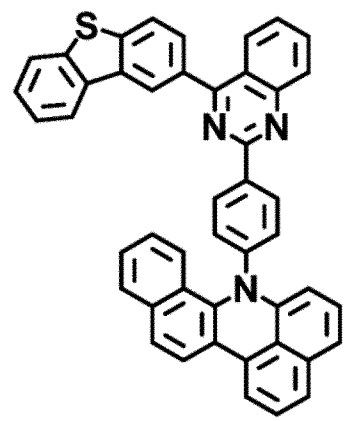
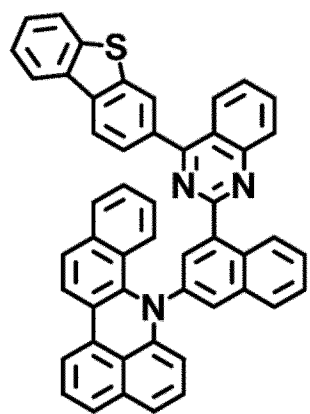
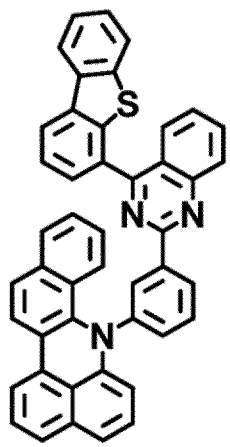
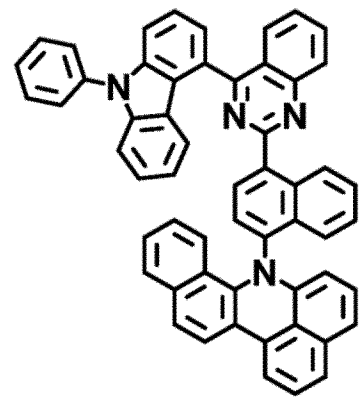

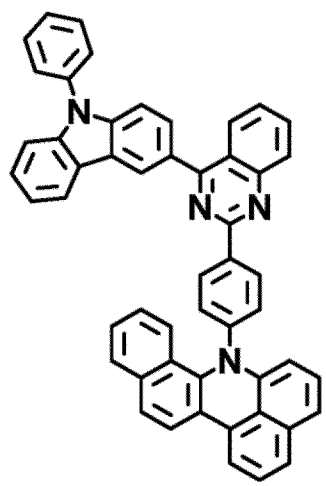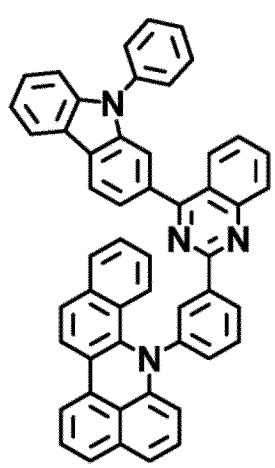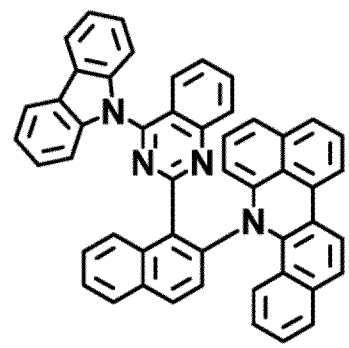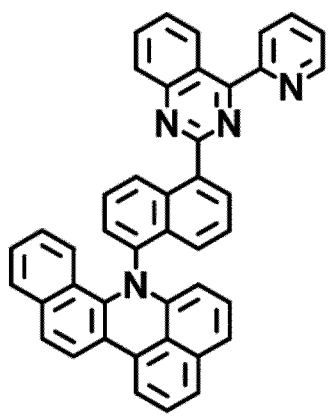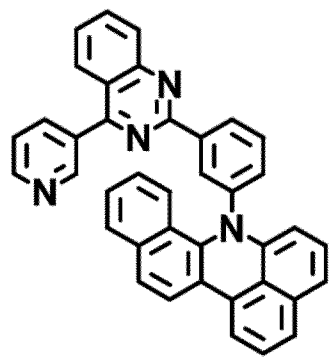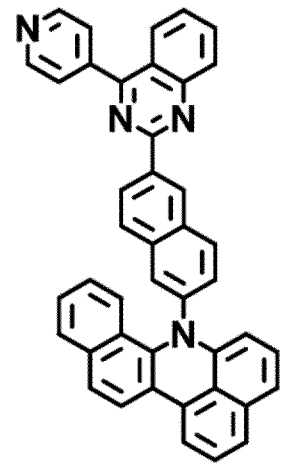

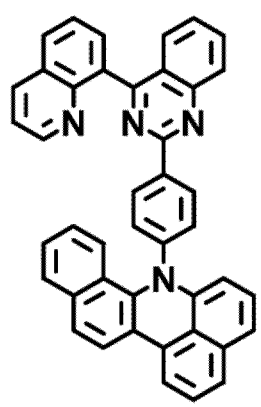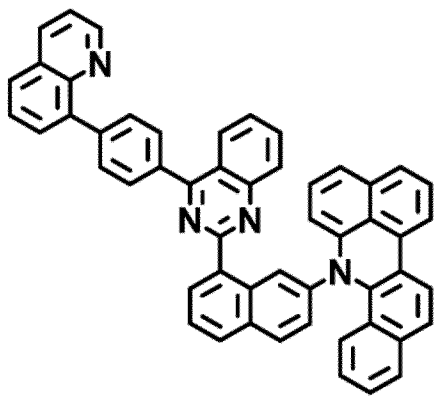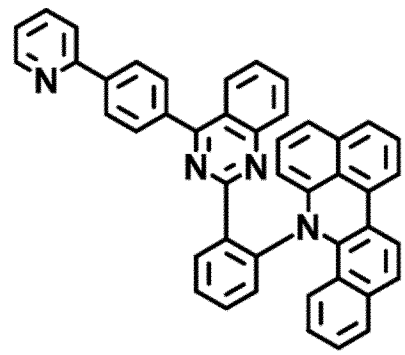
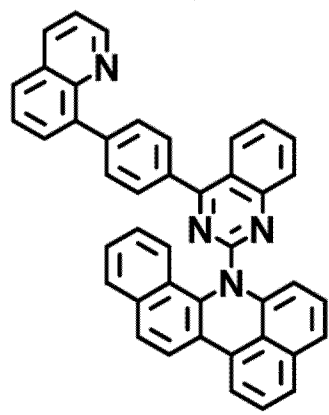
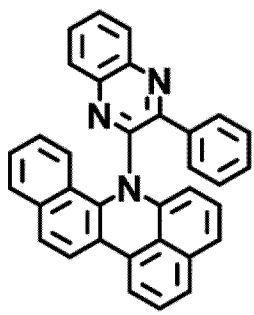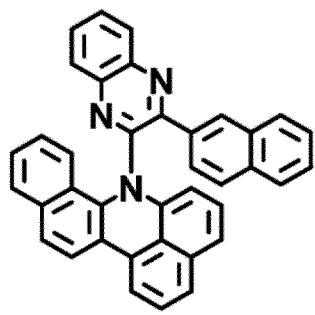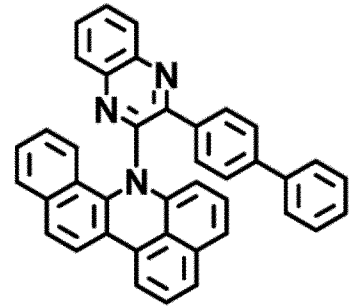
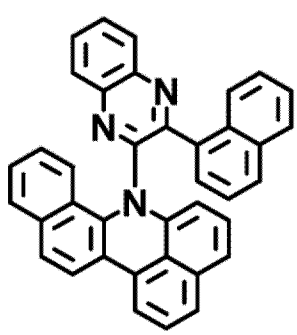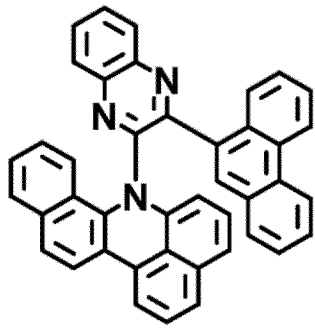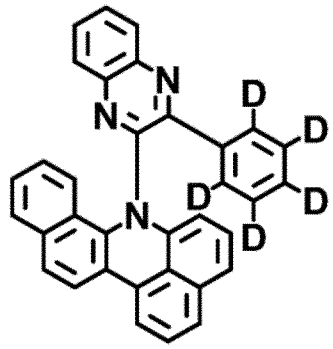

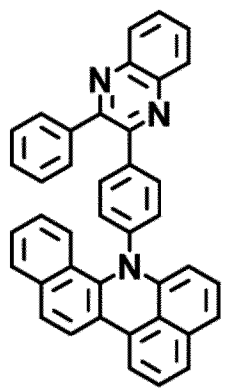
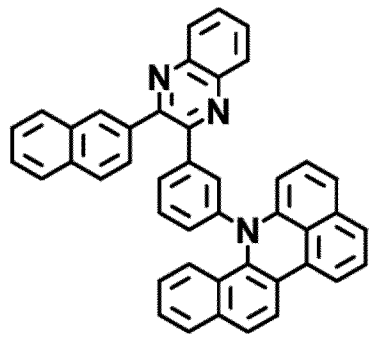
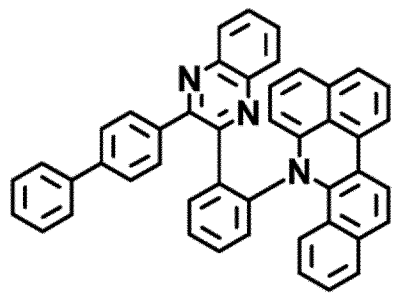
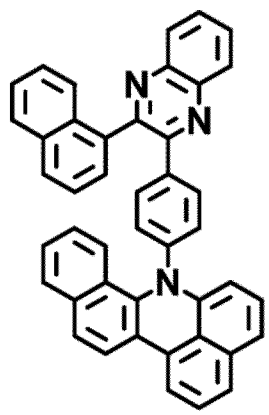
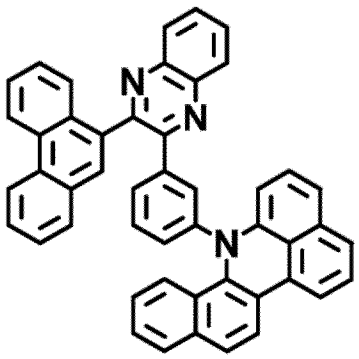
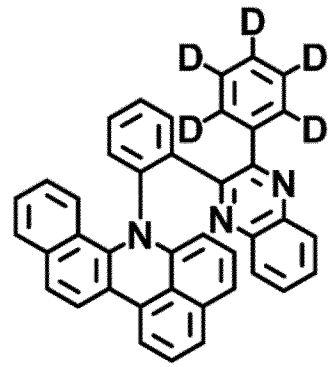
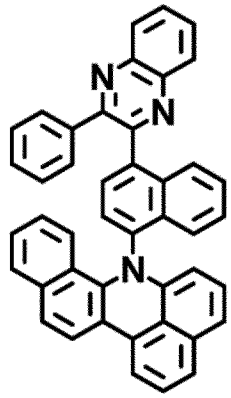
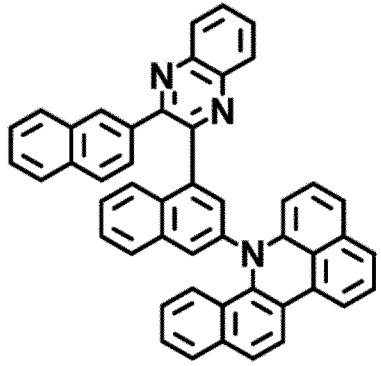
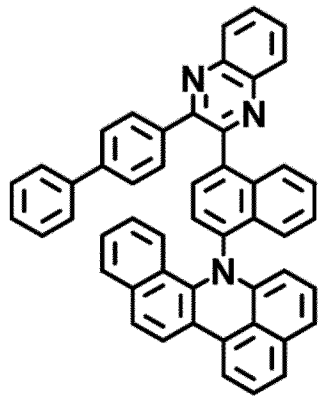
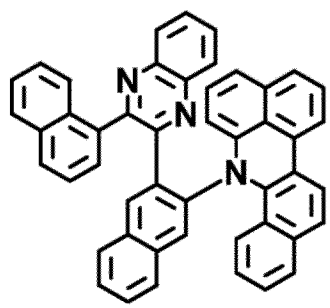
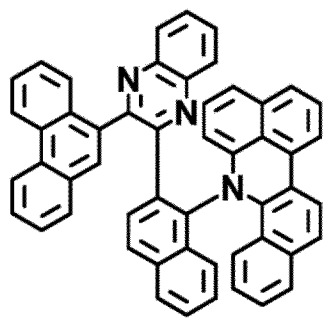
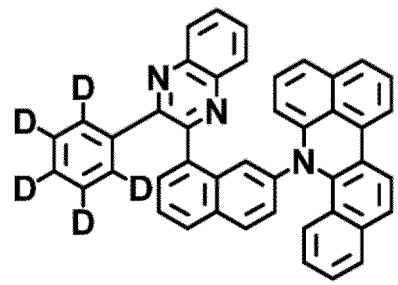

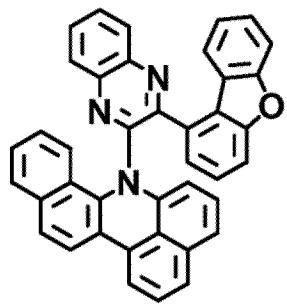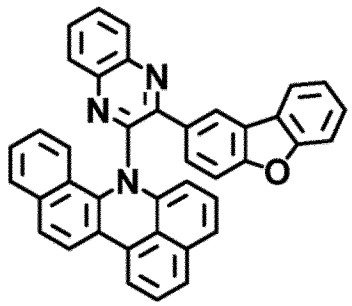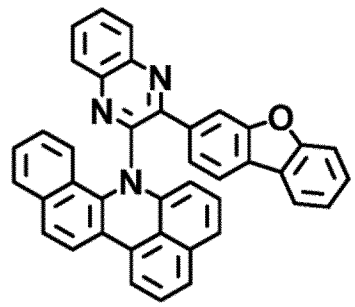
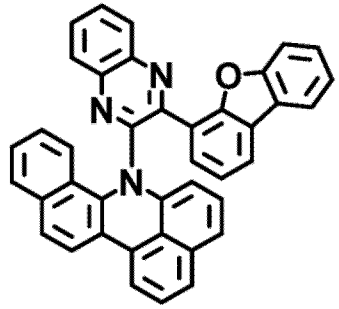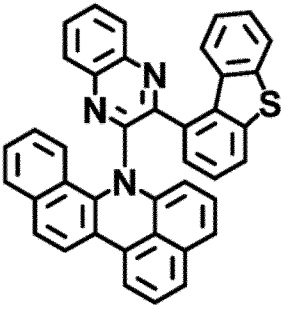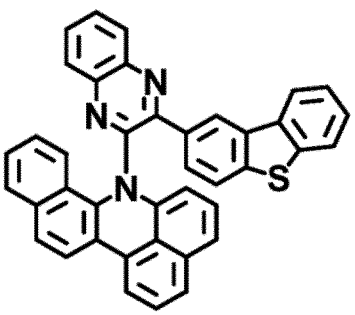
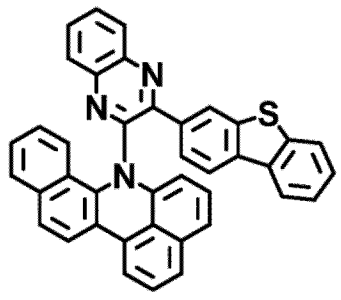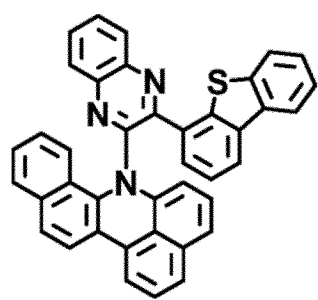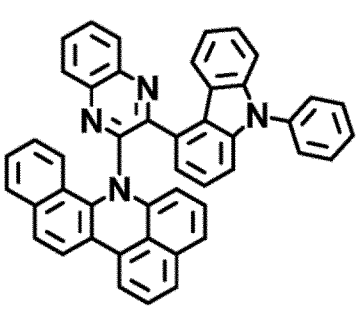
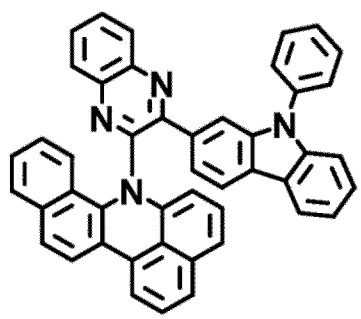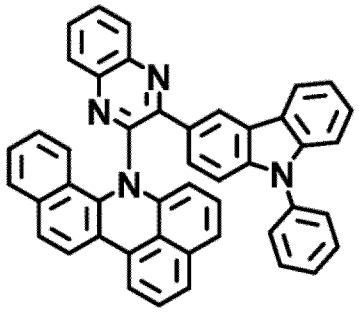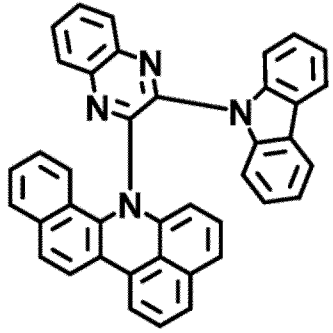
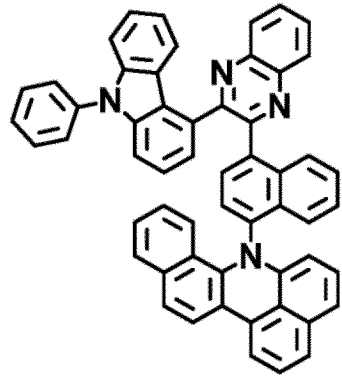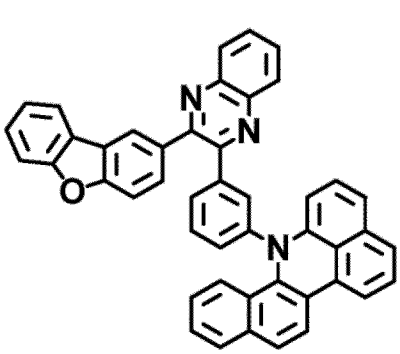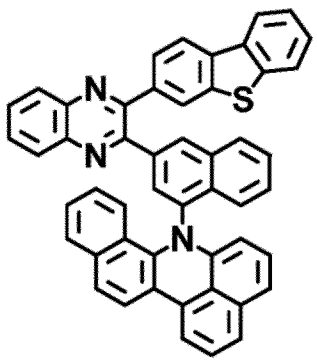

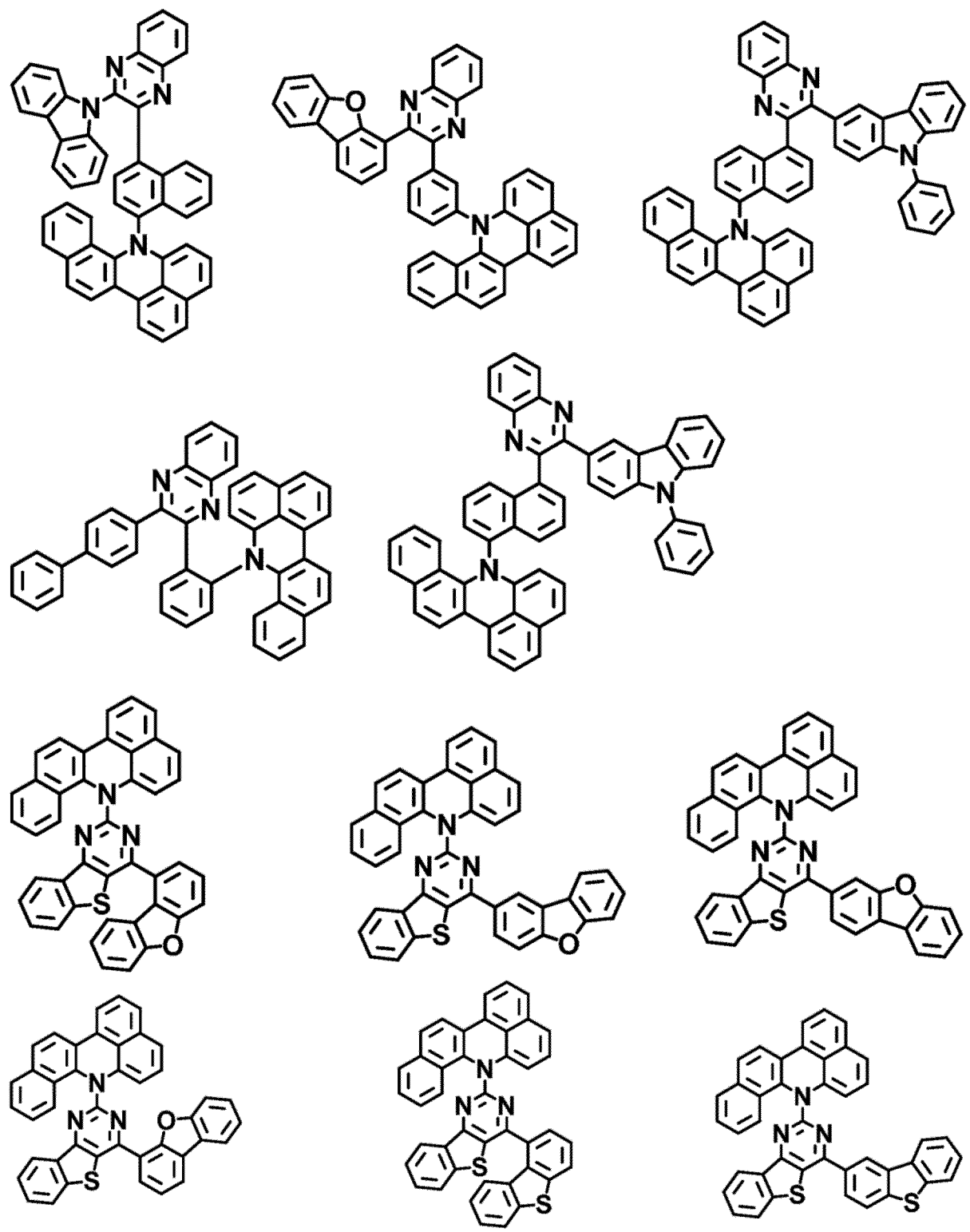

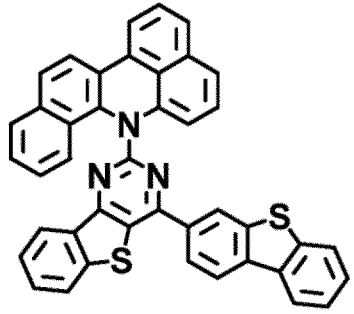 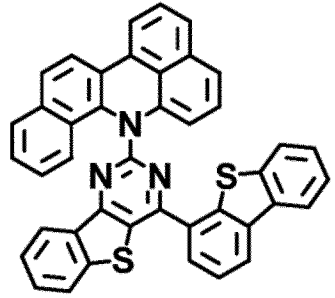 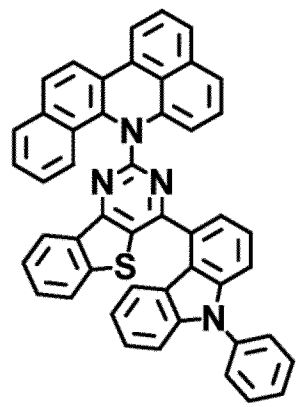
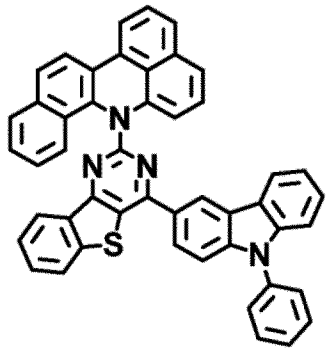 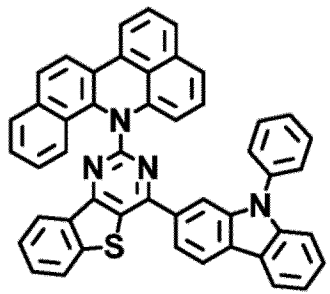 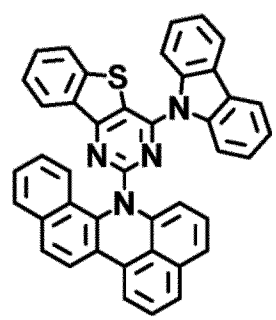
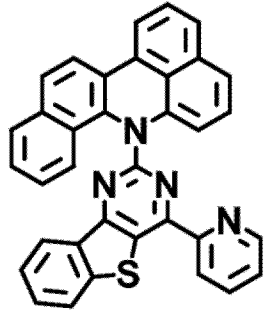 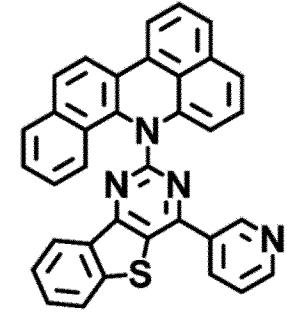 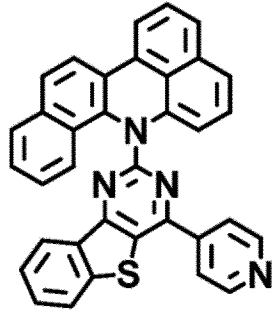
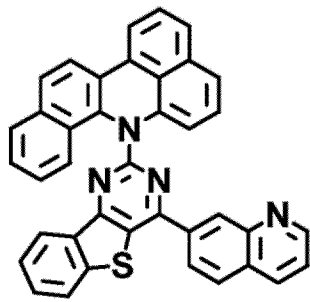 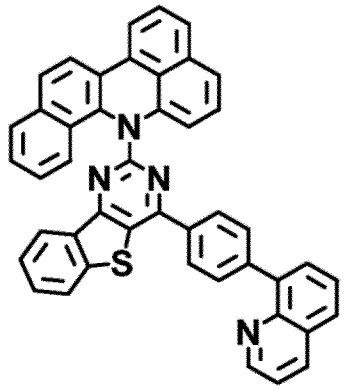 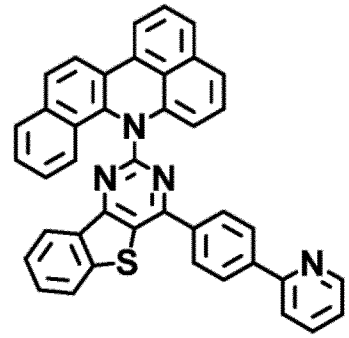

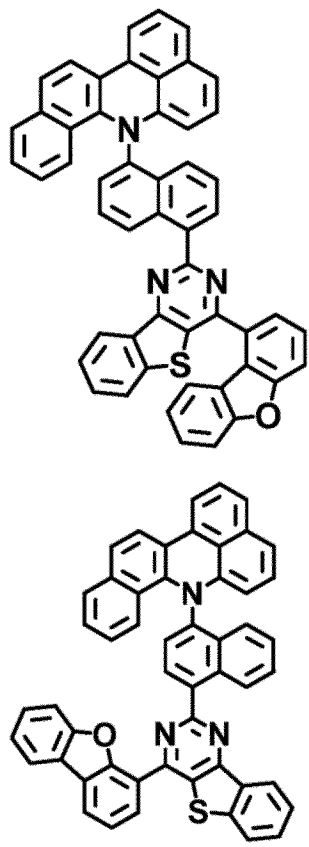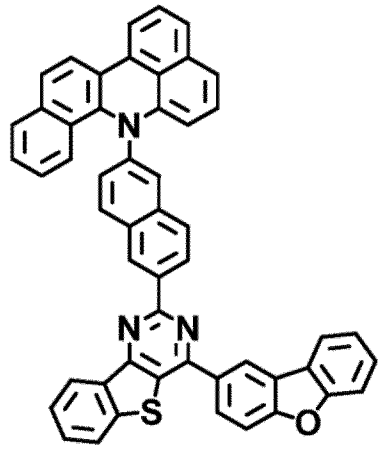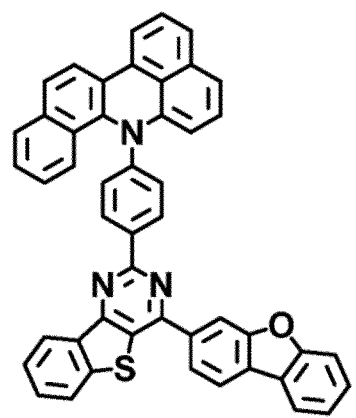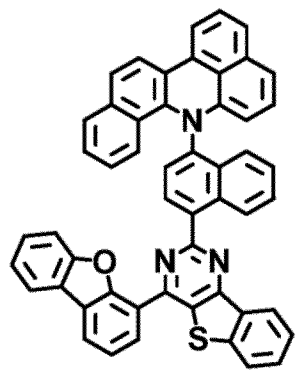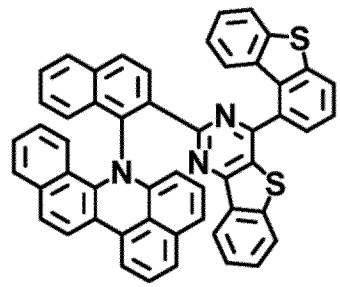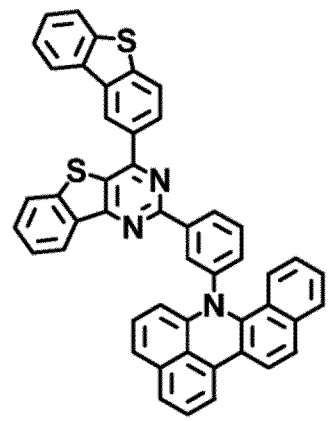

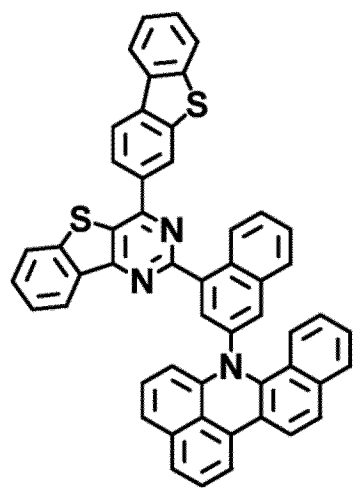 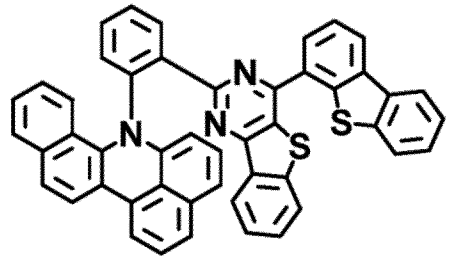 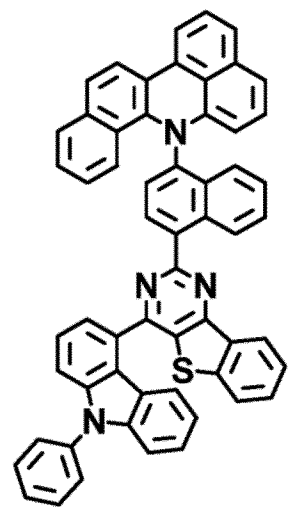
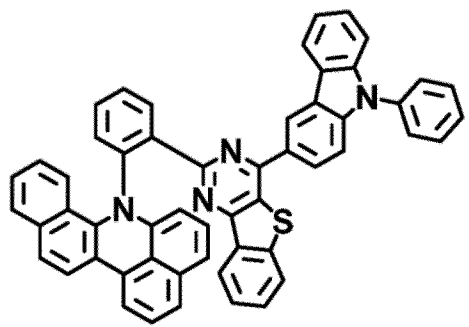 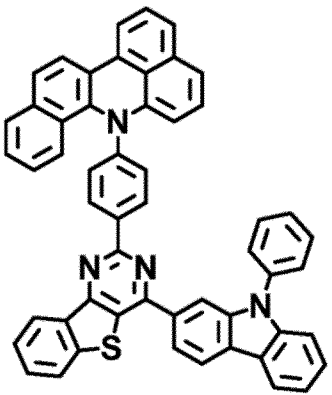 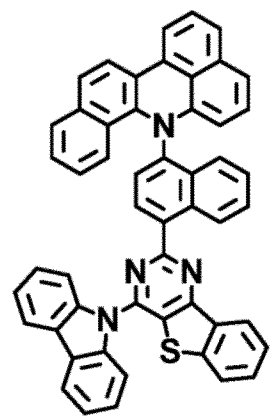

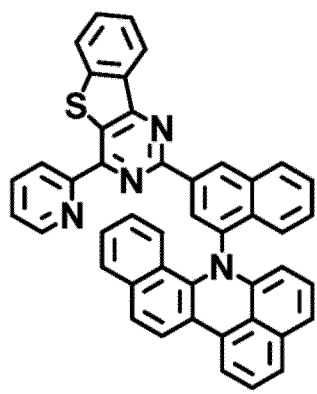 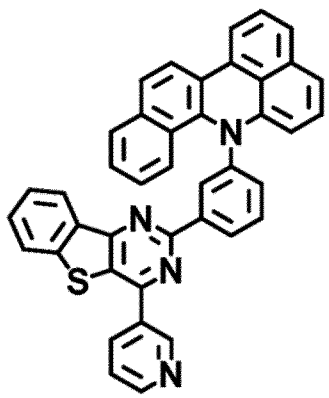 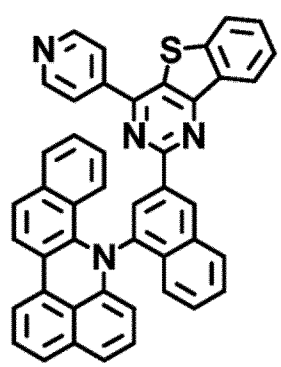
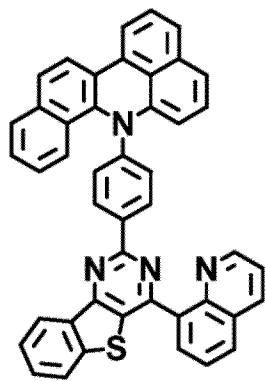 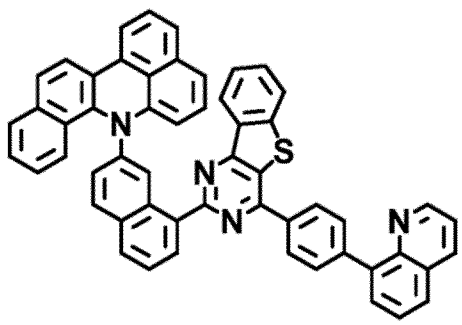 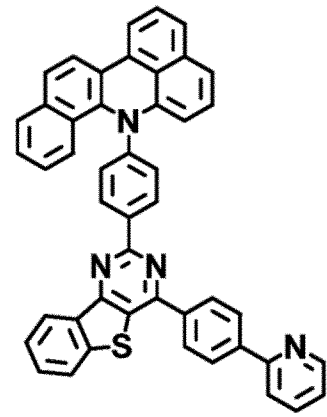

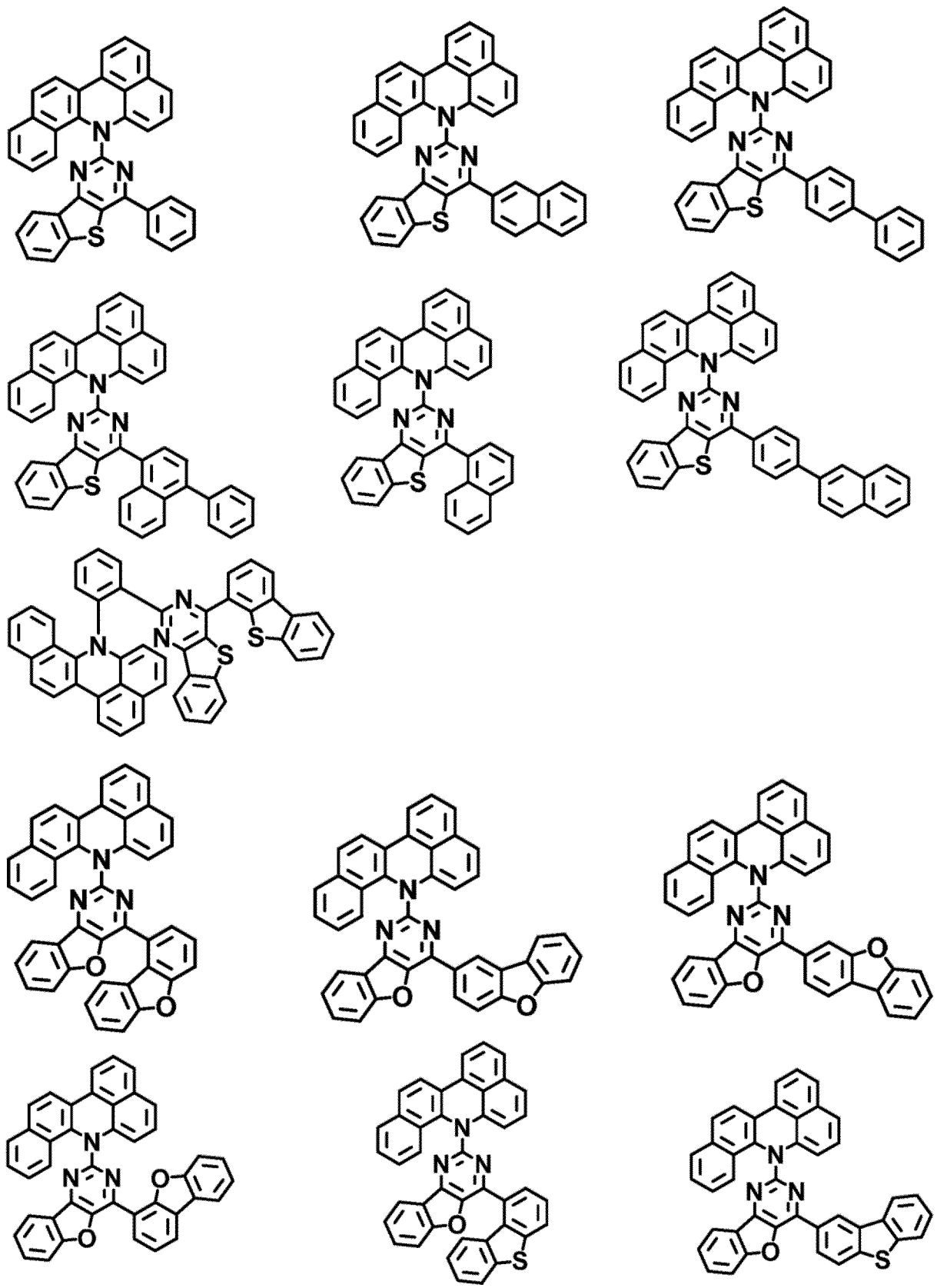

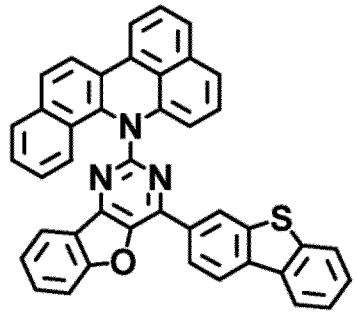
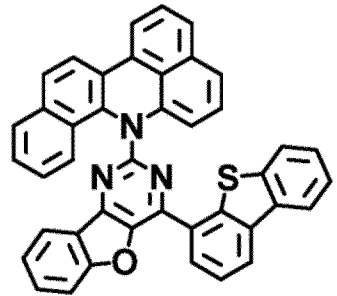
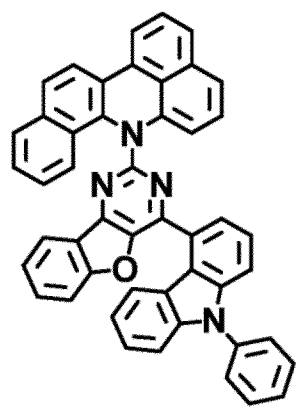
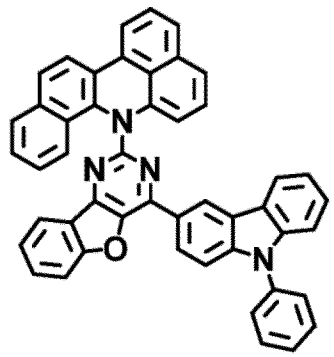
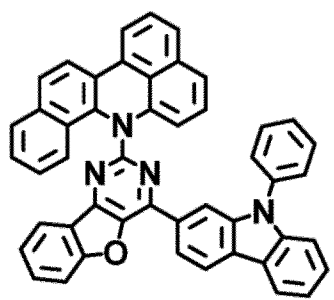
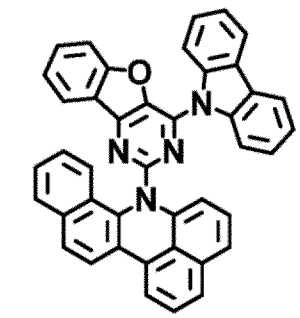
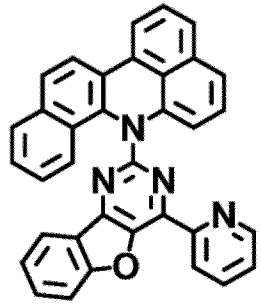
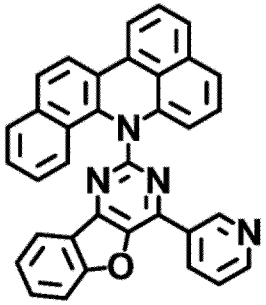
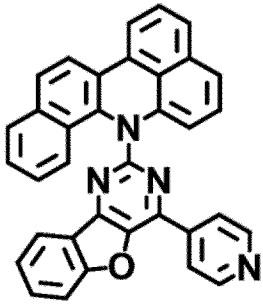
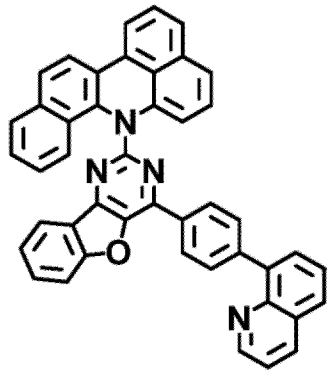
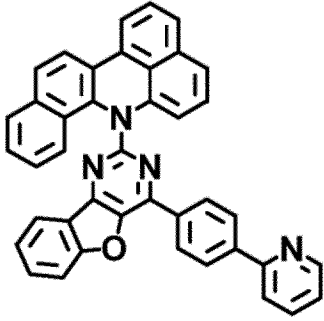

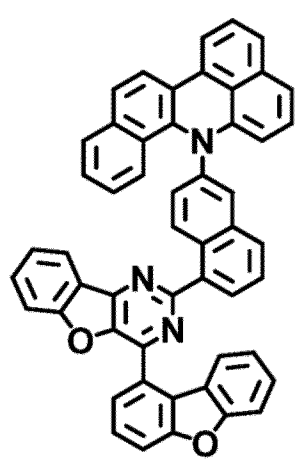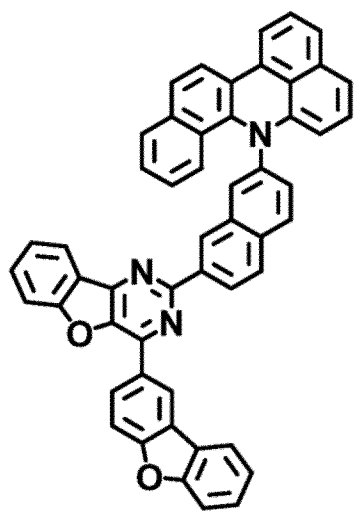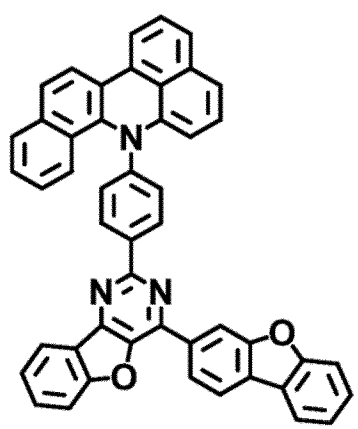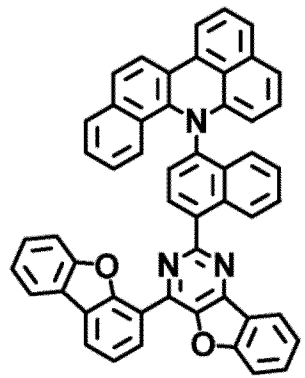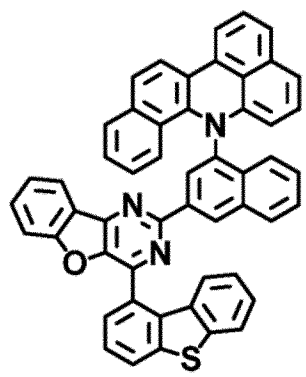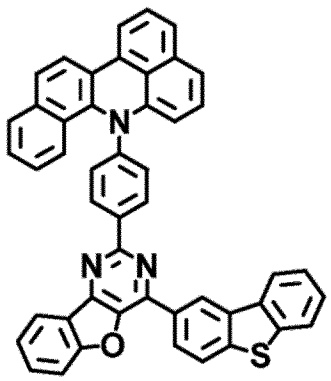

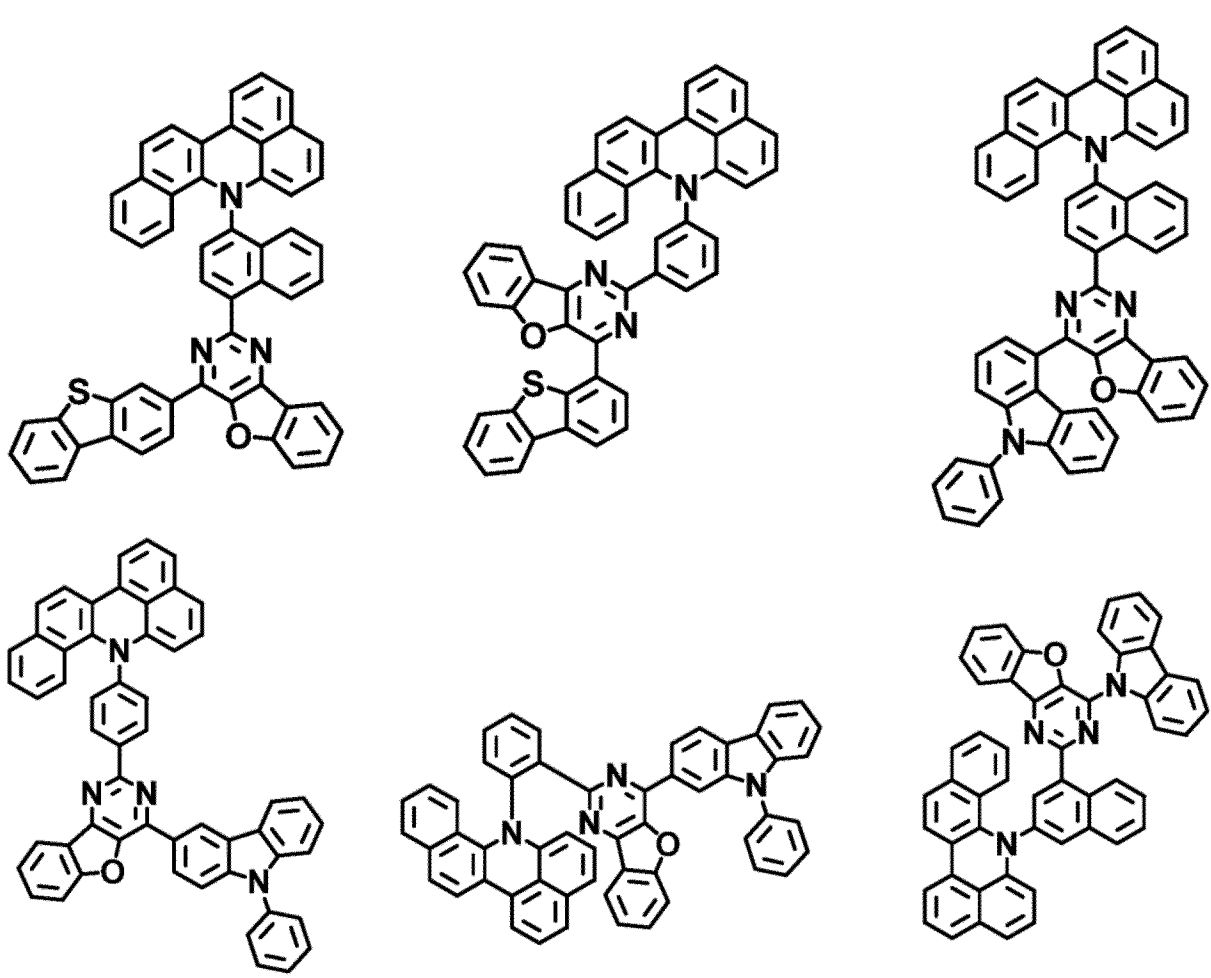

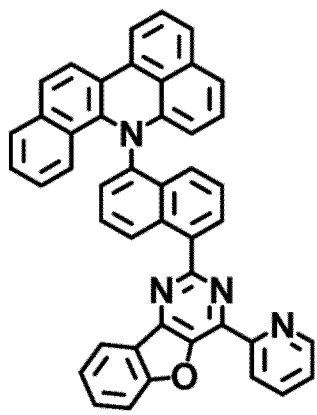 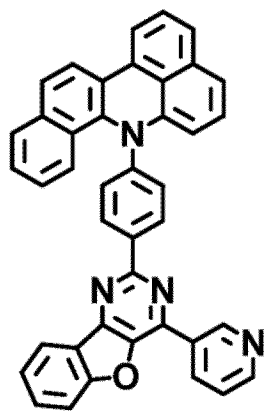 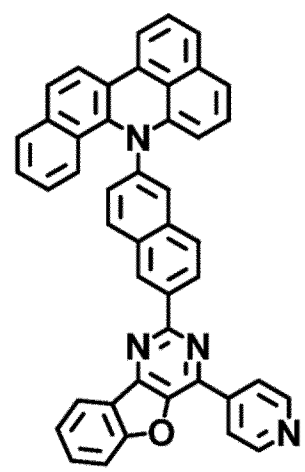
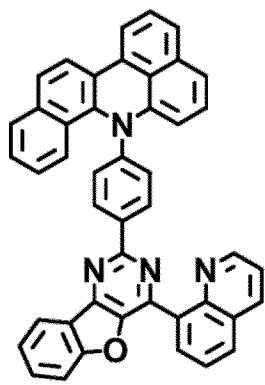 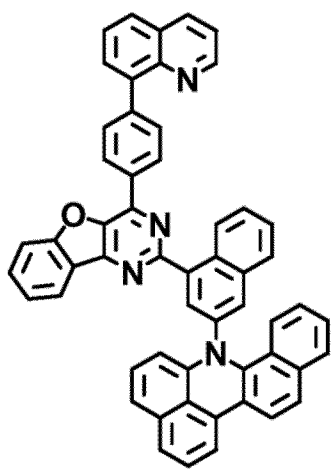 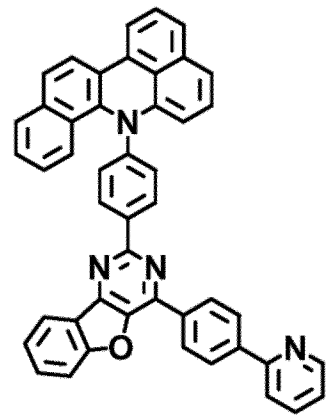

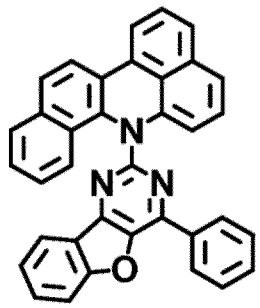 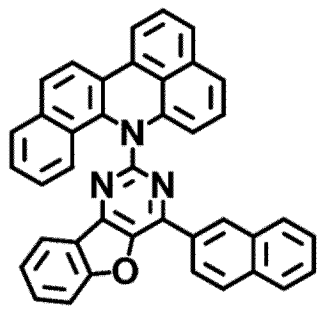 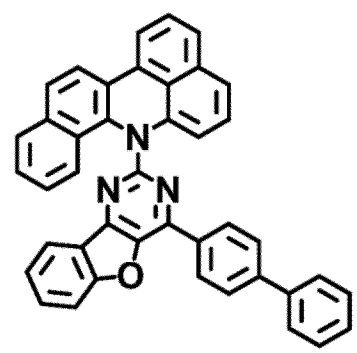
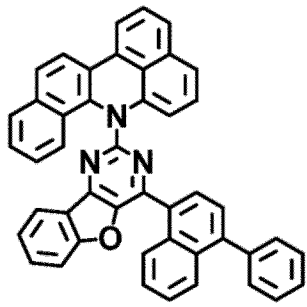 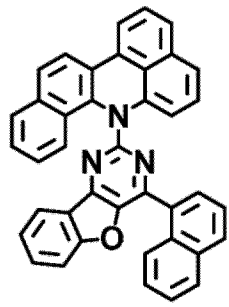 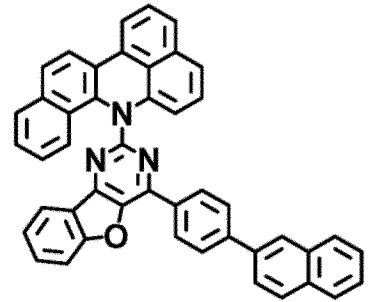
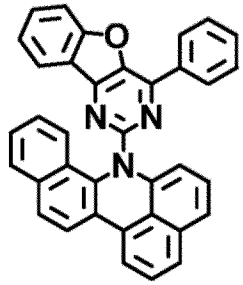 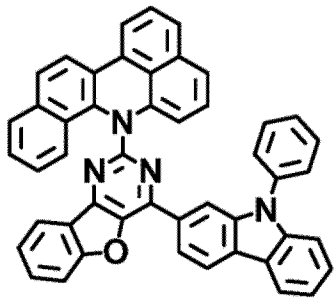

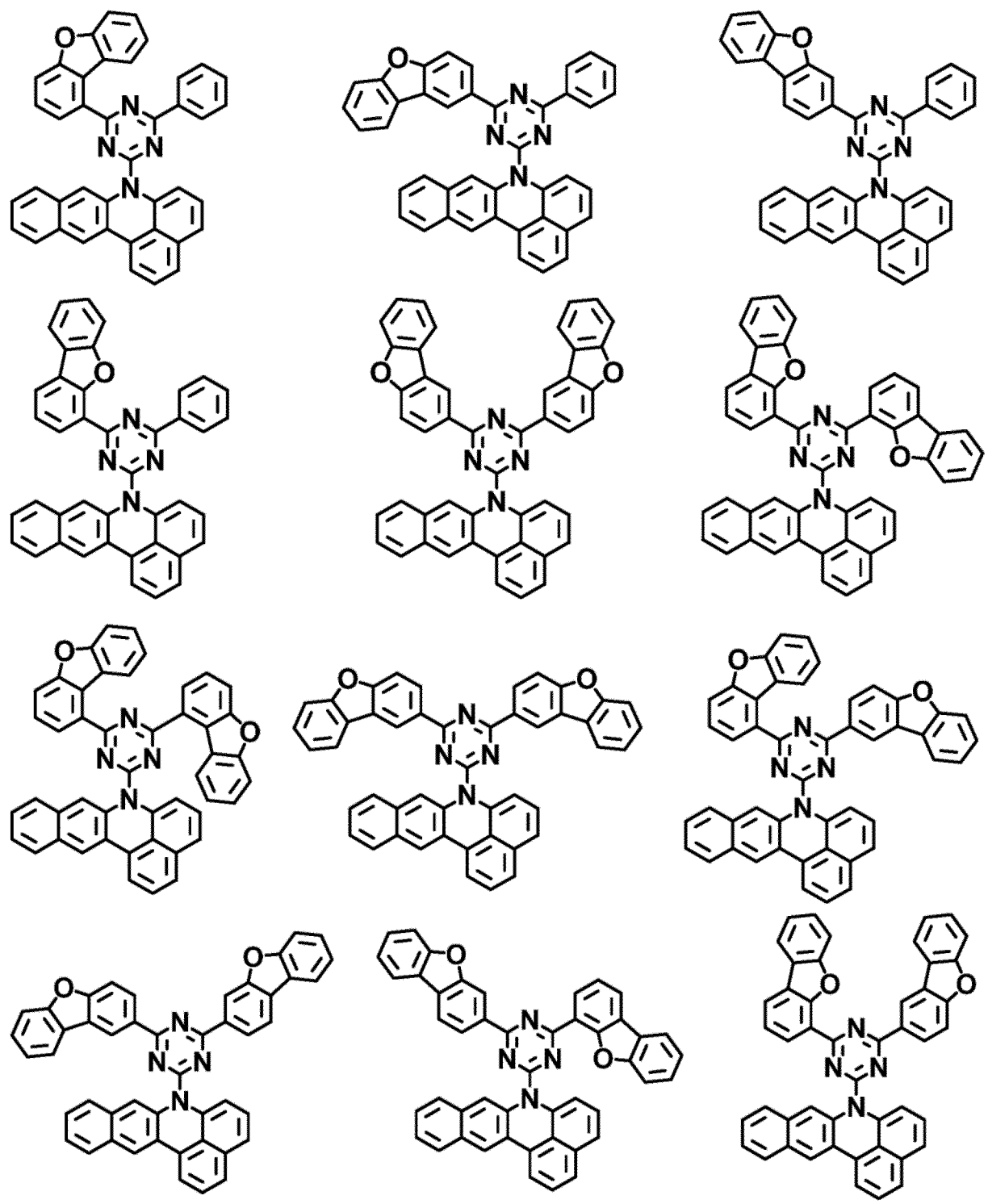

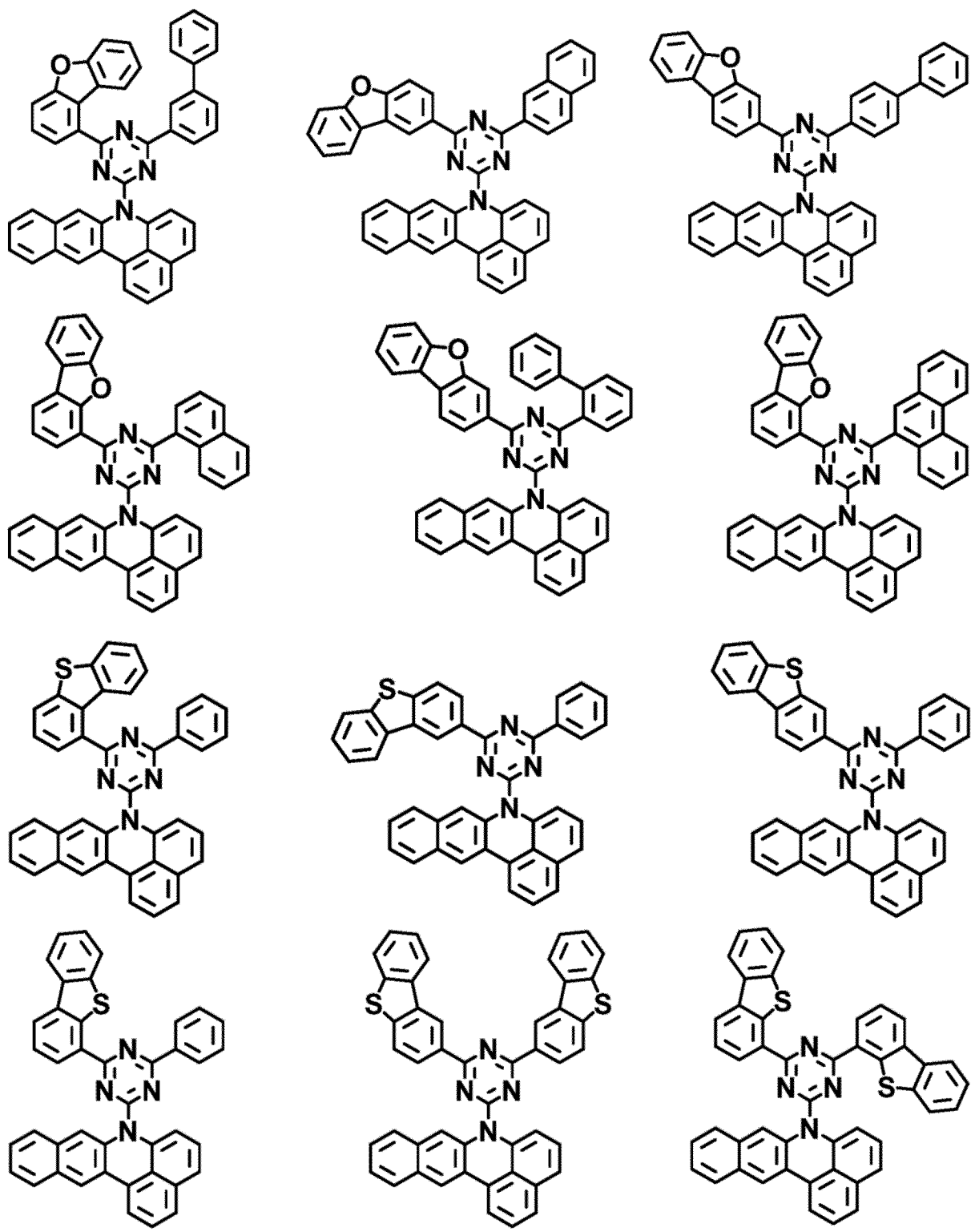

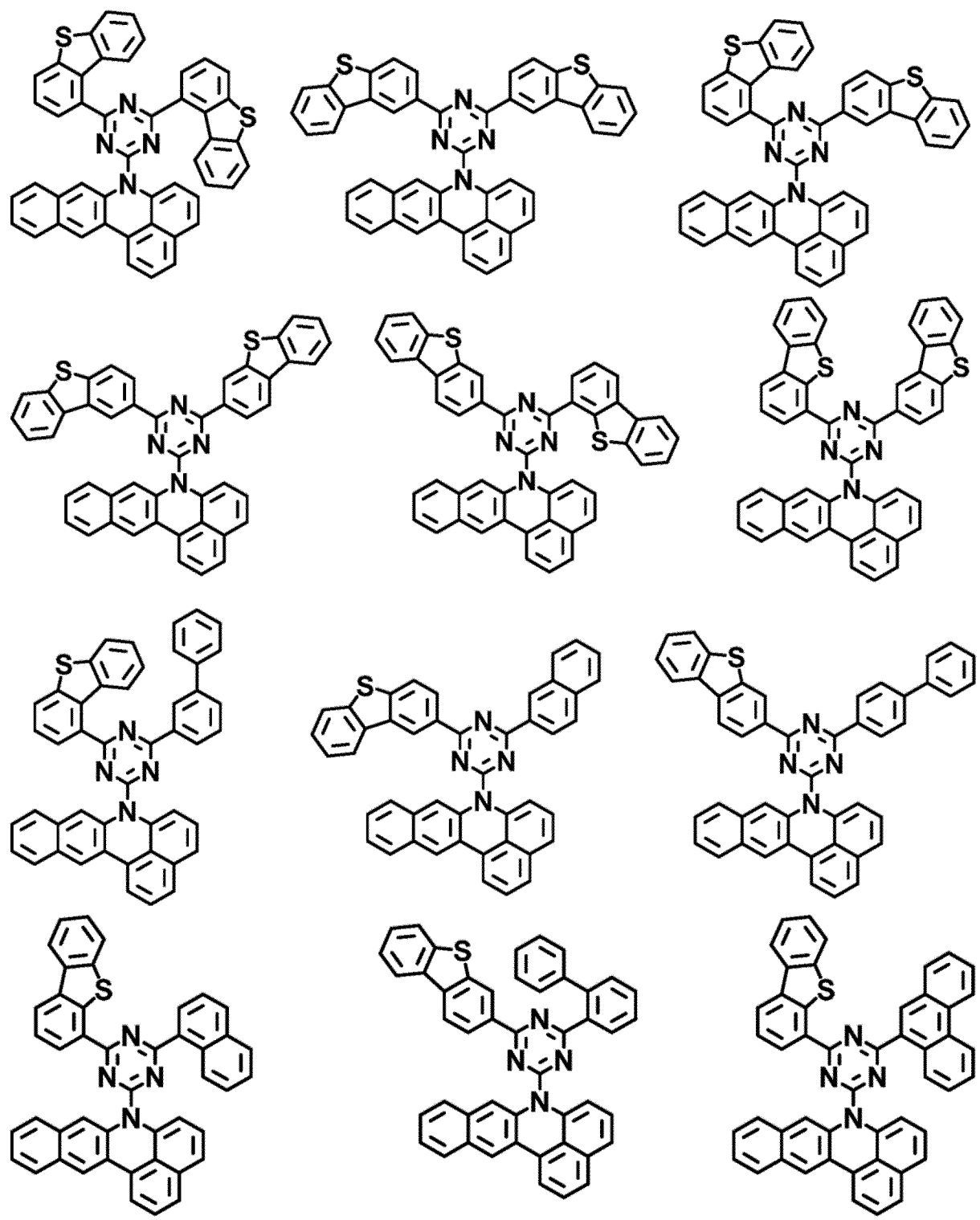

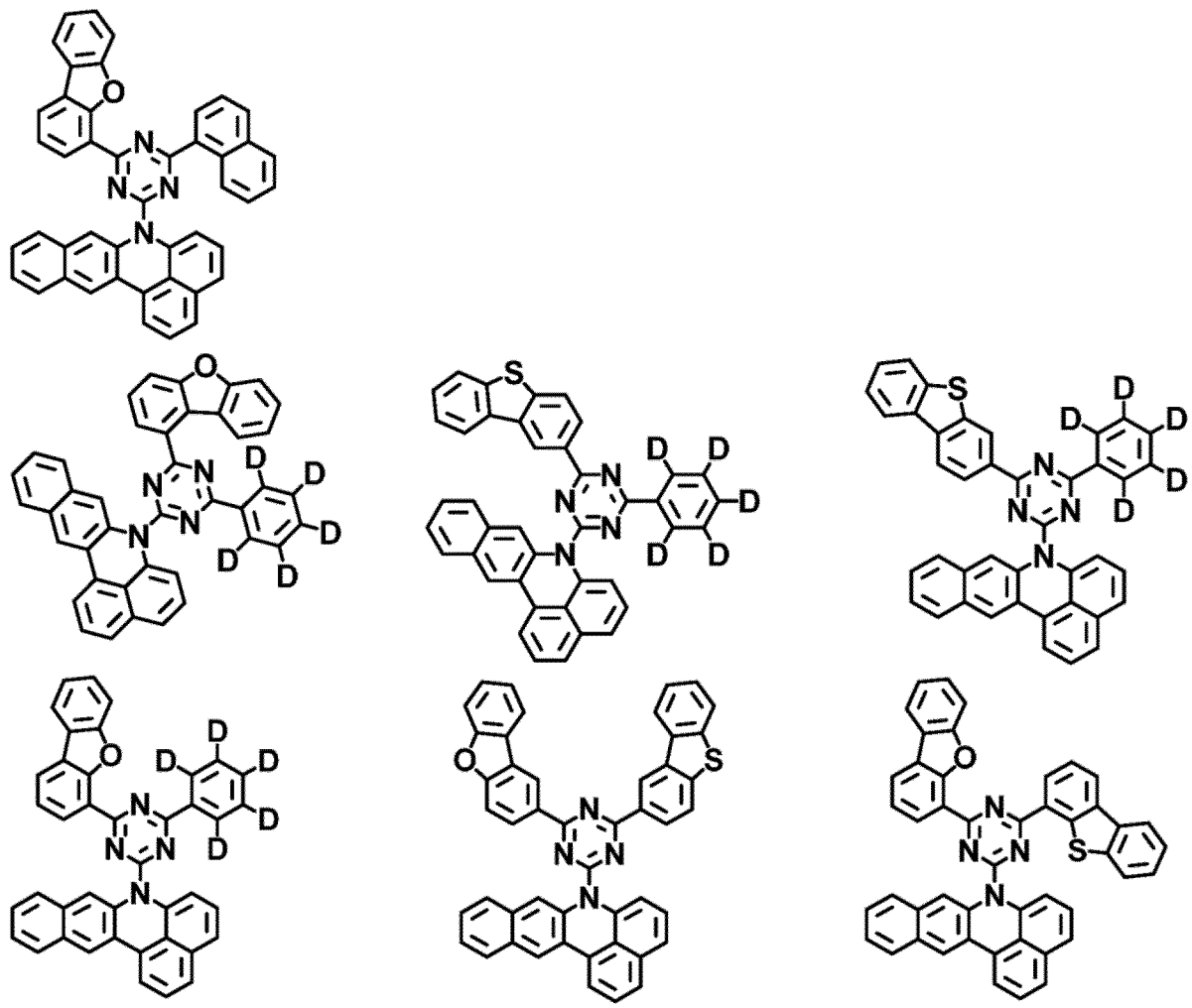

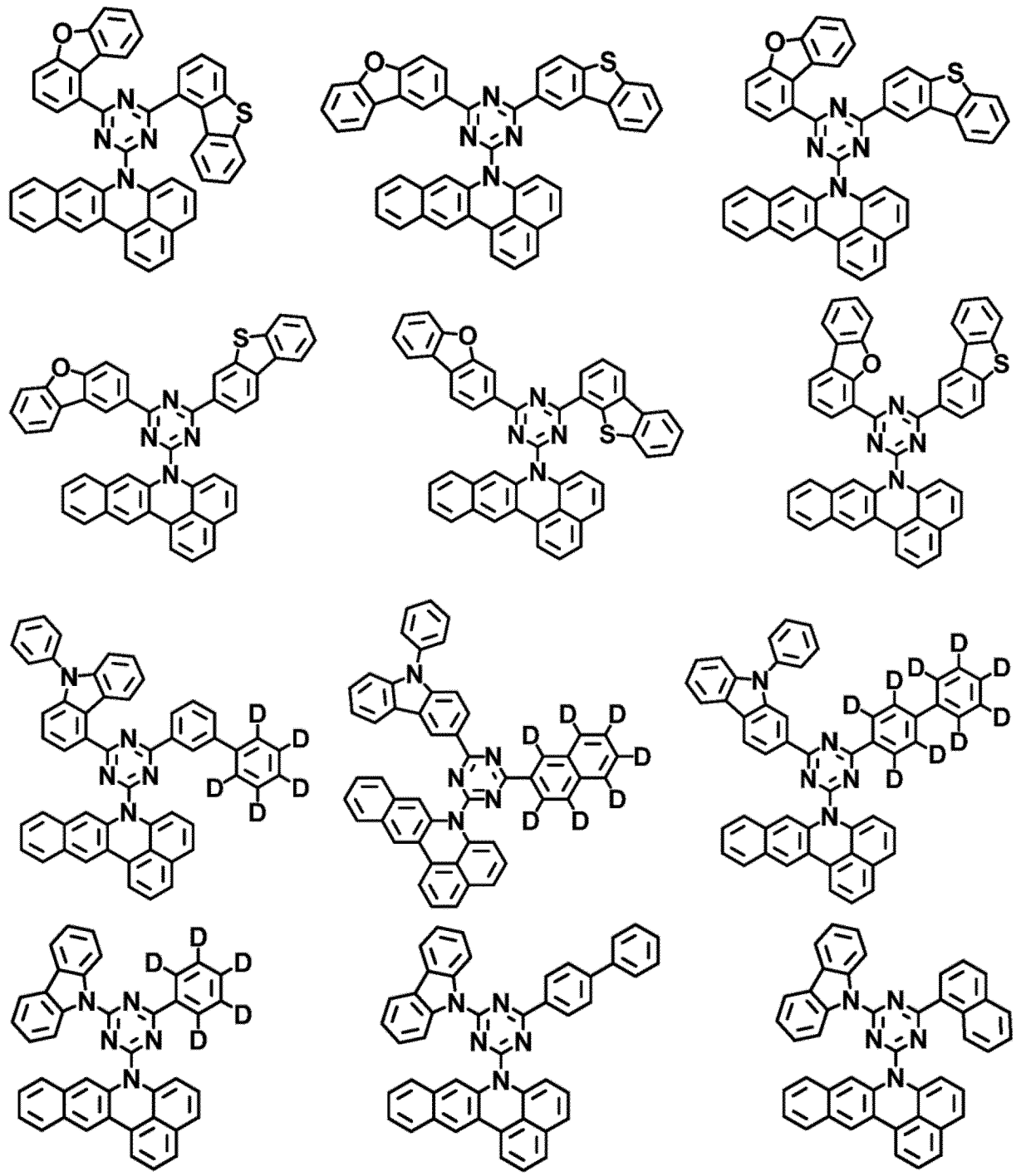

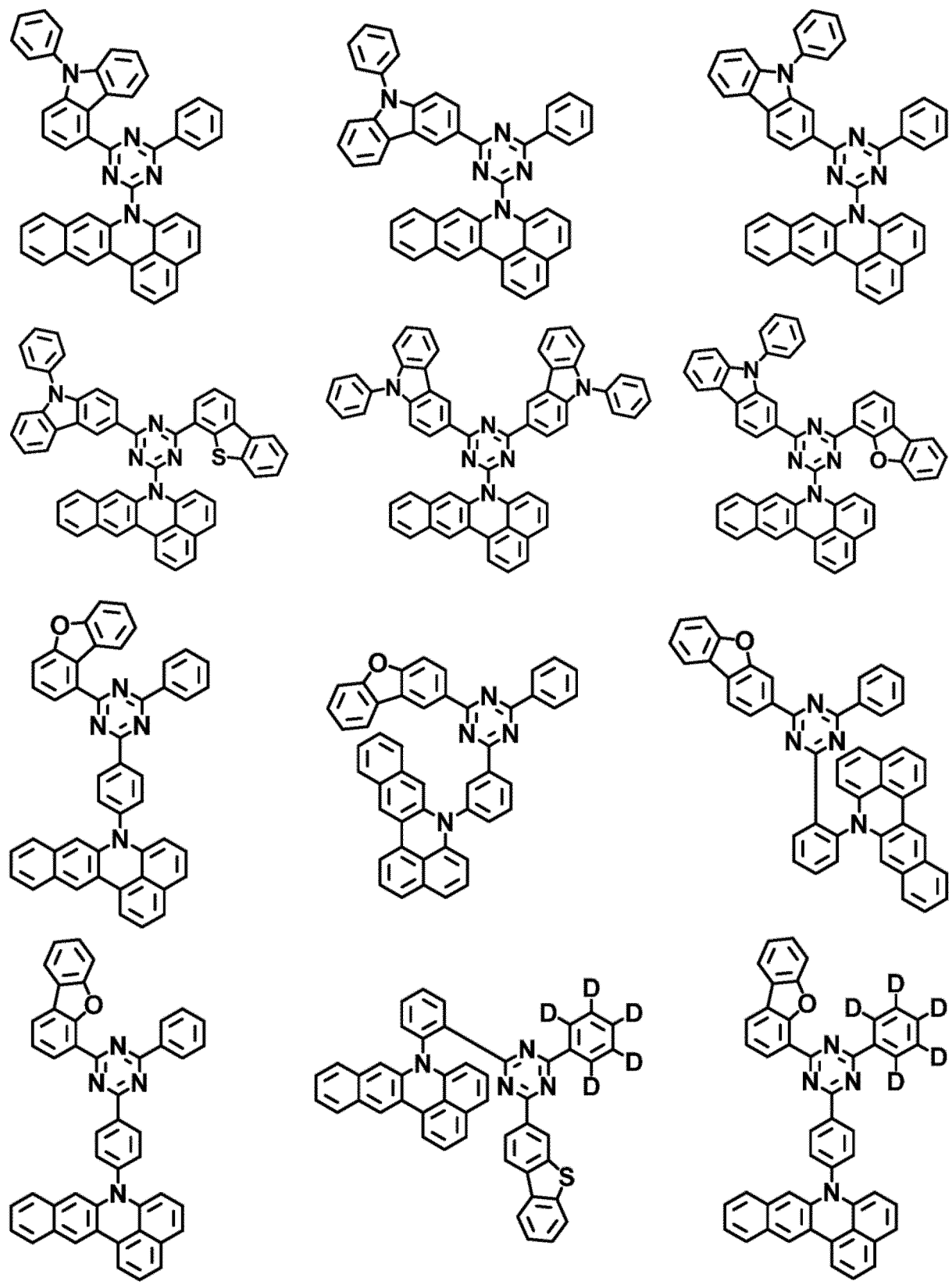

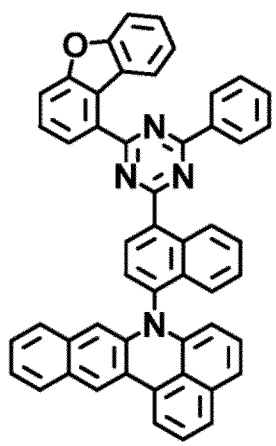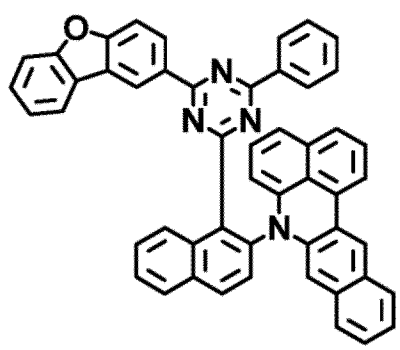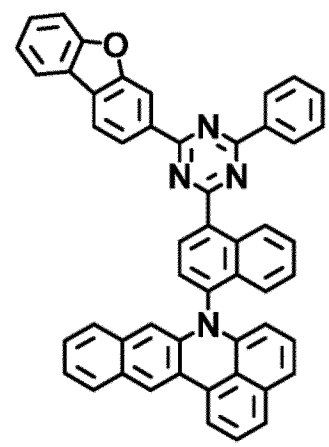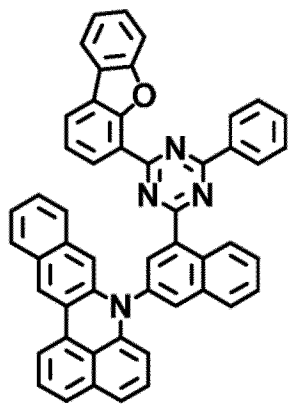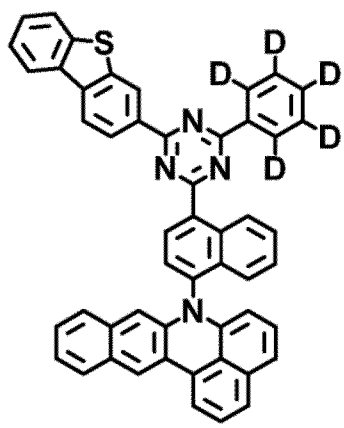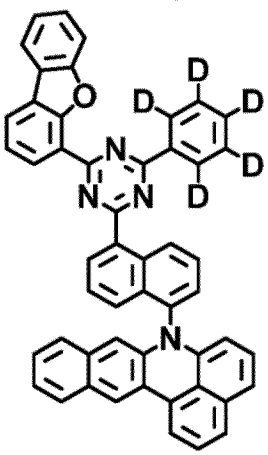

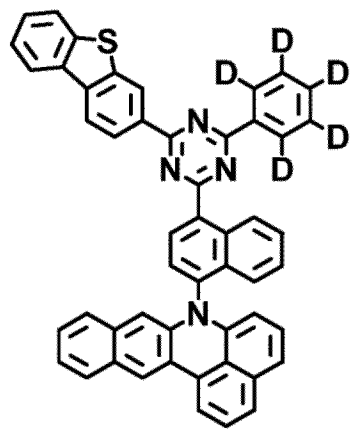
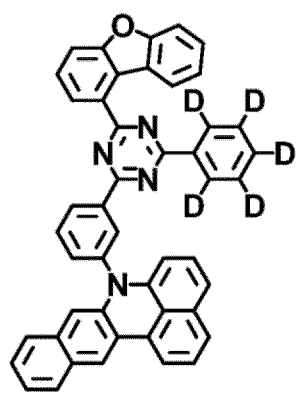
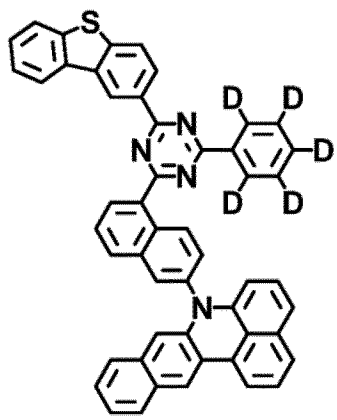
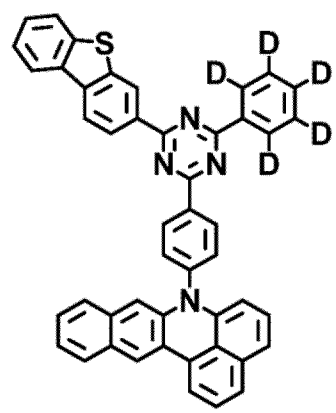

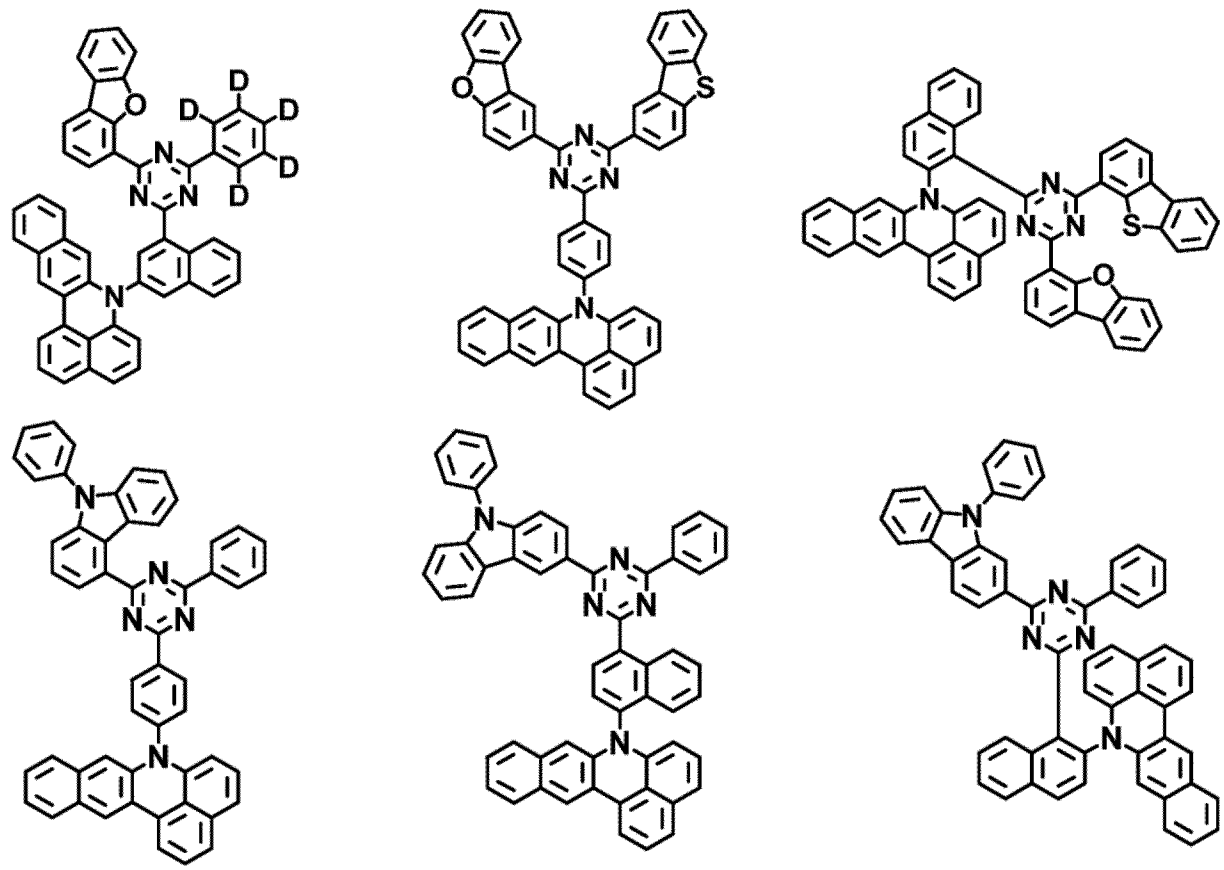

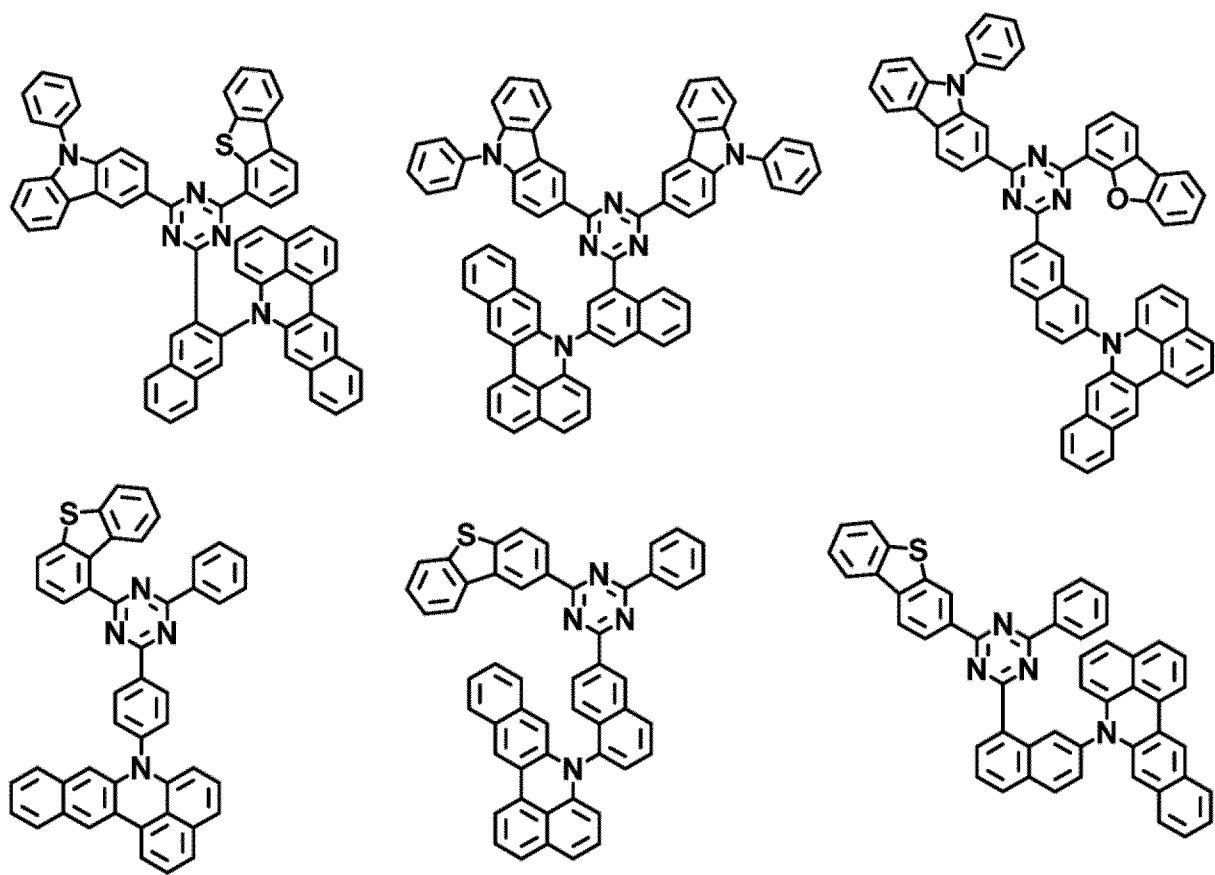

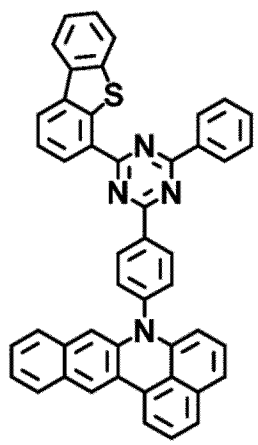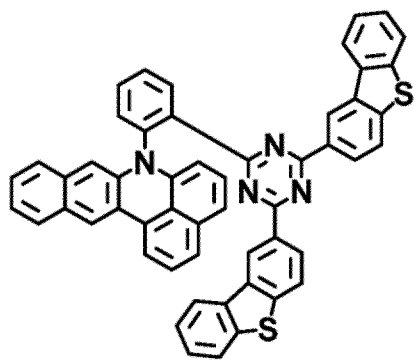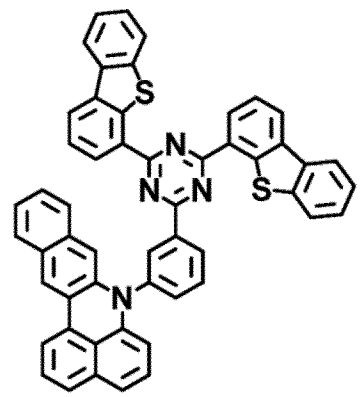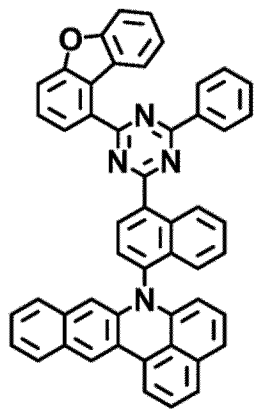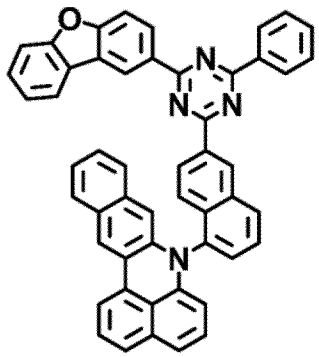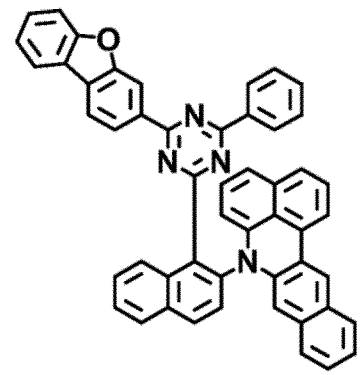

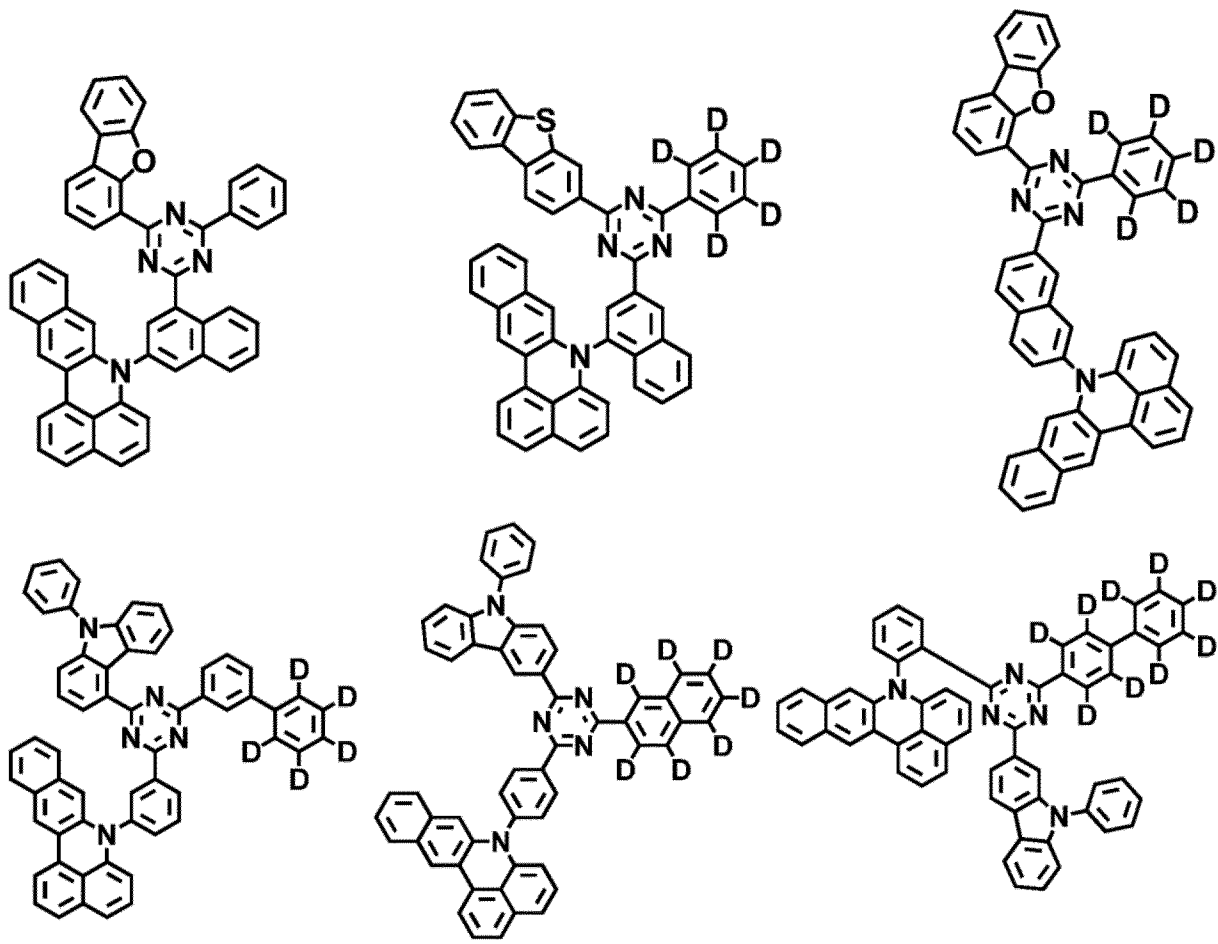

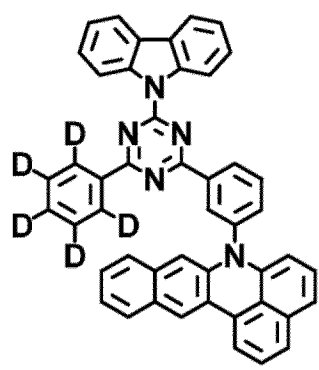
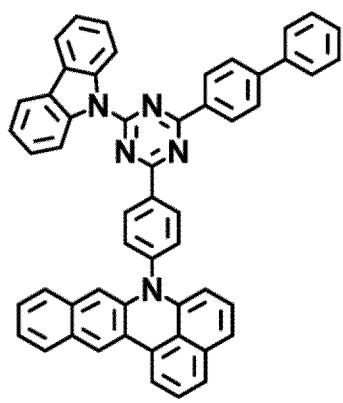
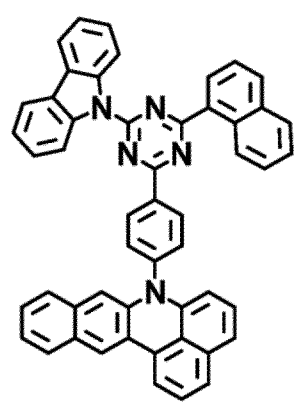
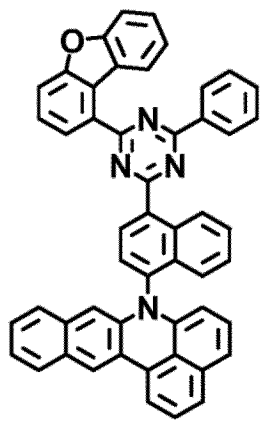
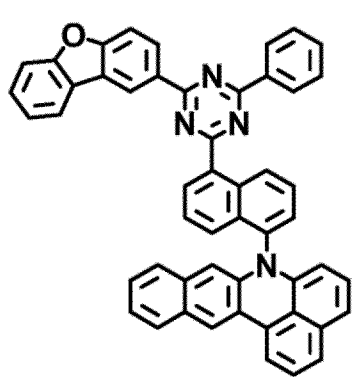
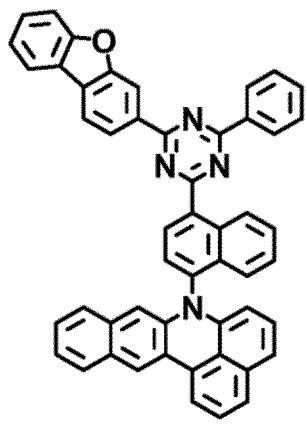
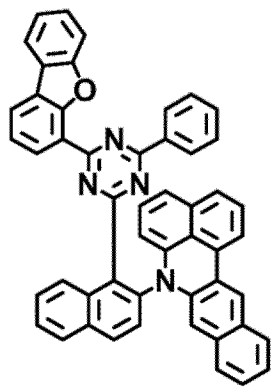
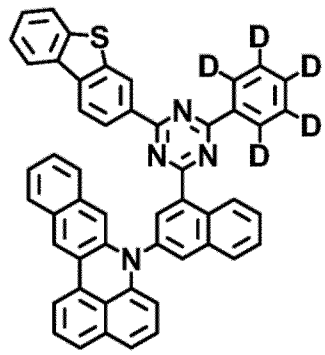
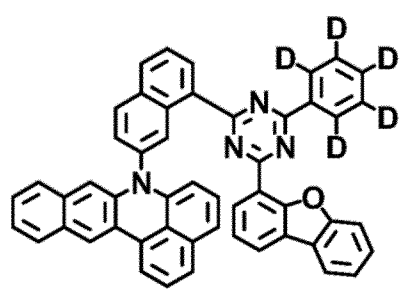
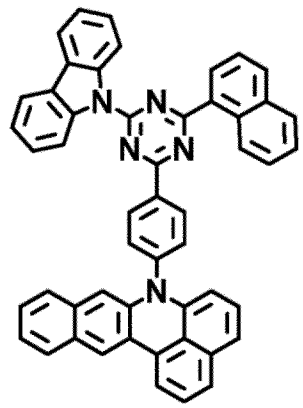

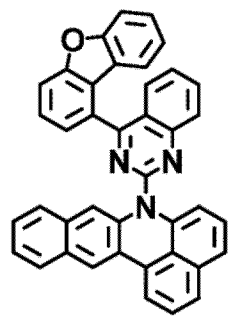 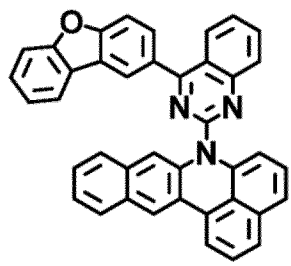 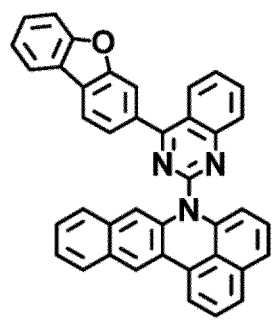
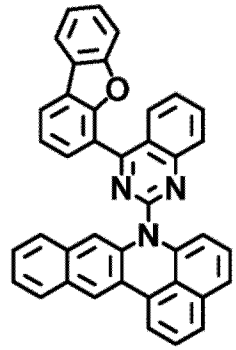 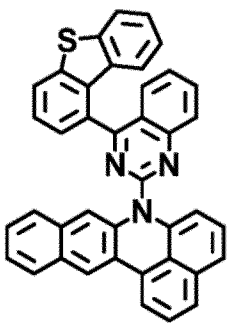 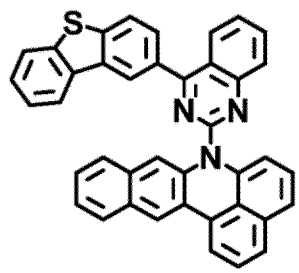
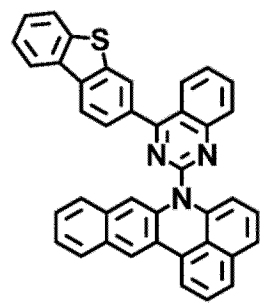 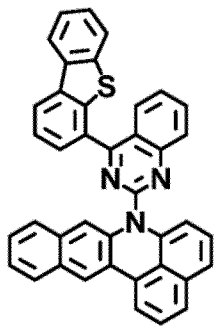 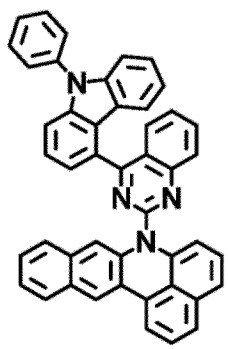

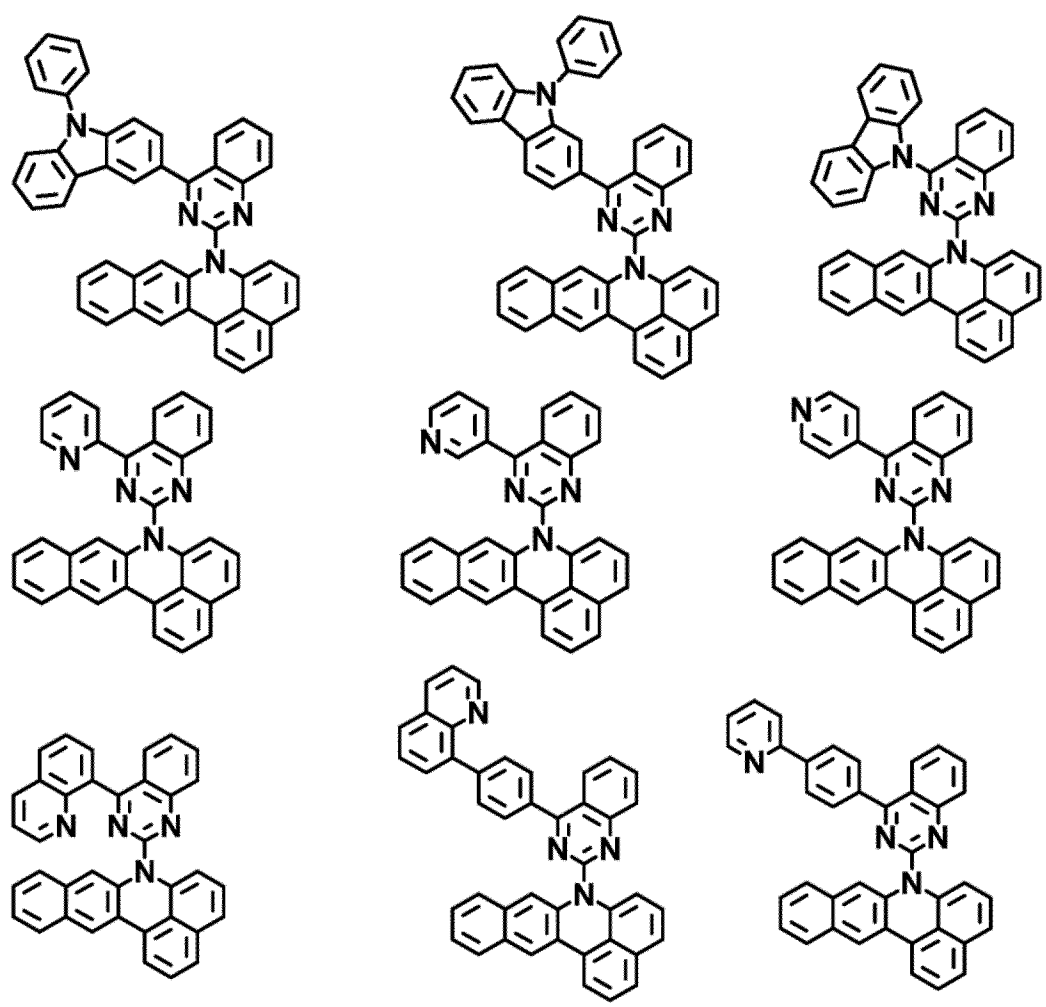

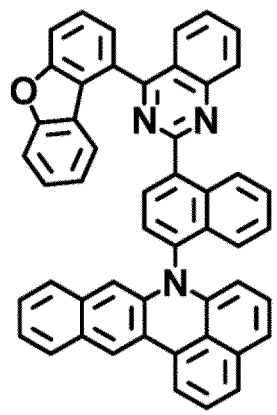 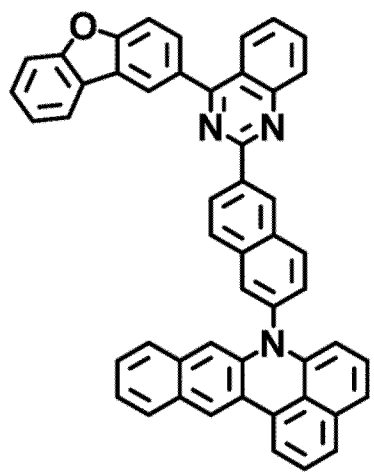 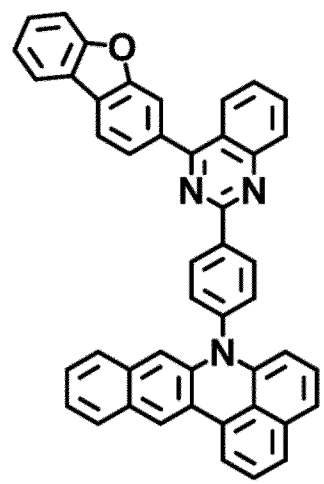
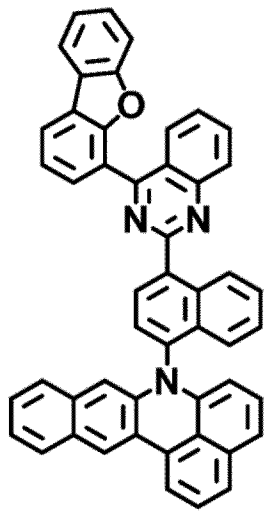 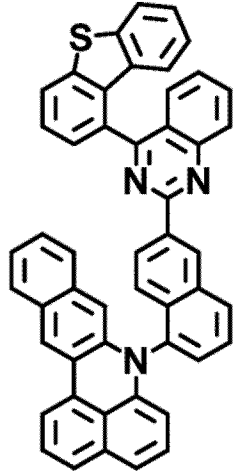 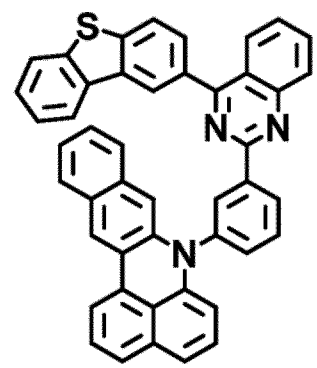

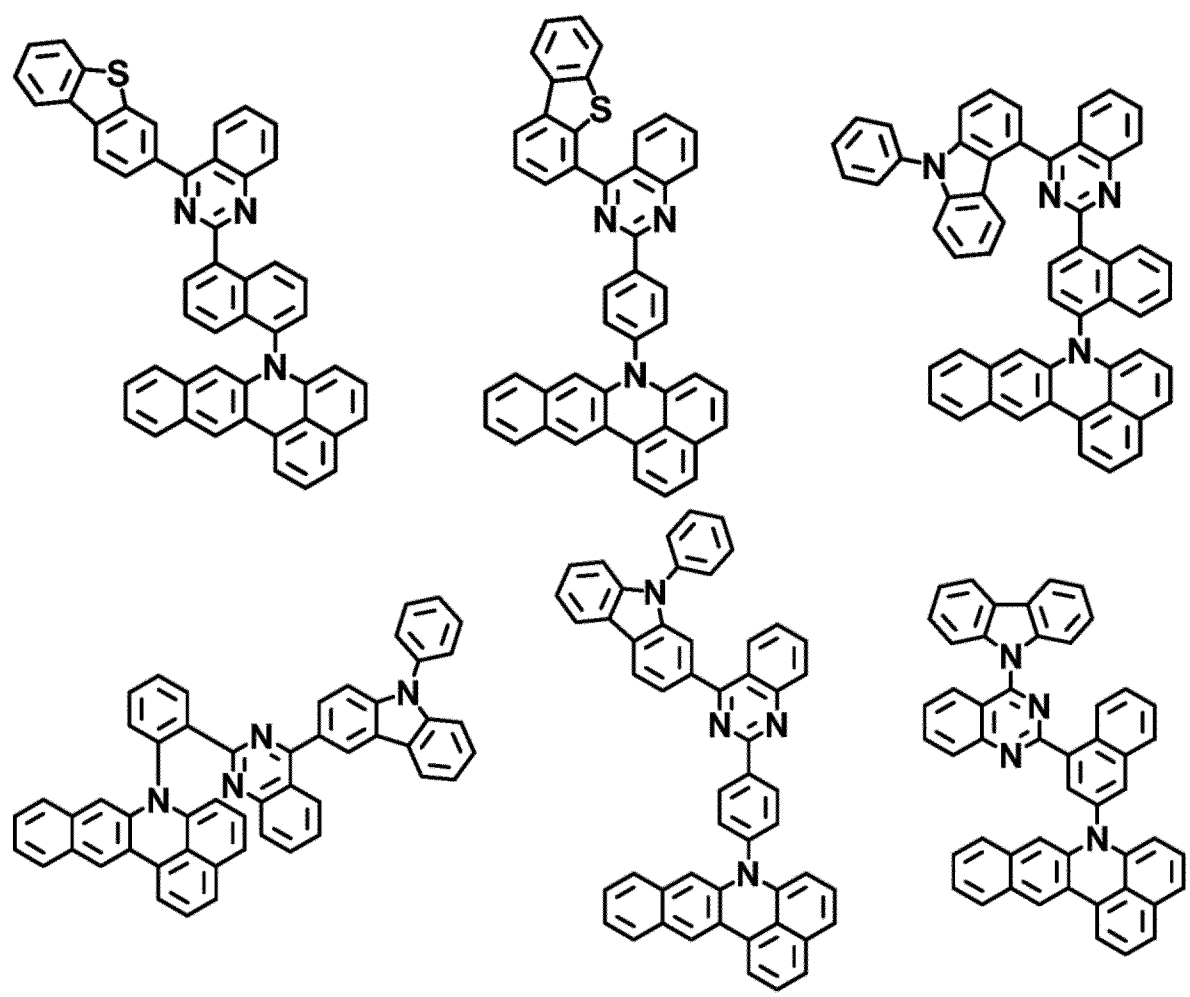

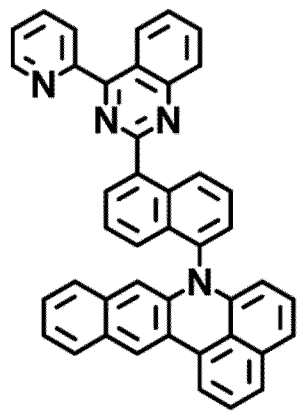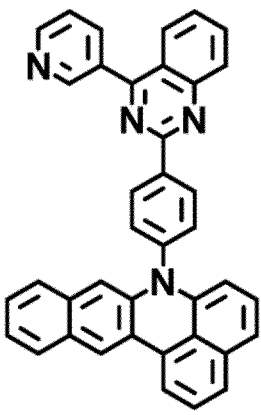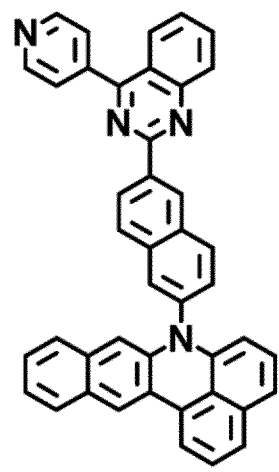
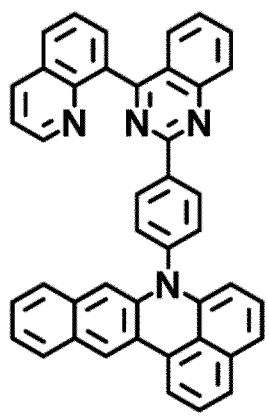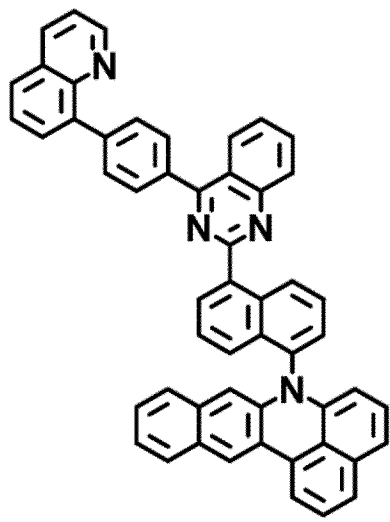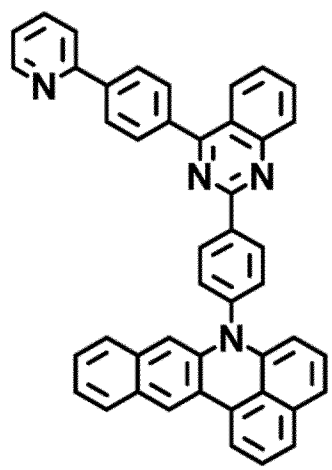

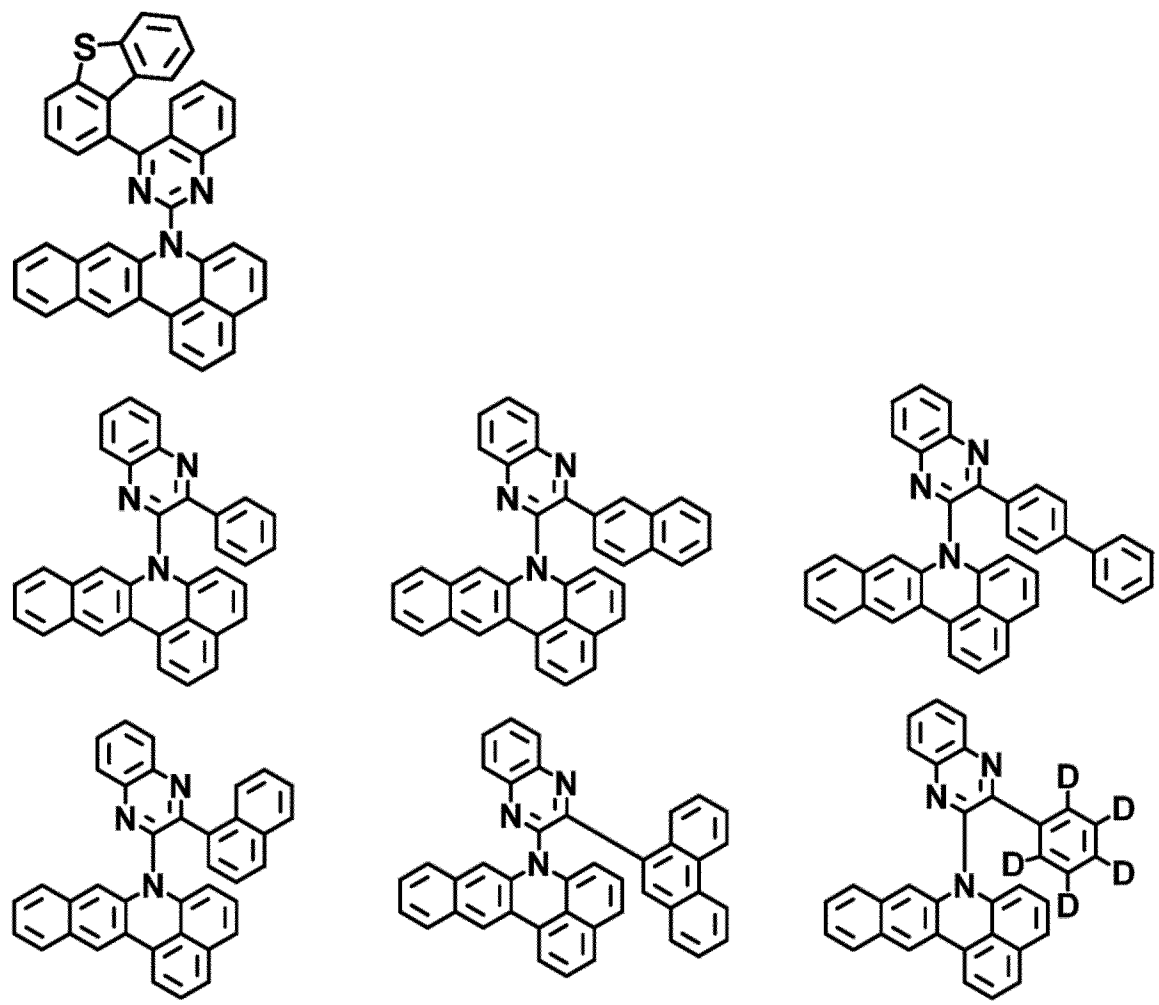

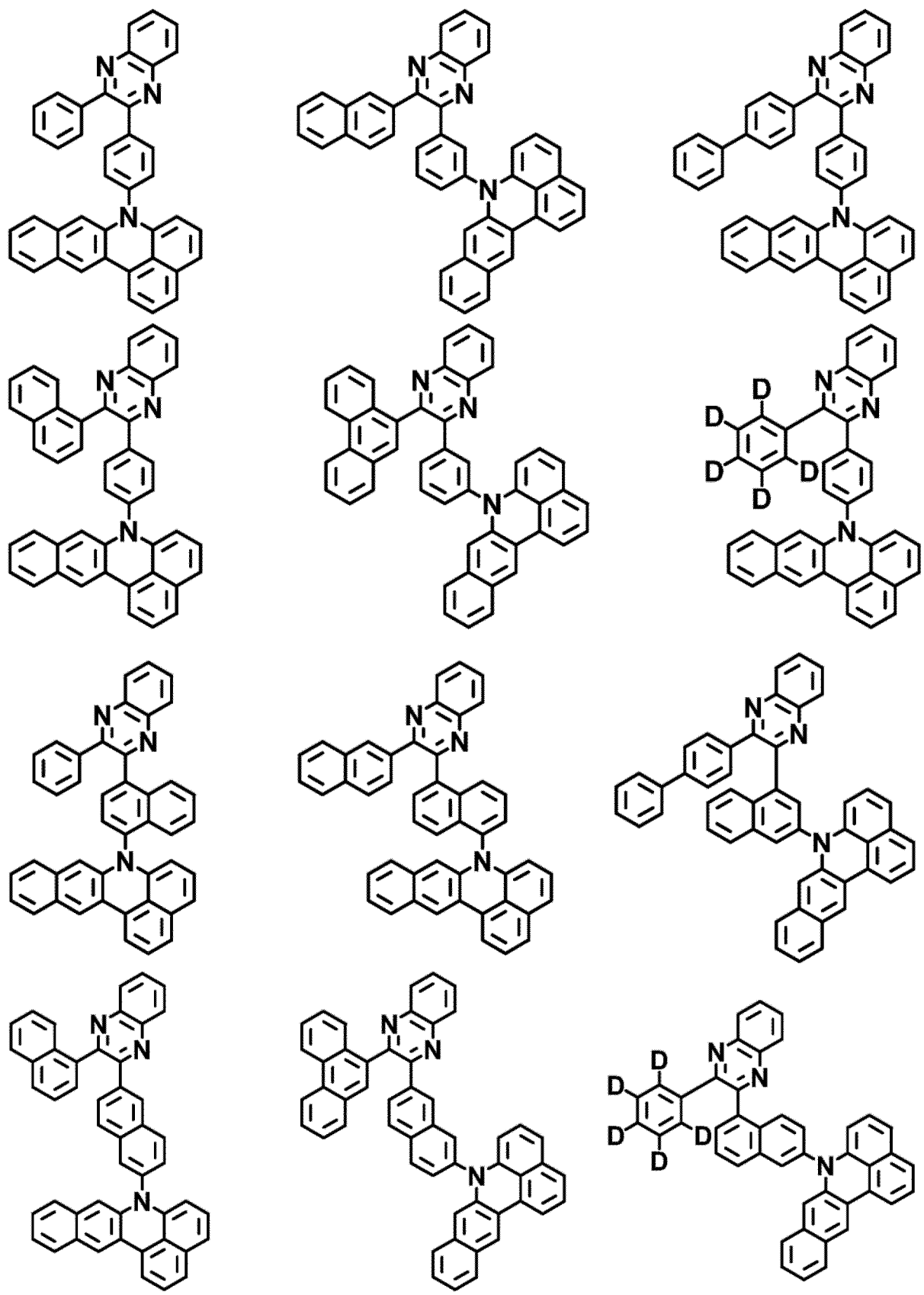

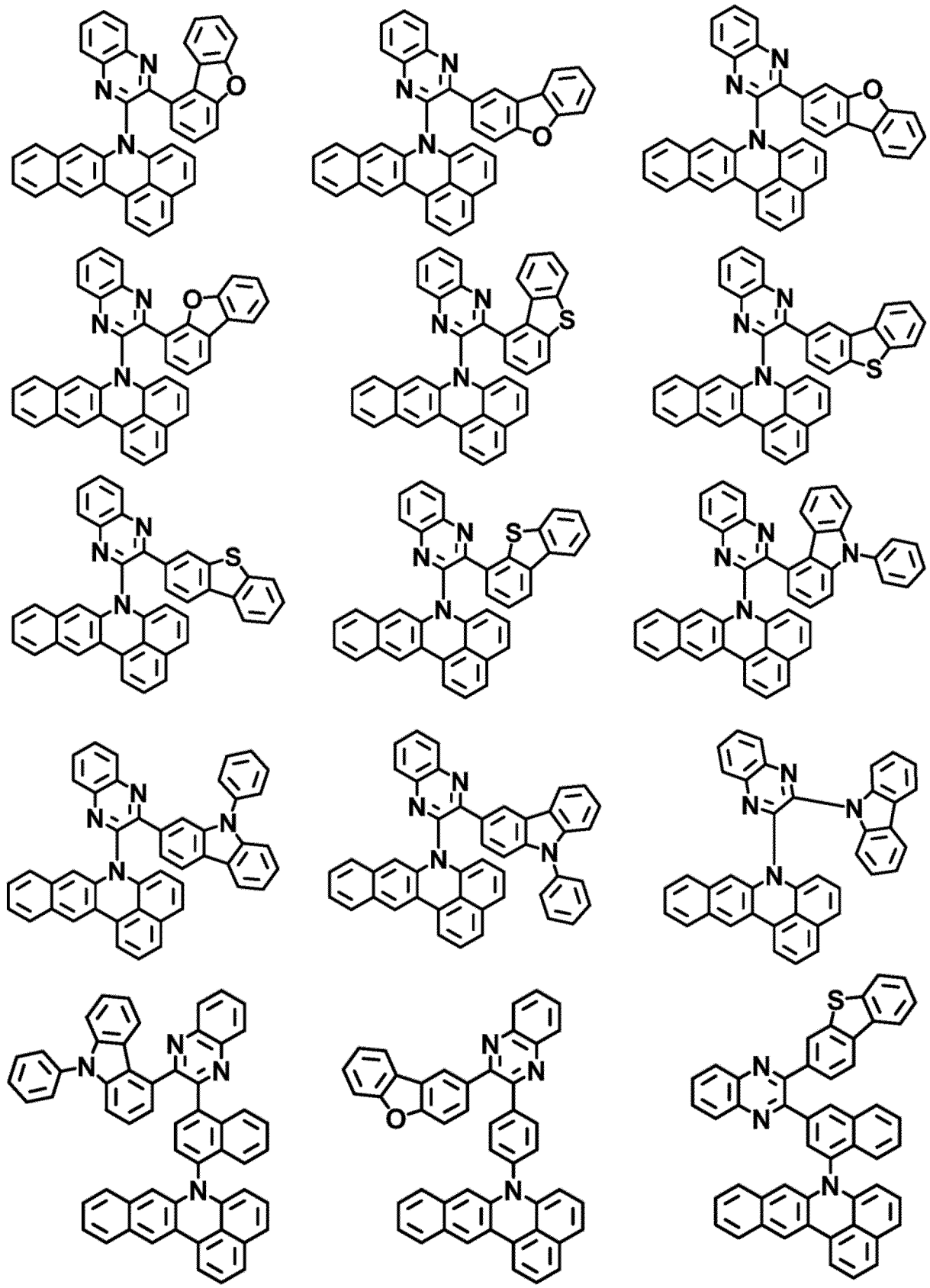

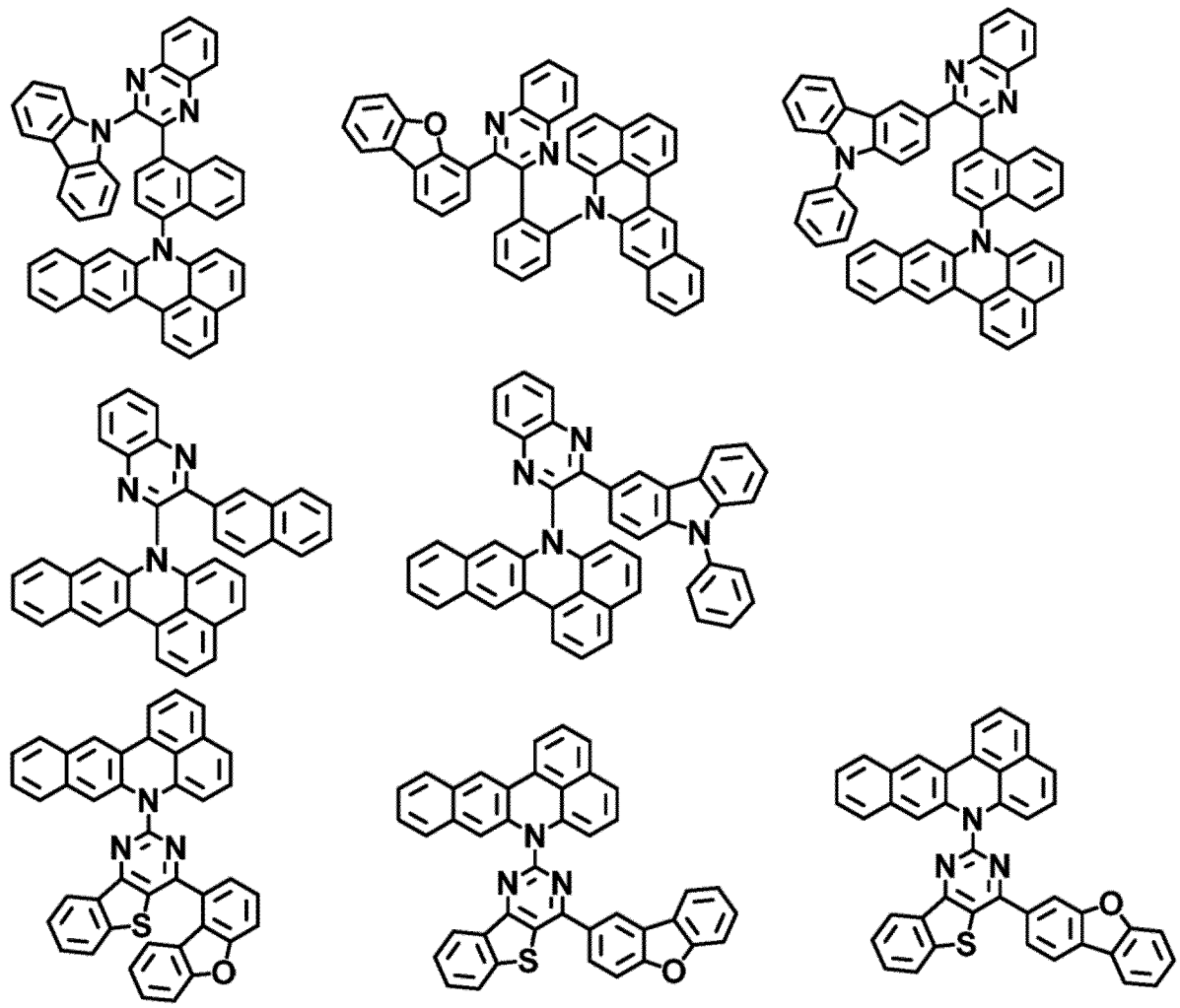

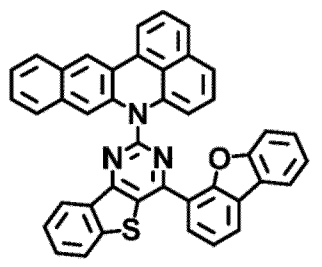 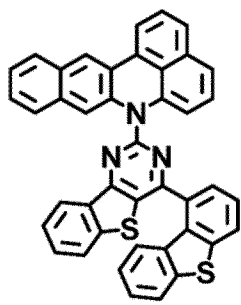 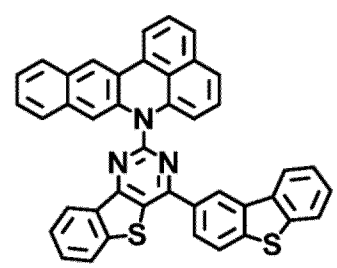
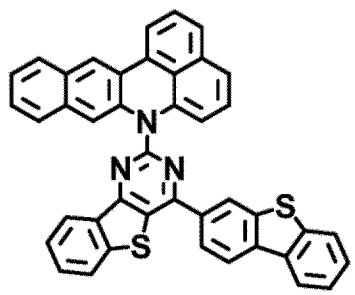 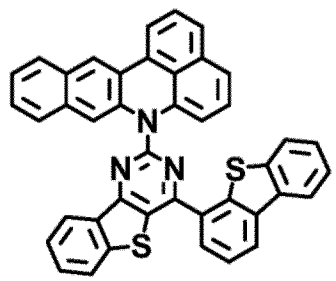 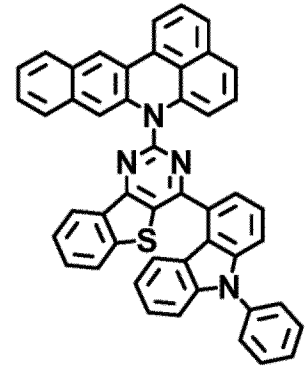
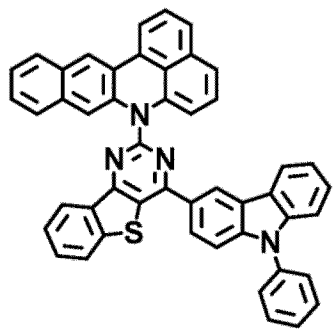 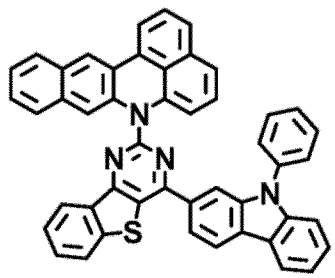 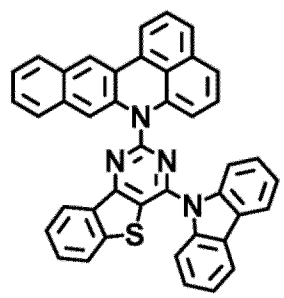

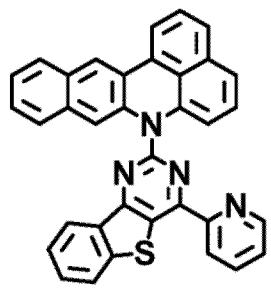 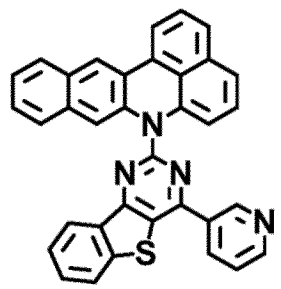 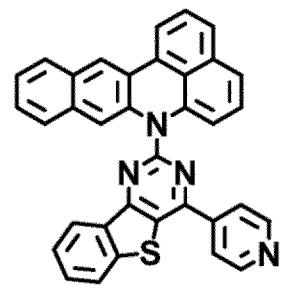
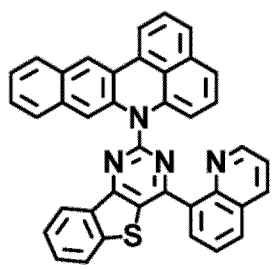 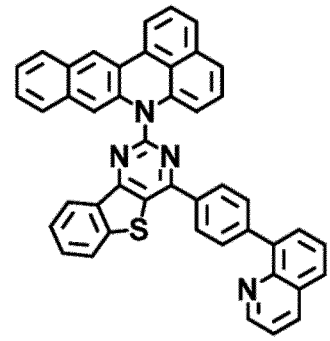 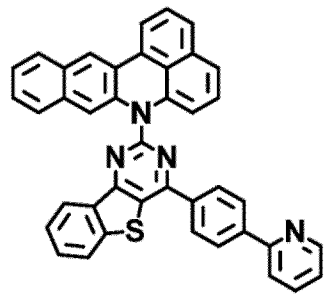
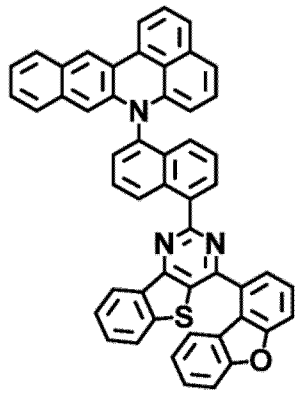 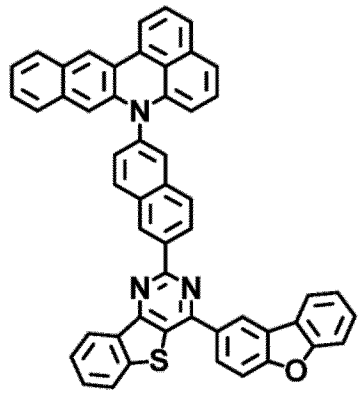 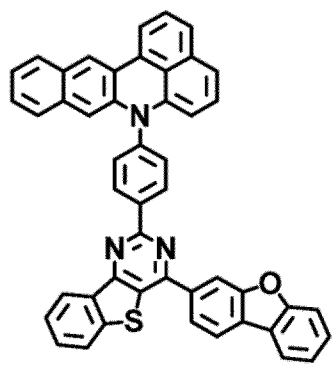

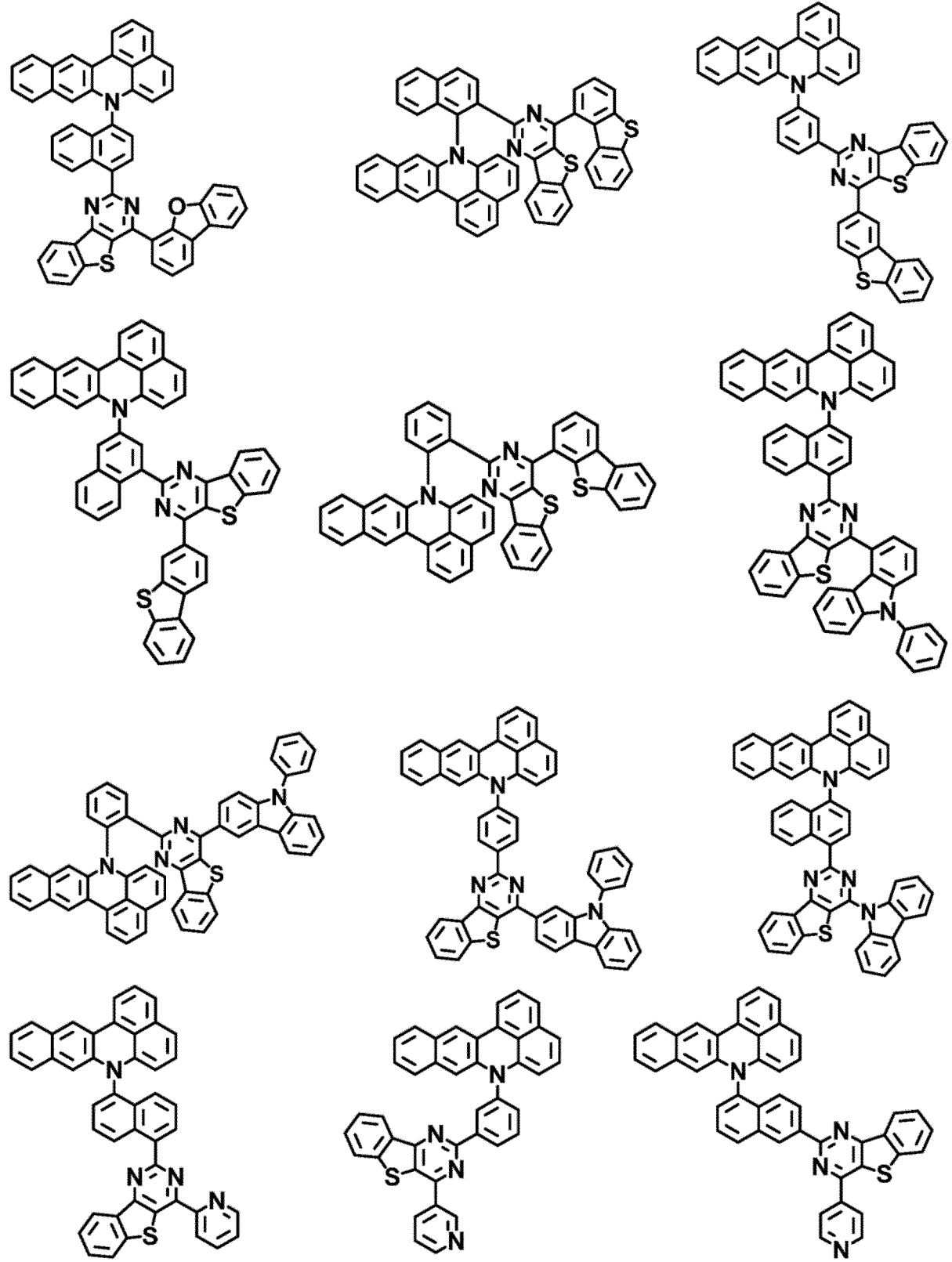

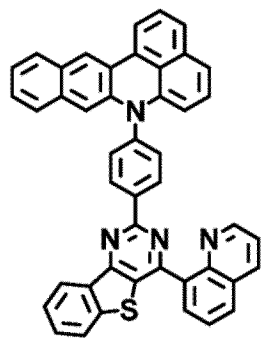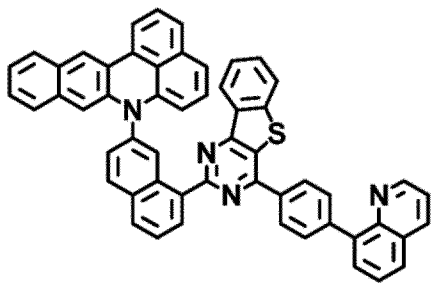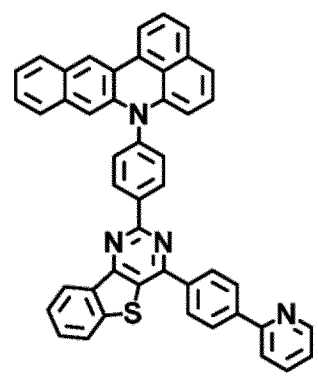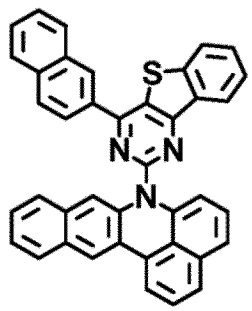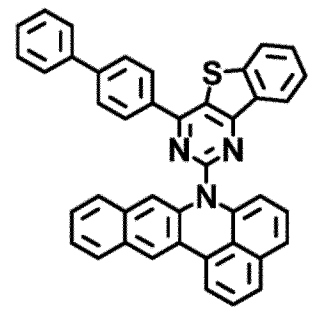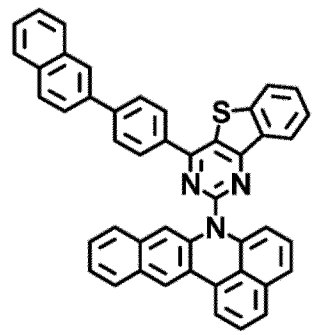

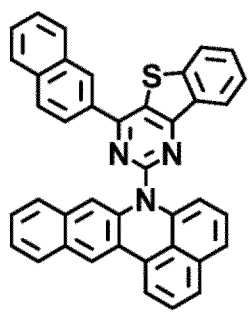 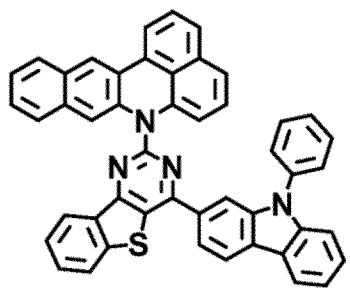
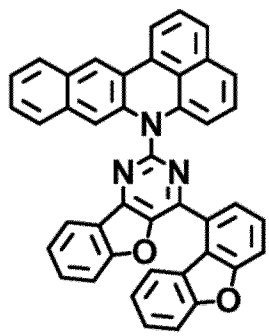 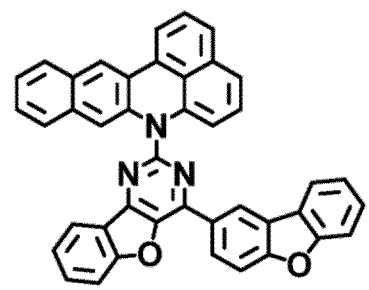 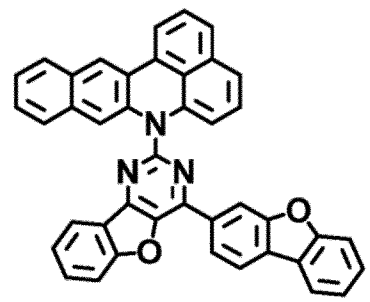
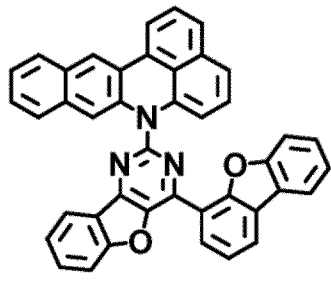 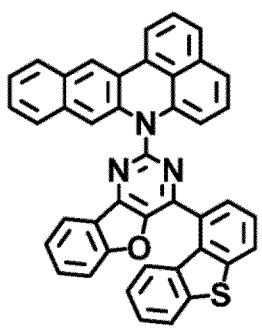 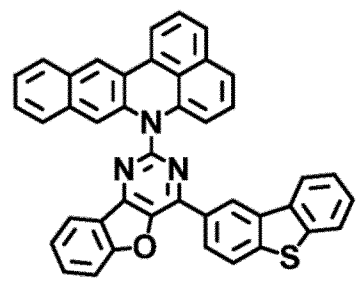

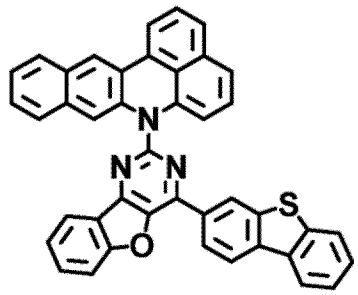 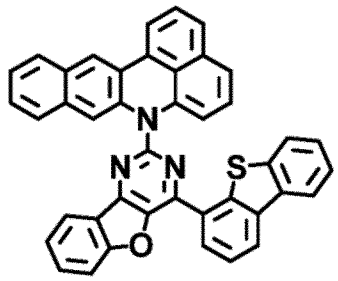 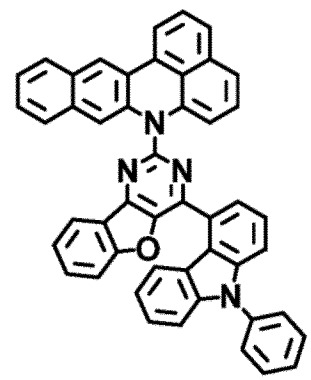
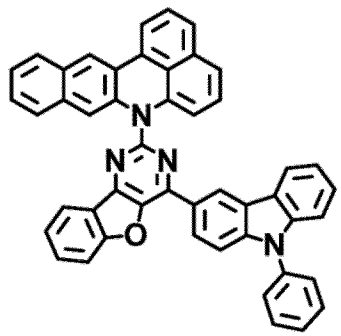 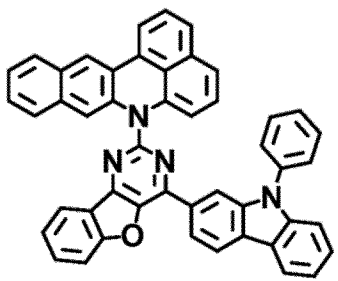 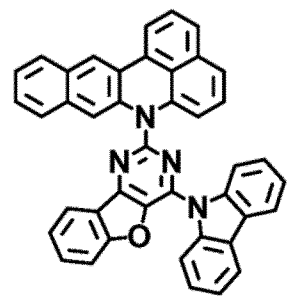
  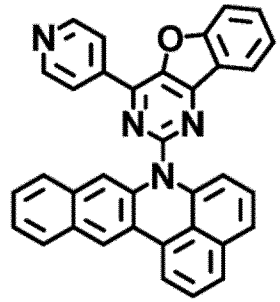

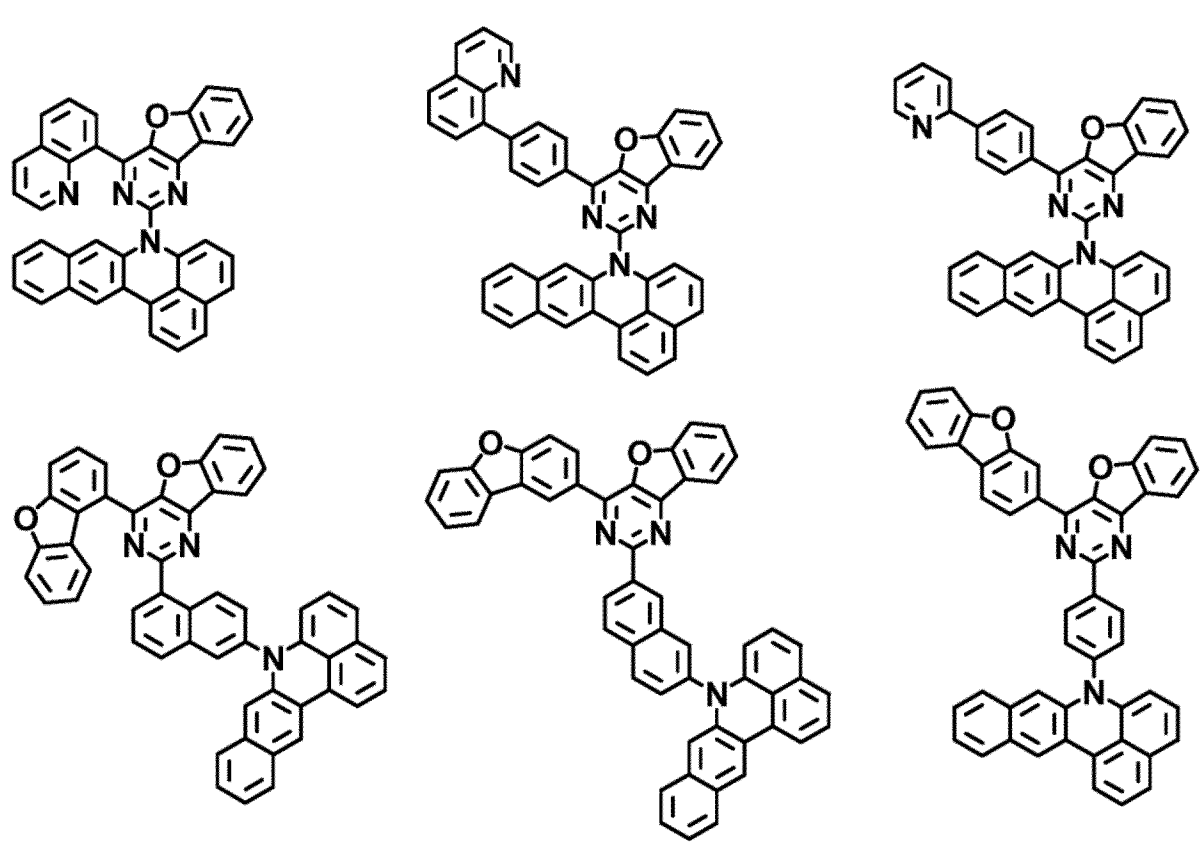

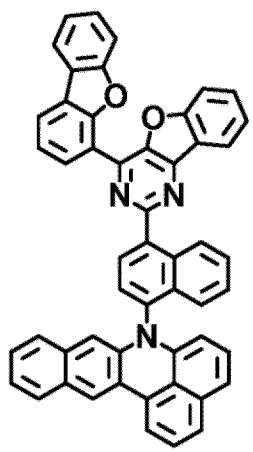 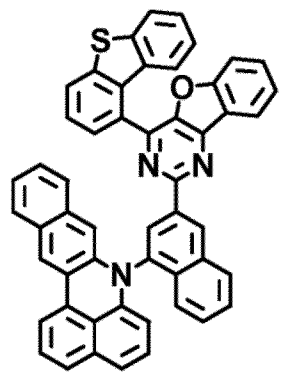 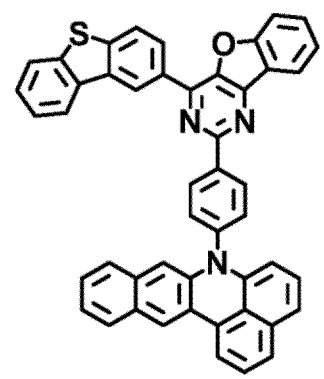
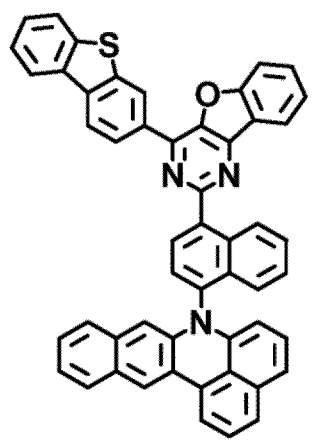 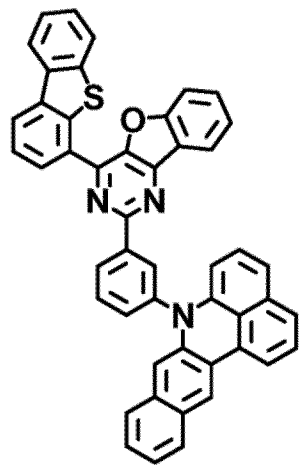 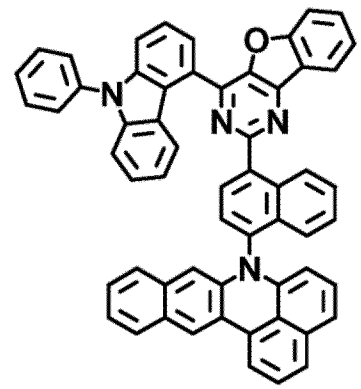

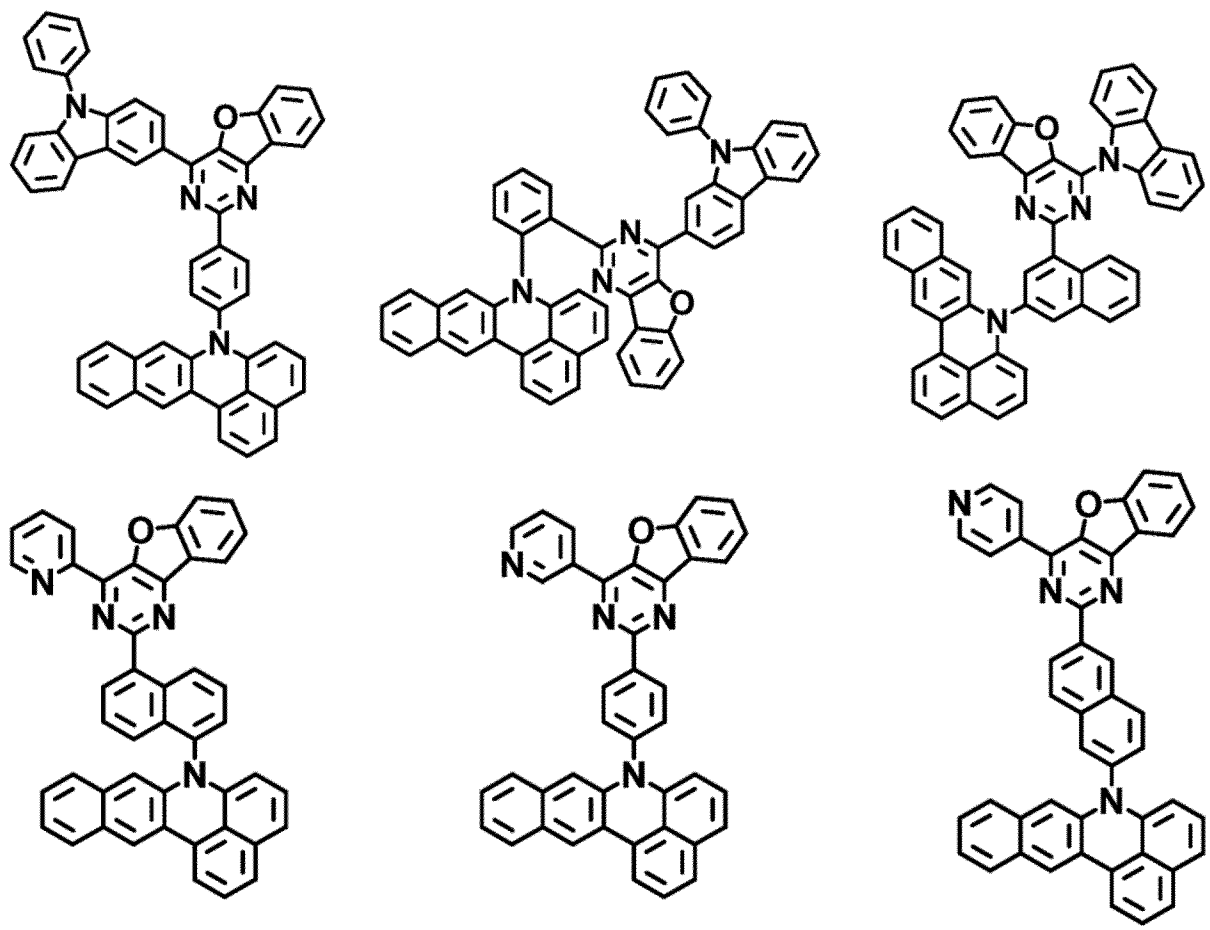

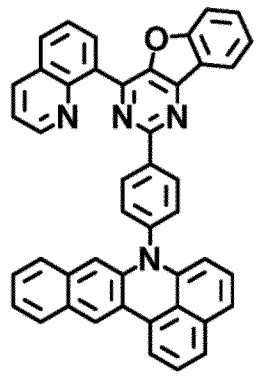 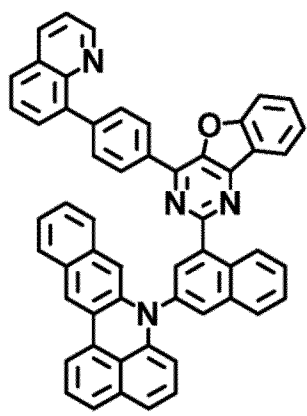 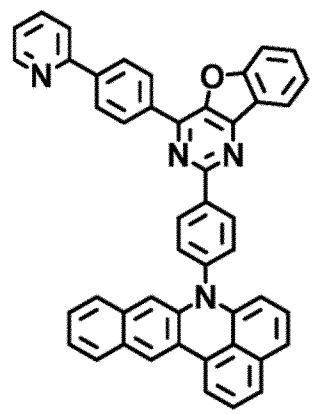
 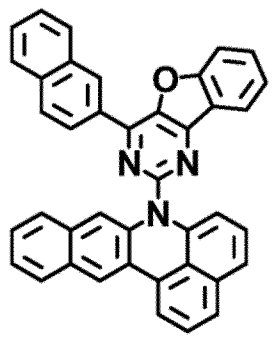 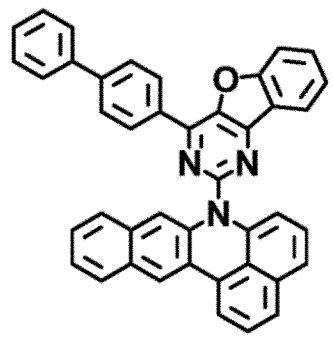
  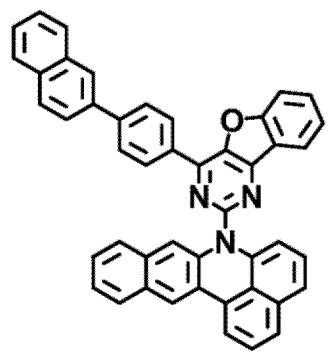
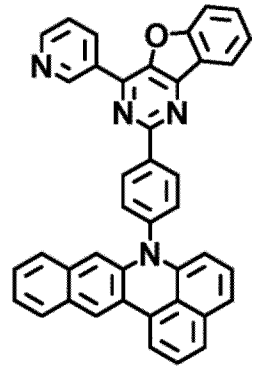

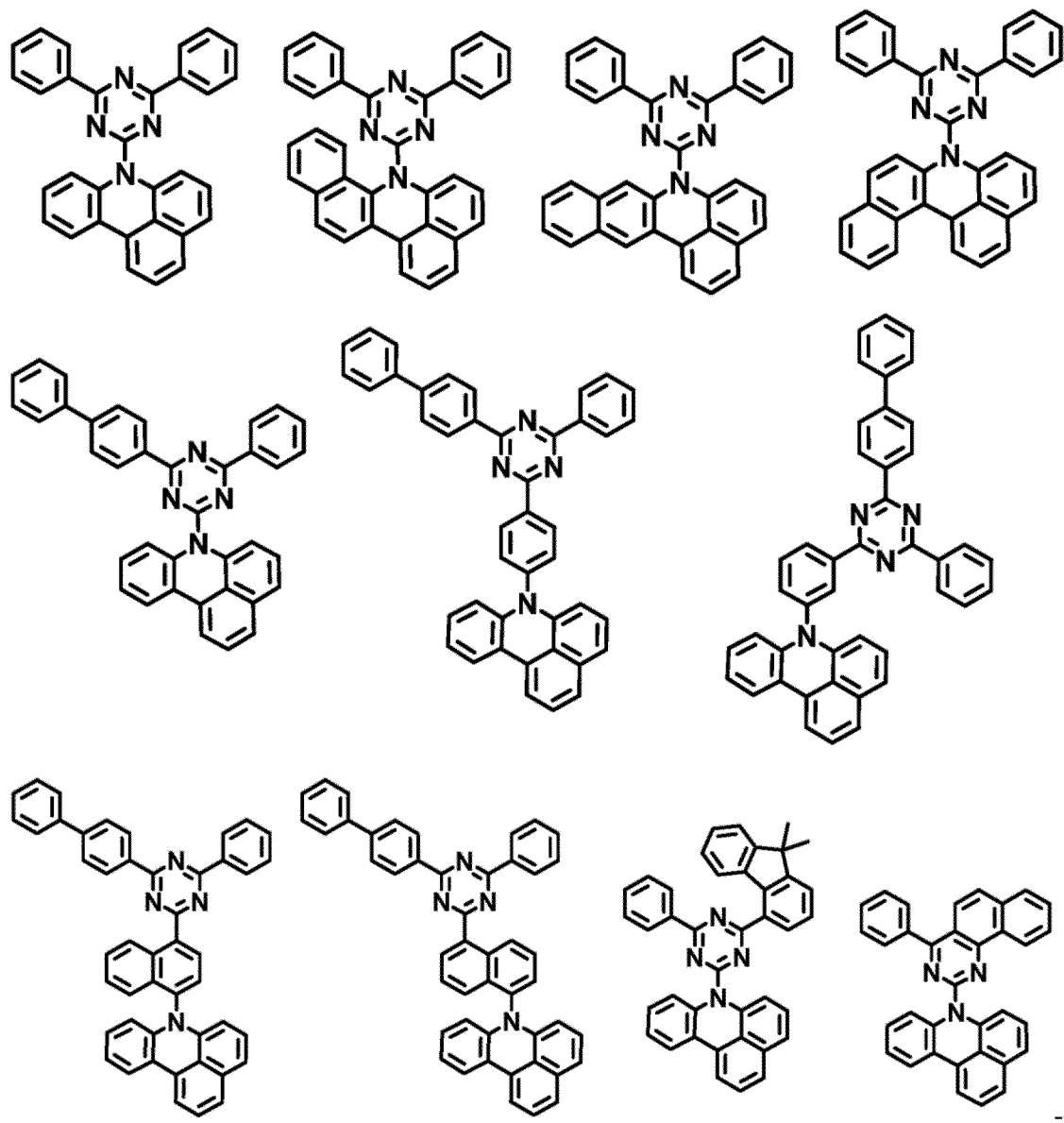

The invention claimed is:
1. A compound of Chemical Formula 1:

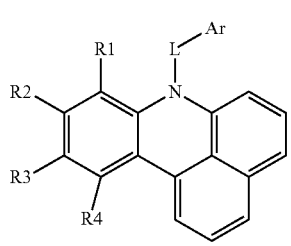

Chemical Formula 1 wherein, in Chemical Formula 1:

R1 to R4 are each independently hydrogen, or groups adjacent to each other can bond to form a substituted or unsubstituted benzene ring;

L is a direct bond or a substituted or unsubstituted arylene group that includes no heteroatoms; and Ar is a group of Chemical Formula D:

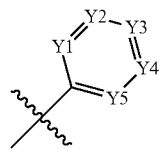

Chemical Formula D wherein in Chemical Formula D:

Y1 to Y5 are the same as or different from each other, and each independently is N or CR;

at least one of Y1 to Y5 is N;

R is hydrogen, deuterium, a halogen group, a substituted or unsubstituted alkyl group, a substituted or unsubstituted alkenyl group, a substituted or unsubstituted aryl group, or a substituted or unsubstituted heteroaryl group, and adjacent Rs can bond to each other to form a substituted or unsubstituted ring; and when R is two or more, the Rs are the same as or different from each other.

2. The compound of claim 1, wherein Chemical Formula 1 is any one of the following Chemical Formulae 3 to 6:

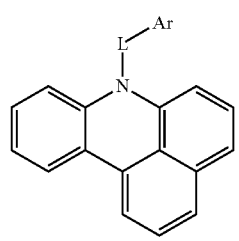

Chemical Formula 3

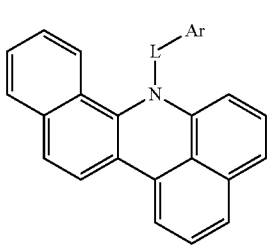

Chemical Formula 4

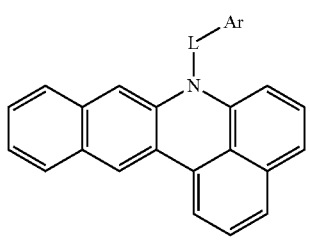

Chemical Formula 5

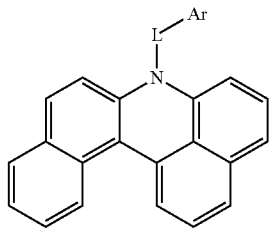

Chemical Formula 6 wherein in Chemical Formulae 3 to 6, Ar and L have the same definitions as in Chemical Formula 1.

3. The compound of claim 1, wherein Ar is a group of any one of the following Chemical Formulae Ar-1 to Ar-4:

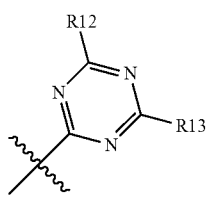

Chemical Formula Ar-1 wherein in Chemical Formula Ar-1:

R12 and R13 are the same as or different from each other, and each independently is hydrogen, deuterium, a halogen group, a substituted or unsubstituted alkyl group, a substituted or unsubstituted aryl group, or a substituted or unsubstituted heteroaryl group;

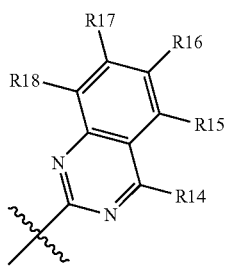

Chemical Formula Ar-2 wherein in Chemical Formula Ar-2:

R14 to R18 are the same as or different from each other, and each independently is hydrogen, deuterium, a halogen group, a substituted or unsubstituted alkyl group, a substituted or unsubstituted alkenyl group, a substituted or unsubstituted aryl group, or a substituted or unsubstituted heteroaryl group, or bond to adjacent groups to form a substituted or unsubstituted ring;

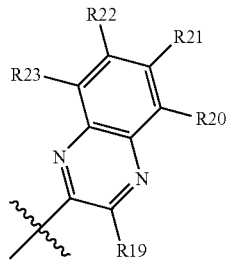

Chemical Formula Ar-3 wherein in Chemical Formula Ar-3:

R19 to R23 are the same as or different from each other, and each independently is hydrogen, deuterium, a halogen group, a substituted or unsubstituted alkyl group, a substituted or unsubstituted alkenyl group, a substituted or unsubstituted aryl group, or a substituted or unsubstituted heteroaryl group;

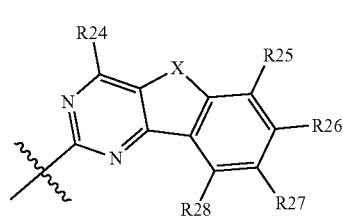

Chemical Formula Ar-4 wherein in Chemical Formula Ar-4:

X is S, O, or C(Rm)(Rn);

Rm and Rn are the same as or different from each other, and each independently is hydrogen, deuterium, an alkyl group, or an aryl group; and R24 to R28 are the same as or different from each other, and each independently is hydrogen, deuterium, a halogen group, a substituted or unsubstituted alkyl group, a substituted or unsubstituted aryl group, or a substituted or unsubstituted heteroaryl group.

4. The compound of claim 3, wherein, when

R1 to R4 are each hydrogen, R12 is a substituted or unsubstituted heteroaryl group, and R14 is a substituted aryl group or a substituted or unsubstituted heteroaryl group.

5. The compound of claim 1, wherein the compound of Chemical Formula 1 is any one compound selected from among the following compounds:

407
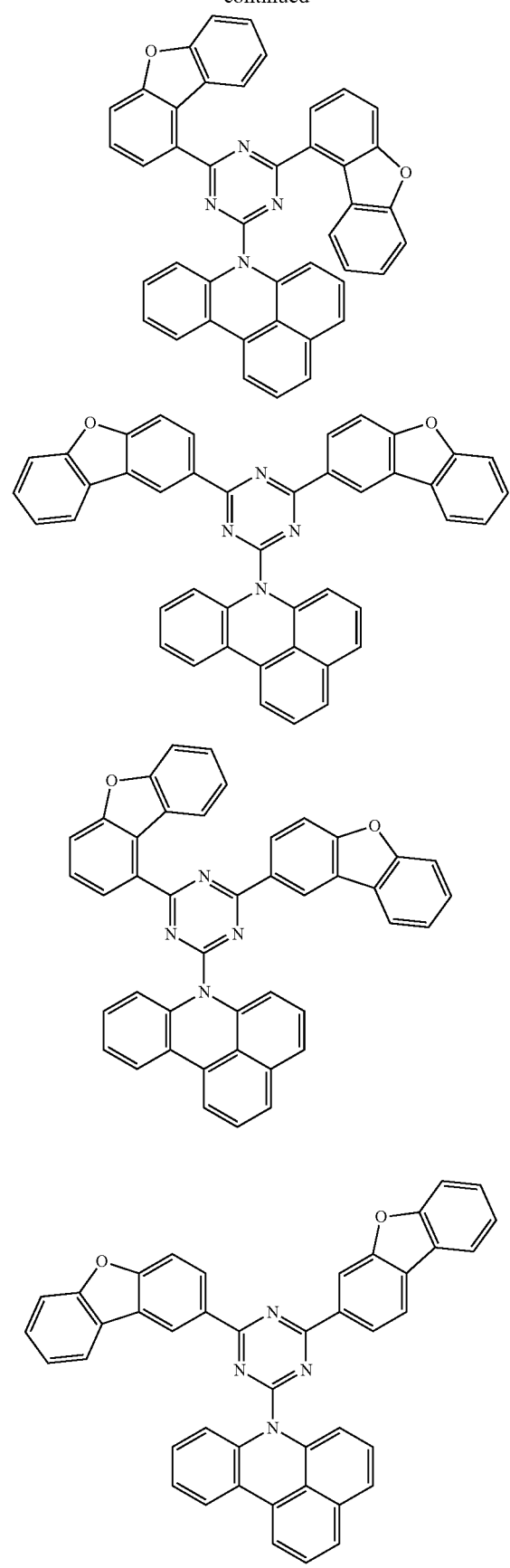
408
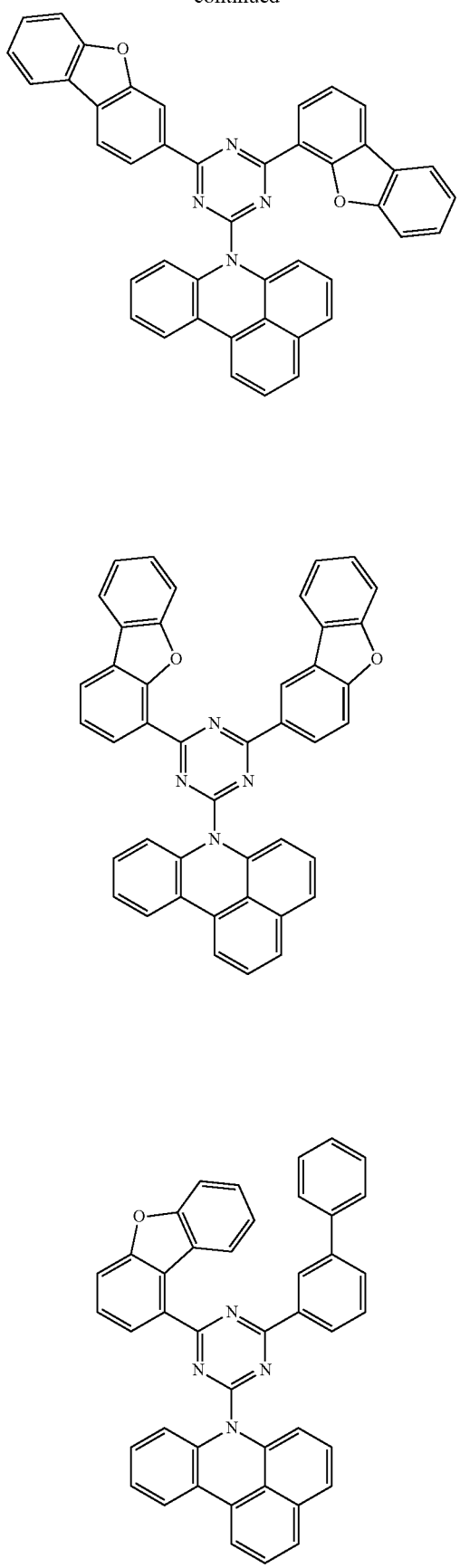

409
-continued
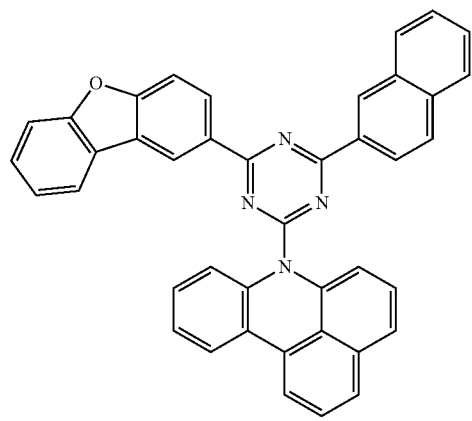
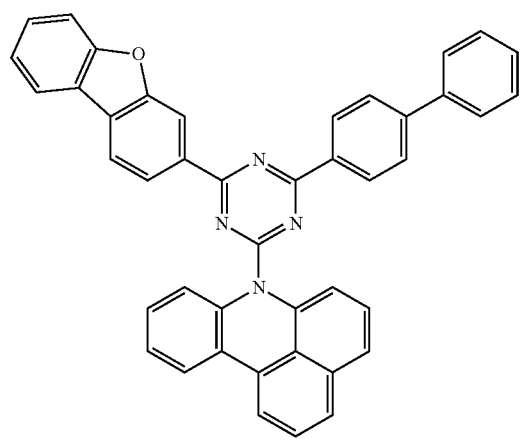
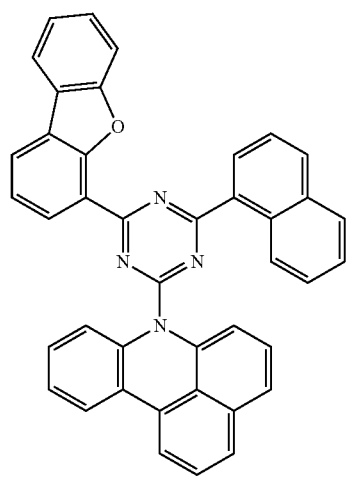
410
-continued
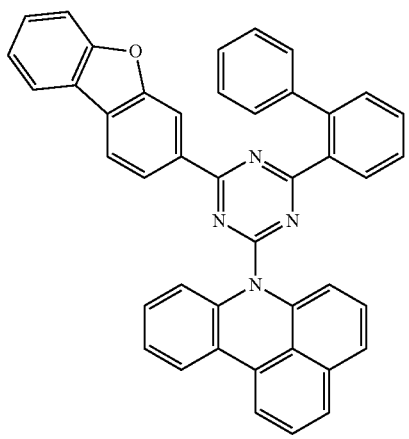
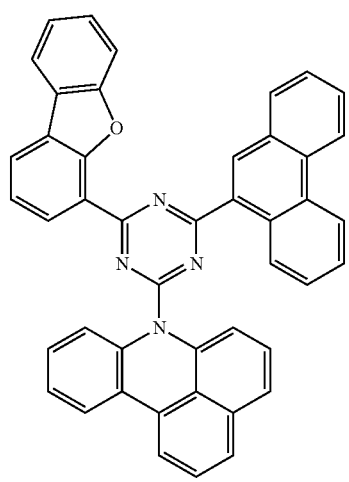
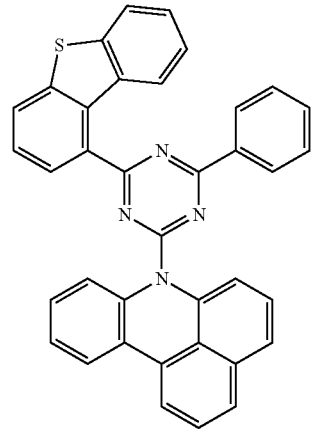
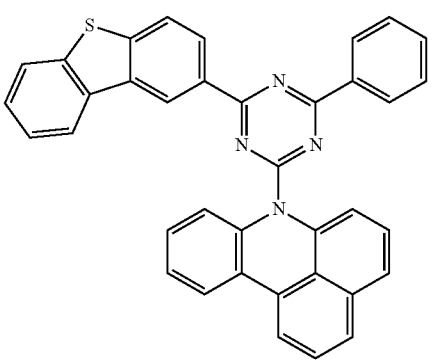

411
-continued
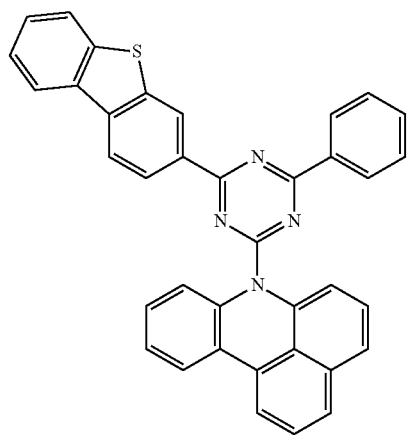
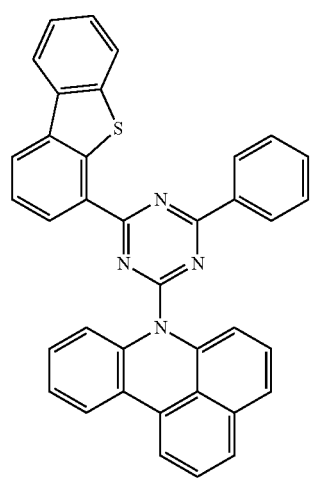
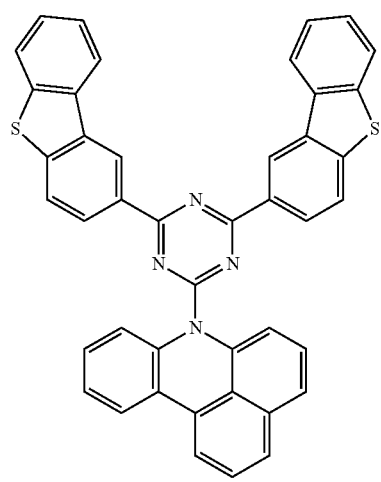
412
-continued
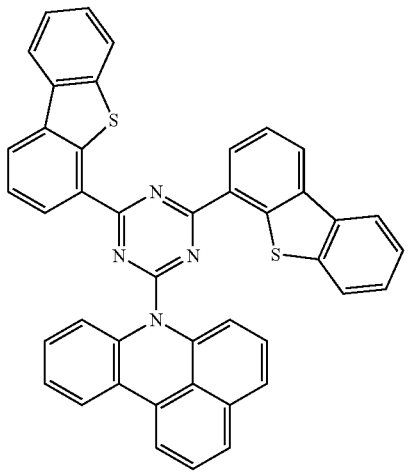
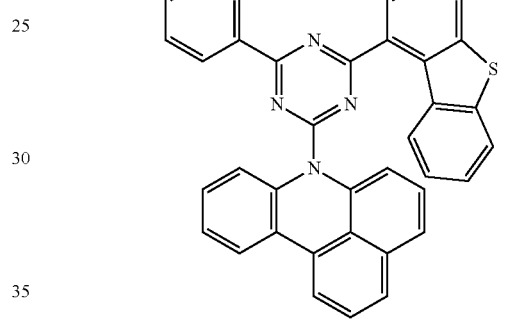
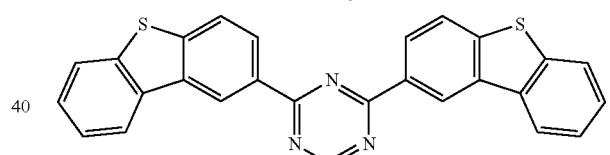
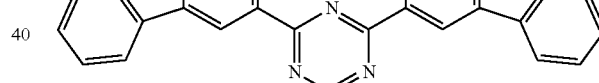
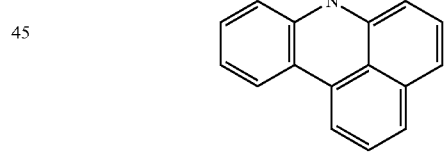
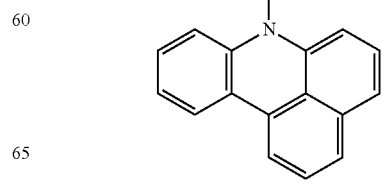

413
-continued
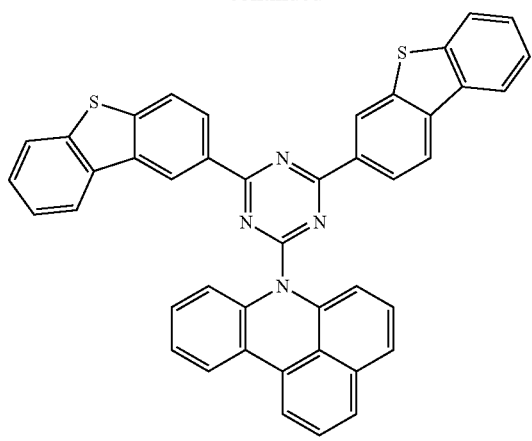
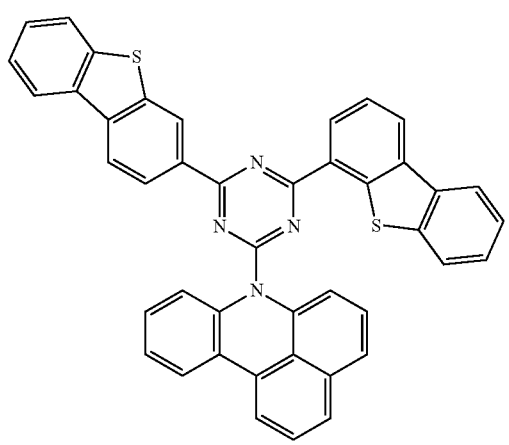
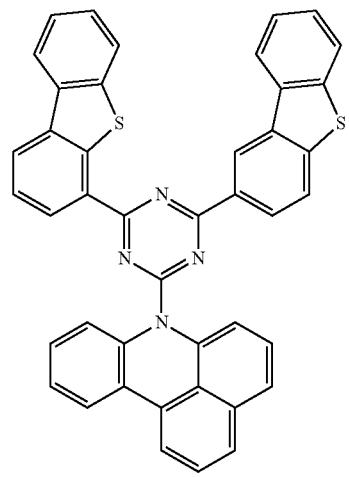
414
-continued
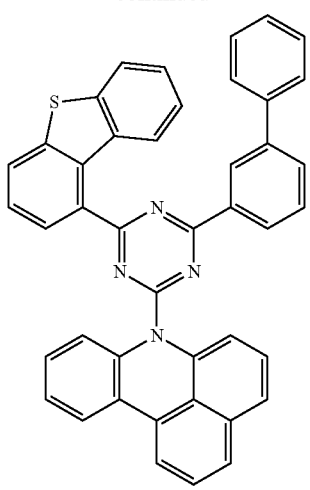
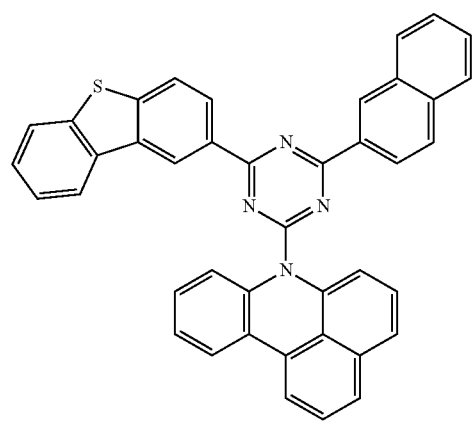
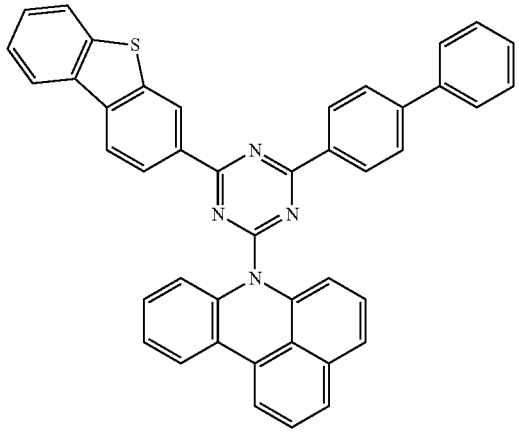

415
-continued
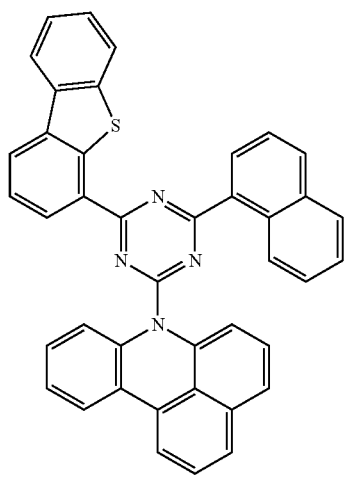
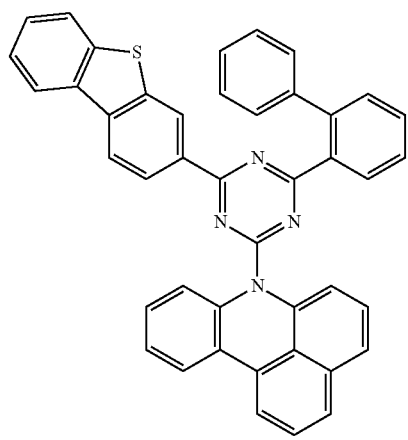
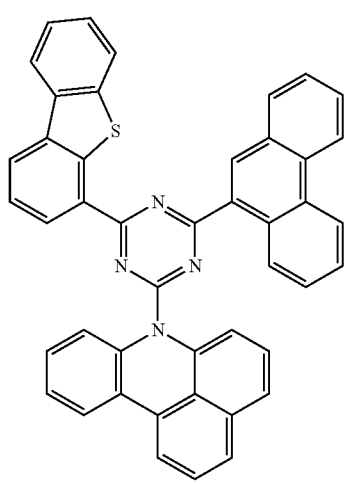
416
-continued
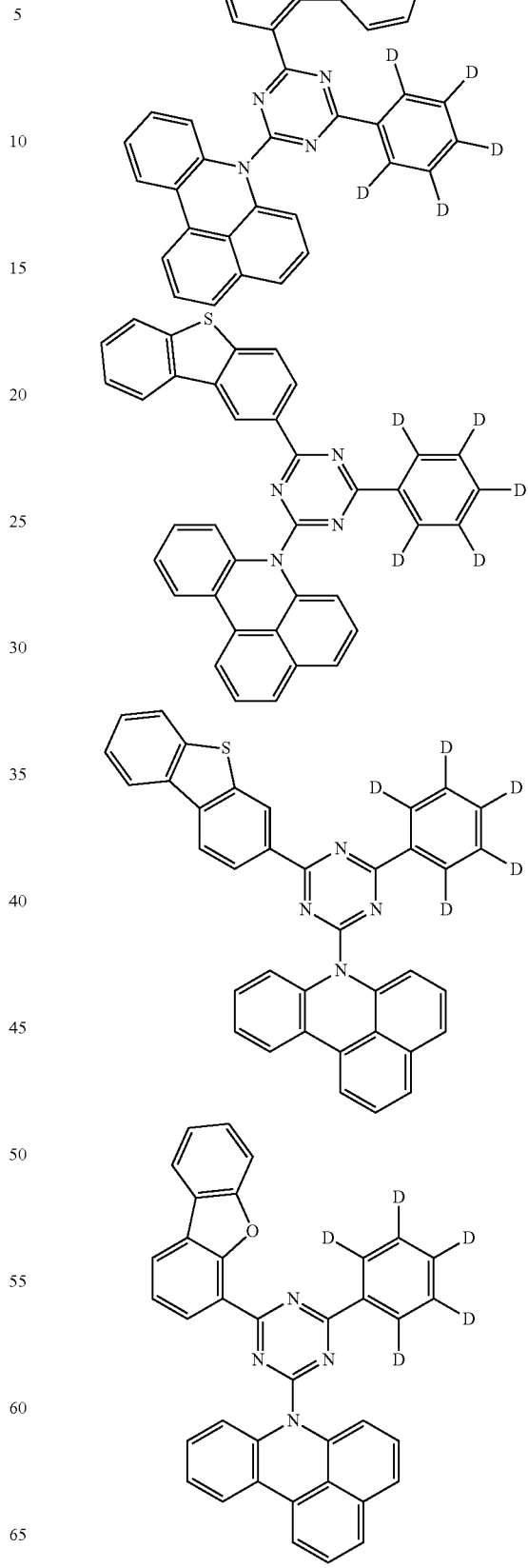

417
-continued
418
-continued
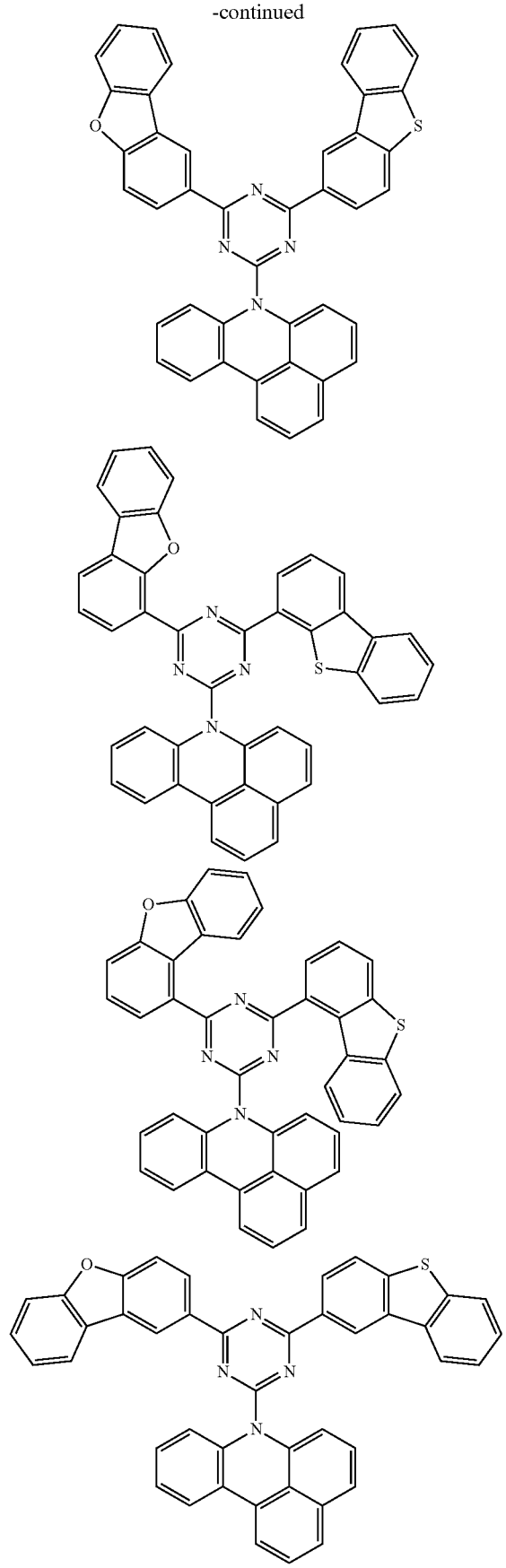
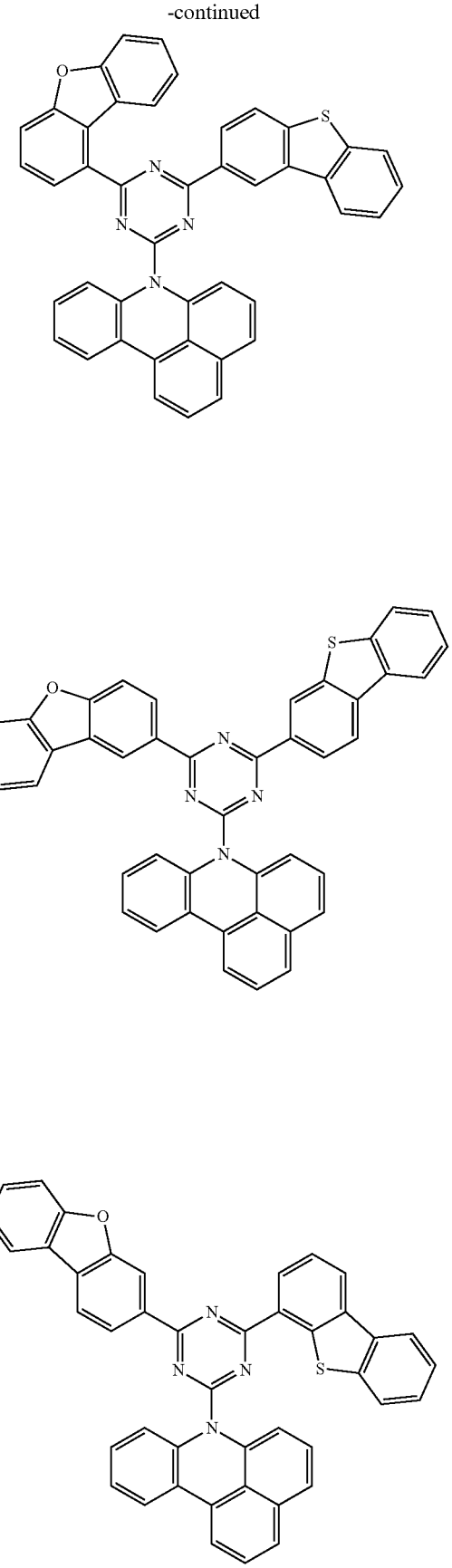

419
-continued
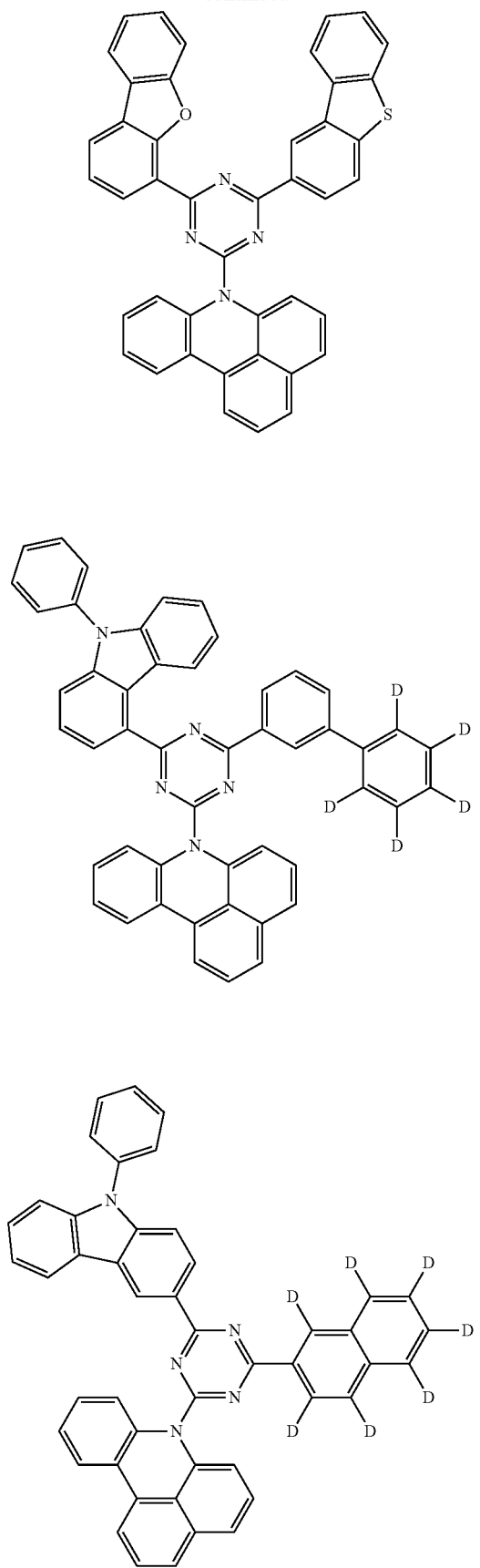
420
-continued
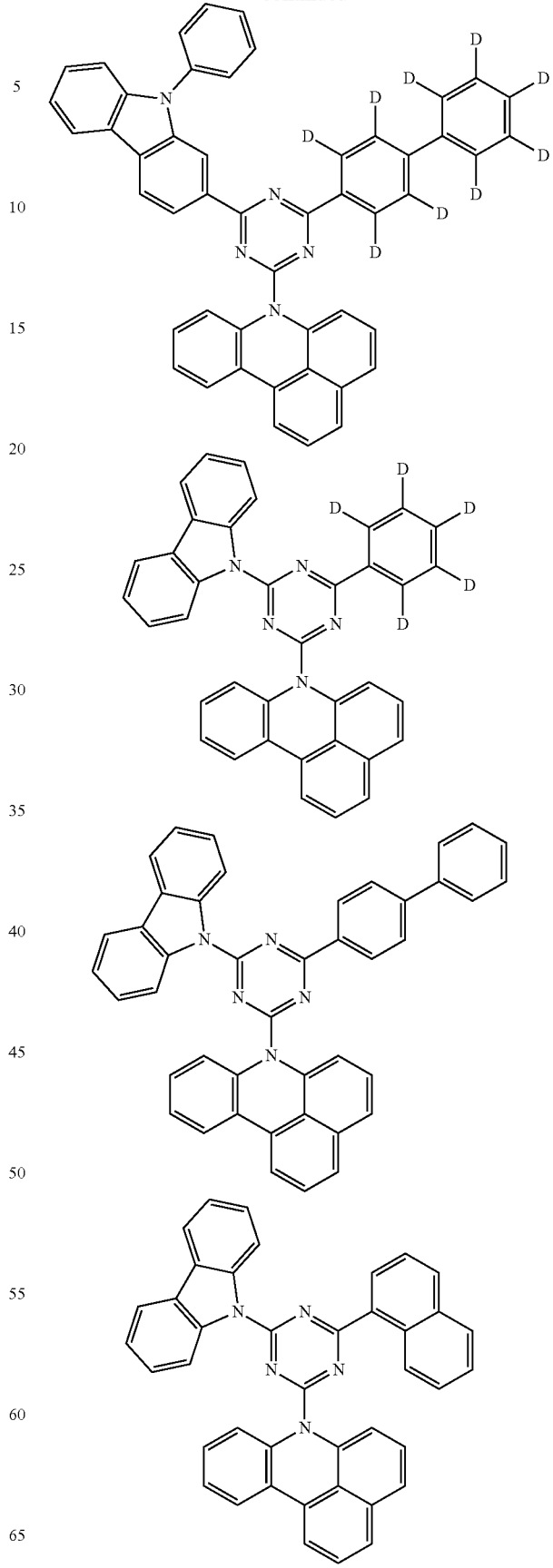

421
-continued
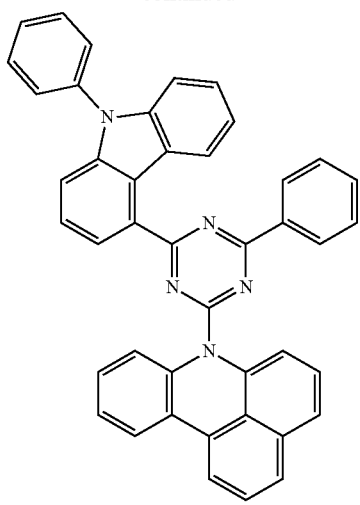
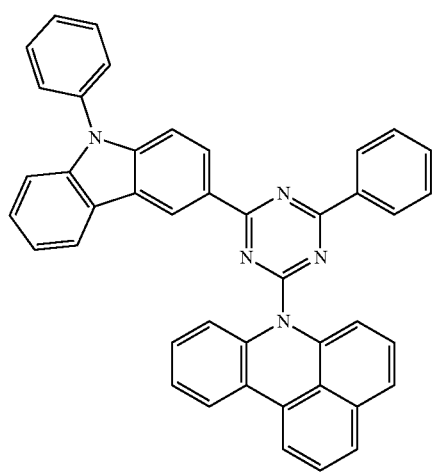
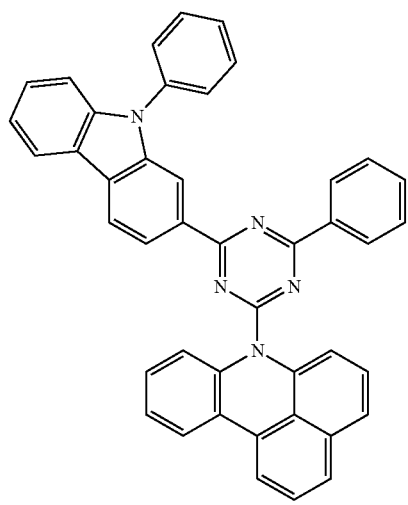
422
-continued
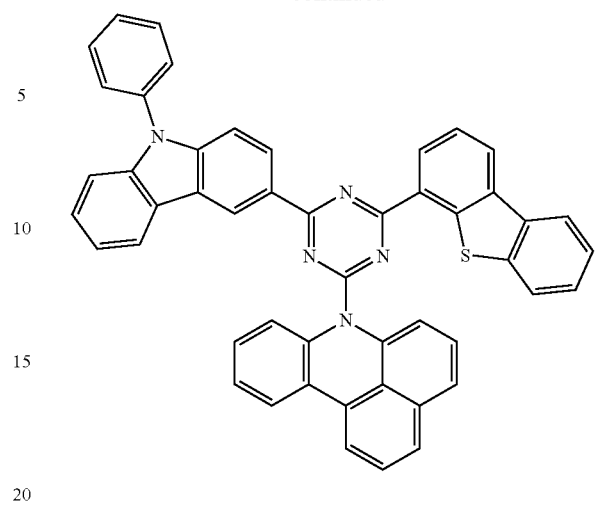
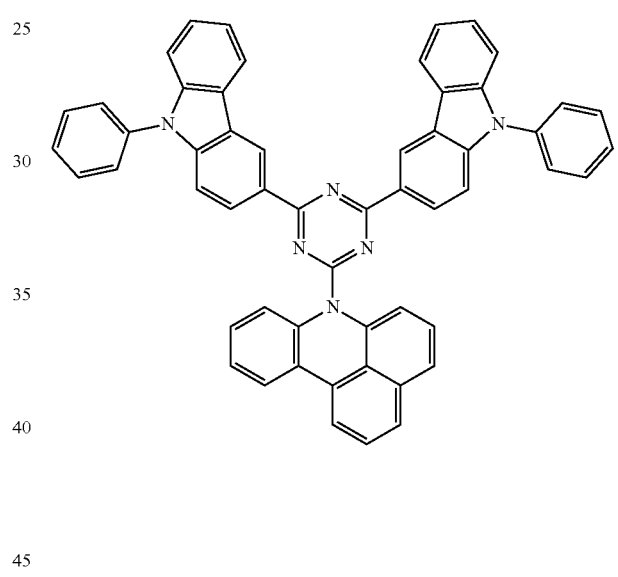
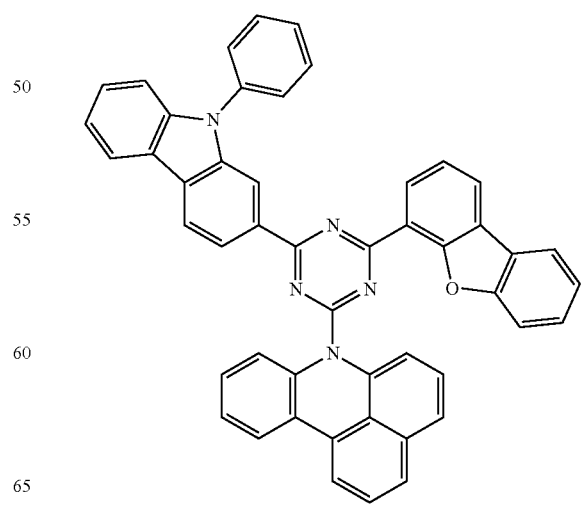

423
-continued
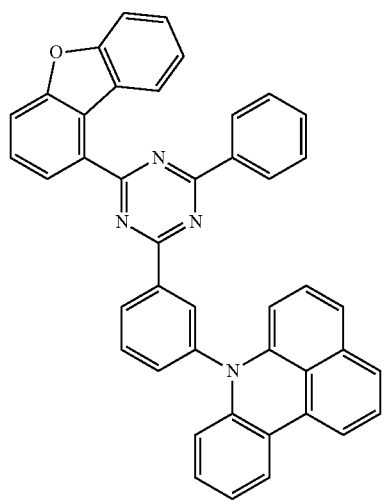
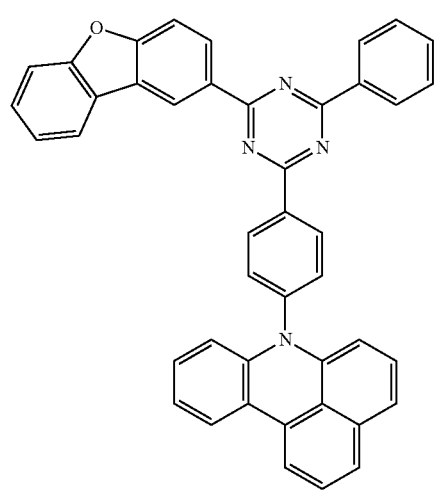
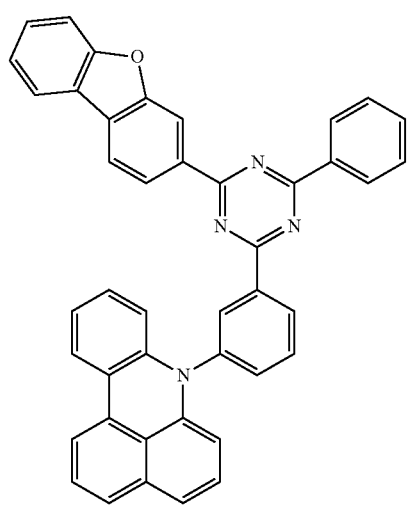
424
-continued
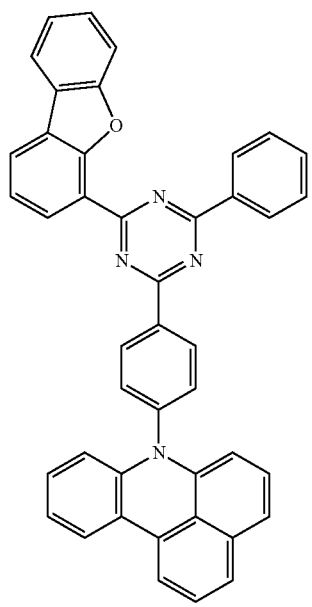
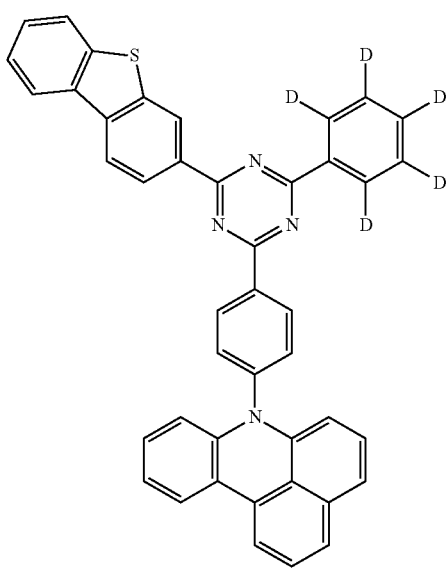
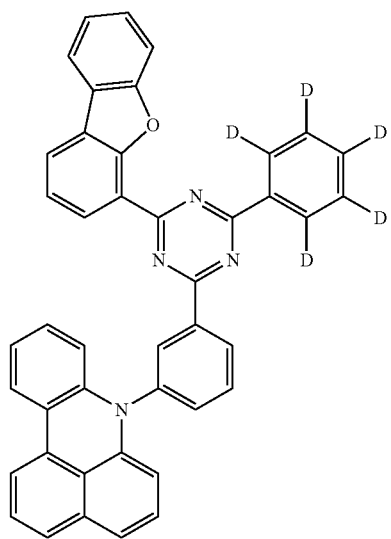

425
-continued
426
-continued
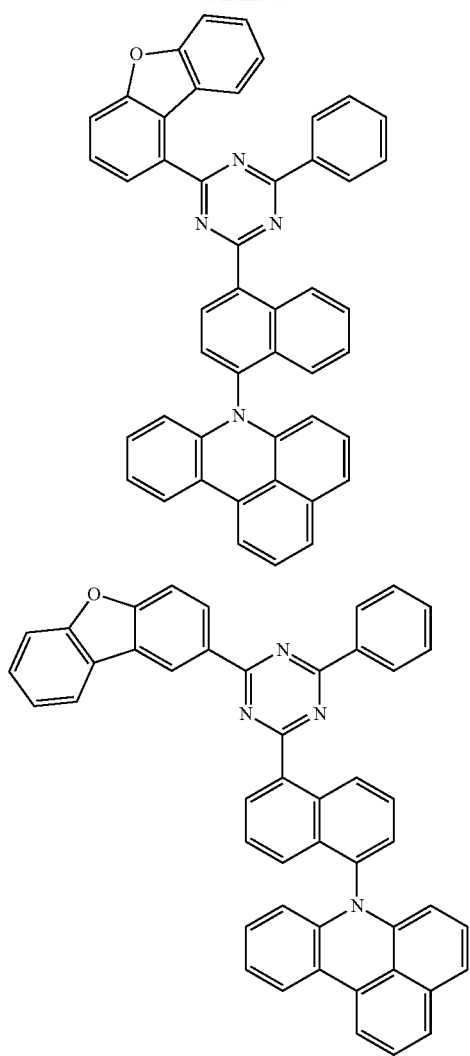
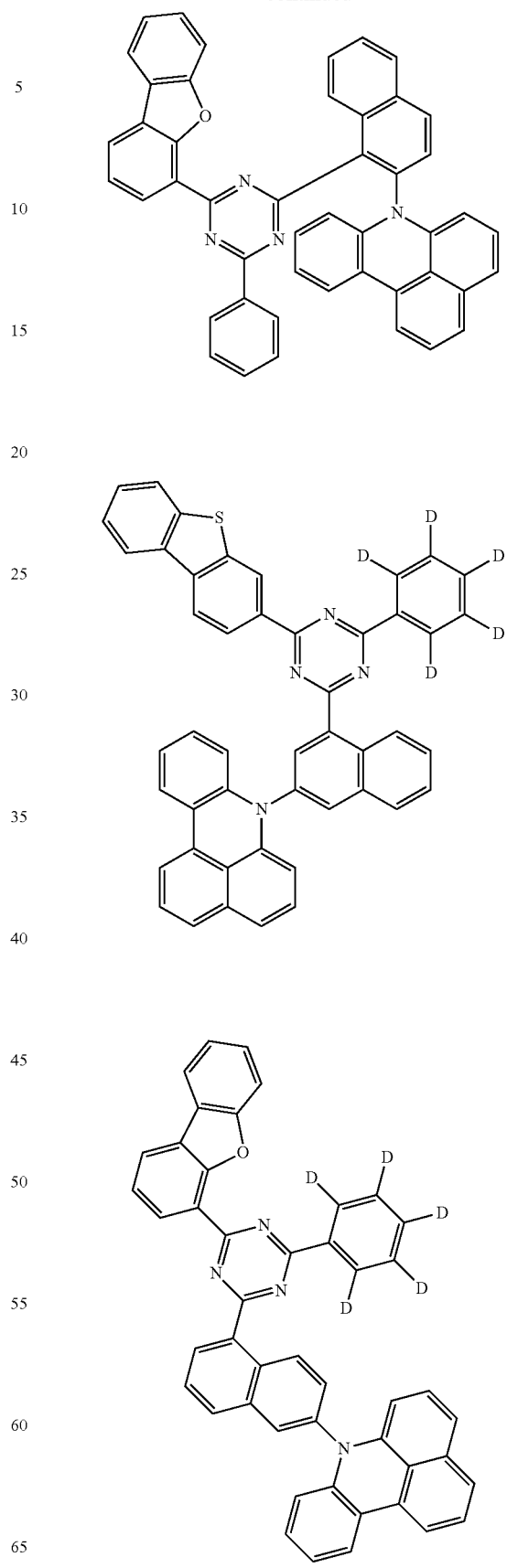

427
-continued
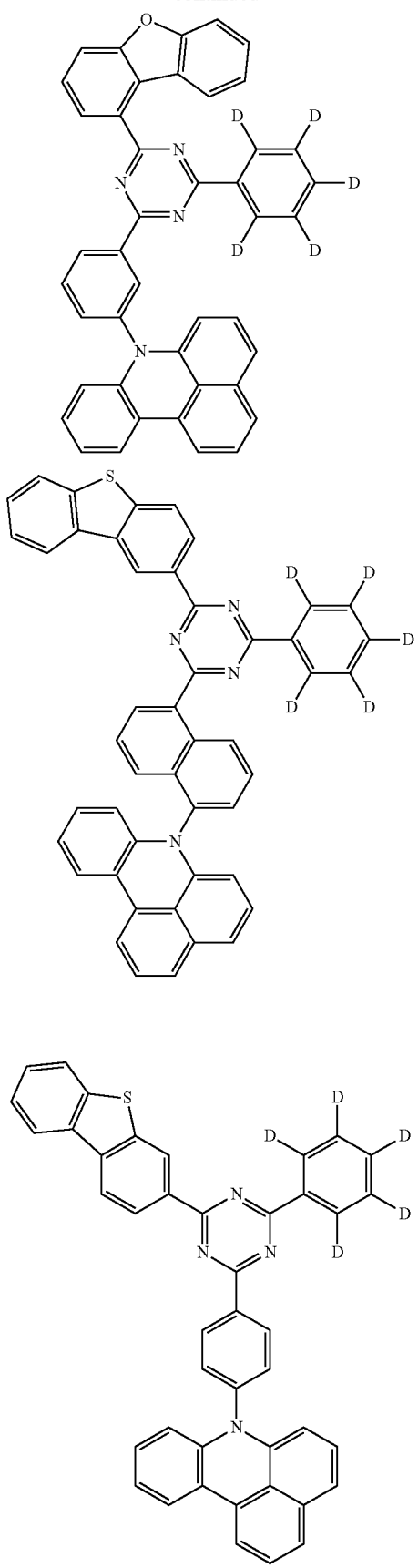
428
-continued
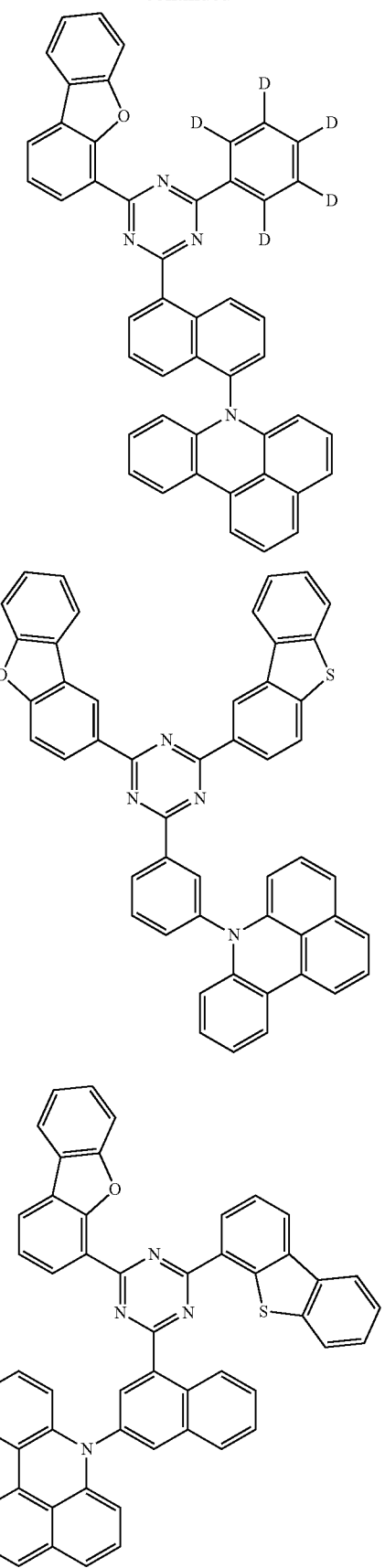

429
-continued
430
-continued
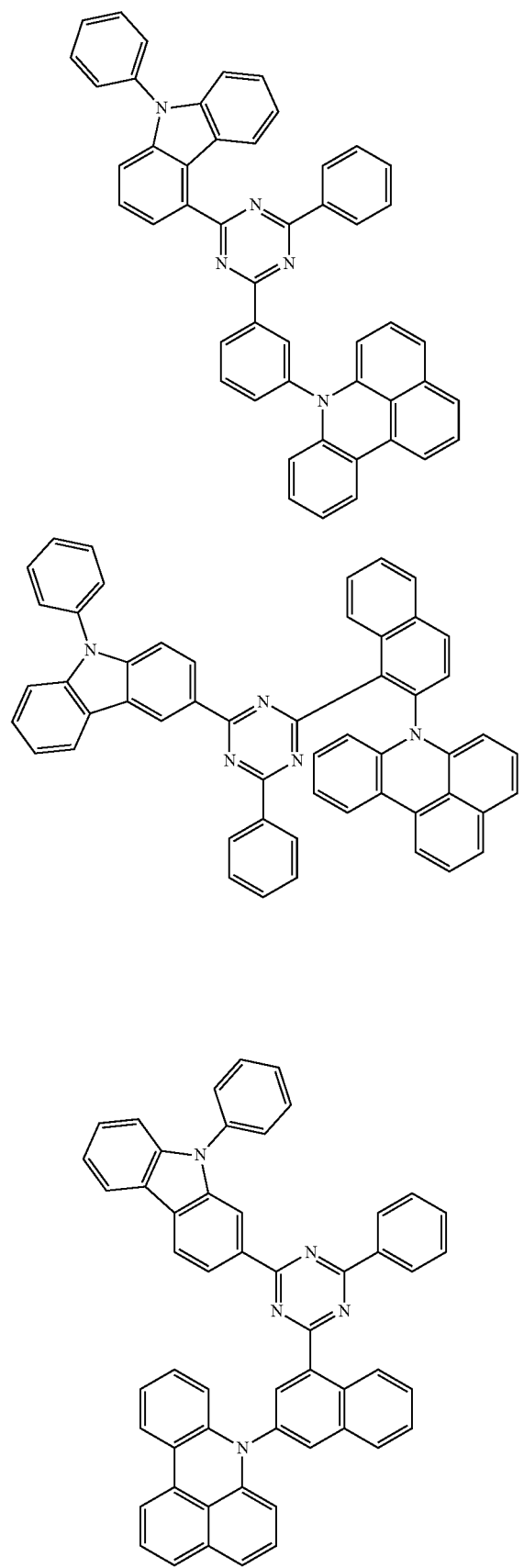
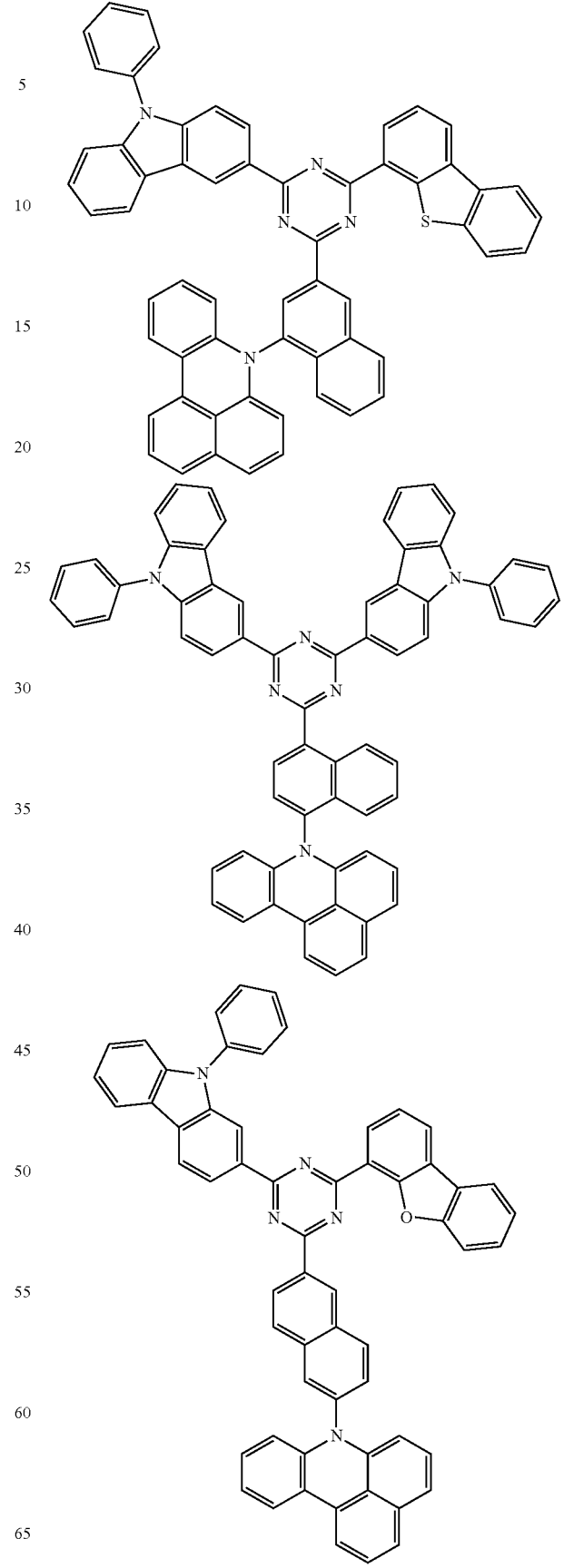

431
-continued
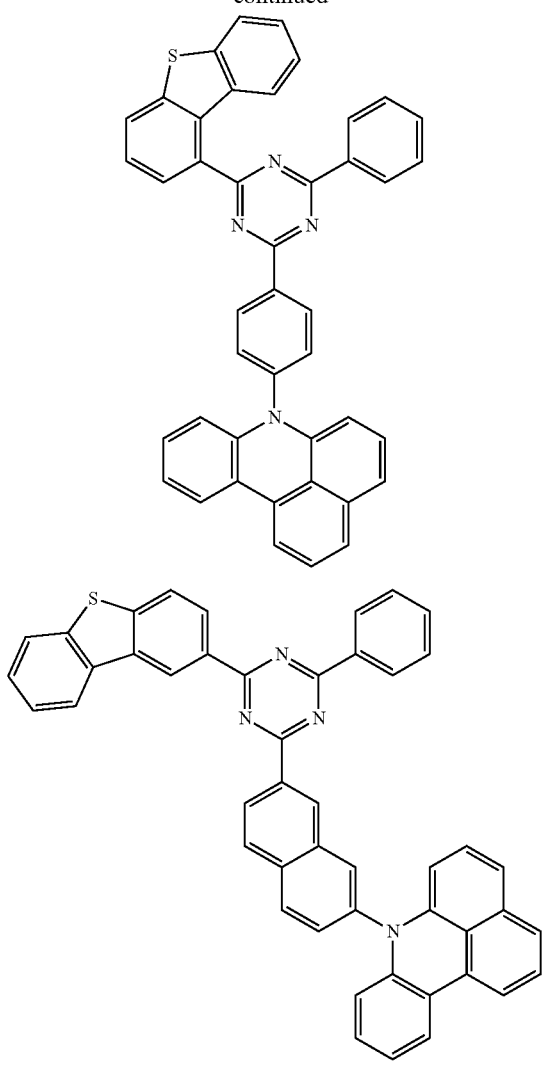
432
-continued
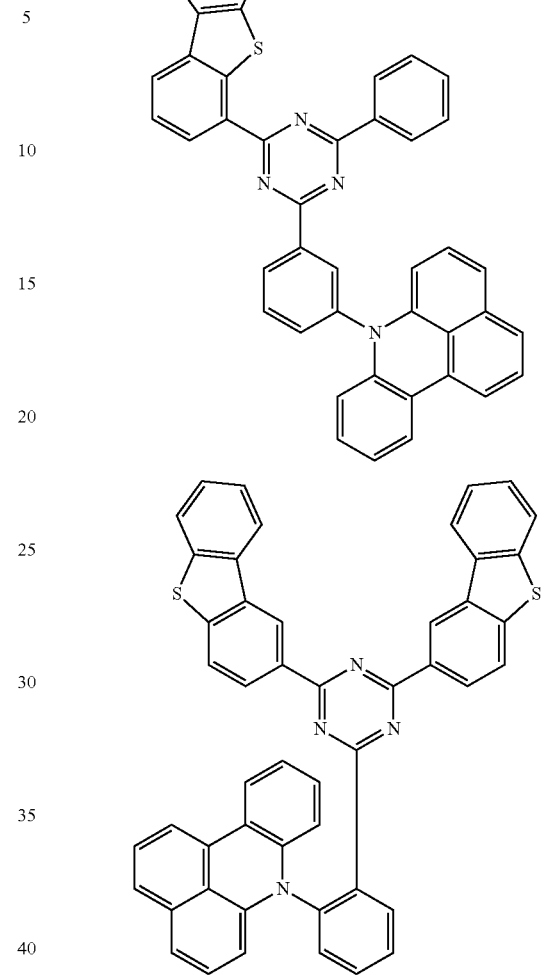
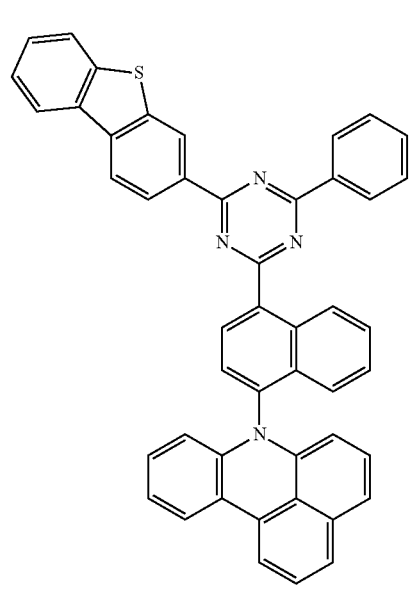
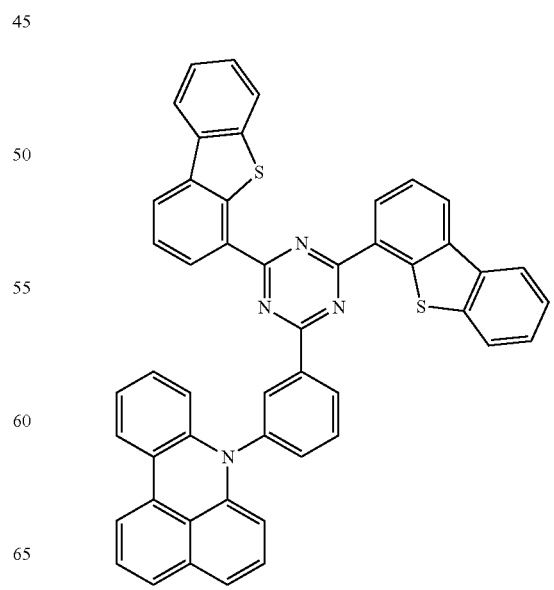

433
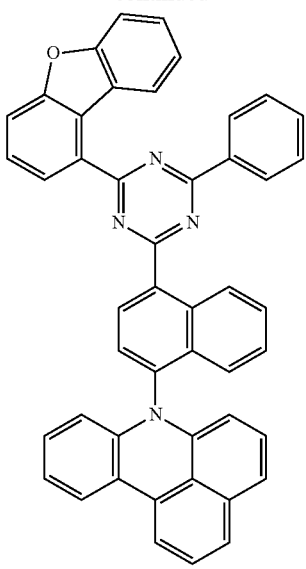
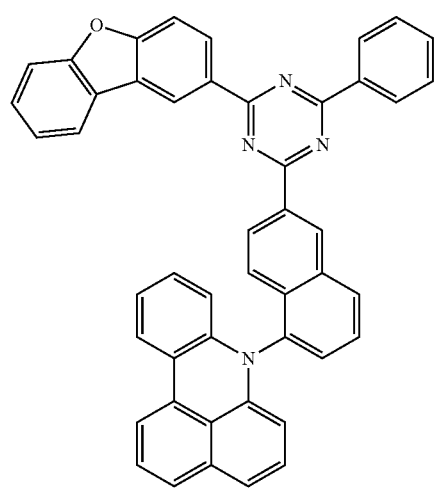
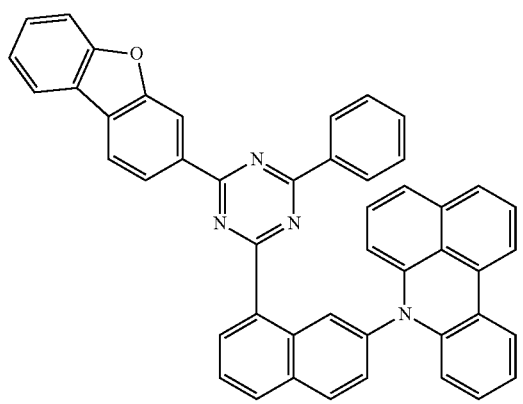
434
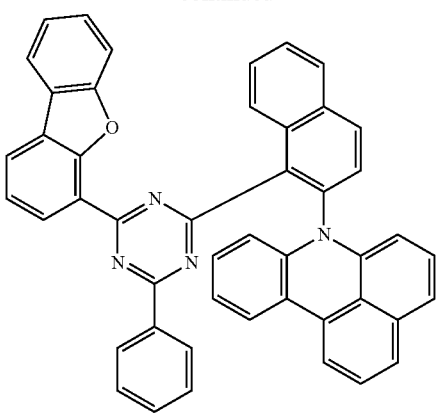
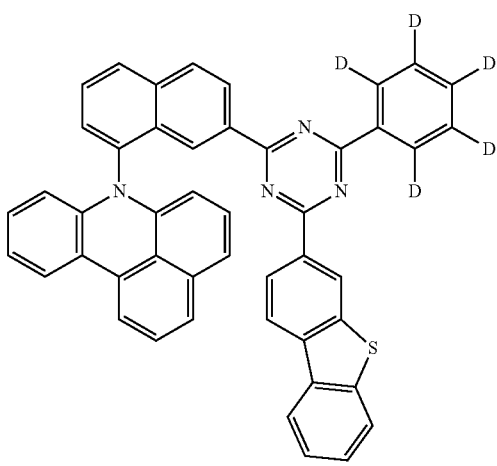
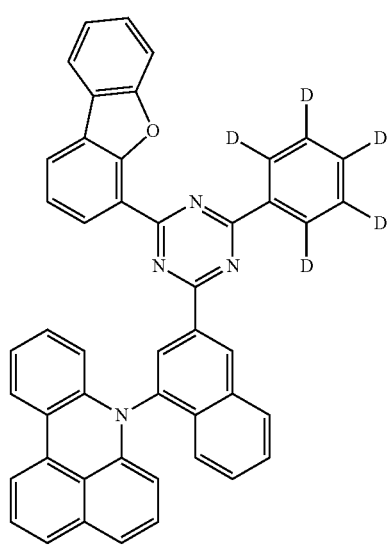

435
-continued
436
-continued
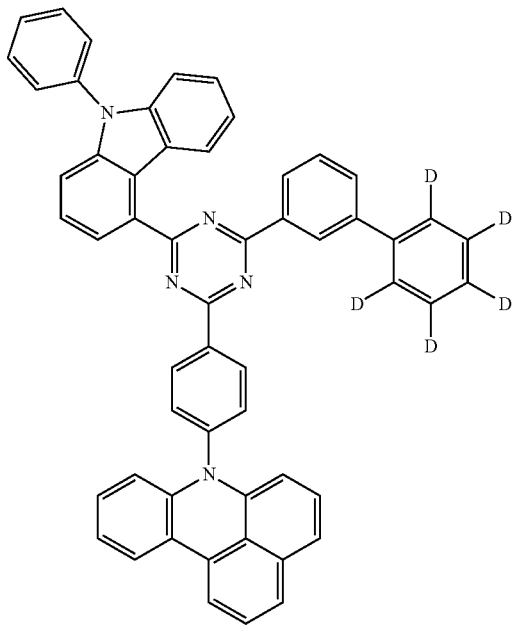
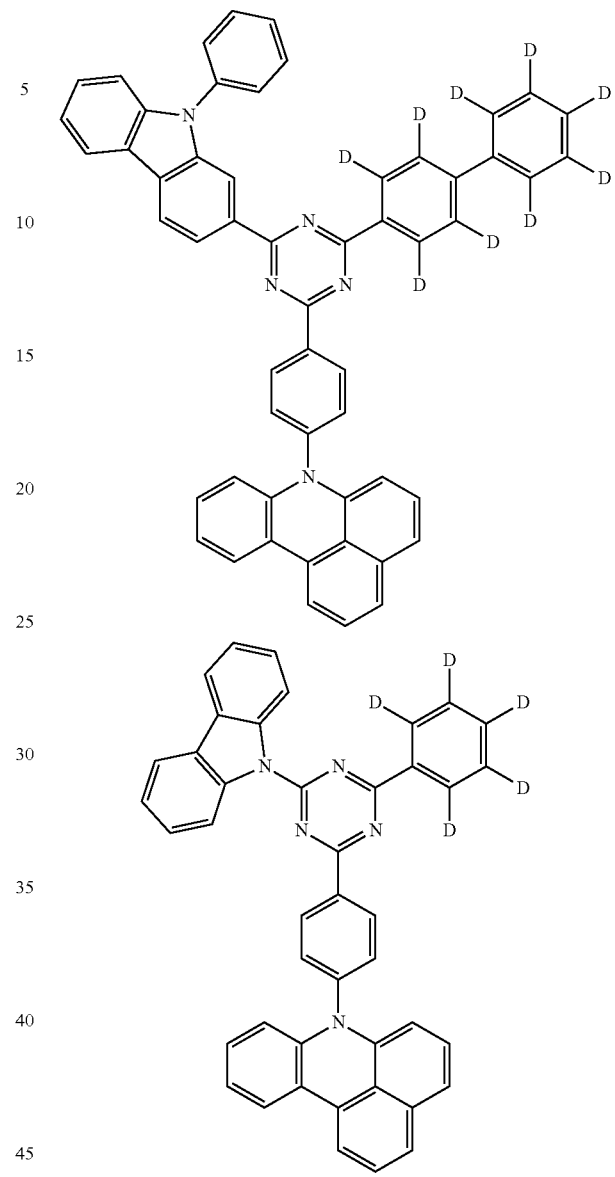
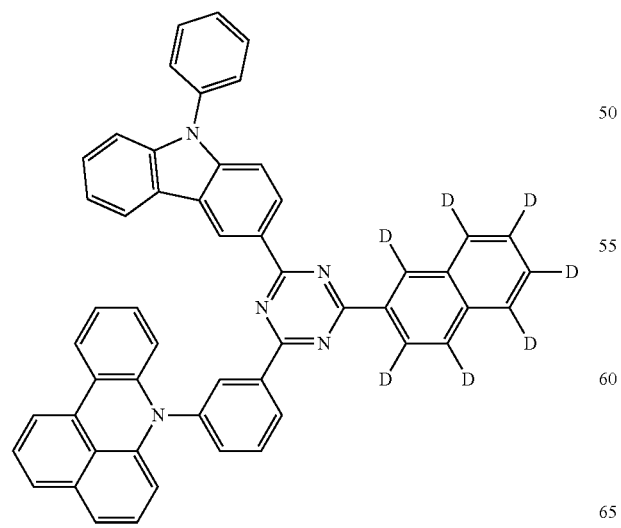

437
-continued
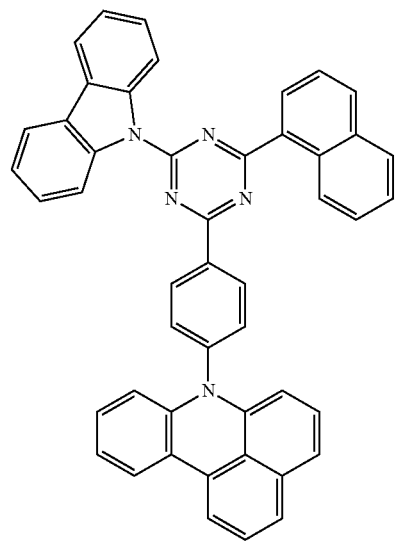
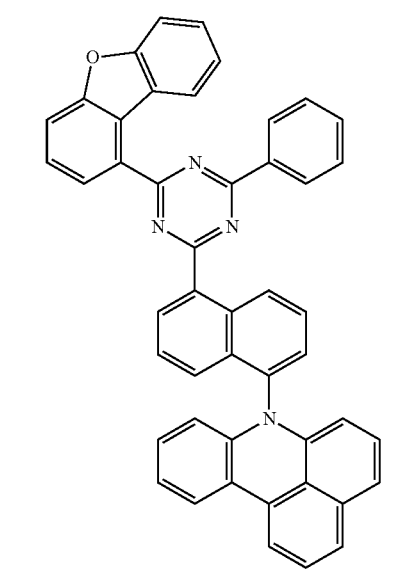
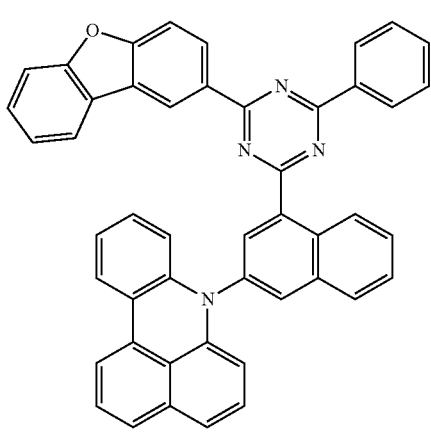
438
-continued
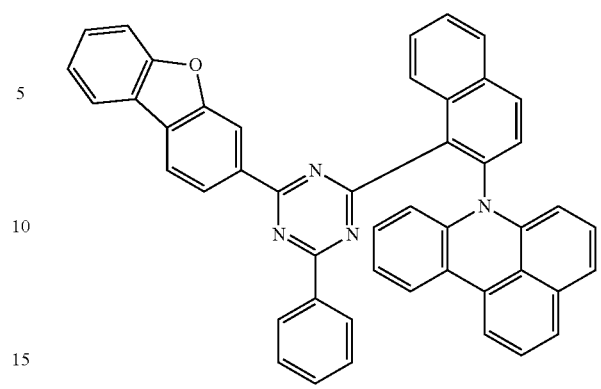
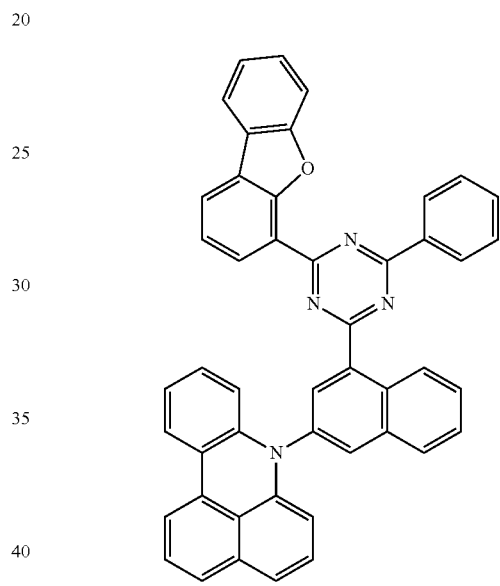
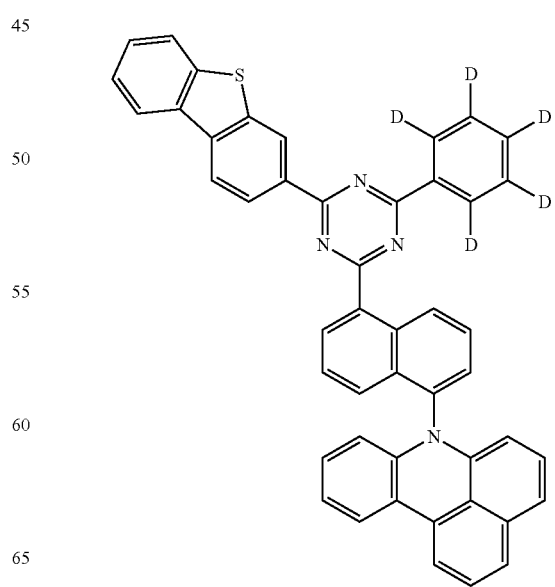

439
-continued
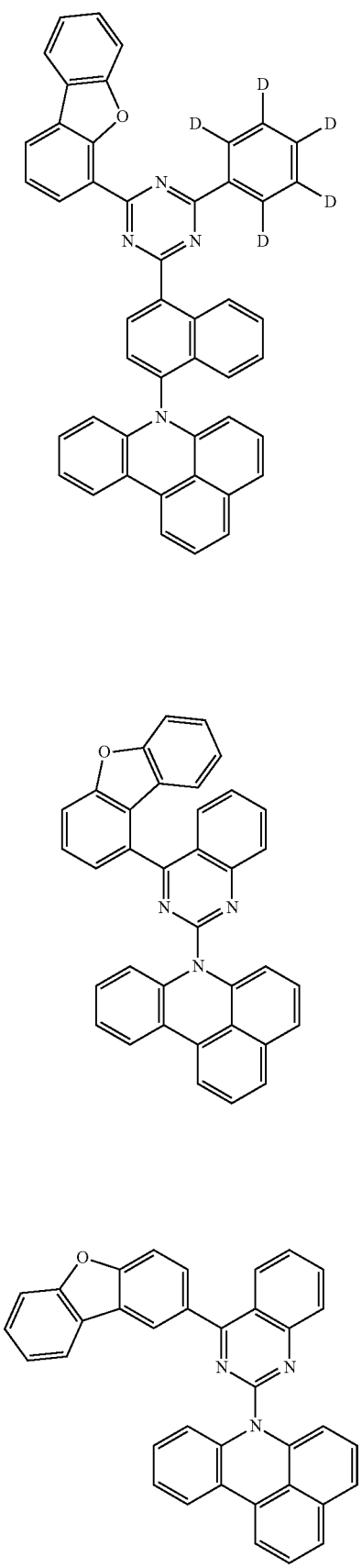
440
-continued
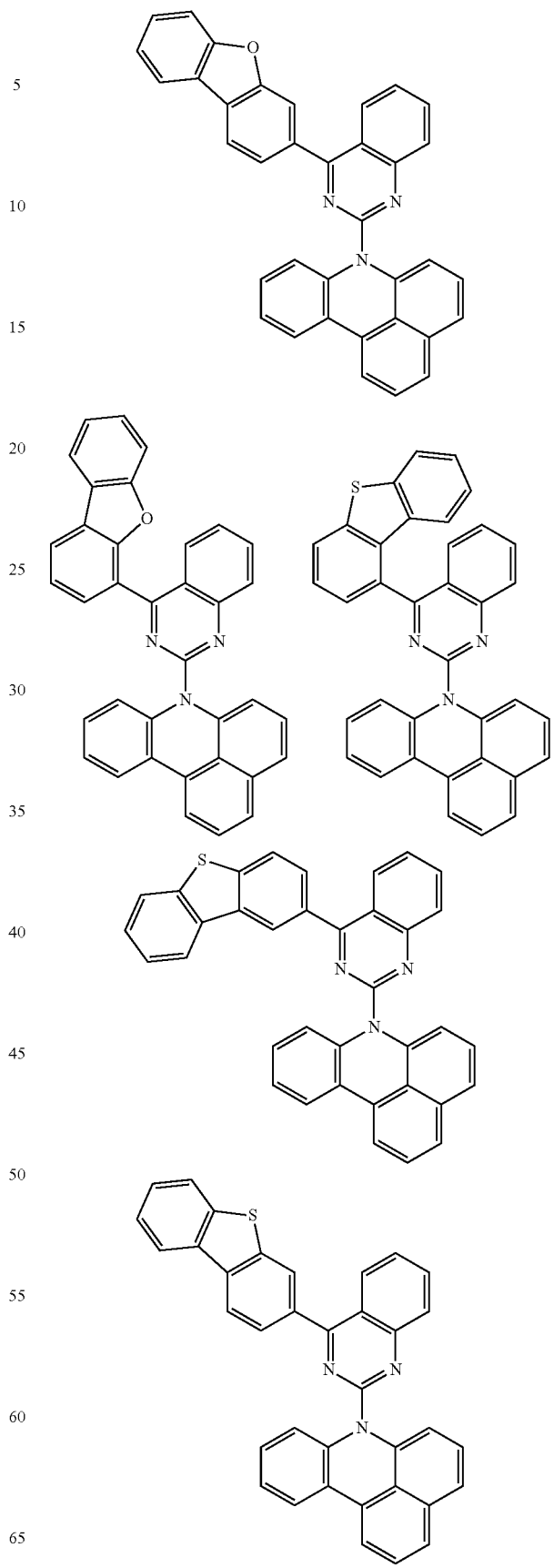

441
-continued
442
-continued
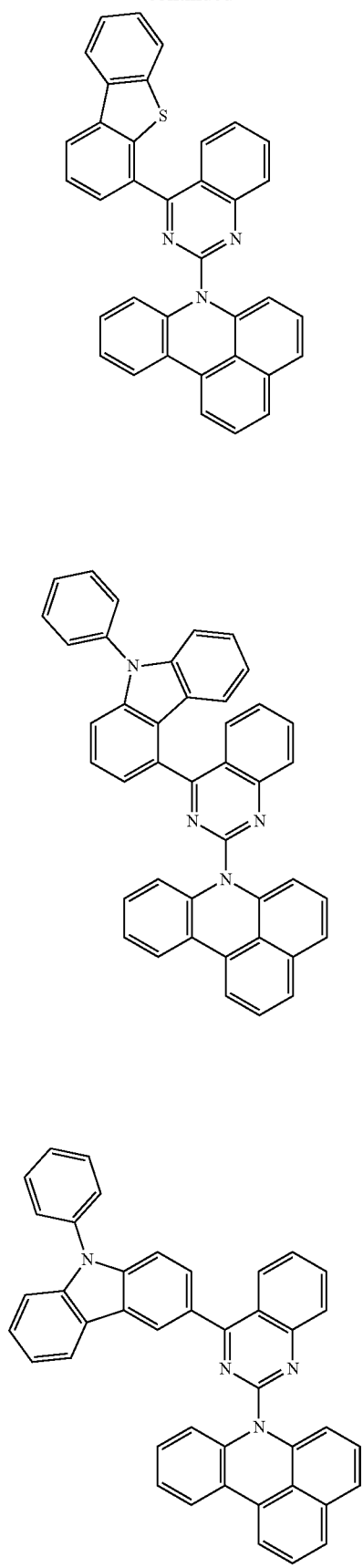
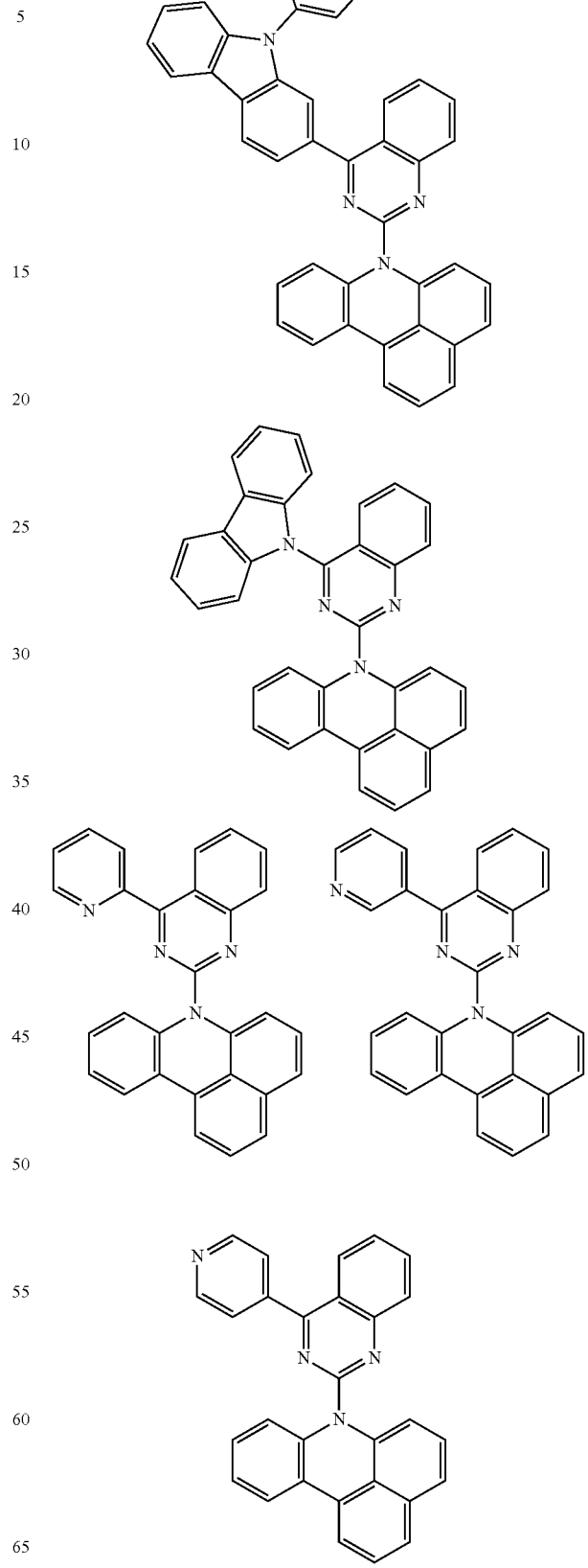

443
-continued
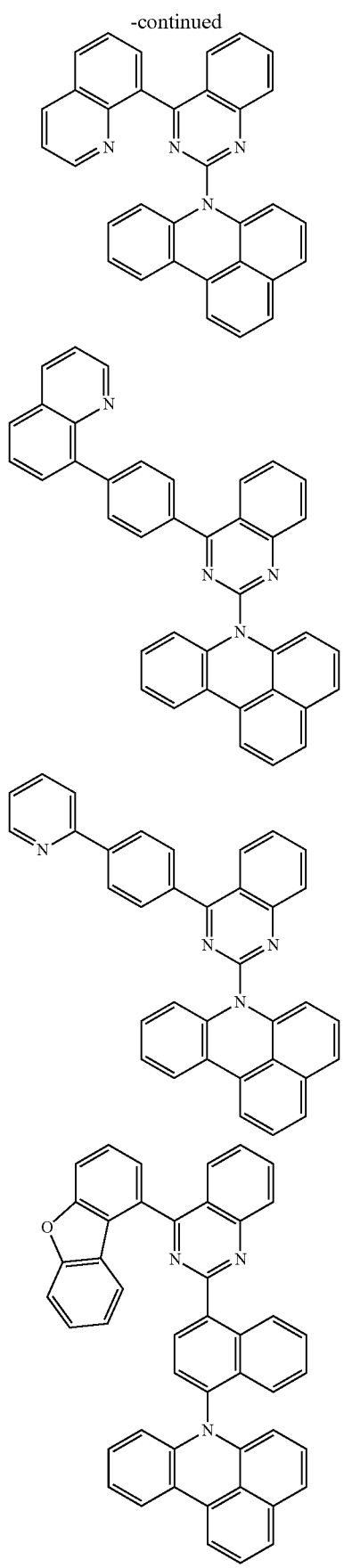
444
-continued
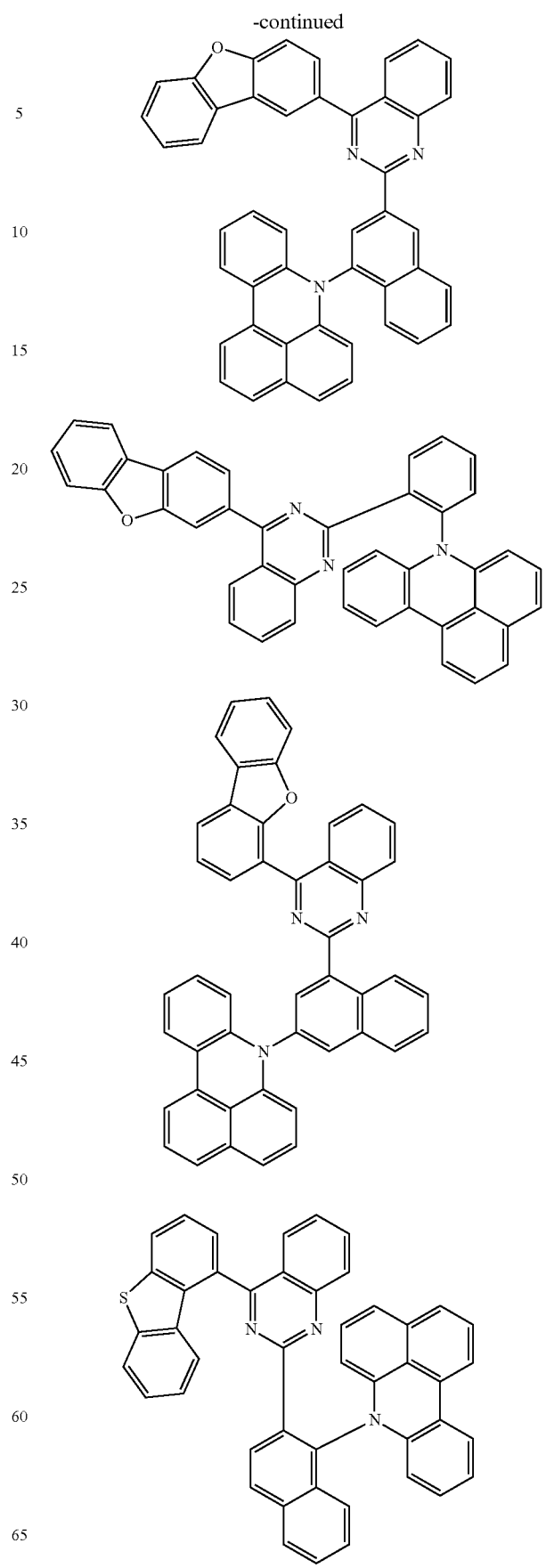

445
-continued
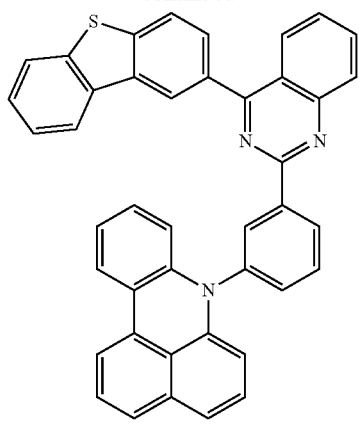
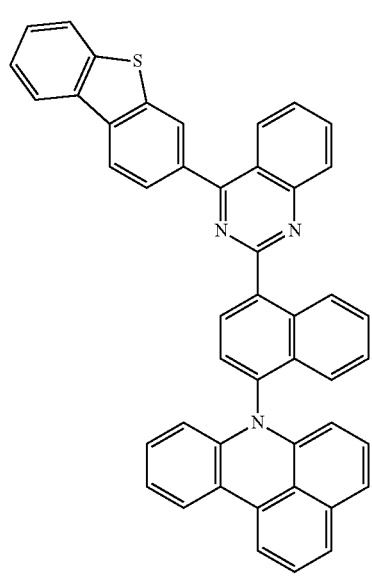
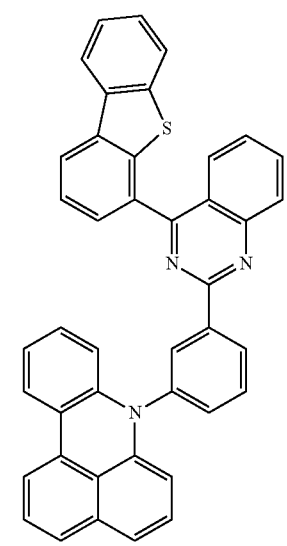
446
-continued
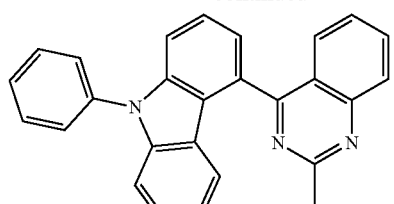
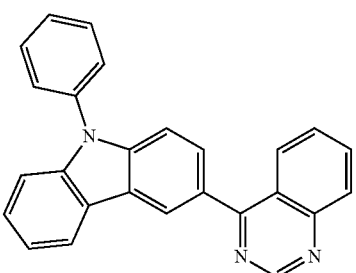
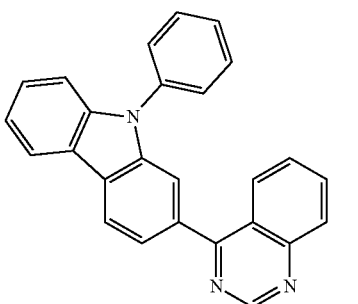

447
-continued
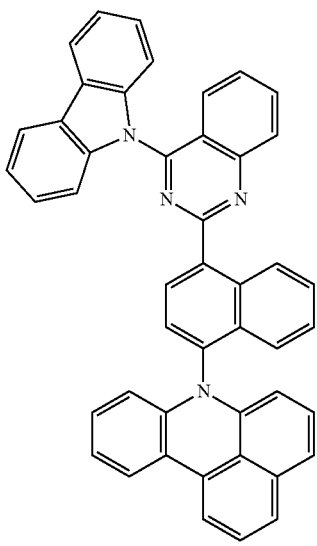
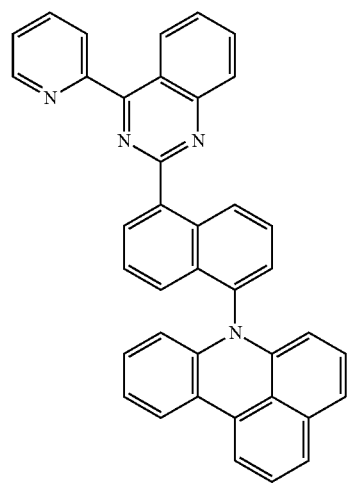
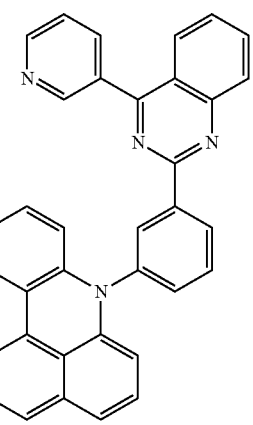
448
-continued
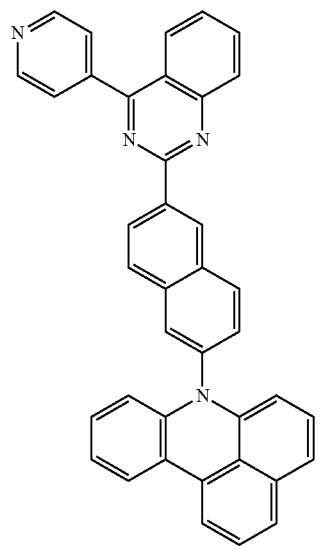
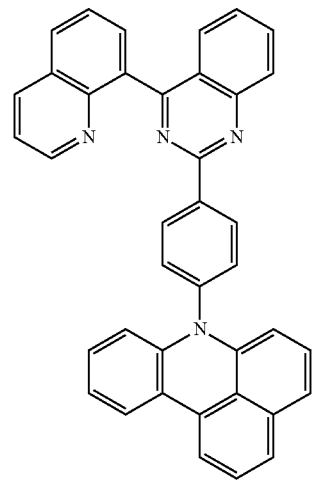
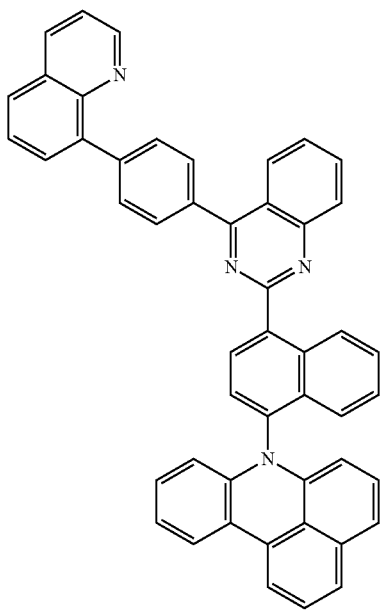

449
-continued
450
-continued
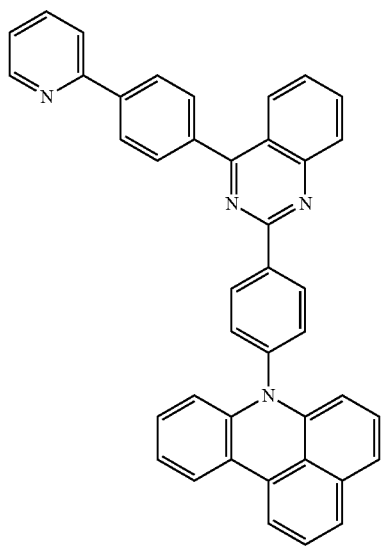
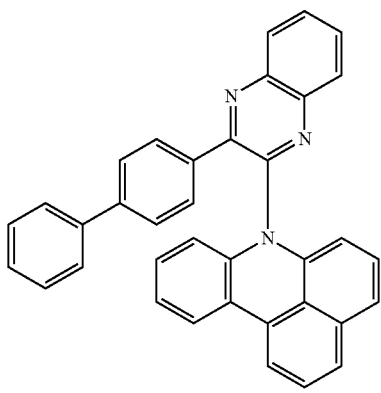
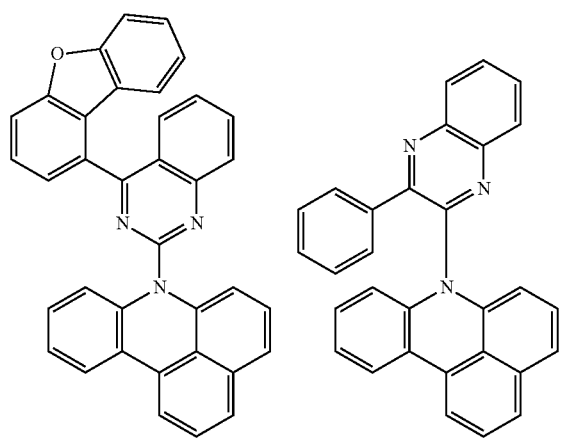
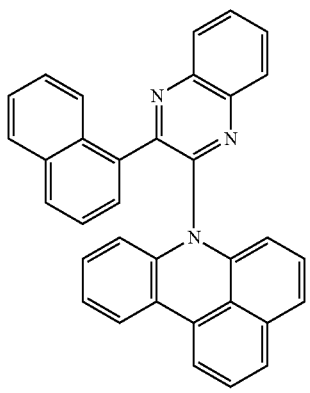
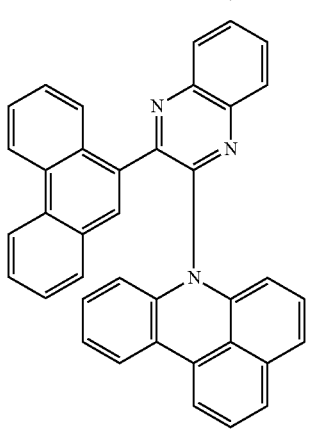
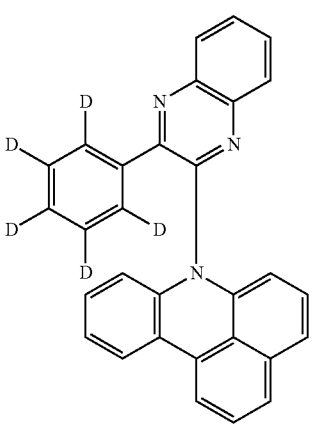

| 451 | 452 |
|---|---|
| -continued | -continued |
| 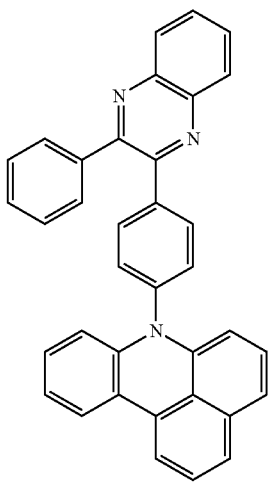 | 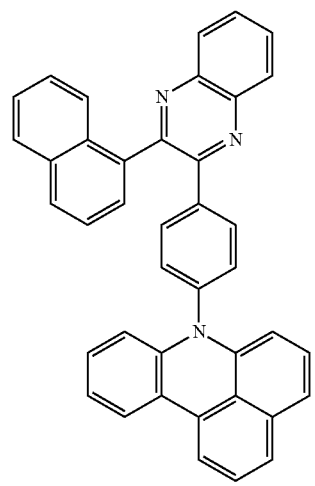 |
| 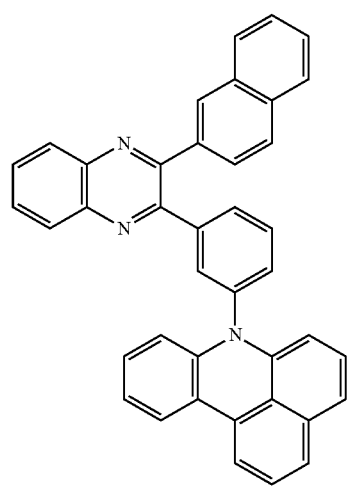 | 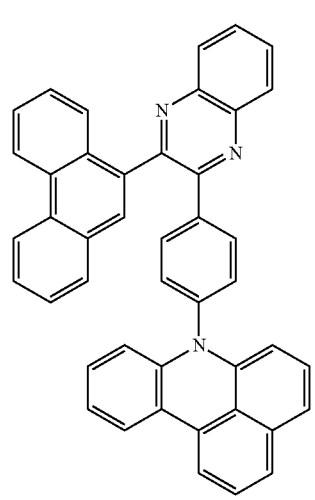 |
| 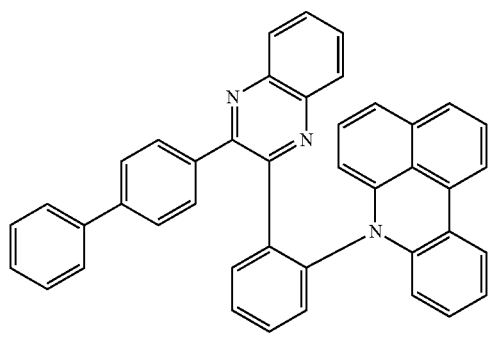 | 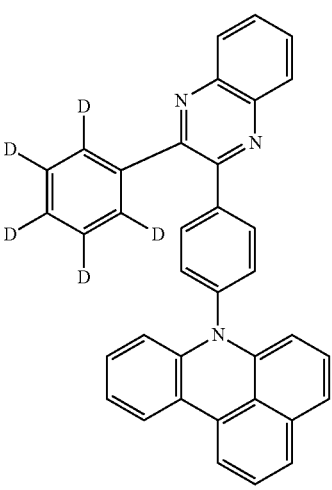 |

453
-continued
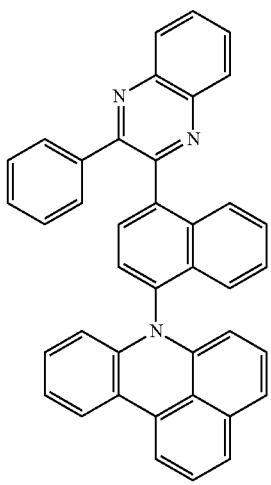
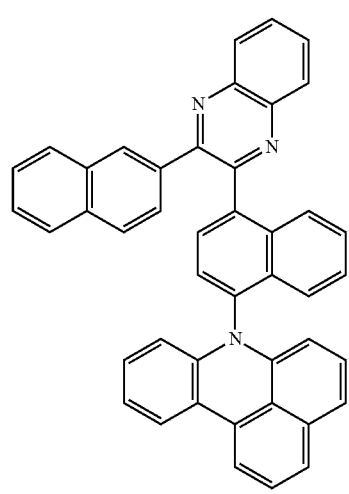
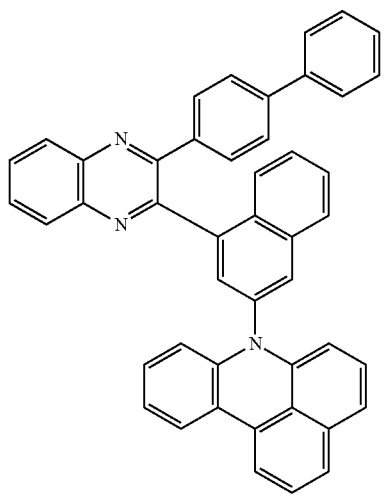
454
-continued
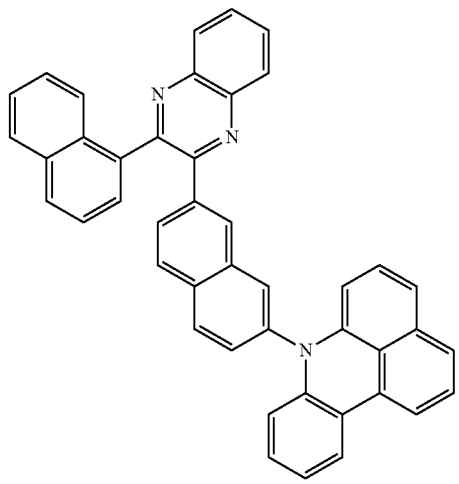
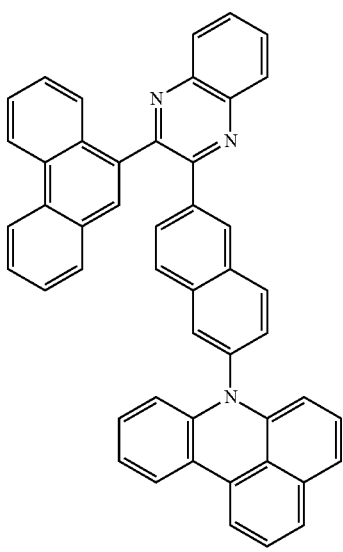
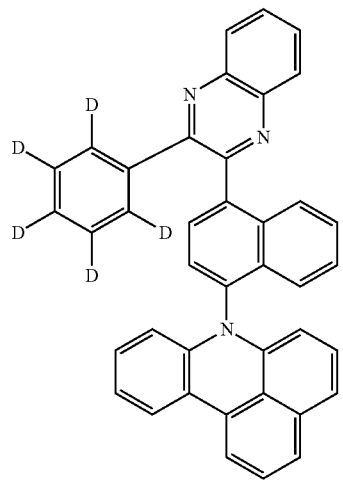

455
-continued
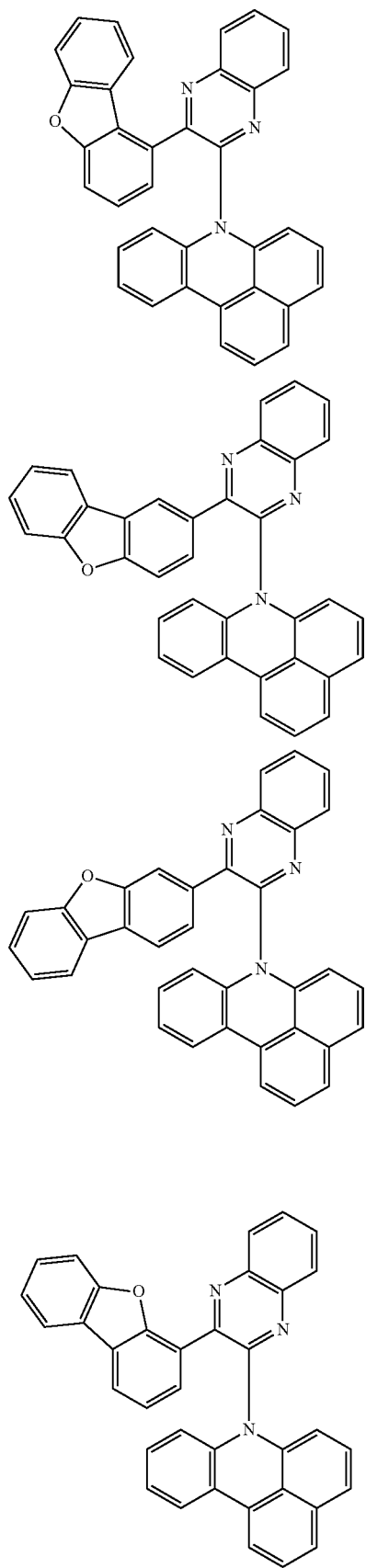
456
-continued
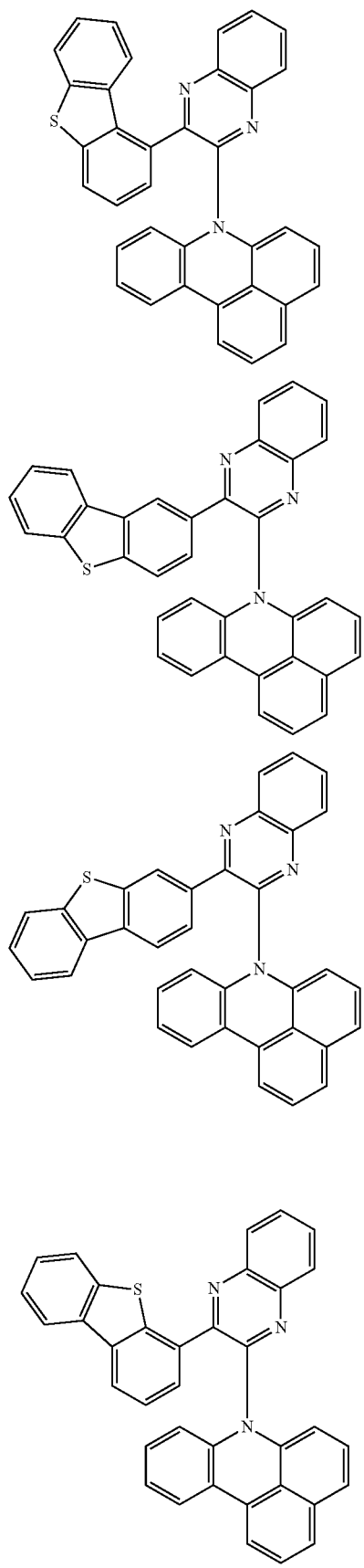

457
-continued
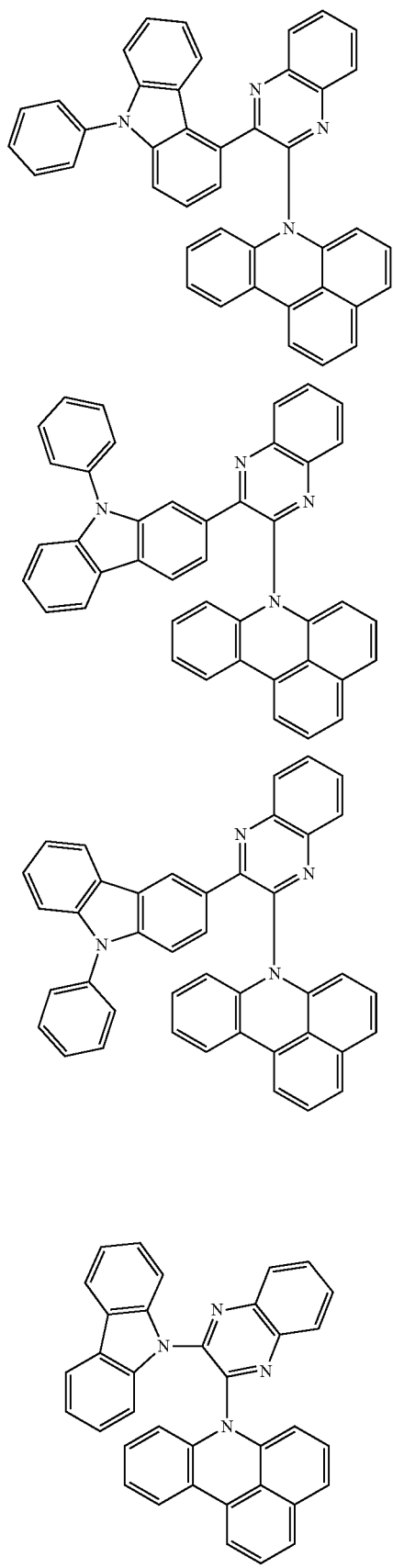
458
-continued
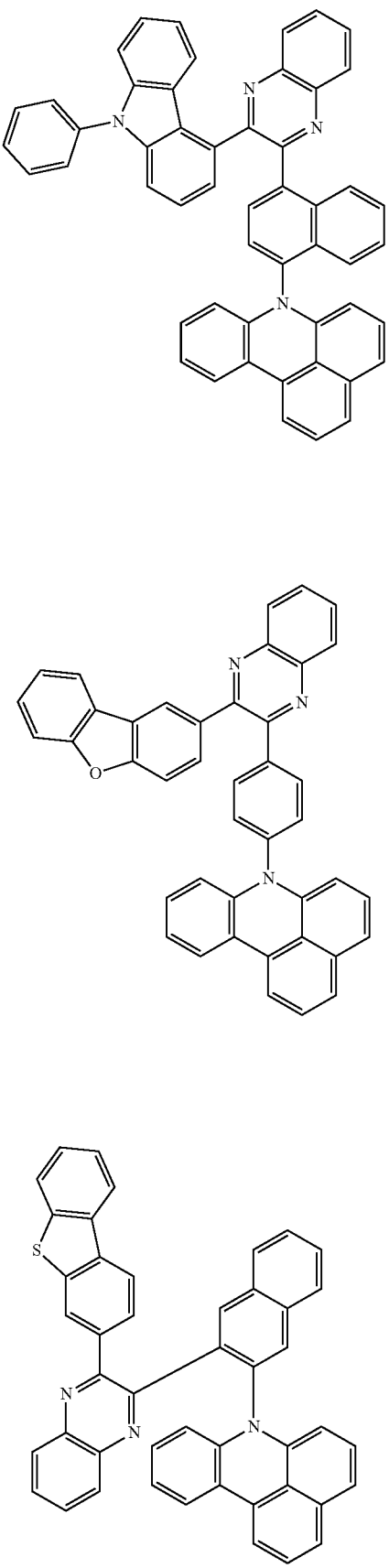

459
-continued
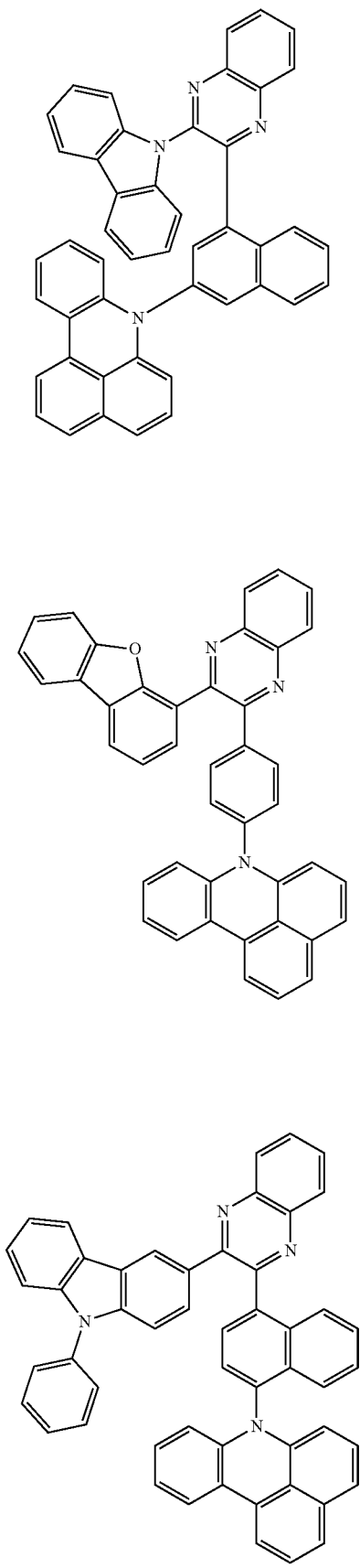
460
-continued
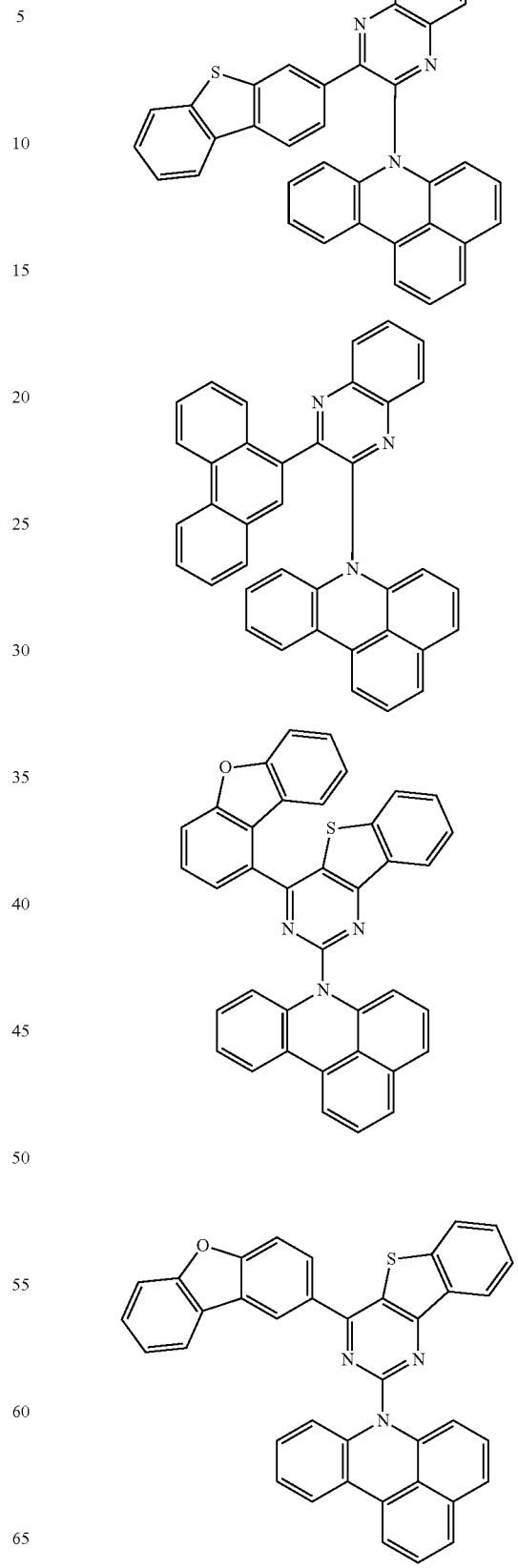

461
-continued
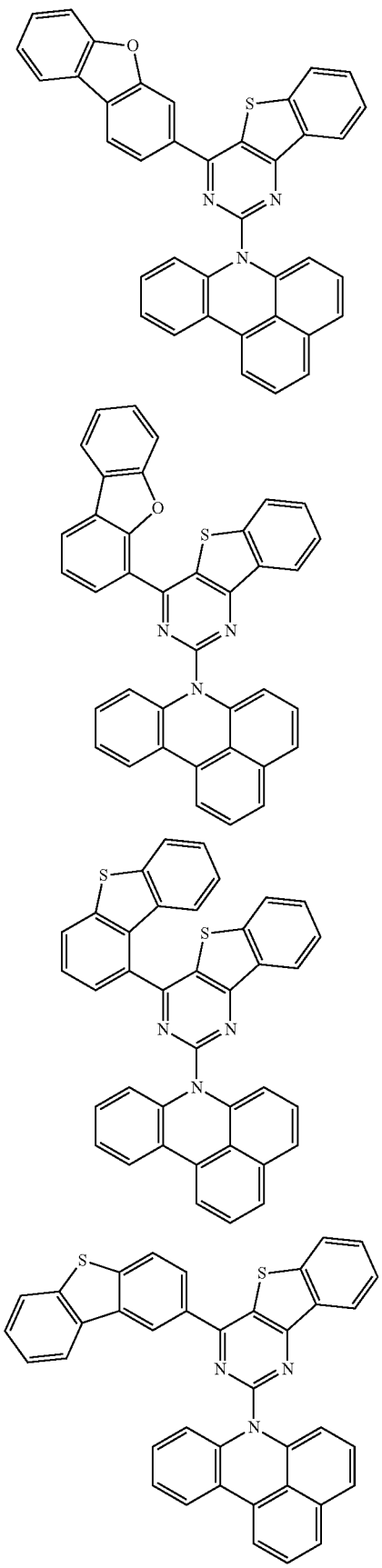
462
-continued
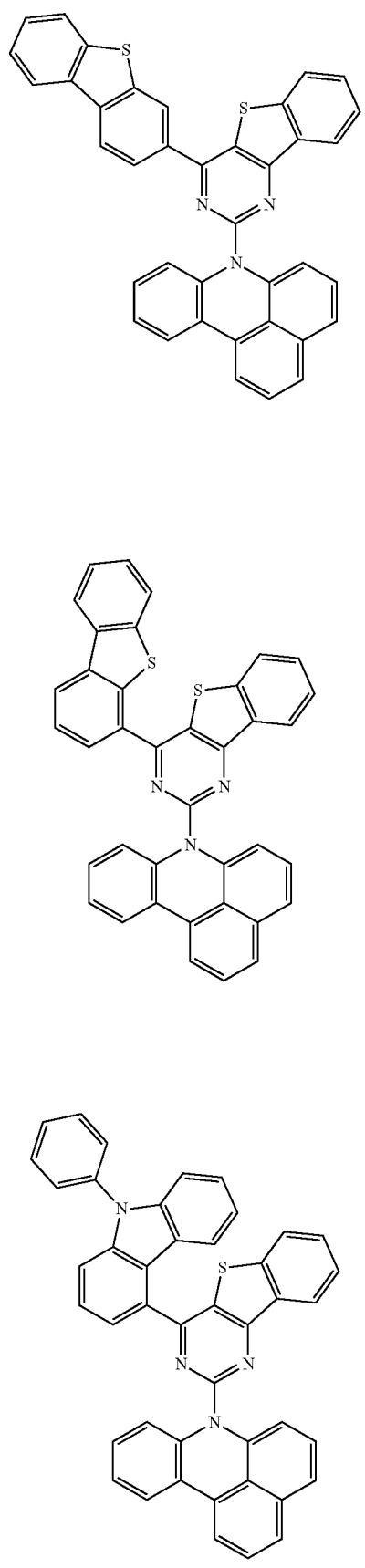

463
-continued
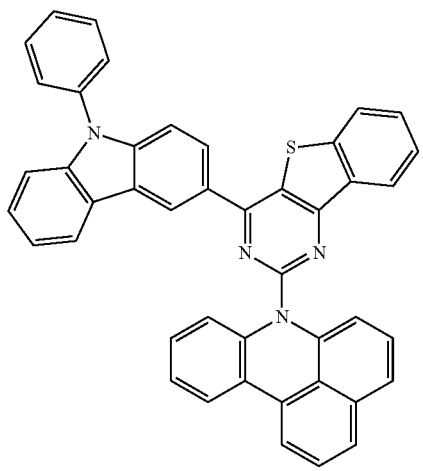
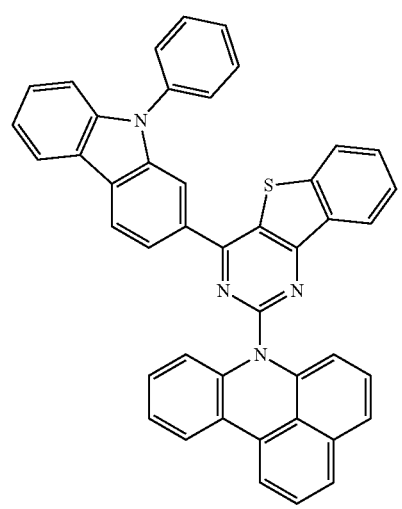
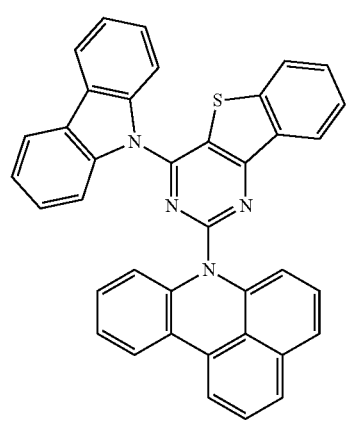
464
-continued
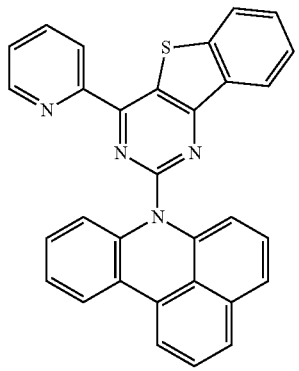
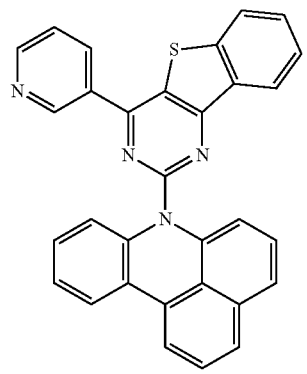
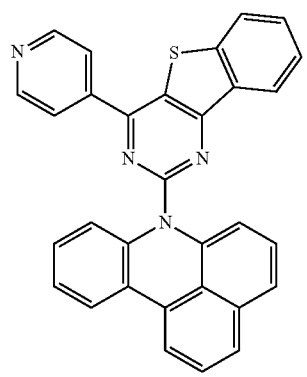
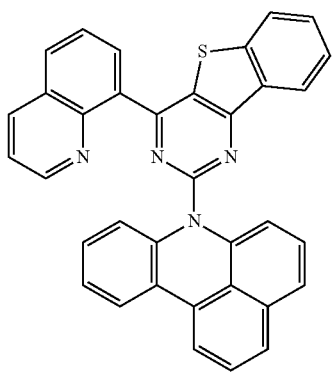

465
-continued
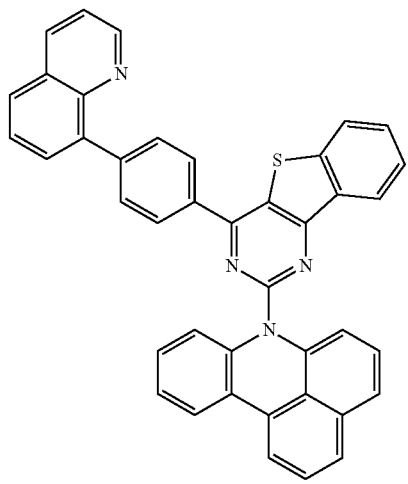
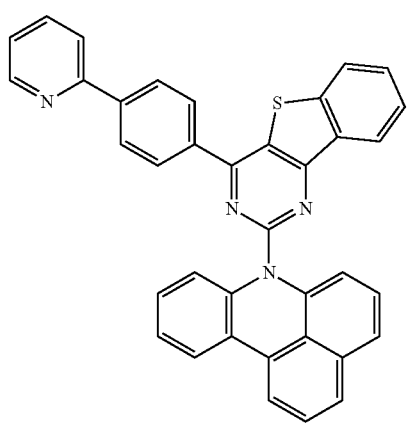
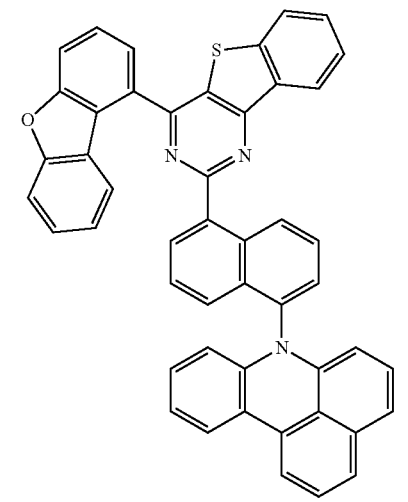
466
-continued
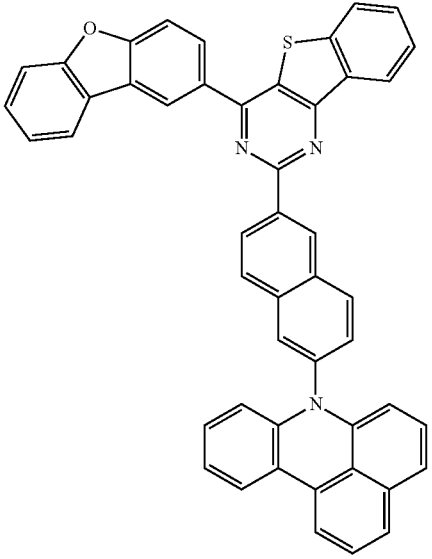
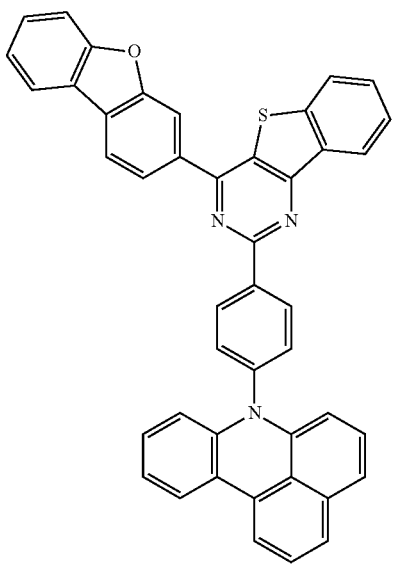
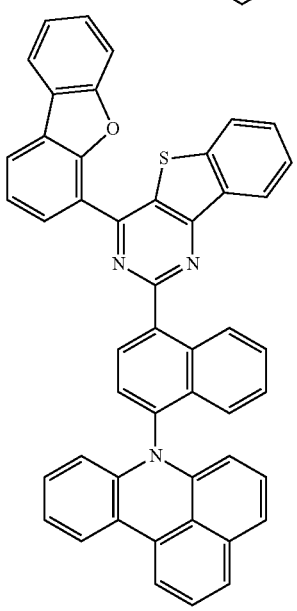

467
-continued
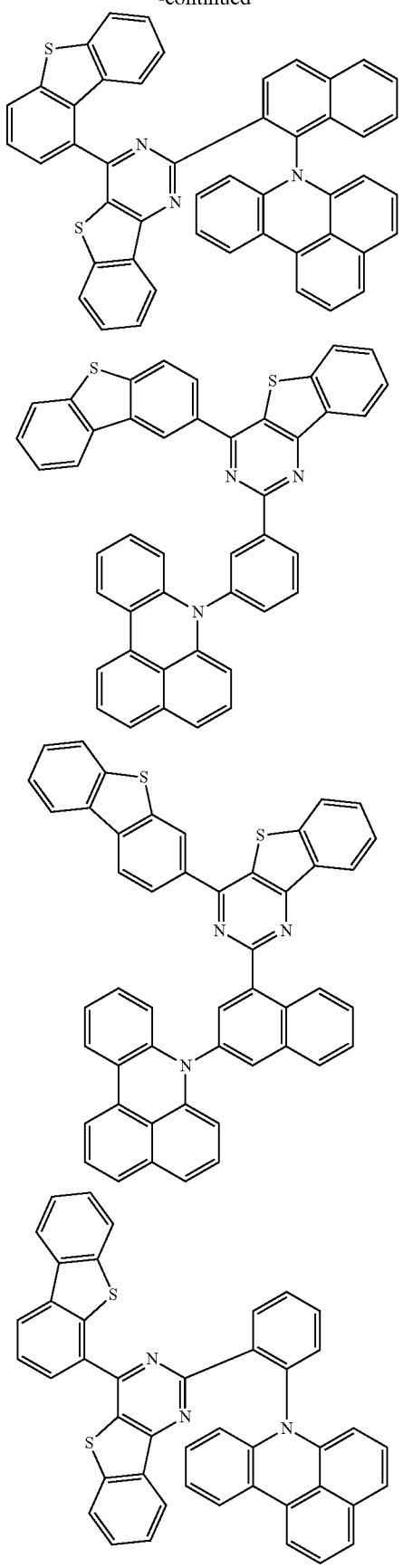
468
-continued
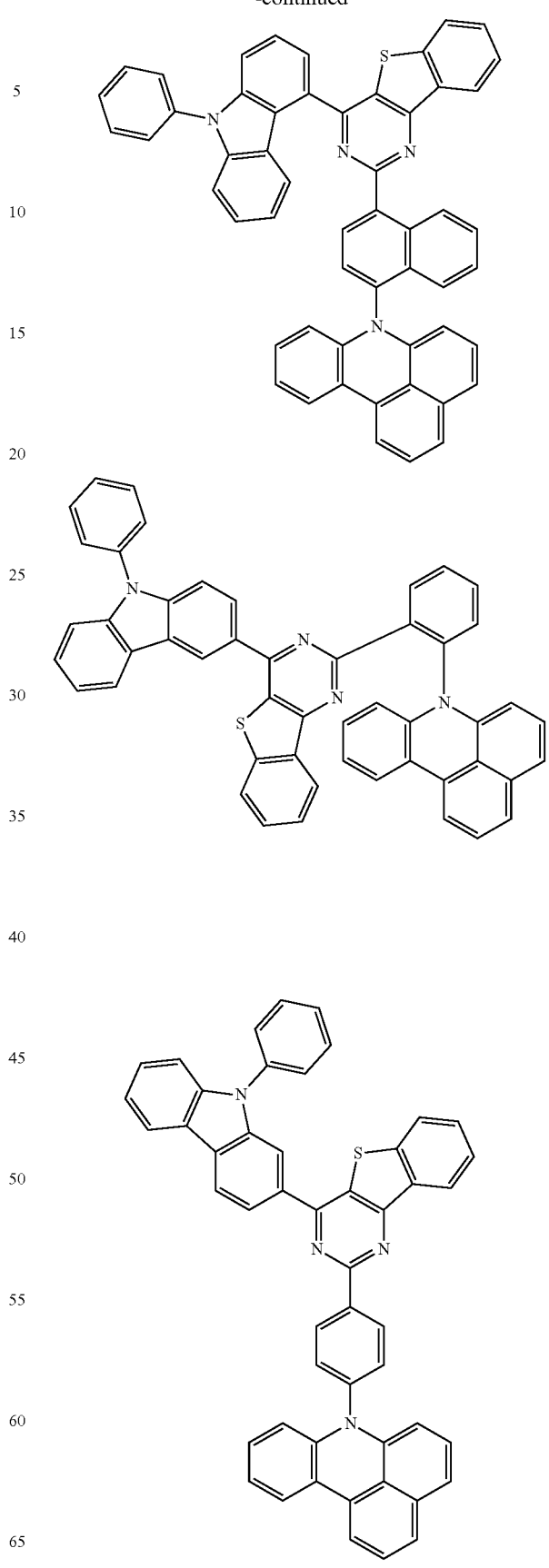

469
-continued
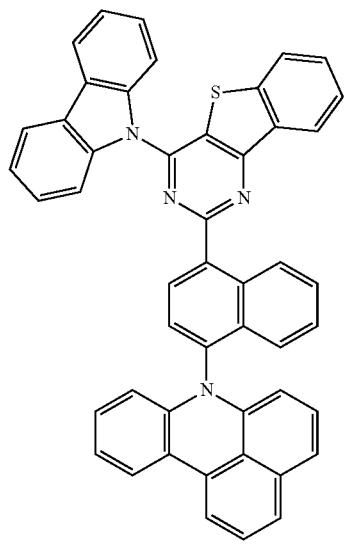
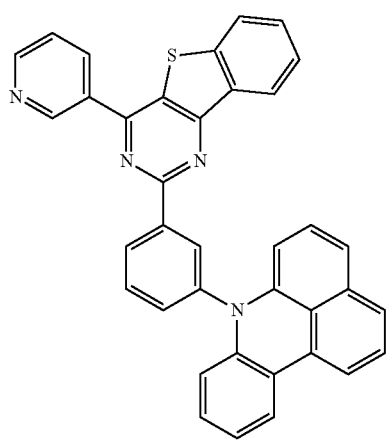
470
-continued
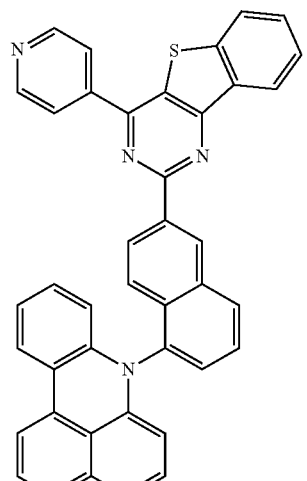
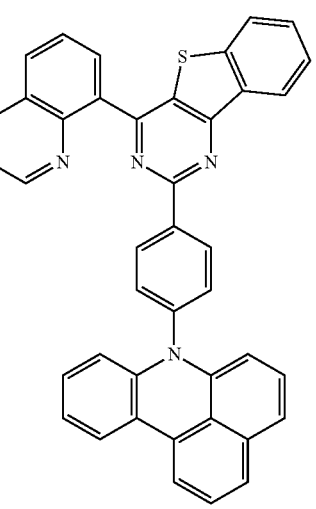
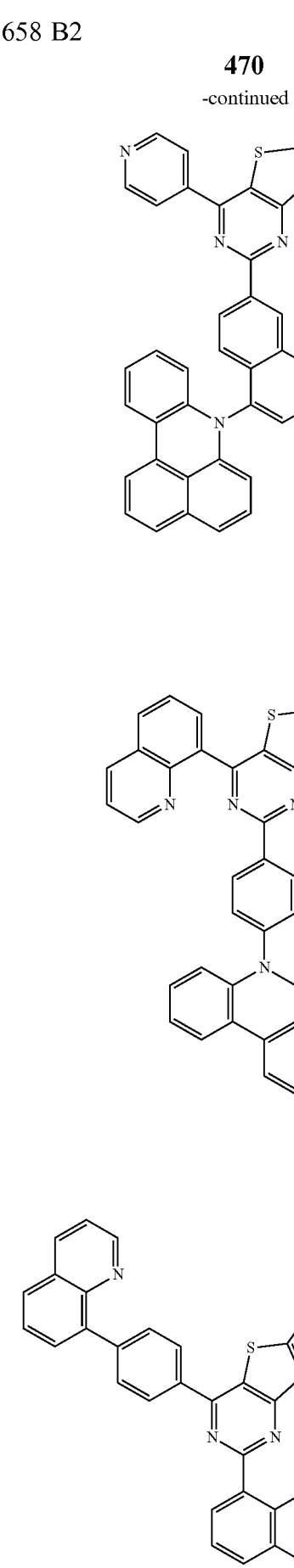

471
-continued
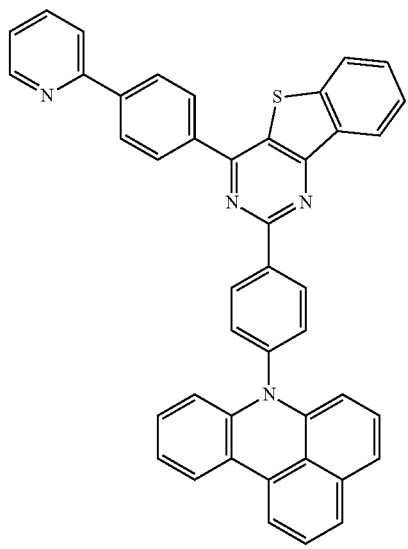
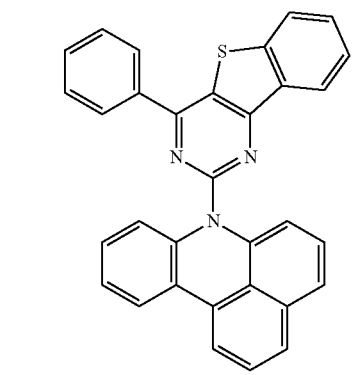
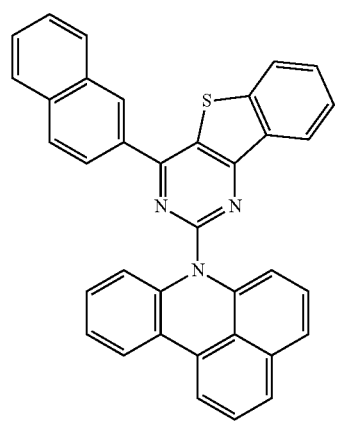
472
-continued
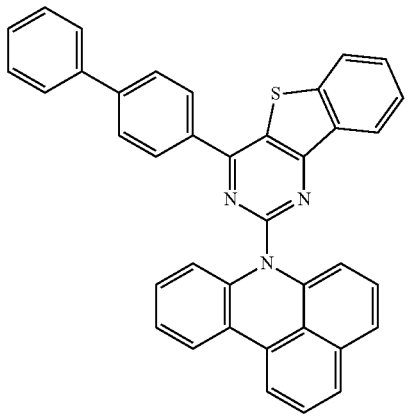
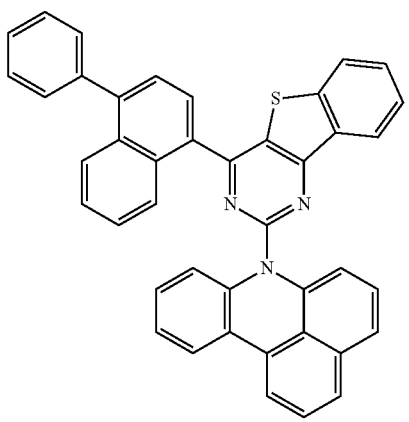
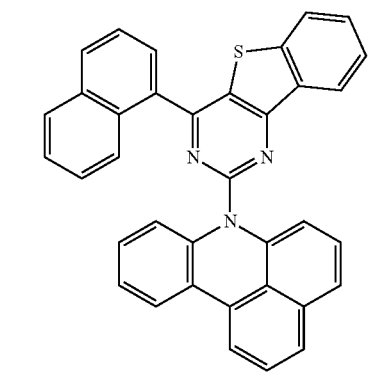
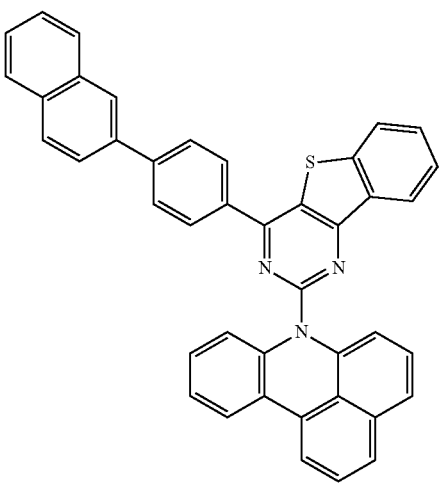

473
-continued
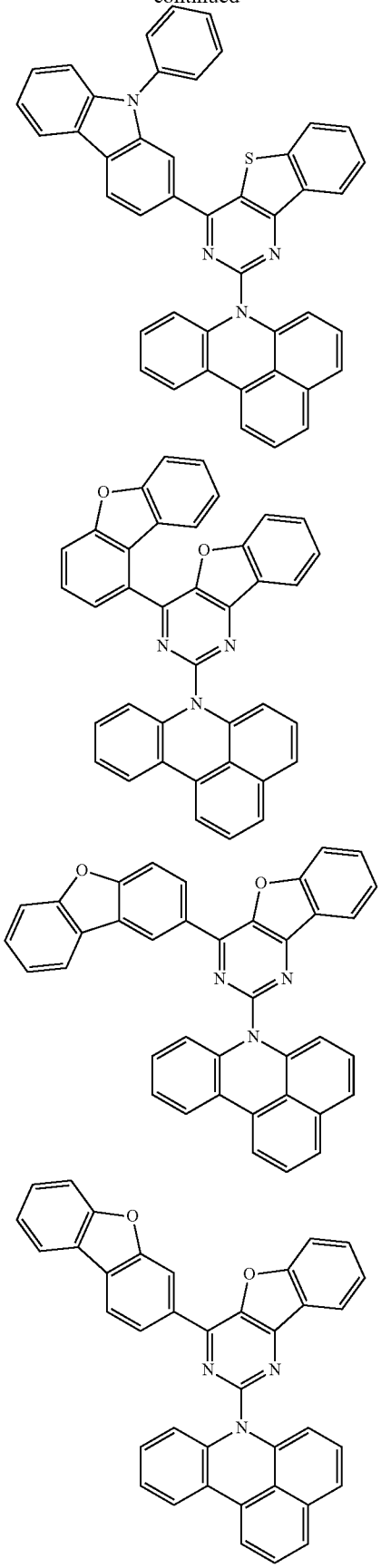
474
-continued
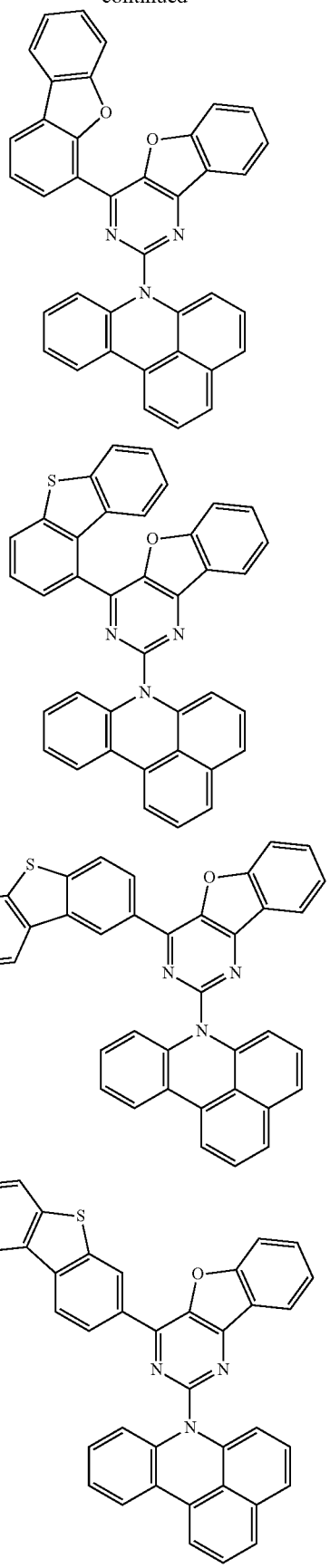

475
-continued
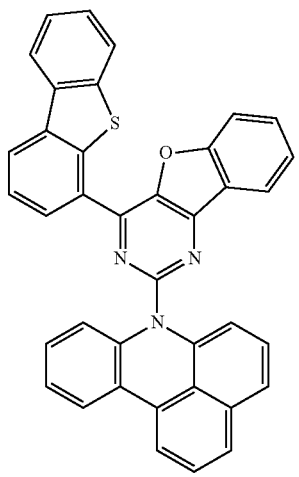
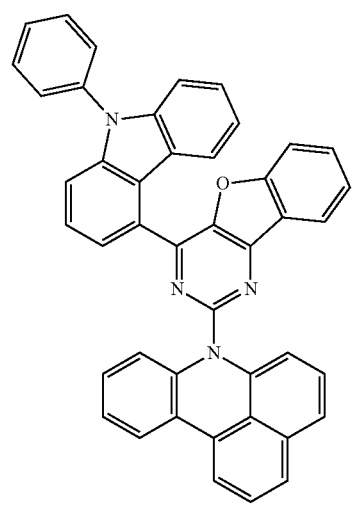
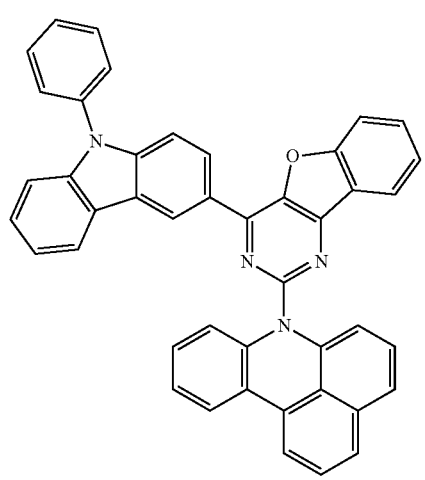
476
-continued
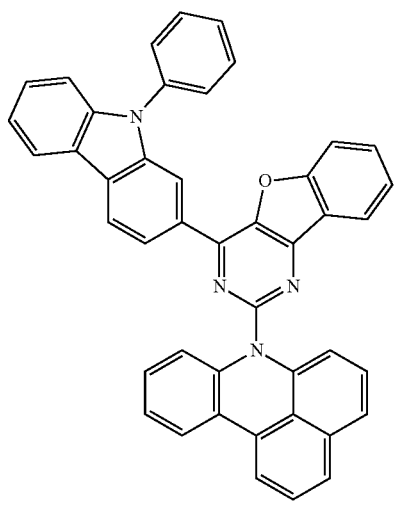
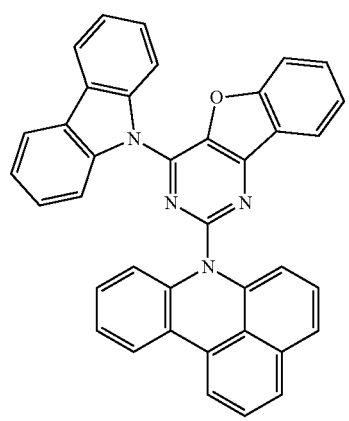
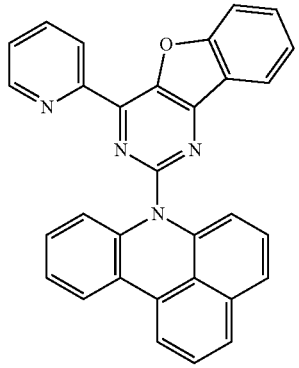
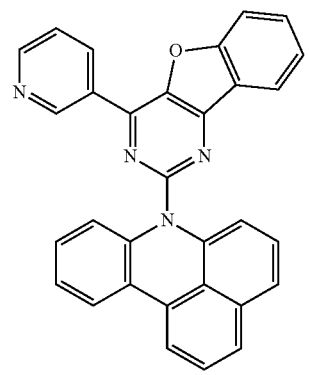

477
-continued
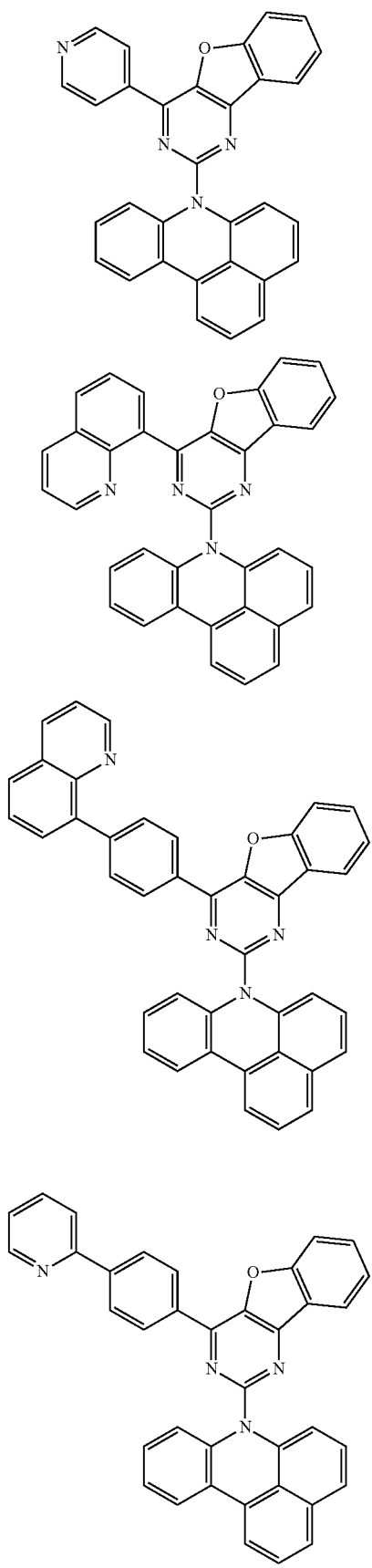
478
-continued
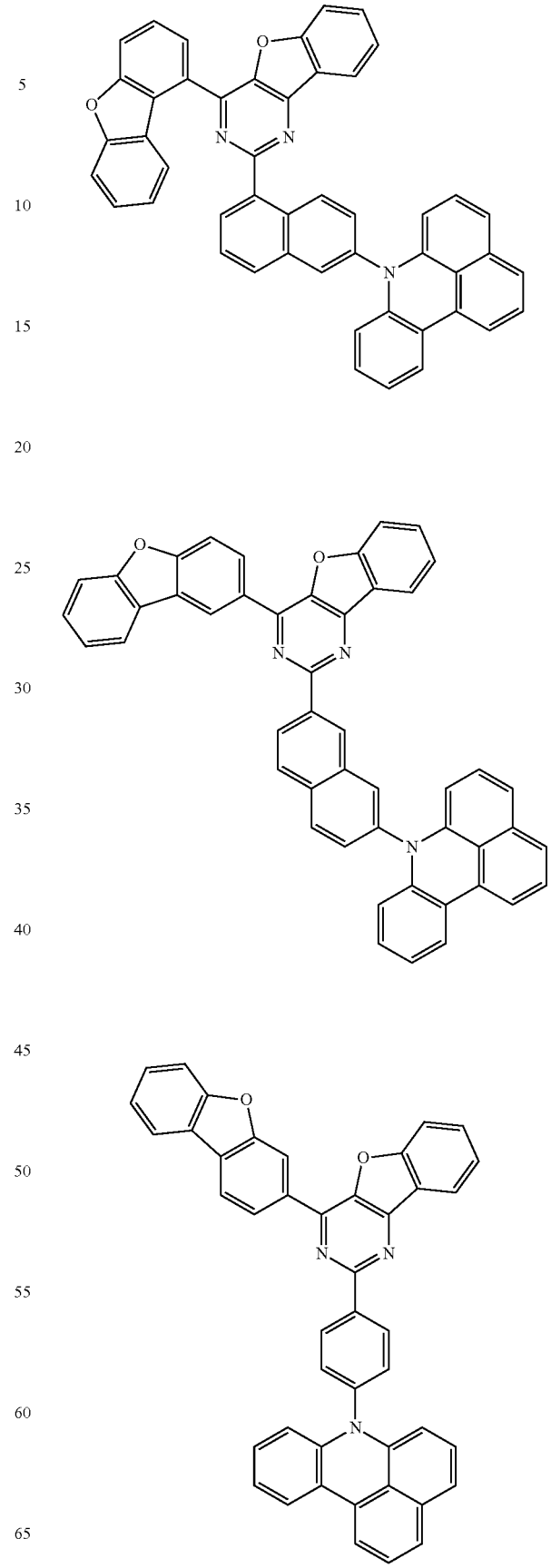

479
-continued
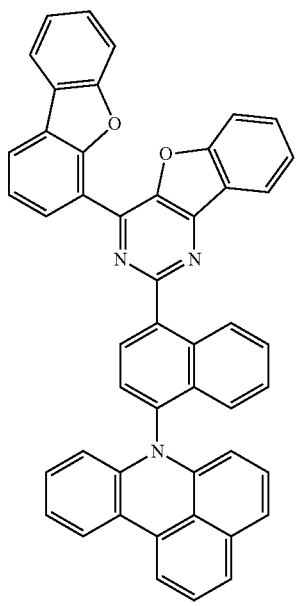
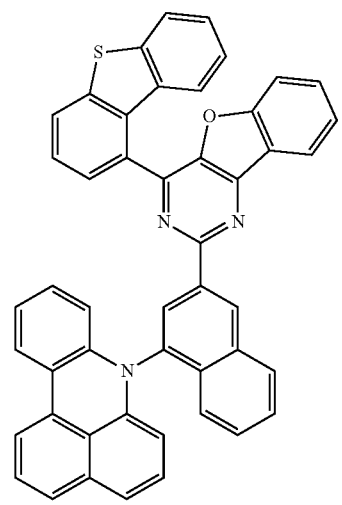
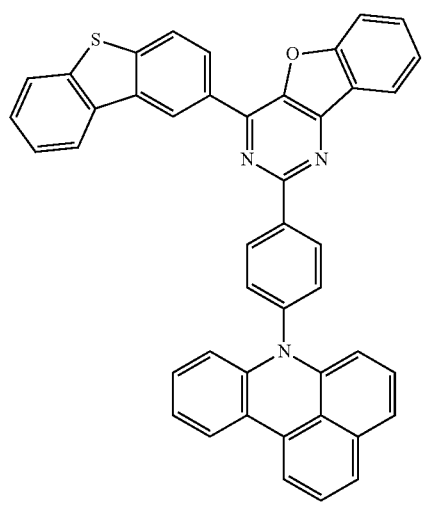
480
-continued
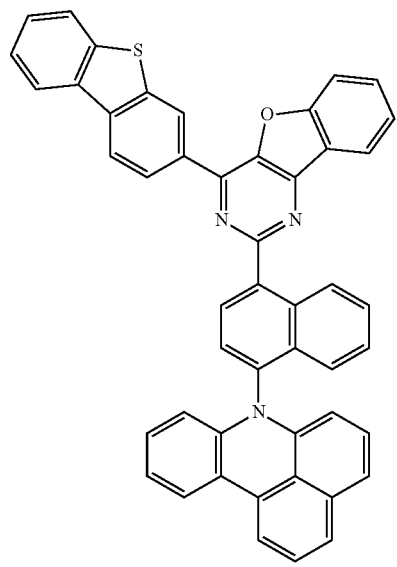
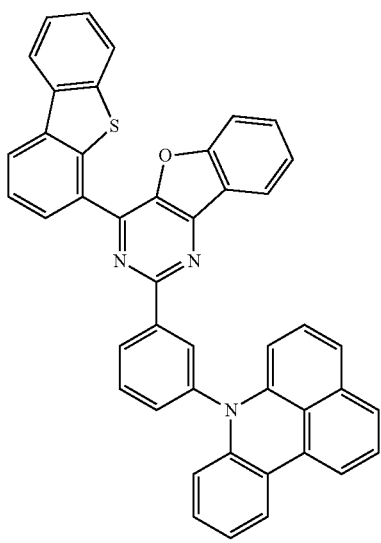
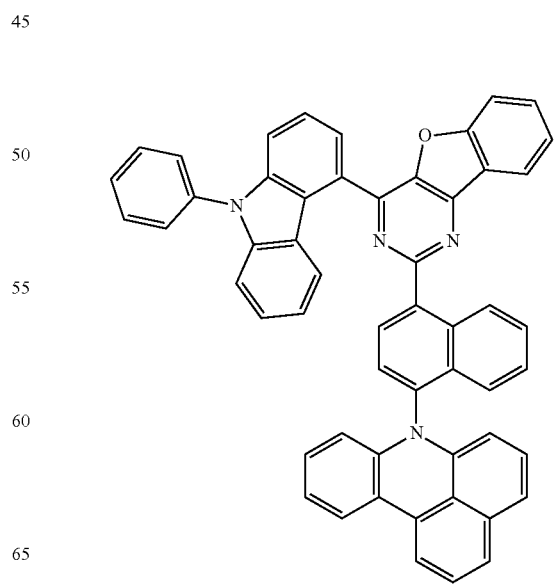

481
-continued
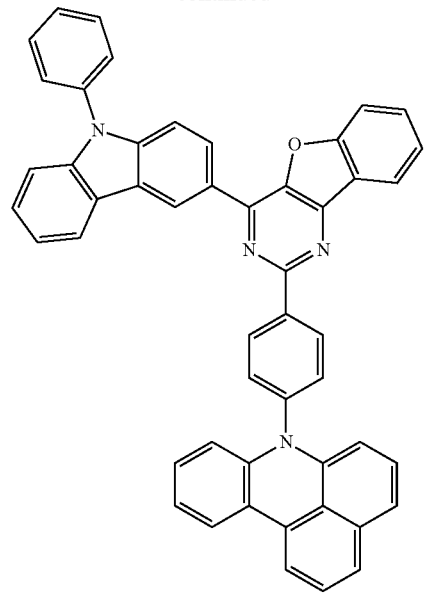
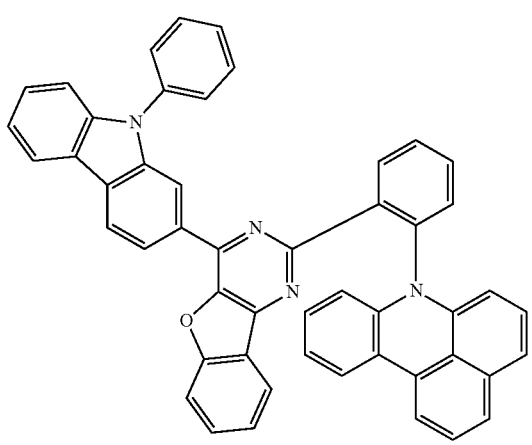
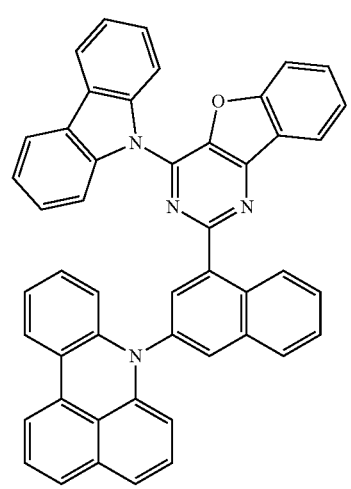
482
-continued
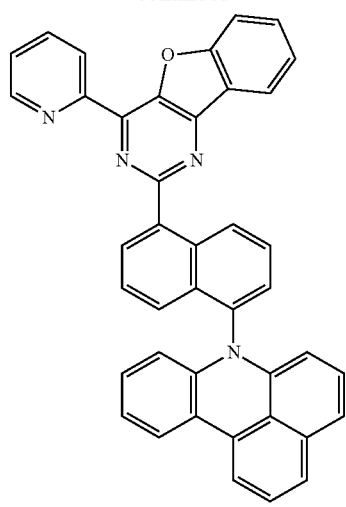
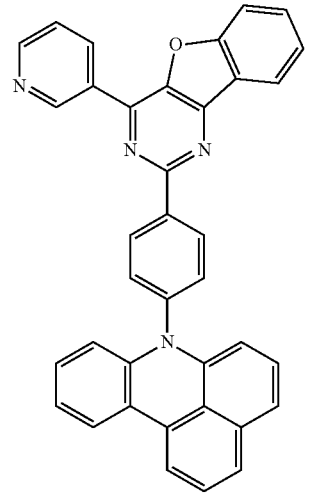
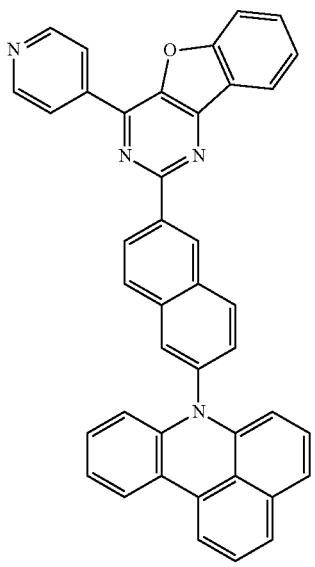

483
-continued
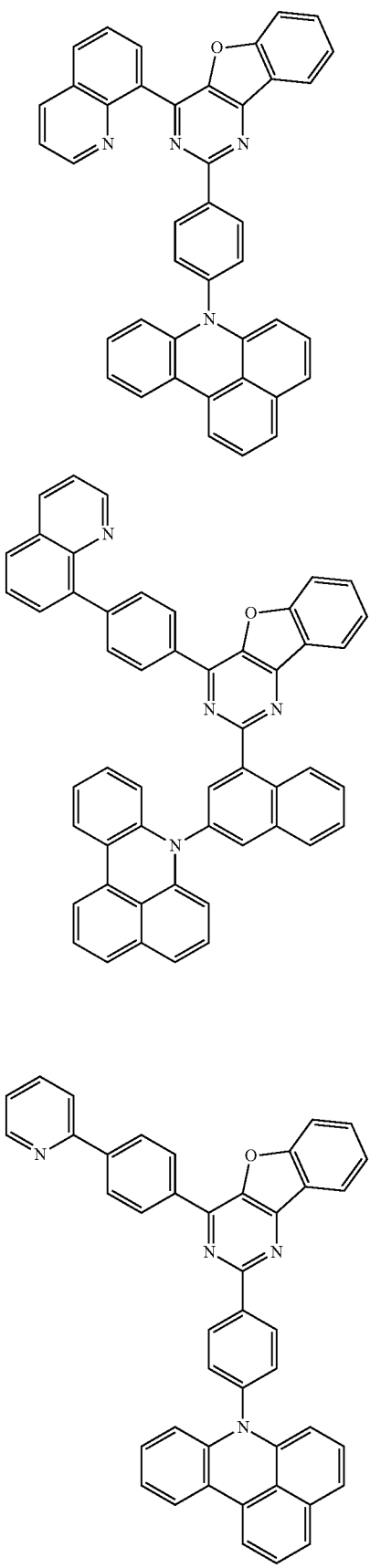
484
-continued
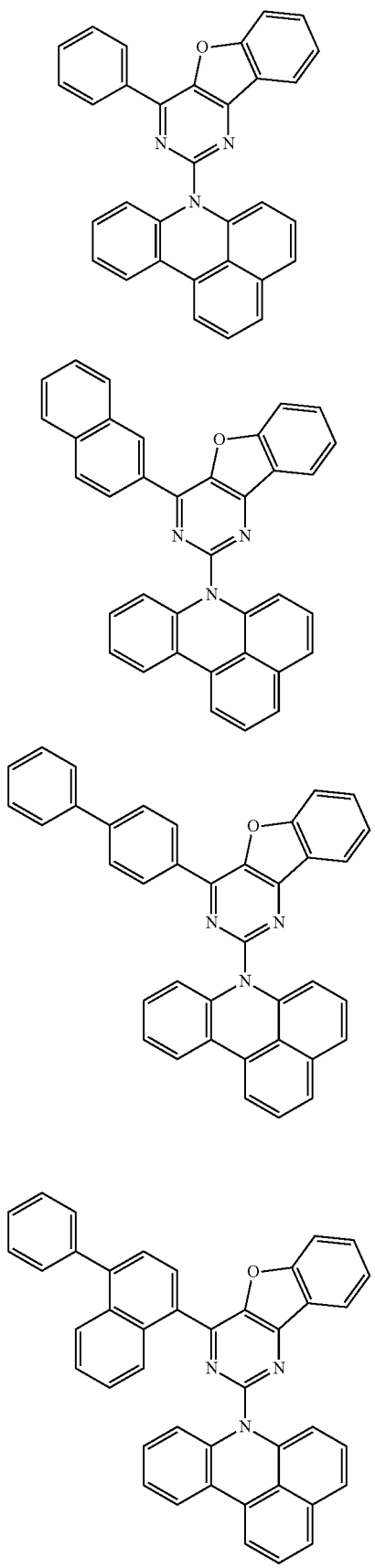

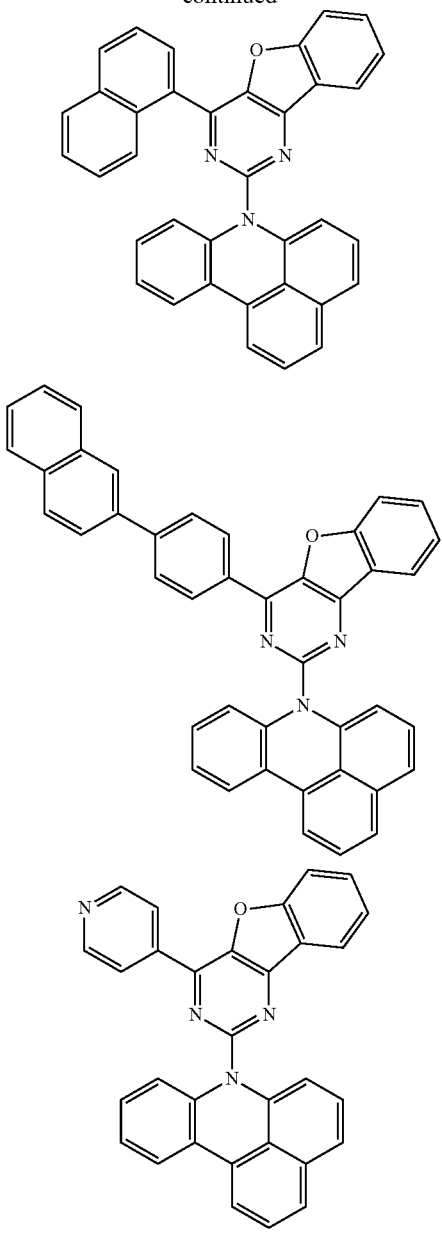

6. An organic light emitting device, comprising:
a first electrode;
a second electrode provided opposite to the first electrode; and
one or more organic material layers provided between the first electrode and the second electrode,
wherein one or more layers of the organic material layers comprise the compound of Chemical Formula 1 of claim 1.

7. The organic light emitting device of claim 6, wherein the organic material layer comprises a hole injection layer or a hole transfer layer, and the hole injection layer or the hole transfer layer comprises the compound of Chemical Formula 1.

8. The organic light emitting device of claim 6, wherein the organic material layer comprises a light emitting layer, and the light emitting layer comprises the compound of Chemical Formula 1.

9. The organic light emitting device of claim 6, wherein the organic material layer comprises an electron transfer layer or an electron injection layer, and the electron transfer layer or the electron injection layer comprises the compound of Chemical Formula 1.

10. The organic light emitting device of claim 6, further comprising one, two or more layers selected from the group consisting of a hole injection layer, a hole transfer layer, an electron transfer layer, an electron injection layer, an electron blocking layer, and a hole blocking layer.

* * * * *

UNITED STATES PATENT AND TRADEMARK OFFICE
CERTIFICATE OF CORRECTION

PATENT NO. : 11,812,658 B2
APPLICATION NO. : 16/982229
DATED : November 7, 2023
INVENTOR(S) : Kim et al.

Page 1 of 93

It is certified that error appears in the above-identified patent and that said Letters Patent is hereby corrected as shown below:

In the Claims

In Claim 5, at Column 486, Line 20, the following compounds should be inserted:

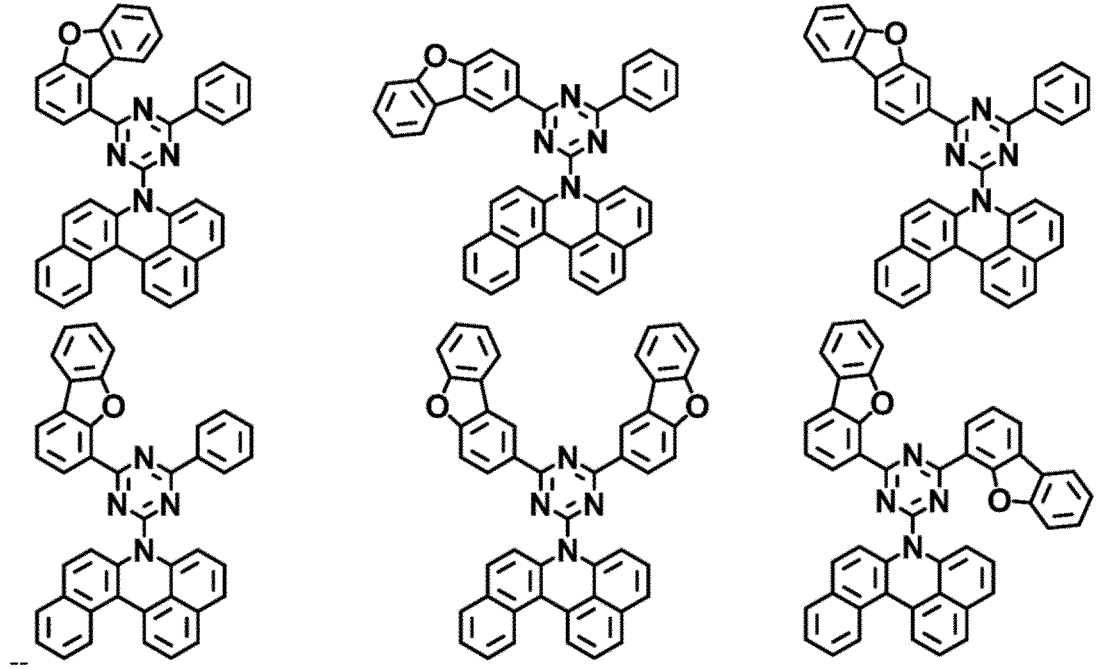

--

Signed and Sealed this
Twenty-ninth Day of October, 2024

Katherine Kelly Vidal
*Director of the United States Patent and Trademark Office*

CERTIFICATE OF CORRECTION (continued)
U.S. Pat. No. 11,812,658 B2